United States Patent
Aponte et al.

(10) Patent No.: US 12,123,010 B2
(45) Date of Patent: *Oct. 22, 2024

(54) PLANTS HAVING INCREASED TOLERANCE TO HERBICIDES

(71) Applicant: BASF SE, Ludwigshafen (DE)

(72) Inventors: Raphael Aponte, Mannheim (DE); Tobias Seiser, Ludwigshafen (DE); Stefan Tresch, Ludwigshafen (DE); Peter Alexander Bowerman, Durham, NC (US); Liliana Parra Rapado, Limburgerhof (DE); Matthias Witschel, Ludwigshafen (DE); Laetitia Souillart, Wuppertal (DE); Manuel Johannes, Hilden (DE); Thomas Mietzner, Annweiler (DE); Jill Marie Paulik, Durham, NC (US)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/049,158

(22) Filed: Oct. 24, 2022

(65) Prior Publication Data

US 2023/0175005 A1 Jun. 8, 2023

Related U.S. Application Data

(63) Continuation of application No. 16/767,917, filed as application No. PCT/IB2018/059413 on Nov. 28, 2018, now Pat. No. 11,479,786.

(60) Provisional application No. 62/592,037, filed on Nov. 29, 2017.

(51) Int. Cl.
*C12N 15/82* (2006.01)
*A01N 43/54* (2006.01)

(52) U.S. Cl.
CPC ......... *C12N 15/8274* (2013.01); *A01N 43/54* (2013.01); *C12Y 103/03004* (2013.01)

(58) Field of Classification Search
None
See application file for complete search history.

(56) References Cited

U.S. PATENT DOCUMENTS

| | | | |
|---|---|---|---|
| 4,940,935 A | 7/1990 | Riley | |
| 5,169,770 A | 12/1992 | Chee et al. | |
| 5,188,642 A | 2/1993 | Shah et al. | |
| 5,268,463 A | 12/1993 | Jefferson | |
| 5,276,268 A | 1/1994 | Strauch et al. | |
| 5,322,783 A | 6/1994 | Tomes et al. | |
| 5,349,127 A | 9/1994 | Dean et al. | |
| 5,366,892 A | 11/1994 | Foncerrada et al. | |
| 5,376,543 A | 12/1994 | Chee et al. | |
| 5,380,831 A | 1/1995 | Adang et al. | |
| 5,399,680 A | 3/1995 | Zhu et al. | |
| 5,424,412 A | 6/1995 | Brown et al. | |
| 5,436,391 A | 7/1995 | Fujimoto et al. | |
| 5,466,785 A | 11/1995 | de Framond | |
| 5,561,236 A | 10/1996 | Leemans et al. | |
| 5,565,350 A | 10/1996 | Kmiec | |
| 5,569,597 A | 10/1996 | Grimsley et al. | |
| 5,593,874 A | 1/1997 | Brown et al. | |
| 5,593,881 A | 1/1997 | Thompson et al. | |
| 5,602,321 A | 2/1997 | John | |
| 5,604,121 A | 2/1997 | Hilder et al. | |
| 5,608,142 A | 3/1997 | Barton et al. | |
| 5,608,144 A | 3/1997 | Baden et al. | |
| 5,608,149 A | 3/1997 | Barry et al. | |
| 5,659,026 A | 8/1997 | Baszczynski et al. | |
| 5,705,628 A | 1/1998 | Hawkins | |
| 5,723,756 A | 3/1998 | Peferoen et al. | |
| 5,737,514 A | 4/1998 | Stiffler | |
| 5,747,450 A | 5/1998 | Ohba et al. | |
| 5,767,373 A | 6/1998 | Ward et al. | |
| 5,773,702 A | 6/1998 | Penner et al. | |
| 5,792,931 A | 8/1998 | Duvick et al. | |
| 5,859,348 A | 1/1999 | Penner et al. | |
| 5,898,071 A | 4/1999 | Hawkins | |
| 5,939,602 A * | 8/1999 | Volrath | .......... C12Y 103/03004 536/23.6 |
| 5,952,544 A | 9/1999 | Browse et al. | |
| 5,981,722 A | 11/1999 | Chen et al. | |

(Continued)

FOREIGN PATENT DOCUMENTS

| | | | |
|---|---|---|---|
| CN | 101232811 A | 7/2008 | |
| CN | 101232813 A | 7/2008 | |

(Continued)

OTHER PUBLICATIONS

"Method of the Year 2011", Nature Methods, vol. 9, Issue 1, Dec. 28, 2011.
Aldemita et al., "Agrobacterium tumefaciens-mediated transformation of japonica and indica rice varieties", Planta, vol. 199, Issue 4, Aug. 1996, pp. 612-617.
Allison et al., "The nucleotide sequence of the coding region of tobacco etch virus genomic RNA: Evidence for the synthesis of a single polyprotein", Virology, vol. 154, Issue 1, Oct. 15, 1986, pp. 9-20.

(Continued)

*Primary Examiner* — Weihua Fan
(74) *Attorney, Agent, or Firm* — MARSHALL, GERSTEIN & BORUN LLP

(57) ABSTRACT

The present invention refers to a method for controlling undesired vegetation at a plant cultivation site, the method comprising the steps of providing, at said site, a plant that comprises at least one nucleic acid comprising a nucleotide sequence encoding protoporphyrinogen oxidase (PPO) which is resistant or tolerant to a PPO-inhibiting herbicide by applying to said site an effective amount of said herbicide. The invention further refers to plants comprising wild-type or mutated PPO enzymes, and methods of obtaining such plants.

20 Claims, 15 Drawing Sheets

Figure 1:
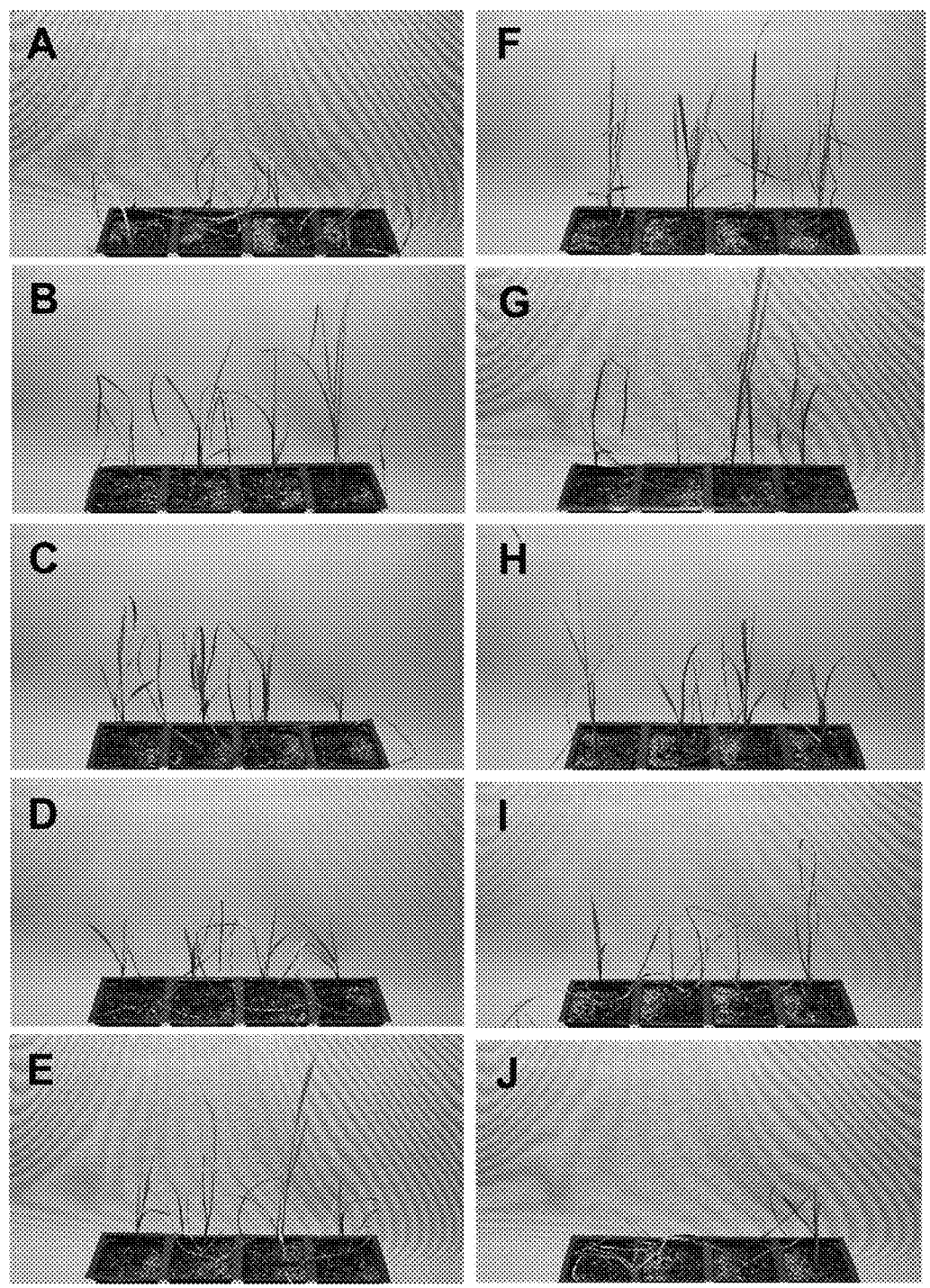

Specification includes a Sequence Listing.

(56) References Cited

U.S. PATENT DOCUMENTS

| | | | |
|---|---|---|---|
| 5,990,387 | A | 11/1999 | Tomes et al. |
| 6,072,050 | A | 6/2000 | Bowen et al. |
| 6,121,512 | A | 9/2000 | Siminszky et al. |
| 6,177,611 | B1 | 1/2001 | Rice |
| 6,232,529 | B1 | 5/2001 | Singletary et al. |
| 6,300,544 | B1 | 10/2001 | Halkier et al. |
| 6,380,465 | B1 | 4/2002 | Barrett |
| 6,534,262 | B1 | 3/2003 | McKernan et al. |
| 6,649,814 | B2 | 11/2003 | Halkier et al. |
| 6,653,529 | B2 | 11/2003 | Peng et al. |
| 11,479,786 | B2 | 10/2022 | Aponte et al. |
| 2005/0060767 | A1 | 3/2005 | Subramanian et al. |
| 2005/0246798 | A1 | 11/2005 | Castle et al. |
| 2007/0004912 | A1 | 1/2007 | Castle et al. |
| 2009/0011936 | A1 | 1/2009 | Hawkes et al. |
| 2009/0049567 | A1 | 2/2009 | Olhoft et al. |
| 2010/0100988 | A1 | 4/2010 | Tranel et al. |
| 2015/0252379 | A1 | 9/2015 | Hutzler et al. |

FOREIGN PATENT DOCUMENTS

| | | |
|---|---|---|
| CN | 101325875 A | 12/2008 |
| CN | 106029890 A | 10/2016 |
| EP | 0242236 A1 | 10/1987 |
| EP | 0293356 A1 | 11/1988 |
| EP | 0337899 A1 | 10/1989 |
| EP | 0374753 A2 | 6/1990 |
| EP | 0427529 A1 | 5/1991 |
| EP | 0451878 A1 | 10/1991 |
| EP | 0397687 B1 | 5/1994 |
| EP | 0424047 B1 | 7/1995 |
| EP | 1198985 A1 | 4/2002 |
| TW | 201231656 A | 8/2012 |
| WO | WO-93/07256 A1 | 4/1993 |
| WO | WO-93/07278 A1 | 4/1993 |
| WO | WO-93/22443 A1 | 11/1993 |
| WO | WO-94/11516 A1 | 5/1994 |
| WO | WO-95/34656 A1 | 12/1995 |
| WO | WO-99/43838 A1 | 9/1999 |
| WO | WO-00/15815 A1 | 3/2000 |
| WO | WO-02/15701 A2 | 2/2002 |
| WO | WO-02/068607 A2 | 9/2002 |
| WO | WO-03/018810 A2 | 3/2003 |
| WO | WO-03/052073 A2 | 6/2003 |
| WO | WO-2005/107437 A2 | 11/2005 |
| WO | WO-2006/024820 A1 | 3/2006 |
| WO | WO-2006/037945 A1 | 4/2006 |
| WO | WO-2006/136596 A2 | 12/2006 |
| WO | WO-2007/000077 A1 | 1/2007 |
| WO | WO-2007/024739 A2 | 3/2007 |
| WO | WO-2007/071900 A1 | 6/2007 |
| WO | WO-2007/096576 A1 | 8/2007 |
| WO | WO-2008/124495 A2 | 10/2008 |
| WO | WO-2008/141154 A2 | 11/2008 |
| WO | WO-2010/049269 A1 | 5/2010 |
| WO | WO-2010/049270 A1 | 5/2010 |
| WO | WO-2011/137088 A1 | 11/2011 |
| WO | WO-2012/080975 A1 | 6/2012 |
| WO | WO-2013/189984 A2 | 12/2013 |
| WO | WO-2015/022636 A2 | 2/2015 |
| WO | WO-2015/022640 A2 | 2/2015 |
| WO | WO-2015/092706 A1 | 6/2015 |

OTHER PUBLICATIONS

Altschul, et al., "Basic local Alignment Search Tool", Journal of Molecular Biology, vol. 215, Issue 3, Oct. 5, 1990, pp. 403-410.

Archer et al., "Current views on chloroplast protein import and hypotheses on the origin of the transport mechanism", Journal of Bioenergetics and Biomembranes, vol. 22, Issue 6, Dec. 1990, pp. 789-810.

Arias, et al., "Molecular evolution of herbicide resistance to phytoene desaturase inhibitors in Hydrilla verticillata and its potential use to generate herbicideresistant crops", Pest Management Science, vol. 61, Issue 3, Jan. 2005, pp. 258-268.

Baim, et al., "A chimeric mammalian transactivator based on the lac repressor that is regulated by temperature and isopropyl beta-D-thiogalactopyranoside", Proceedings of the National Academy of Sciences of the United States of America, vol. 88, Issue 12, Jun. 15, 1991, pp. 5072-5076.

Bairoch, et al., "PROSITE: recent developments", Nucleic Acids Research, vol. 22, Issue 17, Sep. 1994, pp. 3583-3589.

Ballas et al., "Efficient functioning of plant promoters and poly(A) sites in Xenopus oocytes", Nucleic Acids Research, vol. 17, Issue 19, Oct. 11, 1989, pp. 7891-7903.

Bateman, et al., "The Pfam Protein Families Database", Nucleic Acids Research, vol. 30, Issue 1, Jan. 1, 2002, pp. 276-280.

Behrens, et al., "Dicamba Resistance: Enlarging and Preserving Biotechnology-Based Weed Management Strategies", Science, vol. 316, Issue 5828, May 25, 2007, pp. 1185-1188.

Bevan, "Binary Agrobacterium vectors for plant transformation", Nucleic Acids Research, vol. 12, Issue 22, Nov. 26, 1984, pp. 8711-8721.

Block, et al., "Transformation of *Brassica napus* and *Brassica oleracea* Using Agrobacterium tumefaciens and the Expression of the bar and neo Genes in the Transgenic Plants", Plant Physiology, vol. 91, Issue 2, Oct. 1989, 694-701.

Bock, "Transgenic Plastids in Basic Research and Plant Biotechnology", Journal of Molecular Biology, vol. 312, Issue 3, Sep. 21, 2001, pp. 425-438.

Brown et al., "Lac repressor can regulate expression from a hybrid SV40 early promoter containing a lac operator in animal cells", Cell, vol. 49, Issue 5, Jun. 5, 1987, pp. 603-612.

Buchman, et al., "Comparison of intron-dependent and intron-independent gene expression", Molecular and Cellular Biology, vol. 8, Issue 10, Oct. 1988, pp. 4395-4405.

Callis, et al., "Introns increase gene expression in cultured maize cells", Genes & Development, vol. 1, Issue 10, Dec. 1987, pp. 1183-1200.

Camp, et al., "Tissue-Specific Activity of Two Manganese Superoxide Dismutase Promoters in Transgenic Tobacco", Plant Physiology, vol. 112, Issue 2, Oct. 1996, pp. 525-535.

Campanella, et al., "MatGAT: An application that generates similarity/identity matrices using protein or DNA sequences", BMC Bioinformatics, vol. 4, Jul. 10, 2003, 4 pages.

Campbell et al., "Codon Usage in Higher Plants, Green Algae, and Cyanobacteria", Plant Physiology, vol. 92, Issue 1, Jan. 1990, pp. 1-11.

Canevascini, et al., "Tissue-Specific Expression and Promoter Analysis of the Tobacco Itp1 Gene", Plant.

Castle, et al., "Discovery and Directed Evolution of a Glyphosate Tolerance Gene", Science, vol. 304, Issue 5674, May 21, 2004, pp. 1151-1154.

Chan et al., Agrobacterium-mediated production of transgenic rice plants expressing a chimeric alpha-amylase promoter/beta-glucuronidase gene, Plant Mol. Biol., 22(3):491-506 (Jun. 1993).

Chang et al., "Stable genetic transformation of *Arabidopsis thaliana* by Agrobacterium inoculation in planta", The Plant Journal, vol. 5, Issue 4, Apr. 1994, pp. 551-558.

Che, et al., "Localization of Target-Site of the Protoporphyrinogen Oxidase-Inhibiting Herbicide, S-23142, in *Spinacia oleracea* L.", Zeitschrift fur Naturforschung C, vol. 48, Issue 3-4, 1993, pp. 350-355.

Christensen et al., "Sequence analysis and transcriptional regulation by heat shock of polyubiquitin transcripts from maize", Plant Molecular Biology, vol. 12, Issue 6, Jun. 1989, pp. 619-632.

Christensen, et al., "Maize polyubiquitin genes: structure, thermal perturbation of expression and transcript splicing, and promoter activity following transfer to protoplasts by electroporation", Plant Molecular Biology, vol. 18, Issue 4, Feb. 1992, pp. 675-689.

Christopherson et al., "Ecdysteroid-dependent regulation of genes in mammalian cells by a *Drosophila ecdysone* receptor and chimeric transactivators", Proceedings of the National Academy of Sciences, vol. 89, Issue 14, 1992, pp. 6314-6318.

Clark et al., "Mutations at the transit peptide-mature protein junction separate two cleavage events during chloroplast import of the

(56) References Cited

OTHER PUBLICATIONS chlorophyll a/b-binding protein", The Journal of Biological Chemistry, vol. 264, 1989, pp. 17544-17550.
Clough et al., "Floral dip: a simplified method forAgrobacterium-mediated transformation of *Arabidopsis thaliana*", The Plant Journal, vol. 16, Issue 6, Dec. 1998, pp. 735-743.
Cole-Strauss, et al., "Targeted gene repair directed by the chimeric RNA/DNA oligonucleotide in a mammalian cell-free extract", Nucleic Acids Res., 27(5):323-30 (Mar. 1999).
Crossway, et al., "Integration of foreign DNA following microinjection of tobacco mesophyll protoplasts", Molecular and General Genetics MGG, vol. 202, Feb. 1986, pp. 179-185.
Dailey, et al., "Expression of a cloned protoporphyrinogen oxidase", The Journal of Biological Chemistry, vol. 269, Issue 2, Jan. 14, 1994, pp. 813-815.
Dayan, et al., "Biochemical and structural consequences of a glycine deletion in the a-8 helix of protoporphyrinogen oxidase", Biochimica et Biophysica Acta (BBA)—Proteins and Proteomics, vol. 1804, Issue 7, Jul. 2010, pp. 1548-1556.
Deblaere et al., "Efficient octopine Ti plasmid-derived vectors for Agrobacterium-mediated gene transfer to plants", Nucleic Acids Research, vol. 13, Issue 13, Jul. 11, 1985, pp. 4777-4788.
Degenkolb et al., "Structural requirements of tetracycline-Tet repressor interaction: determination of equilibrium binding constants for tetracycline analogs with the Tet repressor", Antimicrobial Agents and Chemotherapy, vol. 35, Issue 8, 1991, pp. 1591-1595.
Della-Cioppa et al., "Protein Trafficking in Plant Cells", Plant Physiology, vol. 84, Issue 4, Aug. 1987, pp. 965-968.
Deuschle et al., "Regulated expression of foreign genes in mammalian cells under the control of coliphage T3 RNA polymerase and lac repressor", Proceedings of the National Academy of Sciences, vol. 86, Issue 14, 1989, pp. 5400-5404.
Deuschle et al., "RNA polymerase II transcription blocked by *Escherichia coli* lac repressor", Science, vol. 248, Issue 4954, Apr. 27, 1990, pp. 480-483.
Dill et al., "Glyphosate-resistant crops: adoption, use and future considerations", Pest Management Science, vol. 64, Issue 4, Apr. 2008, pp. 326-331.
Duke, et al., "Protoporphyrinogen Oxidase-Inhibiting Herbicides", Weed Science, vol. 39, Issue 3, Jul. 1991.
Elroy-Stein et al., "Cap-independent translation of mRNA conferred by encephalomyocarditis virus 5' sequence improves the performance of the vaccinia virus/bacteriophage T7 hybrid expression system", Proceedings of the National Academy of Sciences, vol. 86, Issue 16, Aug. 1989, pp. 6126-6130.
Esvelt, et al., Genomescale engineering for systems and synthetic biology, Molecular Systems Biology, vol. 9, Issue 1, Jan. 1, 2013, 17 pages.
Falciatore, et al., Transformation of nonselectable reporter genes in marine diatoms, Marine Biotechnology, vol. 1, May 1999, pp. 239-251.
Feldmann et al., Agrobacterium-mediated transformation of germinating seeds of *Arabidopsis thaliana*: A non-tissue culture approach, Molecular Genetics and Genomics, vol. 208, Issue 1-2, 1987, pp. 1-9.
Figge et al., "Stringent regulation of stably integrated chloramphenicol acetyl transferase genes by *E. coli* lac repressor in monkey cells", Cell, vol. 52, Issue 5, Mar. 11, 1988, pp. 713-722.
Filho et al., "Mitochondrial and chloroplast targeting sequences in tandem modify protein import specificity in plant organelles", Plant Molecular Biology, vol. 30, Issue 4, Feb. 1996, pp. 769-780.
Frame et al., "Agrobacterium tumefaciens—Mediated Transformation of Maize Embryos Using a Standard Binary Vector System", Plant physiology, vol. 129, Issue 1, 2002, pp. 13-22.
Fuerst et al., "Transfer of the inducible lac repressor/operator system from *Escherichia coli* to a vaccinia virus expression vector", Proceedings of the National Academy of Sciences, vol. 86, Issue 8, pp. 2549-2553.

Gallie et al., "A comparison of eukaryotic viral 5'-leader sequences as enhancers of mRNA expression in vivo", Nucleic Acids Research, vol. 15, Issue 21, Nov. 11, 1987, pp. 8693-8711.
Gallie et al., "The Regulation of Gene Expression in Transformed Maize Aleurone and Endosperm Protoplasts (Analysis of Promoter Activity, Intron Enhancement, and mRNA Untranslated Regions on Expression)", Plant Physiology, vol. 106, Issue 3, Nov. 1994, pp. 929-939.
Gallie et al., "The tobacco etch viral 5? leader and poly(A) tail are functionally synergistic regulators of translation", Gene, vol. 165, Issue 2, 1995, pp. 233-238.
Gasteiger et al., "ExPASy: The proteomics server for in-depth protein knowledge and analysis", Nucleic Acids Research, vol. 31, Issue 13, 2003, pp. 3784-3788.
Geiser et al., "The hypervariable region in the genes coding for entomopathogenic crystal proteins of Bacillus thuringiensis: nucleotide sequence of the kurhd1 gene of subsp. kurstaki HD1", Gene, vol. 48, Isasue 1, 1986, pp. 109-118.
Gill et al., "Negative effect of the transcriptional activator GAL4", Nature, vol. 334, 1988, pp. 721-724.
Gossen et al., "Tight control of gene expression in mammalian cells by tetracycline-responsive promoters", Proceedings of the National Academy of Sciences, vol. 89, Issue 12, 1992, pp. 5547-5551.
Green, "Evolution of Glyphosate-Resistant Crop Technology", Weed Science, vol. 57, Issue 1, Feb. 2009, pp. 108-117.
Green, et al., "New multiple-herbicide crop resistance and formulation technology to augment the utility of glyphosate", Pest Management Science, vol. 64, Issue 4, Apr. 2008, pp. 332-339.
Guerineau, et al., "Effect of deletions in the cauliflower mosaic virus polyadenylation sequence on the choice of the polyadenylation sites in tobacco protoplasts", Molecular and General Genetics MGG, vol. 226, Issue 1-2, Apr. 1991, pp. 141-144.
Guevara-Garcia , et al., "Tissue?specific and wound?inducible pattern of expression of the mannopine synthase promoter is determined by the interaction between positive and negative cis? regulatory elements", The Plant Journal, vol. 4, Issue 3, Sep. 1993, pp. 495-505.
Hansen, et al., "Wound-inducible and organ-specific expression of ORF13 from Agrobacterium rhizogenes; 8196 T-DNA in transgenic tobacco plants", Molecular and General Genetics MGG, vol. 254, Issue 3, Apr. 1997, pp. 337-343.
Hiei, et al., "Efficient transformation of rice (*Oryza sativa* L.) mediated by Agrobacterium and sequence analysis of the boundaries of the T-DNA", The Plant Journal, vol. 6, Issue 2, Aug. 1994, pp. 271-282.
Hofgen, et al., "Storage of competent cells for Agrobacterium transformation", Nucleic Acids Research, vol. 16, Issue 20, Oct. 25, 1988, p. 9877.
Hu, et al., "The inducible lac operator-repressor system is functional in mammalian cells", Cell, vol. 48, Issue 4, Feb. 27, 1987, pp. 555-566.
Hulo, et al., "Recent improvements to the PROSITE database", Nucleic Acids Research, vol. 32, Issue suppl. 1, 2004, D134-D137.
International Application No. PCT/IB2018/059413, International Search Report and Written Opinion, mailed Mar. 19, 2019.
Inui, et al., "Herbicide resistance in transgenic plants with mammalian P450 monooxygenase genes", Pest Management Science, vol. 61, Issue 3, Mar. 2005, pp. 286-291.
Ishida, et al., "High efficiency transformation of maize (*Zea mays* L.) mediated by Agrobacterium tumefaciens", Nature Biotechnology, vol. 14, Issue 6, pp. 745-750 (1996).
Jacobs, et al., "Assay for enzymatic protoporphyrinogen oxidation, a late step in heme synthesis", Enzyme, vol. 28, 1982, pp. 206-219.
Jobling, et al., "Enhanced translation of chimaeric messenger RNAs containing a plant viral untranslated leader sequence", Nature, vol. 325, 1987, pp. 622-625.
Jones, et al., Isolation of the tomato Cf-9 gene for resistance to *Cladosporium fulvum* by transposon tagging, Science, 266(5186):789-93 (Nov. 1994).
Joshi, "Putative polyadenylation signals in nuclear genes of higher plants: a compilation and analysis", Nucleic Acids Research, vol. 15, Issue 23, Dec. 10, 1987, pp. 9627-9640.

(56) References Cited

OTHER PUBLICATIONS

Kataoka, et al., "Isolation and Partial Characterization of Mutant *Chlamydomanas reinhardtii* Resistant to Herbicide S-23142", Journal of Pesticide Science, vol. 15, Issue 3, 1993, pp. 449-451.

Katavic, et al., "In planta transformation of *Arabidopsis thaliana*", Molecular and General Genetics MGG, vol. 245, Issue 3, May 1994, pp. 363-370.

Kawamata, et al., "Temporal and Spatial Pattern of Expression of the Pea Phenylalanine Ammonia-Lyase Genel Promoter in Transgenic Tobacco", Plant and Cell Physiology, vol. 38, Issue 7, Jan. 1, 1997, pp. 792-803.

Klaus, et al., "Generation of marker-free plastid transformants using a transiently cointegrated selection gene", Nature Biotechnology, vol. 22, 2004, pp. 225-229.

Klein, et al., "High-velocity microprojectiles for delivering nucleic acids into living cells", Nature, vol. 327, 1987, pp. 70-73.

Kleinschmidt, et al., "Dynamics of repressor-operator recognition: The Tn10-encoded tetracycline resistance control", Biochemistry, vol. 27, Issue 4, 1988, pp. 1094-1104.

Koncz et al., "The promoter of TL-DNA gene 5 controls the tissue-specific expression of chimaeric genes carried by a novel type of Agrobacterium binary vector", Molecular and General Genetics MGG, vol. 204, Issue 3, Sep. 1986, pp. 383-396.

Krens, et al., "In vitro transformation of plant protoplasts with Ti-plasmid DNA", Nature, vol. 296,1982, pp. 72-74.

Labow, et al., "Conversion of the lac repressor into an allosterically regulated transcriptional activator for mammalian cells", Molecular and Cellular Biology, vol. 10, Issue 7, Jul. 1990, pp. 3343-3356.

Lam, "Analysis of Tissue-Specific Elements in the CaMV 35S Promoter", Plant Promoters and Transcription Factors, Results and Problems in Cell Differentiation book series, vol. 20, 1994, pp. 181-196.

Lamppa, "The chlorophyll a/b-binding protein inserts into the thylakoids independent of its cognate transit peptide", The Journal of Biological Chemistry, vol. 263, 1988, pp. 14996-14999.

Last, et al., "pEmu: an improved promoter for gene expression in cereal cells", Theoretical and Applied Genetics, vol. 81, Issue 5, May 1991, pp. 581-588.

Lawrence, et al., "Alterations in the Chlamydomonas Plastocyanin Transit Peptide Have Distinct Effects on in VitroImport and in Vivo Protein Accumulation", The Journal of Biological Chemistry, vol. 272, Issue 33, 1997, pp. 20357-20363.

Lee, et al., "Cellular Localization of Protoporphyrinogen-Oxidizing Activities of Etiolated Barley (*Hordeum; vulgare* L.) Leaves (Relationship to Mechanism of Action of Protoporphyrinogen Oxidase-Inhibiting; Herbicides)", Plant Physiology, vol. 102, 1993, pp. 881-889.

Letunic, et al., "Recent improvements to the SMART domain-based sequence annotition resource", Nucleic Acids Research, vol. 30, Issue 1, 2002, pp. 242-244.

Li, et al., "Development of PPO inhibitor-resistant cultures and crops", Pest Management Science, vol. 61, Issue 3, Mar. 2005, pp. 277-285.

Lommel, et al., "Identification of the Maize chlorotic mottle virus capsid protein cistron and characterization of its subgenomic messenger RNA", Virology, vol. 181, Issue 1, Mar. 1991, pp. 382-385.

Macejak, et al., "Internal initiation of translation mediated by the 5? leader of a cellular mRNA", Nature, vol. 353, 1991, pp. 90-94.

Maliga, "Progress towards commercialization of plastid transformation technology", Trends in Biotechnology, vol. 21, Issue 1, Jan. 2003, pp. 20-28.

Martin, et al., "Map-based cloning of a protein kinase gene conferring disease resistance in tomato", Science, vol. 262, Issue 5138, 1993, pp. 1432-1436.

Matringe, et al., "p-Hydroxyphenylpyruvate dioxygenase inhibitor-resistant plants", Pest Management Science, vol. 61, Issue 3, Mar. 2005, pp. 269-276.

Matringe, et al., "Protoporphyrinogen oxidase as a molecular target for diphenyl ether herbicides", ?Biochemical Journal, vol. 260, Issue 1, 1989, pp. 231-325.

Matsuoka, et al., "Tissue-specific light-regulated expression directed by the promoter of a C4 gene, maize pyruvate, orthophosphate dikinase, in a C3 plant, rice", Proceedings of the National Academy of Sciences, vol. 90, Issue 20, 1993, pp. 9586-9590.

Mcbride, et al., "Controlled expression of plastid transgenes in plants based on a nuclear DNA-encoded and plastid-targeted T7 RNA polymerase", Proceedings of the National Academy of Sciences, vol. 91 Issue 15, 1994, pp. 7301-7305.

Mcelroy, et al., "Isolation of an efficient actin promoter for use in rice transformation", The Plant Cell, vol. 2, Issue 2, Feb. 1990, pp. 163-171.

Mindrinos, et al., "The *A. thaliana* Disease Resistance Gene RPS2 Encodes a Protein Containing a Nucleotide-Binding Site and Leucine-Rich Repeats", Cell, vol. 78, issue 6, 1994, pp. 1089-1099.

Mlynarova, et al., "High efficiency Agrobacterium-mediated gene transfer to flax", Plant Cell Reports, vol. 13, Issue 5, Feb. 1994, pp. 282-285.

Mogen, et al., "Upstream sequences other than AAUAAA are required for efficient messenger RNA 3'-end formation in plants", The Plant Cell, vol. 2, Issue 12, Dec. 1990, pp. 1261-1272.

Moloney, et al., "High efficiency transformation of *Brassica napus* using Agrobacterium vectors", Plant Cell Reports, vol. 8, Issue 4, Apr. 1989, pp. 238-242.

Mulder, et al., "The InterPro Database, 2003 brings increased coverage and new features", Nucleic Acids Research, vol. 31, Issue 1, 2003, pp. 315-318.

Munroe, et al., "Tales of poly(A): a review", Gene, vol. 91, Issue 2, Jul. 16, 1990, pp. 151-158.

Murashige, et al., "A Revised Medium for Rapid Growth and Bio Assays with Tobacco Tissue Cultures", Physiologia Plantarum, vol. 15, Issue 3, Jul. 1962, pp. 473-497.

Murray, et al., "Codon usage in plant genes", Nucleic Acids Research, vol. 17, Issue 2, Jan. 25, 1989, pp. 477-498.

Nandihalli, et al., "Quantitative Structu re-Activity Relationships of Protoporphyrinogen Oxidase-Inh ibiting Diphenyl Ether Herbicides", Pesticide Biochemistry and Phasiology, vol. 43, Issue 3, 1992, pp. 193-211.

Needleman, et al., "A general method applicable to the search for similarities in the amino acid sequence of two proteins", Journal of Molecular Biology, vol. 48, issue 3, pp. 443-453.

Negrutiu, et al., "Hybrid genes in the analysis of transformation conditions", Plant Molecular Biology, vol. 8, Issue 5, Sep. 1987, pp. 363-373.

Non-Final Rejection in U.S. Appl. No. 16/303,783 dated May 11, 2021.

Odell, et al., "Identification of DNA sequences required for activity of the cauliflower mosaic virus 35S promoter", Nature, vol. 313, pp. 810-812 (1985).

Oliva, et al., "Evidence that tetracycline analogs whose primary target is not the bacterial ribosome cause lysis of *Escherichia coli*", Antimicrobial Agents and Chemotherapy, vol. 36, Issue 5, 1992, pp. 913-919.

Orozco, et al., "Localization of light-inducible and tissue-specific regions of the spinach ribulose bisphosphate carboxylase/oxygenase (rubisco) activase promoter in transgenic tobacco plants", Plant Molecular Biology, vol. 23, Issue 6, Dec. 1993, pp. 1129-1138.

Oshio, et al., "Isolation and Characterization of a Chlamydomonas reinhardtii Mutant Resistant to Photobleaching Herbicides", Zeitschrift für Naturforschung, vol. 48C, Issue 3-4, 1993, pp. 339-344.

Padgette, et al., "Site-directed Mutagenesis of a Conserved Region of the; 5-Enolpyruvylshikimate-3-phosphate Synthase Active Site", Journal of Biological Chemistry, vol. 266, Issue 33, 1991, pp. 22364-22369.

Potrykus, "Gene Transfer to Plants: Assessment of Published Approaches and Results", Annual Review of Plant Physiology and Plant Molecular Biology, vol. 42, 1991, pp. 205-225.

Proudfoot, "Poly (A) Signals", Cell, vol. 64, Issue 4, Feb. 1991, pp. 671-674.

Puchta, et al., "Gene targeting in plants: 25 years later", The International Journal of Developmental Biology, vol. 57, 2013, pp. 629-637.

(56) References Cited

OTHER PUBLICATIONS

Reines, et al., "Elongation factor SII-dependent transcription by RNA polymerase II through a sequence-specific DNA-binding protein", Proceedings of the National Academy of Sciences, vol. 90, Issue 5, 1993, pp. 1917-1921.
Reznikoff, "The lactose operon?controlling elements: a complex paradigm", vol. 6, Issue 17, Sep. 1992, pp. 2419-2422.
Rinehart, et al., "Tissue-Specific and Developmental Regulation of Cotton Gene FbL2A (Demonstration of Promoter Activity in Transgenic Plants)", Plant Physiology, vol. 112, Issue 3, Nov. 1996, pp. 1331-1341.
Romer, et al., "Expression of the Genes Encoding the Early Carotenoid Biosynthetic-Enzymes in Capsicum annuum", Biochemical and Biophysical Research Communications, vol. 196, Issue 3, Nov. 15, 1993, pp. 1414-1421.
Russell, et al., "Tissue-specific expression in transgenic maize of four endosperm promoters from maize and rice", Transgenic Research, Mar. 1997, vol. 6, Issue 2, pp. 157-168.
Sanfacon, et al., "A dissection of the cauliflower mosaic virus polyadenylation signal", Genes & Development, 1991, vol. 5, pp. 141-149.
Sasarmen, et al., "Nucleotide sequence of the hemG gene involved in the protoporphyrinogen oxidase activity of *Escherichia coli* K12", Canadian Journal of Microbiology, vol. 29, Issue 12, 1993, pp. 1155-1161.
Sato, et al., "Chapter 7—Characterization of a mutant of chlamydomonas reinhardtii resistant to protoporphyrinogen oxidase inhibitors", Porphyric Pesticides, vol. 559, Apr. 15, 1994, pp. 91-104.
Schenk, et al., "SeSaM: Sättigungsmutagenese eines Genes", Biospektrum, vol. 12, Mar. 2006, pp. 277-279.
Schmidt, et al., "A novel operon organization involving the genes for chorismate synthase (aromatic biosynthesis pathway) and ribosomal GTPase center proteins (L11, L1, L10, L12: rpIKAJL) in cyanobacterium Synechocystis PCC 6803", The Journal of Biological Chemistry, vol. 268, Issue 36, 1993, pp. 27447-27457.
Schnell, et al., "Signal peptide analogs derived from two chloroplast precursors interact with the signal recognition system of the chloroplast envelope", The Journal of Biological Chemistry, vol. 266, Issue 5, 1991, pp. 3335-3342.
Schubert, et al., "Cloning of the *Alcaligenes eutrophus* genes for synthesis of poly-beta-hydroxybutyric acid (PHB) and synthesis of PHB in *Escherichia coli*", ?Journal of Bacteriology, vol. 170, Issue 12, 1988, pp. 5837-5847.
Schultz, et al., "SMART, a simple modular architecture research tool: Identification of signaling domains", Proceedings of the National Academy of Sciences USA, vol. 95, Issue 11, May 1998, pp. 5857-5864.
Shah, et al., "Engineering Herbicide Tolerance in Transgenic Plants", Science, vol. 233, Issue 4762, Jul. 25, 1986, pp. 478-481.
Shibata, et al., "Isolation And Characterization Of A Chlamydomonas Reinhardtii Mutant Resistant To An Experimental Herbicides-23142, Which Inhibits Chlorophyll Synthesis", Research in Photosynthesis, vol. III, ed. N. Murata, 1992, pp. 567-570.
Shillito, et al., "High Efficiency Direct Gene Transfer to Plants", Bio/Technology, vol. 3, 1985, pp. 1099-1103.
Siminszky, "Plant cytochrome P450-mediated herbicide metabolism", Phytochemistry Reviews, vol. 5, Issue 2-3, Jun. 2006, pp. 445-458.
Skuzeski et al., "Analysis of leaky viral translation termination codons in vivo by transient expression of improved β-glucuronidase vectors", Plant Molecular Biology, vol. 15, Issue 1, Jul. 1990, pp. 65-79.
Smith, et al., "Identification of Common Molecular Subsequences", Journal of Molecular Biology, vol. 147, Issue 1, Mar. 1981, pp. 195-197.
Staub, et al., "Accumulation of D1 polypeptide in tobacco plastids is regulated via the untranslated region of the psbA mRNA", The EMBO Journal, vol. 12, Issue 2, Feb. 1993, pp. 601-606.
Strepp, et al., "Plant nuclear gene knockout reveals a role in plastid division for the homolog of the bacterial; cell division protein FtsZ, an ancestral tubulin", Proceedings of the National Academy of Sciences, vol. 95,; Issue 8, 1998, pp. 4368-4373.
Svab, et al., "Stable transformation of plastids in higher plants", Proceedings of the National Academy of Sciences, vol. 87, Issue 21, 1990, pp. 8526-8530.
Svab, et al., "High-frequency plastid transformation in tobacco by selection for a chimeric aadA gene", Proceedings of the National Academy of Sciences, vol. 90, Issue 3, 1993, pp. 913-917.
Tan, et al., "Imidazolinone-tolerant crops: history, current status and future", Pest Management Science, vol. 61, Issue 3, Mar. 2005, pp. 246-257.
Terpe, et al., "Overview of tag protein fusions: from molecular and biochemical fundamentals to commercial systems", Applied Microbiology and Biotechnology, vol. 60, Issue 5, 2003, pp. 523-533.
Thomas, et al., "Site-directed mutagenesis by gene targeting in mouse embryo-derived stem cells", Cell, vol. 51, Issue 3, Nov. 6, 1987, pp. 503-512.
Van Damme, et al., "Molecular cloning of mannose-binding lectins from Clivia miniata", Plant Molecular Biology, vol. 24, Issue 5, 1994, pp. 825-830.
Velten, et al., "Isolation of a dual plant promoter fragment from the Ti plasmid of Agrobacterium tumefaciens", The EMBO Journal, vol. 3, Issue 12, Dec. 1984, pp. 2723-2730.
Von Heijne, et al., "CHLPEP—A database of chloroplast transit peptides", Plant Molecular Biology Reporter, vol. 9, Issue 2, May 1991, pp. 104-126.
Williams, et al., "Differences in zoospore germination and host penetration in response to temperature among Western Australian isolates of Plasmopara viticola", Australian Journal of Agricultural Research, vol. 58, Issue 7, pp. 702-710.
Wyborski, et al., "Analysis of inducers of the *E.coli* lac repressor system mammalian cells and whole animals", Nucleic Acids Research, vol. 19, Issue 17, Sep. 11, 1991, pp. 4647-4653.
Yamamoto, et al., "Light?responsive elements of the tobacco PSI?D gene are located both upstream and within the transcribed region", The Plant Journal, vol. 12, Issue 2, Aug. 1997, pp. 255-265.
Yamamoto, et al., "The Promoter of a Pine Photosynthetic Gene Allows Expression of a ?-Glucuronidase Reporter Gene in Transgenic Rice Plants in a Light-Independent but Tissue-Specific Manner", Plant and Cell Physiology, vol. 35, Issue 5, Jan. 1, 1994, pp. 773-778.
Yanase, et al., "Porphyrin synthesis involvement in diphenyl ether-like mode of action of TNPP-ethyl, a novel phenylpyrazole herbicide", Pesticide Biochemistry and Physiology, vol. 35, Issue 1, 1989, pp. 70-80.
Yao, et al., "*Drosophila* ultraspiracle modulates ecdysone receptor function via heterodimer formation", Cell, vol. 71, Issue 1, Oct. 1992, pp. 63-72.
Yarranton, 'Inducible vectors for expression in mammalian cells', Current Opinion in Biotechnology, vol. 3, Issue 5, Oct. 1992, pp. 506-511.
Zambretti, et al., "A mutant p53 protein is required for maintenance of the transformed phenotype in cells transformed with p53 plus ras cDNAs", Proceedings of the National Academy of Sciences, vol. 89, Issue 9, pp. 3952-3956 (1992).
Zhao, et al., "Immunological Characterization and Chloroplast Localization of the Tryptophan Biosynthetic Enzymes of the Flowering Plant *Arabidopsis thaliana*", The Journal of Biological Chemistry, vol. 270, Issue 11, pp. 6081-6087.

\* cited by examiner

A)

1

2

3

B)

1

2

3

C)

1

2

3

D)

1

2

3

A)

C)

1
2
3
4
5
6
7
8

Check    200    100    50 g/ha

D)

9

10 check    200    100    50 g/ha

PLANTS HAVING INCREASED TOLERANCE TO HERBICIDES

CROSS-REFERENCE TO RELATED APPLICATION

This application is a continuation U.S. patent application Ser. No. 16/767,917, which is a U.S. National Stage application of International Application No. PCT/IB2018/059413, filed Nov. 28, 2018, which claims priority to U.S. Patent Application No. 62/592,037, filed on Nov. 29, 2017.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "1712288B_Seqlisting.XML", which was created on Oct. 4, 2022 and is 804,387 bytes in size. The subject matter of the Sequence Listing is incorporated herein in its entirety by reference.

FIELD OF THE INVENTION

The present invention relates in general to methods for conferring on plants agricultural level tolerance to herbicides. Particularly, the invention refers to plants having an increased tolerance to PPO-inhibiting herbicides. More specifically, the present invention relates to methods and plants obtained by mutagenesis and cross-breeding and transformation that have an increased tolerance to PPO-inhibiting herbicides.

BACKGROUND OF THE INVENTION

Herbicides that inhibit protoporphyrinogen oxidase (hereinafter referred to as Protox or PPO; EC:1.3.3.4), a key enzyme in the biosynthesis of protoporphyrin IX, have been used for selective weed control since the 1960s. PPO catalyzes the last common step in chlorophyll and heme biosynthesis which is the oxidation of protoporphyrinogen IX to protoporphyrin IX. (Matringe et al. 1989. Biochem. 1. 260: 231). PPO-inhibiting herbicides include many different structural classes of molecules (Duke et al. 1991. Weed Sci. 39: 465; Nandihalli et al. 1992. Pesticide Biochem. Physiol. 43: 193; Matringe et al. 1989. FEBS Lett. 245: 35; Yanase and Andoh. 1989. Pesticide Biochem. Physiol. 35: 70). These herbicidal compounds include the diphenylethers {e.g. lactofen, (+−)-2-ethoxy-1-methyl-2-oxoethyl 5-{2-chloro-4-(trifluoromethyl)phenoxy}-2-nitrobenzoate; acifluorfen, 5-{2-chloro-4-(trifluoromethyl)phenoxy}-2-nitrobenzoic acid; its methyl ester; or oxyfluorfen, 2-chloro-1-(3-ethoxy-4-nitrophenoxy)-4-(trifluorobenzene)}, oxidiazoles, (e.g. oxidiazon, 3-{2,4-dichloro-5-(1-methylethoxy)phenyl}-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-{1-(2,3,4-trichlorophenyl)-4-nitropyrazolyl-5-oxy}propionate; M&B 39279), pyridine derivatives (e.g. LS 82-556), and phenopylate and its O-phenylpyrrolidino- and piperidinocarbamate analogs. Many of these compounds competitively inhibit the normal reaction catalyzed by the enzyme, apparently acting as substrate analogs.

Application of PPO-inhibiting herbicides results in the accumulation of protoporphyrinogen IX in the chloroplast and mitochondria, which is believed to leak into the cytosol where it is oxidized by a peroxidase. When exposed to light, protoporphyrin IX causes formation of singlet oxygen in the cytosol and the formation of other reactive oxygen species, which can cause lipid peroxidation and membrane disruption leading to rapid cell death (Lee et al. 1993. Plant Physiol. 102: 881).

Not all PPO enzymes are sensitive to herbicides which inhibit plant PPO enzymes. Both the Escherichia coli and Bacillus subtilis PPO enzymes (Sasarmen et al. 1993. Can. J. Microbiol. 39: 1155; Dailey et al. 1994. J. Biol. Chem. 269: 813) are resistant to these herbicidal inhibitors. Mutants of the unicellular alga Chlamydomonas reinhardtii resistant to the phenylimide herbicide S-23142 have been reported (Kataoka et al. 1990. J. Pesticide Sci. 15: 449; Shibata et al. 1992. In Research in Photosynthesis, Vol. III, N. Murata, ed. Kluwer:Netherlands. pp. 567-70). At least one of these mutants appears to have an altered PPO activity that is resistant not only to the herbicidal inhibitor on which the mutant was selected, but also to other classes of protox inhibitors (Oshio et al. 1993. Z. Naturforsch. 48c: 339; Sato et al. 1994. In ACS Symposium on Porphyric Pesticides, S. Duke, ed. ACS Press: Washington, D.C.). A mutant tobacco cell line has also been reported that is resistant to the inhibitor S-21432 (Che et al. 1993. Z. Naturforsch. 48c: 350). Auxotrophic E. coli mutants have been used to confirm the herbicide resistance of cloned plant PPO-inhibting herbicides.

Three main strategies are available for making plants tolerant to herbicides, i.e. (1) detoxifying the herbicide with an enzyme which transforms the herbicide, or its active metabolite, into non-toxic products, such as, for example, the enzymes for tolerance to bromoxynil or to basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. et al., J. Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor. The third strategy was described for successfully obtaining plants which were tolerant to PPO inhibitors (see e.g. U.S. Pat. No. 5,767,373 or U.S. Pat. No. 5,939,602, and patent family members thereof.). In addition, US 2010/0100988 and WO 2007/024739 discloses nucleotide sequences encoding amino acid sequences having enzymatic activity such that the amino acid sequences are resistant to PPO inhibitor herbicidal chemicals, in particular 3-phenyluracil inhibitor specific PPO mutants.

WO 2012/080975 discloses plants the tolerance of which to a PPO-inhibiting herbicide named (1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione) had been increased by transforming said plants with nucleic acids encoding mutated PPO mutated enzymes. In particular, WO 2012/080975 discloses that the introduction of nucleic acids which code for a mutated PPO of an Amaranthus type II PPO in which the Arginine at position 128 had been replaced by a leucine, alanine, or valine, and the phenylalanine at position 4 had been replaced by a methionine, cysteine, isoleucine, leucine, or threonine, confers increased tolerance/resistance to a benzoxazinone-derivative herbicide. WO 2013/189984 discloses plants the tolerance of which to PPO inhibitors had been increased by transforming said plants with nucleic acids encoding mutated PPO enzymes, in which the Leucine corresponding to position 397 of an *Amaranthus* type II PPO had been replaced, and the phenylalanine corresponding to position 420 of an *Amaranthus* type II PPO had been replaced. WO2015/02263640 discloses plants the tolerance of which to PPO inhibitors had been increased by transforming said plants with nucleic acids encoding mutated PPO enzymes, in which the Arginine corresponding to position 128 of an *Amaranthus* type II PPO had been replaced, and the phenylalanine corresponding to position 420 of an *Amaranthus* type II PPO had been replaced, but the replacement occurred with amino acids, which are different from those disclosed in WO 2012/080975. WO2015/092706 describes PPO polypeptides from a plurality of organisms, which PPO polypeptides had been mutated to comprise the advantageous mutations employed for the *Amaranthus* type II PPO. WO2015/0226 discloses PPO polypeptides from Alopecurus myosuroides and mutants thereof, which confer tolerance to a broad spectrum of PPO inhibiting herbicides.

The inventors of the present invention have now surprisingly found that those types of mutants confer increased tolerance/resistance to a new class of PPO inhibitors, hereinafter described as uracilpyridines or uracilpyridine herbicides. Thus, to date, the prior art has not described uracilpyridine tolerant plants containing a mutated PPO nucleic acid according to the present invention, which are tolerant/resistant to a broad selection of uracilpyridines. Therefore, what is needed in the art are crop plants and crop plants having increased tolerance to uracilpyridines and containing at least one wildtype and/or mutated PPO nucleic acid according to the present invention. Also needed are methods for controlling weed growth in the vicinity of such crop plants or crop plants. These compositions and methods would allow for the use of spray over techniques when applying herbicides to areas containing crop plants or crop plants.

SUMMARY OF THE INVENTION

The problem is solved by the present invention which refers to a method for controlling undesired vegetation at a plant cultivation site, the method comprising the steps of:
a) providing, at said site, a plant that comprises at least one nucleic acid comprising a nucleotide sequence encoding a protoporphyrinogen oxidase (PPO) polypeptide which is resistant or tolerant to a "PPO inhibiting herbicide";
b) applying to said site an effective amount of said herbicide,
wherein the PPO inhibiting herbicide is a uracilpyridine of formula (I)

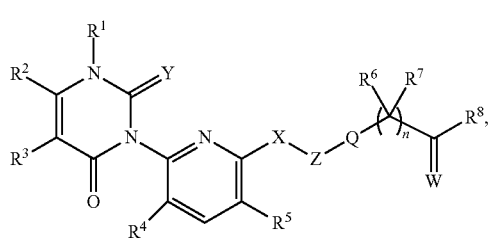

wherein the substituents have the following meanings:
$R^1$ hydrogen, $NH_2$, $C_1$-$C_6$-alkyl or $C_3$-$C_6$-alkynyl;
$R^2$ hydrogen, $C_1$-$C_6$-alkyl or $C_1$-$C_6$-haloalkyl;
$R^3$ hydrogen or $C_1$-$C_6$-alkyl;
$R^4$ H or halogen;
$R^5$ halogen, CN, $NO_2$, $NH_2$, $CF_3$, or C(=S)$NH_2$;
$R^6$ H, halogen, CN, $C_1$-$C_3$-alkyl, $C_1$-$C_3$-haloalkyl, $C_1$-$C_3$-alkoxy, $C_1$-$C_3$-haloalkoxy, $C_1$-$C_3$-alkylthio, ($C_1$-$C_3$-alkyl)amino, di($C_1$-$C_3$-alkyl)amino, $C_1$-$C_3$-alkoxy-$C_1$-$C_3$-alkyl, $C_1$-$C_3$-alkoxycarbonyl;
$R^7$ H, halogen, $C_1$-$C_3$-alkyl, $C_1$-$C_3$-alkoxy;
$R^8$ $OR^9$, $SR^9$, $NR^{10}R^{11}$, $NR^9OR^9$, $NR^9S(O)_2R^{10}$ or $NR^9S(O)_2NR^{10}R^{11}$, wherein
  $R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_1$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
  —N=C$R^{12}R^{13}$, wherein $R^{12}$ and $R^{13}$ independently of one another are H, $C_1$-$C_4$-alkyl or phenyl;
  $C_3$-$C_6$-cycloalkyl, $C_3$-$C_6$-cycloalkyl-$C_1$-$C_6$-alkyl, $C_3$-$C_6$-heterocyclyl, $C_3$-$C_6$-heterocyclyl-$C_1$-$C_6$-alkyl, phenyl, phenyl-$C_1$-$C_4$-alkyl or a 5- or 6 membered heteroaryl,
    wherein each cycloalkyl, heterocyclyl, phenyl or heteroaryl ring can be substituted by one to four substituents selected from $R^{14}$ or a 3- to 7-membered carbocyclus,
      which carbocyclus optionally has in addition to carbon atoms one or two ring members selected from the group consisting of —N($R^{12}$)—, —N=N—, —C(=O)—, —O— and —S—, and
      which carbocyclus is optionally substituted with one to four substituents selected from $R^{14}$;
    wherein $R^{14}$ is halogen, $NO_2$, CN, $C_1$-$C_4$-alkyl, $C_1$-$C_4$-halo-alkyl, $C_1$-$C_4$-alkoxy or $C_1$-$C_4$-alkoxycarbonyl;
  $R^{10}$, $R^{11}$ independently of one another are $R^9$, or together form a 3- to 7-membered carbocyclus,
    which carbocyclus optionally has in addition to carbon atoms one or two ring members selected from the group consisting of —N($R^{12}$—, —N=N—, —C(=O)—, —O— and —S—, and
    which carbocyclus is optionally substituted with one to four substituents selected from $R^{14}$;
n 1 to 3;
Q $CH_2$, O, S, SO, $SO_2$, NH or ($C_1$-$C_3$-alkyl)N;
O or S;
X NH, $NCH_3$, O or S;
Y O or S;
Z phenyl, pyridyl, pyridazinyl, pyrimidinyl or pyrazinyl, each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy, $C_1$-$C_6$-haloalkoxy;

including their agriculturally acceptable salts or derivatives, provided the compounds of formula (I) have a carboxyl group and wherein the effective amount of said herbicide does not kill or inhibit the growth of the herbicide-tolerant plant of a).

In one embodiment, the herbicide resistant or tolerant PPO polypeptide comprises one or more of the following motifs 1, 2, and/or 3:

a. Motif 1: SQ[N/K/H]KRYI, wherein the Arg at position 5 within said motif is substituted by any other amino acid;

b. Motif 2: TLGTLFSS, wherein the Leu at position 2, and/or the Gly at position 3, and/or the Leu at position 5 within said motif is substituted by any other amino acid;

c. Motif 3: [F/Y]TTF[V/I]GG, wherein the Phe at position 4 within said motif is substituted by any other amino acid.

In another embodiment, the herbicide resistant or tolerant PPO polypeptide comprises a variant of the amino acid sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, which variant comprises one or more of the following substitutions:

a. the amino acid corresponding to Arg128 of SEQ ID NO: 1 is substituted by any other amino acid.

b. The amino acid corresponding to Gly211 of SEQ ID NO: 1 is substituted by any other amino acid c. the amino acid corresponding to Leu397 of SEQ ID NO: 1 is substituted by any other amino acid.

d. the amino acid corresponding to Gly398 of SEQ ID NO: 1 is substituted by any other amino acid e. the amino acid corresponding to Leu400 of SEQ ID NO: 1 is substituted by any other amino acid f. the amino acid corresponding to Phe420 of SEQ ID NO: 1 is substituted by any other amino acid.

In still another embodiment, the herbicide resistant or tolerant PPO polypeptide comprises the amino acid sequence of SEQ ID NO: 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, or a variant thereof.

In still another embodiment, the herbicide resistant or tolerant PPO polypeptide comprises the amino acid sequence of SEQ ID NO: 240, 241, 242, 243, 244, 245, 246, 247, 248, 249, 250, 251, 252, 253, 254, 255, 256, 257, 258, 259, 260, 261, 262, or 264.

Another object refers to a method of identifying a nucleotide sequence encoding a mutated PPO which is resistant or tolerant to a uracilpyridine herbicide, the method comprising:

a) generating a library of mutated PPO-encoding nucleic acids, b) screening a population of the resulting mutated PPO-encoding nucleic acids by expressing each of said nucleic acids in a cell or plant and treating said cell or plant with a uracilpyridine, c) comparing the uracilpyridine herbicide-tolerance levels provided by said population of mutated PPO encoding nucleic acids with the uracilpyridine-tolerance level provided by a control PPO-encoding nucleic acid, d) selecting at least one mutated PPO-encoding nucleic acid that provides a significantly increased level of tolerance to a uracilpyridine as compared to that provided by the control PPO-encoding nucleic acid.

In a preferred embodiment, the mutated PPO-encoding nucleic acid selected in step d) provides at least 2-fold as much tolerance to a uracilpyridine as compared to that provided by the control PPO-encoding nucleic acid.

The resistance or tolerance can be determined by generating a transgenic plant comprising a nucleic acid sequence of the library of step a) and comparing said transgenic plant with a control plant.

Another object refers to a method of identifying a plant or algae containing a nucleic acid encoding a mutated PPO which is resistant or tolerant to a uracilpyridine, the method comprising:

a) identifying an effective amount of a uracilpyridine in a culture of plant cells or green algae.

b) treating said plant cells or green algae with a mutagenizing agent, c) contacting said mutagenized cells population with an effective amount of uracilpyridine herbicide, identified in a), d) selecting at least one cell surviving these test conditions, e) PCR-amplification and sequencing of PPO genes from cells selected in d) and comparing such sequences to wild-type PPO gene sequences, respectively.

In a preferred embodiment, the mutagenizing agent is ethylmethanesulfonate.

In another embodiment, the invention refers to a plant cell transformed by and expressing a wild-type or a mutated PPO nucleic acid according to the present invention or a plant which has been mutated to obtain a plant expressing, preferably over-expressing a wild-type or a mutated PPO nucleic acid according to the present invention, wherein expression of said nucleic acid in the plant cell results in increased resistance or tolerance to a uracilpyridine as compared to a wild type variety of the plant cell.

In another embodiment, the invention refers to a plant that expresses a mutagenized or recombinant mutated PPO polypeptide, and wherein said mutated PPO confers upon the plant increased uracilpyridine tolerance as compared to the corresponding wild-type variety of the plant when expressed therein.

In another embodiment, the invention refers to a plant comprising a plant cell according to the present invention, wherein expression of the nucleic acid in the plant results in the plant's increased resistance to uracilpyridine herbicide as compared to a wild type variety of the plant.

The plants of the present invention can be transgenic or non-transgenic.

Preferably, the expression of the nucleic acid of the invention in the plant results in the plant's increased resistance to uracilpyridine herbicides as compared to a wild type variety of the plant.

In another embodiment, the invention refers to a method for growing the plant according to the present invention while controlling weeds in the vicinity of said plant, said method comprising the steps of:
a) growing said plant; and
b) applying a herbicide composition comprising a uracilpyridine herbicide to the plant and weeds, wherein the herbicide normally inhibits protoporphyrinogen oxidase, at a level of the herbicide that would inhibit the growth of a corresponding wild-type plant.

In another embodiment, the invention refers to a seed produced by a transgenic plant comprising a plant cell of the present invention, or to a seed produced by the non-transgenic plant that expresses a mutagenized PPO polypeptide, wherein the seed is true breeding for an increased resistance to a uracilpyridine herbicide as compared to a wild type variety of the seed.

In another embodiment, the invention refers to a method of producing a transgenic plant cell with an increased resistance to a uracilpyridine herbicide as compared to a wild type variety of the plant cell comprising, transforming the plant cell with an expression cassette comprising a wild-type or a mutated PPO nucleic acid.

In another embodiment, the invention refers to a method of producing a transgenic plant comprising, (a) transforming a plant cell with an expression cassette comprising a wild-type or a mutated PPO nucleic acid, and (b) generating a plant with an increased resistance to uracilpyridine herbicide from the plant cell.

Preferably, the expression cassette further comprises a transcription initiation regulatory region and a translation initiation regulatory region that are functional in the plant.

In another embodiment, the invention relates to using the mutated PPO of the invention as selectable marker. The invention provides a method of identifying or selecting a transformed plant cell, plant tissue, plant or part thereof comprising a) providing a transformed plant cell, plant tissue, plant or part thereof, wherein said transformed plant cell, plant tissue, plant or part thereof comprises an isolated nucleic acid encoding a mutated PPO polypeptide of the invention as described hereinafter, wherein the polypeptide is used as a selection marker, and wherein said transformed plant cell, plant tissue, plant or part thereof may optionally comprise a further isolated nucleic acid of interest; b) contacting the transformed plant cell, plant tissue, plant or part thereof with at least one PPO-inhibiting inhibiting compound; c) determining whether the plant cell, plant tissue, plant or part thereof is affected by the inhibitor or inhibiting compound; and d) identifying or selecting the transformed plant cell, plant tissue, plant or part thereof.

The invention is also embodied in purified mutated PPO proteins that contain the mutations described herein, which are useful in molecular modeling studies to design further improvements to herbicide tolerance. Methods of protein purification are well known, and can be readily accomplished using commercially available products or specially designed methods, as set forth for example, in Protein Biotechnology, Walsh and Headon (Wiley, 1994).

In another embodiment, the invention relates to a combination useful for weed control, comprising (a) a polynucleotide encoding a mutated PPO polypeptide according to the present invention, which polynucleotide is capable of being expressed in a plant to thereby provide to that plant tolerance to a uracilpyridine herbicide; and (b) a uracilpyridine herbicide.

In another embodiment, the invention relates to a process for preparing a combination useful for weed control comprising (a) providing a polynucleotide encoding a mutated PPO polypeptide according to the present invention, which polynucleotide is capable of being expressed in a plant to thereby provide to that plant tolerance to a uracilpyridine herbicide; and (b) providing a uracilpyridine herbicide.

In a preferred embodiment, said step of providing a polynucleotide comprises providing a plant containing the polynucleotide.

In another preferred embodiment, said step of providing a polynucleotide comprises providing a seed containing the polynucleotide.

In another preferred embodiment, said process further comprises a step of applying the uracilpyridine herbicide to the seed.

In another embodiment, the invention relates to the use of a combination useful for weed control, comprising (a) a polynucleotide encoding a mutated PPO polypeptide according to the present invention, which polynucleotide is capable of being expressed in a plant to thereby provide to that plant tolerance to a uracilpyridine herbicide; and (b) a uracilpyridine herbicide, to control weeds at a plant cultivation site.

BRIEF DESCRIPTION OF THE DRAWINGS (NB: full name of used uracilpyridines is given in the Example section)

Figure 2:
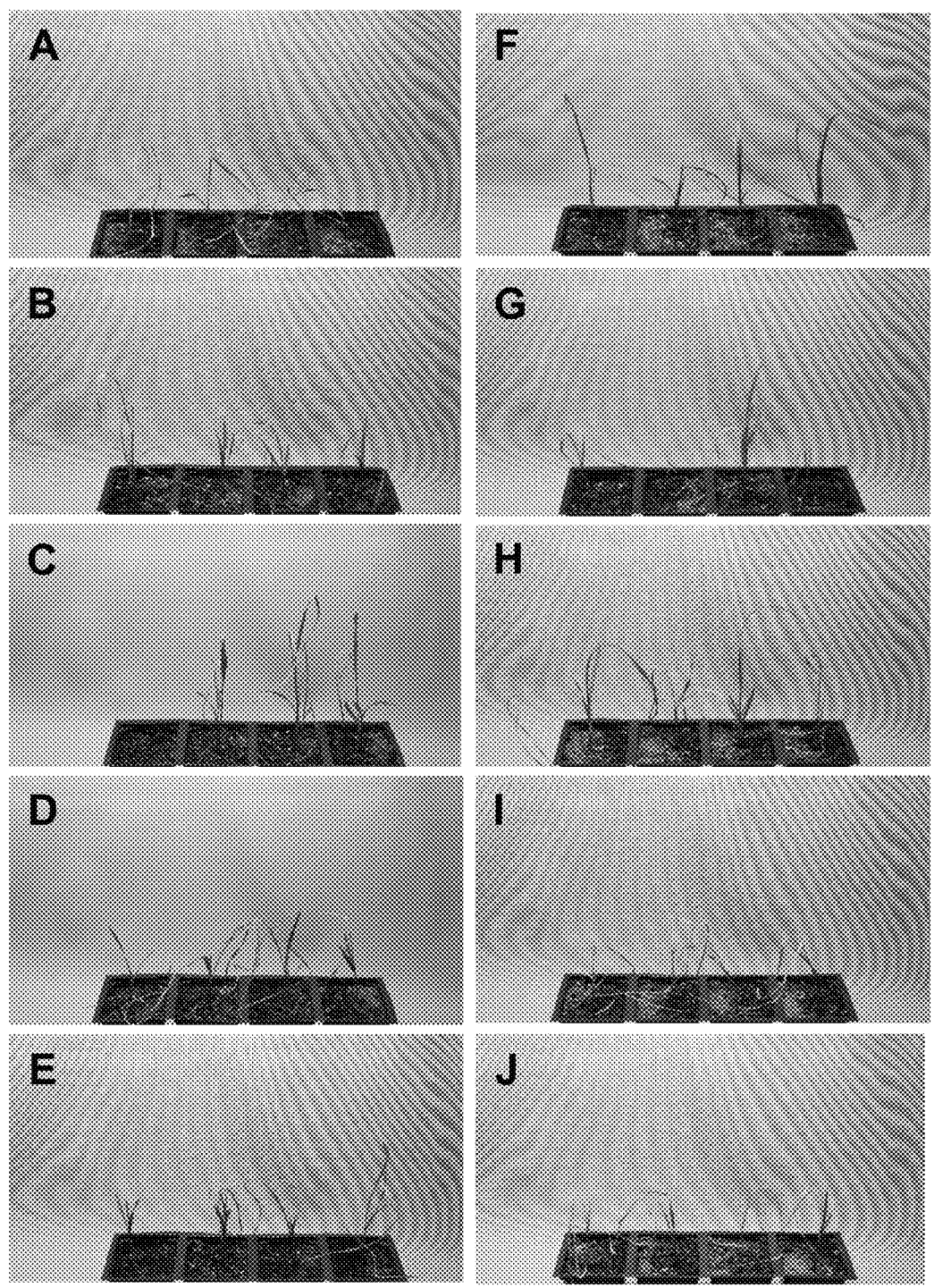

FIG. 1: Rice plants 7 days after treatment with 3.125 g AI/ha of Uracilpyridine 4. A) wild-type, B) R139L mutant, C) R139G mutant, D) G225R mutant, E) G420A mutant, F) F442L mutant, G) F442I mutant, H) F442V mutant, I) L419 mutant, J) L422F mutant FIG. 2: SRice plants 7 days after treatment with 6.25 g AI/ha of Uracilpyridine 2. A) wild-type, B) R139L mutant, C) R139G mutant, D) G225R mutant, E) G420A mutant, F) F442L mutant, G) F442I mutant, H) F442V mutant, I) L419 mutant, J) L422F mutant.

Figure 3:
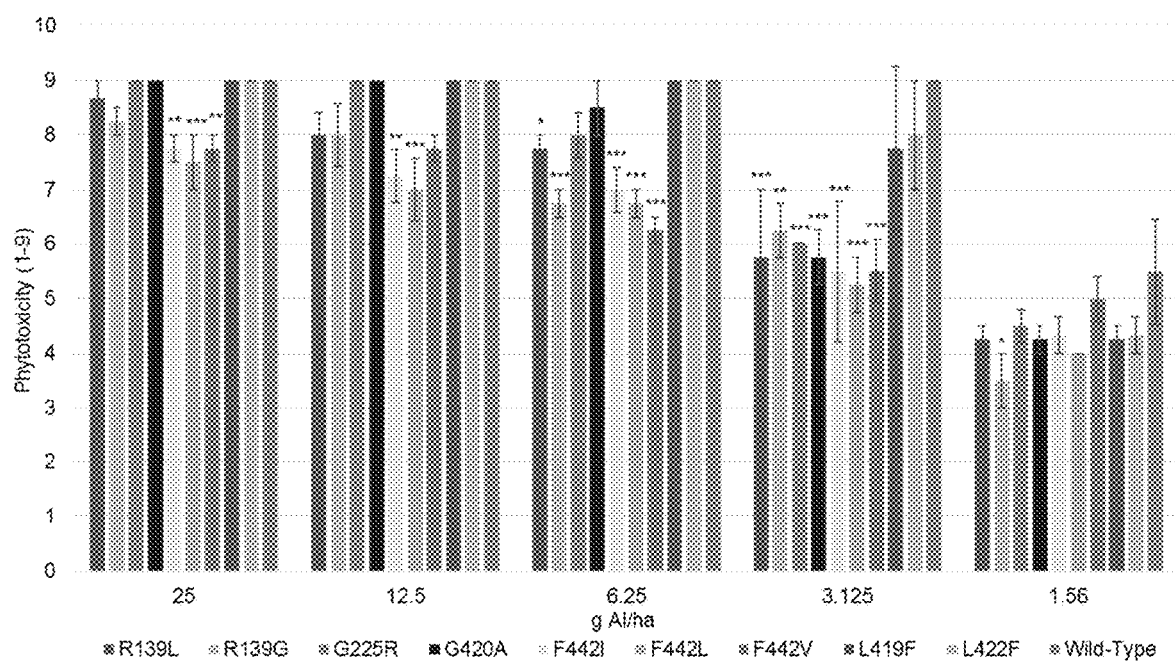
Figure 4:
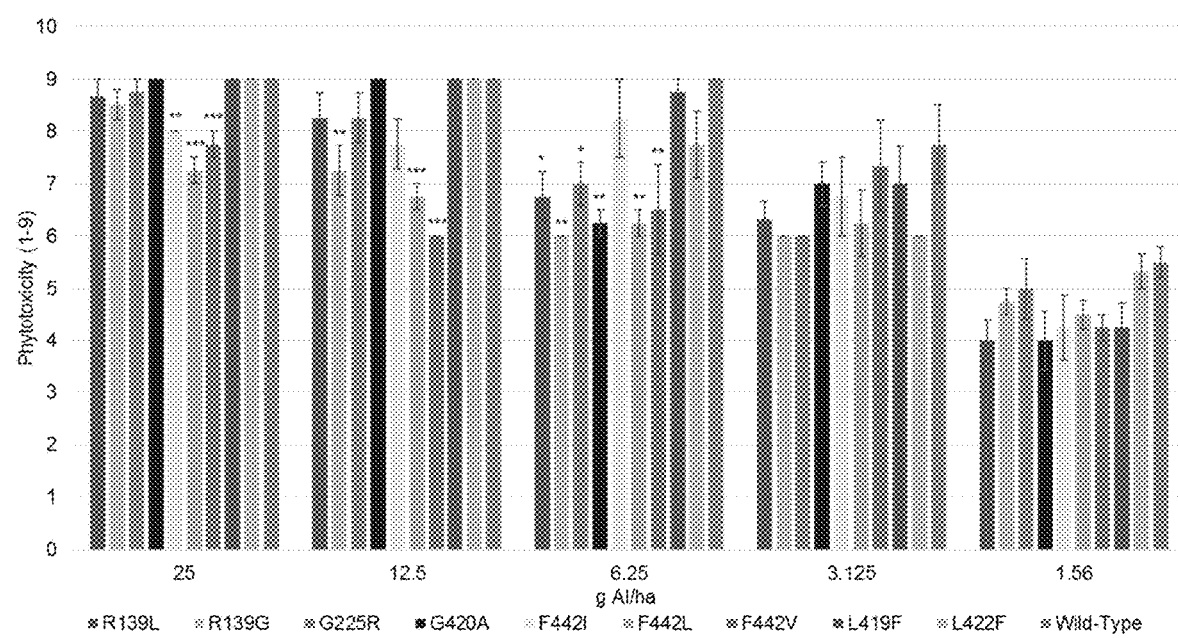

FIG. 3: Response of rice containing mutations in the OsPPO2 gene and wild-type rice to application of Uracilpyridine 4. Each bar represents the average of up to four plants. Phytotoxicity was assessed 7 days after herbicide application. * P-value <0.001,  P-value<0.01, *P-value<0.05 as calculated by ANOVA using a QuasiPoisson distribution FIG. 4: Response of rice containing mutations in the OsPPO2 gene and wild-type rice to application of Uracilpyridine 2. Each bar represents the average of up to four plants. Phytotoxicity was assessed 7 days after herbicide application. * P-value <0.001,  P-value<0.01,*P-value<0.05 as calculated by ANOVA using a QuasiPoisson distribution.

Figure 5:
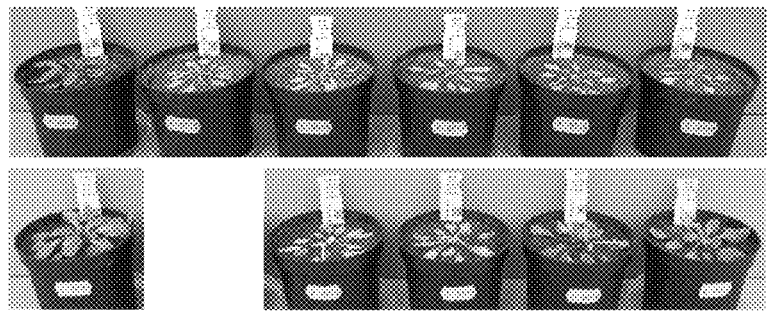
Figure 5:
Figure 5:
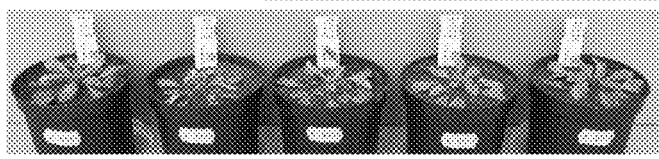
Figure 5:
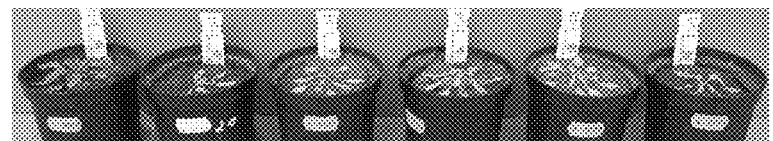
Figure 5:
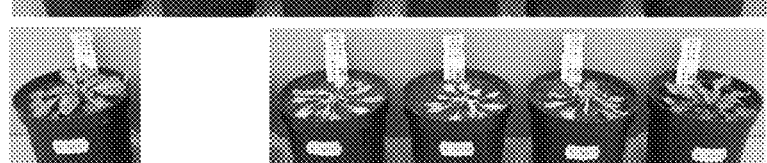
Figure 5:
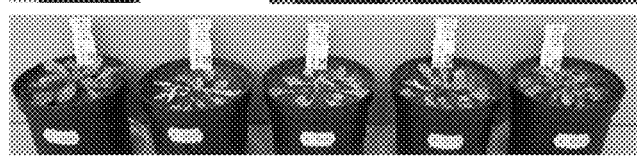
Figure 5:
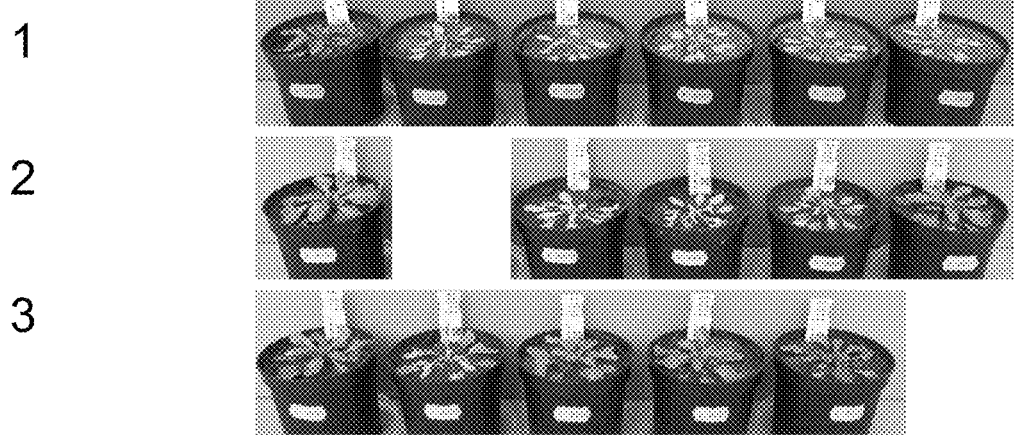
Figure 5:
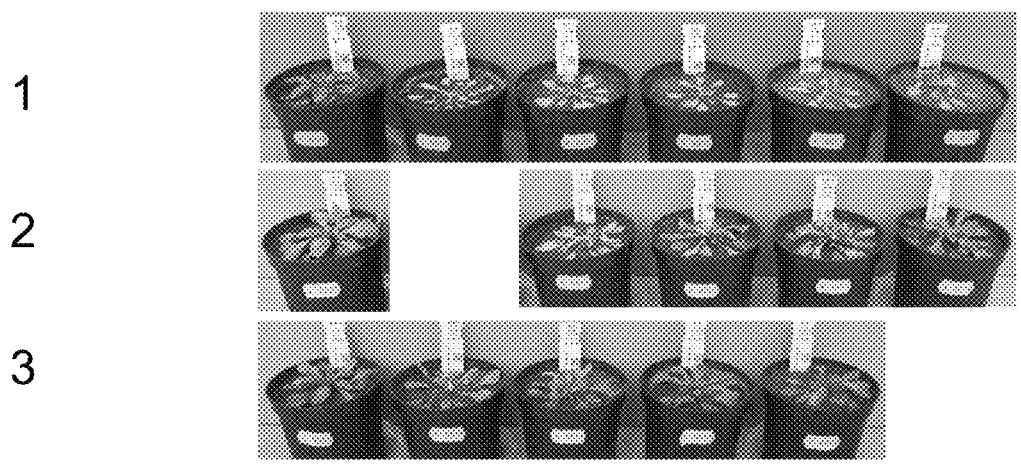
Figure 6:
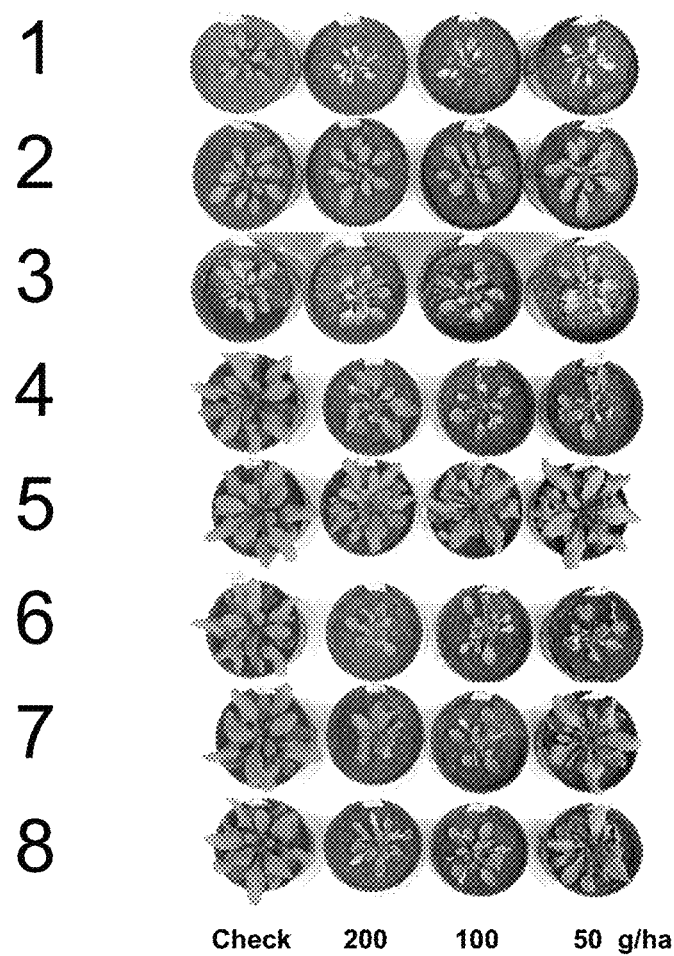
Figure 6:
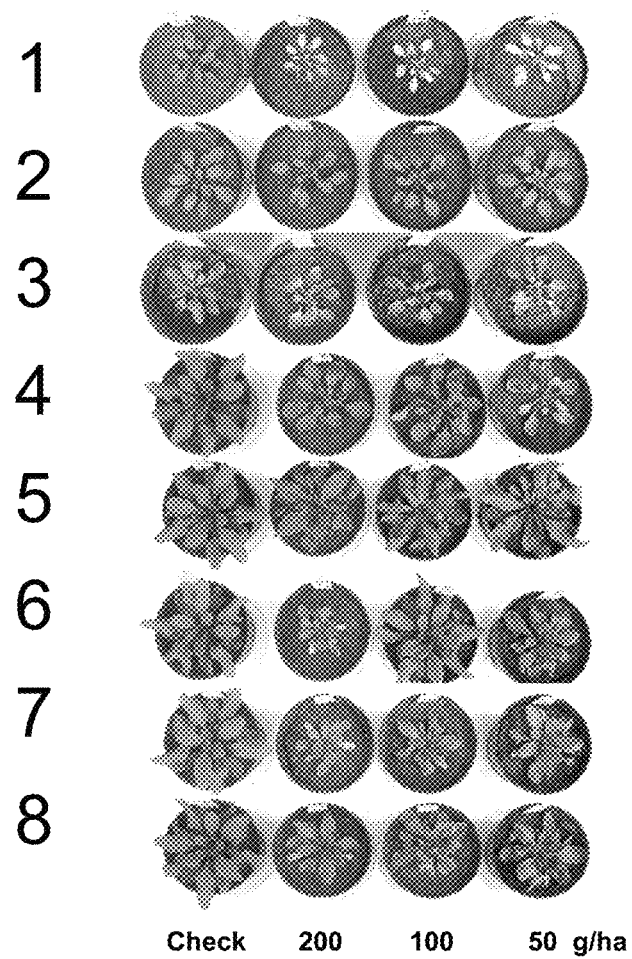
Figure 6:
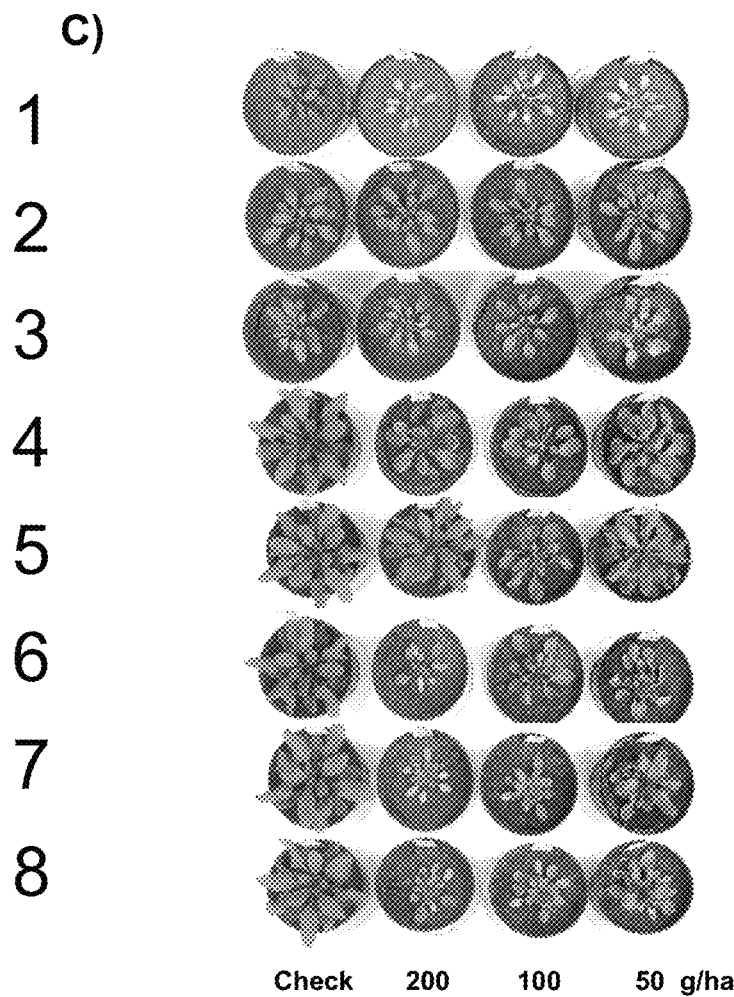
Figure 6:
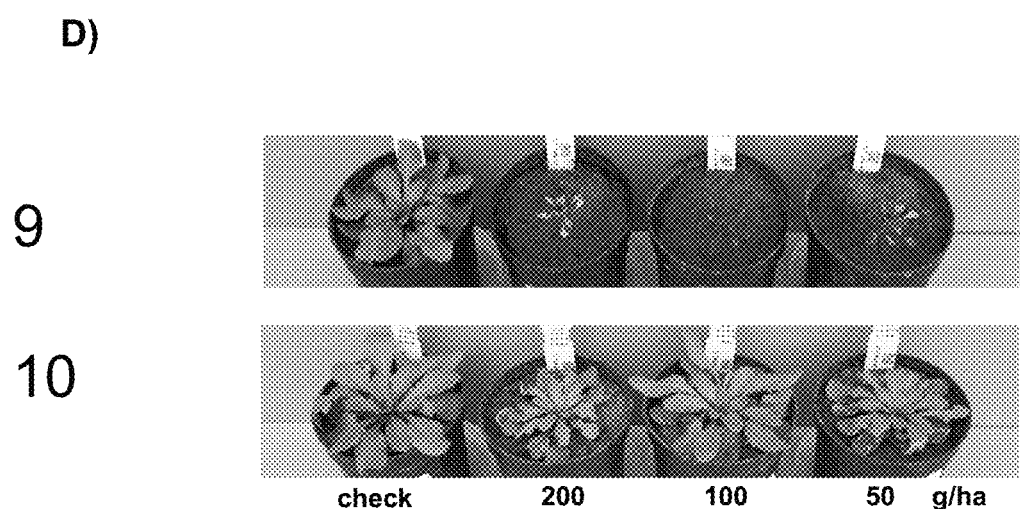
Figure 7:
Figure 8:
Figure 8:
Figure 8:
Figure 8:
Figure 8:
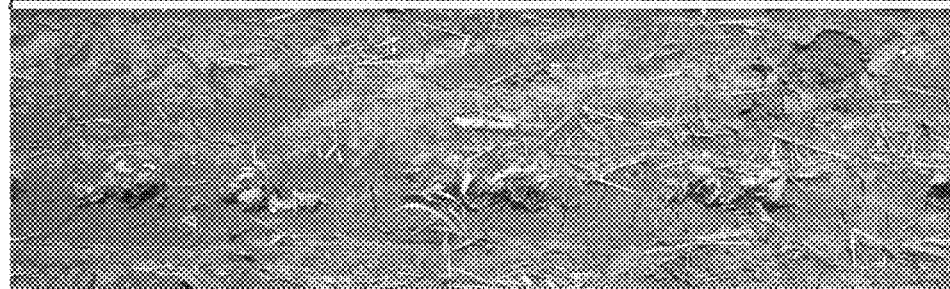
Figure 9:
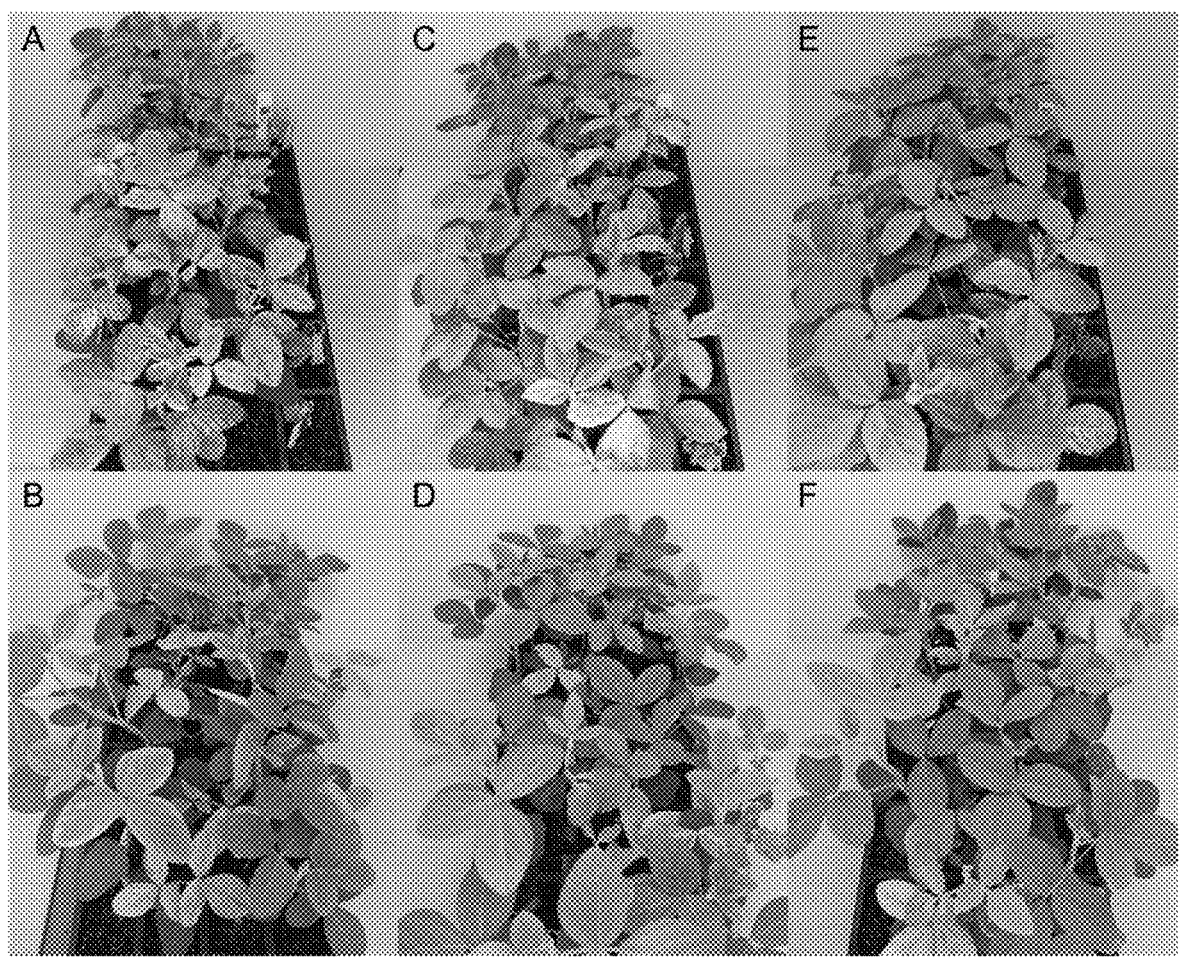

FIG. 5: Transgenic T2 *Arabidopsis* plants harboring *Arabidopsis* PPO tolerance trait, sprayed post in the greenhouse with the following amounts (80, 30, 10, 5, 1 g/ha from right to left) of Uracilpyridine+1% (v/v) MSO. Pictures taken 14 Days After Treatment (DAT). A) is tested with Uracilpyridine 4, B) is tested with Uracilpyridine 5, C) is tested with Uracilpyridine 2, D) is tested with Uracilpyridine 3.
 1=non-transformed *Arabidopsis* plants
 2=Transformants with *Arabidopsis* PPO1 wildtype
 3=Transformants with *Arabidopsis* PPO1 double mutant S305L_Y426M FIG. 6: Transgenic T2 *Arabidopsis* plants harboring various PPO tolerance trait, sprayed post in the greenhouse with the following amounts (200, 100, 50 g/ha) of Uracilpyridine+1% (v/v) MSO. Pictures taken 14 Days After Treatment (DAT). A) is tested with Uracilpyridine 2, B) is tested with Uracilpyridine 4, C) is tested with Uracilpyridine 1, D) is tested with Uracilpyridine 2.
 1=non-transformed *Arabidopsis* plants
 2=transformed with AMATU_PPO2_TPL_hemG (event R) (SEQ ID NO: 246)
 3=transformed with AMATU_PPO2_TPL_hemG (event Q) (SEQ ID NO: 246)
 4=transformed with ALOMY_PPO2_TP_hemG (SEQ ID NO: 248)
 5=transformed with ALOMY_PPO2_R137LF438V
 6=transformed with ALOMY_PPO2_TPL_AMATU_PPO2_R128M_F420I (SEQ ID NO: 258)
 7=transformed with AMATU_PPO2R128M_F420I
 8=transformed with AMATU_PPO2_R128A_F420M FIG. 7: Transgenic Corn plants harboring a PPO inhibitor tolerance trait, sprayed post at the V5 leaf stage with 100 g/ha of Uracilpyridine 2+1% (v/v) MSO. Evaluation performed 14 Days After Treatment (DAT) and is shown as injury (%) relative to non-transgenic treated plants. Application performed on corn in V5 leaf stage with 100 g/ha Uracilpyridine 2. Picture taken at 2 DAT
 1=Corn transformed with AMATU_PPO2R128A_F420L
 2=Corn transformed with AMATU_PPO2R128A_F420I
 3=non-transformed corn plants FIG. 8: Transgenic T3 Soybean plants harboring a PPO inhibitor tolerance trait, sprayed post at the V3 leaf stage with 100 g/ha of Uracilpyridine 2+1% (v/v) MSO. Evaluation performed 14 Days After Treatment (DAT) and is shown as injury (%) relative to non-transgenic treated plants. Application performed on soy at V3 leaf stage with 100 g/ha uracilpyridine 2. Picture taken at 2 DAT
 1=Soy transformed with AMATU_PPO2_R128A, F420I
 2=Soy transformed with AMATU_PPO2_L397E, F420V
 3=Soy transformed with AMATU_PPO2_L397E, F420M
 4=Soy transformed with AMATU_PPO2_L397Q, F420M
 5=non-transformed soy plants FIG. 9: Transgenic T4 Soybean plants harboring a PPO inhibitor tolerance trait, sprayed with g/ha (Panels A-B), 50 g/ha (Panels C-D), 100 g/ha (Panels E-F) of Uracilpyridine 10+1% (v/v) MSO. Evaluation and pictures taken 7 Days After Treatment. Application performed on soybean 14 days after sowing. Panels A, C, & E each show plants harboring a PPO trait containg R128A+F420L, R128A+F420I AMTU PPO2 variants as well as untransformed soybean (last column). Panels B, D, & F each show plants harboring a PPO trait containg L397Q+F420V and L397E+F420M AMTU PPO2 variants.

Figure 10:
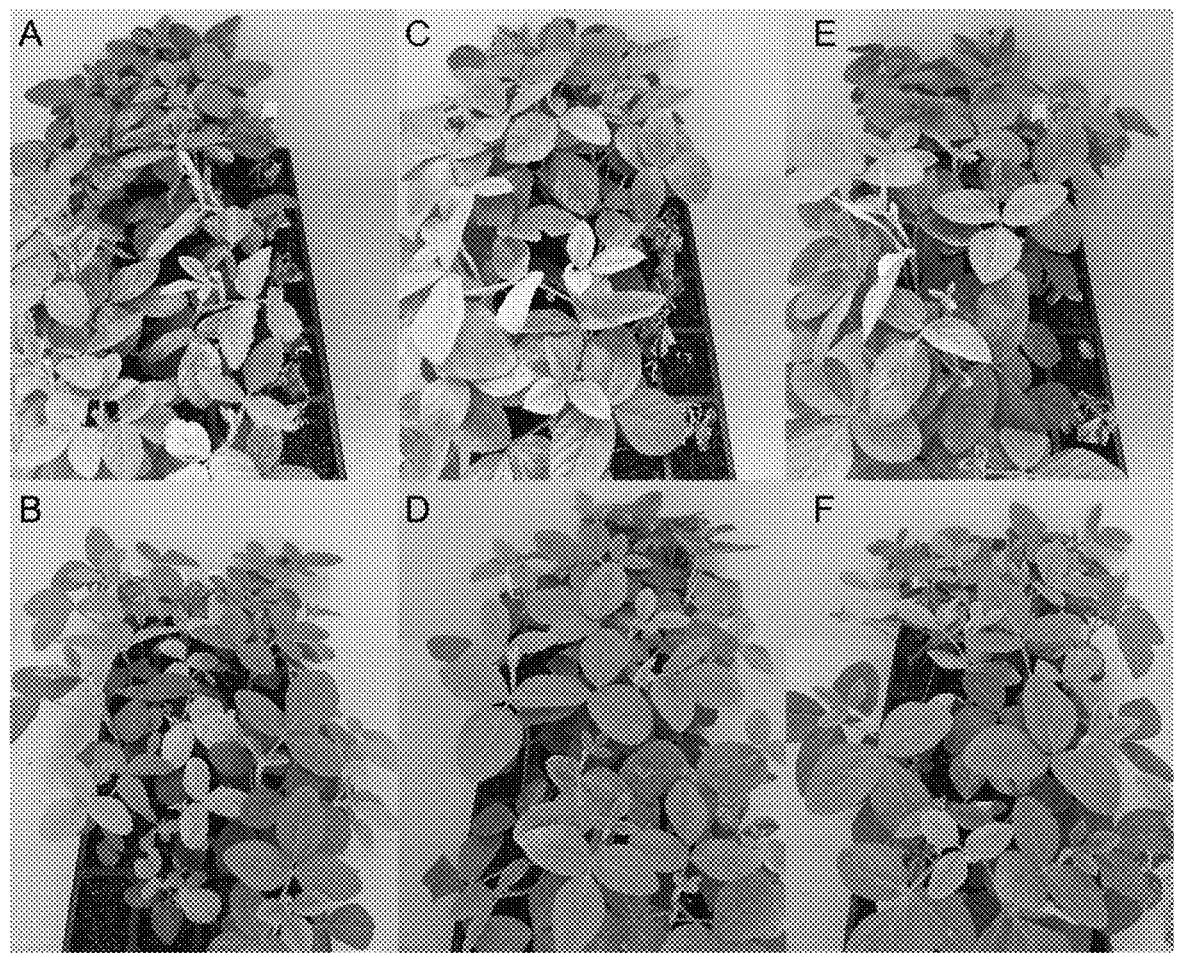

FIG. 10: Transgenic T4 Soybean plants harboring a PPO inhibitor tolerance trait, sprayed with 25 g/ha (Panels A-B), 50 g/ha (Panels C-D), 100 g/ha (Panels E-F) of Uracilpyridine 20+1% (v/v) MSO. Evaluation and pictures taken 7 Days After Treatment. Application performed on soybean 14 days after sowing. Panels A, C, & E each show plants harboring a PPO trait containg R128A+F420L, R128A+F420I AMTU PPO2 variants as well as untransformed soybean (last column). Panels B, D, & F each show plants harboring a PPO trait containing L397Q+F420V and L397E+F420M AMTU PPO2 variants.

Figure 11:
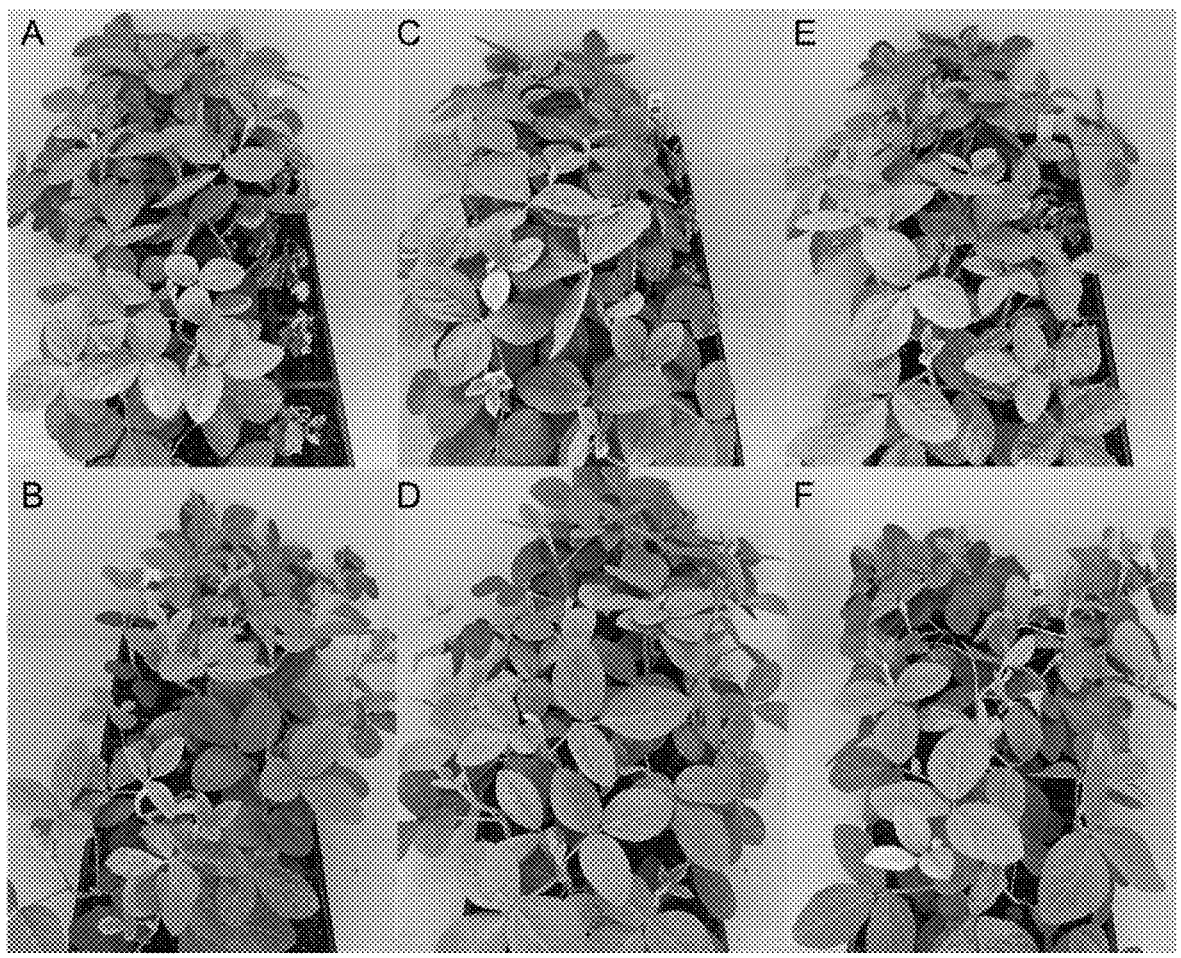

FIG. 11: Transgenic T4 Soybean plants harboring a PPO inhibitor tolerance trait, sprayed with 25 g/ha (Panels A-B), 50 g/ha (Panels C-D), 100 g/ha (Panels E-F) of Uracilpyridine 21+1% (v/v) MSO. Evaluation and pictures taken 7 Days After Treatment. Application performed on soybean 14 days after sowing. Panels A, C, & E each show plants harboring a PPO trait containg R128A+F420L, R128A+F420I AMTU PPO2 variants as well as untransformed soybean (last column). Panels B, D, & F each show plants harboring a PPO trait containg L397Q+F420V and L397E+F420M AMTU PPO2 variants.

Figure 12:
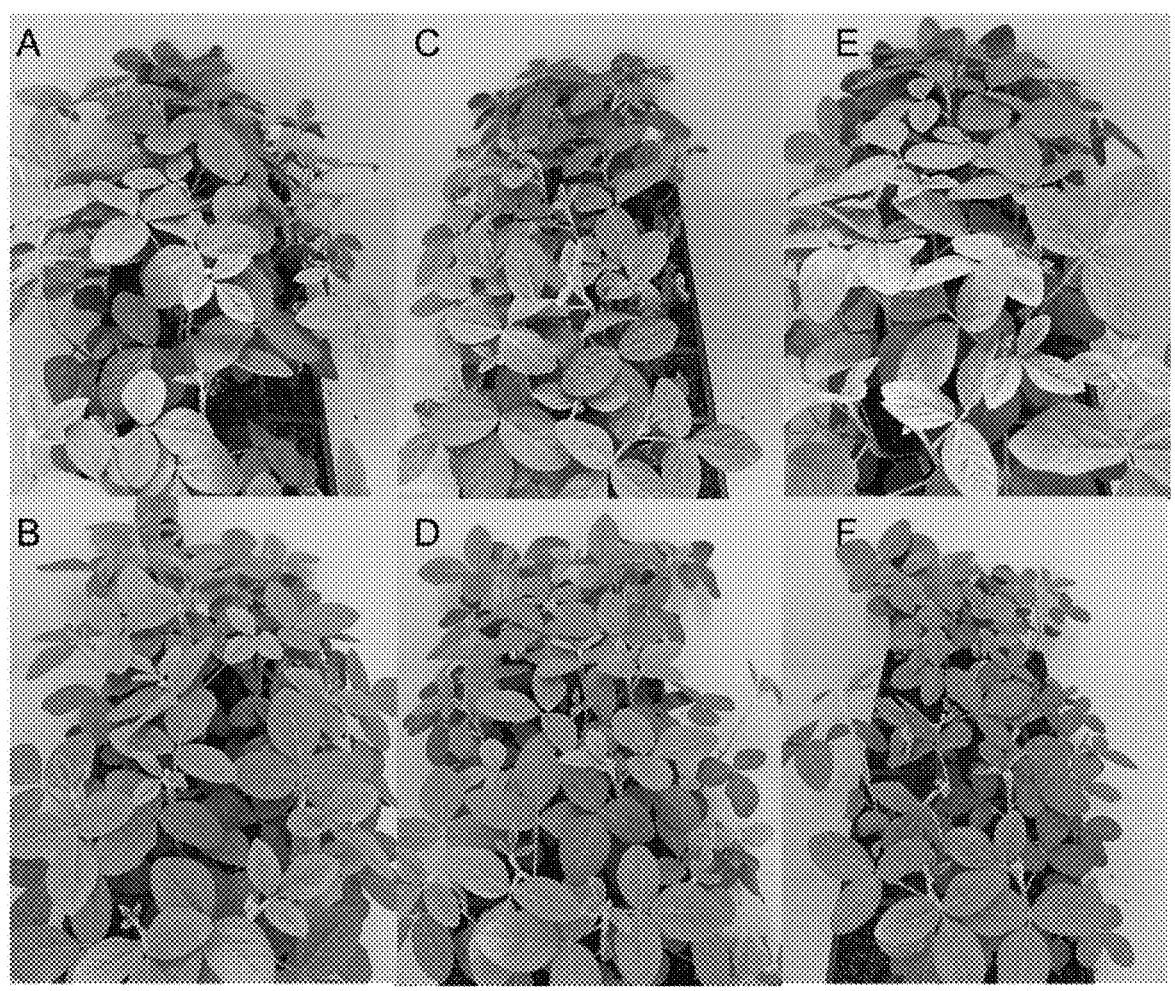

FIG. 12: Transgenic T4 Soybean plants harboring a PPO inhibitor tolerance trait, sprayed with g/ha (Panels A-B), 50 g/ha (Panels C-D), 100 g/ha (Panels E-F) of Uracilpyridine 22+1% (v/v) MSO. Evaluation and pictures taken 7 Days After Treatment. Application performed on soybean 14 days after sowing. Panels A, C, & E each show plants harboring a PPO trait containg R128A+F420L, R128A+F420I AMTU PPO2 variants as well as untransformed soybean (last column). Panels B, D, & F each show plants harboring a PPO trait containg L397Q+F420V and L397E+F420M AMTU PPO2 variants.

DETAILED DESCRIPTION

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The inventors of the present invention have found, that the tolerance or resistance of a plant to a uracilpyridine herbicide could be remarkably increased by overexpressing a nucleic acid encoding PPO polypeptides described hereinafter.

The present invention refers to a method for controlling undesired vegetation at a plant cultivation site, the method comprising the steps of:
 a) providing, at said site, a plant that comprises at least one nucleic acid comprising a nucleotide sequence encoding a protoporphyrinogen oxidase (mutated PPO) which is resistant or tolerant to a PPO-inhibiting herbicide as defined hereinafter,
 b) applying to said site an effective amount of said herbicide, wherein the PPO inhibiting herbicide is a uracilpyridine of formula (I)

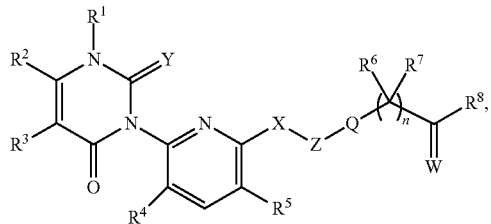

wherein the substituents have the following meanings:
$R^1$ hydrogen, $NH_2$, $C_1$-$C_6$-alkyl or $C_3$-$C_6$-alkynyl;
$R^2$ hydrogen, $C_1$-$C_6$-alkyl or $C_1$-$C_6$-haloalkyl;
$R^3$ hydrogen or $C_1$-$C_6$-alkyl;
$R^4$ H or halogen;
$R^5$ halogen, CN, $NO_2$, $NH_2$, $CF_3$, or $C(=S)NH_2$;
$R^6$ H, halogen, CN, $C_1$-$C_3$-alkyl, $C_1$-$C_3$-haloalkyl, $C_1$-$C_3$-alkoxy, $C_1$-$C_3$-haloalkoxy, $C_1$-$C_3$-alkylthio, ($C_1$-$C_3$-alkyl)amino, di($C_1$-$C_3$-alkyl)amino, $C_1$-$C_3$-alkoxy-$C_1$-$C_3$-alkyl, $C_1$-$C_3$-alkoxycarbonyl;
$R^7$ H, halogen, $C_1$-$C_3$-alkyl, $C_1$-$C_3$-alkoxy;
$R^8$ $OR^9$, $SR^9$, $NR^{10}R^{11}$, $NR^9OR^9$, $NR^9S(O)_2R^{10}$ or $NR^9S(O)_2NR^{10}R^{11}$, wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
—N=$CR^{12}R^{13}$, wherein $R^{12}$ and $R^{13}$ independently of one another are H, $C_1$-$C_4$-alkyl or phenyl;
$C_3$-$C_6$-cycloalkyl, $C_3$-$C_6$-cycloalkyl-$C_1$-$C_6$-alkyl, $C_3$-$C_6$-heterocyclyl, $C_3$-$C_6$-heterocyclyl-$C_1$-$C_6$-alkyl, phenyl, phenyl-$C_1$-$C_4$-alkyl or a 5- or 6 membered heteroaryl,
wherein each cycloalkyl, heterocyclyl, phenyl or heteroaryl ring can be substituted by one to four substituents selected from $R^{14}$ or a 3- to 7-membered carbocyclus,
which carbocyclus optionally has in addition to carbon atoms one or two ring members selected from the group consisting of —N($R^{12}$)—, —N=N—, —C(=O)—, —O— and —S—, and which carbocyclus is optionally substituted with one to four substituents selected from $R^{14}$;
wherein $R^{14}$ is halogen, $NO_2$, CN, $C_1$-$C_4$-alkyl, $C_1$-$C_4$-halo-alkyl, $C_1$-$C_4$-alkoxy or $C_1$-$C_4$-alkoxycarbonyl;
$R^{10}$, $R^{11}$ independently of one another are $R^9$, or together form a 3- to 7-membered carbocyclus,
which carbocyclus optionally has in addition to carbon atoms one or two ring members selected from the group consisting of —N($R^{12}$)—, —N=N—, —C(=O)—, —O— and —S—, and which carbocyclus is optionally substituted with one to four substituents selected from $R^{14}$;
n 1 to 3;
Q $CH_2$, O, S, SO, $SO_2$, NH or ($C_1$-$C_3$-alkyl)N;
W O or S;
X NH, $NCH_3$, O or S;
Y O or S;
Z phenyl, pyridyl, pyridazinyl, pyrimidinyl or pyrazinyl, each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy, $C_1$-$C_6$-haloalkoxy;
including their agriculturally acceptable salts or derivatives, provided the compounds of formula (I) have a carboxyl group.

The term "control of undesired vegetation" is to be understood as meaning the killing of weeds and/or otherwise retarding or inhibiting the normal growth of the weeds. Weeds, in the broadest sense, are understood as meaning all those plants which grow in locations where they are undesired, e.g. (crop) plant cultivation sites. The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus,* and *Taraxacum.* Monocotyledonous weeds include, but are not limited to, weeds of of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera.* In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The term "plant" is used in its broadest sense as it pertains to organic material and is intended to encompass eukaryotic organisms that are members of the Kingdom Plantae, examples of which include but are not limited to vascular plants, vegetables, grains, flowers, trees, herbs, bushes, grasses, vines, ferns, mosses, fungi and algae, etc, as well as clones, offsets, and parts of plants used for asexual propagation (e.g. cuttings, pipings, shoots, rhizomes, underground stems, clumps, crowns, bulbs, corms, tubers, rhizomes, plants/tissues produced in tissue culture, etc.). The term "plant" further encompasses whole plants, ancestors and progeny of the plants and plant parts, including seeds, shoots, stems, leaves, roots (including tubers), flowers, florets, fruits, pedicles, peduncles, stamen, anther, stigma, style, ovary, petal, sepal, carpel, root tip, root cap, root hair, leaf hair, seed hair, pollen grain, microspore, cotyledon, hypocotyl, epicotyl, xylem, phloem, parenchyma, endosperm, a companion cell, a guard cell, and any other known organs, tissues, and cells of a plant, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising Acer spp., Actinidia spp., Abelmoschus spp., Agave sisalana, Agropyron spp., Agrostis stolonifera, Allium spp., Amaranthus spp., Ammophila arenaria, Ananas comosus, Annona spp., Apium graveolens, Arachis spp, Artocarpus spp., Asparagus officinalis, Avena spp. (e.g. Avena sativa, Avena fatua, Avena byzantina, Avena fatua var. sativa, Avena hybrida), Averrhoa carambola, Bambusa sp., Benincasa hispida, Bertholletia excelsea, Beta vulgaris, Brassica spp. (e.g. Brassica napus, Brassica rapa ssp. [canola, oilseed rape, turnip rape]), Cadaba farinosa, Camellia sinensis, Canna indica, Cannabis sativa, Capsicum spp., Carex elata, Carica papaya, Carissa macrocarpa, Carya spp., Carthamus tinctorius, Castanea spp., Ceiba pentandra, Cichorium endivia, Cinnamomum spp., Citrullus lanatus, Citrus spp., Cocos spp., Coffea spp., Colocasia esculenta, Cola spp., Corchorus sp., Coriandrum sativum, Corylus spp., Crataegus spp., Crocus sativus, Cucurbita spp., Cucumis spp., Cynara spp., Daucus carota, Desmodium spp., Dimocarpus longan, Dioscorea spp., Diospyros spp., Echinochloa spp., Elaeis (e.g. Elaeis guineensis, Elaeis oleifera), Eleusine coracana, Eragrostis tef, Erianthus sp., Eriobotrya japonica, Eucalyptus sp., Eugenia uniflora, Fagopyrum spp., Fagus spp., Festuca arundinacea, Ficus carica, Fortunella spp., Fragaria spp., Ginkgo biloba, Glycine spp. (e.g. Glycine max, Soja hispida or Soja max), Gossypium hirsutum, Helianthus spp. (e.g. Helianthus annuus), Hemerocallis fulva, Hibiscus spp., Hordeum spp. (e.g. Hordeum vulgare), Ipomoea batatas, Juglans spp., Lactuca sativa, Lathyrus spp., Lens culinaris, Linum usitatissimum, Litchi chinensis, Lotus spp., Luffa acutangula, Lupinus spp., Luzula sylvatica, Lycopersicon spp. (e.g. Lycopersicon esculentum, Lycopersicon lycopersicum, Lycopersicon pyriforme), Macrotyloma spp., Malus spp., Malpighia emarginata, Mammea americana, Mangifera indica, Manihot spp., Manilkara zapota, Medicago sativa, Melilotus spp., Mentha spp., Miscanthus sinensis, Momordica spp., Morus nigra, Musa spp., Nicotiana spp., Olea spp., Opuntia spp., Ornithopus spp., Oryza spp. (e.g. Oryza sativa, Oryza latifolia), Panicum miliaceum, Panicum virgatum, Passiflora edulis, Pastinaca sativa, Pennisetum sp., Persea spp., Petroselinum crispum, Phalaris arundinacea, Phaseolus spp., Phleum pratense, Phoenix spp., Phragmites australis, Physalis spp., Pinus spp., Pistacia vera, Pisum spp., Poa spp., Populus spp., Prosopis spp., Prunus spp., Psidium spp., Punica granatum, Pyrus communis, Quercus spp., Raphanus sativus, Rheum rhabarbarum, Ribes spp., Ricinus communis, Rubus spp., Saccharum spp., Salix sp., Sambucus spp., Secale cereale, Sesamum spp., Sinapis sp., Solanum spp. (e.g. Solanum tuberosum, Solanum integrifolium or Solanum lycopersicum), Sorghum bicolor, Spinacia spp., Syzygium spp., Tagetes spp., Tamarind us indica, Theobroma cacao, Trifolium spp., Tripsacum dactyloides, Triticosecale rimpaui, Triticum spp. (e.g. Triticum aestivum, Triticum durum, Triticum turgidum, Triticum hybernum, Triticum macha, Triticum sativum, Triticum monococcum or Triticum vulgare), Tropaeolum minus, Tropaeolum majus, Vaccinium spp., Vicia spp., Vigna spp., Viola odorata, Vitis spp., Zea mays, Zizania palustris, Ziziphus spp., amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant. Examples of crop plants include inter alia soybean, sunflower, canola, alfalfa, rapeseed, cotton, tomato, potato or tobacco. Further preferebly, the plant is a monocotyledonous plant, such as sugarcane. Further preferably, the plant is a cereal, such as rice, maize, wheat, barley, millet, rye, sorghum or oats.

In a preferred embodiment, the plant has been previously produced by a process comprising recombinantly preparing a plant by introducing and over-expressing a wild-type or mutated PPO transgene according to the present invention, as described in greater detail hereinfter.

In another preferred embodiment, the plant has been previously produced by a process comprising in situ mutagenizing plant cells, to obtain plant cells which express a mutated PPO.

As disclosed herein, the nucleic acids of the invention find use in enhancing the herbicide tolerance of plants that comprise in their genomes a gene encoding a herbicide-tolerant wild-type or mutated PPO protein. Such a gene may be an endogenous gene or a transgene, as described hereinafter.

Therefore, in another embodiment the present invention refers to a method of increasing or enhancing the uracil-pyridine herbicide tolerance or resistance of a plant, the method comprising overexpressing a nucleic acid encoding a PPO polypeptide which comprises one or more of the following motifs 1, 2, and/or 3:
  a. Motif 1: SQ[N/K/H]KRYI, wherein the Arg at position 5 within said motif is substituted by any other amino acid;
  b. Motif 2: TLGTLFSS, wherein the Leu at position 2 and/or the Gly at position 3, and/or the Leu at position 5 within said motif is substituted by any other amino acid;
  c. Motif 3: [F/Y]TTF[V/I]GG, wherein the Phe at position 4 within said motif is substituted by any other amino acid.

In another embodiment the present invention refers to a method of increasing or enhancing the uracilpyridine herbicide tolerance or resistance of a plant, the method comprising overexpressing a nucleic acid encoding a herbicide resistant or tolerant PPO polypeptide which comprises a variant of the amino acid sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, which variant comprises one or more of the following substitutions:
  a. the amino acid corresponding to Arg128 of SEQ ID NO: 1 is substituted by any other amino acid.

b. The amino acid corresponding to Gly211 of SEQ ID NO: 1 is substituted by any other amino acid
c. the amino acid corresponding to Leu397 of SEQ ID NO: 1 is substituted by any other amino acid
d. the amino acid corresponding to Gly398 of SEQ ID NO: 1 is substituted by any other amino acid
e. the amino acid corresponding to Leu400 of SEQ ID NO: 1 is substituted by any other amino acid
f. the amino acid corresponding to Phe420 of SEQ ID NO: 1 is substituted by any other amino acid.

In another embodiment the present invention refers to a method of increasing or enhancing the uracilpyridine herbicide tolerance or resistance of a plant, the method comprising overexpressing a nucleic acid encoding a herbicide resistant or tolerant PPO polypeptide which comprises the amino acid sequence of SEQ ID NO: 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, or a variant thereof.

In another embodiment the present invention refers to a method of increasing or enhancing the uracilpyridine herbicide tolerance or resistance of a plant, the method comprising overexpressing a nucleic acid encoding a herbicide resistant or tolerant PPO polypeptide which comprises the amino acid sequence of SEQ ID NO: 240, 241, 242, 243, 244, 245, 246, 247, 248, 249, 250, 251, 252, 253, 254, 255, 256, 257, 258, 259, 260, 261, 262, or 264.

Additionally, in certain embodiments, the nucleic acids of the present invention can be stacked with any combination of polynucleotide sequences of interest in order to create plants with a desired phenotype. For example, the nucleic acids of the present invention may be stacked with any other polynucleotides encoding polypeptides having pesticidal and/or insecticidal activity, such as, for example, the *Bacillus thuringiensis* toxin proteins (described in U.S. Pat. Nos. 5,366,892; 5,747,450; 5,737,514; 5,723,756; 5,593,881; and Geiser et al (1986) Gene 48: 109), By way of example, polynucleotides that may be stacked with the nucleic acids of the present invention include nucleic acids encoding polypeptides conferring resistance to pests/pathogens such as viruses, nematodes, insects or fungi, and the like. Exemplary polynucleotides that may be stacked with nucleic acids of the invention include polynucleotides encoding: polypeptides having pesticidal and/or insecticidal activity, such as other *Bacillus thuringiensis* toxic proteins (described in U.S. Pat. Nos. 5,366,892; 5,747,450; 5,737, 514; 5,723,756; 5,593,881; and Geiser et al., (1986) Gene 48:109), lectins (Van Damme et al. (1994) Plant Mol. Biol. 24:825, pentin (described in U.S. Pat. No. 5,981,722), and the like; traits desirable for disease or herbicide resistance (e.g., fumonisin detoxification genes (U.S. Pat. No. 5,792, 931); avirulence and disease resistance genes (Jones et al. (1994) Science 266:789; Martin et al., (1993) Science 262: 1432; Mindrinos et al. (1994) Cell 78:1089); acetolactate synthase (ALS) mutants that lead to herbicide resistance such as the S4 and/or Hra mutations; glyphosate resistance (e.g., 5-enol-pyrovyl-shikimate-3-phosphate-synthase (EPSPS) gene, described in U.S. Pat. Nos. 4,940,935 and 5,188,642; or the glyphosate N-acetyltransferase (GAT) gene, described in Castle et al. (2004) Science, 304:1151-1154; and in U.S. Patent App. Pub. Nos. 20070004912, 20050246798, and 20050060767)); glufosinate resistance (e.g, phosphinothricin acetyl transferase genes PAT and BAR, described in U.S. Pat. Nos. 5,561,236 and 5,276,268); resistance to herbicides including sulfonyl urea, DHT (2,4D), and PPO herbicides (e.g., glyphosate acetyl transferase, aryloxy alkanoate dioxygenase, acetolactate synthase, and protoporphyrinogen oxidase); a cytochrome P450 or variant thereof that confers herbicide resistance or tolerance to, inter alia, HPPD herbicides (U.S. patent application Ser. No. 12/156,247; U.S. Pat. Nos. 6,380,465; 6,121,512; 5,349,127; 6,649,814; and 6,300,544; and PCT Patent App. Pub. No. WO2007000077); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)); the disclosures of which are herein incorporated by reference.

In a preferred embodiment, the plant comprises at least one additional heterologous nucleic acid comprising a nucleotide sequence encoding a herbicide tolerance enzyme selected, for example, from the group consisting of 5-enolpyruvylshikimate-3-phosphate synthase (EPSPS), Glyphosate acetyl transferase (GAT), cytochrome P450 monooxygenase, phosphinothricin acetyltransferase (PAT), Acetohydroxyacid synthase (AHAS; EC 4.1.3.18, also known as acetolactate synthase or ALS), hydroxyphenyl pyruvate dioxygenase (HPPD), Phytoene desaturase (PD) and dicamba degrading enzymes as disclosed in WO 02/068607, or phenoxyaceticacid- and phenoxypropionicacid-derivative degrading enzymes as disclosed in WO 2008141154 or WO 2005107437. The combinations generated can also include multiple copies of any one of the polynucleotides of interest.

Generally, the term "herbicide" is used herein to mean an active ingredient that kills, controls or otherwise adversely modifies the growth of plants. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art. Herbicidal activity is exhibited by herbicides useful for the the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the herbicide postemergence to relatively immature undesirable vegetation to achieve the maximum control of weeds.

By a "herbicide-tolerant" or "herbicide-resistant" plant, it is intended that a plant that is tolerant or resistant to at least one herbicide at a level that would normally kill, or inhibit the growth of, a normal or wild-type plant. By "herbicide-tolerant wildtype or mutated PPO protein" or "herbicide-resistant wildtype or mutated PPO protein", it is intended that such a PPO protein displays higher PPO activity, relative to the PPO activity of a wild-type PPO protein, when in the presence of at least one herbicide that is known to interfere with PPO activity and at a concentration or level of the herbicide that is known to inhibit the PPO activity of the wild-type mutated PPO protein. Furthermore, the PPO activity of such a herbicide-tolerant or herbicide-resistant mutated PPO protein may be referred to herein as "herbicide-tolerant" or "herbicide-resistant" PPO activity.

In a particularly preferred embodiment, the herbicides useful for the present invention refer uracilpyridines of formula (I)

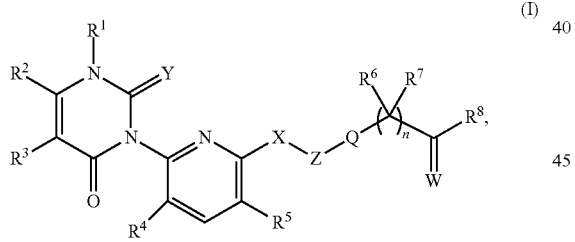

(I)

wherein the substituents have the following meanings:

$R^1$ hydrogen, $NH_2$, $C_1$-$C_6$-alkyl or $C_3$-$C_6$-alkynyl;
$R^2$ hydrogen, $C_1$-$C_6$-alkyl or $C_1$-$C_6$-haloalkyl;
$R^3$ hydrogen or $C_1$-$C_6$-alkyl;
$R^4$ H or halogen;
$R^5$ halogen, CN, $NO_2$, $NH_2$, $CF_3$ or C(=S)$NH_2$;
$R^6$ H, halogen, CN, $C_1$-$C_3$-alkyl, $C_1$-$C_3$-haloalkyl, $C_1$-$C_3$-alkoxy, $C_1$-$C_3$-haloalkoxy, $C_1$-$C_3$-alkylthio, ($C_1$-$C_3$-alkyl)amino, di($C_1$-$C_3$-alkyl)amino, $C_1$-$C_3$-alkoxy-$C_1$-$C_3$-alkyl, $C_1$-$C_3$-alkoxycarbonyl;
$R^7$ H, halogen, $C_1$-$C_3$-alkyl, $C_1$-$C_3$-alkoxy;
$R^8$ $OR^9$, $SR^9$, $NR^{10}R^{11}$, $NR^9OR^9$, $NR^9S(O)_2R^{10}$ or $NR^9S(O)_2NR^{10}R^{11}$, wherein
  $R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
  —N=$CR^{12}R^{13}$, wherein $R^{12}$ and $R^{13}$ independently of one another are H, $C_1$-$C_4$-alkyl or phenyl;
  $C_3$-$C_6$-cycloalkyl, $C_3$-$C_6$-cycloalkyl-$C_1$-$C_6$-alkyl, $C_3$-$C_6$-heterocyclyl, $C_3$-$C_6$-heterocyclyl-$C_1$-$C_6$-alkyl, phenyl, phenyl-$C_1$-$C_4$-alkyl or a 5- or 6 membered heteroaryl,
    wherein each cycloalkyl, heterocyclyl, phenyl or heteroaryl ring can be substituted by one to four substituents selected from $R^{14}$ or a 3- to 7-membered carbocyclus,
      which carbocyclus optionally has in addition to carbon atoms one or two ring members selected from the group consisting of —N=N—, —C(=O)—, —O— and —S—, and
      which carbocyclus is optionally substituted with one to four substituents selected from $R^{14}$;
      wherein $R^{14}$ is halogen, $NO_2$, CN, $C_1$-$C_4$ alkyl, $C_1$-$C_4$-halo-alkyl, $C_1$-$C_4$-alkoxy or $C_1$-$C_4$-alkoxycarbonyl;
  $R^{10}$, $R^{11}$ independently of one another are $R^9$, or together form a 3- to 7-membered carbocyclus,
    which carbocyclus optionally has in addition to carbon atoms one or two ring members selected from the group consisting of —N($R^{12}$)—, —N=N—, —C(=O)—, —O— and —S—, and
    which carbocyclus is optionally substituted with one to four substituents selected from $R^{14}$;
n 1 to 3;
Q $CH_2$, O, S, SO, $SO_2$, NH or ($C_1$-$C_3$-alkyl)N;
W O or S;
X NH, $NC_3$, O or S;
Y O or S;
Z phenyl, pyridyl, pyridazinyl, pyrimidinyl or pyrazinyl, each of which is optionally substituted by 1 to 4 substituents selected from the group consisting of halogen, CN, $C_1$-$C_6$-alkyl, $C_1$-$C_6$-haloalkyl, $C_1$-$C_6$-alkoxy, $C_1$-$C_6$-haloalkoxy;
including their agriculturally acceptable salts or derivatives, provided the compounds of formula (I) have a carboxyl group.

If the uracilpyridines of formula (I), the herbicidal compounds B and/or the safeners C as described herein are capable of forming geometrical isomers, for example E/Z isomers, it is possible to use both, the pure isomers and mixtures thereof, in the compositions according to the invention.

If the uracilpyridines of formula (I), the herbicidal compounds B and/or the safeners C as described herein have one or more centres of chirality and, as a consequence, are present as enantiomers or diastereomers, it is possible to use both, the pure enantiomers and diastereomers and their mixtures, in the compositions according to the invention.

Within the substituents of the uracilpyridines of formula (I), instead of hydrogene also the corresponding isotope deuterium can be used.

If the uracilpyridines of formula (I), the herbicidal compounds B and/or the safeners C as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diethylammonium, diisopropylammonium, trimethylammonium, triethylammonium, tris(isopropyl)ammonium, heptylammonium, dodecylammonium, tetradecylammonium, tetramethylammonium, tetraethylammonium, tetrabutylammonium, 2-hydroxyethyl-ammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl) sulfoxonium, and finally the salts of polybasic amines such as N,N-bis-(3-aminopropyl)methylamine and diethylenetriamine.

Also preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Uracilpyridines of formula (I), herbicidal compounds B and/or safeners C as described herein having a carboxyl group can be employed in the form of the acid, in the form of an agriculturally suitable salt as mentioned above or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters, tefuryl ((tetrahydrofuran-2-yl)methyl) esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

The organic moieties mentioned in the definition of the variables $R^1$ to $R^{14}$ and $R^a$ to $R^e$, are—like the term halogen—collective terms for individual enumerations of the individual group members. The term halogen denotes in each case fluorine, chlorine, bromine or iodine. AH hydrocarbon chains, e.g. all alkyl, alkenyl, alkynyl, alkoxy chains, can be straight-chain or branched, the prefix $C_n$-$C_m$ denoting in each case the possible number of carbon atoms in the group.

Examples of such meanings are:

$C_1$-$C_3$-alkyl and also the $C_1$-$C_3$-alkyl moieties of di($C_1$-$C_3$-alkyl)amino, $C_1$-$C_3$-alkoxy-$C_1$-$C_3$-alkyl: for example $CH_3$, $C_2H_5$, n-propyl and $CH(CH_3)_2$;

$C_1$-$C_4$-alkyl and also the $C_1$-$C_4$-alkyl moieties of phenyl-$C_1$-$C_4$-alkyl: for example $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-cyanoalkyl, $C_1$-$C_6$-alkyoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy) $C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl, $C_3$-$C_6$-cycloalkyl-$C_1$-$C_6$-alkyl, $C_3$-$C_6$-heterocyclyl-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_3$-haloalkyl: $C_1$-$C_3$-alkyl as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl;

$C_1$-$C_4$-haloalkyl: $C_1$-$C_4$-alkyl as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-alkenyl and also the $C_3$-$C_6$-alkenyl moieties of $C_3$-$C_6$-alkenyloxy-$C_1$-$C_6$-alkyl, $C_3$-$C_6$-alkenyloxy-$C_1$-$C_6$-alkoxy-$C_1$-$C_6$-alkyl, $C_3$-$C_6$-alkenyloxycarbonyl-$C_1$-$C_6$-alkyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-haloalkenyl and also the $C_3$-$C_6$-haloalkenyl moieties of $C_3$-$C_6$-haloalkenyloxy-$C_1$-$C_6$-alkyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl and also the $C_3$-$C_6$-alkynyl moieties of $C_3$-$C_6$-alkynyloxycarbonyl-$C_1$-$C_6$-alkyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_3$-alkoxy and also the $C_1$-$C_3$-alkoxy moieties of $C_1$-$C_3$-alkoxy-$C_1$-$C_3$-alkyl, $C_1$-$C_3$-alkoxycarbonyl: for example methoxy, ethoxy, propoxy;

$C_1$-$C_4$-alkoxy and also the $C_1$-$C_4$-alkoxy moieties of $C_1$-$C_4$-alkoxycarbonyl: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-alkyoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_3$-$C_6$-alkenyloxy-$C_1$-$C_6$-alkoxy-$C_1$-$C_6$-alkyl, $C_1$-$C_6$-alkoxycarbonyl-$C_1$-$C_6$-alkyl: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

$C_1$-$C_3$-haloalkoxy: a $C_1$-$C_3$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy;

$C_1$-$C_4$-haloalkoxy: a $C_1$-$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$-$C_6$-haloalkoxy and also the $C_1$-$C_6$-haloalkoxy moieties of $C_1$-$C_6$-haloalkoxy-$C_1$-$C_6$-alkyl, $C_1$-$C_6$-haloalkoxycarbonyl-$C_1$-$C_6$-alkyl: a $C_1$-$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_3$-alkylthio: for example methylthio, ethylthio, propylthio, 1-methylethylthio;

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio and also the $C_1$-$C_6$-alkylthio moieties of $C_1$-$C_6$-alkylthio-$C_1$-$C_6$-alkyl: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylsulfinyl ($C_1$-$C_6$-alkyl-S(=O)—) and also the $C_1$-$C_6$-alkylsulfinyl moieties of $C_1$-$C_6$-alkylsulfinyl-$C_1$-$C_6$-alkyl: for example methylsulfinyl, ethylsulfinyl, propylsulfinyl, 1-methylethylsulfinyl, butylsulfinyl, 1-methylpropylsulfinyl, 2-methylpropylsulfinyl, 1,1-di-methylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethyl-propylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutyl-sulfinyl, 2,2-dimethylbutylsulfinyl, 2,3-dimethylbutylsulfinyl, 3,3-dimethylbutyl-sulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-alkylsulfonyl ($C_1$-$C_6$-alkyl-S(O)$_2$—) and also the $C_1$-$C_6$-alkylsulfonyl moieties of $C_1$-$C_6$-alkylsulfonyl-$C_1$-$C_6$-alkyl: for example methylsulfonyl, ethylsulfonyl, propylsulfonyl, 1-methylethylsulfonyl, butylsulfonyl, 1-methylpropylsulfonyl, 2-methyl-propylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethyl-propylsulfonyl, 1,2,2-trimethylpropylsulfonyl, 1-ethyl-1-methylpropylsulfonyl and 1-ethyl-2-methylpropylsulfonyl;

($C_1$-$C_3$-alkyl)amino: for example methylamino, ethylamino, propylamino, 1-methylethyl-amino;

($C_1$-$C_4$-alkyl)amino: for example methylamino, ethylamino, propylamino, 1-methylethyl-amino, butylamino, 1-methylpropylamino, 2-methylpropylamino or 1,1-dimethylethylamino;

($C_1$-$C_6$-alkyl)amino: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutyl-amino 3,3-dimethylbutyl-amino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di($C_1$-$C_6$-alkyl)amino: di($C_1$-$C_4$-alkyl)amino as mentioned above, and also, for example, N-methyl-N-pentylamino, N-methyl-N-(1-methylbutyl)amino, N-methyl-N-(2-methyl-butyl)amino, N-methyl-N-(3-methylbutypamino, N-methyl-N-(2,2-dimethylpropyl)amino, N-methyl-N-(1-ethylpropyl)amino, N-methyl-N-hexylamino, N-methyl-N-(1,1-dimethyl-propyl) amino, N-methyl-N-(1,2-dimethylpropyl)amino, N-methyl-N-(1-methylpentyl)amino, N-methyl-N-(2-methylpentyl)amino, N-methyl-N-(3-methylpentypamino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethyl-butypamino, N-methyl-N-(2,3-dimethylbutyl)amino, N-methyl-N-(3,3-dimethylbutyl)amino, N-methyl-N-(1-ethylbutypamino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl)amino, N-ethyl-N-(3-methylpentypamino, N-ethyl-N-(4-methylpentyl)amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl)amino, N-ethyl-N-(1-ethylbutyl)amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

$C_3$-$C_6$-cycloalkyl and also the cycloalkyl moieties of $C_3$-$C_6$-cycloalkyl-$C_1$-$C_6$-alkyl: monocyclic saturated hydrocarbons having 3 to 6 ring members, such as cyclopropyl, cyclobutyl, cyclopentyl and cyclohexyl;

$C_3$-$C_6$-heterocyclyl and also the heterocyclyl moieties of $C_3$-$C_6$-heterocyclyl-$C_1$-$C_6$-alkyl: aliphatic heterocycle having 3 to 6 ring members which, in addition to carbon atoms, contains 1 to 4 nitrogen atoms, or 1 to 3 nitrogen atoms and an oxygen or sulphur atom, or an oxygen or a sulphur atom, for example three- or four-membered heterocycles like 2-oxetanyl, 3-oxetanyl, 2-thietanyl, 3-thietanyl, 1-azetidinyl, 2-azetidinyl, 1-azetinyl, 2-azetinyl; five-membered saturated heterocycles like 2-tetrahydrofuranyl, 3-tetrahydrofuranyl, 2-tetrahydrothienyl, 3-tetrahydrothienyl, 1-pyrrolidinyl,2-pyrrolidinyl, 3-pyrrolidinyl, 3-isoxazolidinyl, 4-isoxazolidinyl, 5-isoxazolidinyl, 2-isothiazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 3-oxazolidinyl, 1,2,4-oxadiazolidin-3-yl, 1,2,4-oxadiazolidin-5-yl, 3-thiazolidinyl, 1,2,4-thiadiazolidin-3-yl, 1,2,4-thiadiazolidin-5-yl, 1,2,4-triazolidin-3-yl, 1,2,4-oxadiazolidin-2-yl, 1,2,4-oxadiazolidin-4-yl, 1,3,4-oxadiazolidin-2-yl, 1,2,4-thiadiazolidin-2-yl, 1,2,4-thiadiazolidin-4-yl, 1,3,4-thiadiazolidin-2-yl, 1,2,4-triazolidin-1-yl, 1,3,4-triazolidin-2-yl; six-membered saturated heterocycles like 1-piperidinyl, 2-piperidinyl, 3-piperidinyl, 4-piperidinyl, 1,3-dioxan-5-yl, 1,4-dioxanyl, 1,3-dithian-5-yl, 1,3-dithianyl, 1,3-oxathian-5-yl, 1,4-oxathianyl, 2-tetrahydropyranyl, 3-tetrahydropyranyl, 4-tetrahydropyranyl, 2-tetrahydrothiopyranyl, 3-tetrahydrothiopyranyl,4-tetrahydrothiopyranyl, 1-hexahydropyridazinyl, 3-hexahydropyridazinyl, 4-hexahydropyridazinyl, 1-hexahydropyrimidinyl, 2-hexahydropyrimidinyl, 4-hexahydropyrimidinyl, 5-hexahydropyrimidinyl, 1-piperazinyl, 2-piperazinyl, 1,3,5-hexahydrotriazin-1-yl, 1,3,5-hexahydrotriazin-2-yl, 1,2,4-hexahydrotriazin-1-yl, 1,2,4-hexahydrotriazin-3-yl, tetrahydro-1,3-oxazin-1-yl, tetrahydro-1,3-oxazin-2-yl, tetrahydro-1,3-oxazin-6-yl, 1-morpholinyl, 2-morpholinyl, 3-morpholinyl;

5- or 6 membered heteroaryl: aromatic heteroaryl having 5 or 6 ring members which, in addition to carbon atoms, contains 1 to 4 nitrogen atoms, or 1 to 3 nitrogen atoms and an oxygen or sulphur atom, or an oxygen or a sulphur atom, for example 5-membered aromatic rings like furyl (for example 2-furyl, 3-furyl, thienyl (for example 2-thienyl, 3-thienl), pyrrolyl (for example pyrrol-2-yl, pyrrol-3-0, pyrazolyl (for example pyrazol-3-yl, pyrazol-4-isoxazolyl (for example isoxazol-3-yl, isoxazol-4-yl, isoxazol-5-0, isothiazolyl (for example isothiazol-3-yl, isothiazol-4-yl, isothiazol-5-0, imidazolyl (for example imidazole-2-yl, oxazolyl (for example oxazol-2-yl, oxazol-4-yl, oxazol-5-0, thiazolyl (for example thiazol-2-yl, thiazol-4-yl, oxadiazolyl (for example 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-0, thiadiazolyl (for example 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-0, triazolyl (for example 1,2,3-triazol-4-yl, 1,2,4-triazol-3-0; 1-tetrazolyl; 6-membered aromatic rings like pyridyl (for example pyridine-2-yl, pyridine-3-yl, pyridine-4-0, pyrazinyl (for example pyridazin-3-yl, pyridazin-4-0, pyrimidinyl (for example pyrimidin-2-yl, pyrimidin-4-yl, pyrazin-2-yl, triazinyl (for example 1,3,5-triazin-2-yl, 1,2,4-triazin-3-yl, 1,2,4-triazin-5-yl, 1,2,4-triazin-6-yl);

3- to 7-membered carbocyclus: a three- to seven-membered monocyclic, saturated, partial unsaturated or aromatic cycle having three to seven ring members which comprises apart from carbon atoms optionally one or two ring members selected from the group consisting of —N($R^{12}$)—, —N═N—, —C(═O)—, —O— and —S—.

The preferred embodiments of the invention mentioned herein below have to be understood as being preferred either independently from each other or in combination with one another.

According to a preferred embodiment of the invention preference is also given to those uracilpyridines of formula (I), wherein the variables, either independently of one another or in combination with one another, have the following meanings:

Preferred are the uracilpyridines of formula (I) wherein
$R^1$ is hydrogen, $NH_2$ or $C_1$-$C_6$-alkyl;
preferably is $NH_2$ or $C_1$-$C_4$-alkyl;
particularly preferred is $NH_2$ or $CH_3$;
also preferably is $C_1$-$C_6$-alkyl;
particularly preferred is $C_1$-$C_4$-alkyl;
especially preferred is $CH_3$.

Also preferred are the uracilpyridines of formula (I) wherein
$R^2$ is $C_1$-$C_6$-alkyl or $C_1$-$C_6$-haloalkyl;
preferably is $C_1$-$C_4$-alkyl or $C_1$-$C_4$-haloalkyl;
more preferred is $C_1$-$C_4$-haloalkyl;
particularly preferred is $C_1$-$C_2$-haloalkyl;
especially preferred is $CF_3$.

Also preferred are the uracilpyridines of formula (I) wherein
$R^3$ is H;
also preferably is $C_1$-$C_6$-alkyl,
particularly preferred is $C_1$-$C_4$-alkyl,
especially preferred is $CH_3$.

Also preferred are the uracilpyridines of formula (I) wherein
$R^4$ is H, F or Cl;
particularly preferred is H or F;
especially preferred is H;
also particularly preferred is H or Cl;
especially preferred is Cl;
also particularly preferred is F or Cl;
especially preferred is F.

Also preferred are the uracilpyridines of formula (I) wherein
$R^5$ is halogen or CN;
preferably F, Cl, Br or CN;
particularly preferred is F, Cl or CN;
especially preferred is Cl or CN;
more preferred is Cl;
also more preferred is CN;
also especially preferred is F or Cl;
more preferred is F.

Also preferred are the uracilpyridines of formula (I) wherein
$R^6$ is H, $C_1$-$C_3$-alkyl, $C_1$-$C_3$-haloalkyl, $C_1$-$C_3$-alkoxy, $C_1$-$C_3$-haloalkoxy or $C_1$-$C_3$-alkylthio;
particularly preferred is H, $C_1$-$C_3$-alkyl, $C_1$-$C_3$-haloalkyl or $C_1$-$C_3$-alkoxy;
especially preferred is H, $C_1$-$C_3$-alkyl or $C_1$-$C_3$-alkoxy;
more preferred is H, $CH_3$ or $OCH_3$.

Also preferred are the uracilpyridines of formula (I) wherein
$R^7$ is H, halogen or $C_1$-$C_3$-alkyl;
particularly preferred is H, F or $CH_3$;
especially preferred is H.

Also preferred are the uracilpyridines of formula (I) wherein
$R^8$ is $OR^9$, $SR^9$, $NR^{10}R^{11}$, $NR^9S(O)_2R^{10}$ or $NR^9S(O)_2NR^{10}R^{11}$
particularly preferred is $OR^9$, $NR^{10}R^{11}$, $NR^9S(O)_2R^{10}$ or $NR^9S(O)_2NR^{10}R^{11}$;
especially preferred $OR^9$, $NR^9S(O)_2R^{10}$ or $NR^9S(O)_2NR^{10}R^{11}$;
especially preferred is $OR^9$ or $NR^9S(O)_2R^{10}$.

Also preferred are the uracilpyridines of formula (I) wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl) amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl) aminocarbonyl-$C_1$-$C_6$-alkyl, di($C_1$-$C_6$-alkyl)aminocarbonyl-$C_1$-$C_6$-alkyl,
—N=$CR^{12}R^{13}$,
wherein $R^{12}$ and $R^{13}$ independently of one another are H, $C_1$-$C_4$-alkyl or phenyl; $C_3$-$C_6$-cycloalkyl, $C_3$-$C_6$-cycloalkyl-$C_1$-$C_6$-alkyl, $C_3$-$C_6$-heterocyclyl, phenyl, phenyl-$C_1$-$C_4$-alkyl or a 5- or 6- membered heteroaryl,
wherein each cycloalkyl, heterocyclyl, phenyl or heteroaryl ring can be substituted by one to four substituents selected from $R^{14}$ or a 3- to 7-membered carbocyclus,
which carbocyclus optionally has in addition to carbon atoms one or two ring members selected from the group consisting of —N($R^{12}$)—, —N=N—, C(=O)—, —O— and —S—, and
which carbocyclus is optionally substituted with one to four substituents selected from $R^{14}$,
wherein $R^{14}$ is halogen, $NO_2$, CN, $C_1$-$C_4$ alkyl, $C_1$-$C_4$-haloalkyl, $C_1$-$C_4$-alkoxy or $C_1$-$C_4$-alkoxycarbonyl;
preferably is hydrogen, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, di($C_1$-$C_6$-alkoxy)$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl or $C_3$-$C_6$-cycloalkyl-$C_1$-$C_6$-alkyl;
particularly preferred is hydrogen, $C_1$-$C_6$-alkyl, $C_3$-$C_6$-alkenyl, $C_3$-$C_6$-alkynyl or $C_1$-$C_6$-haloalkyl;
also particularly preferred is hydrogen, $C_1$-$C_6$-alkyl, $C_3$-$C_6$-alkenyl or $C_3$-$C_6$-alkynyl;
especially preferred is hydrogen, $C_1$-$C_6$-alkyl, or $C_3$-$C_6$-alkynyl;
more preferred is hydrogen, $CH_3$, $C_2H_5$, $CH_2CH=CH_2$ or $CH_2C\equiv CH$;
most preferred is hydrogen, $CH_3$, $C_2H_5$ or $CH_2C\equiv CH$.

Also preferred are the uracilpyridines of formula (I) wherein
$R^{10}$ is H, $C_1$-$C_6$-alkyl or $C_3$-$C_6$-cycloalkyl;
particularly preferred is H or $C_1$-$C_6$-alkyl;
more preferred is H;
also more preferred is $C_1$-$C_6$-alkyl.

Also preferred are the uracilpyridines of formula (I) wherein
$R^{11}$ is H, $C_1$-$C_6$-alkyl or $C_1$-$C_6$-alkoxycarbonyl-$C_1$-$C_6$-alkyl;
particularly preferred is H or $C_1$-$C_6$-alkyl;
more preferred is H;
also more preferred is $C_1$-$C_6$-alkyl.

Also preferred are the uracilpyridines of formula (I) wherein
$R^{12}$ is phenyl or $C_1$-$C_4$-alkyl;
particularly preferred is phenyl or $CH_3$;
also particularly preferred is phenyl;
also particularly preferred is $C_1$-$C_4$-alkyl.

Also preferred are the uracilpyridines of formula (I) wherein
$R^{13}$ is phenyl or $C_1$-$C_4$-alkyl;
particularly preferred is phenyl or $CH_3$;
also particularly preferred is phenyl;
also particularly preferred is $C_1$-$C_4$-alkyl.

Also preferred are the uracilpyridines of formula (I) wherein
$R^{14}$ is halogen or $C_1$-$C_4$-alkyl;
particularly preferred is F, Cl or $CH_3$;
also particularly preferred is halogen;
especially preferred is F or Cl;
also particularly preferred is $C_1$-$C_6$-alkyl;
especially preferred is $CH_3$.

Also preferred are the uracilpyridines of formula (I) wherein
n is 1 or 2;
particularly preferred is 2;
also particularly preferred is 1.

Also preferred are the uracilpyridines of formula (I) wherein
Q is O, S, SO, SO$_2$, NH or (C$_1$-C$_3$-alkyl)N;
preferably is O or S;
particularly preferred is O.

Also preferred are the uracilpyridines of formula (I) wherein
W is O,
also preferably is S.

Also preferred are the uracilpyridines of formula (I) wherein
X is O,
also preferably is S.

Also preferred are the uracilpyridines of formula (I) wherein
Y is O,
also preferably is S.

Also preferred are the uracilpyridines of formula (I) wherein
Z is phenyl or pyridyl,
each of which is optionally substituted by 1 to 4 substituents selected from the group consisting of halogen, CN, C$_1$-C$_6$-alkyl, C$_1$-C$_6$-haloalkyl, C$_1$-C$_6$-alkoxy and C$_1$-C$_6$-haloalkoxy;
preferably is phenyl,
which is optionally substituted by 1 to 4 substituents selected from the group consisting of halogen, CN, C$_1$-C$_6$-alkyl, C$_1$-C$_6$-haloalkyl, C$_1$-C$_6$-alkoxy and C$_1$-C$_6$-haloalkoxy;
also preferably is pyridyl,
which is optionally substituted by 1 to 4 substituents selected from the group consisting of halogen, CN, C$_1$ C$_6$ alkyl, C$_1$-C$_6$-haloalkyl, C$_1$-C$_6$-alkoxy and C$_1$-C$_6$-haloalkoxy.

Also preferred are the uracilpyridines of formula (I) wherein
Z is phenyl or pyridyl,
each of which is optionally substituted by 1 to 4 substituents selected from the group consisting of halogen, CN, C$_1$ C$_6$ alkyl, C$_1$-C$_6$-haloalkyl, C$_1$-C$_6$-alkoxy and C$_1$-C$_6$-haloalkoxy;
preferably is phenyl or pyridyl,
each of which is optionally substituted by 1 to 4 substituents selected from the group consisting of halogen, C$_1$-C$_6$-alkyl, C$_1$-C$_6$-haloalkyl, C$_1$-C$_6$-alkoxy or C$_1$-C$_6$-haloalkoxy;
particularly preferred is phenyl or pyridyl,
each of which is optionally substituted by 1 to 4 substituents selected from the group consisting of halogen or C$_1$-C$_6$-alkyl;
especially preferred is phenyl or pyridyl,
each of which is optionally substituted by 1 to 4 substituents selected from the group consisting of F, Cl or CH$_3$;
more preferred is phenyl or pyridyl,
each of which is unsubstituted.

Also preferred are the uracilpyridines of formula (I) wherein
Z is phenyl,
which is optionally substituted by 1 to 4 substituents selected from the group consisting of halogen, CN, C$_1$ C$_6$ alkyl, C$_1$-C$_6$-haloalkyl, C$_1$-C$_6$-alkoxy and C$_1$-C$_6$-haloalkoxy;
preferably is phenyl,
which is optionally substituted by 1 to 4 substituents selected from the group consisting of halogen, C$_1$-C$_6$-alkyl, C$_1$-C$_6$-haloalkyl, C$_1$-C$_6$-alkoxy or C$_1$-C$_6$-haloalkoxy;
particularly preferred is phenyl,
which is optionally substituted by 1 to 4 substituents selected from the group consisting of halogen or C$_1$-C$_6$-alkyl;
especially preferred is phenyl
which is optionally substituted by 1 to 4 substituents selected from the group consisting of F, Cl or CH$_3$;
more preferred is unsubstituted phenyl.

Also preferred are the uracilpyridines of formula (I) wherein
Z is pyridyl,
which is optionally substituted by 1 to 3 substituents selected from the group consisting of halogen, CN, C$_1$ C$_6$ alkyl, C$_1$-C$_6$-haloalkyl, C$_1$-C$_6$-alkoxy and C$_1$-C$_6$-haloalkoxy;
preferably is pyridyl,
which is optionally substituted by 1 to 3 substituents selected from the group consisting of halogen, C$_1$-C$_6$-alkyl, C$_1$-C$_6$-haloalkyl, C$_1$-C$_6$-alkoxy or C$_1$-C$_6$-haloalkoxy;
particularly preferred is pyridyl,
which is optionally substituted by 1 to 3 substituents selected from the group consisting of halogen or C$_1$-C$_6$-alkyl;
especially preferred is pyridyl,
which is optionally substituted by 1 to 3 substituents selected from the group consisting of F, Cl or CH$_3$;
more preferred is unsubstituted pyridyl.

Also preferred are the uracilpyridines of formula (I) wherein
Z is selected from the group consisting of $Z^1$ to $Z^{29}$

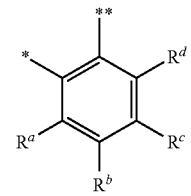

Z-1

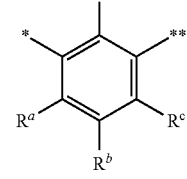

Z-2

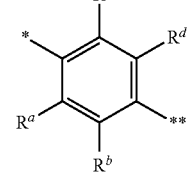

Z-3

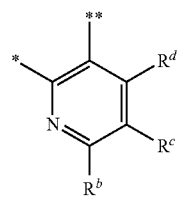 Z-4
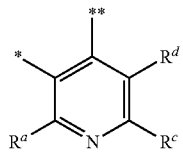 Z-5
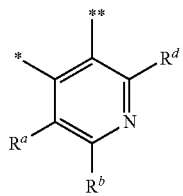 Z-6
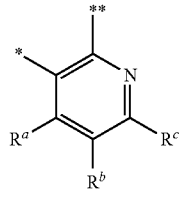 Z-7
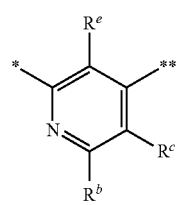 Z-8
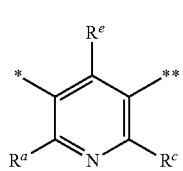 Z-9
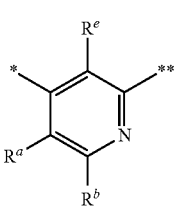 Z-10
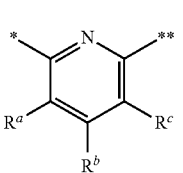 Z-11
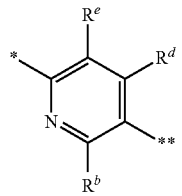 Z-12
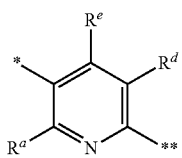 Z-13
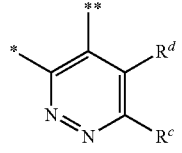 Z-14
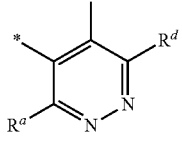 Z-15
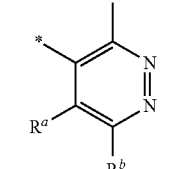 Z-16
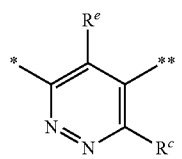 Z-17
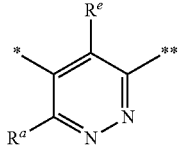 Z-18
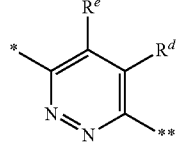 Z-19
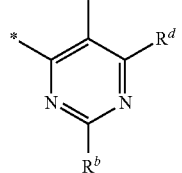 Z-20

-continued

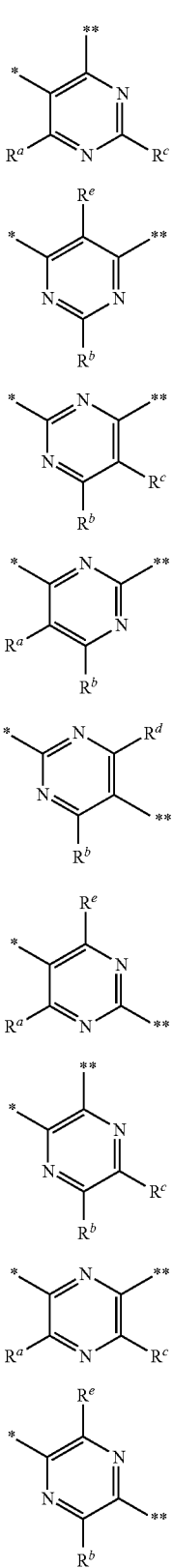

wherein
* denotes the point of attachment of Z to X;
* denotes the point of attachment of Z to Q; and $R^a$, $R^b$, $R^c$, $R^d$ and $R^e$ independently of one another are
H, halogen, CN, $C_1$-$C_6$-alkyl, $C_1$-$C_6$-haloalkyl, $C_1$-$C_6$-alkoxy, $C_1$-$C_6$-haloalkoxy; preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H.

Also preferred are the uracilpyridines of formula (I) wherein
Z is selected from the group consisting of $Z^1$, $Z^2$, $Z^3$, $Z^4$, $Z^5$, $Z^6$, $Z^7$, $Z^8$, $Z^9$, $Z^{10}$, $Z^{11}$, $Z^{12}$, $Z^{13}$ and $Z^{21}$ as defined above;
particularly preferred is selected from the group consisting of $Z^1$, $Z^2$, $Z^4$, $Z^5$, $Z^6$, $Z^7$, $Z^8$, $Z^9$, $Z^{10}$, $Z^{11}$ and $L^{21}$ as defined above;
more particularly preferred is selected from the group consisting of $Z^1$, $Z^4$, $Z^5$, $Z^6$, $Z^7$ and $Z^{21}$ as defined above;
especially preferred is selected from the group consisting of $Z^1$, $Z^4$, $Z^5$, $Z^6$ and $Z^7$ as defined above;
more preferred is selected from the group consisting of $Z^1$ and $Z^7$ as defined above.

Also preferred are the uracilpyridines of formula (I) wherein
Z is selected from the group consisting of $Z^1$, $Z^2$, $Z^3$, $Z^4$, $Z^5$, $Z^6$, $Z^7$, $Z^8$, $Z^9$, $Z^{19}$, $Z^{11}$, $Z^{12}$, $Z^{13}$ and $Z^{21}$ as defined above; wherein
$R^a$, $R^b$, $R^c$, $R^d$ and $R^e$ independently of one another are
H, halogen, CN, $C_1$-$C_6$-alkyl, $C_1$-$C_6$-haloalkyl, $C_1$-$C_6$-alkoxy, $C_1$-$C_6$-haloalkoxy;
preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H;
particularly preferred is selected from the group consisting of $Z^1$, $Z^2$, $Z^4$, $Z^5$, $Z^6$, $Z^7$, $Z^8$, $Z^9$, $Z^{19}$, $Z^{11}$ and $Z^{21}$ as defined above, wherein
$R^a$, $R^b$, $R^c$, $R^d$ and $R^e$ independently of one another are
H, halogen, CN, $C_1$-$C_6$-alkyl, $C_1$-$C_6$-haloalkyl, $C_1$-$C_6$-alkoxy, $C_1$-$C_6$-haloalkoxy;
preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H;
more particularly preferred is selected from the group consisting of $Z^1$, $Z^4$, $Z^5$, $Z^6$, $Z^7$, and $Z^{21}$ as defined above, wherein
$R^a$, $R^b$, $R^c$, $R^d$ and $R^e$ independently of one another are
H, halogen, CN, $C_1$-$C_6$-alkyl, $C_1$-$C_6$-haloalkyl, $C_1$-$C_6$-alkoxy, $C_1$-$C_6$-haloalkoxy;
preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H;
especially preferred is selected from the group consisting of $Z^1$, $Z^4$, $Z^5$, $Z^6$ and $Z^7$ as defined above, wherein
$R^a$, $R^b$, $R^c$, $R^d$ and $R^e$ independently of one another are
H, halogen, CN, $C_1$-$C_6$-alkyl, $C_1$-$C_6$-haloalkyl, $C_1$-$C_6$-alkoxy, $C_1$-$C_6$-haloalkoxy;
preferably H, halogen, $C_1$-$C_6$-alkyl, $C_1$-$C_6$-haloalkyl, $C_1$-$C_6$-alkoxy or $C_1$-$C_6$-haloalkoxy;
particularly preferred H, halogen or $C_1$-$C_6$-alkyl;
especially preferred H, F, Cl, or $CH_3$;
more preferred H;

more preferred is selected from the group consisting of $Z^1$ and $Z^7$ as defined above, wherein $R^a$, $R^b$, $R^c$, $R^d$ and $R^e$ independently of one another are
H, halogen, CN, $C_1$-$C_6$-alkyl, $C_1$-$C_6$-haloalkyl, $C_1$-$C_6$-alkoxy, $C_1$-$C_6$-haloalkoxy;
preferably H, halogen, $C_1$-$C_6$-alkyl, $C_1$-$C_6$-haloalkyl, $C_1$-$C_6$-alkoxy or $C_1$-$C_6$ haloalkoxy;
particularly preferred H, halogen or $C_1$-$C_6$-alkyl;
especially preferred H, F, Cl, or $CH_3$;
more preferred H.

Also preferred are the uracilpyridines of formula (I) wherein
$R^1$ is $C_1$-$C_6$-alkyl,
$R^2$ is $C_1$-$C_4$-haloalkyl,
$R^3$ is H, and
Y is O.

Also preferred are the uracilpyridines of formula (I) wherein
$R^4$ is H or F, and
$R^5$ is F, Cl, Br or CN.

Also preferred are the uracilpyridines of formula (I) wherein
$R^4$ is H or F, and
$R^5$ is F, Cl or CN.

Also preferred are the uracilpyridines of formula (I) wherein
$R^6$ is H, $C_1$-$C_3$-alkyl or $C_1$-$C_3$-alkoxy, and
$R^7$ is H.

Also preferred are the uracilpyridines of formula (I) wherein
$R^8$ is $OR^9NR^9S(O)_2R^{10}$ or $NR^9S(O)_2NR^{10}R^{11}$, wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, di($C_1$-$C_6$-alkoxy)$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl or $C_3$-$C_6$-cycloalkyl-$C_1$-$C_6$-alkyl; and
$R^{10}$, $R^{11}$ are $C_1$-$C_6$-alkyl.

Also preferred are the uracilpyridines of formula (I) wherein
n is 1.

Also preferred are the uracilpyridines of formula (I) wherein
Q, W and X are O.

Also preferred are the uracilpyridines of formula (I) wherein
$R^1$ is hydrogen, $NH_2$ or $C_1$-$C_6$-alkyl;
$R^2$ is $C_1$-$C_6$-alkyl or $C_1$-$C_6$-haloalkyl;
$R^3$ is H;
$R^4$ is H or halogen;
$R^5$ is halogen or CN;
$R^6$ is H, $C_1$-$C_3$-alkyl, $C_1$-$C_3$-haloalkyl, $C_1$-$C_3$-alkoxy, $C_1$-$C_3$-haloalkoxy or $C_1$-$C_3$-alkylthio;
$R^7$ is H;
$R^8$ is $OR^9$, $SR^9$, $NR^{10}R^{11}$, $NR^9S(O)_2R^{10}$ or $NR^9S(O)_2NR^{10}R^{11}$; wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, di($C_3$-$C_6$-alkoxy)$C_3$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_1$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$ alkyl)aminocarbonyl-$C_1$-$C_6$-alkyl, di($C_1$-$C_6$-alkyl)aminocarbonyl-$C_1$-$C_6$-alkyl, —N=$CR^{12}R^{13}$,
wherein $R^{12}$ and $R^{13}$ independently of one another are H, $C_1$-$C_4$-alkyl or phenyl;
$C_3$-$C_6$-cycloalkyl, $C_3$-$C_6$-cycloalkyl-$C_1$-$C_6$-alkyl, $C_3$-$C_6$-heterocyclyl, phenyl, phenyl-$C_1$-$C_4$-alkyl or a 5- or 6 membered heteroaryl,
wherein each cycloalkyl, heterocyclyl, phenyl or heteroaryl ring can be substituted by one to four substituents selected from $R^{14}$ or a 3- to 7-membered carbocyclus,
which carbocyclus optionally has in addition to carbon atoms one or two ring members selected from the group consisting of —N($R^{12}$)—, —N=N—, —C(=O)—, —O— and —S—, and
which carbocyclus is optionally substituted with one to four substituents selected from $R^{14}$;
$R^{10}$ is $C_1$-$C_6$-alkyl;
$R^{11}$ is H or $C_1$-$C_6$-alkyl;
$R^{12}$ is phenyl or $CH_3$;
$R^{13}$ is phenyl or $CH_3$;
$R^{14}$ is halogen or $C_1$-$C_6$-alkyl;
n is 1 or 2;
Q is O, S, SO, $SO_2$, NH or ($C_1$-$C_3$-alkyl)N;
W is O;
X is O;
Y is O;
Z $Z^1$, $Z^2$, $Z^3$, $Z^4$, $Z^5$, $Z^6$, $Z^7$, $Z^8$, $Z^9$, $Z^{10}$, $Z^{11}$, $Z^{12}$, $^{13}$ and $Z^{21}$ as defined above, wherein
$R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;

particularly preferred are the uracilpyridines of formula (I) wherein
$R^1$ is $NH_2$ or $C_1$-$C_4$-alkyl;
$R^2$ is $C_1$-$C_4$-alkyl or $C_1$-$C_4$-haloalkyl;
$R^3$ is H;
$R^4$ is H or halogen;
$R^5$ is halogen or CN;
$R^6$ is H, $C_1$-$C_3$-alkyl, $C_1$-$C_3$-haloalkyl or $C_1$-$C_3$-alkoxy;
$R^7$ is H;
$R^8$ $OR^9$, $NR^{19}R^{11}$, $NR^9S(O)_2R^{10}$ or $NR^9S(O)_2NR^{10}R^{11}$;
wherein
$R^9$ is hydrogen, $C_1$-$C_6$-alkyl, $C_3$-$C_6$-alkenyl, $C_3$-$C_6$-alkynyl, $C_1$-$C_6$-haloalkyl, $C_1$-$C_6$-alkoxy-$C_1$-$C_6$-alkyl, di($C_1$-$C_6$-alkoxy)$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl or $C_3$-$C_6$-cycloalkyl-$C_1$-$C_6$-alkyl;
$R^{10}$ is $C_1$-$C_6$-alkyl;
$R^{11}$ is H or $C_1$-$C_6$-alkyl;
n is 1;
Q is O, S, SO, $SO_2$, NH or ($C_1$-$C_3$-alkyl)N;
W is O;
X is O;
Y is O;
Z is selected from the group consisting of $Z^1$, $Z^2$, $Z^4$, $Z^5$, $Z^6$, $Z^7$, $Z^8$, $Z^9$, $Z^{10}$, $Z^{11}$ and $Z^{21}$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;

especially preferred are the uracilpyridines of formula (I) wherein
$R^1$ is $NH_2$ or $CH_3$;
$R^2$ is $C_1$-$C_4$-haloalkyl;
$R^3$ is H;
$R^4$ is H, F or Cl;
$R^5$ is F, Cl, Br or CN;
$R^6$ is H, $C_1$-$C_3$-alkyl or $C_1$-$C_3$-alkoxy;
$R^7$ is H;
$R^8$ is $OR^9$ or $NR^9S(O)_2R^{10}$, wherein
   $R^9$ is hydrogen, $C_1$-$C_6$-alkyl, $C_3$-$C_6$-alkenyl, $C_3$-$C_6$-alkynyl or $C_1$-$C_6$-haloalkyl, and
   $R^{10}$ is $C_1$-$C_6$-alkyl;
n is 1;
Q is O or S;
W is O;
X is O;
Y is O;
Z is selected from the group consisting of $Z^1$, $Z^4$, $Z^5$, $Z^6$, $Z^7$ and $Z^{21}$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;

also especially preferred are the uracilpyridines of formula (I) wherein
$R^1$ is $NH_2$ or $CH_3$;
$R^2$ is $C_1$-$C_4$-haloalkyl;
$R^3$ is H;
$R^4$ is H, F or Cl;
$R^5$ is F, Cl or CN;
$R^6$ is H, $C_1$-$C_3$-alkyl or $C_1$-$C_3$-alkoxy;
$R^7$ is H;
$R^8$ is $OR^9$ or $NR^9S(O)_2R^{10}$, wherein
   $R^9$ is hydrogen, $C_1$-$C_6$-alkyl, $C_3$-$C_6$-alkenyl, $C_3$-$C_6$-alkynyl or $C_1$-$C_6$-haloalkyl, and
   $R^{10}$ is $C_1$-$C_6$-alkyl;
n is 1;
Q is 0 or S;
W is O;
X is O;
Y is O;
Z is selected from the group consisting of $Z^1$, $Z^4$, $Z^5$, $Z^6$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy;

more preferred are the uracilpyridines of formula (I) wherein
$R^1$ is $CH_3$;
$R^2$ is $CF_3$;
$R^3$ is H;
$R^4$ is H, F or Cl;
$R^5$ is F, Cl, Br or CN;
$R^6$ is H, $CH_3$ or $OCH_3$;
$R^7$ is H;
$R^8$ is $OR^9$ or $NR^9S(O)_2V$; wherein
   $R^9$ is hydrogen, $C_1$-$C_6$-alkyl, $C_3$-$C_6$-alkenyl, or $C_3$-$C_6$-alkynyl, and
   $R^{10}$ is $C_1$-$C_6$-alkyl;
n is 1;
Q is O;
W is O;
X is O;
Y is O;
Z is selected from the group consisting of $Z^1$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy.

also more preferred are the uracilpyridines of formula (I) wherein
$R^1$ is $CH_3$;
$R^2$ is $CF_3$;
$R^3$ is H;
$R^4$ is H, F or Cl;
$R^5$ is F, Cl or CN;
$R^6$ is H, $CH_3$ or $OCH_3$;
$R^7$ is H;
$R^8$ is $OR^9$ or $NR^9S(O)_2R^{10}$; wherein
   $R^9$ is hydrogen, $C_1$-$C_6$-alkyl, or $C_3$-$C_6$-alkynyl, and
   $R^{10}$ is $C_1$-$C_6$-alkyl;
n is 1;
Q is O;
W is O;
X is O;
Y is O;
Z is selected from the group consisting of $Z^1$ and $Z^7$ as defined above, wherein $R^a$, $R^b$, $R^c$, $R^d$ and $R^e$ independently of one another are H, halogen, CN, $C_1$-$C_6$-alkyl, $C_1$-$C_6$-haloalkyl, $C_1$-$C_6$-alkoxy, $C_1$-$C_6$-haloalkoxy.

Also preferred are the uracilpyridines of formula (I) wherein
$R^1$ is $CH_3$;
$R^2$ is $CF_3$;
$R^3$ is H;
$R^4$ is H, F or Cl;
$R^5$ is F, Cl, Br or CN;
$R^6$ is H, $CH_3$ or $OCH_3$;
$R^7$ is H;
$R^8$ $OR^9$, $SR^9$, $NR^{10}R^{11}$, $NR^9OR^9$, $NR^9S(O)_2R^{10}$ or $NR^9S(O)_2NR^{10}R^{11}$, wherein
   $R^9$ is hydrogen, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_1$-$C_6$-cyanoalkyl, $C_1$-$C_6$-alkoxy-$C_1$-$C_6$-alkyl, $C_1$-$C_6$-alkoxy-$C_1$-$C_6$alkoxy-$C_1$-$C_6$-alkyl, di($C_1$-$C_6$-alkoxy)$C_1$-$C_6$-alkyl, $C_1$-$C_6$-haloalkoxy-$C_1$-$C_6$-alkyl, $C_3$-$C_6$-alkenyloxy-$C_1$-$C_6$-alkyl, $C_3$-$C_6$-haloalkenyloxy-$C_1$-$C_6$-alkyl, $C_3$-$C_6$-alkenyloxy-$C_1$-$C_6$-alkoxy-$C_1$-$C_6$-alkyl, $C_1$-$C_6$-alkylthio-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-alkenyloxycarbonyl-$C_1$-$C_6$-alkyl, $C_3$-$C_6$-alkynyloxycarbonyl-$C_1$-$C_6$-alkyl, amino, ($C_1$-$C_6$-alkyl)amino, di($C_1$-$C_6$-alkyl)amino, ($C_1$-$C_6$-alkylcarbonyl)amino, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, aminocarbonyl-$C_1$-$C_6$-alkyl, ($C_1$-$C_6$-alkyl)aminocarbonyl-$C_1$-$C_6$-alkyl, di($C_1$-$C_6$-alkyl)aminocarbonyl-$C_1$-$C_6$-alkyl,
   —N=$CR^{12}R^{13}$, wherein $R^{12}$ and $R^{13}$ independently of one another are H, $C_1$-$C_4$-alkyl or phenyl;
   $C_3$-$C_6$-cycloalkyl, $C_3$-$C_6$-cycloalkyl-$C_1$-$C_6$-alkyl, $C_3$-$C_6$-heterocyclyl, $C_3$-$C_6$-heterocyclyl-$C_3$-$C_3$-alkyl, phenyl, phenyl-$C_1$-$C_6$-alkyl or a 5- or 6 membered heteroaryl,
     wherein each cycloalkyl, heterocyclyl, phenyl or heteroaryl ring can be substituted by one to four substituents selected from $R^{14}$ or a 3- to 7-membered carbocyclus,
     which carbocyclus optionally has in addition to carbon atoms one or two ring members selected from the group consisting of —N(R$^{12}$)—, —N═N—, C(═O)—, —O— and —S—, and
which carbocyclus is optionally substituted with one to four substituents selected from R$^{14}$;
wherein R$^{14}$ is halogen, NO$_2$, CN, C$_1$-C$_4$-alkyl, C$_1$-C$_4$-haloalkyl, C$_1$-C$_4$-alkoxy or C$_1$-C$_4$-alkoxycarbonyl;

R$^{10}$, R$^{11}$ independently of one another are R$^9$, or together form a 3- to 7-membered carbocyclus,
which carbocyclus optionally has in addition to carbon atoms one or two ring members selected from the group consisting of —N(R$^{12}$)—, —N═N—, —C(═O)—, —O— and —S—, and
which carbocyclus is optionally substituted with one to four substituents selected from R$^{14}$;

n is 1;
Q is O;
W is O;
X is O;
Y is O;
Z is selected from the group consisting of Z$^1$ and Z$^7$ as defined above, wherein R$^a$, R$^b$, R$^c$, R$^d$ and R$^e$ independently of one another are H, halogen, CN, C$_1$-C$_6$-alkyl, C$_1$-C$_6$-haloalkyl, C$_1$-C$_6$-alkoxy, C$_1$-C$_6$-haloalkoxy.

Also preferred are the uracilpyridines of formula (I) wherein
R$^1$ is CH$_3$;
R$^2$ is CF$_3$;
R$^3$ is H;
R$^4$ is H, F or Cl;
R$^5$ is F, Cl or CN;
R$^6$ is H, CH$_3$ or OCH$_3$;
R$^7$ is H;
R$^8$ OR$^9$, SR$^9$, NR$^{10}$R$^{11}$, NR$^9$OR$^9$, NR$^9$S(O)$_2$R$^{10}$ or NR$^9$S(O)$_2$NR$^{10}$R$^{11}$, wherein
R$^9$ is hydrogen, C$_1$-C$_6$-alkyl, C$_3$-C$_6$-alkenyl, C$_3$-C$_6$-alkynyl, C$_1$-C$_6$-haloalkyl, C$_3$-C$_6$-haloalkenyl, C$_3$-C$_6$-haloalkynyl, C$_1$-C$_6$-cyanoalkyl, C$_1$-C$_6$-alkoxy-C$_1$-C$_6$-alkyl, C$_1$-C$_6$-alkoxy-C$_1$-C$_6$-alkoxy-C$_1$-C$_6$-alkyl, di(C$_1$-C$_6$-alkoxy)C$_1$-C$_6$-alkyl, C$_1$-C$_6$haloalkoxy-C$_1$-C$_6$-alkyl, C$_3$-C$_6$-alkenyloxy-C$_1$-C$_6$-alkyl, C$_1$-C$_6$-haloalkenyloxy-C$_1$-C$_6$-alkyl, C$_3$-C$_6$-alkenyloxy-C$_1$-C$_6$-alkoxy-C$_1$-C$_6$alkyl, C$_1$-C$_6$-alkylthio-C$_1$-C$_6$-alkyl, C$_1$-C$_6$-alkylsulfonyl-C$_1$-C$_6$-alkyl, C$_1$-C$_6$-alkylcarbonyl-C$_3$-C$_6$-alkyl, C$_1$-C$_6$-alkoxycarbonyl-C$_1$-C$_6$-alkyl, C$_1$-C$_6$-haloalkoxycarbonyl-C$_1$-C$_6$-alkyl, C$_3$-C$_6$-alkenyloxycarbonyl-C$_1$-C$_6$-alkyl, C$_1$-C$_6$-alkynyloxycarbonyl-C$_1$-C$_6$-alkyl, amino, (C$_1$-C$_6$-alkyl)amino, di(C$_1$-C$_6$-alkyl)amino, (C$_1$-C$_6$-alkylcarbonyl)amino, amino-C$_1$-C$_6$-alkyl, (C$_1$-C$_6$-alkyl)amino-C$_1$-C$_6$-alkyl, di(C$_1$-C$_6$-alkyl)amino-C$_1$-C$_6$-alkyl, aminocarbonyl-C$_1$-C$_6$-alkyl, (C$_1$-C$_6$-alkyl)aminocarbonyl-C$_1$-C$_6$-alkyl, di(C$_1$-C$_6$alkyl)aminocarbonyl-C$_1$-C$_6$-alkyl, —N═CR$^{12}$R$^{13}$, wherein R$^{12}$ and R$^{13}$ independently of one another are H, C$_1$-C$_4$-alkyl or phenyl;
C$_3$-C$_6$-cycloalkyl, C$_3$-C$_6$ cycloalkyl C$_1$-C$_6$ alkyl, C$_3$-C$_6$-heterocyclyl, C$_3$-C$_6$-heterocyclyl-C$_1$-C$_6$-alkyl, phenyl, phenyl-C$_1$-C$_4$-alkyl or a 5- or 6 membered heteroaryl,
wherein each cycloalkyl, heterocyclyl, phenyl or heteroaryl ring can be substituted by one to four substituents selected from R$^{14}$ or a 3- to 7-membered carbocyclus,
which carbocyclus optionally has in addition to carbon atoms one or two ring members selected from the group consisting of
—(R$^{12}$)—, —N═N—, —C(═O)—, —O— and —S—, and
which carbocyclus is optionally substituted with one to four substituents selected from R$^{14}$;
wherein R$^{14}$ is halogen, NO$_2$, CN, C$_1$-C$_4$-alkyl, C$_1$-C$_4$-haloalkyl, C$_1$-C$_4$-alkoxy or C$_1$-C$_4$-alkoxycarbonyl;

R$^{10}$, R$^{11}$ independently of one another are R$^9$, or together form a 3- to 7-membered carbocyclus,
which carbocyclus optionally has in addition to carbon atoms one or two ring members selected from the group consisting of —N(R$^{12}$)—, —N═N—, —C(═O)—, —O— and —S—, and
which carbocyclus is optionally substituted with one to four substituents selected from R$^{14}$;

n is 1;
Q is O;
W is O;
X is O;
Y is O;
Z is selected from the group consisting of Z$^1$ and Z$^7$ as defined above, wherein R$^a$, R$^b$, R$^c$, R$^d$ and R$^e$ independently of one another are H, halogen, CN, C$_1$-C$_6$-alkyl, C$_1$-C$_6$-haloalkyl, C$_1$-C$_6$-alkoxy, C$_1$-C$_6$-haloalkoxy.

Particular preference is given to uracilpyrimidines of formula (I.a) (corresponds to formula (I) wherein R$^1$ is CH$_3$, R$^2$ is CF$_3$, R$^3$ is H, R$^7$ is H, n is 1, Q, W, X and Y are O, and Z is Z-1 as defined, wherein R$^a$, R$^b$, R$^c$ and R$^d$ are H:

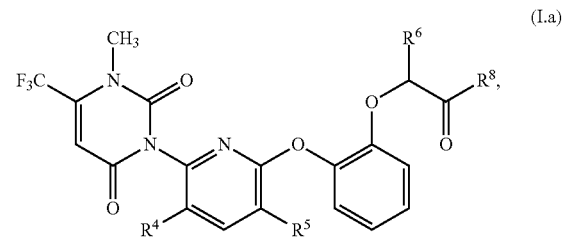

(I.a)

wherein the variables R$^4$, R$^5$, R$^6$ and R$^8$ have the meanings, in particular the preferred meanings, as defined above.

Special preference is given to the compounds of the formulae (I.a.1) to (I.a.672), preferably (I.a.1) to (I.a.504), of Table A, where the definitions of the variables R$^4$, R$^5$, R$^6$ and W are of particular importance for the compounds according to the invention not only in combination with one another but in each case also on their own:

TABLE A

| No. | R$^4$ | R$^5$ | R$^6$ | R$^8$ |
|---|---|---|---|---|
| I.a.1 | H | F | H | OH |
| I.a.2 | H | F | H | OCH$_3$ |
| I.a.3 | H | F | H | OC$_2$H$_5$ |
| I.a.4 | H | F | H | OCH(CH$_3$)$_2$ |
| I.a.5 | H | F | H | OCH$_2$CH$_2$CH$_3$ |
| I.a.6 | H | F | H | OCH$_2$CH(CH$_3$)$_2$ |
| I.a.7 | H | F | H | OCH$_2$CH═CH$_2$ |
| I.a.8 | H | F | H | OCH$_2$C≡CH |
| I.a.9 | H | F | H | OCH$_2$CF$_3$ |
| I.a.10 | H | F | H | OCH$_2$CHF$_2$ |
| I.a.11 | H | F | H | OC$_6$H$_5$ |
| I.a.12 | H | F | H | OCH$_2$(C$_6$H$_5$) |
| I.a.13 | H | F | H | OCH$_2$OCH$_3$ |
| I.a.14 | H | F | H | OCH$_2$OCH$_2$CH$_3$ |
| I.a.15 | H | F | H | OCH$_2$CH$_2$OCH$_3$ |

TABLE A-continued

| No. | $R^4$ | $R^5$ | $R^6$ | $R^8$ |
|---|---|---|---|---|
| I.a.16 | H | F | H | $OCH_2CH_2OCH_2CH_3$ |
| I.a.17 | H | F | H | $OCH_2(CO)OCH_3$ |
| I.a.18 | H | F | H | $OCH_2(CO)OCH_2CH_3$ |
| I.a.19 | H | F | H | $OCH(CH_3)(CO)OCH_3$ |
| I.a.20 | H | F | H | $OCH(CH_3)(CO)OCH_2CH_3$ |
| I.a.21 | H | F | H | $OCH_2$-cyclopropyl |
| I.a.22 | H | F | H | $OCH_2$-cyclobutyl |
| I.a.23 | H | F | H | $SCH_3$ |
| I.a.24 | H | F | H | $SC_2H_5$ |
| I.a.25 | H | F | H | $NHSO_2CH_3$ |
| I.a.26 | H | F | H | $NHSO_2CH(CH_3)_2$ |
| I.a.27 | H | F | H | $NHSO_2N(CH_3)_2$ |
| I.a.28 | H | F | H | $NHSO_2N(CH_3)[CH(CH_3)_2]$ |
| I.a.29 | H | F | $CH_3$ | OH |
| I.a.30 | H | F | $CH_3$ | $OCH_3$ |
| I.a.31 | H | F | $CH_3$ | $OC_2H_5$ |
| I.a.32 | H | F | $CH_3$ | $OCH(CH_3)_2$ |
| I.a.33 | H | F | $CH_3$ | $OCH_2CH_2CH_3$ |
| I.a.34 | H | F | $CH_3$ | $OCH_2CH(CH_3)_2$ |
| I.a.35 | H | F | $CH_3$ | $OCH_2CH=CH_2$ |
| I.a.36 | H | F | $CH_3$ | $OCH_2C\equiv CH$ |
| I.a.37 | H | F | $CH_3$ | $OCH_2CF_3$ |
| I.a.38 | H | F | $CH_3$ | $OCH_2CHF_2$ |
| I.a.39 | H | F | $CH_3$ | $OC_6H_5$ |
| I.a.40 | H | F | $CH_3$ | $OCH_2(C_6H_5)$ |
| I.a.41 | H | F | $CH_3$ | $OCH_2OCH_3$ |
| I.a.42 | H | F | $CH_3$ | $OCH_2OCH_2CH_3$ |
| I.a.43 | H | F | $CH_3$ | $OCH_2CH_2OCH_3$ |
| I.a.44 | H | F | $CH_3$ | $OCH_2CH_2OCH_2CH_3$ |
| I.a.45 | H | F | $CH_3$ | $OCH_2(CO)OCH_3$ |
| I.a.46 | H | F | $CH_3$ | $OCH_2(CO)OCH_2CH_3$ |
| I.a.47 | H | F | $CH_3$ | $OCH(CH_3)(CO)OCH_3$ |
| I.a.48 | H | F | $CH_3$ | $OCH(CH_3)(CO)OCH_2CH_3$ |
| I.a.49 | H | F | $CH_3$ | $OCH_2$-cyclopropyl |
| I.a.50 | H | F | $CH_3$ | $OCH_2$-cyclobutyl |
| I.a.51 | H | F | $CH_3$ | $SCH_3$ |
| I.a.52 | H | F | $CH_3$ | $SC_2H_5$ |
| I.a.53 | H | F | $CH_3$ | $NHSO_2CH_3$ |
| I.a.54 | H | F | $CH_3$ | $NHSO_2CH(CH_3)_2$ |
| I.a.55 | H | F | $CH_3$ | $NHSO_2N(CH_3)_2$ |
| I.a.56 | H | F | $CH_3$ | $NHSO_2N(CH_3)[CH(CH_3)_2]$ |
| I.a.57 | H | F | $OCH_3$ | OH |
| I.a.58 | H | F | $OCH_3$ | $OCH_3$ |
| I.a.59 | H | F | $OCH_3$ | $OC_2H_5$ |
| I.a.60 | H | F | $OCH_3$ | $OCH(CH_3)_2$ |
| I.a.61 | H | F | $OCH_3$ | $OCH_2CH_2CH_3$ |
| I.a.62 | H | F | $OCH_3$ | $OCH_2CH(CH_3)_2$ |
| I.a.63 | H | F | $OCH_3$ | $OCH_2CH=CH_2$ |
| I.a.64 | H | F | $OCH_3$ | $OCH_2C\equiv CH$ |
| I.a.65 | H | F | $OCH_3$ | $OCH_2CF_3$ |
| I.a.66 | H | F | $OCH_3$ | $OCH_2CHF_2$ |
| I.a.67 | H | F | $OCH_3$ | $OC_6H_5$ |
| I.a.68 | H | F | $OCH_3$ | $OCH_2(C_6H_5)$ |
| I.a.69 | H | F | $OCH_3$ | $OCH_2OCH_3$ |
| I.a.70 | H | F | $OCH_3$ | $OCH_2OCH_2CH_3$ |
| I.a.71 | H | F | $OCH_3$ | $OCH_2CH_2OCH_3$ |
| I.a.72 | H | F | $OCH_3$ | $OCH_2CH_2OCH_2CH_3$ |
| I.a.73 | H | F | $OCH_3$ | $OCH_2(CO)OCH_3$ |
| I.a.74 | H | F | $OCH_3$ | $OCH_2(CO)OCH_2CH_3$ |
| I.a.75 | H | F | $OCH_3$ | $OCH(CH_3)(CO)OCH_3$ |
| I.a.76 | H | F | $OCH_3$ | $OCH(CH_3)(CO)OCH_2CH_3$ |
| I.a.77 | H | F | $OCH_3$ | $OCH_2$-cyclopropyl |
| I.a.78 | H | F | $OCH_3$ | $OCH_2$-cyclobutyl |
| I.a.79 | H | F | $OCH_3$ | $SCH_3$ |
| I.a.80 | H | F | $OCH_3$ | $SC_2H_5$ |
| I.a.81 | H | F | $OCH_3$ | $NHSO_2CH_3$ |
| I.a.82 | H | F | $OCH_3$ | $NHSO_2CH(CH_3)_2$ |
| I.a.83 | H | F | $OCH_3$ | $NHSO_2N(CH_3)_2$ |
| I.a.84 | H | F | $OCH_3$ | $NHSO_2N(CH_3)[CH(CH_3)_2]$ |
| I.a.85 | H | Cl | H | OH |
| I.a.86 | H | Cl | H | $OCH_3$ |
| I.a.87 | H | Cl | H | $OC_2H_5$ |
| I.a.88 | H | Cl | H | $OCH(CH_3)_2$ |
| I.a.89 | H | Cl | H | $OCH_2CH_2CH_3$ |
| I.a.90 | H | Cl | H | $OCH_2CH(CH_3)_2$ |
| I.a.91 | H | Cl | H | $OCH_2CH=CH_2$ |
| I.a.92 | H | Cl | H | $OCH_2C\equiv CH$ |
| I.a.93 | H | Cl | H | $OCH_2CF_3$ |
| I.a.94 | H | Cl | H | $OCH_2CHF_2$ |
| I.a.95 | H | Cl | H | $OC_6H_5$ |
| I.a.96 | H | Cl | H | $OCH_2(C_6H_5)$ |
| I.a.97 | H | Cl | H | $OCH_2OCH_3$ |
| I.a.98 | H | Cl | H | $OCH_2OCH_2CH_3$ |
| I.a.99 | H | Cl | H | $OCH_2CH_2OCH_3$ |
| I.a.100 | H | Cl | H | $OCH_2CH_2OCH_2CH_3$ |
| I.a.101 | H | Cl | H | $OCH_2(CO)OCH_3$ |
| I.a.102 | H | Cl | H | $OCH_2(CO)OCH_2CH_3$ |
| I.a.103 | H | Cl | H | $OCH(CH_3)(CO)OCH_3$ |
| I.a.104 | H | Cl | H | $OCH(CH_3)(CO)OCH_2CH_3$ |
| I.a.105 | H | Cl | H | $OCH_2$-cyclopropyl |
| I.a.106 | H | Cl | H | $OCH_2$-cyclobutyl |
| I.a.107 | H | Cl | H | $SCH_3$ |
| I.a.108 | H | Cl | H | $SC_2H_5$ |
| I.a.109 | H | Cl | H | $NHSO_2CH_3$ |
| I.a.110 | H | Cl | H | $NHSO_2CH(CH_3)_2$ |
| I.a.ll | H | Cl | H | $NHSO_2N(CH_3)_2$ |
| I.a.112 | H | Cl | H | $NHSO_2N(CH_3)[CH(CH_3)_2]$ |
| I.a.113 | H | Cl | $CH_3$ | OH |
| I.a.114 | H | Cl | $CH_3$ | $OCH_3$ |
| I.a.115 | H | Cl | $CH_3$ | $OC_2H_5$ |
| I.a.116 | H | Cl | $CH_3$ | $OCH(CH_3)_2$ |
| I.a.117 | H | Cl | $CH_3$ | $OCH_2CH_2CH_3$ |
| I.a.118 | H | Cl | $CH_3$ | $OCH_2CH(CH_3)_2$ |
| I.a.119 | H | Cl | $CH_3$ | $OCH_2CH=CH_2$ |
| I.a.120 | H | Cl | $CH_3$ | $OCH_2C\equiv CH$ |
| I.a.121 | H | Cl | $CH_3$ | $OCH_2CF_3$ |
| I.a.122 | H | Cl | $CH_3$ | $OCH_2CHF_2$ |
| I.a.123 | H | Cl | $CH_3$ | $OC_6H_5$ |
| I.a.124 | H | Cl | $CH_3$ | $OCH_2(C_6H_5)$ |
| I.a.125 | H | Cl | $CH_3$ | $OCH_2OCH_3$ |
| I.a.126 | H | Cl | $CH_3$ | $OCH_2OCH_2CH_3$ |
| I.a.127 | H | Cl | $CH_3$ | $OCH_2CH_2OCH_3$ |
| I.a.128 | H | Cl | $CH_3$ | $OCH_2CH_2OCH_2CH_3$ |
| I.a.129 | H | Cl | $CH_3$ | $OCH_2(CO)OCH_3$ |
| I.a.130 | H | Cl | $CH_3$ | $OCH_2(CO)OCH_2CH_3$ |
| I.a.131 | H | Cl | $CH_3$ | $OCH(CH_3)(CO)OCH_3$ |
| I.a.132 | H | Cl | $CH_3$ | $OCH(CH_3)(CO)OCH_2CH_3$ |
| I.a.133 | H | Cl | $CH_3$ | $OCH_2$-cyclopropyl |
| I.a.134 | H | Cl | $CH_3$ | $OCH_2$-cyclobutyl |
| I.a.135 | H | Cl | $CH_3$ | $SCH_3$ |
| I.a.136 | H | Cl | $CH_3$ | $SC_2H_5$ |
| I.a.137 | H | Cl | $CH_3$ | $NHSO_2CH_3$ |
| I.a.138 | H | Cl | $CH_3$ | $NHSO_2CH(CH_3)_2$ |
| I.a.139 | H | Cl | $CH_3$ | $NHSO_2N(CH_3)_2$ |
| I.a.140 | H | Cl | $CH_3$ | $NHSO_2N(CH_3)[CH(CH_3)_2]$ |
| I.a.141 | H | Cl | $OCH_3$ | OH |
| I.a.142 | H | Cl | $OCH_3$ | $OCH_3$ |
| I.a.143 | H | Cl | $OCH_3$ | $OC_2H_5$ |
| I.a.144 | H | Cl | $OCH_3$ | $OCH(CH_3)_2$ |
| I.a.145 | H | Cl | $OCH_3$ | $OCH_2CH_2CH_3$ |
| I.a.146 | H | Cl | $OCH_3$ | $OCH_2CH(CH_3)_2$ |
| I.a.147 | H | Cl | $OCH_3$ | $OCH_2CH=CH_2$ |
| I.a.148 | H | Cl | $OCH_3$ | $OCH_2C\equiv CH$ |
| I.a.149 | H | Cl | $OCH_3$ | $OCH_2CF_3$ |
| I.a.150 | H | Cl | $OCH_3$ | $OCH_2CHF_2$ |
| I.a.151 | H | Cl | $OCH_3$ | $OC_6H_5$ |
| I.a.152 | H | Cl | $OCH_3$ | $OCH_2(C_6H_5)$ |
| I.a.153 | H | Cl | $OCH_3$ | $OCH_2OCH_3$ |
| I.a.154 | H | Cl | $OCH_3$ | $OCH_2OCH_2CH_3$ |
| I.a.155 | H | Cl | $OCH_3$ | $OCH_2CH_2OCH_3$ |
| I.a.156 | H | Cl | $OCH_3$ | $OCH_2CH_2OCH_2CH_3$ |
| I.a.157 | H | Cl | $OCH_3$ | $OCH_2(CO)OCH_3$ |
| I.a.158 | H | Cl | $OCH_3$ | $OCH_2(CO)OCH_2CH_3$ |
| I.a.159 | H | Cl | $OCH_3$ | $OCH(CH_3)(CO)OCH_3$ |
| I.a.160 | H | Cl | $OCH_3$ | $OCH(CH_3)(CO)OCH_2CH_3$ |
| I.a.161 | H | Cl | $OCH_3$ | $OCH_2$-cyclopropyl |
| I.a.162 | H | Cl | $OCH_3$ | $OCH_2$-cyclobutyl |
| I.a.163 | H | Cl | $OCH_3$ | $SCH_3$ |
| I.a.164 | H | Cl | $OCH_3$ | $SC_2H_5$ |
| I.a.165 | H | Cl | $OCH_3$ | $NHSO_2CH_3$ |
| I.a.166 | H | Cl | $OCH_3$ | $NHSO_2CH(CH_3)_2$ |
| I.a.167 | H | Cl | $OCH_3$ | $NHSO_2N(CH_3)_2$ |
| I.a.168 | H | Cl | $OCH_3$ | $NHSO_2N(CH_3)[CH(CH_3)_2]$ |
| I.a.169 | H | CN | H | OH |
| I.a.170 | H | CN | H | $OCH_3$ |
| I.a.171 | H | CN | H | $OC_2H_5$ |

TABLE A-continued

| No. | $R^4$ | $R^5$ | $R^6$ | $R^8$ |
|---|---|---|---|---|
| I.a.172 | H | CN | H | $OCH(CH_3)_2$ |
| I.a.173 | H | CN | H | $OCH_2CH_2CH_3$ |
| I.a.174 | H | CN | H | $OCH_2CH(CH_3)_2$ |
| I.a.175 | H | CN | H | $OCH_2CH=CH_2$ |
| I.a.176 | H | CN | H | $OCH_2C\equiv CH$ |
| I.a.177 | H | CN | H | $OCH_2CF_3$ |
| I.a.178 | H | CN | H | $OCH_2CHF_2$ |
| I.a.179 | H | CN | H | $OC_6H_5$ |
| I.a.180 | H | CN | H | $OCH_2(C_6H_5)$ |
| I.a.181 | H | CN | H | $OCH_2OCH_3$ |
| I.a.182 | H | CN | H | $OCH_2OCH_2CH_3$ |
| I.a.183 | H | CN | H | $OCH_2CH_2OCH_3$ |
| I.a.184 | H | CN | H | $OCH_2CH_2OCH_2CH_3$ |
| I.a.185 | H | CN | H | $OCH_2(CO)OCH_3$ |
| I.a.186 | H | CN | H | $OCH_2(CO)OCH_2CH_3$ |
| I.a.187 | H | CN | H | $OCH(CH_3)(CO)OCH_3$ |
| I.a.188 | H | CN | H | $OCH(CH_3)(CO)OCH_2CH_3$ |
| I.a.189 | H | CN | H | $OCH_2$-cyclopropyl |
| I.a.190 | H | CN | H | $OCH_2$-cyclobutyl |
| I.a.191 | H | CN | H | $SCH_3$ |
| I.a.192 | H | CN | H | $SC_2H_5$ |
| I.a.193 | H | CN | H | $NHSO_2CH_3$ |
| I.a.194 | H | CN | H | $NHSO_2CH(CH_3)_2$ |
| I.a.195 | H | CN | H | $NHSO_2N(CH_3)_2$ |
| I.a.196 | H | CN | H | $NHSO_2N(CH_3)[CH(CH_3)_2]$ |
| I.a.197 | H | CN | $CH_3$ | OH |
| I.a.198 | H | CN | $CH_3$ | $OCH_3$ |
| I.a.199 | H | CN | $CH_3$ | $OC_2H_5$ |
| I.a.200 | H | CN | $CH_3$ | $OCH(CH_3)_2$ |
| I.a.201 | H | CN | $CH_3$ | $OCH_2CH_2CH_3$ |
| I.a.202 | H | CN | $CH_3$ | $OCH_2CH(CH_3)_2$ |
| I.a.203 | H | CN | $CH_3$ | $OCH_2CH=CH_2$ |
| I.a.204 | H | CN | $CH_3$ | $OCH_2C\equiv CH$ |
| I.a.205 | H | CN | $CH_3$ | $OCH_2CF_3$ |
| I.a.206 | H | CN | $CH_3$ | $OCH_2CHF_2$ |
| I.a.207 | H | CN | $CH_3$ | $OC_6H_5$ |
| I.a.208 | H | CN | $CH_3$ | $OCH_2(C_6H_5)$ |
| I.a.209 | H | CN | $CH_3$ | $OCH_2OCH_3$ |
| I.a.210 | H | CN | $CH_3$ | $OCH_2OCH_2CH_3$ |
| I.a.211 | H | CN | $CH_3$ | $OCH_2CH_2OCH_3$ |
| I.a.212 | H | CN | $CH_3$ | $OCH_2CH_2OCH_2CH_3$ |
| I.a.213 | H | CN | $CH_3$ | $OCH_2(CO)OCH_3$ |
| I.a.214 | H | CN | $CH_3$ | $OCH_2(CO)OCH_2CH_3$ |
| I.a.215 | H | CN | $CH_3$ | $OCH(CH_3)(CO)OCH_3$ |
| I.a.216 | H | CN | $CH_3$ | $OCH(CH_3)(CO)OCH_2CH_3$ |
| I.a.217 | H | CN | $CH_3$ | $OCH_2$-cyclopropyl |
| I.a.218 | H | CN | $CH_3$ | $OCH_2$-cyclobutyl |
| I.a.219 | H | CN | $CH_3$ | $SCH_3$ |
| I.a.220 | H | CN | $CH_3$ | $SC_2H_5$ |
| I.a.221 | H | CN | $CH_3$ | $NHSO_2CH_3$ |
| I.a.222 | H | CN | $CH_3$ | $NHSO_2CH(CH_3)_2$ |
| I.a.223 | H | CN | $CH_3$ | $NHSO_2N(CH_3)_2$ |
| I.a.224 | H | CN | $CH_3$ | $NHSO_2N(CH_3)[CH(CH_3)_2]$ |
| I.a.225 | H | CN | $OCH_3$ | OH |
| I.a.226 | H | CN | $OCH_3$ | $OCH_3$ |
| I.a.227 | H | CN | $OCH_3$ | $OC_2H_5$ |
| I.a.228 | H | CN | $OCH_3$ | $OCH(CH_3)_2$ |
| I.a.229 | H | CN | $OCH_3$ | $OCH_2CH_2CH_3$ |
| I.a.230 | H | CN | $OCH_3$ | $OCH_2CH(CH_3)_2$ |
| I.a.231 | H | CN | $OCH_3$ | $OCH_2CH=CH_2$ |
| I.a.232 | H | CN | $OCH_3$ | $OCH_2C\equiv CH$ |
| I.a.233 | H | CN | $OCH_3$ | $OCH_2CF_3$ |
| I.a.234 | H | CN | $OCH_3$ | $OCH_2CHF_2$ |
| I.a.235 | H | CN | $OCH_3$ | $OC_6H_5$ |
| I.a.236 | H | CN | $OCH_3$ | $OCH_2(C_6H_5)$ |
| I.a.237 | H | CN | $OCH_3$ | $OCH_2OCH_3$ |
| I.a.238 | H | CN | $OCH_3$ | $OCH_2OCH_2CH_3$ |
| I.a.239 | H | CN | $OCH_3$ | $OCH_2CH_2OCH_3$ |
| I.a.240 | H | CN | $OCH_3$ | $OCH_2CH_2OCH_2CH_3$ |
| I.a.241 | H | CN | $OCH_3$ | $OCH_2(CO)OCH_3$ |
| I.a.242 | H | CN | $OCH_3$ | $OCH_2(CO)OCH_2CH_3$ |
| I.a.243 | H | CN | $OCH_3$ | $OCH(CH_3)(CO)OCH_3$ |
| I.a.244 | H | CN | $OCH_3$ | $OCH(CH_3)(CO)OCH_2CH_3$ |
| I.a.245 | H | CN | $OCH_3$ | $OCH_2$-cyclopropyl |
| I.a.246 | H | CN | $OCH_3$ | $OCH_2$-cyclobutyl |
| I.a.247 | H | CN | $OCH_3$ | $SCH_3$ |
| I.a.248 | H | CN | $OCH_3$ | $SC_2H_5$ |
| I.a.249 | H | CN | $OCH_3$ | $NHSO_2CH_3$ |
| I.a.250 | H | CN | $OCH_3$ | $NHSO_2CH(CH_3)_2$ |
| I.a.251 | H | CN | $OCH_3$ | $NHSO_2N(CH_3)_2$ |
| I.a.252 | H | CN | $OCH_3$ | $NHSO_2N(CH_3)[CH(CH_3)_2]$ |
| I.a.253 | F | F | H | OH |
| I.a.254 | F | F | H | $OCH_3$ |
| I.a.255 | F | F | H | $OC_2H_5$ |
| I.a.256 | F | F | H | $OCH(CH_3)_2$ |
| I.a.257 | F | F | H | $OCH_2CH_2CH_3$ |
| I.a.258 | F | F | H | $OCH_2CH(CH_3)_2$ |
| I.a.259 | F | F | H | $OCH_2CH=CH_2$ |
| I.a.260 | F | F | H | $OCH_2C\equiv CH$ |
| I.a.261 | F | F | H | $OCH_2CF_3$ |
| I.a.262 | F | F | H | $OCH_2CHF_2$ |
| I.a.263 | F | F | H | $OC_6H_5$ |
| I.a.264 | F | F | H | $OCH_2(C_6H_5)$ |
| I.a.265 | F | F | H | $OCH_2OCH_3$ |
| I.a.266 | F | F | H | $OCH_2OCH_2CH_3$ |
| I.a.267 | F | F | H | $OCH_2CH_2OCH_3$ |
| I.a.268 | F | F | H | $OCH_2CH_2OCH_2CH_3$ |
| I.a.269 | F | F | H | $OCH_2(CO)OCH_3$ |
| I.a.270 | F | F | H | $OCH_2(CO)OCH_2CH_3$ |
| I.a.271 | F | F | H | $OCH(CH_3)(CO)OCH_3$ |
| I.a.272 | F | F | H | $OCH(CH_3)(CO)OCH_2CH_3$ |
| I.a.273 | F | F | H | $OCH_2$-cyclopropyl |
| I.a.274 | F | F | H | $OCH_2$-cyclobutyl |
| I.a.275 | F | F | H | $SCH_3$ |
| I.a.276 | F | F | H | $SC_2H_5$ |
| I.a.277 | F | F | H | $NHSO_2CH_3$ |
| I.a.278 | F | F | H | $NHSO_2CH(CH_3)_2$ |
| I.a.279 | F | F | H | $NHSO_2N(CH_3)_2$ |
| I.a.280 | F | F | H | $NHSO_2N(CH_3)[CH(CH_3)_2]$ |
| I.a.281 | F | F | $CH_3$ | OH |
| I.a.282 | F | F | $CH_3$ | $OCH_3$ |
| I.a.283 | F | F | $CH_3$ | $OC_2H_5$ |
| I.a.284 | F | F | $CH_3$ | $OCH_2CH_2CH_3$ |
| I.a.285 | F | F | $CH_3$ | $OCH_2CH_2CH_3$ |
| I.a.286 | F | F | $CH_3$ | $OCH_2CH(CH_3)_2$ |
| I.a.287 | F | F | $CH_3$ | $OCH_2CH=CH_2$ |
| I.a.288 | F | F | $CH_3$ | $OCH_2C\equiv CH$ |
| I.a.289 | F | F | $CH_3$ | $OCH_2CF_3$ |
| I.a.290 | F | F | $CH_3$ | $OCH_2CHF_2$ |
| I.a.291 | F | F | $CH_3$ | $OC_6H_5$ |
| I.a.292 | F | F | $CH_3$ | $OCH_2(C_6H_5)$ |
| I.a.293 | F | F | $CH_3$ | $OCH_2OCH_3$ |
| I.a.294 | F | F | $CH_3$ | $OCH_2OCH_2CH_3$ |
| I.a.295 | F | F | $CH_3$ | $OCH_2CH_2OCH_3$ |
| I.a.296 | F | F | $CH_3$ | $OCH_2CH_2OCH_2CH_3$ |
| I.a.297 | F | F | $CH_3$ | $OCH_2(CO)OCH_3$ |
| I.a.298 | F | F | $CH_3$ | $OCH_2(CO)OCH_2CH_3$ |
| I.a.299 | F | F | $CH_3$ | $OCH(CH_3)(CO)OCH_3$ |
| I.a.300 | F | F | $CH_3$ | $OCH(CH_3)(CO)OCH_2CH_3$ |
| I.a.301 | F | F | $CH_3$ | $OCH_2$-cyclopropyl |
| I.a.302 | F | F | $CH_3$ | $OCH_2$-cyclobutyl |
| I.a.303 | F | F | $CH_3$ | $SCH_3$ |
| I.a.304 | F | F | $CH_3$ | $SC_2H_5$ |
| I.a.305 | F | F | $CH_3$ | $NHSO_2CH_3$ |
| I.a.306 | F | F | $CH_3$ | $NHSO_2CH(CH_3)_2$ |
| I.a.307 | F | F | $CH_3$ | $NHSO_2N(CH_3)_2$ |
| I.a.308 | F | F | $CH_3$ | $NHSO_2N(CH_3)[CH(CH_3)_2]$ |
| I.a.309 | F | F | $OCH_3$ | OH |
| I.a.310 | F | F | $OCH_3$ | $OCH_3$ |
| I.a.311 | F | F | $OCH_3$ | $OC_2H_5$ |
| I.a.312 | F | F | $OCH_3$ | $OCH(CH_3)_2$ |
| I.a.313 | F | F | $OCH_3$ | $OCH_2CH_2CH_3$ |
| I.a.314 | F | F | $OCH_3$ | $OCH_2CH(CH_3)_2$ |
| I.a.315 | F | F | $OCH_3$ | $OCH_2CH=CH_2$ |
| I.a.316 | F | F | $OCH_3$ | $OCH_2C\equiv CH$ |
| I.a.317 | F | F | $OCH_3$ | $OCH_2CF_3$ |
| I.a.318 | F | F | $OCH_3$ | $OCH_2CHF_2$ |
| I.a.319 | F | F | $OCH_3$ | $OC_6H_5$ |
| I.a.320 | F | F | $OCH_3$ | $OCH_2(C_6H_5)$ |
| I.a.321 | F | F | $OCH_3$ | $OCH_2OCH_3$ |
| I.a.322 | F | F | $OCH_3$ | $OCH_2OCH_2CH_3$ |
| I.a.323 | F | F | $OCH_3$ | $OCH_2CH_2OCH_3$ |
| I.a.324 | F | F | $OCH_3$ | $OCH_2CH_2OCH_2CH_3$ |
| I.a.325 | F | F | $OCH_3$ | $OCH_2(CO)OCH_3$ |
| I.a.326 | F | F | $OCH_3$ | $OCH_2(CO)OCH_2CH_3$ |
| I.a.327 | F | F | $OCH_3$ | $OCH(CH_3)(CO)OCH_3$ |

TABLE A-continued

| No. | R⁴ | R⁵ | R⁶ | R⁸ |
|---|---|---|---|---|
| I.a.328 | F | F | OCH₃ | OCH(CH₃)(CO)OCH₂CH₃ |
| I.a.329 | F | F | OCH₃ | OCH₂-cyclopropyl |
| I.a.330 | F | F | OCH₃ | OCH₂-cyclobutyl |
| I.a.331 | F | F | OCH₃ | SCH₃ |
| I.a.332 | F | F | OCH₃ | SC₂H₅ |
| I.a.333 | F | F | OCH₃ | NHSO₂CH₃ |
| I.a.334 | F | F | OCH₃ | NHSO₂CH(CH₃)₂ |
| I.a.335 | F | F | OCH₃ | NHSO₂N(CH₃)₂ |
| I.a.336 | F | F | OCH₃ | NHSO₂N(CH₃)[CH(CH₃)₂] |
| I.a.337 | F | Cl | H | OH |
| I.a.338 | F | Cl | H | OCH₃ |
| I.a.339 | F | Cl | H | OC₂H₅ |
| I.a.340 | F | Cl | H | OCH(CH₃)₂ |
| I.a.341 | F | Cl | H | OCH₂CH₂CH₃ |
| I.a.342 | F | Cl | H | OCH₂CH(CH₃)₂ |
| I.a.343 | F | Cl | H | OCH₂CH=CH₂ |
| I.a.344 | F | Cl | H | OCH₂C≡CH |
| I.a.345 | F | Cl | H | OCH₂CF₃ |
| I.a.346 | F | Cl | H | OCH₂CHF₂ |
| I.a.347 | F | Cl | H | OC₆H₅ |
| I.a.348 | F | Cl | H | OCH₂(C₆H₅) |
| I.a.349 | F | Cl | H | OCH₂OCH₃ |
| I.a.350 | F | Cl | H | OCH₂OCH₂CH₃ |
| I.a.351 | F | Cl | H | OCH₂CH₂OCH₃ |
| I.a.352 | F | Cl | H | OCH₂CH₂OCH₂CH₃ |
| I.a.353 | F | Cl | H | OCH₂(CO)OCH₃ |
| I.a.354 | F | Cl | H | OCH₂(CO)OCH₂CH₃ |
| I.a.355 | F | Cl | H | OCH(CH₃)(CO)OCH₃ |
| I.a.356 | F | Cl | H | OCH(CH₃)(CO)OCH₂CH₃ |
| I.a.357 | F | Cl | H | OCH₂-cyclopropyl |
| I.a.358 | F | Cl | H | OCH₂-cyclobutyl |
| I.a.359 | F | Cl | H | SCH₃ |
| I.a.360 | F | Cl | H | SC₂H₅ |
| I.a.361 | F | Cl | H | NHSO₂CH₃ |
| I.a.362 | F | Cl | H | NHSO₂CH(CH₃)₂ |
| I.a.363 | F | Cl | H | NHSO₂N(CH₃)₂ |
| I.a.364 | F | Cl | H | NHSO₂N(CH₃)[CH(CH₃)₂] |
| I.a.365 | F | Cl | CH₃ | OH |
| I.a.366 | F | Cl | CH₃ | OCH₃ |
| I.a.367 | F | Cl | CH₃ | OC₂H₅ |
| I.a.368 | F | Cl | CH₃ | OCH(CH₃)₂ |
| I.a.369 | F | Cl | CH₃ | OCH₂CH₂CH₃ |
| I.a.370 | F | Cl | CH₃ | OCH₂CH(CH₃)₂ |
| I.a.371 | F | Cl | CH₃ | OCH₂CH=CH₂ |
| I.a.372 | F | Cl | CH₃ | OCH₂C≡CH |
| I.a.373 | F | Cl | CH₃ | OCH₂CF₃ |
| I.a.374 | F | Cl | CH₃ | OCH₂CHF₂ |
| I.a.375 | F | Cl | CH₃ | OC₆H₅ |
| I.a.376 | F | Cl | CH₃ | OCH₂(C₆H₅) |
| I.a.377 | F | Cl | CH₃ | OCH₂OCH₃ |
| I.a.378 | F | Cl | CH₃ | OCH₂OCH₂CH₃ |
| I.a.379 | F | Cl | CH₃ | OCH₂CH₂OCH₃ |
| I.a.380 | F | Cl | CH₃ | OCH₂CH₂OCH₂CH₃ |
| I.a.381 | F | Cl | CH₃ | OCH₂(CO)OCH₃ |
| I.a.382 | F | Cl | CH₃ | OCH₂(CO)OCH₂CH₃ |
| I.a.383 | F | Cl | CH₃ | OCH(CH₃)(CO)OCH₃ |
| I.a.384 | F | Cl | CH₃ | OCH(CH₃)(CO)OCH₂CH₃ |
| I.a.385 | F | Cl | CH₃ | OCH₂-cyclopropyl |
| I.a.386 | F | Cl | CH₃ | OCH₂-cyclobutyl |
| I.a.387 | F | Cl | CH₃ | SCH₃ |
| I.a.388 | F | Cl | CH₃ | SC₂H₅ |
| I.a.389 | F | Cl | CH₃ | NHSO₂CH₃ |
| I.a.390 | F | Cl | CH₃ | NHSO₂CH(CH₃)₂ |
| I.a.391 | F | Cl | CH₃ | NHSO₂N(CH₃)₂ |
| I.a.392 | F | Cl | CH₃ | NHSO₂N(CH₃)[CH(CH₃)₂] |
| I.a.393 | F | Cl | OCH₃ | OH |
| I.a.394 | F | Cl | OCH₃ | OCH₃ |
| I.a.395 | F | Cl | OCH₃ | OC₂H₅ |
| I.a.396 | F | Cl | OCH₃ | OCH(CH₃)₂ |
| I.a.397 | F | Cl | OCH₃ | OCH₂CH₂CH₃ |
| I.a.398 | F | Cl | OCH₃ | OCH₂CH(CH₃)₂ |
| I.a.399 | F | Cl | OCH₃ | OCH₂CH=CH₂ |
| I.a.400 | F | Cl | OCH₃ | OCH₂C≡CH |
| I.a.401 | F | Cl | OCH₃ | OCH₂CF₃ |
| I.a.402 | F | Cl | OCH₃ | OCH₂CHF₂ |
| I.a.403 | F | Cl | OCH₃ | OC₆H₅ |
| I.a.404 | F | Cl | OCH₃ | OCH₂(C₆H₅) |
| I.a.405 | F | Cl | OCH₃ | OCH₂OCH₃ |
| I.a.406 | F | Cl | OCH₃ | OCH₂OCH₂CH₃ |
| I.a.407 | F | Cl | OCH₃ | OCH₂CH₂OCH₃ |
| I.a.408 | F | Cl | OCH₃ | OCH₂CH₂OCH₂CH₃ |
| I.a.409 | F | Cl | OCH₃ | OCH₂(CO)OCH₃ |
| I.a.410 | F | Cl | OCH₃ | OCH₂(CO)OCH₂CH₃ |
| I.a.411 | F | Cl | OCH₃ | OCH(CH₃)(CO)OCH₃ |
| I.a.412 | F | Cl | OCH₃ | OCH(CH₃)(CO)OCH₂CH₃ |
| I.a.413 | F | Cl | OCH₃ | OCH₂-cyclopropyl |
| I.a.414 | F | Cl | OCH₃ | OCH₂-cyclobutyl |
| I.a.415 | F | Cl | OCH₃ | SCH₃ |
| I.a.416 | F | Cl | OCH₃ | SC₂H₅ |
| I.a.417 | F | Cl | OCH₃ | NHSO₂CH₃ |
| I.a.418 | F | Cl | OCH₃ | NHSO₂CH(CH₃)₂ |
| I.a.419 | F | Cl | OCH₃ | NHSO₂N(CH₃)₂ |
| I.a.420 | F | Cl | OCH₃ | NHSO₂N(CH₃)[CH(CH₃)₂] |
| I.a.421 | F | CN | H | OH |
| I.a.422 | F | CN | H | OCH₂ |
| I.a.423 | F | CN | H | OC₂H₅ |
| I.a.424 | F | CN | H | OCH(CH₃)₂ |
| I.a.425 | F | CN | H | OCH₂CH₂CH₃ |
| I.a.426 | F | CN | H | OCH₂CH(CH₃)₂ |
| I.a.427 | F | CN | H | OCH₂CH=CH₂ |
| I.a.428 | F | CN | H | OCH₂C≡CH |
| I.a.429 | F | CN | H | OCH₂CF₃ |
| I.a.430 | F | CN | H | OCH₂CHF₂ |
| I.a.431 | F | CN | H | OC₆H₅ |
| I.a.432 | F | CN | H | OCH₂(C₆H₅) |
| I.a.433 | F | CN | H | OCH₂OCH₃ |
| I.a.434 | F | CN | H | OCH₂OCH₂CH₃ |
| I.a.435 | F | CN | H | OCH₂CH₂OCH₃ |
| I.a.436 | F | CN | H | OCH₂CH₂OCH₂CH₃ |
| I.a.437 | F | CN | H | OCH₂(CO)OCH₃ |
| I.a.438 | F | CN | H | OCH₂(CO)OCH₂CH₃ |
| I.a.439 | F | CN | H | OCH(CH₃)(CO)OCH₃ |
| I.a.440 | F | CN | H | OCH(CH₃)(CO)OCH₂CH₃ |
| I.a.441 | F | CN | H | OCH₂-cyclopropyl |
| I.a.442 | F | CN | H | OCH₂-cyclobutyl |
| I.a.443 | F | CN | H | SCH₃ |
| I.a.444 | F | CN | H | SC₂H₅ |
| I.a.445 | F | CN | H | NHSO₂CH₃ |
| I.a.446 | F | CN | H | NHSO₂CH(CH₃)₂ |
| I.a.447 | F | CN | H | NHSO₂N(CH₃)₂ |
| I.a.448 | F | CN | H | NHSO₂N(CH₃)[CH(CH₃)₂] |
| I.a.449 | F | CN | CH₃ | OH |
| I.a.450 | F | CN | CH₃ | OCH₃ |
| I.a.451 | F | CN | CH₃ | OC₂H₅ |
| I.a.452 | F | CN | CH₃ | OCH(CH₃)₂ |
| I.a.453 | F | CN | CH₃ | OCH₂CH₂CH₃ |
| I.a.454 | F | CN | CH₃ | OCH₂CH(CH₃)₂ |
| I.a.455 | F | CN | CH₃ | OCH₂CH=CH₂ |
| I.a.456 | F | CN | CH₃ | OCH₂C≡CH |
| I.a.457 | F | CN | CH₃ | OCH₂CF₃ |
| I.a.458 | F | CN | CH₃ | OCH₂CHF₂ |
| I.a.459 | F | CN | CH₃ | OC₆H₅ |
| I.a.460 | F | CN | CH₃ | OCH₂(C₆H₅) |
| I.a.461 | F | CN | CH₃ | OCH₂OCH₃ |
| I.a.462 | F | CN | CH₃ | OCH₂OCH₂CH₃ |
| I.a.463 | F | CN | CH₃ | OCH₂CH₂OCH₃ |
| I.a.464 | F | CN | CH₃ | OCH₂CH₂OCH₂CH₃ |
| I.a.465 | F | CN | CH₃ | OCH₂(CO)OCH₃ |
| I.a.466 | F | CN | CH₃ | OCH₂(CO)OCH₂CH₃ |
| I.a.467 | F | CN | CH₃ | OCH(CH₃)(CO)OCH₃ |
| I.a.468 | F | CN | CH₃ | OCH(CH₃)(CO)OCH₂CH₃ |
| I.a.469 | F | CN | CH₃ | OCH₂-cyclopropyl |
| I.a.470 | F | CN | CH₃ | OCH₂-cyclobutyl |
| I.a.471 | F | CN | CH₃ | SCH₃ |
| I.a.472 | F | CN | CH₃ | SC₂H₅ |
| I.a.473 | F | CN | CH₃ | NHSO₂CH₃ |
| I.a.474 | F | CN | CH₃ | NHSO₂CH(CH₃)₂ |
| I.a.475 | F | CN | CH₃ | NHSO₂N(CH₃)₂ |
| I.a.476 | F | CN | CH₃ | NHSO₂N(CH₃)[CH(CH₃)₂] |
| I.a.477 | F | CN | OCH₃ | OH |
| I.a.478 | F | CN | OCH₃ | OCH₃ |
| I.a.479 | F | CN | OCH₃ | OC₂H₅ |
| I.a.480 | F | CN | OCH₃ | OCH(CH₃)₂ |
| I.a.481 | F | CN | OCH₃ | OCH₂CH₂CH₃ |
| I.a.482 | F | CN | OCH₃ | OCH₂CH(CH₃)₂ |
| I.a.483 | F | CN | OCH₃ | OCH₂CH=CH₂ |

TABLE A-continued

| No. | $R^4$ | $R^5$ | $R^6$ | $R^8$ |
|---|---|---|---|---|
| I.a.484 | F | CN | $OCH_3$ | $OCH_2C\equiv CH$ |
| I.a.485 | F | CN | $OCH_3$ | $OCH_2CF_3$ |
| I.a.486 | F | CN | $OCH_3$ | $OCH_2CHF_2$ |
| I.a.487 | F | CN | $OCH_3$ | $OC_6H_5$ |
| I.a.488 | F | CN | $OCH_3$ | $OCH_2(C_6H_5)$ |
| I.a.489 | F | CN | $OCH_3$ | $OCH_2OCH_3$ |
| I.a.490 | F | CN | $OCH_3$ | $OCH_2OCH_2CH_3$ |
| I.a.491 | F | CN | $OCH_3$ | $OCH_2CH_2OCH_3$ |
| I.a.492 | F | CN | $OCH_3$ | $OCH_2CH_2OCH_2CH_3$ |
| I.a.493 | F | CN | $OCH_3$ | $OCH_2(CO)OCH_3$ |
| I.a.494 | F | CN | $OCH_3$ | $OCH_2(CO)OCH_2CH_3$ |
| I.a.495 | F | CN | $OCH_3$ | $OCH(CH_3)(CO)OCH_3$ |
| I.a.496 | F | CN | $OCH_3$ | $OCH(CH_3)(CO)OCH_2CH_3$ |
| I.a.497 | F | CN | $OCH_3$ | $OCH_2$-cyclopropyl |
| I.a.498 | F | CN | $OCH_3$ | $OCH_2$-cyclobutyl |
| I.a.499 | F | CN | $OCH_3$ | $SCH_3$ |
| I.a.500 | F | CN | $OCH_3$ | $SC_2H_5$ |
| I.a.501 | F | CN | $OCH_3$ | $NHSO_2CH_3$ |
| I.a.502 | F | CN | $OCH_3$ | $NHSO_2CH(CH_3)_2$ |
| I.a.503 | F | CN | $OCH_3$ | $NHSO_2N(CH_3)_2$ |
| I.a.504 | F | CN | $OCH_3$ | $NHSO_2N(CH_3)[CH(CH_3)_2]$ |
| I.a.505 | H | Br | H | OH |
| I.a.506 | H | Br | H | $OCH_3$ |
| I.a.507 | H | Br | H | $OC_2H_5$ |
| I.a.508 | H | Br | H | $OCH(CH_3)_2$ |
| I.a.509 | H | Br | H | $OCH_2CH_2CH_3$ |
| I.a.510 | H | Br | H | $OCH_2CH(CH_3)_2$ |
| I.a.511 | H | Br | H | $OCH_2CH=CH_2$ |
| I.a.512 | H | Br | H | $OCH_2C\equiv CH$ |
| I.a.513 | H | Br | H | $OCH_2CF_3$ |
| I.a.514 | H | Br | H | $OCH_2CHF_2$ |
| I.a.515 | H | Br | H | $OC_6H_5$ |
| I.a.516 | H | Br | H | $OCH_2(C_6H_5)$ |
| I.a.517 | H | Br | H | $OCH_2OCH_3$ |
| I.a.518 | H | Br | H | $OCH_2OCH_2CH_3$ |
| I.a.519 | H | Br | H | $OCH_2CH_2OCH_3$ |
| I.a.520 | H | Br | H | $OCH_2CH_2OCH_2CH_3$ |
| I.a.521 | H | Br | H | $OCH_2(CO)OCH_3$ |
| I.a.522 | H | Br | H | $OCH_2(CO)OCH_2CH_3$ |
| I.a.523 | H | Br | H | $OCH(CH_3)(CO)OCH_3$ |
| I.a.524 | H | Br | H | $OCH(CH_3)(CO)OCH_2CH_3$ |
| I.a.525 | H | Br | H | $OCH_2$-cyclopropyl |
| I.a.526 | H | Br | H | $OCH_2$-cyclobutyl |
| I.a.527 | H | Br | H | $SCH_3$ |
| I.a.528 | H | Br | H | $SC_2H_5$ |
| I.a.529 | H | Br | H | $NHSO_2CH_3$ |
| I.a.530 | H | Br | H | $NHSO_2CH(CH_3)_2$ |
| I.a.531 | H | Br | H | $NHSO_2N(CH_3)_2$ |
| I.a.532 | H | Br | H | $NHSO_2N(CH_3)[CH(CH_3)_2]$ |
| I.a.533 | H | Br | $CH_3$ | OH |
| I.a.534 | H | Br | $CH_3$ | $OCH_3$ |
| I.a.535 | H | Br | $CH_3$ | $OC_2H_5$ |
| I.a.536 | H | Br | $CH_3$ | $OCH(CH_3)_2$ |
| I.a.537 | H | Br | $CH_3$ | $OCH_2CH_2CH_3$ |
| I.a.538 | H | Br | $CH_3$ | $OCH_2CH(CH_3)_2$ |
| I.a.539 | H | Br | $CH_3$ | $OCH_2CH=CH_2$ |
| I.a.540 | H | Br | $CH_3$ | $OCH_2C\equiv CH$ |
| I.a.541 | H | Br | $CH_3$ | $OCH_2CF_3$ |
| I.a.542 | H | Br | $CH_3$ | $OCH_2CHF_2$ |
| I.a.543 | H | Br | $CH_3$ | $OC_6H_5$ |
| I.a.544 | H | Br | $CH_3$ | $OCH_2(C_6H_5)$ |
| I.a.545 | H | Br | $CH_3$ | $OCH_2OCH_3$ |
| I.a.546 | H | Br | $CH_3$ | $OCH_2OCH_2CH_3$ |
| I.a.547 | H | Br | $CH_3$ | $OCH_2CH_2OCH_3$ |
| I.a.548 | H | Br | $CH_3$ | $OCH_2CH_2OCH_2CH_3$ |
| I.a.549 | H | Br | $CH_3$ | $OCH_2(CO)OCH_3$ |
| I.a.550 | H | Br | $CH_3$ | $OCH_2(CO)OCH_2CH_3$ |
| I.a.551 | H | Br | $CH_3$ | $OCH(CH_3)(CO)OCH_3$ |
| I.a.552 | H | Br | $CH_3$ | $OCH(CH_3)(CO)OCH_2CH_3$ |
| I.a.553 | H | Br | $CH_3$ | $OCH_2$-cyclopropyl |
| I.a.554 | H | Br | $CH_3$ | $OCH_2$-cyclobutyl |
| I.a.555 | H | Br | $CH_3$ | $SCH_3$ |
| I.a.556 | H | Br | $CH_3$ | $SC_2H_5$ |
| I.a.557 | H | Br | $CH_3$ | $NHSO_2CH_3$ |
| I.a.558 | H | Br | $CH_3$ | $NHSO_2CH(CH_3)_2$ |
| I.a.559 | H | Br | $CH_3$ | $NHSO_2N(CH_3)_2$ |
| I.a.560 | H | Br | $CH_3$ | $NHSO_2N(CH_3)[CH(CH_3)_2]$ |
| I.a.561 | H | Br | $OCH_3$ | OH |
| I.a.562 | H | Br | $OCH_3$ | $OCH_3$ |
| I.a.563 | H | Br | $OCH_3$ | $OC_2H_5$ |
| I.a.564 | H | Br | $OCH_3$ | $OCH(CH_3)_2$ |
| I.a.565 | H | Br | $OCH_3$ | $OCH_2CH_2CH_3$ |
| I.a.566 | H | Br | $OCH_3$ | $OCH_2CH(CH_3)_2$ |
| I.a.567 | H | Br | $OCH_3$ | $OCH_2CH=CH_2$ |
| I.a.568 | H | Br | $OCH_3$ | $OCH_2C\equiv CH$ |
| I.a.569 | H | Br | $OCH_3$ | $OCH_2CF_3$ |
| I.a.570 | H | Br | $OCH_3$ | $OCH_2CHF_2$ |
| I.a.571 | H | Br | $OCH_3$ | $OC_6H_5$ |
| I.a.572 | H | Br | $OCH_3$ | $OCH_2(C_6H_5)$ |
| I.a.573 | H | Br | $OCH_3$ | $OCH_2OCH_3$ |
| I.a.574 | H | Br | $OCH_3$ | $OCH_2OCH_2CH_3$ |
| I.a.575 | H | Br | $OCH_3$ | $OCH_2CH_2OCH_3$ |
| I.a.576 | H | Br | $OCH_3$ | $OCH_2CH_2OCH_2CH_3$ |
| I.a.577 | H | Br | $OCH_3$ | $OCH_2(CO)OCH_3$ |
| I.a.578 | H | Br | $OCH_3$ | $OCH_2(CO)OCH_2CH_3$ |
| I.a.579 | H | Br | $OCH_3$ | $OCH(CH_3)(CO)OCH_3$ |
| I.a.580 | H | Br | $OCH_3$ | $OCH(CH_3)(CO)OCH_2CH_3$ |
| I.a.581 | H | Br | $OCH_3$ | $OCH_2$-cyclopropyl |
| I.a.582 | H | Br | $OCH_3$ | $OCH_2$-cyclobutyl |
| I.a.583 | H | Br | $OCH_3$ | $SCH_3$ |
| I.a.584 | H | Br | $OCH_3$ | $SC_2H_5$ |
| I.a.585 | H | Br | $OCH_3$ | $NHSO_2CH_3$ |
| I.a.586 | H | Br | $OCH_3$ | $NHSO_2CH(CH_3)_2$ |
| I.a.587 | H | Br | $OCH_3$ | $NHSO_2N(CH_3)_2$ |
| I.a.588 | H | Br | $OCH_3$ | $NHSO_2N(CH_3)[CH(CH_3)_2]$ |
| I.a.589 | F | Br | H | OH |
| I.a.590 | F | Br | H | $OCH_3$ |
| I.a.591 | F | Br | H | $OC_2H_5$ |
| I.a.592 | F | Br | H | $OCH(CH_3)_2$ |
| I.a.593 | F | Br | H | $OCH_2CH_2CH_3$ |
| I.a.594 | F | Br | H | $OCH_2CH(CH_3)_2$ |
| I.a.595 | F | Br | H | $OCH_2CH=CH_2$ |
| I.a.596 | F | Br | H | $OCH_2C\equiv CH$ |
| I.a.597 | F | Br | H | $OCH_2CF_3$ |
| I.a.598 | F | Br | H | $OCH_2CHF_2$ |
| I.a.599 | F | Br | H | $OC_6H_5$ |
| I.a.600 | F | Br | H | $OCH_2(C_6H_5)$ |
| I.a.601 | F | Br | H | $OCH_2OCH_3$ |
| I.a.602 | F | Br | H | $OCH_2OCH_2CH_3$ |
| I.a.603 | F | Br | H | $OCH_2CH_2OCH_3$ |
| I.a.604 | F | Br | H | $OCH_2CH_2OCH_2CH_3$ |
| I.a.605 | F | Br | H | $OCH_2(CO)OCH_3$ |
| I.a.606 | F | Br | H | $OCH_2(CO)OCH_2CH_3$ |
| I.a.607 | F | Br | H | $OCH(CH_3)(CO)OCH_3$ |
| I.a.608 | F | Br | H | $OCH(CH_3)(CO)OCH_2CH_3$ |
| I.a.609 | F | Br | H | $OCH_2$-cyclopropyl |
| I.a.610 | F | Br | H | $OCH_2$-cyclobutyl |
| I.a.611 | F | Br | H | $SCH_3$ |
| I.a.612 | F | Br | H | $SC_2H_5$ |
| I.a.613 | F | Br | H | $NHSO_2CH_3$ |
| I.a.614 | F | Br | H | $NHSO_2CH(CH_3)_2$ |
| I.a.615 | F | Br | H | $NHSO_2N(CH_3)_2$ |
| I.a.616 | F | Br | H | $NHSO_2N(CH_3)[CH(CH_3)_2]$ |
| I.a.617 | F | Br | $CH_3$ | OH |
| I.a.618 | F | Br | $CH_3$ | $OCH_3$ |
| I.a.619 | F | Br | $CH_3$ | $OC_2H_5$ |
| I.a.620 | F | Br | $CH_3$ | $OCH(CH_3)_2$ |
| I.a.621 | F | Br | $CH_3$ | $OCH_2CH_2CH_3$ |
| I.a.622 | F | Br | $CH_3$ | $OCH_2CH(CH_3)_2$ |
| I.a.623 | F | Br | $CH_3$ | $OCH_2CH=CH_2$ |
| I.a.624 | F | Br | $CH_3$ | $OCH_2C\equiv CH$ |
| I.a.625 | F | Br | $CH_3$ | $OCH_2CF_3$ |
| I.a.626 | F | Br | $CH_3$ | $OCH_2CHF_2$ |
| I.a.627 | F | Br | $CH_3$ | $OC_6H_5$ |
| I.a.628 | F | Br | $CH_3$ | $OCH_2(C_6H_5)$ |
| I.a.629 | F | Br | $CH_3$ | $OCH_2OCH_3$ |
| I.a.630 | F | Br | $CH_3$ | $OCH_2OCH_2CH_3$ |
| I.a.631 | F | Br | $CH_3$ | $OCH_2CH_2OCH_3$ |
| I.a.632 | F | Br | $CH_3$ | $OCH_2CH_2OCH_2CH_3$ |
| I.a.633 | F | Br | $CH_3$ | $OCH_2(CO)OCH_3$ |
| I.a.634 | F | Br | $CH_3$ | $OCH_2(CO)OCH_2CH_3$ |
| I.a.635 | F | Br | $CH_3$ | $OCH(CH_3)(CO)OCH_3$ |
| I.a.636 | F | Br | $CH_3$ | $OCH(CH_3)(CO)OCH_2CH_2$ |
| I.a.637 | F | Br | $CH_3$ | $OCH_2$-cyclopropyl |
| I.a.638 | F | Br | $CH_3$ | $OCH_2$-cyclobutyl |
| I.a.639 | F | Br | $CH_3$ | $SCH_3$ |

TABLE A-continued

| No. | R⁴ | R⁵ | R⁶ | R⁸ |
|---|---|---|---|---|
| I.a.640 | F | Br | CH₃ | SC₂H₅ |
| I.a.641 | F | Br | CH₃ | NHSO₂CH₃ |
| I.a.642 | F | Br | CH₃ | NHSO₂CH(CH₃)₂ |
| I.a.643 | F | Br | CH₃ | NHSO₂N(CH₃)₂ |
| I.a.644 | F | Br | CH₃ | NHSO₂N(CH₃)[CH(CH₃)₂] |
| I.a.645 | F | Br | OCH₃ | OH |
| I.a.646 | F | Br | OCH₃ | OCH₃ |
| I.a.647 | F | Br | OCH₃ | OC₂H₅ |
| I.a.648 | F | Br | OCH₃ | OCH(CH₃)₂ |
| I.a.649 | F | Br | OCH₃ | OCH₂CH₂CH₃ |
| I.a.650 | F | Br | OCH₃ | OCH₂CH(CH₃)₂ |
| I.a.651 | F | Br | OCH₃ | OCH₂CH=CH₂ |
| I.a.652 | F | Br | OCH₃ | OCH₂C≡CH |
| I.a.653 | F | Br | OCH₃ | OCH₂CF₃ |
| I.a.654 | F | Br | OCH₃ | OCH₂CHF₂ |
| I.a.655 | F | Br | OCH₃ | OC₆H₅ |
| I.a.656 | F | Br | OCH₃ | OCH₂(C₆H₅) |
| I.a.657 | F | Br | OCH₃ | OCH₂OCH₃ |
| I.a.658 | F | Br | OCH₃ | OCH₂OCH₂CH₃ |
| I.a.659 | F | Br | OCH₃ | OCH₂CH₂OCH₃ |
| I.a.660 | F | Br | OCH₃ | OCH₂CH₂OCH₂CH₃ |
| I.a.661 | F | Br | OCH₃ | OCH₂(CO)OCH₃ |
| I.a.662 | F | Br | OCH₃ | OCH₂(CO)OCH₂CH₃ |
| I.a.663 | F | Br | OCH₃ | OCH(CH₃)(CO)OCH₃ |
| I.a.664 | F | Br | OCH₃ | OCH(CH₃)(CO)OCH₂CH₃ |
| I.a.665 | F | Br | OCH₃ | OCH₂-cyclopropyl |
| I.a.666 | F | Br | OCH₃ | OCH₂-cyclobutyl |
| I.a.667 | F | Br | OCH₃ | SCH₃ |
| I.a.668 | F | Br | OCH₃ | SC₂H₅ |
| I.a.669 | F | Br | OCH₃ | NHSO₂CH₃ |
| I.a.670 | F | Br | OCH₃ | NHSO₂CH(CH₃)₂ |
| I.a.671 | F | Br | OCH₃ | NHSO₂N(CH₃)₂ |
| I.a.672 | F | Br | OCH₃ | NHSO₂N(CH₃)[CH(CH₃)₂] |

Also preferred are the uracilpyridines of formula (I.b), preferably the uracilpyridines of formulae (I.b.1) to (I.b.672), particularly preferred the uracilpyridines of formulae (I.b.1) to (I.b.504), which differ from the corresponding uracilpyridines of formulae (I.a.1) to (I.a.672) only in that Q is S:

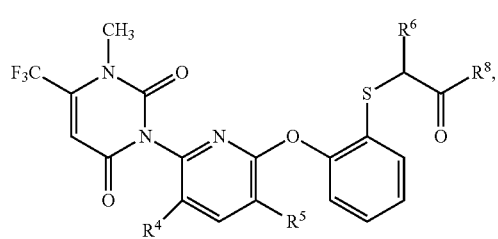

(I.b)

Also preferred are the uracilpyridines of formula (I.c), preferably the uracilpyridines of formulae (I.c.1) to (I.c.672), particularly preferred the uracilpyridines of formulae (I.c.1) to (I.c.504), which differ from the corresponding uracilpyridines of formulae (I.a.1) to (I.a.672) only in that Z is Z-2, wherein $R^a$, $R^b$, $R^c$ and $R^e$ are H:

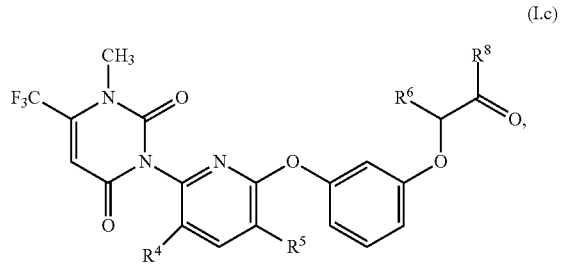

(I.c)

Also preferred are the uracilpyridines of formula (I.d), preferably the uracilpyridines of formulae (I.d.1) to (I.d.672), particularly preferred the uracilpyridines of formulae (I.d.1) to (I.d.504), which differ from the corresponding uracilpyridines of formulae (I.a.1) to (I.a.672) only in that Z is Z-3, wherein $R^a$, $R^b$, $R^d$ and $R^e$ are H:

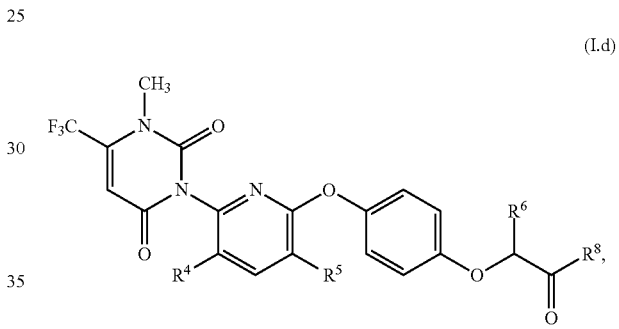

(I.d)

Also preferred are the uracilpyridines of formula (I.e), preferably the uracilpyridines of formulae (I.e.1) to (I.e.672), particularly preferred the uracilpyridines of formulae (I.e.1) to (I.e.504), which differ from the corresponding uracilpyridines of formulae (I.a.1) to (I.a.672) only in that Z is Z-4, wherein $R^b$, $R^c$ and $R^d$ are H:

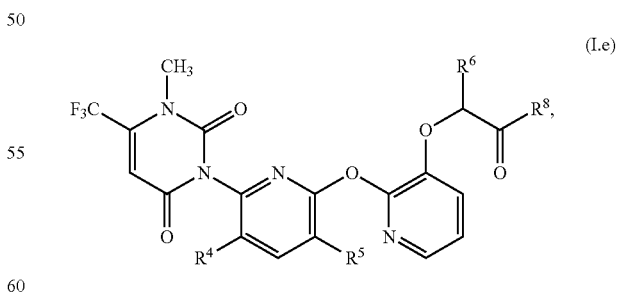

(I.e)

Also preferred are the uracilpyridines of formula (I.f), preferably the uracilpyridines of formulae (I.f.1) to (I.f.672), particularly preferred the uracilpyridines of formulae (I.f.1) to (I.f.504), which differ from the corresponding uracilpyridines of formulae (I.a.1) to (I.a.672) only in that Z is Z-5, wherein $R^a$, $R^c$ and $R^d$ are H:

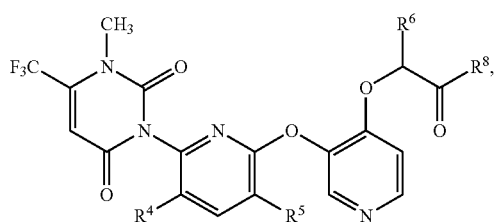

(I.f)

Also preferred are the uracilpyridines of formula (I.g), preferably the uracilpyridines of formulae (I.g.1) to (I.g.672), particularly preferred the uracilpyridines of formulae (I.g.1) to (I.g.504), which differ from the corresponding uracilpyridines of formulae (I.a.1) to (I.a.672) only in that Z is Z-6, wherein $R^a$, $R^b$ and $R^d$ are H:

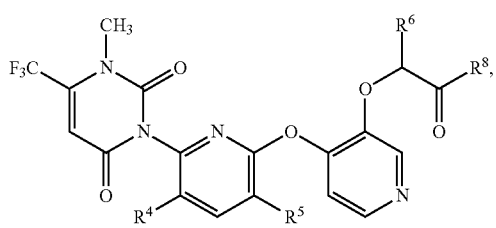

(I.g)

Also preferred are the uracilpyridines of formula (I.h), preferably the uracilpyridines of formulae (I.h.1) to (I.h.672), particularly preferred the uracilpyridines of formulae (I.h.1) to (I.h.504), which differ from the corresponding uracilpyridines of formulae (I.a.1) to (I.a.672) only in that Z is Z-7, wherein $R^a$, $R^b$ and $R^c$ are H:

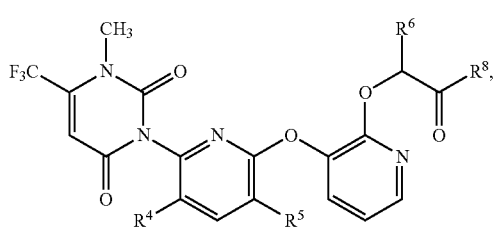

(I.h)

Also preferred are the uracilpyridines of formula (I.i) preferably the uracilpyridines of formulae (I.i.1) to (I.i.672), particularly preferred the uracilpyridines of formulae (I.i.1) to (I.i.504), which differ from the corresponding uracilpyridines of formulae (I.a.1) to (I.a.672) only in that Z is Z-7, wherein $R^a$, $R^b$ and $R^c$ are H, and Q is S:

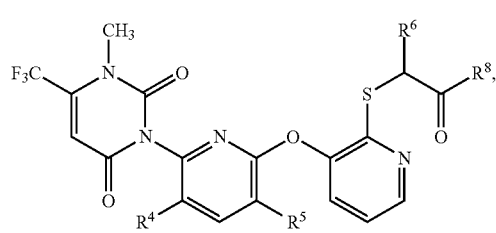

(I.i)

Also preferred are the uracilpyridines of formula (I.k), preferably the uracilpyridines of formulae (I.k.1) to (I.k.672), particularly preferred the uracilpyridines of formulae (I.k.1) to (I.k.504), which differ from the corresponding uracilpyridines of formulae (I.a.1) to (I.a.672) only in that Z is Z-8, wherein $R^b$, $R^c$ and $R^e$ are H:

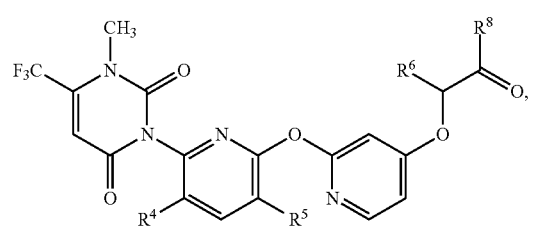

(I.k)

Also preferred are the uracilpyridines of formula (I.l), preferably the uracilpyridines of formulae (I.l.1) to (I.l.672), particularly preferred the uracilpyridines of formulae (I.l.1) to (I.l.504), which differ from the corresponding uracilpyridines of formulae (I.a.1) to (I.a.672) only in that Z is Z-9, wherein $R^a$, $R^c$ and $R^e$ are H:

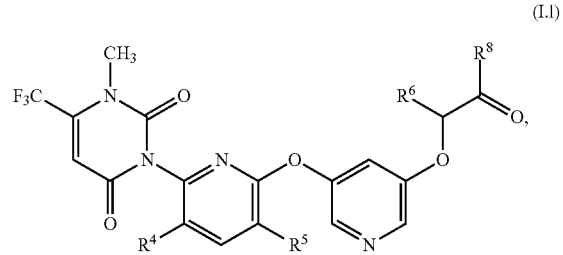

(I.l)

Also preferred are the uracilpyridines of formula (I.m), preferably the uracilpyridines of formulae (I.m.1) to (I.m.672), particularly preferred the uracilpyridines of formulae (I.m.1) to (I.m.504), which differ from the corresponding uracilpyridines of formulae (I.a.1) to (I.a.672) only in that Z is Z-10, wherein $R^a$, $R^b$ and $R^e$ are H:

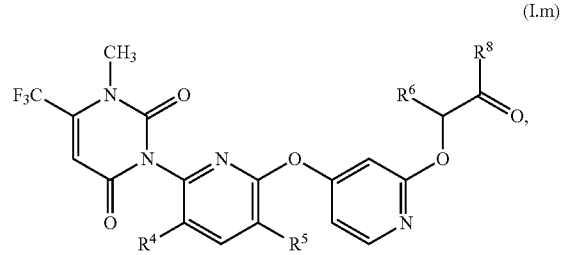

(I.m)

Also preferred are the uracilpyridines of formula (I.n), preferably the uracilpyridines of formulae (I.n.1) to (I.n.672), particularly preferred the uracilpyridines of formulae (I.n.1) to (I.n.504), which differ from the corresponding uracilpyridines of formulae (I.a.1) to (I.a.672) only in that Z is Z-11, wherein $R^a$, $R^b$ and $R^c$ are H:

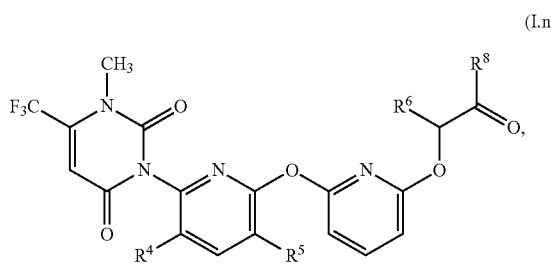

(I.n)

Also preferred are the uracilpyridines of formula (I.o), preferably the uracilpyridines of formulae (I.o.1) to (I.o.672), particularly preferred the uracilpyridines of formulae (I.o.1) to (I.o.504), which differ from the corresponding uracilpyridines of formulae (I.a.1) to (I.a.672) only in that Z is Z-12, wherein $R^b$, $R^d$ and $R^e$ are H:

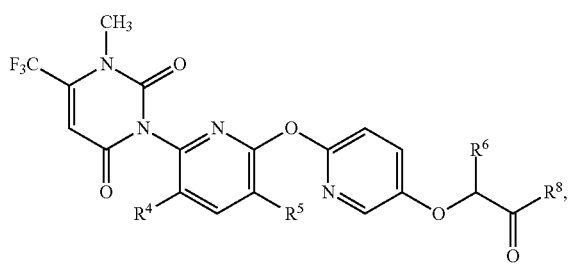

(I.o)

Also preferred are the uracilpyridines of formula (I.p), preferably the uracilpyridines of formulae (I.p.1) to (I.p.672), particularly preferred the uracilpyridines of formulae (I.p.1) to (I.p.504), which differ from the corresponding uracilpyridines of formulae (I.a.1) to (I.a.672) only in that Z is Z-13, wherein $R^a$, $R^d$ and $R^e$ are H:

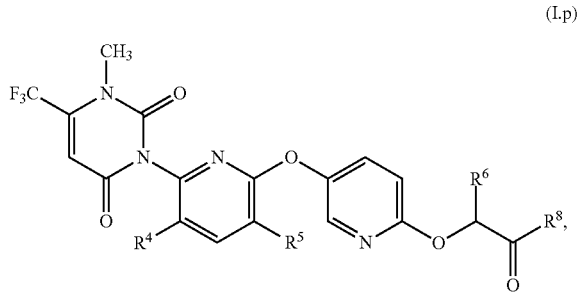

(I.p)

Also preferred are the uracilpyridines of formula (I.q), preferably the uracilpyridines of formulae (I.q.1) to (I.q.672), particularly preferred the uracilpyridines of formulae (I.q.1) to (I.q.504), which differ from the corresponding uracilpyridines of formulae (I.a.1) to (I.a.672) only in that Z is Z-21, wherein $R^a$ and $R^c$ are H:

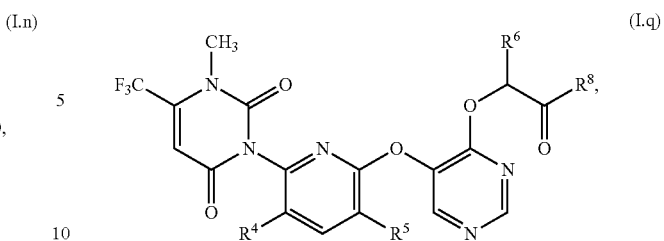

(I.q)

To widen the spectrum of action and to achieve synergistic effects, the uracilpyridines of formula (I) may be mixed with a large number of representatives of other herbicidal or growth-regulating active ingredient groups and then applied concomitantly. Suitable components for mixtures are, for example, herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

It may furthermore be beneficial to apply the uracilpyridines of formula (I) alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

In one embodiment of the present invention the compositions according to the present invention comprise at least one uracilpyridine of formula (I) (compound A) and at least one further active compound selected from herbicides B, preferably herbicides B of class b1) to b15), and safeners C (compound C).

In another embodiment of the present invention the compositions according to the present invention comprise at least one uracilpyridine of formula (I) and at least one further active compound B (herbicide B).

The further herbicidal compound B (component B) is preferably selected from the herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitosis inhibitors;

b10) inhibitors of the synthesis of very long chain fatty acids (VLCFA inhibitors);
b11) cellulose biosynthesis inhibitors;
b12) decoupler herbicides;
b13) auxinic herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;
including their agriculturally acceptable salts or derivatives.

Preference is given to those compositions according to the present invention comprising at least one herbicide B selected from herbicides of class b2, b3, b4, b5, b6, b7, b9, b10 and b13.

Specific preference is given to those compositions according to the present invention which comprise at least one herbicide B selected from the herbicides of class b4, b6, b7, b9, b10 and b13.

Particular preference is given to those compositions according to the present invention which comprise at least one herbicide B selected from the herbicides of class b4, b6, b10 and b13.

Examples of herbicides B which can be used in combination with the uracilpyridines of formula (I) of formula (I) according to the present invention are:

b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2",4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2",4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron,
imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam,
pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8),
sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;
among these, a preferred embodiment of the invention relates to those compositions comprising at least one imidazolinone herbicide;

b3) from the group of the photosynthesis inhibitors:
amicarbazone, inhibitors of the photosystem II, e.g. 1-(6-tert-butylpyrimidin-4-yl)-2-hydroxy-4-methoxy-3-methyl-2H-pyrrol-5-one (CAS 1654744-66-7), 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butyl- 1-methyl-pyrazol-3-yl)-4-chloro-2-hydroxy-3-methyl-2H-pyrrol-5-one (CAS 1654057-29-0), 1-(5-tert-butyl-1-methyl-pyrazol-3-yl)-3-chloro-2-hydroxy-4-methyl-2H-pyrrol-5-one (CAS 1654747-80-4), 4-hydroxy-1-methoxy-5-methyl-344-(trifluoromethyl)-2-pyridydimidazolidin-2-one; (CAS 2023785-78-4), 4-hydroxy-1,5-dimethyl-344-(trifluoromethyl)-2-pyridydimidazolidin-2-one (CAS 2023785-79-5), 5-ethoxy-4-hydroxy-1-methyl-3-[4-(trifluoromethyl)-2-pyridy]imidazolidin-2-one (CAS 1701416-69-4), 4-hydroxy-1-methyl-344-(trifluoromethyl)-2-pyridydimidazolidin-2-one (CAS 1708087-22-2), 4-hydroxy-1,5-dimethyl-3-[1-methyl-5-(trifluoromethy)pyrazol-3-yl]imidazolidin-2-one (CAS 2023785-80-8), 1-(5-tert-butylisoxazol-3-yl)-4-ethoxy-5-hydroxy-3-methyl-imidazolidin-2-one (CAS 1844836-64-1), triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, chlorphtalim, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)-pyrimidine (CAS 180608-33-7), HPPD inhibitors: benzobicyclon, benzofenap, bicyclopyrone, clomazone, fenquinotrione, isoxaflutole, mesotrione, oxotrione (CAS 1486617-21-3), pyrasulfotole, pyrazolynate, pyrazoxyfen, sulcotrione, tefuryltrione, tembotrione, tolpyralate, topramezone, bleacher, unknown target: aclonifen, amitrole flumeturon and 2-chloro-3-methylsulfanyl-N-(1-methyltetrazol-5-yl)-4-(trifluoromethyl)benzamide (CAS 1361139-71-0), 2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7);

b6) from the group of the EPSP synthase inhibitors:

glyphosate, glyphosate-isopropylammonium, glyposate-potassium and glyphosate-trimesium (sulfosate);

b7) from the group of the glutamine synthase inhibitors:

bilanaphos (bialaphos), bilanaphos-sodium, glufosinate, glufosinate-P and glufosinate-ammonium;

b8) from the group of the DHP synthase inhibitors:

asulam;

b9) from the group of the mitosis inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: carbetamide, chlorpropham, flamprop, flamprop-isopropyl, flamprop-methyl, flamprop-M-isopropyl, flamprop-M-methyl and propham; among these, compounds of group K1, in particular dinitroanilines are preferred;

b10) from the group of the VLCFA inhibitors:

chloroacetamides such as acetochlor, alachlor, amidochlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, napro-anilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9 the isoxazoline compounds of the formula (I)I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors:

chlorthiamid, dichlobenil, flupoxam, indaziflam, isoxaben, triaziflam and 1-cyclohexyl-5-pentafluorphenyloxy-1⁴-[1,2,4,6]thiatriazin-3-ylamine (CAS 175899-01-1);

b12) from the group of the decoupler herbicides:

dinoseb, dinoterb and DNOC and its salts;

b13) from the group of the auxinic herbicides:

2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, flopyrauxifen, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, florpyrauxifen, florpyrauxifen-benzyl (CAS 1390661-72-9) and 4-amino-3-chloro-5-fluoro-6-(7-fluoro-1H-indol-6-yl)picolinic acid (CAS 1629965-65-6);

b14) from the group of the auxin transport inhibitors:

diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanolammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl) ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl. Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl. Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and aminopyralid-tris(2-hydroxypropyl)ammonium.

Suitable salts of glyphosate are for example glyphosate-ammonium, glyphosate-diammonium, glyphoste-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinmerac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

Particularly preferred herbicides B are the herbicides B as defined above; in particular the herbicides B.1-B.202, especially the herbicides B.1-B.201 listed below in table B:

TABLE B

| | Herbicide B |
|---|---|
| A.1 | clethodim |
| A.2 | clodinafop-propargyl |
| A.3 | cycloxydim |
| A.4 | cyhalofop-butyl |
| A.5 | fenoxaprop-ethyl |
| A.6 | fenoxaprop-P-ethyl |
| A.7 | metamifop |
| A.8 | pinoxaden |
| A.9 | profoxydim |
| A.10 | sethoxydim |
| A.11 | tepraloxydim |
| A.12 | tralkoxydim |
| A.13 | esprocarb |
| A.14 | ethofumesate |
| A.15 | molinate |
| A.16 | prosulfocarb |
| A.17 | thiobencarb |
| A.18 | triallate |

TABLE B-continued

| | Herbicide B |
|---|---|
| A.19 | bensulfuron-methyl |
| A.20 | bispyribac-sodium |
| A.21 | cloransulam-methyl |
| A.22 | chlorsulfuron |
| A.23 | clorimuron |
| A.24 | cyclosulfamuron |
| A.25 | diclosulam |
| A.26 | florasulam |
| A.27 | flumetsulam |
| A.28 | flupyrsulfuron-methyl-sodium |
| A.29 | foramsulfuron |
| A.30 | imazamox |
| A.31 | imazamox-ammonium |
| A.32 | imazapic |
| A.33 | imazapic-ammonium |
| A.34 | imazapic-isopropylammonium |
| A.35 | imazapyr |
| A.36 | imazapyr-ammonium |
| A.37 | imazapyr-isopropylammonium |
| A.38 | imazaquin |
| A.39 | imazaquin-ammonium |
| A.40 | imazethapyr |
| A.41 | imazethapyr-ammonium |
| A.42 | imazethapyr-isopropylammonium |
| A.43 | imazosulfuron |
| A.44 | iodosulfuron-methyl-sodium |
| A.45 | iofensulfuron |
| A.46 | iofensulfuron-sodium |
| A.47 | mesosulfuron-methyl |
| A.48 | metazosulfuron |
| A.49 | metsulfuron-methyl |
| A.50 | metosulam |
| A.51 | nicosulfuron |
| A.52 | penoxsulam |
| A.53 | propoxycarbazon-sodium |
| A.54 | pyrazosulfuron-ethyl |
| A.55 | pyribenzoxim |
| A.56 | pyriftalid |
| A.57 | pyroxsulam |
| A.58 | propyrisulfuron |
| A.59 | rimsulfuron |
| A.60 | sulfosulfuron |
| A.61 | thiencarbazone-methyl |
| A.62 | thifensulfuron-methyl |
| A.63 | tribenuron-methyl |
| A.64 | tritosulfuron |
| A.65 | triafamone |
| A.66 | ametryne |
| A.67 | atrazine |
| A.68 | bentazon |
| A.69 | bromoxynil |
| A.70 | bromoxynil-octanoate |
| A.71 | bromoxynil-heptanoate |
| A.72 | bromoxynil-potassium |
| A.73 | diuron |
| A.74 | fluometuron |
| A.75 | hexazinone |
| A.76 | isoproturon |
| A.77 | linuron |
| A.78 | metamitron |
| A.79 | metribuzin |
| A.80 | propanil |
| A.81 | simazin |
| A.82 | terbuthylazine |
| A.83 | terbutryn |
| A.84 | paraquat-dichloride |
| A.85 | acifluorfen |
| A.86 | butafenacil |
| A.87 | carfentrazone-ethyl |
| A.88 | flumioxazin |
| A.89 | fomesafen |
| A.90 | oxadiargyl |
| A.91 | oxyfluorfen |
| A.92 | pyraflufen |
| A.93 | pyraflufen-ethyl |
| A.94 | saflufenacil |
| A.95 | sulfentrazone |
| A.96 | trifludimoxazin |
| A.97 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6 |
| A.98 | benzobicyclon |
| A.99 | bicyclopyrone |
| A.100 | clomazone |
| A.101 | diflufenican |
| A.102 | flurochloridone |
| A.103 | isoxaflutole |
| A.104 | mesotrione |
| A.105 | norflurazone |
| A.106 | picolinafen |
| A.107 | sulcotrione |
| A.108 | tefuryltrione |
| A.109 | tembotrione |
| A.110 | tolpyralate |
| A.111 | topramezone |
| A.112 | topramezone-sodium |
| A.113 | amitrole |
| A.114 | fluometuron |
| A.115 | fenquinotrione |
| A.116 | glyphosate |
| A.117 | glyphosate-ammonium |
| A.118 | glyphosate-dimethylammonium |
| A.119 | glyphosate-isopropylammonium |
| A.120 | glyphosate-trimesium (sulfosate) |
| A.121 | glyphosate-potassium |
| A.122 | glufosinate |
| A.123 | glufosinate-ammonium |
| A.124 | glufosinate-P |
| A.125 | glufosinate-P-ammonium |
| A.126 | pendimethalin |
| A.127 | trifluralin |
| A.128 | acetochlor |
| A.129 | butachlor |
| A.130 | cafenstrole |
| A.131 | dimethenamid-P |
| A.132 | fentrazamide |
| A.133 | flufenacet |
| A.134 | mefenacet |
| A.135 | metazachlor |
| A.136 | metolachlor |
| A.137 | S-metolachlor |
| A.138 | pretilachlor |
| A.139 | fenoxasulfone |
| A.140 | indaziflam |
| A.141 | isoxaben |
| A.142 | triaziflam |
| A.143 | ipfencarbazone |
| A.144 | pyroxasulfone |
| A.145 | 2,4-D |
| A.146 | 2,4-D-isobutyl |
| A.147 | 2,4-D-dimethylammonium |
| A.148 | 2,4-D-N,N,N-trimethylethanolammonium |
| A.149 | aminopyralid |
| A.150 | aminopyralid-methyl |
| A.151 | aminopyralid-dimethyl-ammonium |
| A.152 | aminopyralid-tris(2-hydroxypropyl)ammonium |
| A.153 | clopyralid |
| A.154 | clopyralid-methyl |
| A.155 | clopyralid-olamine |
| A.156 | dicamba |
| A.157 | dicamba-butotyl |
| A.158 | dicamba-diglycolamine |

TABLE B-continued

| | Herbicide B |
|---|---|
| A.159 | dicamba-dimethylammonium |
| A.160 | dicamba-diolamine |
| A.161 | dicamba-isopropylammonium |
| A.162 | dicamba-potassium |
| A.163 | dicamba-sodium |
| A.164 | dicamba-trolamine |
| A.165 | dicamba-N,N-bis-(3-aminopropyl)methylamine |
| A.166 | dicamba-diethylenetriamine |
| A.167 | fluroxypyr |
| A.168 | fluroxypyr-meptyl |
| A.169 | halauxifen |
| A.170 | halauxifen-methyl |
| A.171 | MCPA |
| A.172 | MCPA-2-ethylhexyl |
| A.173 | MCPA-dimethylammonium |
| A.174 | quinclorac |
| A.175 | quinclorac-dimethylammonium |
| A.176 | quinmerac |
| A.177 | quinmerac-dimethylammonium |
| A.178 | florpyrauxifen |
| A.179 | florpyrauxifen-benzyl (CAS 1390661-72-9) |
| A.180 | aminocyclopyrachlor |
| A.181 | aminocyclopyrachlor-potassium |
| A.182 | aminocyclopyrachlor-methyl |
| A.183 | diflufenzopyr |
| A.184 | diflufenzopyr-sodium |
| A.185 | dymron |
| A.186 | indanofan |
| A.187 | oxaziclomefone |
| A.188 | II.1 |
| A.189 | II.2 |
| A.190 | II.3 |
| A.191 | II.4 |
| A.192 | II.5 |
| A.193 | II.6 |
| A.194 | II.7 |
| A.195 | II.8 |
| A.196 | II.9 |
| A.197 | 4-amino-3-chloro-5-fluoro-6-(7-fluoro-1H-indol-6-yl) picolinic acid (CAS 1629965-65-6) |
| A.198 | flopyrauxifen |
| A.199 | oxotrione (CAS 1486617-21-3) |
| A.200 | cinmethylin |
| A.201 | 2-chloro-3-methylsulfanyl-N-(1-methyltetrazol-5-yl)-4-(trifluoromethyl)benzamide (CAS 1361139-71-0) |
| A.202 | 2-(2,4-dichlorophenyl)-methyl-4,4-dimethyl-3-isoxazolidone (CAS 81777-95-9) |

Moreover, it may be useful to apply the uracilpyridines of formula (I) in combination with safeners. Safeners are chemical compounds which prevent or reduce damage on useful plants without having a major impact on the herbicidal action of the uracilpyridines of formula (I) towards unwanted plants. They can be applied either before sowings (e.g. on seed treatments, shoots or seedlings) or in the pre-emergence application or post-emergence application of the useful plant. The safeners and the uracilpyridines of formula (I) and optionally the herbicides B can be applied simultaneously or in succession.

In another embodiment of the present invention the compositions according to the present invention comprise at least one uracilpyridine of formula (I) and at least one safener C (component C).

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (M0N4660, CAS 71526-07-3), 2,2,5-trimethyl-3-(dichloroacetyl)-1,3-oxazolidine (R-29148, CAS 52836-31-4), metcamifen and BPCMS (CAS 54091-06-4); especially preferred benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (M0N4660, CAS 71526-07-3), 2,2,5-trimethyl-3-(dichloroacetyl)-1,3-oxazolidine (R-29148, CAS 52836-31-4) and metcamifen.

Particularly preferred safeners C, which, as component C, are constituent of the composition according to the invention are the safeners C as defined above; in particular the safeners C.1-C.17 listed below in table C:

TABLE C

| | Safener C |
|---|---|
| C.1 | benoxacor |
| C.2 | cloquintocet |
| C.3 | cloquintocet-mexyl |
| C.4 | cyprosulfamide |
| C.5 | dichlormid |
| C.6 | fenchlorazole |
| C.7 | fenchlorazole-ethyl |
| C.8 | fenclorim |
| C.9 | furilazole |
| C.10 | isoxadifen |
| C.11 | isoxadifen-ethyl |
| C.12 | mefenpyr |
| C.13 | mefenpyr-diethyl |
| C.14 | naphtalic acid anhydride |
| C.15 | 4-(dichloroacetyl)-1-oxa-4-azaspiro[4.5]decane (CAS 71526-07-3) |
| C.16 | 2,2,5-trimethyl-3-(dichloroacetyl)-1,3-oxazolidine (CAS 52836-31-4) |
| C.17 | metcamifen |

The active compounds B of groups b1) to b15) and the active compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

According to a preferred embodiment of the invention, the composition comprises as herbicidal active compound B or component B at least one, preferably exactly one herbicide B.

According to another preferred embodiment of the invention, the composition comprises as herbicidal active compounds B or component B at least two, preferably exactly two herbicides B different from each other.

According to another preferred embodiment of the invention, the composition comprises as herbicidal active compounds B or component B at least three, preferably exactly three herbicides B different from each other.

According to another preferred embodiment of the invention, the composition comprises as herbicidal active compounds B or component B at least four, preferably exactly four herbicides B different from each other.

According to another preferred embodiment of the invention, the composition comprises as safening component C or component C at least one, preferably exactly one safener C.

According to another preferred embodiment of the invention, the composition comprises as component B at least one, preferably exactly one herbicide B, and as component C at least one, preferably exactly one, safener C.

According to another preferred embodiment of the invention, the composition comprises at least two, preferably exactly two, herbicides B different from each other, and as component C at least one, preferably exactly one, safener C.

According to another preferred embodiment of the invention, the composition comprises at least three, preferably exactly three, herbicides B different from each other, and as component C at least one, preferably exactly one, safener C.

According to another preferred embodiment of the invention, the composition comprises as component A at least one, preferably exactly one compound of formula (I), preferably of formula (I.a) or (I.h), and as component B at least one, preferably exactly one, herbicide B.

According to another preferred embodiment of the invention, the composition comprises as component A at least one, preferably exactly one compound of formula (I), preferably of formula (I.a) or (I.h), and at least two, preferably exactly two, herbicides B different from each other.

According to another preferred embodiment of the invention, the composition comprises as component A at least one, preferably exactly one compound of formula (I), preferably of formula (I.a) or (I.h), and at least three, preferably exactly three, herbicides B different from each other.

According to another preferred embodiment of the invention, the composition comprises as component A at least one, preferably exactly one compound of formula (I), preferably of formula (I.a) or (I.h), and at least four, preferably exactly four, herbicides B different from each other.

According to another preferred embodiment of the invention, the composition comprises as component A at least one, preferably exactly one compound of formula (I), preferably of formula (I.a) or (I.h), and as component C at least one, preferably exactly one, safener C.

According to another preferred embodiment of the invention, the composition comprises as component A at least one, preferably exactly one compound of formula (I), preferably of formula (I.a) or (I.h), as component B at least one, preferably exactly one, herbicide B, and as component C at least one, preferably exactly one safener C.

According to another preferred embodiment of the invention, the composition comprises as component A at least one, preferably exactly one compound of formula (I), preferably of formula (I.a) or (I.h), at least two, preferably exactly two herbicides B different from each other, and as component C at least one, preferably exactly one, safener C.

According to another preferred embodiment of the invention, the composition comprises as component A at least one, preferably exactly one compound of formula (I), preferably of formula (I.a) or (I.h), at least three, preferably exactly three herbicides B different from each other, and as component C at least one, preferably exactly one, safener C.

According to another preferred embodiment of the invention, the composition comprises, in addition to an uracilpyridine of formula (I), especially an active compound from the group consisting of (I.a.87), (I.a.109), (I.a.115), (I.a.255), (I.a.277), (I.a.283), (I.a.339), (I.a.361), (I.a.367), (I.h.87), (I.h.109), (I.h.115), (I.h.255), (I.h.277), (I.h.283), (I.h.339), (I.h.361) and (I.h.367), at least one and especially exactly one herbicidally active compound from group b4), in particular selected from the group consisting of acifluorfen, butafencil, carfenetrazone-ethyl, flumioxazin, fomesafen, oxadiargyl, oxyfluorfen, pyraflufen, pyraflufen-ethyl, saflufenacil, sulfentrazone, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6).

According to another preferred embodiment of the invention, the composition comprises, in addition to an uracilpyridine of formula (I), especially an active compound from the group consisting of (I.a.87), (I.a.109), (I.a.115), (I.a.255), (I.a.277), (I.a.283), (I.a.339), (I.a.361), (I.a.367), (I.h.87), (I.h.109), (I.h.115), (I.h.255), (I.h.277), (I.h.283), (I.h.339), (I.h.361) and (I.h.367), at least one and especially exactly one herbicidally active compound from group b6), in particular selected from the group consisting of glyphosate, glyphosate-ammonium, glyphosate-dimethylammonium, glyphosate-isopropylammonium and glyphosate-trimesium (sulfosate) and glyphosate-potassium.

According to another preferred embodiment of the invention, the composition comprises, in addition to an uracilpyridine of formula (I), especially an active compound from the group consisting of (I.a.87), (I.a.109), (I.a.115), (I.a.255), (I.a.277), (I.a.283), (I.a.339), (I.a.361), (I.a.367), (I.h.87), (I.h.109), (I.h.115), (I.h.255), (I.h.277), (I.h.283), (I.h.339), (I.h.361) and (I.h.367), at least one and especially exactly one herbicidally active compound from group b10), in particular selected from the group consisting of acetochlor, butachlor, cafenstrole, dimethenamid-P, fentrazamide, flufenacet, mefenacet, metazachlor, metolachlor, S-metolachlor, fenoxasulfone, ipfencarbazone and pyroxasulfone. Likewise, preference is given to compositions comprising in addition to an uracilpyridine of formula (I), especially an active compound from the group consisting of (I.a.87), (I.a.109), (I.a.115), (I.a.255), (I.a.277), (I.a.283), (I.a.339), (I.a.361), (I.a.367), (I.h.87), (I.h.109), (I.h.115), (I.h.255), (I.h.277), (I.h.283), (I.h.339), (I.h.361) and (I.h.367), at least one and especially exactly one herbicidally active compound from group b10), in particular selected from the group consisting of isoxazoline compounds of the formulae II.1, II.2, II.3, II.4, II.5, II.6, II.7, II.8 and II.9 as defined above.

According to another preferred embodiment of the invention, the composition comprises, in addition to an uracil-pyridine of formula (I), especially an active compound from the group consisting of (I.a.87), (I.a.109), (I.a.115), (I.a.255), (I.a.277), (I.a.283), (I.a.339), (I.a.361), (I.a.367), (I.h.87), (I.h.109), (I.h.115), (I.h.255), (I.h.277), (I.h.283), (I.h.339), (I.h.361) and (I.h.367), at least one and especially exactly one herbicidally active compound from group b13), in particular selected from the group consisting of 2,4-D, 2,4-D-isobutyl, 2,4-D-dimethylammonium, 2,4-D-N,N,N-trimethylethanolammonium, aminocyclopyrachlor, aminocyclopyrachlor-potassium, aminocyclopyrachlor-methyl, aminopyralid, aminopyralid-methyl, aminopyralid-dimethylammonium, aminopyralid-tris(2-hydroxypropyl)ammonium, clopyralid, clopyralid-methyl, clopyralid-olamine, dicamba, dicamba-butotyl, dicamba-diglycolamine, dicamba-dimethylammonium, dicamba-diolamine, dicamba-isopropylammonium, dicamba-potassium, dicamba-sodium, dicamba-trolamine, dicamba-N,N-bis-(3-aminopropyl)methylamine, dicamba-diethylenetriamine, flopyrauxifen, fluroxypyr, fluroxypyr-meptyl, halauxifen, halauxifen-methyl, MCPA, MCPA-2-ethylhexyl, MCPA-dimethylammonium, quinclorac, quinclorac-dimethylammonium, quinmerac, quinmerac-dimethylammonium, florpyrauxifen, florpyrauxifen-benzyl (CAS 1390661-72-9), and 4-amino-3-chloro-5-fluoro-6-(7-fluoro-1H-indol-6-yl)picolinic acid.

Here and below, the term "binary compositions" includes compositions comprising one or more, for example 1, 2 or 3, active compounds of the formula (I) and either one or more, for example 1, 2 or 3, herbicides B or one or more safeners C.

Correspondingly, the term "ternary compositions" includes compositions comprising one or more, for example 1, 2 or 3, active compounds of the formula (I), one or more, for example 1, 2 or 3, herbicides B and one or more, for example 1, 2 or 3, safeners C.

In binary compositions comprising at least one compound of the formula (I) as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:125 to 125:1.

In binary compositions comprising at least one compound of the formula (I) as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising at least one uracilpyridine of formula (I) as component A, at least one herbicide B and at least one safener C, the relative proportions by weight of the components A:B are generally in the range of from 1:1000 to 1000:1, preferably in the range of from 1:500 to 500:1, in particular in the range of from 1:250 to 250:1 and particularly preferably in the range of from 1:125 to 125:1, the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1, and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. The weight ratio of components A+B to component C is preferably in the range of from 1:500 to 500:1, in particular in the range of from 1:250 to 250:1 and particularly preferably in the range of from 1:75 to 75:1.

The weight ratios of the individual components in the preferred mixtures mentioned below are within the limits given herein, in particular within the preferred limits.

Particularly preferred are the compositions mentioned below comprising the uracilpyridines of formula (I) as defined and the substance(s) as defined in the respective row of table 1;
  especially preferred comprising as only herbicidal active compounds the uracilpyridines of formula (I) as defined and the substance(s) as defined in the respective row of table 1;
  most preferably comprising as only active compounds the uracilpyridines of formula (I) as defined and the substance(s) as defined in the respective row of table 1.

Particularly preferred are compositions 1.1 to 1.3653, especially compositions 1.1 to 1.3635, comprising the uracilpyridine (Ia.339) and the substance(s) as defined in the respective row of table 1:

TABLE 1

(compositions 1.1 to 1.3635):

| comp. no. | herbicide B | safener C |
| --- | --- | --- |
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |

TABLE 1-continued (compositions 1.1 to 1.3635):

| comp. no. | herbicide B | safener C |
|---|---|---|
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.145 | — |
| 1.146 | B.146 | — |
| 1.147 | B.147 | — |
| 1.148 | B.148 | — |
| 1.149 | B.149 | — |
| 1.150 | B.150 | — |
| 1.151 | B.151 | — |
| 1.152 | B.152 | — |
| 1.153 | B.153 | — |
| 1.154 | B.154 | — |
| 1.155 | B.155 | — |
| 1.156 | B.156 | — |
| 1.157 | B.157 | — |
| 1.158 | B.158 | — |
| 1.159 | B.159 | — |
| 1.160 | B.160 | — |
| 1.161 | B.161 | — |
| 1.162 | B.162 | — |
| 1.163 | B.163 | — |
| 1.164 | B.164 | — |
| 1.165 | B.165 | — |
| 1.166 | B.166 | — |
| 1.167 | B.167 | — |
| 1.168 | B.168 | — |
| 1.169 | B.169 | — |
| 1.170 | B.170 | — |
| 1.171 | B.171 | — |
| 1.172 | B.172 | — |
| 1.173 | B.173 | — |
| 1.174 | B.174 | — |
| 1.175 | B.175 | — |
| 1.176 | B.176 | — |
| 1.177 | B.177 | — |
| 1.178 | B.178 | — |
| 1.179 | B.179 | — |
| 1.180 | B.180 | — |
| 1.181 | B.181 | — |
| 1.182 | B.182 | — |
| 1.183 | B.183 | — |
| 1.184 | B.184 | — |
| 1.185 | B.185 | — |
| 1.186 | B.186 | — |
| 1.187 | B.187 | — |
| 1.188 | B.188 | — |
| 1.189 | B.189 | — |
| 1.190 | B.190 | — |
| 1.191 | B.191 | — |
| 1.192 | B.192 | — |
| 1.193 | B.193 | — |
| 1.194 | B.194 | — |
| 1.195 | B.195 | — |

TABLE 1-continued (compositions 1.1 to 1.3635):

| comp. no. | herbicide B | safener C |
|---|---|---|
| 1.196 | B.196 | — |
| 1.197 | B.197 | — |
| 1.198 | B.198 | — |
| 1.199 | B.199 | — |
| 1.200 | B.200 | — |
| 1.201 | B.201 | — |
| 1.202 | B.1 | C.1 |
| 1.203 | B.2 | C.1 |
| 1.204 | B.3 | C.1 |
| 1.205 | B.4 | C.1 |
| 1.206 | B.5 | C.1 |
| 1.207 | B.6 | C.1 |
| 1.208 | B.7 | C.1 |
| 1.209 | B.8 | C.1 |
| 1.210 | B.9 | C.1 |
| 1.211 | B.10 | C.1 |
| 1.212 | B.11 | C.1 |
| 1.213 | B.12 | C.1 |
| 1.214 | B.13 | C.1 |
| 1.215 | B.14 | C.1 |
| 1.216 | B.15 | C.1 |
| 1.217 | B.16 | C.1 |
| 1.218 | B.17 | C.1 |
| 1.219 | B.18 | C.1 |
| 1.220 | B.19 | C.1 |
| 1.221 | B.20 | C.1 |
| 1.222 | B.21 | C.1 |
| 1.223 | B.22 | C.1 |
| 1.224 | B.23 | C.1 |
| 1.225 | B.24 | C.1 |
| 1.226 | B.25 | C.1 |
| 1.227 | B.26 | C.1 |
| 1.228 | B.27 | C.1 |
| 1.229 | B.28 | C.1 |
| 1.230 | B.29 | C.1 |
| 1.231 | B.30 | C.1 |
| 1.232 | B.31 | C.1 |
| 1.233 | B.32 | C.1 |
| 1.234 | B.33 | C.1 |
| 1.235 | B.34 | C.1 |
| 1.236 | B.35 | C.1 |
| 1.237 | B.36 | C.1 |
| 1.238 | B.37 | C.1 |
| 1.239 | B.38 | C.1 |
| 1.240 | B.39 | C.1 |
| 1.241 | B.40 | C.1 |
| 1.242 | B.41 | C.1 |
| 1.243 | B.42 | C.1 |
| 1.244 | B.43 | C.1 |
| 1.245 | B.44 | C.1 |
| 1.246 | B.45 | C.1 |
| 1.247 | B.46 | C.1 |
| 1.248 | B.47 | C.1 |
| 1.249 | B.48 | C.1 |
| 1.250 | B.49 | C.1 |
| 1.251 | B.50 | C.1 |
| 1.252 | B.51 | C.1 |
| 1.253 | B.52 | C.1 |
| 1.254 | B.53 | C.1 |
| 1.255 | B.54 | C.1 |
| 1.256 | B.55 | C.1 |
| 1.257 | B.56 | C.1 |
| 1.258 | B.57 | C.1 |
| 1.259 | B.58. | C.1 |
| 1.260 | B.59 | C.1 |
| 1.261 | B.60 | C.1 |
| 1.262 | B.61 | C.1 |
| 1.263 | B.62 | C.1 |
| 1.264 | B.63 | C.1 |
| 1.265 | B.64 | C.1 |
| 1.266 | B.65 | C.1 |
| 1.267 | B.66 | C.1 |
| 1.268 | B.67 | C.1 |
| 1.269 | B.68 | C.1 |
| 1.270 | B.69 | C.1 |
| 1.271 | B.70 | C.1 |
| 1.272 | B.71 | C.1 |
| 1.273 | B.72 | C.1 |
| 1.274 | B.73 | C.1 |
| 1.275 | B.74 | C.1 |
| 1.276 | B.75 | C.1 |
| 1.277 | B.76 | C.1 |
| 1.278 | B.77 | C.1 |
| 1.279 | B.78 | C.1 |
| 1.280 | B.79 | C.1 |
| 1.281 | B.80 | C.1 |
| 1.282 | B.81 | C.1 |
| 1.283 | B.82 | C.1 |
| 1.284 | B.83 | C.1 |
| 1.285 | B.84 | C.1 |
| 1.286 | B.85 | C.1 |
| 1.287 | B.86 | C.1 |
| 1.288 | B.87 | C.1 |
| 1.289 | B.88 | C.1 |
| 1.290 | B.89 | C.1 |
| 1.291 | B.90 | C.1 |
| 1.292 | B.91 | C.1 |
| 1.293 | B.92 | C.1 |
| 1.294 | B.93 | C.1 |
| 1.295 | B.94 | C.1 |
| 1.296 | B.95 | C.1 |
| 1.297 | B.96 | C.1 |
| 1.298 | B.97 | C.1 |
| 1.299 | B.98 | C.1 |
| 1.300 | B.99 | C.1 |
| 1.301 | B.100 | C.1 |
| 1.302 | B.101 | C.1 |
| 1.303 | B.102 | C.1 |
| 1.304 | B.103 | C.1 |
| 1.305 | B.104 | C.1 |
| 1.306 | B.105 | C.1 |
| 1.307 | B.106 | C.1 |
| 1.308 | B.107 | C.1 |
| 1.309 | B.108 | C.1 |
| 1.310 | B.109 | C.1 |
| 1.311 | B.110 | C.1 |
| 1.312 | B.111 | C.1 |
| 1.313 | B.112 | C.1 |
| 1.314 | B.113 | C.1 |
| 1.315 | B.114 | C.1 |
| 1.316 | B.115 | C.1 |
| 1.317 | B.116 | C.1 |
| 1.318 | B.117 | C.1 |
| 1.319 | B.118 | C.1 |
| 1.320 | B.119 | C.1 |
| 1.321 | B.120 | C.1 |
| 1.322 | B.121 | C.1 |
| 1.323 | B.122 | C.1 |
| 1.324 | B.123 | C.1 |
| 1.325 | B.124 | C.1 |
| 1.326 | B.125 | C.1 |
| 1.327 | B.126 | C.1 |
| 1.328 | B.127 | C.1 |
| 1.329 | B.128 | C.1 |
| 1.330 | B.129 | C.1 |
| 1.331 | B.130 | C.1 |
| 1.332 | B.131 | C.1 |
| 1.333 | B.132 | C.1 |
| 1.334 | B.133 | C.1 |
| 1.335 | B.134 | C.1 |
| 1.336 | B.135 | C.1 |
| 1.337 | B.136 | C.1 |
| 1.338 | B.137 | C.1 |
| 1.339 | B.138 | C.1 |
| 1.340 | B.139 | C.1 |
| 1.341 | B.140 | C.1 |
| 1.342 | B.141 | C.1 |
| 1.343 | B.142 | C.1 |
| 1.344 | B.143 | C.1 |
| 1.345 | B.144 | C.1 |
| 1.346 | B.145 | C.1 |
| 1.347 | B.146 | C.1 |

TABLE 1-continued (compositions 1.1 to 1.3635):

| comp. no. | herbicide B | safener C |
|---|---|---|
| 1.348 | B.147 | C.1 |
| 1.349 | B.148 | C.1 |
| 1.350 | B.149 | C.1 |
| 1.351 | B.150 | C.1 |
| 1.352 | B.151 | C.1 |
| 1.353 | B.152 | C.1 |
| 1.354 | B.153 | C.1 |
| 1.355 | B.154 | C.1 |
| 1.356 | B.155 | C.1 |
| 1.357 | B.156 | C.1 |
| 1.358 | B.157 | C.1 |
| 1.359 | B.158 | C.1 |
| 1.360 | B.159 | C.1 |
| 1.361 | B.160 | C.1 |
| 1.362 | B.161 | C.1 |
| 1.363 | B.162 | C.1 |
| 1.364 | B.163 | C.1 |
| 1.365 | B.164 | C.1 |
| 1.366 | B.165 | C.1 |
| 1.367 | B.166 | C.1 |
| 1.368 | B.167 | C.1 |
| 1.369 | B.168 | C.1 |
| 1.370 | B.169 | C.1 |
| 1.371 | B.170 | C.1 |
| 1.372 | B.171 | C.1 |
| 1.373 | B.172 | C.1 |
| 1.374 | B.173 | C.1 |
| 1.375 | B.174 | C.1 |
| 1.376 | B.175 | C.1 |
| 1.377 | B.176 | C.1 |
| 1.378 | B.177 | C.1 |
| 1.379 | B.178 | C.1 |
| 1.380 | B.179 | C.1 |
| 1.381 | B.180 | C.1 |
| 1.382 | B.181 | C.1 |
| 1.383 | B.182 | C.1 |
| 1.384 | B.183 | C.1 |
| 1.385 | B.184 | C.1 |
| 1.386 | B.185 | C.1 |
| 1.387 | B.186 | C.1 |
| 1.388 | B.187 | C.1 |
| 1.389 | B.188 | C.1 |
| 1.390 | B.189 | C.1 |
| 1.391 | B.190 | C.1 |
| 1.392 | B.191 | C.1 |
| 1.393 | B.192 | C.1 |
| 1.394 | B.193 | C.1 |
| 1.395 | B.194 | C.1 |
| 1.396 | B.195 | C.1 |
| 1.397 | B.196 | C.1 |
| 1.398 | B.197 | C.1 |
| 1.399 | B.198 | C.1 |
| 1.400 | B.199 | C.1 |
| 1.401 | B.200 | C.1 |
| 1.402 | B.201 | C.1 |
| 1.403 | B.1 | C.2 |
| 1.404 | B.2 | C.2 |
| 1.405 | B.3 | C.2 |
| 1.406 | B.4 | C.2 |
| 1.407 | B.5 | C.2 |
| 1.408 | B.6 | C.2 |
| 1.409 | B.7 | C.2 |
| 1.410 | B.8 | C.2 |
| 1.411 | B.9 | C.2 |
| 1.412 | B.10 | C.2 |
| 1.413 | B.11 | C.2 |
| 1.414 | B.12 | C.2 |
| 1.415 | B.13 | C.2 |
| 1.416 | B.14 | C.2 |
| 1.417 | B.15 | C.2 |
| 1.418 | B.16 | C.2 |
| 1.419 | B.17 | C.2 |
| 1.420 | B.18 | C.2 |
| 1.421 | B.19 | C.2 |
| 1.422 | B.20 | C.2 |
| 1.423 | B.21 | C.2 |
| 1.424 | B.22 | C.2 |
| 1.425 | B.23 | C.2 |
| 1.426 | B.24 | C.2 |
| 1.427 | B.25 | C.2 |
| 1.428 | B.26 | C.2 |
| 1.429 | B.27 | C.2 |
| 1.430 | B.28 | C.2 |
| 1.431 | B.29 | C.2 |
| 1.432 | B.30 | C.2 |
| 1.433 | B.31 | C.2 |
| 1.434 | B.32 | C.2 |
| 1.435 | B.33 | C.2 |
| 1.436 | B.34 | C.2 |
| 1.437 | B.35 | C.2 |
| 1.438 | B.36 | C.2 |
| 1.439 | B.37 | C.2 |
| 1.440 | B.38 | C.2 |
| 1.441 | B.39 | C.2 |
| 1.442 | B.40 | C.2 |
| 1.443 | B.41 | C.2 |
| 1.444 | B.42 | C.2 |
| 1.445 | B.43 | C.2 |
| 1.446 | B.44 | C.2 |
| 1.447 | B.45 | C.2 |
| 1.448 | B.46 | C.2 |
| 1.449 | B.47 | C.2 |
| 1.450 | B.48 | C.2 |
| 1.451 | B.49 | C.2 |
| 1.452 | B.50 | C.2 |
| 1.453 | B.51 | C.2 |
| 1.454 | B.52 | C.2 |
| 1.455 | B.53 | C.2 |
| 1.456 | B.54 | C.2 |
| 1.457 | B.55 | C.2 |
| 1.458 | B.56 | C.2 |
| 1.459 | B.57 | C.2 |
| 1.460 | B.58. | C.2 |
| 1.461 | B.59 | C.2 |
| 1.462 | B.60 | C.2 |
| 1.463 | B.61 | C.2 |
| 1.464 | B.62 | C.2 |
| 1.465 | B.63 | C.2 |
| 1.466 | B.64 | C.2 |
| 1.467 | B.65 | C.2 |
| 1.468 | B.66 | C.2 |
| 1.469 | B.67 | C.2 |
| 1.470 | B.68 | C.2 |
| 1.471 | B.69 | C.2 |
| 1.472 | B.70 | C.2 |
| 1.473 | B.71 | C.2 |
| 1.474 | B.72 | C.2 |
| 1.475 | B.73 | C.2 |
| 1.476 | B.74 | C.2 |
| 1.477 | B.75 | C.2 |
| 1.478 | B.76 | C.2 |
| 1.479 | B.77 | C.2 |
| 1.480 | B.78 | C.2 |
| 1.481 | B.79 | C.2 |
| 1.482 | B.80 | C.2 |
| 1.483 | B.81 | C.2 |
| 1.484 | B.82 | C.2 |
| 1.485 | B.83 | C.2 |
| 1.486 | B.84 | C.2 |
| 1.487 | B.85 | C.2 |
| 1.488 | B.86 | C.2 |
| 1.489 | B.87 | C.2 |
| 1.490 | B.88 | C.2 |
| 1.491 | B.89 | C.2 |
| 1.492 | B.90 | C.2 |
| 1.493 | B.91 | C.2 |
| 1.494 | B.92 | C.2 |
| 1.495 | B.93 | C.2 |
| 1.496 | B.94 | C.2 |
| 1.497 | B.95 | C.2 |
| 1.498 | B.96 | C.2 |
| 1.499 | B.97 | C.2 |

TABLE 1-continued (compositions 1.1 to 1.3635):

| comp. no. | herbicide B | safener C |
|---|---|---|
| 1.500 | B.98 | C.2 |
| 1.501 | B.99 | C.2 |
| 1.502 | B.100 | C.2 |
| 1.503 | B.101 | C.2 |
| 1.504 | B.102 | C.2 |
| 1.505 | B.103 | C.2 |
| 1.506 | B.104 | C.2 |
| 1.507 | B.105 | C.2 |
| 1.508 | B.106 | C.2 |
| 1.509 | B.107 | C.2 |
| 1.510 | B.108 | C.2 |
| 1.511 | B.109 | C.2 |
| 1.512 | B.110 | C.2 |
| 1.513 | B.111 | C.2 |
| 1.514 | B.112 | C.2 |
| 1.515 | B.113 | C.2 |
| 1.516 | B.114 | C.2 |
| 1.517 | B.115 | C.2 |
| 1.518 | B.116 | C.2 |
| 1.519 | B.117 | C.2 |
| 1.520 | B.118 | C.2 |
| 1.521 | B.119 | C.2 |
| 1.522 | B.120 | C.2 |
| 1.523 | B.121 | C.2 |
| 1.524 | B.122 | C.2 |
| 1.525 | B.123 | C.2 |
| 1.526 | B.124 | C.2 |
| 1.527 | B.125 | C.2 |
| 1.528 | B.126 | C.2 |
| 1.529 | B.127 | C.2 |
| 1.530 | B.128 | C.2 |
| 1.531 | B.129 | C.2 |
| 1.532 | B.130 | C.2 |
| 1.533 | B.131 | C.2 |
| 1.534 | B.132 | C.2 |
| 1.535 | B.133 | C.2 |
| 1.536 | B.134 | C.2 |
| 1.537 | B.135 | C.2 |
| 1.538 | B.136 | C.2 |
| 1.539 | B.137 | C.2 |
| 1.540 | B.138 | C.2 |
| 1.541 | B.139 | C.2 |
| 1.542 | B.140 | C.2 |
| 1.543 | B.141 | C.2 |
| 1.544 | B.142 | C.2 |
| 1.545 | B.143 | C.2 |
| 1.546 | B.144 | C.2 |
| 1.547 | B.145 | C.2 |
| 1.548 | B.146 | C.2 |
| 1.549 | B.147 | C.2 |
| 1.550 | B.148 | C.2 |
| 1.551 | B.149 | C.2 |
| 1.552 | B.150 | C.2 |
| 1.553 | B.151 | C.2 |
| 1.554 | B.152 | C.2 |
| 1.555 | B.153 | C.2 |
| 1.556 | B.154 | C.2 |
| 1.557 | B.155 | C.2 |
| 1.558 | B.156 | C.2 |
| 1.559 | B.157 | C.2 |
| 1.560 | B.158 | C.2 |
| 1.561 | B.159 | C.2 |
| 1.562 | B.160 | C.2 |
| 1.563 | B.161 | C.2 |
| 1.564 | B.162 | C.2 |
| 1.565 | B.163 | C.2 |
| 1.566 | B.164 | C.2 |
| 1.567 | B.165 | C.2 |
| 1.568 | B.166 | C.2 |
| 1.569 | B.167 | C.2 |
| 1.570 | B.168 | C.2 |
| 1.571 | B.169 | C.2 |
| 1.572 | B.170 | C.2 |
| 1.573 | B.171 | C.2 |
| 1.574 | B.172 | C.2 |
| 1.575 | B.173 | C.2 |
| 1.576 | B.174 | C.2 |
| 1.577 | B.175 | C.2 |
| 1.578 | B.176 | C.2 |
| 1.579 | B.177 | C.2 |
| 1.580 | B.178 | C.2 |
| 1.581 | B.179 | C.2 |
| 1.582 | B.180 | C.2 |
| 1.583 | B.181 | C.2 |
| 1.584 | B.182 | C.2 |
| 1.585 | B.183 | C.2 |
| 1.586 | B.184 | C.2 |
| 1.587 | B.185 | C.2 |
| 1.588 | B.186 | C.2 |
| 1.589 | B.187 | C.2 |
| 1.590 | B.188 | C.2 |
| 1.591 | B.189 | C.2 |
| 1.592 | B.190 | C.2 |
| 1.593 | B.191 | C.2 |
| 1.594 | B.192 | C.2 |
| 1.595 | B.193 | C.2 |
| 1.596 | B.194 | C.2 |
| 1.597 | B.195 | C.2 |
| 1.598 | B.196 | C.2 |
| 1.599 | B.197 | C.2 |
| 1.600 | B.198 | C.2 |
| 1.601 | B.199 | C.2 |
| 1.602 | B.200 | C.2 |
| 1.603 | B.201 | C.2 |
| 1.604 | B.1 | C.3 |
| 1.605 | B.2 | C.3 |
| 1.606 | B.3 | C.3 |
| 1.607 | B.4 | C.3 |
| 1.608 | B.5 | C.3 |
| 1.609 | B.6 | C.3 |
| 1.610 | B.7 | C.3 |
| 1.611 | B.8 | C.3 |
| 1.612 | B.9 | C.3 |
| 1.613 | B.10 | C.3 |
| 1.614 | B.11 | C.3 |
| 1.615 | B.12 | C.3 |
| 1.616 | B.13 | C.3 |
| 1.617 | B.14 | C.3 |
| 1.618 | B.15 | C.3 |
| 1.619 | B.16 | C.3 |
| 1.620 | B.17 | C.3 |
| 1.621 | B.18 | C.3 |
| 1.622 | B.19 | C.3 |
| 1.623 | B.20 | C.3 |
| 1.624 | B.21 | C.3 |
| 1.625 | B.22 | C.3 |
| 1.626 | B.23 | C.3 |
| 1.627 | B.24 | C.3 |
| 1.628 | B.25 | C.3 |
| 1.629 | B.26 | C.3 |
| 1.630 | B.27 | C.3 |
| 1.631 | B.28 | C.3 |
| 1.632 | B.29 | C.3 |
| 1.633 | B.30 | C.3 |
| 1.634 | B.31 | C.3 |
| 1.635 | B.32 | C.3 |
| 1.636 | B.33 | C.3 |
| 1.637 | B.34 | C.3 |
| 1.638 | B.35 | C.3 |
| 1.639 | B.36 | C.3 |
| 1.640 | B.37 | C.3 |
| 1.641 | B.38 | C.3 |
| 1.642 | B.39 | C.3 |
| 1.643 | B.40 | C.3 |
| 1.644 | B.41 | C.3 |
| 1.645 | B.42 | C.3 |
| 1.646 | B.43 | C.3 |
| 1.647 | B.44 | C.3 |
| 1.648 | B.45 | C.3 |
| 1.649 | B.46 | C.3 |
| 1.650 | B.47 | C.3 |
| 1.651 | B.48 | C.3 |

TABLE 1-continued (compositions 1.1 to 1.3635):

| comp. no. | herbicide B | safener C |
|---|---|---|
| 1.652 | B.49 | C.3 |
| 1.653 | B.50 | C.3 |
| 1.654 | B.51 | C.3 |
| 1.655 | B.52 | C.3 |
| 1.656 | B.53 | C.3 |
| 1.657 | B.54 | C.3 |
| 1.658 | B.55 | C.3 |
| 1.659 | B.56 | C.3 |
| 1.660 | B.57 | C.3 |
| 1.661 | B.58. | C.3 |
| 1.662 | B.59 | C.3 |
| 1.663 | B.60 | C.3 |
| 1.664 | B.61 | C.3 |
| 1.665 | B.62 | C.3 |
| 1.666 | B.63 | C.3 |
| 1.667 | B.64 | C.3 |
| 1.668 | B.65 | C.3 |
| 1.669 | B.66 | C.3 |
| 1.670 | B.67 | C.3 |
| 1.671 | B.68 | C.3 |
| 1.672 | B.69 | C.3 |
| 1.673 | B.70 | C.3 |
| 1.674 | B.71 | C.3 |
| 1.675 | B.72 | C.3 |
| 1.676 | B.73 | C.3 |
| 1.677 | B.74 | C.3 |
| 1.678 | B.75 | C.3 |
| 1.679 | B.76 | C.3 |
| 1.680 | B.77 | C.3 |
| 1.681 | B.78 | C.3 |
| 1.682 | B.79 | C.3 |
| 1.683 | B.80 | C.3 |
| 1.684 | B.81 | C.3 |
| 1.685 | B.82 | C.3 |
| 1.686 | B.83 | C.3 |
| 1.687 | B.84 | C.3 |
| 1.688 | B.85 | C.3 |
| 1.689 | B.86 | C.3 |
| 1.690 | B.87 | C.3 |
| 1.691 | B.88 | C.3 |
| 1.692 | B.89 | C.3 |
| 1.693 | B.90 | C.3 |
| 1.694 | B.91 | C.3 |
| 1.695 | B.92 | C.3 |
| 1.696 | B.93 | C.3 |
| 1.697 | B.94 | C.3 |
| 1.698 | B.95 | C.3 |
| 1.699 | B.96 | C.3 |
| 1.700 | B.97 | C.3 |
| 1.701 | B.98 | C.3 |
| 1.702 | B.99 | C.3 |
| 1.703 | B.100 | C.3 |
| 1.704 | B.101 | C.3 |
| 1.705 | B.102 | C.3 |
| 1.706 | B.103 | C.3 |
| 1.707 | B.104 | C.3 |
| 1.708 | B.105 | C.3 |
| 1.709 | B.106 | C.3 |
| 1.710 | B.107 | C.3 |
| 1.711 | B.108 | C.3 |
| 1.712 | B.109 | C.3 |
| 1.713 | B.110 | C.3 |
| 1.714 | B.111 | C.3 |
| 1.715 | B.112 | C.3 |
| 1.716 | B.113 | C.3 |
| 1.717 | B.114 | C.3 |
| 1.718 | B.115 | C.3 |
| 1.719 | B.116 | C.3 |
| 1.720 | B.117 | C.3 |
| 1.721 | B.118 | C.3 |
| 1.722 | B.119 | C.3 |
| 1.723 | B.120 | C.3 |
| 1.724 | B.121 | C.3 |
| 1.725 | B.122 | C.3 |
| 1.726 | B.123 | C.3 |
| 1.727 | B.124 | C.3 |
| 1.728 | B.125 | C.3 |
| 1.729 | B.126 | C.3 |
| 1.730 | B.127 | C.3 |
| 1.731 | B.128 | C.3 |
| 1.732 | B.129 | C.3 |
| 1.733 | B.130 | C.3 |
| 1.734 | B.131 | C.3 |
| 1.735 | B.132 | C.3 |
| 1.736 | B.133 | C.3 |
| 1.737 | B.134 | C.3 |
| 1.738 | B.135 | C.3 |
| 1.739 | B.136 | C.3 |
| 1.740 | B.137 | C.3 |
| 1.741 | B.138 | C.3 |
| 1.742 | B.139 | C.3 |
| 1.743 | B.140 | C.3 |
| 1.744 | B.141 | C.3 |
| 1.745 | B.142 | C.3 |
| 1.746 | B.143 | C.3 |
| 1.747 | B.144 | C.3 |
| 1.748 | B.145 | C.3 |
| 1.749 | B.146 | C.3 |
| 1.750 | B.147 | C.3 |
| 1.751 | B.148 | C.3 |
| 1.752 | B.149 | C.3 |
| 1.753 | B.150 | C.3 |
| 1.754 | B.151 | C.3 |
| 1.755 | B.152 | C.3 |
| 1.756 | B.153 | C.3 |
| 1.757 | B.154 | C.3 |
| 1.758 | B.155 | C.3 |
| 1.759 | B.156 | C.3 |
| 1.760 | B.157 | C.3 |
| 1.761 | B.158 | C.3 |
| 1.762 | B.159 | C.3 |
| 1.763 | B.160 | C.3 |
| 1.764 | B.161 | C.3 |
| 1.765 | B.162 | C.3 |
| 1.766 | B.163 | C.3 |
| 1.767 | B.164 | C.3 |
| 1.768 | B.165 | C.3 |
| 1.769 | B.166 | C.3 |
| 1.770 | B.167 | C.3 |
| 1.771 | B.168 | C.3 |
| 1.772 | B.169 | C.3 |
| 1.773 | B.170 | C.3 |
| 1.774 | B.171 | C.3 |
| 1.775 | B.172 | C.3 |
| 1.776 | B.173 | C.3 |
| 1.777 | B.174 | C.3 |
| 1.778 | B.175 | C.3 |
| 1.779 | B.176 | C.3 |
| 1.780 | B.177 | C.3 |
| 1.781 | B.178 | C.3 |
| 1.782 | B.179 | C.3 |
| 1.783 | B.180 | C.3 |
| 1.784 | B.181 | C.3 |
| 1.785 | B.182 | C.3 |
| 1.786 | B.183 | C.3 |
| 1.787 | B.184 | C.3 |
| 1.788 | B.185 | C.3 |
| 1.789 | B.186 | C.3 |
| 1.790 | B.187 | C.3 |
| 1.791 | B.188 | C.3 |
| 1.792 | B.189 | C.3 |
| 1.793 | B.190 | C.3 |
| 1.794 | B.191 | C.3 |
| 1.795 | B.192 | C.3 |
| 1.796 | B.193 | C.3 |
| 1.797 | B.194 | C.3 |
| 1.798 | B.195 | C.3 |
| 1.799 | B.196 | C.3 |
| 1.800 | B.197 | C.3 |
| 1.801 | B.198 | C.3 |
| 1.802 | B.199 | C.3 |
| 1.803 | B.200 | C.3 |

TABLE 1-continued (compositions 1.1 to 1.3635):

| comp. no. | herbicide B | safener C |
|---|---|---|
| 1.804 | B.201 | C.3 |
| 1.805 | B.1 | C.4 |
| 1.806 | B.2 | C.4 |
| 1.807 | B.3 | C.4 |
| 1.808 | B.4 | C.4 |
| 1.809 | B.5 | C.4 |
| 1.810 | B.6 | C.4 |
| 1.811 | B.7 | C.4 |
| 1.812 | B.8 | C.4 |
| 1.813 | B.9 | C.4 |
| 1.814 | B.10 | C.4 |
| 1.815 | B.11 | C.4 |
| 1.816 | B.12 | C.4 |
| 1.817 | B.13 | C.4 |
| 1.818 | B.14 | C.4 |
| 1.819 | B.15 | C.4 |
| 1.820 | B.16 | C.4 |
| 1.821 | B.17 | C.4 |
| 1.822 | B.18 | C.4 |
| 1.823 | B.19 | C.4 |
| 1.824 | B.20 | C.4 |
| 1.825 | B.21 | C.4 |
| 1.826 | B.22 | C.4 |
| 1.827 | B.23 | C.4 |
| 1.828 | B.24 | C.4 |
| 1.829 | B.25 | C.4 |
| 1.830 | B.26 | C.4 |
| 1.831 | B.27 | C.4 |
| 1.832 | B.28 | C.4 |
| 1.833 | B.29 | C.4 |
| 1.834 | B.30 | C.4 |
| 1.835 | B.31 | C.4 |
| 1.836 | B.32 | C.4 |
| 1.837 | B.33 | C.4 |
| 1.838 | B.34 | C.4 |
| 1.839 | B.35 | C.4 |
| 1.840 | B.36 | C.4 |
| 1.841 | B.37 | C.4 |
| 1.842 | B.38 | C.4 |
| 1.843 | B.39 | C.4 |
| 1.844 | B.40 | C.4 |
| 1.845 | B.41 | C.4 |
| 1.846 | B.42 | C.4 |
| 1.847 | B.43 | C.4 |
| 1.848 | B.44 | C.4 |
| 1.849 | B.45 | C.4 |
| 1.850 | B.46 | C.4 |
| 1.851 | B.47 | C.4 |
| 1.852 | B.48 | C.4 |
| 1.853 | B.49 | C.4 |
| 1.854 | B.50 | C.4 |
| 1.855 | B.51 | C.4 |
| 1.856 | B.52 | C.4 |
| 1.857 | B.53 | C.4 |
| 1.858 | B.54 | C.4 |
| 1.859 | B.55 | C.4 |
| 1.860 | B.56 | C.4 |
| 1.861 | B.57 | C.4 |
| 1.862 | B.58. | C.4 |
| 1.863 | B.59 | C.4 |
| 1.864 | B.60 | C.4 |
| 1.865 | B.61 | C.4 |
| 1.866 | B.62 | C.4 |
| 1.867 | B.63 | C.4 |
| 1.868 | B.64 | C.4 |
| 1.869 | B.65 | C.4 |
| 1.870 | B.66 | C.4 |
| 1.871 | B.67 | C.4 |
| 1.872 | B.68 | C.4 |
| 1.873 | B.69 | C.4 |
| 1.874 | B.70 | C.4 |
| 1.875 | B.71 | C.4 |
| 1.876 | B.72 | C.4 |
| 1.877 | B.73 | C.4 |
| 1.878 | B.74 | C.4 |
| 1.879 | B.75 | C.4 |
| 1.880 | B.76 | C.4 |
| 1.881 | B.77 | C.4 |
| 1.882 | B.78 | C.4 |
| 1.883 | B.79 | C.4 |
| 1.884 | B.80 | C.4 |
| 1.885 | B.81 | C.4 |
| 1.886 | B.82 | C.4 |
| 1.887 | B.83 | C.4 |
| 1.888 | B.84 | C.4 |
| 1.889 | B.85 | C.4 |
| 1.890 | B.86 | C.4 |
| 1.891 | B.87 | C.4 |
| 1.892 | B.88 | C.4 |
| 1.893 | B.89 | C.4 |
| 1.894 | B.90 | C.4 |
| 1.895 | B.91 | C.4 |
| 1.896 | B.92 | C.4 |
| 1.897 | B.93 | C.4 |
| 1.898 | B.94 | C.4 |
| 1.899 | B.95 | C.4 |
| 1.900 | B.96 | C.4 |
| 1.901 | B.97 | C.4 |
| 1.902 | B.98 | C.4 |
| 1.903 | B.99 | C.4 |
| 1.904 | B.100 | C.4 |
| 1.905 | B.101 | C.4 |
| 1.906 | B.102 | C.4 |
| 1.907 | B.103 | C.4 |
| 1.908 | B.104 | C.4 |
| 1.909 | B.105 | C.4 |
| 1.910 | B.106 | C.4 |
| 1.911 | B.107 | C.4 |
| 1.912 | B.108 | C.4 |
| 1.913 | B.109 | C.4 |
| 1.914 | B.110 | C.4 |
| 1.915 | B.111 | C.4 |
| 1.916 | B.112 | C.4 |
| 1.917 | B.113 | C.4 |
| 1.918 | B.114 | C.4 |
| 1.919 | B.115 | C.4 |
| 1.920 | B.116 | C.4 |
| 1.921 | B.117 | C.4 |
| 1.922 | B.118 | C.4 |
| 1.923 | B.119 | C.4 |
| 1.924 | B.120 | C.4 |
| 1.925 | B.121 | C.4 |
| 1.926 | B.122 | C.4 |
| 1.927 | B.123 | C.4 |
| 1.928 | B.124 | C.4 |
| 1.929 | B.125 | C.4 |
| 1.930 | B.126 | C.4 |
| 1.931 | B.127 | C.4 |
| 1.932 | B.128 | C.4 |
| 1.933 | B.129 | C.4 |
| 1.934 | B.130 | C.4 |
| 1.935 | B.131 | C.4 |
| 1.936 | B.132 | C.4 |
| 1.937 | B.133 | C.4 |
| 1.938 | B.134 | C.4 |
| 1.939 | B.135 | C.4 |
| 1.940 | B.136 | C.4 |
| 1.941 | B.137 | C.4 |
| 1.942 | B.138 | C.4 |
| 1.943 | B.139 | C.4 |
| 1.944 | B.140 | C.4 |
| 1.945 | B.141 | C.4 |
| 1.946 | B.142 | C.4 |
| 1.947 | B.143 | C.4 |
| 1.948 | B.144 | C.4 |
| 1.949 | B.145 | C.4 |
| 1.950 | B.146 | C.4 |
| 1.951 | B.147 | C.4 |
| 1.952 | B.148 | C.4 |
| 1.953 | B.149 | C.4 |
| 1.954 | B.150 | C.4 |
| 1.955 | B.151 | C.4 |

TABLE 1-continued (compositions 1.1 to 1.3635):

| comp. no. | herbicide B | safener C |
|---|---|---|
| 1.956 | B.152 | C.4 |
| 1.957 | B.153 | C.4 |
| 1.958 | B.154 | C.4 |
| 1.959 | B.155 | C.4 |
| 1.960 | B.156 | C.4 |
| 1.961 | B.157 | C.4 |
| 1.962 | B.158 | C.4 |
| 1.963 | B.159 | C.4 |
| 1.964 | B.160 | C.4 |
| 1.965 | B.161 | C.4 |
| 1.966 | B.162 | C.4 |
| 1.967 | B.163 | C.4 |
| 1.968 | B.164 | C.4 |
| 1.969 | B.165 | C.4 |
| 1.970 | B.166 | C.4 |
| 1.971 | B.167 | C.4 |
| 1.972 | B.168 | C.4 |
| 1.973 | B.169 | C.4 |
| 1.974 | B.170 | C.4 |
| 1.975 | B.171 | C.4 |
| 1.976 | B.172 | C.4 |
| 1.977 | B.173 | C.4 |
| 1.978 | B.174 | C.4 |
| 1.979 | B.175 | C.4 |
| 1.980 | B.176 | C.4 |
| 1.981 | B.177 | C.4 |
| 1.982 | B.178 | C.4 |
| 1.983 | B.179 | C.4 |
| 1.984 | B.180 | C.4 |
| 1.985 | B.181 | C.4 |
| 1.986 | B.182 | C.4 |
| 1.987 | B.183 | C.4 |
| 1.988 | B.184 | C.4 |
| 1.989 | B.185 | C.4 |
| 1.990 | B.186 | C.4 |
| 1.991 | B.187 | C.4 |
| 1.992 | B.188 | C.4 |
| 1.993 | B.189 | C.4 |
| 1.994 | B.190 | C.4 |
| 1.995 | B.191 | C.4 |
| 1.996 | B.192 | C.4 |
| 1.997 | B.193 | C.4 |
| 1.998 | B.194 | C.4 |
| 1.999 | B.195 | C.4 |
| 1.1000 | B.196 | C.4 |
| 1.1001 | B.197 | C.4 |
| 1.1002 | B.198 | C.4 |
| 1.1003 | B.199 | C.4 |
| 1.1004 | B.200 | C.4 |
| 1.1005 | B.201 | C.4 |
| 1.1006 | B.1 | C.5 |
| 1.1007 | B.2 | C.5 |
| 1.1008 | B.3 | C.5 |
| 1.1009 | B.4 | C.5 |
| 1.1010 | B.5 | C.5 |
| 1.1011 | B.6 | C.5 |
| 1.1012 | B.7 | C.5 |
| 1.1013 | B.8 | C.5 |
| 1.1014 | B.9 | C.5 |
| 1.1015 | B.10 | C.5 |
| 1.1016 | B.11 | C.5 |
| 1.1017 | B.12 | C.5 |
| 1.1018 | B.13 | C.5 |
| 1.1019 | B.14 | C.5 |
| 1.1020 | B.15 | C.5 |
| 1.1021 | B.16 | C.5 |
| 1.1022 | B.17 | C.5 |
| 1.1023 | B.18 | C.5 |
| 1.1024 | B.19 | C.5 |
| 1.1025 | B.20 | C.5 |
| 1.1026 | B.21 | C.5 |
| 1.1027 | B.22 | C.5 |
| 1.1028 | B.23 | C.5 |
| 1.1029 | B.24 | C.5 |
| 1.1030 | B.25 | C.5 |
| 1.1031 | B.26 | C.5 |
| 1.1032 | B.27 | C.5 |
| 1.1033 | B.28 | C.5 |
| 1.1034 | B.29 | C.5 |
| 1.1035 | B.30 | C.5 |
| 1.1036 | B.31 | C.5 |
| 1.1037 | B.32 | C.5 |
| 1.1038 | B.33 | C.5 |
| 1.1039 | B.34 | C.5 |
| 1.1040 | B.35 | C.5 |
| 1.1041 | B.36 | C.5 |
| 1.1042 | B.37 | C.5 |
| 1.1043 | B.38 | C.5 |
| 1.1044 | B.39 | C.5 |
| 1.1045 | B.40 | C.5 |
| 1.1046 | B.41 | C.5 |
| 1.1047 | B.42 | C.5 |
| 1.1048 | B.43 | C.5 |
| 1.1049 | B.44 | C.5 |
| 1.1050 | B.45 | C.5 |
| 1.1051 | B.46 | C.5 |
| 1.1052 | B.47 | C.5 |
| 1.1053 | B.48 | C.5 |
| 1.1054 | B.49 | C.5 |
| 1.1055 | B.50 | C.5 |
| 1.1056 | B.51 | C.5 |
| 1.1057 | B.52 | C.5 |
| 1.1058 | B.53 | C.5 |
| 1.1059 | B.54 | C.5 |
| 1.1060 | B.55 | C.5 |
| 1.1061 | B.56 | C.5 |
| 1.1062 | B.57 | C.5 |
| 1.1063 | B.58. | C.5 |
| 1.1064 | B.59 | C.5 |
| 1.1065 | B.60 | C.5 |
| 1.1066 | B.61 | C.5 |
| 1.1067 | B.62 | C.5 |
| 1.1068 | B.63 | C.5 |
| 1.1069 | B.64 | C.5 |
| 1.1070 | B.65 | C.5 |
| 1.1071 | B.66 | C.5 |
| 1.1072 | B.67 | C.5 |
| 1.1073 | B.68 | C.5 |
| 1.1074 | B.69 | C.5 |
| 1.1075 | B.70 | C.5 |
| 1.1076 | B.71 | C.5 |
| 1.1077 | B.72 | C.5 |
| 1.1078 | B.73 | C.5 |
| 1.1079 | B.74 | C.5 |
| 1.1080 | B.75 | C.5 |
| 1.1081 | B.76 | C.5 |
| 1.1082 | B.77 | C.5 |
| 1.1083 | B.78 | C.5 |
| 1.1084 | B.79 | C.5 |
| 1.1085 | B.80 | C.5 |
| 1.1086 | B.81 | C.5 |
| 1.1087 | B.82 | C.5 |
| 1.1088 | B.83 | C.5 |
| 1.1089 | B.84 | C.5 |
| 1.1090 | B.85 | C.5 |
| 1.1091 | B.86 | C.5 |
| 1.1092 | B.87 | C.5 |
| 1.1093 | B.88 | C.5 |
| 1.1094 | B.89 | C.5 |
| 1.1095 | B.90 | C.5 |
| 1.1096 | B.91 | C.5 |
| 1.1097 | B.92 | C.5 |
| 1.1098 | B.93 | C.5 |
| 1.1099 | B.94 | C.5 |
| 1.1100 | B.95 | C.5 |
| 1.1101 | B.96 | C.5 |
| 1.1102 | B.97 | C.5 |
| 1.1103 | B.98 | C.5 |
| 1.1104 | B.99 | C.5 |
| 1.1105 | B.100 | C.5 |
| 1.1106 | B.101 | C.5 |
| 1.1107 | B.102 | C.5 |

TABLE 1-continued (compositions 1.1 to 1.3635):

| comp. no. | herbicide B | safener C |
|---|---|---|
| 1.1108 | B.103 | C.5 |
| 1.1109 | B.104 | C.5 |
| 1.1110 | B.105 | C.5 |
| 1.1111 | B.106 | C.5 |
| 1.1112 | B.107 | C.5 |
| 1.1113 | B.108 | C.5 |
| 1.1114 | B.109 | C.5 |
| 1.1115 | B.110 | C.5 |
| 1.1116 | B.111 | C.5 |
| 1.1117 | B.112 | C.5 |
| 1.1118 | B.113 | C.5 |
| 1.1119 | B.114 | C.5 |
| 1.1120 | B.115 | C.5 |
| 1.1121 | B.116 | C.5 |
| 1.1122 | B.117 | C.5 |
| 1.1123 | B.118 | C.5 |
| 1.1124 | B.119 | C.5 |
| 1.1125 | B.120 | C.5 |
| 1.1126 | B.121 | C.5 |
| 1.1127 | B.122 | C.5 |
| 1.1128 | B.123 | C.5 |
| 1.1129 | B.124 | C.5 |
| 1.1130 | B.125 | C.5 |
| 1.1131 | B.126 | C.5 |
| 1.1132 | B.127 | C.5 |
| 1.1133 | B.128 | C.5 |
| 1.1134 | B.129 | C.5 |
| 1.1135 | B.130 | C.5 |
| 1.1136 | B.131 | C.5 |
| 1.1137 | B.132 | C.5 |
| 1.1138 | B.133 | C.5 |
| 1.1139 | B.134 | C.5 |
| 1.1140 | B.135 | C.5 |
| 1.1141 | B.136 | C.5 |
| 1.1142 | B.137 | C.5 |
| 1.1143 | B.138 | C.5 |
| 1.1144 | B.139 | C.5 |
| 1.1145 | B.140 | C.5 |
| 1.1146 | B.141 | C.5 |
| 1.1147 | B.142 | C.5 |
| 1.1148 | B.143 | C.5 |
| 1.1149 | B.144 | C.5 |
| 1.1150 | B.145 | C.5 |
| 1.1151 | B.146 | C.5 |
| 1.1152 | B.147 | C.5 |
| 1.1153 | B.148 | C.5 |
| 1.1154 | B.149 | C.5 |
| 1.1155 | B.150 | C.5 |
| 1.1156 | B.151 | C.5 |
| 1.1157 | B.152 | C.5 |
| 1.1158 | B.153 | C.5 |
| 1.1159 | B.154 | C.5 |
| 1.1160 | B.155 | C.5 |
| 1.1161 | B.156 | C.5 |
| 1.1162 | B.157 | C.5 |
| 1.1163 | B.158 | C.5 |
| 1.1164 | B.159 | C.5 |
| 1.1165 | B.160 | C.5 |
| 1.1166 | B.161 | C.5 |
| 1.1167 | B.162 | C.5 |
| 1.1168 | B.163 | C.5 |
| 1.1169 | B.164 | C.5 |
| 1.1170 | B.165 | C.5 |
| 1.1171 | B.166 | C.5 |
| 1.1172 | B.167 | C.5 |
| 1.1173 | B.168 | C.5 |
| 1.1174 | B.169 | C.5 |
| 1.1175 | B.170 | C.5 |
| 1.1176 | B.171 | C.5 |
| 1.1177 | B.172 | C.5 |
| 1.1178 | B.173 | C.5 |
| 1.1179 | B.174 | C.5 |
| 1.1180 | B.175 | C.5 |
| 1.1181 | B.176 | C.5 |
| 1.1182 | B.177 | C.5 |
| 1.1183 | B.178 | C.5 |
| 1.1184 | B.179 | C.5 |
| 1.1185 | B.180 | C.5 |
| 1.1186 | B.181 | C.5 |
| 1.1187 | B.182 | C.5 |
| 1.1188 | B.183 | C.5 |
| 1.1189 | B.184 | C.5 |
| 1.1190 | B.185 | C.5 |
| 1.1191 | B.186 | C.5 |
| 1.1192 | B.187 | C.5 |
| 1.1193 | B.188 | C.5 |
| 1.1194 | B.189 | C.5 |
| 1.1195 | B.190 | C.5 |
| 1.1196 | B.191 | C.5 |
| 1.1197 | B.192 | C.5 |
| 1.1198 | B.193 | C.5 |
| 1.1199 | B.194 | C.5 |
| 1.1200 | B.195 | C.5 |
| 1.1201 | B.196 | C.5 |
| 1.1202 | B.197 | C.5 |
| 1.1203 | B.198 | C.5 |
| 1.1204 | B.199 | C.5 |
| 1.1205 | B.200 | C.5 |
| 1.1206 | B.201 | C.5 |
| 1.1207 | B.1 | C.6 |
| 1.1208 | B.2 | C.6 |
| 1.1209 | B.3 | C.6 |
| 1.1210 | B.4 | C.6 |
| 1.1211 | B.5 | C.6 |
| 1.1212 | B.6 | C.6 |
| 1.1213 | B.7 | C.6 |
| 1.1214 | B.8 | C.6 |
| 1.1215 | B.9 | C.6 |
| 1.1216 | B.10 | C.6 |
| 1.1217 | B.11 | C.6 |
| 1.1218 | B.12 | C.6 |
| 1.1219 | B.13 | C.6 |
| 1.1220 | B.14 | C.6 |
| 1.1221 | B.15 | C.6 |
| 1.1222 | B.16 | C.6 |
| 1.1223 | B.17 | C.6 |
| 1.1224 | B.18 | C.6 |
| 1.1225 | B.19 | C.6 |
| 1.1226 | B.20 | C.6 |
| 1.1227 | B.21 | C.6 |
| 1.1228 | B.22 | C.6 |
| 1.1229 | B.23 | C.6 |
| 1.1230 | B.24 | C.6 |
| 1.1231 | B.25 | C.6 |
| 1.1232 | B.26 | C.6 |
| 1.1233 | B.27 | C.6 |
| 1.1234 | B.28 | C.6 |
| 1.1235 | B.29 | C.6 |
| 1.1236 | B.30 | C.6 |
| 1.1237 | B.31 | C.6 |
| 1.1238 | B.32 | C.6 |
| 1.1239 | B.33 | C.6 |
| 1.1240 | B.34 | C.6 |
| 1.1241 | B.35 | C.6 |
| 1.1242 | B.36 | C.6 |
| 1.1243 | B.37 | C.6 |
| 1.1244 | B.38 | C.6 |
| 1.1245 | B.39 | C.6 |
| 1.1246 | B.40 | C.6 |
| 1.1247 | B.41 | C.6 |
| 1.1248 | B.42 | C.6 |
| 1.1249 | B.43 | C.6 |
| 1.1250 | B.44 | C.6 |
| 1.1251 | B.45 | C.6 |
| 1.1252 | B.46 | C.6 |
| 1.1253 | B.47 | C.6 |
| 1.1254 | B.48 | C.6 |
| 1.1255 | B.49 | C.6 |
| 1.1256 | B.50 | C.6 |
| 1.1257 | B.51 | C.6 |
| 1.1258 | B.52 | C.6 |
| 1.1259 | B.53 | C.6 |

TABLE 1-continued (compositions 1.1 to 1.3635):

| comp. no. | herbicide B | safener C |
|---|---|---|
| 1.1260 | B.54 | C.6 |
| 1.1261 | B.55 | C.6 |
| 1.1262 | B.56 | C.6 |
| 1.1263 | B.57 | C.6 |
| 1.1264 | B.58. | C.6 |
| 1.1265 | B.59 | C.6 |
| 1.1266 | B.60 | C.6 |
| 1.1267 | B.61 | C.6 |
| 1.1268 | B.62 | C.6 |
| 1.1269 | B.63 | C.6 |
| 1.1270 | B.64 | C.6 |
| 1.1271 | B.65 | C.6 |
| 1.1272 | B.66 | C.6 |
| 1.1273 | B.67 | C.6 |
| 1.1274 | B.68 | C.6 |
| 1.1275 | B.69 | C.6 |
| 1.1276 | B.70 | C.6 |
| 1.1277 | B.71 | C.6 |
| 1.1278 | B.72 | C.6 |
| 1.1279 | B.73 | C.6 |
| 1.1280 | B.74 | C.6 |
| 1.1281 | B.75 | C.6 |
| 1.1282 | B.76 | C.6 |
| 1.1283 | B.77 | C.6 |
| 1.1284 | B.78 | C.6 |
| 1.1285 | B.79 | C.6 |
| 1.1286 | B.80 | C.6 |
| 1.1287 | B.81 | C.6 |
| 1.1288 | B.82 | C.6 |
| 1.1289 | B.83 | C.6 |
| 1.1290 | B.84 | C.6 |
| 1.1291 | B.85 | C.6 |
| 1.1292 | B.86 | C.6 |
| 1.1293 | B.87 | C.6 |
| 1.1294 | B.88 | C.6 |
| 1.1295 | B.89 | C.6 |
| 1.1296 | B.90 | C.6 |
| 1.1297 | B.91 | C.6 |
| 1.1298 | B.92 | C.6 |
| 1.1299 | B.93 | C.6 |
| 1.1300 | B.94 | C.6 |
| 1.1301 | B.95 | C.6 |
| 1.1302 | B.96 | C.6 |
| 1.1303 | B.97 | C.6 |
| 1.1304 | B.98 | C.6 |
| 1.1305 | B.99 | C.6 |
| 1.1306 | B.100 | C.6 |
| 1.1307 | B.101 | C.6 |
| 1.1308 | B.102 | C.6 |
| 1.1309 | B.103 | C.6 |
| 1.1310 | B.104 | C.6 |
| 1.1311 | B.105 | C.6 |
| 1.1312 | B.106 | C.6 |
| 1.1313 | B.107 | C.6 |
| 1.1314 | B.108 | C.6 |
| 1.1315 | B.109 | C.6 |
| 1.1316 | B.110 | C.6 |
| 1.1317 | B.111 | C.6 |
| 1.1318 | B.112 | C.6 |
| 1.1319 | B.113 | C.6 |
| 1.1320 | B.114 | C.6 |
| 1.1321 | B.115 | C.6 |
| 1.1322 | B.116 | C.6 |
| 1.1323 | B.117 | C.6 |
| 1.1324 | B.118 | C.6 |
| 1.1325 | B.119 | C.6 |
| 1.1326 | B.120 | C.6 |
| 1.1327 | B.121 | C.6 |
| 1.1328 | B.122 | C.6 |
| 1.1329 | B.123 | C.6 |
| 1.1330 | B.124 | C.6 |
| 1.1331 | B.125 | C.6 |
| 1.1332 | B.126 | C.6 |
| 1.1333 | B.127 | C.6 |
| 1.1334 | B.128 | C.6 |
| 1.1335 | B.129 | C.6 |
| 1.1336 | B.130 | C.6 |
| 1.1337 | B.131 | C.6 |
| 1.1338 | B.132 | C.6 |
| 1.1339 | B.133 | C.6 |
| 1.1340 | B.134 | C.6 |
| 1.1341 | B.135 | C.6 |
| 1.1342 | B.136 | C.6 |
| 1.1343 | B.137 | C.6 |
| 1.1344 | B.138 | C.6 |
| 1.1345 | B.139 | C.6 |
| 1.1346 | B.140 | C.6 |
| 1.1347 | B.141 | C.6 |
| 1.1348 | B.142 | C.6 |
| 1.1349 | B.143 | C.6 |
| 1.1350 | B.144 | C.6 |
| 1.1351 | B.145 | C.6 |
| 1.1352 | B.146 | C.6 |
| 1.1353 | B.147 | C.6 |
| 1.1354 | B.148 | C.6 |
| 1.1355 | B.149 | C.6 |
| 1.1356 | B.150 | C.6 |
| 1.1357 | B.151 | C.6 |
| 1.1358 | B.152 | C.6 |
| 1.1359 | B.153 | C.6 |
| 1.1360 | B.154 | C.6 |
| 1.1361 | B.155 | C.6 |
| 1.1362 | B.156 | C.6 |
| 1.1363 | B.157 | C.6 |
| 1.1364 | B.158 | C.6 |
| 1.1365 | B.159 | C.6 |
| 1.1366 | B.160 | C.6 |
| 1.1367 | B.161 | C.6 |
| 1.1368 | B.162 | C.6 |
| 1.1369 | B.163 | C.6 |
| 1.1370 | B.164 | C.6 |
| 1.1371 | B.165 | C.6 |
| 1.1372 | B.166 | C.6 |
| 1.1373 | B.167 | C.6 |
| 1.1374 | B.168 | C.6 |
| 1.1375 | B.169 | C.6 |
| 1.1376 | B.170 | C.6 |
| 1.1377 | B.171 | C.6 |
| 1.1378 | B.172 | C.6 |
| 1.1379 | B.173 | C.6 |
| 1.1380 | B.174 | C.6 |
| 1.1381 | B.175 | C.6 |
| 1.1382 | B.176 | C.6 |
| 1.1383 | B.177 | C.6 |
| 1.1384 | B.178 | C.6 |
| 1.1385 | B.179 | C.6 |
| 1.1386 | B.180 | C.6 |
| 1.1387 | B.181 | C.6 |
| 1.1388 | B.182 | C.6 |
| 1.1389 | B.183 | C.6 |
| 1.1390 | B.184 | C.6 |
| 1.1391 | B.185 | C.6 |
| 1.1392 | B.186 | C.6 |
| 1.1393 | B.187 | C.6 |
| 1.1394 | B.188 | C.6 |
| 1.1395 | B.189 | C.6 |
| 1.1396 | B.190 | C.6 |
| 1.1397 | B.191 | C.6 |
| 1.1398 | B.192 | C.6 |
| 1.1399 | B.193 | C.6 |
| 1.1400 | B.194 | C.6 |
| 1.1401 | B.195 | C.6 |
| 1.1402 | B.196 | C.6 |
| 1.1403 | B.197 | C.6 |
| 1.1404 | B.198 | C.6 |
| 1.1405 | B.199 | C.6 |
| 1.1406 | B.200 | C.6 |
| 1.1407 | B.201 | C.6 |
| 1.1408 | B.1 | C.7 |
| 1.1409 | B.2 | C.7 |
| 1.1410 | B.3 | C.7 |
| 1.1411 | B.4 | C.7 |

TABLE 1-continued (compositions 1.1 to 1.3635):

| comp. no. | herbicide B | safener C |
|---|---|---|
| 1.1412 | B.5 | C.7 |
| 1.1413 | B.6 | C.7 |
| 1.1414 | B.7 | C.7 |
| 1.1415 | B.8 | C.7 |
| 1.1416 | B.9 | C.7 |
| 1.1417 | B.10 | C.7 |
| 1.1418 | B.11 | C.7 |
| 1.1419 | B.12 | C.7 |
| 1.1420 | B.13 | C.7 |
| 1.1421 | B.14 | C.7 |
| 1.1422 | B.15 | C.7 |
| 1.1423 | B.16 | C.7 |
| 1.1424 | B.17 | C.7 |
| 1.1425 | B.18 | C.7 |
| 1.1426 | B.19 | C.7 |
| 1.1427 | B.20 | C.7 |
| 1.1428 | B.21 | C.7 |
| 1.1429 | B.22 | C.7 |
| 1.1430 | B.23 | C.7 |
| 1.1431 | B.24 | C.7 |
| 1.1432 | B.25 | C.7 |
| 1.1433 | B.26 | C.7 |
| 1.1434 | B.27 | C.7 |
| 1.1435 | B.28 | C.7 |
| 1.1436 | B.29 | C.7 |
| 1.1437 | B.30 | C.7 |
| 1.1438 | B.31 | C.7 |
| 1.1439 | B.32 | C.7 |
| 1.1440 | B.33 | C.7 |
| 1.1441 | B.34 | C.7 |
| 1.1442 | B.35 | C.7 |
| 1.1443 | B.36 | C.7 |
| 1.1444 | B.37 | C.7 |
| 1.1445 | B.38 | C.7 |
| 1.1446 | B.39 | C.7 |
| 1.1447 | B.40 | C.7 |
| 1.1448 | B.41 | C.7 |
| 1.1449 | B.42 | C.7 |
| 1.1450 | B.43 | C.7 |
| 1.1451 | B.44 | C.7 |
| 1.1452 | B.45 | C.7 |
| 1.1453 | B.46 | C.7 |
| 1.1454 | B.47 | C.7 |
| 1.1455 | B.48 | C.7 |
| 1.1456 | B.49 | C.7 |
| 1.1457 | B.50 | C.7 |
| 1.1458 | B.51 | C.7 |
| 1.1459 | B.52 | C.7 |
| 1.1460 | B.53 | C.7 |
| 1.1461 | B.54 | C.7 |
| 1.1462 | B.55 | C.7 |
| 1.1463 | B.56 | C.7 |
| 1.1464 | B.57 | C.7 |
| 1.1465 | B.58. | C.7 |
| 1.1466 | B.59 | C.7 |
| 1.1467 | B.60 | C.7 |
| 1.1468 | B.61 | C.7 |
| 1.1469 | B.62 | C.7 |
| 1.1470 | B.63 | C.7 |
| 1.1471 | B.64 | C.7 |
| 1.1472 | B.65 | C.7 |
| 1.1473 | B.66 | C.7 |
| 1.1474 | B.67 | C.7 |
| 1.1475 | B.68 | C.7 |
| 1.1476 | B.69 | C.7 |
| 1.1477 | B.70 | C.7 |
| 1.1478 | B.71 | C.7 |
| 1.1479 | B.72 | C.7 |
| 1.1480 | B.73 | C.7 |
| 1.1481 | B.74 | C.7 |
| 1.1482 | B.75 | C.7 |
| 1.1483 | B.76 | C.7 |
| 1.1484 | B.77 | C.7 |
| 1.1485 | B.78 | C.7 |
| 1.1486 | B.79 | C.7 |
| 1.1487 | B.80 | C.7 |
| 1.1488 | B.81 | C.7 |
| 1.1489 | B.82 | C.7 |
| 1.1490 | B.83 | C.7 |
| 1.1491 | B.84 | C.7 |
| 1.1492 | B.85 | C.7 |
| 1.1493 | B.86 | C.7 |
| 1.1494 | B.87 | C.7 |
| 1.1495 | B.88 | C.7 |
| 1.1496 | B.89 | C.7 |
| 1.1497 | B.90 | C.7 |
| 1.1498 | B.91 | C.7 |
| 1.1499 | B.92 | C.7 |
| 1.1500 | B.93 | C.7 |
| 1.1501 | B.94 | C.7 |
| 1.1502 | B.95 | C.7 |
| 1.1503 | B.96 | C.7 |
| 1.1504 | B.97 | C.7 |
| 1.1505 | B.98 | C.7 |
| 1.1506 | B.99 | C.7 |
| 1.1507 | B.100 | C.7 |
| 1.1508 | B.101 | C.7 |
| 1.1509 | B.102 | C.7 |
| 1.1510 | B.103 | C.7 |
| 1.1511 | B.104 | C.7 |
| 1.1512 | B.105 | C.7 |
| 1.1513 | B.106 | C.7 |
| 1.1514 | B.107 | C.7 |
| 1.1515 | B.108 | C.7 |
| 1.1516 | B.109 | C.7 |
| 1.1517 | B.110 | C.7 |
| 1.1518 | B.111 | C.7 |
| 1.1519 | B.112 | C.7 |
| 1.1520 | B.113 | C.7 |
| 1.1521 | B.114 | C.7 |
| 1.1522 | B.115 | C.7 |
| 1.1523 | B.116 | C.7 |
| 1.1524 | B.117 | C.7 |
| 1.1525 | B.118 | C.7 |
| 1.1526 | B.119 | C.7 |
| 1.1527 | B.120 | C.7 |
| 1.1528 | B.121 | C.7 |
| 1.1529 | B.122 | C.7 |
| 1.1530 | B.123 | C.7 |
| 1.1531 | B.124 | C.7 |
| 1.1532 | B.125 | C.7 |
| 1.1533 | B.126 | C.7 |
| 1.1534 | B.127 | C.7 |
| 1.1535 | B.128 | C.7 |
| 1.1536 | B.129 | C.7 |
| 1.1537 | B.130 | C.7 |
| 1.1538 | B.131 | C.7 |
| 1.1539 | B.132 | C.7 |
| 1.1540 | B.133 | C.7 |
| 1.1541 | B.134 | C.7 |
| 1.1542 | B.135 | C.7 |
| 1.1543 | B.136 | C.7 |
| 1.1544 | B.137 | C.7 |
| 1.1545 | B.138 | C.7 |
| 1.1546 | B.139 | C.7 |
| 1.1547 | B.140 | C.7 |
| 1.1548 | B.141 | C.7 |
| 1.1549 | B.142 | C.7 |
| 1.1550 | B.143 | C.7 |
| 1.1551 | B.144 | C.7 |
| 1.1552 | B.145 | C.7 |
| 1.1553 | B.146 | C.7 |
| 1.1554 | B.147 | C.7 |
| 1.1555 | B.148 | C.7 |
| 1.1556 | B.149 | C.7 |
| 1.1557 | B.150 | C.7 |
| 1.1558 | B.151 | C.7 |
| 1.1559 | B.152 | C.7 |
| 1.1560 | B.153 | C.7 |
| 1.1561 | B.154 | C.7 |
| 1.1562 | B.155 | C.7 |
| 1.1563 | B.156 | C.7 |

TABLE 1-continued (compositions 1.1 to 1.3635):

| comp. no. | herbicide B | safener C |
|---|---|---|
| 1.1564 | B.157 | C.7 |
| 1.1565 | B.158 | C.7 |
| 1.1566 | B.159 | C.7 |
| 1.1567 | B.160 | C.7 |
| 1.1568 | B.161 | C.7 |
| 1.1569 | B.162 | C.7 |
| 1.1570 | B.163 | C.7 |
| 1.1571 | B.164 | C.7 |
| 1.1572 | B.165 | C.7 |
| 1.1573 | B.166 | C.7 |
| 1.1574 | B.167 | C.7 |
| 1.1575 | B.168 | C.7 |
| 1.1576 | B.169 | C.7 |
| 1.1577 | B.170 | C.7 |
| 1.1578 | B.171 | C.7 |
| 1.1579 | B.172 | C.7 |
| 1.1580 | B.173 | C.7 |
| 1.1581 | B.174 | C.7 |
| 1.1582 | B.175 | C.7 |
| 1.1583 | B.176 | C.7 |
| 1.1584 | B.177 | C.7 |
| 1.1585 | B.178 | C.7 |
| 1.1586 | B.179 | C.7 |
| 1.1587 | B.180 | C.7 |
| 1.1588 | B.181 | C.7 |
| 1.1589 | B.182 | C.7 |
| 1.1590 | B.183 | C.7 |
| 1.1591 | B.184 | C.7 |
| 1.1592 | B.185 | C.7 |
| 1.1593 | B.186 | C.7 |
| 1.1594 | B.187 | C.7 |
| 1.1595 | B.188 | C.7 |
| 1.1596 | B.189 | C.7 |
| 1.1597 | B.190 | C.7 |
| 1.1598 | B.191 | C.7 |
| 1.1599 | B.192 | C.7 |
| 1.1600 | B.193 | C.7 |
| 1.1601 | B.194 | C.7 |
| 1.1602 | B.195 | C.7 |
| 1.1603 | B.196 | C.7 |
| 1.1604 | B.197 | C.7 |
| 1.1605 | B.198 | C.7 |
| 1.1606 | B.199 | C.7 |
| 1.1607 | B.200 | C.7 |
| 1.1608 | B.201 | C.7 |
| 1.1609 | B.1 | C.8 |
| 1.1610 | B.2 | C.8 |
| 1.1611 | B.3 | C.8 |
| 1.1612 | B.4 | C.8 |
| 1.1613 | B.5 | C.8 |
| 1.1614 | B.6 | C.8 |
| 1.1615 | B.7 | C.8 |
| 1.1616 | B.8 | C.8 |
| 1.1617 | B.9 | C.8 |
| 1.1618 | B.10 | C.8 |
| 1.1619 | B.11 | C.8 |
| 1.1620 | B.12 | C.8 |
| 1.1621 | B.13 | C.8 |
| 1.1622 | B.14 | C.8 |
| 1.1623 | B.15 | C.8 |
| 1.1624 | B.16 | C.8 |
| 1.1625 | B.17 | C.8 |
| 1.1626 | B.18 | C.8 |
| 1.1627 | B.19 | C.8 |
| 1.1628 | B.20 | C.8 |
| 1.1629 | B.21 | C.8 |
| 1.1630 | B.22 | C.8 |
| 1.1631 | B.23 | C.8 |
| 1.1632 | B.24 | C.8 |
| 1.1633 | B.25 | C.8 |
| 1.1634 | B.26 | C.8 |
| 1.1635 | B.27 | C.8 |
| 1.1636 | B.28 | C.8 |
| 1.1637 | B.29 | C.8 |
| 1.1638 | B.30 | C.8 |
| 1.1639 | B.31 | C.8 |
| 1.1640 | B.32 | C.8 |
| 1.1641 | B.33 | C.8 |
| 1.1642 | B.34 | C.8 |
| 1.1643 | B.35 | C.8 |
| 1.1644 | B.36 | C.8 |
| 1.1645 | B.37 | C.8 |
| 1.1646 | B.38 | C.8 |
| 1.1647 | B.39 | C.8 |
| 1.1648 | B.40 | C.8 |
| 1.1649 | B.41 | C.8 |
| 1.1650 | B.42 | C.8 |
| 1.1651 | B.43 | C.8 |
| 1.1652 | B.44 | C.8 |
| 1.1653 | B.45 | C.8 |
| 1.1654 | B.46 | C.8 |
| 1.1655 | B.47 | C.8 |
| 1.1656 | B.48 | C.8 |
| 1.1657 | B.49 | C.8 |
| 1.1658 | B.50 | C.8 |
| 1.1659 | B.51 | C.8 |
| 1.1660 | B.52 | C.8 |
| 1.1661 | B.53 | C.8 |
| 1.1662 | B.54 | C.8 |
| 1.1663 | B.55 | C.8 |
| 1.1664 | B.56 | C.8 |
| 1.1665 | B.57 | C.8 |
| 1.1666 | B.58. | C.8 |
| 1.1667 | B.59 | C.8 |
| 1.1668 | B.60 | C.8 |
| 1.1669 | B.61 | C.8 |
| 1.1670 | B.62 | C.8 |
| 1.1671 | B.63 | C.8 |
| 1.1672 | B.64 | C.8 |
| 1.1673 | B.65 | C.8 |
| 1.1674 | B.66 | C.8 |
| 1.1675 | B.67 | C.8 |
| 1.1676 | B.68 | C.8 |
| 1.1677 | B.69 | C.8 |
| 1.1678 | B.70 | C.8 |
| 1.1679 | B.71 | C.8 |
| 1.1680 | B.72 | C.8 |
| 1.1681 | B.73 | C.8 |
| 1.1682 | B.74 | C.8 |
| 1.1683 | B.75 | C.8 |
| 1.1684 | B.76 | C.8 |
| 1.1685 | B.77 | C.8 |
| 1.1686 | B.78 | C.8 |
| 1.1687 | B.79 | C.8 |
| 1.1688 | B.80 | C.8 |
| 1.1689 | B.81 | C.8 |
| 1.1690 | B.82 | C.8 |
| 1.1691 | B.83 | C.8 |
| 1.1692 | B.84 | C.8 |
| 1.1693 | B.85 | C.8 |
| 1.1694 | B.86 | C.8 |
| 1.1695 | B.87 | C.8 |
| 1.1696 | B.88 | C.8 |
| 1.1697 | B.89 | C.8 |
| 1.1698 | B.90 | C.8 |
| 1.1699 | B.91 | C.8 |
| 1.1700 | B.92 | C.8 |
| 1.1701 | B.93 | C.8 |
| 1.1702 | B.94 | C.8 |
| 1.1703 | B.95 | C.8 |
| 1.1704 | B.96 | C.8 |
| 1.1705 | B.97 | C.8 |
| 1.1706 | B.98 | C.8 |
| 1.1707 | B.99 | C.8 |
| 1.1708 | B.100 | C.8 |
| 1.1709 | B.101 | C.8 |
| 1.1710 | B.102 | C.8 |
| 1.1711 | B.103 | C.8 |
| 1.1712 | B.104 | C.8 |
| 1.1713 | B.105 | C.8 |
| 1.1714 | B.106 | C.8 |
| 1.1715 | B.107 | C.8 |

TABLE 1-continued (compositions 1.1 to 1.3635):

| comp. no. | herbicide B | safener C |
|---|---|---|
| 1.1716 | B.108 | C.8 |
| 1.1717 | B.109 | C.8 |
| 1.1718 | B.110 | C.8 |
| 1.1719 | B.111 | C.8 |
| 1.1720 | B.112 | C.8 |
| 1.1721 | B.113 | C.8 |
| 1.1722 | B.114 | C.8 |
| 1.1723 | B.115 | C.8 |
| 1.1724 | B.116 | C.8 |
| 1.1725 | B.117 | C.8 |
| 1.1726 | B.118 | C.8 |
| 1.1727 | B.119 | C.8 |
| 1.1728 | B.120 | C.8 |
| 1.1729 | B.121 | C.8 |
| 1.1730 | B.122 | C.8 |
| 1.1731 | B.123 | C.8 |
| 1.1732 | B.124 | C.8 |
| 1.1733 | B.125 | C.8 |
| 1.1734 | B.126 | C.8 |
| 1.1735 | B.127 | C.8 |
| 1.1736 | B.128 | C.8 |
| 1.1737 | B.129 | C.8 |
| 1.1738 | B.130 | C.8 |
| 1.1739 | B.131 | C.8 |
| 1.1740 | B.132 | C.8 |
| 1.1741 | B.133 | C.8 |
| 1.1742 | B.134 | C.8 |
| 1.1743 | B.135 | C.8 |
| 1.1744 | B.136 | C.8 |
| 1.1745 | B.137 | C.8 |
| 1.1746 | B.138 | C.8 |
| 1.1747 | B.139 | C.8 |
| 1.1748 | B.140 | C.8 |
| 1.1749 | B.141 | C.8 |
| 1.1750 | B.142 | C.8 |
| 1.1751 | B.143 | C.8 |
| 1.1752 | B.144 | C.8 |
| 1.1753 | B.145 | C.8 |
| 1.1754 | B.146 | C.8 |
| 1.1755 | B.147 | C.8 |
| 1.1756 | B.148 | C.8 |
| 1.1757 | B.149 | C.8 |
| 1.1758 | B.150 | C.8 |
| 1.1759 | B.151 | C.8 |
| 1.1760 | B.152 | C.8 |
| 1.1761 | B.153 | C.8 |
| 1.1762 | B.154 | C.8 |
| 1.1763 | B.155 | C.8 |
| 1.1764 | B.156 | C.8 |
| 1.1765 | B.157 | C.8 |
| 1.1766 | B.158 | C.8 |
| 1.1767 | B.159 | C.8 |
| 1.1768 | B.160 | C.8 |
| 1.1769 | B.161 | C.8 |
| 1.1770 | B.162 | C.8 |
| 1.1771 | B.163 | C.8 |
| 1.1772 | B.164 | C.8 |
| 1.1773 | B.165 | C.8 |
| 1.1774 | B.166 | C.8 |
| 1.1775 | B.167 | C.8 |
| 1.1776 | B.168 | C.8 |
| 1.1777 | B.169 | C.8 |
| 1.1778 | B.170 | C.8 |
| 1.1779 | B.171 | C.8 |
| 1.1780 | B.172 | C.8 |
| 1.1781 | B.173 | C.8 |
| 1.1782 | B.174 | C.8 |
| 1.1783 | B.175 | C.8 |
| 1.1784 | B.176 | C.8 |
| 1.1785 | B.177 | C.8 |
| 1.1786 | B.178 | C.8 |
| 1.1787 | B.179 | C.8 |
| 1.1788 | B.180 | C.8 |
| 1.1789 | B.181 | C.8 |
| 1.1790 | B.182 | C.8 |
| 1.1791 | B.183 | C.8 |
| 1.1792 | B.184 | C.8 |
| 1.1793 | B.185 | C.8 |
| 1.1794 | B.186 | C.8 |
| 1.1795 | B.187 | C.8 |
| 1.1796 | B.188 | C.8 |
| 1.1797 | B.189 | C.8 |
| 1.1798 | B.190 | C.8 |
| 1.1799 | B.191 | C.8 |
| 1.1800 | B.192 | C.8 |
| 1.1801 | B.193 | C.8 |
| 1.1802 | B.194 | C.8 |
| 1.1803 | B.195 | C.8 |
| 1.1804 | B.196 | C.8 |
| 1.1805 | B.197 | C.8 |
| 1.1806 | B.198 | C.8 |
| 1.1807 | B.199 | C.8 |
| 1.1808 | B.200 | C.8 |
| 1.1809 | B.201 | C.8 |
| 1.1810 | B.1 | C.9 |
| 1.1811 | B.2 | C.9 |
| 1.1812 | B.3 | C.9 |
| 1.1813 | B.4 | C.9 |
| 1.1814 | B.5 | C.9 |
| 1.1815 | B.6 | C.9 |
| 1.1816 | B.7 | C.9 |
| 1.1817 | B.8 | C.9 |
| 1.1818 | B.9 | C.9 |
| 1.1819 | B.10 | C.9 |
| 1.1820 | B.11 | C.9 |
| 1.1821 | B.12 | C.9 |
| 1.1822 | B.13 | C.9 |
| 1.1823 | B.14 | C.9 |
| 1.1824 | B.15 | C.9 |
| 1.1825 | B.16 | C.9 |
| 1.1826 | B.17 | C.9 |
| 1.1827 | B.18 | C.9 |
| 1.1828 | B.19 | C.9 |
| 1.1829 | B.20 | C.9 |
| 1.1830 | B.21 | C.9 |
| 1.1831 | B.22 | C.9 |
| 1.1832 | B.23 | C.9 |
| 1.1833 | B.24 | C.9 |
| 1.1834 | B.25 | C.9 |
| 1.1835 | B.26 | C.9 |
| 1.1836 | B.27 | C.9 |
| 1.1837 | B.28 | C.9 |
| 1.1838 | B.29 | C.9 |
| 1.1839 | B.30 | C.9 |
| 1.1840 | B.31 | C.9 |
| 1.1841 | B.32 | C.9 |
| 1.1842 | B.33 | C.9 |
| 1.1843 | B.34 | C.9 |
| 1.1844 | B.35 | C.9 |
| 1.1845 | B.36 | C.9 |
| 1.1846 | B.37 | C.9 |
| 1.1847 | B.38 | C.9 |
| 1.1848 | B.39 | C.9 |
| 1.1849 | B.40 | C.9 |
| 1.1850 | B.41 | C.9 |
| 1.1851 | B.42 | C.9 |
| 1.1852 | B.43 | C.9 |
| 1.1853 | B.44 | C.9 |
| 1.1854 | B.45 | C.9 |
| 1.1855 | B.46 | C.9 |
| 1.1856 | B.47 | C.9 |
| 1.1857 | B.48 | C.9 |
| 1.1858 | B.49 | C.9 |
| 1.1859 | B.50 | C.9 |
| 1.1860 | B.51 | C.9 |
| 1.1861 | B.52 | C.9 |
| 1.1862 | B.53 | C.9 |
| 1.1863 | B.54 | C.9 |
| 1.1864 | B.55 | C.9 |
| 1.1865 | B.56 | C.9 |
| 1.1866 | B.57 | C.9 |
| 1.1867 | B.58. | C.9 |

TABLE 1-continued (compositions 1.1 to 1.3635):

| comp. no. | herbicide B | safener C |
|---|---|---|
| 1.1868 | B.59 | C.9 |
| 1.1869 | B.60 | C.9 |
| 1.1870 | B.61 | C.9 |
| 1.1871 | B.62 | C.9 |
| 1.1872 | B.63 | C.9 |
| 1.1873 | B.64 | C.9 |
| 1.1874 | B.65 | C.9 |
| 1.1875 | B.66 | C.9 |
| 1.1876 | B.67 | C.9 |
| 1.1877 | B.68 | C.9 |
| 1.1878 | B.69 | C.9 |
| 1.1879 | B.70 | C.9 |
| 1.1880 | B.71 | C.9 |
| 1.1881 | B.72 | C.9 |
| 1.1882 | B.73 | C.9 |
| 1.1883 | B.74 | C.9 |
| 1.1884 | B.75 | C.9 |
| 1.1885 | B.76 | C.9 |
| 1.1886 | B.77 | C.9 |
| 1.1887 | B.78 | C.9 |
| 1.1888 | B.79 | C.9 |
| 1.1889 | B.80 | C.9 |
| 1.1890 | B.81 | C.9 |
| 1.1891 | B.82 | C.9 |
| 1.1892 | B.83 | C.9 |
| 1.1893 | B.84 | C.9 |
| 1.1894 | B.85 | C.9 |
| 1.1895 | B.86 | C.9 |
| 1.1896 | B.87 | C.9 |
| 1.1897 | B.88 | C.9 |
| 1.1898 | B.89 | C.9 |
| 1.1899 | B.90 | C.9 |
| 1.1900 | B.91 | C.9 |
| 1.1901 | B.92 | C.9 |
| 1.1902 | B.93 | C.9 |
| 1.1903 | B.94 | C.9 |
| 1.1904 | B.95 | C.9 |
| 1.1905 | B.96 | C.9 |
| 1.1906 | B.97 | C.9 |
| 1.1907 | B.98 | C.9 |
| 1.1908 | B.99 | C.9 |
| 1.1909 | B.100 | C.9 |
| 1.1910 | B.101 | C.9 |
| 1.1911 | B.102 | C.9 |
| 1.1912 | B.103 | C.9 |
| 1.1913 | B.104 | C.9 |
| 1.1914 | B.105 | C.9 |
| 1.1915 | B.106 | C.9 |
| 1.1916 | B.107 | C.9 |
| 1.1917 | B.108 | C.9 |
| 1.1918 | B.109 | C.9 |
| 1.1919 | B.110 | C.9 |
| 1.1920 | B.111 | C.9 |
| 1.1921 | B.112 | C.9 |
| 1.1922 | B.113 | C.9 |
| 1.1923 | B.114 | C.9 |
| 1.1924 | B.115 | C.9 |
| 1.1925 | B.116 | C.9 |
| 1.1926 | B.117 | C.9 |
| 1.1927 | B.118 | C.9 |
| 1.1928 | B.119 | C.9 |
| 1.1929 | B.120 | C.9 |
| 1.1930 | B.121 | C.9 |
| 1.1931 | B.122 | C.9 |
| 1.1932 | B.123 | C.9 |
| 1.1933 | B.124 | C.9 |
| 1.1934 | B.125 | C.9 |
| 1.1935 | B.126 | C.9 |
| 1.1936 | B.127 | C.9 |
| 1.1937 | B.128 | C.9 |
| 1.1938 | B.129 | C.9 |
| 1.1939 | B.130 | C.9 |
| 1.1940 | B.131 | C.9 |
| 1.1941 | B.132 | C.9 |
| 1.1942 | B.133 | C.9 |
| 1.1943 | B.134 | C.9 |
| 1.1944 | B.135 | C.9 |
| 1.1945 | B.136 | C.9 |
| 1.1946 | B.137 | C.9 |
| 1.1947 | B.138 | C.9 |
| 1.1948 | B.139 | C.9 |
| 1.1949 | B.140 | C.9 |
| 1.1950 | B.141 | C.9 |
| 1.1951 | B.142 | C.9 |
| 1.1952 | B.143 | C.9 |
| 1.1953 | B.144 | C.9 |
| 1.1954 | B.145 | C.9 |
| 1.1955 | B.146 | C.9 |
| 1.1956 | B.147 | C.9 |
| 1.1957 | B.148 | C.9 |
| 1.1958 | B.149 | C.9 |
| 1.1959 | B.150 | C.9 |
| 1.1960 | B.151 | C.9 |
| 1.1961 | B.152 | C.9 |
| 1.1962 | B.153 | C.9 |
| 1.1963 | B.154 | C.9 |
| 1.1964 | B.155 | C.9 |
| 1.1965 | B.156 | C.9 |
| 1.1966 | B.157 | C.9 |
| 1.1967 | B.158 | C.9 |
| 1.1968 | B.159 | C.9 |
| 1.1969 | B.160 | C.9 |
| 1.1970 | B.161 | C.9 |
| 1.1971 | B.162 | C.9 |
| 1.1972 | B.163 | C.9 |
| 1.1973 | B.164 | C.9 |
| 1.1974 | B.165 | C.9 |
| 1.1975 | B.166 | C.9 |
| 1.1976 | B.167 | C.9 |
| 1.1977 | B.168 | C.9 |
| 1.1978 | B.169 | C.9 |
| 1.1979 | B.170 | C.9 |
| 1.1980 | B.171 | C.9 |
| 1.1981 | B.172 | C.9 |
| 1.1982 | B.173 | C.9 |
| 1.1983 | B.174 | C.9 |
| 1.1984 | B.175 | C.9 |
| 1.1985 | B.176 | C.9 |
| 1.1986 | B.177 | C.9 |
| 1.1987 | B.178 | C.9 |
| 1.1988 | B.179 | C.9 |
| 1.1989 | B.180 | C.9 |
| 1.1990 | B.181 | C.9 |
| 1.1991 | B.182 | C.9 |
| 1.1992 | B.183 | C.9 |
| 1.1993 | B.184 | C.9 |
| 1.1994 | B.185 | C.9 |
| 1.1995 | B.186 | C.9 |
| 1.1996 | B.187 | C.9 |
| 1.1997 | B.188 | C.9 |
| 1.1998 | B.189 | C.9 |
| 1.1999 | B.190 | C.9 |
| 1.2000 | B.191 | C.9 |
| 1.2001 | B.192 | C.9 |
| 1.2002 | B.193 | C.9 |
| 1.2003 | B.194 | C.9 |
| 1.2004 | B.195 | C.9 |
| 1.2005 | B.196 | C.9 |
| 1.2006 | B.197 | C.9 |
| 1.2007 | B.198 | C.9 |
| 1.2008 | B.199 | C.9 |
| 1.2009 | B.200 | C.9 |
| 1.2010 | B.201 | C.9 |
| 1.2011 | B.1 | C.10 |
| 1.2012 | B.2 | C.10 |
| 1.2013 | B.3 | C.10 |
| 1.2014 | B.4 | C.10 |
| 1.2015 | B.5 | C.10 |
| 1.2016 | B.6 | C.10 |
| 1.2017 | B.7 | C.10 |
| 1.2018 | B.8 | C.10 |
| 1.2019 | B.9 | C.10 |

TABLE 1-continued (compositions 1.1 to 1.3635):

| comp. no. | herbicide B | safener C |
|---|---|---|
| 1.2020 | B.10 | C.10 |
| 1.2021 | B.11 | C.10 |
| 1.2022 | B.12 | C.10 |
| 1.2023 | B.13 | C.10 |
| 1.2024 | B.14 | C.10 |
| 1.2025 | B.15 | C.10 |
| 1.2026 | B.16 | C.10 |
| 1.2027 | B.17 | C.10 |
| 1.2028 | B.18 | C.10 |
| 1.2029 | B.19 | C.10 |
| 1.2030 | B.20 | C.10 |
| 1.2031 | B.21 | C.10 |
| 1.2032 | B.22 | C.10 |
| 1.2033 | B.23 | C.10 |
| 1.2034 | B.24 | C.10 |
| 1.2035 | B.25 | C.10 |
| 1.2036 | B.26 | C.10 |
| 1.2037 | B.27 | C.10 |
| 1.2038 | B.28 | C.10 |
| 1.2039 | B.29 | C.10 |
| 1.2040 | B.30 | C.10 |
| 1.2041 | B.31 | C.10 |
| 1.2042 | B.32 | C.10 |
| 1.2043 | B.33 | C.10 |
| 1.2044 | B.34 | C.10 |
| 1.2045 | B.35 | C.10 |
| 1.2046 | B.36 | C.10 |
| 1.2047 | B.37 | C.10 |
| 1.2048 | B.38 | C.10 |
| 1.2049 | B.39 | C.10 |
| 1.2050 | B.40 | C.10 |
| 1.2051 | B.41 | C.10 |
| 1.2052 | B.42 | C.10 |
| 1.2053 | B.43 | C.10 |
| 1.2054 | B.44 | C.10 |
| 1.2055 | B.45 | C.10 |
| 1.2056 | B.46 | C.10 |
| 1.2057 | B.47 | C.10 |
| 1.2058 | B.48 | C.10 |
| 1.2059 | B.49 | C.10 |
| 1.2060 | B.50 | C.10 |
| 1.2061 | B.51 | C.10 |
| 1.2062 | B.52 | C.10 |
| 1.2063 | B.53 | C.10 |
| 1.2064 | B.54 | C.10 |
| 1.2065 | B.55 | C.10 |
| 1.2066 | B.56 | C.10 |
| 1.2067 | B.57 | C.10 |
| 1.2068 | B.58. | C.10 |
| 1.2069 | B.59 | C.10 |
| 1.2070 | B.60 | C.10 |
| 1.2071 | B.61 | C.10 |
| 1.2072 | B.62 | C.10 |
| 1.2073 | B.63 | C.10 |
| 1.2074 | B.64 | C.10 |
| 1.2075 | B.65 | C.10 |
| 1.2076 | B.66 | C.10 |
| 1.2077 | B.67 | C.10 |
| 1.2078 | B.68 | C.10 |
| 1.2079 | B.69 | C.10 |
| 1.2080 | B.70 | C.10 |
| 1.2081 | B.71 | C.10 |
| 1.2082 | B.72 | C.10 |
| 1.2083 | B.73 | C.10 |
| 1.2084 | B.74 | C.10 |
| 1.2085 | B.75 | C.10 |
| 1.2086 | B.76 | C.10 |
| 1.2087 | B.77 | C.10 |
| 1.2088 | B.78 | C.10 |
| 1.2089 | B.79 | C.10 |
| 1.2090 | B.80 | C.10 |
| 1.2091 | B.81 | C.10 |
| 1.2092 | B.82 | C.10 |
| 1.2093 | B.83 | C.10 |
| 1.2094 | B.84 | C.10 |
| 1.2095 | B.85 | C.10 |
| 1.2096 | B.86 | C.10 |
| 1.2097 | B.87 | C.10 |
| 1.2098 | B.88 | C.10 |
| 1.2099 | B.89 | C.10 |
| 1.2100 | B.90 | C.10 |
| 1.2101 | B.91 | C.10 |
| 1.2102 | B.92 | C.10 |
| 1.2103 | B.93 | C.10 |
| 1.2104 | B.94 | C.10 |
| 1.2105 | B.95 | C.10 |
| 1.2106 | B.96 | C.10 |
| 1.2107 | B.97 | C.10 |
| 1.2108 | B.98 | C.10 |
| 1.2109 | B.99 | C.10 |
| 1.2110 | B.100 | C.10 |
| 1.2111 | B.101 | C.10 |
| 1.2112 | B.102 | C.10 |
| 1.2113 | B.103 | C.10 |
| 1.2114 | B.104 | C.10 |
| 1.2115 | B.105 | C.10 |
| 1.2116 | B.106 | C.10 |
| 1.2117 | B.107 | C.10 |
| 1.2118 | B.108 | C.10 |
| 1.2119 | B.109 | C.10 |
| 1.2120 | B.110 | C.10 |
| 1.2121 | B.111 | C.10 |
| 1.2122 | B.112 | C.10 |
| 1.2123 | B.113 | C.10 |
| 1.2124 | B.114 | C.10 |
| 1.2125 | B.115 | C.10 |
| 1.2126 | B.116 | C.10 |
| 1.2127 | B.117 | C.10 |
| 1.2128 | B.118 | C.10 |
| 1.2129 | B.119 | C.10 |
| 1.2130 | B.120 | C.10 |
| 1.2131 | B.121 | C.10 |
| 1.2132 | B.122 | C.10 |
| 1.2133 | B.123 | C.10 |
| 1.2134 | B.124 | C.10 |
| 1.2135 | B.125 | C.10 |
| 1.2136 | B.126 | C.10 |
| 1.2137 | B.127 | C.10 |
| 1.2138 | B.128 | C.10 |
| 1.2139 | B.129 | C.10 |
| 1.2140 | B.130 | C.10 |
| 1.2141 | B.131 | C.10 |
| 1.2142 | B.132 | C.10 |
| 1.2143 | B.133 | C.10 |
| 1.2144 | B.134 | C.10 |
| 1.2145 | B.135 | C.10 |
| 1.2146 | B.136 | C.10 |
| 1.2147 | B.137 | C.10 |
| 1.2148 | B.138 | C.10 |
| 1.2149 | B.139 | C.10 |
| 1.2150 | B.140 | C.10 |
| 1.2151 | B.141 | C.10 |
| 1.2152 | B.142 | C.10 |
| 1.2153 | B.143 | C.10 |
| 1.2154 | B.144 | C.10 |
| 1.2155 | B.145 | C.10 |
| 1.2156 | B.146 | C.10 |
| 1.2157 | B.147 | C.10 |
| 1.2158 | B.148 | C.10 |
| 1.2159 | B.149 | C.10 |
| 1.2160 | B.150 | C.10 |
| 1.2161 | B.151 | C.10 |
| 1.2162 | B.152 | C.10 |
| 1.2163 | B.153 | C.10 |
| 1.2164 | B.154 | C.10 |
| 1.2165 | B.155 | C.10 |
| 1.2166 | B.156 | C.10 |
| 1.2167 | B.157 | C.10 |
| 1.2168 | B.158 | C.10 |
| 1.2169 | B.159 | C.10 |
| 1.2170 | B.160 | C.10 |
| 1.2171 | B.161 | C.10 |

TABLE 1-continued (compositions 1.1 to 1.3635):

| comp. no. | herbicide B | safener C |
|---|---|---|
| 1.2172 | B.162 | C.10 |
| 1.2173 | B.163 | C.10 |
| 1.2174 | B.164 | C.10 |
| 1.2175 | B.165 | C.10 |
| 1.2176 | B.166 | C.10 |
| 1.2177 | B.167 | C.10 |
| 1.2178 | B.168 | C.10 |
| 1.2179 | B.169 | C.10 |
| 1.2180 | B.170 | C.10 |
| 1.2181 | B.171 | C.10 |
| 1.2182 | B.172 | C.10 |
| 1.2183 | B.173 | C.10 |
| 1.2184 | B.174 | C.10 |
| 1.2185 | B.175 | C.10 |
| 1.2186 | B.176 | C.10 |
| 1.2187 | B.177 | C.10 |
| 1.2188 | B.178 | C.10 |
| 1.2189 | B.179 | C.10 |
| 1.2190 | B.180 | C.10 |
| 1.2191 | B.181 | C.10 |
| 1.2192 | B.182 | C.10 |
| 1.2193 | B.183 | C.10 |
| 1.2194 | B.184 | C.10 |
| 1.2195 | B.185 | C.10 |
| 1.2196 | B.186 | C.10 |
| 1.2197 | B.187 | C.10 |
| 1.2198 | B.188 | C.10 |
| 1.2199 | B.189 | C.10 |
| 1.2200 | B.190 | C.10 |
| 1.2201 | B.191 | C.10 |
| 1.2202 | B.192 | C.10 |
| 1.2203 | B.193 | C.10 |
| 1.2204 | B.194 | C.10 |
| 1.2205 | B.195 | C.10 |
| 1.2206 | B.196 | C.10 |
| 1.2207 | B.197 | C.10 |
| 1.2208 | B.198 | C.10 |
| 1.2209 | B.199 | C.10 |
| 1.2210 | B.200 | C.10 |
| 1.2211 | B.201 | C.10 |
| 1.2212 | B.1 | C.11 |
| 1.2213 | B.2 | C.11 |
| 1.2214 | B.3 | C.11 |
| 1.2215 | B.4 | C.11 |
| 1.2216 | B.5 | C.11 |
| 1.2217 | B.6 | C.11 |
| 1.2218 | B.7 | C.11 |
| 1.2219 | B.8 | C.11 |
| 1.2220 | B.9 | C.11 |
| 1.2221 | B.10 | C.11 |
| 1.2222 | B.11 | C.11 |
| 1.2223 | B.12 | C.11 |
| 1.2224 | B.13 | C.11 |
| 1.2225 | B.14 | C.11 |
| 1.2226 | B.15 | C.11 |
| 1.2227 | B.16 | C.11 |
| 1.2228 | B.17 | C.11 |
| 1.2229 | B.18 | C.11 |
| 1.2230 | B.19 | C.11 |
| 1.2231 | B.20 | C.11 |
| 1.2232 | B.21 | C.11 |
| 1.2233 | B.22 | C.11 |
| 1.2234 | B.23 | C.11 |
| 1.2235 | B.24 | C.11 |
| 1.2236 | B.25 | C.11 |
| 1.2237 | B.26 | C.11 |
| 1.2238 | B.27 | C.11 |
| 1.2239 | B.28 | C.11 |
| 1.2240 | B.29 | C.11 |
| 1.2241 | B.30 | C.11 |
| 1.2242 | B.31 | C.11 |
| 1.2243 | B.32 | C.11 |
| 1.2244 | B.33 | C.11 |
| 1.2245 | B.34 | C.11 |
| 1.2246 | B.35 | C.11 |
| 1.2247 | B.36 | C.11 |
| 1.2248 | B.37 | C.11 |
| 1.2249 | B.38 | C.11 |
| 1.2250 | B.39 | C.11 |
| 1.2251 | B.40 | C.11 |
| 1.2252 | B.41 | C.11 |
| 1.2253 | B.42 | C.11 |
| 1.2254 | B.43 | C.11 |
| 1.2255 | B.44 | C.11 |
| 1.2256 | B.45 | C.11 |
| 1.2257 | B.46 | C.11 |
| 1.2258 | B.47 | C.11 |
| 1.2259 | B.48 | C.11 |
| 1.2260 | B.49 | C.11 |
| 1.2261 | B.50 | C.11 |
| 1.2262 | B.51 | C.11 |
| 1.2263 | B.52 | C.11 |
| 1.2264 | B.53 | C.11 |
| 1.2265 | B.54 | C.11 |
| 1.2266 | B.55 | C.11 |
| 1.2267 | B.56 | C.11 |
| 1.2268 | B.57 | C.11 |
| 1.2269 | B.58. | C.11 |
| 1.2270 | B.59 | C.11 |
| 1.2271 | B.60 | C.11 |
| 1.2272 | B.61 | C.11 |
| 1.2273 | B.62 | C.11 |
| 1.2274 | B.63 | C.11 |
| 1.2275 | B.64 | C.11 |
| 1.2276 | B.65 | C.11 |
| 1.2277 | B.66 | C.11 |
| 1.2278 | B.67 | C.11 |
| 1.2279 | B.68 | C.11 |
| 1.2280 | B.69 | C.11 |
| 1.2281 | B.70 | C.11 |
| 1.2282 | B.71 | C.11 |
| 1.2283 | B.72 | C.11 |
| 1.2284 | B.73 | C.11 |
| 1.2285 | B.74 | C.11 |
| 1.2286 | B.75 | C.11 |
| 1.2287 | B.76 | C.11 |
| 1.2288 | B.77 | C.11 |
| 1.2289 | B.78 | C.11 |
| 1.2290 | B.79 | C.11 |
| 1.2291 | B.80 | C.11 |
| 1.2292 | B.81 | C.11 |
| 1.2293 | B.82 | C.11 |
| 1.2294 | B.83 | C.11 |
| 1.2295 | B.84 | C.11 |
| 1.2296 | B.85 | C.11 |
| 1.2297 | B.86 | C.11 |
| 1.2298 | B.87 | C.11 |
| 1.2299 | B.88 | C.11 |
| 1.2300 | B.89 | C.11 |
| 1.2301 | B.90 | C.11 |
| 1.2302 | B.91 | C.11 |
| 1.2303 | B.92 | C.11 |
| 1.2304 | B.93 | C.11 |
| 1.2305 | B.94 | C.11 |
| 1.2306 | B.95 | C.11 |
| 1.2307 | B.96 | C.11 |
| 1.2308 | B.97 | C.11 |
| 1.2309 | B.98 | C.11 |
| 1.2310 | B.99 | C.11 |
| 1.2311 | B.100 | C.11 |
| 1.2312 | B.101 | C.11 |
| 1.2313 | B.102 | C.11 |
| 1.2314 | B.103 | C.11 |
| 1.2315 | B.104 | C.11 |
| 1.2316 | B.105 | C.11 |
| 1.2317 | B.106 | C.11 |
| 1.2318 | B.107 | C.11 |
| 1.2319 | B.108 | C.11 |
| 1.2320 | B.109 | C.11 |
| 1.2321 | B.110 | C.11 |
| 1.2322 | B.111 | C.11 |
| 1.2323 | B.112 | C.11 |

TABLE 1-continued (compositions 1.1 to 1.3635):

| comp. no. | herbicide B | safener C |
|---|---|---|
| 1.2324 | B.113 | C.11 |
| 1.2325 | B.114 | C.11 |
| 1.2326 | B.115 | C.11 |
| 1.2327 | B.116 | C.11 |
| 1.2328 | B.117 | C.11 |
| 1.2329 | B.118 | C.11 |
| 1.2330 | B.119 | C.11 |
| 1.2331 | B.120 | C.11 |
| 1.2332 | B.121 | C.11 |
| 1.2333 | B.122 | C.11 |
| 1.2334 | B.123 | C.11 |
| 1.2335 | B.124 | C.11 |
| 1.2336 | B.125 | C.11 |
| 1.2337 | B.126 | C.11 |
| 1.2338 | B.127 | C.11 |
| 1.2339 | B.128 | C.11 |
| 1.2340 | B.129 | C.11 |
| 1.2341 | B.130 | C.11 |
| 1.2342 | B.131 | C.11 |
| 1.2343 | B.132 | C.11 |
| 1.2344 | B.133 | C.11 |
| 1.2345 | B.134 | C.11 |
| 1.2346 | B.135 | C.11 |
| 1.2347 | B.136 | C.11 |
| 1.2348 | B.137 | C.11 |
| 1.2349 | B.138 | C.11 |
| 1.2350 | B.139 | C.11 |
| 1.2351 | B.140 | C.11 |
| 1.2352 | B.141 | C.11 |
| 1.2353 | B.142 | C.11 |
| 1.2354 | B.143 | C.11 |
| 1.2355 | B.144 | C.11 |
| 1.2356 | B.145 | C.11 |
| 1.2357 | B.146 | C.11 |
| 1.2358 | B.147 | C.11 |
| 1.2359 | B.148 | C.11 |
| 1.2360 | B.149 | C.11 |
| 1.2361 | B.150 | C.11 |
| 1.2362 | B.151 | C.11 |
| 1.2363 | B.152 | C.11 |
| 1.2364 | B.153 | C.11 |
| 1.2365 | B.154 | C.11 |
| 1.2366 | B.155 | C.11 |
| 1.2367 | B.156 | C.11 |
| 1.2368 | B.157 | C.11 |
| 1.2369 | B.158 | C.11 |
| 1.2370 | B.159 | C.11 |
| 1.2371 | B.160 | C.11 |
| 1.2372 | B.161 | C.11 |
| 1.2373 | B.162 | C.11 |
| 1.2374 | B.163 | C.11 |
| 1.2375 | B.164 | C.11 |
| 1.2376 | B.165 | C.11 |
| 1.2377 | B.166 | C.11 |
| 1.2378 | B.167 | C.11 |
| 1.2379 | B.168 | C.11 |
| 1.2380 | B.169 | C.11 |
| 1.2381 | B.170 | C.11 |
| 1.2382 | B.171 | C.11 |
| 1.2383 | B.172 | C.11 |
| 1.2384 | B.173 | C.11 |
| 1.2385 | B.174 | C.11 |
| 1.2386 | B.175 | C.11 |
| 1.2387 | B.176 | C.11 |
| 1.2388 | B.177 | C.11 |
| 1.2389 | B.178 | C.11 |
| 1.2390 | B.179 | C.11 |
| 1.2391 | B.180 | C.11 |
| 1.2392 | B.181 | C.11 |
| 1.2393 | B.182 | C.11 |
| 1.2394 | B.183 | C.11 |
| 1.2395 | B.184 | C.11 |
| 1.2396 | B.185 | C.11 |
| 1.2397 | B.186 | C.11 |
| 1.2398 | B.187 | C.11 |
| 1.2399 | B.188 | C.11 |
| 1.2400 | B.189 | C.11 |
| 1.2401 | B.190 | C.11 |
| 1.2402 | B.191 | C.11 |
| 1.2403 | B.192 | C.11 |
| 1.2404 | B.193 | C.11 |
| 1.2405 | B.194 | C.11 |
| 1.2406 | B.195 | C.11 |
| 1.2407 | B.196 | C.11 |
| 1.2408 | B.197 | C.11 |
| 1.2409 | B.198 | C.11 |
| 1.2410 | B.199 | C.11 |
| 1.2411 | B.200 | C.11 |
| 1.2412 | B.201 | C.11 |
| 1.2413 | B.1 | C.12 |
| 1.2414 | B.2 | C.12 |
| 1.2415 | B.3 | C.12 |
| 1.2416 | B.4 | C.12 |
| 1.2417 | B.5 | C.12 |
| 1.2418 | B.6 | C.12 |
| 1.2419 | B.7 | C.12 |
| 1.2420 | B.8 | C.12 |
| 1.2421 | B.9 | C.12 |
| 1.2422 | B.10 | C.12 |
| 1.2423 | B.11 | C.12 |
| 1.2424 | B.12 | C.12 |
| 1.2425 | B.13 | C.12 |
| 1.2426 | B.14 | C.12 |
| 1.2427 | B.15 | C.12 |
| 1.2428 | B.16 | C.12 |
| 1.2429 | B.17 | C.12 |
| 1.2430 | B.18 | C.12 |
| 1.2431 | B.19 | C.12 |
| 1.2432 | B.20 | C.12 |
| 1.2433 | B.21 | C.12 |
| 1.2434 | B.22 | C.12 |
| 1.2435 | B.23 | C.12 |
| 1.2436 | B.24 | C.12 |
| 1.2437 | B.25 | C.12 |
| 1.2438 | B.26 | C.12 |
| 1.2439 | B.27 | C.12 |
| 1.2440 | B.28 | C.12 |
| 1.2441 | B.29 | C.12 |
| 1.2442 | B.30 | C.12 |
| 1.2443 | B.31 | C.12 |
| 1.2444 | B.32 | C.12 |
| 1.2445 | B.33 | C.12 |
| 1.2446 | B.34 | C.12 |
| 1.2447 | B.35 | C.12 |
| 1.2448 | B.36 | C.12 |
| 1.2449 | B.37 | C.12 |
| 1.2450 | B.38 | C.12 |
| 1.2451 | B.39 | C.12 |
| 1.2452 | B.40 | C.12 |
| 1.2453 | B.41 | C.12 |
| 1.2454 | B.42 | C.12 |
| 1.2455 | B.43 | C.12 |
| 1.2456 | B.44 | C.12 |
| 1.2457 | B.45 | C.12 |
| 1.2458 | B.46 | C.12 |
| 1.2459 | B.47 | C.12 |
| 1.2460 | B.48 | C.12 |
| 1.2461 | B.49 | C.12 |
| 1.2462 | B.50 | C.12 |
| 1.2463 | B.51 | C.12 |
| 1.2464 | B.52 | C.12 |
| 1.2465 | B.53 | C.12 |
| 1.2466 | B.54 | C.12 |
| 1.2467 | B.55 | C.12 |
| 1.2468 | B.56 | C.12 |
| 1.2469 | B.57 | C.12 |
| 1.2470 | B.58. | C.12 |
| 1.2471 | B.59 | C.12 |
| 1.2472 | B.60 | C.12 |
| 1.2473 | B.61 | C.12 |
| 1.2474 | B.62 | C.12 |
| 1.2475 | B.63 | C.12 |

TABLE 1-continued (compositions 1.1 to 1.3635):

| comp. no. | herbicide B | safener C |
|---|---|---|
| 1.2476 | B.64 | C.12 |
| 1.2477 | B.65 | C.12 |
| 1.2478 | B.66 | C.12 |
| 1.2479 | B.67 | C.12 |
| 1.2480 | B.68 | C.12 |
| 1.2481 | B.69 | C.12 |
| 1.2482 | B.70 | C.12 |
| 1.2483 | B.71 | C.12 |
| 1.2484 | B.72 | C.12 |
| 1.2485 | B.73 | C.12 |
| 1.2486 | B.74 | C.12 |
| 1.2487 | B.75 | C.12 |
| 1.2488 | B.76 | C.12 |
| 1.2489 | B.77 | C.12 |
| 1.2490 | B.78 | C.12 |
| 1.2491 | B.79 | C.12 |
| 1.2492 | B.80 | C.12 |
| 1.2493 | B.81 | C.12 |
| 1.2494 | B.82 | C.12 |
| 1.2495 | B.83 | C.12 |
| 1.2496 | B.84 | C.12 |
| 1.2497 | B.85 | C.12 |
| 1.2498 | B.86 | C.12 |
| 1.2499 | B.87 | C.12 |
| 1.2500 | B.88 | C.12 |
| 1.2501 | B.89 | C.12 |
| 1.2502 | B.90 | C.12 |
| 1.2503 | B.91 | C.12 |
| 1.2504 | B.92 | C.12 |
| 1.2505 | B.93 | C.12 |
| 1.2506 | B.94 | C.12 |
| 1.2507 | B.95 | C.12 |
| 1.2508 | B.96 | C.12 |
| 1.2509 | B.97 | C.12 |
| 1.2510 | B.98 | C.12 |
| 1.2511 | B.99 | C.12 |
| 1.2512 | B.100 | C.12 |
| 1.2513 | B.101 | C.12 |
| 1.2514 | B.102 | C.12 |
| 1.2515 | B.103 | C.12 |
| 1.2516 | B.104 | C.12 |
| 1.2517 | B.105 | C.12 |
| 1.2518 | B.106 | C.12 |
| 1.2519 | B.107 | C.12 |
| 1.2520 | B.108 | C.12 |
| 1.2521 | B.109 | C.12 |
| 1.2522 | B.110 | C.12 |
| 1.2523 | B.111 | C.12 |
| 1.2524 | B.112 | C.12 |
| 1.2525 | B.113 | C.12 |
| 1.2526 | B.114 | C.12 |
| 1.2527 | B.115 | C.12 |
| 1.2528 | B.116 | C.12 |
| 1.2529 | B.117 | C.12 |
| 1.2530 | B.118 | C.12 |
| 1.2531 | B.119 | C.12 |
| 1.2532 | B.120 | C.12 |
| 1.2533 | B.121 | C.12 |
| 1.2534 | B.122 | C.12 |
| 1.2535 | B.123 | C.12 |
| 1.2536 | B.124 | C.12 |
| 1.2537 | B.125 | C.12 |
| 1.2538 | B.126 | C.12 |
| 1.2539 | B.127 | C.12 |
| 1.2540 | B.128 | C.12 |
| 1.2541 | B.129 | C.12 |
| 1.2542 | B.130 | C.12 |
| 1.2543 | B.131 | C.12 |
| 1.2544 | B.132 | C.12 |
| 1.2545 | B.133 | C.12 |
| 1.2546 | B.134 | C.12 |
| 1.2547 | B.135 | C.12 |
| 1.2548 | B.136 | C.12 |
| 1.2549 | B.137 | C.12 |
| 1.2550 | B.138 | C.12 |
| 1.2551 | B.139 | C.12 |
| 1.2552 | B.140 | C.12 |
| 1.2553 | B.141 | C.12 |
| 1.2554 | B.142 | C.12 |
| 1.2555 | B.143 | C.12 |
| 1.2556 | B.144 | C.12 |
| 1.2557 | B.145 | C.12 |
| 1.2558 | B.146 | C.12 |
| 1.2559 | B.147 | C.12 |
| 1.2560 | B.148 | C.12 |
| 1.2561 | B.149 | C.12 |
| 1.2562 | B.150 | C.12 |
| 1.2563 | B.151 | C.12 |
| 1.2564 | B.152 | C.12 |
| 1.2565 | B.153 | C.12 |
| 1.2566 | B.154 | C.12 |
| 1.2567 | B.155 | C.12 |
| 1.2568 | B.156 | C.12 |
| 1.2569 | B.157 | C.12 |
| 1.2570 | B.158 | C.12 |
| 1.2571 | B.159 | C.12 |
| 1.2572 | B.160 | C.12 |
| 1.2573 | B.161 | C.12 |
| 1.2574 | B.162 | C.12 |
| 1.2575 | B.163 | C.12 |
| 1.2576 | B.164 | C.12 |
| 1.2577 | B.165 | C.12 |
| 1.2578 | B.166 | C.12 |
| 1.2579 | B.167 | C.12 |
| 1.2580 | B.168 | C.12 |
| 1.2581 | B.169 | C.12 |
| 1.2582 | B.170 | C.12 |
| 1.2583 | B.171 | C.12 |
| 1.2584 | B.172 | C.12 |
| 1.2585 | B.173 | C.12 |
| 1.2586 | B.174 | C.12 |
| 1.2587 | B.175 | C.12 |
| 1.2588 | B.176 | C.12 |
| 1.2589 | B.177 | C.12 |
| 1.2590 | B.178 | C.12 |
| 1.2591 | B.179 | C.12 |
| 1.2592 | B.180 | C.12 |
| 1.2593 | B.181 | C.12 |
| 1.2594 | B.182 | C.12 |
| 1.2595 | B.183 | C.12 |
| 1.2596 | B.184 | C.12 |
| 1.2597 | B.185 | C.12 |
| 1.2598 | B.186 | C.12 |
| 1.2599 | B.187 | C.12 |
| 1.2600 | B.188 | C.12 |
| 1.2601 | B.189 | C.12 |
| 1.2602 | B.190 | C.12 |
| 1.2603 | B.191 | C.12 |
| 1.2604 | B.192 | C.12 |
| 1.2605 | B.193 | C.12 |
| 1.2606 | B.194 | C.12 |
| 1.2607 | B.195 | C.12 |
| 1.2608 | B.196 | C.12 |
| 1.2609 | B.197 | C.12 |
| 1.2610 | B.198 | C.12 |
| 1.2611 | B.199 | C.12 |
| 1.2612 | B.200 | C.12 |
| 1.2613 | B.201 | C.12 |
| 1.2614 | B.1 | C.13 |
| 1.2615 | B.2 | C.13 |
| 1.2616 | B.3 | C.13 |
| 1.2617 | B.4 | C.13 |
| 1.2618 | B.5 | C.13 |
| 1.2619 | B.6 | C.13 |
| 1.2620 | B.7 | C.13 |
| 1.2621 | B.8 | C.13 |
| 1.2622 | B.9 | C.13 |
| 1.2623 | B.10 | C.13 |
| 1.2624 | B.11 | C.13 |
| 1.2625 | B.12 | C.13 |
| 1.2626 | B.13 | C.13 |
| 1.2627 | B.14 | C.13 |

TABLE 1-continued (compositions 1.1 to 1.3635):

| comp. no. | herbicide B | safener C |
|---|---|---|
| 1.2628 | B.15 | C.13 |
| 1.2629 | B.16 | C.13 |
| 1.2630 | B.17 | C.13 |
| 1.2631 | B.18 | C.13 |
| 1.2632 | B.19 | C.13 |
| 1.2633 | B.20 | C.13 |
| 1.2634 | B.21 | C.13 |
| 1.2635 | B.22 | C.13 |
| 1.2636 | B.23 | C.13 |
| 1.2637 | B.24 | C.13 |
| 1.2638 | B.25 | C.13 |
| 1.2639 | B.26 | C.13 |
| 1.2640 | B.27 | C.13 |
| 1.2641 | B.28 | C.13 |
| 1.2642 | B.29 | C.13 |
| 1.2643 | B.30 | C.13 |
| 1.2644 | B.31 | C.13 |
| 1.2645 | B.32 | C.13 |
| 1.2646 | B.33 | C.13 |
| 1.2647 | B.34 | C.13 |
| 1.2648 | B.35 | C.13 |
| 1.2649 | B.36 | C.13 |
| 1.2650 | B.37 | C.13 |
| 1.2651 | B.38 | C.13 |
| 1.2652 | B.39 | C.13 |
| 1.2653 | B.40 | C.13 |
| 1.2654 | B.41 | C.13 |
| 1.2655 | B.42 | C.13 |
| 1.2656 | B.43 | C.13 |
| 1.2657 | B.44 | C.13 |
| 1.2658 | B.45 | C.13 |
| 1.2659 | B.46 | C.13 |
| 1.2660 | B.47 | C.13 |
| 1.2661 | B.48 | C.13 |
| 1.2662 | B.49 | C.13 |
| 1.2663 | B.50 | C.13 |
| 1.2664 | B.51 | C.13 |
| 1.2665 | B.52 | C.13 |
| 1.2666 | B.53 | C.13 |
| 1.2667 | B.54 | C.13 |
| 1.2668 | B.55 | C.13 |
| 1.2669 | B.56 | C.13 |
| 1.2670 | B.57 | C.13 |
| 1.2671 | B.58. | C.13 |
| 1.2672 | B.59 | C.13 |
| 1.2673 | B.60 | C.13 |
| 1.2674 | B.61 | C.13 |
| 1.2675 | B.62 | C.13 |
| 1.2676 | B.63 | C.13 |
| 1.2677 | B.64 | C.13 |
| 1.2678 | B.65 | C.13 |
| 1.2679 | B.66 | C.13 |
| 1.2680 | B.67 | C.13 |
| 1.2681 | B.68 | C.13 |
| 1.2682 | B.69 | C.13 |
| 1.2683 | B.70 | C.13 |
| 1.2684 | B.71 | C.13 |
| 1.2685 | B.72 | C.13 |
| 1.2686 | B.73 | C.13 |
| 1.2687 | B.74 | C.13 |
| 1.2688 | B.75 | C.13 |
| 1.2689 | B.76 | C.13 |
| 1.2690 | B.77 | C.13 |
| 1.2691 | B.78 | C.13 |
| 1.2692 | B.79 | C.13 |
| 1.2693 | B.80 | C.13 |
| 1.2694 | B.81 | C.13 |
| 1.2695 | B.82 | C.13 |
| 1.2696 | B.83 | C.13 |
| 1.2697 | B.84 | C.13 |
| 1.2698 | B.85 | C.13 |
| 1.2699 | B.86 | C.13 |
| 1.2700 | B.87 | C.13 |
| 1.2701 | B.88 | C.13 |
| 1.2702 | B.89 | C.13 |
| 1.2703 | B.90 | C.13 |
| 1.2704 | B.91 | C.13 |
| 1.2705 | B.92 | C.13 |
| 1.2706 | B.93 | C.13 |
| 1.2707 | B.94 | C.13 |
| 1.2708 | B.95 | C.13 |
| 1.2709 | B.96 | C.13 |
| 1.2710 | B.97 | C.13 |
| 1.2711 | B.98 | C.13 |
| 1.2712 | B.99 | C.13 |
| 1.2713 | B.100 | C.13 |
| 1.2714 | B.101 | C.13 |
| 1.2715 | B.102 | C.13 |
| 1.2716 | B.103 | C.13 |
| 1.2717 | B.104 | C.13 |
| 1.2718 | B.105 | C.13 |
| 1.2719 | B.106 | C.13 |
| 1.2720 | B.107 | C.13 |
| 1.2721 | B.108 | C.13 |
| 1.2722 | B.109 | C.13 |
| 1.2723 | B.110 | C.13 |
| 1.2724 | B.111 | C.13 |
| 1.2725 | B.112 | C.13 |
| 1.2726 | B.113 | C.13 |
| 1.2727 | B.114 | C.13 |
| 1.2728 | B.115 | C.13 |
| 1.2729 | B.116 | C.13 |
| 1.2730 | B.117 | C.13 |
| 1.2731 | B.118 | C.13 |
| 1.2732 | B.119 | C.13 |
| 1.2733 | B.120 | C.13 |
| 1.2734 | B.121 | C.13 |
| 1.2735 | B.122 | C.13 |
| 1.2736 | B.123 | C.13 |
| 1.2737 | B.124 | C.13 |
| 1.2738 | B.125 | C.13 |
| 1.2739 | B.126 | C.13 |
| 1.2740 | B.127 | C.13 |
| 1.2741 | B.128 | C.13 |
| 1.2742 | B.129 | C.13 |
| 1.2743 | B.130 | C.13 |
| 1.2744 | B.131 | C.13 |
| 1.2745 | B.132 | C.13 |
| 1.2746 | B.133 | C.13 |
| 1.2747 | B.134 | C.13 |
| 1.2748 | B.135 | C.13 |
| 1.2749 | B.136 | C.13 |
| 1.2750 | B.137 | C.13 |
| 1.2751 | B.138 | C.13 |
| 1.2752 | B.139 | C.13 |
| 1.2753 | B.140 | C.13 |
| 1.2754 | B.141 | C.13 |
| 1.2755 | B.142 | C.13 |
| 1.2756 | B.143 | C.13 |
| 1.2757 | B.144 | C.13 |
| 1.2758 | B.145 | C.13 |
| 1.2759 | B.146 | C.13 |
| 1.2760 | B.147 | C.13 |
| 1.2761 | B.148 | C.13 |
| 1.2762 | B.149 | C.13 |
| 1.2763 | B.150 | C.13 |
| 1.2764 | B.151 | C.13 |
| 1.2765 | B.152 | C.13 |
| 1.2766 | B.153 | C.13 |
| 1.2767 | B.154 | C.13 |
| 1.2768 | B.155 | C.13 |
| 1.2769 | B.156 | C.13 |
| 1.2770 | B.157 | C.13 |
| 1.2771 | B.158 | C.13 |
| 1.2772 | B.159 | C.13 |
| 1.2773 | B.160 | C.13 |
| 1.2774 | B.161 | C.13 |
| 1.2775 | B.162 | C.13 |
| 1.2776 | B.163 | C.13 |
| 1.2777 | B.164 | C.13 |
| 1.2778 | B.165 | C.13 |
| 1.2779 | B.166 | C.13 |

TABLE 1-continued (compositions 1.1 to 1.3635):

| comp. no. | herbicide B | safener C |
|---|---|---|
| 1.2780 | B.167 | C.13 |
| 1.2781 | B.168 | C.13 |
| 1.2782 | B.169 | C.13 |
| 1.2783 | B.170 | C.13 |
| 1.2784 | B.171 | C.13 |
| 1.2785 | B.172 | C.13 |
| 1.2786 | B.173 | C.13 |
| 1.2787 | B.174 | C.13 |
| 1.2788 | B.175 | C.13 |
| 1.2789 | B.176 | C.13 |
| 1.2790 | B.177 | C.13 |
| 1.2791 | B.178 | C.13 |
| 1.2792 | B.179 | C.13 |
| 1.2793 | B.180 | C.13 |
| 1.2794 | B.181 | C.13 |
| 1.2795 | B.182 | C.13 |
| 1.2796 | B.183 | C.13 |
| 1.2797 | B.184 | C.13 |
| 1.2798 | B.185 | C.13 |
| 1.2799 | B.186 | C.13 |
| 1.2800 | B.187 | C.13 |
| 1.2801 | B.188 | C.13 |
| 1.2802 | B.189 | C.13 |
| 1.2803 | B.190 | C.13 |
| 1.2804 | B.191 | C.13 |
| 1.2805 | B.192 | C.13 |
| 1.2806 | B.193 | C.13 |
| 1.2807 | B.194 | C.13 |
| 1.2808 | B.195 | C.13 |
| 1.2809 | B.196 | C.13 |
| 1.2810 | B.197 | C.13 |
| 1.2811 | B.198 | C.13 |
| 1.2812 | B.199 | C.13 |
| 1.2813 | B.200 | C.13 |
| 1.2814 | B.201 | C.13 |
| 1.2815 | B.1 | C.14 |
| 1.2816 | B.2 | C.14 |
| 1.2817 | B.3 | C.14 |
| 1.2818 | B.4 | C.14 |
| 1.2819 | B.5 | C.14 |
| 1.2820 | B.6 | C.14 |
| 1.2821 | B.7 | C.14 |
| 1.2822 | B.8 | C.14 |
| 1.2823 | B.9 | C.14 |
| 1.2824 | B.10 | C.14 |
| 1.2825 | B.11 | C.14 |
| 1.2826 | B.12 | C.14 |
| 1.2827 | B.13 | C.14 |
| 1.2828 | B.14 | C.14 |
| 1.2829 | B.15 | C.14 |
| 1.2830 | B.16 | C.14 |
| 1.2831 | B.17 | C.14 |
| 1.2832 | B.18 | C.14 |
| 1.2833 | B.19 | C.14 |
| 1.2834 | B.20 | C.14 |
| 1.2835 | B.21 | C.14 |
| 1.2836 | B.22 | C.14 |
| 1.2837 | B.23 | C.14 |
| 1.2838 | B.24 | C.14 |
| 1.2839 | B.25 | C.14 |
| 1.2840 | B.26 | C.14 |
| 1.2841 | B.27 | C.14 |
| 1.2842 | B.28 | C.14 |
| 1.2843 | B.29 | C.14 |
| 1.2844 | B.30 | C.14 |
| 1.2845 | B.31 | C.14 |
| 1.2846 | B.32 | C.14 |
| 1.2847 | B.33 | C.14 |
| 1.2848 | B.34 | C.14 |
| 1.2849 | B.35 | C.14 |
| 1.2850 | B.36 | C.14 |
| 1.2851 | B.37 | C.14 |
| 1.2852 | B.38 | C.14 |
| 1.2853 | B.39 | C.14 |
| 1.2854 | B.40 | C.14 |
| 1.2855 | B.41 | C.14 |
| 1.2856 | B.42 | C.14 |
| 1.2857 | B.43 | C.14 |
| 1.2858 | B.44 | C.14 |
| 1.2859 | B.45 | C.14 |
| 1.2860 | B.46 | C.14 |
| 1.2861 | B.47 | C.14 |
| 1.2862 | B.48 | C.14 |
| 1.2863 | B.49 | C.14 |
| 1.2864 | B.50 | C.14 |
| 1.2865 | B.51 | C.14 |
| 1.2866 | B.52 | C.14 |
| 1.2867 | B.53 | C.14 |
| 1.2868 | B.54 | C.14 |
| 1.2869 | B.55 | C.14 |
| 1.2870 | B.56 | C.14 |
| 1.2871 | B.57 | C.14 |
| 1.2872 | B.58. | C.14 |
| 1.2873 | B.59 | C.14 |
| 1.2874 | B.60 | C.14 |
| 1.2875 | B.61 | C.14 |
| 1.2876 | B.62 | C.14 |
| 1.2877 | B.63 | C.14 |
| 1.2878 | B.64 | C.14 |
| 1.2879 | B.65 | C.14 |
| 1.2880 | B.66 | C.14 |
| 1.2881 | B.67 | C.14 |
| 1.2882 | B.68 | C.14 |
| 1.2883 | B.69 | C.14 |
| 1.2884 | B.70 | C.14 |
| 1.2885 | B.71 | C.14 |
| 1.2886 | B.72 | C.14 |
| 1.2887 | B.73 | C.14 |
| 1.2888 | B.74 | C.14 |
| 1.2889 | B.75 | C.14 |
| 1.2890 | B.76 | C.14 |
| 1.2891 | B.77 | C.14 |
| 1.2892 | B.78 | C.14 |
| 1.2893 | B.79 | C.14 |
| 1.2894 | B.80 | C.14 |
| 1.2895 | B.81 | C.14 |
| 1.2896 | B.82 | C.14 |
| 1.2897 | B.83 | C.14 |
| 1.2898 | B.84 | C.14 |
| 1.2899 | B.85 | C.14 |
| 1.2900 | B.86 | C.14 |
| 1.2901 | B.87 | C.14 |
| 1.2902 | B.88 | C.14 |
| 1.2903 | B.89 | C.14 |
| 1.2904 | B.90 | C.14 |
| 1.2905 | B.91 | C.14 |
| 1.2906 | B.92 | C.14 |
| 1.2907 | B.93 | C.14 |
| 1.2908 | B.94 | C.14 |
| 1.2909 | B.95 | C.14 |
| 1.2910 | B.96 | C.14 |
| 1.2911 | B.97 | C.14 |
| 1.2912 | B.98 | C.14 |
| 1.2913 | B.99 | C.14 |
| 1.2914 | B.100 | C.14 |
| 1.2915 | B.101 | C.14 |
| 1.2916 | B.102 | C.14 |
| 1.2917 | B.103 | C.14 |
| 1.2918 | B.104 | C.14 |
| 1.2919 | B.105 | C.14 |
| 1.2920 | B.106 | C.14 |
| 1.2921 | B.107 | C.14 |
| 1.2922 | B.108 | C.14 |
| 1.2923 | B.109 | C.14 |
| 1.2924 | B.110 | C.14 |
| 1.2925 | B.111 | C.14 |
| 1.2926 | B.112 | C.14 |
| 1.2927 | B.113 | C.14 |
| 1.2928 | B.114 | C.14 |
| 1.2929 | B.115 | C.14 |
| 1.2930 | B.116 | C.14 |
| 1.2931 | B.117 | C.14 |

TABLE 1-continued (compositions 1.1 to 1.3635):

| comp. no. | herbicide B | safener C |
|---|---|---|
| 1.2932 | B.118 | C.14 |
| 1.2933 | B.119 | C.14 |
| 1.2934 | B.120 | C.14 |
| 1.2935 | B.121 | C.14 |
| 1.2936 | B.122 | C.14 |
| 1.2937 | B.123 | C.14 |
| 1.2938 | B.124 | C.14 |
| 1.2939 | B.125 | C.14 |
| 1.2940 | B.126 | C.14 |
| 1.2941 | B.127 | C.14 |
| 1.2942 | B.128 | C.14 |
| 1.2943 | B.129 | C.14 |
| 1.2944 | B.130 | C.14 |
| 1.2945 | B.131 | C.14 |
| 1.2946 | B.132 | C.14 |
| 1.2947 | B.133 | C.14 |
| 1.2948 | B.134 | C.14 |
| 1.2949 | B.135 | C.14 |
| 1.2950 | B.136 | C.14 |
| 1.2951 | B.137 | C.14 |
| 1.2952 | B.138 | C.14 |
| 1.2953 | B.139 | C.14 |
| 1.2954 | B.140 | C.14 |
| 1.2955 | B.141 | C.14 |
| 1.2956 | B.142 | C.14 |
| 1.2957 | B.143 | C.14 |
| 1.2958 | B.144 | C.14 |
| 1.2959 | B.145 | C.14 |
| 1.2960 | B.146 | C.14 |
| 1.2961 | B.147 | C.14 |
| 1.2962 | B.148 | C.14 |
| 1.2963 | B.149 | C.14 |
| 1.2964 | B.150 | C.14 |
| 1.2965 | B.151 | C.14 |
| 1.2966 | B.152 | C.14 |
| 1.2967 | B.153 | C.14 |
| 1.2968 | B.154 | C.14 |
| 1.2969 | B.155 | C.14 |
| 1.2970 | B.156 | C.14 |
| 1.2971 | B.157 | C.14 |
| 1.2972 | B.158 | C.14 |
| 1.2973 | B.159 | C.14 |
| 1.2974 | B.160 | C.14 |
| 1.2975 | B.161 | C.14 |
| 1.2976 | B.162 | C.14 |
| 1.2977 | B.163 | C.14 |
| 1.2978 | B.164 | C.14 |
| 1.2979 | B.165 | C.14 |
| 1.2980 | B.166 | C.14 |
| 1.2981 | B.167 | C.14 |
| 1.2982 | B.168 | C.14 |
| 1.2983 | B.169 | C.14 |
| 1.2984 | B.170 | C.14 |
| 1.2985 | B.171 | C.14 |
| 1.2986 | B.172 | C.14 |
| 1.2987 | B.173 | C.14 |
| 1.2988 | B.174 | C.14 |
| 1.2989 | B.175 | C.14 |
| 1.2990 | B.176 | C.14 |
| 1.2991 | B.177 | C.14 |
| 1.2992 | B.178 | C.14 |
| 1.2993 | B.179 | C.14 |
| 1.2994 | B.180 | C.14 |
| 1.2995 | B.181 | C.14 |
| 1.2996 | B.182 | C.14 |
| 1.2997 | B.183 | C.14 |
| 1.2998 | B.184 | C.14 |
| 1.2999 | B.185 | C.14 |
| 1.3000 | B.186 | C.14 |
| 1.3001 | B.187 | C.14 |
| 1.3002 | B.188 | C.14 |
| 1.3003 | B.189 | C.14 |
| 1.3004 | B.190 | C.14 |
| 1.3005 | B.191 | C.14 |
| 1.3006 | B.192 | C.14 |
| 1.3007 | B.193 | C.14 |
| 1.3008 | B.194 | C.14 |
| 1.3009 | B.195 | C.14 |
| 1.3010 | B.196 | C.14 |
| 1.3011 | B.197 | C.14 |
| 1.3012 | B.198 | C.14 |
| 1.3013 | B.199 | C.14 |
| 1.3014 | B.200 | C.14 |
| 1.3015 | B.201 | C.14 |
| 1.3016 | B.1 | C.15 |
| 1.3017 | B.2 | C.15 |
| 1.3018 | B.3 | C.15 |
| 1.3019 | B.4 | C.15 |
| 1.3020 | B.5 | C.15 |
| 1.3021 | B.6 | C.15 |
| 1.3022 | B.7 | C.15 |
| 1.3023 | B.8 | C.15 |
| 1.3024 | B.9 | C.15 |
| 1.3025 | B.10 | C.15 |
| 1.3026 | B.11 | C.15 |
| 1.3027 | B.12 | C.15 |
| 1.3028 | B.13 | C.15 |
| 1.3029 | B.14 | C.15 |
| 1.3030 | B.15 | C.15 |
| 1.3031 | B.16 | C.15 |
| 1.3032 | B.17 | C.15 |
| 1.3033 | B.18 | C.15 |
| 1.3034 | B.19 | C.15 |
| 1.3035 | B.20 | C.15 |
| 1.3036 | B.21 | C.15 |
| 1.3037 | B.22 | C.15 |
| 1.3038 | B.23 | C.15 |
| 1.3039 | B.24 | C.15 |
| 1.3040 | B.25 | C.15 |
| 1.3041 | B.26 | C.15 |
| 1.3042 | B.27 | C.15 |
| 1.3043 | B.28 | C.15 |
| 1.3044 | B.29 | C.15 |
| 1.3045 | B.30 | C.15 |
| 1.3046 | B.31 | C.15 |
| 1.3047 | B.32 | C.15 |
| 1.3048 | B.33 | C.15 |
| 1.3049 | B.34 | C.15 |
| 1.3050 | B.35 | C.15 |
| 1.3051 | B.36 | C.15 |
| 1.3052 | B.37 | C.15 |
| 1.3053 | B.38 | C.15 |
| 1.3054 | B.39 | C.15 |
| 1.3055 | B.40 | C.15 |
| 1.3056 | B.41 | C.15 |
| 1.3057 | B.42 | C.15 |
| 1.3058 | B.43 | C.15 |
| 1.3059 | B.44 | C.15 |
| 1.3060 | B.45 | C.15 |
| 1.3061 | B.46 | C.15 |
| 1.3062 | B.47 | C.15 |
| 1.3063 | B.48 | C.15 |
| 1.3064 | B.49 | C.15 |
| 1.3065 | B.50 | C.15 |
| 1.3066 | B.51 | C.15 |
| 1.3067 | B.52 | C.15 |
| 1.3068 | B.53 | C.15 |
| 1.3069 | B.54 | C.15 |
| 1.3070 | B.55 | C.15 |
| 1.3071 | B.56 | C.15 |
| 1.3072 | B.57 | C.15 |
| 1.3073 | B.58. | C.15 |
| 1.3074 | B.59 | C.15 |
| 1.3075 | B.60 | C.15 |
| 1.3076 | B.61 | C.15 |
| 1.3077 | B.62 | C.15 |
| 1.3078 | B.63 | C.15 |
| 1.3079 | B.64 | C.15 |
| 1.3080 | B.65 | C.15 |
| 1.3081 | B.66 | C.15 |
| 1.3082 | B.67 | C.15 |
| 1.3083 | B.68 | C.15 |

TABLE 1-continued (compositions 1.1 to 1.3635):

| comp. no. | herbicide B | safener C |
|---|---|---|
| 1.3084 | B.69 | C.15 |
| 1.3085 | B.70 | C.15 |
| 1.3086 | B.71 | C.15 |
| 1.3087 | B.72 | C.15 |
| 1.3088 | B.73 | C.15 |
| 1.3089 | B.74 | C.15 |
| 1.3090 | B.75 | C.15 |
| 1.3091 | B.76 | C.15 |
| 1.3092 | B.77 | C.15 |
| 1.3093 | B.78 | C.15 |
| 1.3094 | B.79 | C.15 |
| 1.3095 | B.80 | C.15 |
| 1.3096 | B.81 | C.15 |
| 1.3097 | B.82 | C.15 |
| 1.3098 | B.83 | C.15 |
| 1.3099 | B.84 | C.15 |
| 1.3100 | B.85 | C.15 |
| 1.3101 | B.86 | C.15 |
| 1.3102 | B.87 | C.15 |
| 1.3103 | B.88 | C.15 |
| 1.3104 | B.89 | C.15 |
| 1.3105 | B.90 | C.15 |
| 1.3106 | B.91 | C.15 |
| 1.3107 | B.92 | C.15 |
| 1.3108 | B.93 | C.15 |
| 1.3109 | B.94 | C.15 |
| 1.3110 | B.95 | C.15 |
| 1.3111 | B.96 | C.15 |
| 1.3112 | B.97 | C.15 |
| 1.3113 | B.98 | C.15 |
| 1.3114 | B.99 | C.15 |
| 1.3115 | B.100 | C.15 |
| 1.3116 | B.101 | C.15 |
| 1.3117 | B.102 | C.15 |
| 1.3118 | B.103 | C.15 |
| 1.3119 | B.104 | C.15 |
| 1.3120 | B.105 | C.15 |
| 1.3121 | B.106 | C.15 |
| 1.3122 | B.107 | C.15 |
| 1.3123 | B.108 | C.15 |
| 1.3124 | B.109 | C.15 |
| 1.3125 | B.110 | C.15 |
| 1.3126 | B.111 | C.15 |
| 1.3127 | B.112 | C.15 |
| 1.3128 | B.113 | C.15 |
| 1.3129 | B.114 | C.15 |
| 1.3130 | B.115 | C.15 |
| 1.3131 | B.116 | C.15 |
| 1.3132 | B.117 | C.15 |
| 1.3133 | B.118 | C.15 |
| 1.3134 | B.119 | C.15 |
| 1.3135 | B.120 | C.15 |
| 1.3136 | B.121 | C.15 |
| 1.3137 | B.122 | C.15 |
| 1.3138 | B.123 | C.15 |
| 1.3139 | B.124 | C.15 |
| 1.3140 | B.125 | C.15 |
| 1.3141 | B.126 | C.15 |
| 1.3142 | B.127 | C.15 |
| 1.3143 | B.128 | C.15 |
| 1.3144 | B.129 | C.15 |
| 1.3145 | B.130 | C.15 |
| 1.3146 | B.131 | C.15 |
| 1.3147 | B.132 | C.15 |
| 1.3148 | B.133 | C.15 |
| 1.3149 | B.134 | C.15 |
| 1.3150 | B.135 | C.15 |
| 1.3151 | B.136 | C.15 |
| 1.3152 | B.137 | C.15 |
| 1.3153 | B.138 | C.15 |
| 1.3154 | B.139 | C.15 |
| 1.3155 | B.140 | C.15 |
| 1.3156 | B.141 | C.15 |
| 1.3157 | B.142 | C.15 |
| 1.3158 | B.143 | C.15 |
| 1.3159 | B.144 | C.15 |
| 1.3160 | B.145 | C.15 |
| 1.3161 | B.146 | C.15 |
| 1.3162 | B.147 | C.15 |
| 1.3163 | B.148 | C.15 |
| 1.3164 | B.149 | C.15 |
| 1.3165 | B.150 | C.15 |
| 1.3166 | B.151 | C.15 |
| 1.3167 | B.152 | C.15 |
| 1.3168 | B.153 | C.15 |
| 1.3169 | B.154 | C.15 |
| 1.3170 | B.155 | C.15 |
| 1.3171 | B.156 | C.15 |
| 1.3172 | B.157 | C.15 |
| 1.3173 | B.158 | C.15 |
| 1.3174 | B.159 | C.15 |
| 1.3175 | B.160 | C.15 |
| 1.3176 | B.161 | C.15 |
| 1.3177 | B.162 | C.15 |
| 1.3178 | B.163 | C.15 |
| 1.3179 | B.164 | C.15 |
| 1.3180 | B.165 | C.15 |
| 1.3181 | B.166 | C.15 |
| 1.3182 | B.167 | C.15 |
| 1.3183 | B.168 | C.15 |
| 1.3184 | B.169 | C.15 |
| 1.3185 | B.170 | C.15 |
| 1.3186 | B.171 | C.15 |
| 1.3187 | B.172 | C.15 |
| 1.3188 | B.173 | C.15 |
| 1.3189 | B.174 | C.15 |
| 1.3190 | B.175 | C.15 |
| 1.3191 | B.176 | C.15 |
| 1.3192 | B.177 | C.15 |
| 1.3193 | B.178 | C.15 |
| 1.3194 | B.179 | C.15 |
| 1.3195 | B.180 | C.15 |
| 1.3196 | B.181 | C.15 |
| 1.3197 | B.182 | C.15 |
| 1.3198 | B.183 | C.15 |
| 1.3199 | B.184 | C.15 |
| 1.3200 | B.185 | C.15 |
| 1.3201 | B.186 | C.15 |
| 1.3202 | B.187 | C.15 |
| 1.3203 | B.188 | C.15 |
| 1.3204 | B.189 | C.15 |
| 1.3205 | B.190 | C.15 |
| 1.3206 | B.191 | C.15 |
| 1.3207 | B.192 | C.15 |
| 1.3208 | B.193 | C.15 |
| 1.3209 | B.194 | C.15 |
| 1.3210 | B.195 | C.15 |
| 1.3211 | B.196 | C.15 |
| 1.3212 | B.197 | C.15 |
| 1.3213 | B.198 | C.15 |
| 1.3214 | B.199 | C.15 |
| 1.3215 | B.200 | C.15 |
| 1.3216 | B.201 | C.15 |
| 1.3217 | B.1 | C.16 |
| 1.3218 | B.2 | C.16 |
| 1.3219 | B.3 | C.16 |
| 1.3220 | B.4 | C.16 |
| 1.3221 | B.5 | C.16 |
| 1.3222 | B.6 | C.16 |
| 1.3223 | B.7 | C.16 |
| 1.3224 | B.8 | C.16 |
| 1.3225 | B.9 | C.16 |
| 1.3226 | B.10 | C.16 |
| 1.3227 | B.11 | C.16 |
| 1.3228 | B.12 | C.16 |
| 1.3229 | B.13 | C.16 |
| 1.3230 | B.14 | C.16 |
| 1.3231 | B.15 | C.16 |
| 1.3232 | B.16 | C.16 |
| 1.3233 | B.17 | C.16 |
| 1.3234 | B.18 | C.16 |
| 1.3235 | B.19 | C.16 |

TABLE 1-continued (compositions 1.1 to 1.3635):

| comp. no. | herbicide B | safener C |
|---|---|---|
| 1.3236 | B.20 | C.16 |
| 1.3237 | B.21 | C.16 |
| 1.3238 | B.22 | C.16 |
| 1.3239 | B.23 | C.16 |
| 1.3240 | B.24 | C.16 |
| 1.3241 | B.25 | C.16 |
| 1.3242 | B.26 | C.16 |
| 1.3243 | B.27 | C.16 |
| 1.3244 | B.28 | C.16 |
| 1.3245 | B.29 | C.16 |
| 1.3246 | B.30 | C.16 |
| 1.3247 | B.31 | C.16 |
| 1.3248 | B.32 | C.16 |
| 1.3249 | B.33 | C.16 |
| 1.3250 | B.34 | C.16 |
| 1.3251 | B.35 | C.16 |
| 1.3252 | B.36 | C.16 |
| 1.3253 | B.37 | C.16 |
| 1.3254 | B.38 | C.16 |
| 1.3255 | B.39 | C.16 |
| 1.3256 | B.40 | C.16 |
| 1.3257 | B.41 | C.16 |
| 1.3258 | B.42 | C.16 |
| 1.3259 | B.43 | C.16 |
| 1.3260 | B.44 | C.16 |
| 1.3261 | B.45 | C.16 |
| 1.3262 | B.46 | C.16 |
| 1.3263 | B.47 | C.16 |
| 1.3264 | B.48 | C.16 |
| 1.3265 | B.49 | C.16 |
| 1.3266 | B.50 | C.16 |
| 1.3267 | B.51 | C.16 |
| 1.3268 | B.52 | C.16 |
| 1.3269 | B.53 | C.16 |
| 1.3270 | B.54 | C.16 |
| 1.3271 | B.55 | C.16 |
| 1.3272 | B.56 | C.16 |
| 1.3273 | B.57 | C.16 |
| 1.3274 | B.58. | C.16 |
| 1.3275 | B.59 | C.16 |
| 1.3276 | B.60 | C.16 |
| 1.3277 | B.61 | C.16 |
| 1.3278 | B.62 | C.16 |
| 1.3279 | B.63 | C.16 |
| 1.3280 | B.64 | C.16 |
| 1.3281 | B.65 | C.16 |
| 1.3282 | B.66 | C.16 |
| 1.3283 | B.67 | C.16 |
| 1.3284 | B.68 | C.16 |
| 1.3285 | B.69 | C.16 |
| 1.3286 | B.70 | C.16 |
| 1.3287 | B.71 | C.16 |
| 1.3288 | B.72 | C.16 |
| 1.3289 | B.73 | C.16 |
| 1.3290 | B.74 | C.16 |
| 1.3291 | B.75 | C.16 |
| 1.3292 | B.76 | C.16 |
| 1.3293 | B.77 | C.16 |
| 1.3294 | B.78 | C.16 |
| 1.3295 | B.79 | C.16 |
| 1.3296 | B.80 | C.16 |
| 1.3297 | B.81 | C.16 |
| 1.3298 | B.82 | C.16 |
| 1.3299 | B.83 | C.16 |
| 1.3300 | B.84 | C.16 |
| 1.3301 | B.85 | C.16 |
| 1.3302 | B.86 | C.16 |
| 1.3303 | B.87 | C.16 |
| 1.3304 | B.88 | C.16 |
| 1.3305 | B.89 | C.16 |
| 1.3306 | B.90 | C.16 |
| 1.3307 | B.91 | C.16 |
| 1.3308 | B.92 | C.16 |
| 1.3309 | B.93 | C.16 |
| 1.3310 | B.94 | C.16 |
| 1.3311 | B.95 | C.16 |
| 1.3312 | B.96 | C.16 |
| 1.3313 | B.97 | C.16 |
| 1.3314 | B.98 | C.16 |
| 1.3315 | B.99 | C.16 |
| 1.3316 | B.100 | C.16 |
| 1.3317 | B.101 | C.16 |
| 1.3318 | B.102 | C.16 |
| 1.3319 | B.103 | C.16 |
| 1.3320 | B.104 | C.16 |
| 1.3321 | B.105 | C.16 |
| 1.3322 | B.106 | C.16 |
| 1.3323 | B.107 | C.16 |
| 1.3324 | B.108 | C.16 |
| 1.3325 | B.109 | C.16 |
| 1.3326 | B.110 | C.16 |
| 1.3327 | B.111 | C.16 |
| 1.3328 | B.112 | C.16 |
| 1.3329 | B.113 | C.16 |
| 1.3330 | B.114 | C.16 |
| 1.3331 | B.115 | C.16 |
| 1.3332 | B.116 | C.16 |
| 1.3333 | B.117 | C.16 |
| 1.3334 | B.118 | C.16 |
| 1.3335 | B.119 | C.16 |
| 1.3336 | B.120 | C.16 |
| 1.3337 | B.121 | C.16 |
| 1.3338 | B.122 | C.16 |
| 1.3339 | B.123 | C.16 |
| 1.3340 | B.124 | C.16 |
| 1.3341 | B.125 | C.16 |
| 1.3342 | B.126 | C.16 |
| 1.3343 | B.127 | C.16 |
| 1.3344 | B.128 | C.16 |
| 1.3345 | B.129 | C.16 |
| 1.3346 | B.130 | C.16 |
| 1.3347 | B.131 | C.16 |
| 1.3348 | B.132 | C.16 |
| 1.3349 | B.133 | C.16 |
| 1.3350 | B.134 | C.16 |
| 1.3351 | B.135 | C.16 |
| 1.3352 | B.136 | C.16 |
| 1.3353 | B.137 | C.16 |
| 1.3354 | B.138 | C.16 |
| 1.3355 | B.139 | C.16 |
| 1.3356 | B.140 | C.16 |
| 1.3357 | B.141 | C.16 |
| 1.3358 | B.142 | C.16 |
| 1.3359 | B.143 | C.16 |
| 1.3360 | B.144 | C.16 |
| 1.3361 | B.145 | C.16 |
| 1.3362 | B.146 | C.16 |
| 1.3363 | B.147 | C.16 |
| 1.3364 | B.148 | C.16 |
| 1.3365 | B.149 | C.16 |
| 1.3366 | B.150 | C.16 |
| 1.3367 | B.151 | C.16 |
| 1.3368 | B.152 | C.16 |
| 1.3369 | B.153 | C.16 |
| 1.3370 | B.154 | C.16 |
| 1.3371 | B.155 | C.16 |
| 1.3372 | B.156 | C.16 |
| 1.3373 | B.157 | C.16 |
| 1.3374 | B.158 | C.16 |
| 1.3375 | B.159 | C.16 |
| 1.3376 | B.160 | C.16 |
| 1.3377 | B.161 | C.16 |
| 1.3378 | B.162 | C.16 |
| 1.3379 | B.163 | C.16 |
| 1.3380 | B.164 | C.16 |
| 1.3381 | B.165 | C.16 |
| 1.3382 | B.166 | C.16 |
| 1.3383 | B.167 | C.16 |
| 1.3384 | B.168 | C.16 |
| 1.3385 | B.169 | C.16 |
| 1.3386 | B.170 | C.16 |
| 1.3387 | B.171 | C.16 |

TABLE 1-continued (compositions 1.1 to 1.3635):

| comp. no. | herbicide B | safener C |
|---|---|---|
| 1.3388 | B.172 | C.16 |
| 1.3389 | B.173 | C.16 |
| 1.3390 | B.174 | C.16 |
| 1.3391 | B.175 | C.16 |
| 1.3392 | B.176 | C.16 |
| 1.3393 | B.177 | C.16 |
| 1.3394 | B.178 | C.16 |
| 1.3395 | B.179 | C.16 |
| 1.3396 | B.180 | C.16 |
| 1.3397 | B.181 | C.16 |
| 1.3398 | B.182 | C.16 |
| 1.3399 | B.183 | C.16 |
| 1.3400 | B.184 | C.16 |
| 1.3401 | B.185 | C.16 |
| 1.3402 | B.186 | C.16 |
| 1.3403 | B.187 | C.16 |
| 1.3404 | B.188 | C.16 |
| 1.3405 | B.189 | C.16 |
| 1.3406 | B.190 | C.16 |
| 1.3407 | B.191 | C.16 |
| 1.3408 | B.192 | C.16 |
| 1.3409 | B.193 | C.16 |
| 1.3410 | B.194 | C.16 |
| 1.3411 | B.195 | C.16 |
| 1.3412 | B.196 | C.16 |
| 1.3413 | B.197 | C.16 |
| 1.3414 | B.198 | C.16 |
| 1.3415 | B.199 | C.16 |
| 1.3416 | B.200 | C.16 |
| 1.3417 | B.201 | C.16 |
| 1.3418 | B.1 | C.17 |
| 1.3419 | B.2 | C.17 |
| 1.3420 | B.3 | C.17 |
| 1.3421 | B.4 | C.17 |
| 1.3422 | B.5 | C.17 |
| 1.3423 | B.6 | C.17 |
| 1.3424 | B.7 | C.17 |
| 1.3425 | B.8 | C.17 |
| 1.3426 | B.9 | C.17 |
| 1.3427 | B.10 | C.17 |
| 1.3428 | B.11 | C.17 |
| 1.3429 | B.12 | C.17 |
| 1.3430 | B.13 | C.17 |
| 1.3431 | B.14 | C.17 |
| 1.3432 | B.15 | C.17 |
| 1.3433 | B.16 | C.17 |
| 1.3434 | B.17 | C.17 |
| 1.3435 | B.18 | C.17 |
| 1.3436 | B.19 | C.17 |
| 1.3437 | B.20 | C.17 |
| 1.3438 | B.21 | C.17 |
| 1.3439 | B.22 | C.17 |
| 1.3440 | B.23 | C.17 |
| 1.3441 | B.24 | C.17 |
| 1.3442 | B.25 | C.17 |
| 1.3443 | B.26 | C.17 |
| 1.3444 | B.27 | C.17 |
| 1.3445 | B.28 | C.17 |
| 1.3446 | B.29 | C.17 |
| 1.3447 | B.30 | C.17 |
| 1.3448 | B.31 | C.17 |
| 1.3449 | B.32 | C.17 |
| 1.3450 | B.33 | C.17 |
| 1.3451 | B.34 | C.17 |
| 1.3452 | B.35 | C.17 |
| 1.3453 | B.36 | C.17 |
| 1.3454 | B.37 | C.17 |
| 1.3455 | B.38 | C.17 |
| 1.3456 | B.39 | C.17 |
| 1.3457 | B.40 | C.17 |
| 1.3458 | B.41 | C.17 |
| 1.3459 | B.42 | C.17 |
| 1.3460 | B.43 | C.17 |
| 1.3461 | B.44 | C.17 |
| 1.3462 | B.45 | C.17 |
| 1.3463 | B.46 | C.17 |
| 1.3464 | B.47 | C.17 |
| 1.3465 | B.48 | C.17 |
| 1.3466 | B.49 | C.17 |
| 1.3467 | B.50 | C.17 |
| 1.3468 | B.51 | C.17 |
| 1.3469 | B.52 | C.17 |
| 1.3470 | B.53 | C.17 |
| 1.3471 | B.54 | C.17 |
| 1.3472 | B.55 | C.17 |
| 1.3473 | B.56 | C.17 |
| 1.3474 | B.57 | C.17 |
| 1.3475 | B.58. | C.17 |
| 1.3476 | B.59 | C.17 |
| 1.3477 | B.60 | C.17 |
| 1.3478 | B.61 | C.17 |
| 1.3479 | B.62 | C.17 |
| 1.3480 | B.63 | C.17 |
| 1.3481 | B.64 | C.17 |
| 1.3482 | B.65 | C.17 |
| 1.3483 | B.66 | C.17 |
| 1.3484 | B.67 | C.17 |
| 1.3485 | B.68 | C.17 |
| 1.3486 | B.69 | C.17 |
| 1.3487 | B.70 | C.17 |
| 1.3488 | B.71 | C.17 |
| 1.3489 | B.72 | C.17 |
| 1.3490 | B.73 | C.17 |
| 1.3491 | B.74 | C.17 |
| 1.3492 | B.75 | C.17 |
| 1.3493 | B.76 | C.17 |
| 1.3494 | B.77 | C.17 |
| 1.3495 | B.78 | C.17 |
| 1.3496 | B.79 | C.17 |
| 1.3497 | B.80 | C.17 |
| 1.3498 | B.81 | C.17 |
| 1.3499 | B.82 | C.17 |
| 1.3500 | B.83 | C.17 |
| 1.3501 | B.84 | C.17 |
| 1.3502 | B.85 | C.17 |
| 1.3503 | B.86 | C.17 |
| 1.3504 | B.87 | C.17 |
| 1.3505 | B.88 | C.17 |
| 1.3506 | B.89 | C.17 |
| 1.3507 | B.90 | C.17 |
| 1.3508 | B.91 | C.17 |
| 1.3509 | B.92 | C.17 |
| 1.3510 | B.93 | C.17 |
| 1.3511 | B.94 | C.17 |
| 1.3512 | B.95 | C.17 |
| 1.3513 | B.96 | C.17 |
| 1.3514 | B.97 | C.17 |
| 1.3515 | B.98 | C.17 |
| 1.3516 | B.99 | C.17 |
| 1.3517 | B.100 | C.17 |
| 1.3518 | B.101 | C.17 |
| 1.3519 | B.102 | C.17 |
| 1.3520 | B.103 | C.17 |
| 1.3521 | B.104 | C.17 |
| 1.3522 | B.105 | C.17 |
| 1.3523 | B.106 | C.17 |
| 1.3524 | B.107 | C.17 |
| 1.3525 | B.108 | C.17 |
| 1.3526 | B.109 | C.17 |
| 1.3527 | B.110 | C.17 |
| 1.3528 | B.111 | C.17 |
| 1.3529 | B.112 | C.17 |
| 1.3530 | B.113 | C.17 |
| 1.3531 | B.114 | C.17 |
| 1.3532 | B.115 | C.17 |
| 1.3533 | B.116 | C.17 |
| 1.3534 | B.117 | C.17 |
| 1.3535 | B.118 | C.17 |
| 1.3536 | B.119 | C.17 |
| 1.3537 | B.120 | C.17 |
| 1.3538 | B.121 | C.17 |
| 1.3539 | B.122 | C.17 |

TABLE 1-continued (compositions 1.1 to 1.3635):

| comp. no. | herbicide B | safener C |
|---|---|---|
| 1.3540 | B.123 | C.17 |
| 1.3541 | B.124 | C.17 |
| 1.3542 | B.125 | C.17 |
| 1.3543 | B.126 | C.17 |
| 1.3544 | B.127 | C.17 |
| 1.3545 | B.128 | C.17 |
| 1.3546 | B.129 | C.17 |
| 1.3547 | B.130 | C.17 |
| 1.3548 | B.131 | C.17 |
| 1.3549 | B.132 | C.17 |
| 1.3550 | B.133 | C.17 |
| 1.3551 | B.134 | C.17 |
| 1.3552 | B.135 | C.17 |
| 1.3553 | B.136 | C.17 |
| 1.3554 | B.137 | C.17 |
| 1.3555 | B.138 | C.17 |
| 1.3556 | B.139 | C.17 |
| 1.3557 | B.140 | C.17 |
| 1.3558 | B.141 | C.17 |
| 1.3559 | B.142 | C.17 |
| 1.3560 | B.143 | C.17 |
| 1.3561 | B.144 | C.17 |
| 1.3562 | B.145 | C.17 |
| 1.3563 | B.146 | C.17 |
| 1.3564 | B.147 | C.17 |
| 1.3565 | B.148 | C.17 |
| 1.3566 | B.149 | C.17 |
| 1.3567 | B.150 | C.17 |
| 1.3568 | B.151 | C.17 |
| 1.3569 | B.152 | C.17 |
| 1.3570 | B.153 | C.17 |
| 1.3571 | B.154 | C.17 |
| 1.3572 | B.155 | C.17 |
| 1.3573 | B.156 | C.17 |
| 1.3574 | B.157 | C.17 |
| 1.3575 | B.158 | C.17 |
| 1.3576 | B.159 | C.17 |
| 1.3577 | B.160 | C.17 |
| 1.3578 | B.161 | C.17 |
| 1.3579 | B.162 | C.17 |
| 1.3580 | B.163 | C.17 |
| 1.3581 | B.164 | C.17 |
| 1.3582 | B.165 | C.17 |
| 1.3583 | B.166 | C.17 |
| 1.3584 | B.167 | C.17 |
| 1.3585 | B.168 | C.17 |
| 1.3586 | B.169 | C.17 |
| 1.3587 | B.170 | C.17 |
| 1.3588 | B.171 | C.17 |
| 1.3589 | B.172 | C.17 |
| 1.3590 | B.173 | C.17 |
| 1.3591 | B.174 | C.17 |
| 1.3592 | B.175 | C.17 |
| 1.3593 | B.176 | C.17 |
| 1.3594 | B.177 | C.17 |
| 1.3595 | B.178 | C.17 |
| 1.3596 | B.179 | C.17 |
| 1.3597 | B.180 | C.17 |
| 1.3598 | B.181 | C.17 |
| 1.3599 | B.182 | C.17 |
| 1.3600 | B.183 | C.17 |
| 1.3601 | B.184 | C.17 |
| 1.3602 | B.185 | C.17 |
| 1.3603 | B.186 | C.17 |
| 1.3604 | B.187 | C.17 |
| 1.3605 | B.188 | C.17 |
| 1.3606 | B.189 | C.17 |
| 1.3607 | B.190 | C.17 |
| 1.3608 | B.191 | C.17 |
| 1.3609 | B.192 | C.17 |
| 1.3610 | B.193 | C.17 |
| 1.3611 | B.194 | C.17 |
| 1.3612 | B.195 | C.17 |
| 1.3613 | B.196 | C.17 |
| 1.3614 | B.197 | C.17 |
| 1.3615 | B.198 | C.17 |
| 1.3616 | B.199 | C.17 |
| 1.3617 | B.200 | C.17 |
| 1.3618 | B.201 | C.17 |
| 1.3619 | — | C.1 |
| 1.3620 | — | C.2 |
| 1.3621 | — | C.3 |
| 1.3622 | — | C.4 |
| 1.3623 | — | C.5 |
| 1.3624 | — | C.6 |
| 1.3625 | — | C.7 |
| 1.3626 | — | C.8 |
| 1.3627 | — | C.9 |
| 1.3628 | — | C.10 |
| 1.3629 | — | C.11 |
| 1.3630 | — | C.12 |
| 1.3631 | — | C.13 |
| 1.3632 | — | C.14 |
| 1.3633 | — | C.15 |
| 1.3634 | — | C.16 |
| 1.3635 | — | C.17 |
| 1.3636 | B.202 | — |
| 1.3637 | B.202 | C.1 |
| 1.3638 | B.202 | C.2 |
| 1.3639 | B.202 | C.3 |
| 1.3640 | B.202 | C.4 |
| 1.3641 | B.202 | C.5 |
| 1.3642 | B.202 | C.6 |
| 1.3643 | B.202 | C.7 |
| 1.3644 | B.202 | C.8 |
| 1.3645 | B.202 | C.9 |
| 1.3646 | B.202 | C.10 |
| 1.3647 | B.202 | C.11 |
| 1.3648 | B.202 | C.12 |
| 1.3649 | B.202 | C.13 |
| 1.3650 | B.202 | C.14 |
| 1.3651 | B.202 | C.15 |
| 1.3652 | B.202 | C.16 |
| 1.3653 | B.202 | C.17 |

The specific number for each single composition is deductible as follows: Composition 1.200 for example comprises the uracilpyridine I.a.339 and cinmethylin (B.200) (see table 1, entry 1.200; as well as table B, entry B.200).

Composition 2.200 for example comprises the uracilpyridine I.a.109 (see the definition for compositions 2.1 to 2.3653, preferably 2.1 to 2.3635, below) and cinmethylin (B.200) (see table 1, entry 1.200; as well as table B, entry B.200).

Composition 7.200 for example comprises imazapyr (B.35) (see the definition for compositions 7.1 to 7.3653, preferably 7.1 to 7.3635, below), the uracilpyridine I.a.339 and cinmethylin (B.200) (see table 1, entry 1.200; as well as table B, entry B.200).

Also especially preferred are compositions 2.1 to 2.3653, more preferred 2.1. to 2.3635, which differ from the corresponding compositions 1.1 to 1.3653, more preferred 1.1 to 1.3635, only in that they comprise as the active compound A the uracilpyridine of formula (I.a.109).

Also especially preferred are compositions 3.1 to 3.3653, more preferred 3.1. to 3.3635, which differ from the corresponding compositions 1.1 to 1.3653, more preferred 1.1 to 1.3635, only in that they additionally comprise B.2 as further herbicide B.

Also especially preferred are compositions 4.1 to 4.3653, more preferred 4.1. to 4.3635, which differ from the corresponding compositions 1.1 to 1.3653, more preferred 1.1 to 1.3635, only in that they additionally comprise B.8 as further herbicide B.

Also especially preferred are compositions 5.1 to 5.3653, more preferred 5.1. to 5.3635, which differ from the corresponding compositions 1.1 to 1.3653, more preferred 1.1 to 1.3635, only in that they additionally comprise B.30 further herbicide B.

Also especially preferred are compositions 6.1 to 6.3653, more preferred 6.1. to 6.3635, which differ from the corresponding compositions 1.1 to 1.3653, more preferred 1.1 to 1.3635, only in that they additionally comprise B.32 as further herbicide B.

Also especially preferred are compositions 7.1 to 7.3653, more preferred 7.1. to 7.3635, which differ from the corresponding compositions 1.1 to 1.3653, more preferred 1.1 to 1.3635, only in that they additionally comprise B.35 further herbicide B.

Also especially preferred are compositions 8.1 to 8.3653, more preferred 8.1. to 8.3635, which differ from the corresponding compositions 1.1 to 1.3653, more preferred 1.1 to 1.3635, only in that they additionally comprise B.38 as further herbicide B.

Also especially preferred are compositions 9.1 to 9.3653, more preferred 9.1. to 9.3635, which differ from the corresponding compositions 1.1 to 1.3653, more preferred 1.1 to 1.3635, only in that they additionally comprise B.40 further herbicide B.

Also especially preferred are compositions 10.1 to 10.3653, more preferred 10.1. to 10.3635, which differ from the corresponding compositions 1.1 to 1.3653, more preferred 1.1 to 1.3635, only in that they additionally comprise B.51 as further herbicide B.

Also especially preferred are compositions 11.1 to 11.3653, more preferred 11.1. to 11.3635, which differ from the corresponding compositions 1.1 to 1.3653, more preferred 1.1 to 1.3635, only in that they additionally comprise B.55 as further herbicide B.

Also especially preferred are compositions 12.1 to 12.3653, more preferred 12.1. to 12.3635, which differ from the corresponding compositions 1.1 to 1.3653, more preferred 1.1 to 1.3635, only in that they additionally comprise B.56 as further herbicide B.

Also especially preferred are compositions 13.1 to 13.3653, more preferred 13.1. to 13.3635, which differ from the corresponding compositions 1.1 to 1.3653, more preferred 1.1 to 1.3635, only in that they additionally comprise B.64 as further herbicide B.

Also especially preferred are compositions 14.1 to 14.3653, more preferred 14.1. to 14.3635, which differ from the corresponding compositions 1.1 to 1.3653, more preferred 1.1 to 1.3635, only in that they additionally comprise B.66 as further herbicide B.

Also especially preferred are compositions 15.1 to 15.3653, more preferred 15.1. to 15.3635, which differ from the corresponding compositions 1.1 to 1.3653, more preferred 1.1 to 1.3635, only in that they additionally comprise B.67 as further herbicide B.

Also especially preferred are compositions 16.1 to 16.3653, more preferred 16.1. to 16.3635, which differ from the corresponding compositions 1.1 to 1.3653, more preferred 1.1 to 1.3635, only in that they additionally comprise B.68 as further herbicide B.

Also especially preferred are compositions 17.1 to 17.3653, more preferred 17.1. to 17.3635, which differ from the corresponding compositions 1.1 to 1.3653, more preferred 1.1 to 1.3635, only in that they additionally comprise B.69 as further herbicide B.

Also especially preferred are compositions 18.1 to 18.3653, more preferred 18.1. to 18.3635, which differ from the corresponding compositions 1.1 to 1.3653, more preferred 1.1 to 1.3635, only in that they additionally comprise B.73 as further herbicide B.

Also especially preferred are compositions 19.1 to 19.3653, more preferred 19.1. to 19.3635, which differ from the corresponding compositions 1.1 to 1.3653, more preferred 1.1 to 1.3635, only in that they additionally comprise B.76 as further herbicide B.

Also especially preferred are compositions 20.1 to 20.3653, more preferred 20.1. to 20.3635, which differ from the corresponding compositions 1.1 to 1.3653, more preferred 1.1 to 1.3635, only in that they additionally comprise B.81 as further herbicide B.

Also especially preferred are compositions 21.1 to 21.3653, more preferred 21.1. to 21.3635, which differ from the corresponding compositions 1.1 to 1.3653, more preferred 1.1 to 1.3635, only in that they additionally comprise B.82 as further herbicide B.

Also especially preferred are compositions 22.1 to 22.3653, more preferred 22.1. to 22.3635, which differ from the corresponding compositions 1.1 to 1.3653, more preferred 1.1 to 1.3635, only in that they additionally comprise B.85 as further herbicide B.

Also especially preferred are compositions 23.1 to 23.3653, more preferred 23.1. to 23.3635, which differ from the corresponding compositions 1.1 to 1.3653, more preferred 1.1 to 1.3635, only in that they additionally comprise B.88 as further herbicide B.

Also especially preferred are compositions 24.1 to 24.3653, more preferred 24.1. to 24.3635, which differ from the corresponding compositions 1.1 to 1.3653, more preferred 1.1 to 1.3635, only in that they additionally comprise B.89 as further herbicide B.

Also especially preferred are compositions 25.1 to 25.3653, more preferred 25.1. to 25.3635, which differ from the corresponding compositions 1.1 to 1.3653, more preferred 1.1 to 1.3635, only in that they additionally comprise B.94 as further herbicide B.

Also especially preferred are compositions 26.1 to 26.3653, more preferred 26.1. to 26.3635, which differ from the corresponding compositions 1.1 to 1.3653, more preferred 1.1 to 1.3635, only in that they additionally comprise B.95 as further herbicide B.

Also especially preferred are compositions 27.1 to 27.3653, more preferred 27.1. to 27.3635, which differ from the corresponding compositions 1.1 to 1.3653, more preferred 1.1 to 1.3635, only in that they additionally comprise B.98 as further herbicide B.

Also especially preferred are compositions 28.1 to 28.3653, more preferred 28.1. to 28.3635, which differ from the corresponding compositions 1.1 to 1.3653, more preferred 1.1 to 1.3635, only in that they additionally comprise B.100 as further herbicide B.

Also especially preferred are compositions 29.1 to 29.3653, more preferred 29.1. to 29.3635, which differ from the corresponding compositions 1.1 to 1.3653, more preferred 1.1 to 1.3635, only in that they additionally comprise B.103 as further herbicide B.

Also especially preferred are compositions 30.1 to 30.3653, more preferred 30.1. to 30.3635, which differ from the corresponding compositions 1.1 to 1.3653, more preferred 1.1 to 1.3635, only in that they additionally comprise B.103 and B.67 as further herbicides B.

Also especially preferred are compositions 31.1 to 31.3653, more preferred 31.1. to 31.3635, which differ from the corresponding compositions 1.1 to 1.3653, more preferred 1.1 to 1.3635, only in that they additionally comprise B.103 and B.76 as further herbicides B.

Also especially preferred are compositions 32.1 to 32.3653, more preferred 32.1. to 32.3635, which differ from the corresponding compositions 1.1 to 1.3653, more preferred 1.1 to 1.3635, only in that they additionally comprise B.103 and B.82 as further herbicides B.

Also especially preferred are compositions 33.1 to 33.3653, more preferred 33.1. to 33.3635, which differ from the corresponding compositions 1.1 to 1.3653, more preferred 1.1 to 1.3635, only in that they additionally comprise B.104 as further herbicide B.

Also especially preferred are compositions 34.1 to 34.3653, more preferred 34.1. to 34.3635, which differ from the corresponding compositions 1.1 to 1.3653, more preferred 1.1 to 1.3635, only in that they additionally comprise B.104 and B.67 as further herbicides B.

Also especially preferred are compositions 35.1 to 35.3653, more preferred 35.1. to 35.3635, which differ from the corresponding compositions 1.1 to 1.3653, more preferred 1.1 to 1.3635, only in that they additionally comprise B.104 and B.76 as further herbicides B.

Also especially preferred are compositions 36.1 to 36.3653, more preferred 36.1. to 36.3635, which differ from the corresponding compositions 1.1 to 1.3653, more preferred 1.1 to 1.3635, only in that they additionally comprise B.104 and B.82 as further herbicides B.

Also especially preferred are compositions 37.1 to 37.3653, more preferred 37.1. to 37.3635, which differ from the corresponding compositions 1.1 to 1.3653, more preferred 1.1 to 1.3635, only in that they additionally comprise B.106 as further herbicide B.

Also especially preferred are compositions 38.1 to 38.3653, more preferred 38.1. to 38.3635, which differ from the corresponding compositions 1.1 to 1.3653, more preferred 1.1 to 1.3635, only in that they additionally comprise B.107 as further herbicide B.

Also especially preferred are compositions 39.1 to 39.3653, more preferred 39.1. to 39.3635, which differ from the corresponding compositions 1.1 to 1.3653, more preferred 1.1 to 1.3635, only in that they additionally comprise B. 107 and B.67 as further herbicides B.

Also especially preferred are compositions 40.1 to 40.3653, more preferred 40.1. to 40.3635, which differ from the corresponding compositions 1.1 to 1.3653, more preferred 1.1 to 1.3635, only in that they additionally comprise B. 107 and B.76 as further herbicides B.

Also especially preferred are compositions 41.1 to 41.3653, more preferred 41.1. to 41.3635, which differ from the corresponding compositions 1.1 to 1.3653, more preferred 1.1 to 1.3635, only in that they additionally comprise B. 107 and B.82 as further herbicides B.

Also especially preferred are compositions 42.1 to 42.3653, more preferred 42.1. to 42.3635, which differ from the corresponding compositions 1.1 to 1.3653, more preferred 1.1 to 1.3635, only in that they additionally comprise B.109 as further herbicide B.

Also especially preferred are compositions 43.1 to 43.3653, more preferred 43.1. to 43.3635, which differ from the corresponding compositions 1.1 to 1.3653, more preferred 1.1 to 1.3635, only in that they additionally comprise B.111 as further herbicide B.

Also especially preferred are compositions 44.1 to 44.3653, more preferred 44.1. to 44.3635, which differ from the corresponding compositions 1.1 to 1.3653, more preferred 1.1 to 1.3635, only in that they additionally comprise B.111 and B.67 as further herbicides B.

Also especially preferred are compositions 45.1 to 45.3653, more preferred 45.1. to 45.3635, which differ from the corresponding compositions 1.1 to 1.3653, more preferred 1.1 to 1.3635, only in that they additionally comprise B.111 and B.76 as further herbicides B.

Also especially preferred are compositions 46.1 to 46.3653, more preferred 46.1. to 46.3635, which differ from the corresponding compositions 1.1 to 1.3653, more preferred 1.1 to 1.3635, only in that they additionally comprise B.111 and B.82 as further herbicides B.

Also especially preferred are compositions 47.1 to 47.3653, more preferred 47.1. to 47.3635, which differ from the corresponding compositions 1.1 to 1.3653, more preferred 1.1 to 1.3635, only in that they additionally comprise B. 116 as further herbicide B.

Also especially preferred are compositions 48.1 to 48.3653, more preferred 48.1. to 48.3635, which differ from the corresponding compositions 1.1 to 1.3653, more preferred 1.1 to 1.3635, only in that they additionally comprise B.116 and B.67 as further herbicides B.

Also especially preferred are compositions 49.1 to 49.3653, more preferred 49.1. to 49.3635, which differ from the corresponding compositions 1.1 to 1.3653, more preferred 1.1 to 1.3635, only in that they additionally comprise B.116 and B.94 as further herbicides B.

Also especially preferred are compositions 50.1 to 50.3653, more preferred 50.1. to 50.3635, which differ from the corresponding compositions 1.1 to 1.3653, more preferred 1.1 to 1.3635, only in that they additionally comprise B.116 and B.103 as further herbicides B.

Also especially preferred are compositions 51.1 to 51.3653, more preferred 51.1. to 51.3635, which differ from the corresponding compositions 1.1 to 1.3653, more preferred 1.1 to 1.3635, only in that they additionally comprise B.116 and B.128 as further herbicides B.

Also especially preferred are compositions 52.1 to 52.3653, more preferred 52.1. to 52.3635, which differ from the corresponding compositions 1.1 to 1.3653, more preferred 1.1 to 1.3635, only in that they additionally comprise B.116 and B.104 as further herbicides B.

Also especially preferred are compositions 53.1 to 53.3653, more preferred 53.1. to 53.3635, which differ from the corresponding compositions 1.1 to 1.3653, more preferred 1.1 to 1.3635, only in that they additionally comprise B.116 and B.107 as further herbicides B.

Also especially preferred are compositions 54.1 to 54.3653, more preferred 54.1. to 54.3635, which differ from the corresponding compositions 1.1 to 1.3653, more preferred 1.1 to 1.3635, only in that they additionally comprise B.116 and B.111 as further herbicides B.

Also especially preferred are compositions 55.1 to 55.3653, more preferred 55.1. to 55.3635, which differ from the corresponding compositions 1.1 to 1.3653, more preferred 1.1 to 1.3635, only in that they additionally comprise B.122 as further herbicide B.

Also especially preferred are compositions 56.1 to 56.3653, more preferred 56.1. to 56.3635, which differ from the corresponding compositions 1.1 to 1.3653, more preferred 1.1 to 1.3635, only in that they additionally comprise B.126 as further herbicide B.

Also especially preferred are compositions 57.1 to 57.3653, more preferred 57.1. to 57.3635, which differ from the corresponding compositions 1.1 to 1.3653, more preferred 1.1 to 1.3635, only in that they additionally comprise B.128 as further herbicide B.

Also especially preferred are compositions 58.1 to 58.3653, more preferred 58.1. to 58.3635, which differ from the corresponding compositions 1.1 to 1.3653, more preferred 1.1 to 1.3635, only in that they additionally comprise B.131 as further herbicide B.

Also especially preferred are compositions 59.1 to 59.3653, more preferred 59.1. to 59.3635, which differ from the corresponding compositions 1.1 to 1.3653, more preferred 1.1 to 1.3635, only in that they additionally comprise B.132 as further herbicide B.

Also especially preferred are compositions 60.1 to 60.3653, more preferred 60.1. to 60.3635, which differ from the corresponding compositions 1.1 to 1.3653, more preferred 1.1 to 1.3635, only in that they additionally comprise B.133 as further herbicide B.

Also especially preferred are compositions 61.1 to 61.3653, more preferred 61.1. to 61.3635, which differ from the corresponding compositions 1.1 to 1.3653, more preferred 1.1 to 1.3635, only in that they additionally comprise B.135 as further herbicide B.

Also especially preferred are compositions 62.1 to 62.3653, more preferred 62.1. to 62.3635, which differ from the corresponding compositions 1.1 to 1.3653, more preferred 1.1 to 1.3635, only in that they additionally comprise B.137 as further herbicide B.

Also especially preferred are compositions 63.1 to 63.3653, more preferred 63.1. to 63.3635, which differ from the corresponding compositions 1.1 to 1.3653, more preferred 11.1 to 1.3635, only in that they additionally comprise B.138 as further herbicide B.

Also especially preferred are compositions 64.1 to 64.3653, more preferred 64.1. to 64.3635, which differ from the corresponding compositions 1.1 to 1.3653, more preferred 1.1 to 1.3635, only in that they additionally comprise B.140 as further herbicide B.

Also especially preferred are compositions 65.1 to 65.3653, more preferred 65.1. to 65.3635, which differ from the corresponding compositions 1.1 to 1.3653, more preferred 1.1 to 1.3635, only in that they additionally comprise B.145 as further herbicide B.

Also especially preferred are compositions 66.1 to 66.3653, more preferred 66.1. to 66.3635, which differ from the corresponding compositions 1.1 to 1.3653, more preferred 1.1 to 1.3635, only in that they additionally comprise B.153 as further herbicide B.

Also especially preferred are compositions 67.1 to 67.3653, more preferred 67.1. to 67.3635, which differ from the corresponding compositions 1.1 to 1.3653, more preferred 1.1 to 1.3635, only in that they additionally comprise B.156 as further herbicide B.

Also especially preferred are compositions 68.1 to 68.3653, more preferred 68.1. to 68.3635, which differ from the corresponding compositions 1.1 to 1.3653, more preferred 1.1 to 1.3635, only in that they additionally comprise B.171 as further herbicide B.

Also especially preferred are compositions 69.1 to 69.3653, more preferred 69.1. to 69.3635, which differ from the corresponding compositions 1.1 to 1.3653, more preferred 1.1 to 1.3635, only in that they additionally comprise B.174 as further herbicide B.

Also especially preferred are compositions 70.1 to 70.3653, more preferred 70.1. to 70.3635, which differ from the corresponding compositions 1.1 to 1.3653, more preferred 1.1 to 1.3635, only in that they comprise as the active compound A the uracilpyridine of formula (I.a.115).

Also especially preferred are compositions 71.1 to 71.3653, more preferred 71.1. to 71.3635, which differ from the corresponding compositions 1.1 to 1.3653, more preferred 1.1 to 1.3635, only in that they comprise as the active compound A the uracilpyridine of formula (I.a.255).

Also especially preferred are compositions 72.1 to 72.3653, more preferred 72.1. to 72.3635, which differ from the corresponding compositions 1.1 to 1.3653, more preferred 1.1 to 1.3635, only in that they comprise as the active compound A the uracilpyridine of formula (I.a.277).

Also especially preferred are compositions 73.1 to 73.3653, more preferred 73.1. to 73.3635, which differ from the corresponding compositions 1.1 to 1.3653, more preferred 1.1 to 1.3635, only in that they comprise as the active compound A the uracilpyridine of formula (I.a.283).

Also especially preferred are compositions 74.1 to 74.3653, more preferred 74.1. to 74.3635, which differ from the corresponding compositions 1.1 to 1.3653, more preferred 1.1 to 1.3635, only in that they comprise as the active compound A the uracilpyridine of formula (I.a.87).

Also especially preferred are compositions 75.1 to 75.3653, more preferred 75.1. to 75.3635, which differ from the corresponding compositions 1.1 to 1.3653, more preferred 1.1 to 1.3635, only in that they comprise as the active compound A the uracilpyridine of formula (I.a.361).

Also especially preferred are compositions 76.1 to 76.3653, more preferred 76.1. to 76.3635, which differ from the corresponding compositions 1.1 to 1.3653, more preferred 1.1 to 1.3635, only in that they comprise as the active compound A the uracilpyridine of formula (I.a.367).

Also especially preferred are compositions 77.1 to 77.3653, more preferred 77.1. to 77.3635, which differ from the corresponding compositions 1.1 to 1.3653, more preferred 1.1 to 1.3635, only in that they comprise as the active compound A the uracilpyridine of formula (I.h.87).

Also especially preferred are compositions 78.1 to 78.3653, more preferred 78.1. to 78.3635, which differ from the corresponding compositions 1.1 to 1.3653, more preferred 1.1 to 1.3635, only in that they comprise as the active compound A the uracilpyridine of formula (I.h.109).

Also especially preferred are compositions 79.1 to 79.3653, more preferred 79.1. to 79.3635, which differ from the corresponding compositions 1.1 to 1.3653, more preferred 1.1 to 1.3635, only in that they comprise as the active compound A the uracilpyridine of formula (I.h.115).

Also especially preferred are compositions 80.1 to 80.3653, more preferred 80.1. to 80.3635, which differ from the corresponding compositions 1.1 to 1.3653, more preferred 1.1 to 1.3635, only in that they comprise as the active compound A the uracilpyridine of formula (I.h.255).

Also especially preferred are compositions 81.1 to 81.3653, more preferred 81.1. to 81.3635, which differ from the corresponding compositions 1.1 to 1.3653, more preferred 1.1 to 1.3635, only in that they comprise as the active compound A the uracilpyridine of formula (I.h.277).

Also especially preferred are compositions 82.1 to 82.3653, more preferred 82.1. to 82.3635, which differ from the corresponding compositions 1.1 to 1.3653, more preferred 1.1 to 1.3635, only in that they comprise as the active compound A the uracilpyridine of formula (I.h.283).

Also especially preferred are compositions 83.1 to 83.3653, more preferred 83.1. to 83.3635, which differ from the corresponding compositions 1.1 to 1.3653, more preferred 1.1 to 1.3635, only in that they comprise as the active compound A the uracilpyridine of formula (I.h.339).

Also especially preferred are compositions 84.1 to 84.3653, more preferred 84.1. to 84.3635, which differ from the corresponding compositions 1.1 to 1.3653, more preferred 1.1 to 1.3635, only in that they comprise as the active compound A the uracilpyridine of formula (I.h.361).

Also especially preferred are compositions 85.1 to 85.3653, more preferred 85.1. to 85.3635, which differ from the corresponding compositions 1.1 to 1.3653, more preferred 1.1 to 1.3635, only in that they comprise as the active compound A the uracilpyridine of formula (I.h.367).

Also especially preferred are compositions 86.1 to 86.3653, more preferred 86.1. to 86.3635, which differ from the corresponding compositions 1.1 to 1.3653, more preferred 1.1 to 1.3635, only in they comprise as the active compound A the uracilpyridine of formula (I.h.339) and additionally comprise B.2 as further herbicide B.

Also especially preferred are compositions 87.1 to 87.3653, more preferred 87.1. to 87.3635, which differ from the corresponding compositions 1.1 to 1.3653, more preferred 1.1 to 1.3635, only in that they comprise as the active compound A the uracilpyridine of formula (I.h.339) and additionally comprise B.8 as further herbicide B.

Also especially preferred are compositions 88.1 to 88.3653, more preferred 88.1. to 88.3635, which differ from the corresponding compositions 1.1 to 1.3653, more preferred 1.1 to 1.3635, only in that they comprise as the active compound A the uracilpyridine of formula (I.h.339) and additionally comprise B.30 further herbicide B.

Also especially preferred are compositions 89.1 to 89.3653, more preferred 89.1. to 89.3635, which differ from the corresponding compositions 1.1 to 1.3653, more preferred 1.1 to 1.3635, only in that they comprise as the active compound A the uracilpyridine of formula (I.h.339) and additionally comprise B.32 as further herbicide B.

Also especially preferred are compositions 90.1 to 90.3653, more preferred 90.1. to 90.3635, which differ from the corresponding compositions 1.1 to 1.3653, more preferred 1.1 to 1.3635, only in that they comprise as the active compound A the uracilpyridine of formula (I.h.339) and additionally comprise B.35 further herbicide B.

Also especially preferred are compositions 91.1 to 91.3653, more preferred 91.1. to 91.3635, which differ from the corresponding compositions 1.1 to 1.3653, more preferred 1.1 to 1.3635, only in that they comprise as the active compound A the uracilpyridine of formula (I.h.339) and additionally comprise B.38 as further herbicide B.

Also especially preferred are compositions 92.1 to 92.3653, more preferred 92.1. to 92.3635, which differ from the corresponding compositions 1.1 to 1.3653, more preferred 1.1 to 1.3635, only in that they comprise as the active compound A the uracilpyridine of formula (I.h.339) and additionally comprise B.40 further herbicide B.

Also especially preferred are compositions 93.1 to 93.3653, more preferred 93.1. to 93.3635, which differ from the corresponding compositions 1.1 to 1.3653, more preferred 1.1 to 1.3635, only in that they comprise as the active compound A the uracilpyridine of formula (I.h.339) and additionally comprise B.51 as further herbicide B.

Also especially preferred are compositions 94.1 to 94.3653, more preferred 94.1. to 94.3635, which differ from the corresponding compositions 1.1 to 1.3653, more preferred 1.1 to 1.3635, only in that they comprise as the active compound A the uracilpyridine of formula (I.h.339) and additionally comprise B.55 as further herbicide B.

Also especially preferred are compositions 95.1 to 95.3653, more preferred 95.1. to 95.3635, which differ from the corresponding compositions 1.1 to 1.3653, more preferred 1.1 to 1.3635, only in that they comprise as the active compound A the uracilpyridine of formula (I.h.339) and additionally comprise B.56 as further herbicide B.

Also especially preferred are compositions 96.1 to 96.3653, more preferred 96.1. to 96.3635, which differ from the corresponding compositions 1.1 to 1.3653, more preferred 1.1 to 1.3635, only in that they comprise as the active compound A the uracilpyridine of formula (I.h.339) and additionally comprise B.64 as further herbicide B.

Also especially preferred are compositions 97.1 to 97.3653, more preferred 97.1. to 97.3635, which differ from the corresponding compositions 1.1 to 1.3653, more preferred 1.1 to 1.3635, only in that they comprise as the active compound A the uracilpyridine of formula (I.h.339) and additionally comprise B.66 as further herbicide B.

Also especially preferred are compositions 98.1 to 98.3653, more preferred 98.1. to 98.3635, which differ from the corresponding compositions 1.1 to 1.3653, more preferred 1.1 to 1.3635, only in that they comprise as the active compound A the uracilpyridine of formula (I.h.339) and additionally comprise B.67 as further herbicide B.

Also especially preferred are compositions 99.1 to 99.3653, more preferred 99.1. to 99.3635, which differ from the corresponding compositions 1.1 to 1.3653, more preferred 1.1 to 1.3635, only in that they comprise as the active compound A the uracilpyridine of formula (I.h.339) and additionally comprise B.68 as further herbicide B.

Also especially preferred are compositions 100.1 to 100.3653, more preferred 100.1. to 100.3635, which differ from the corresponding compositions 1.1 to 1.3653, more preferred 1.1 to 1.3635, only in that they comprise as the active compound A the uracilpyridine of formula (I.h.339) and additionally comprise B.69 as further herbicide B.

Also especially preferred are compositions 101.1 to 101.3653, more preferred 101.1. to 101.3635, which differ from the corresponding compositions 1.1 to 1.3653, more preferred 1.1 to 1.3635, only in that they comprise as the active compound A the uracilpyridine of formula (I.h.339) and additionally comprise B.73 as further herbicide B.

Also especially preferred are compositions 102.1 to 102.3653, more preferred 102.1. to 102.3635, which differ from the corresponding compositions 1.1 to 1.3653, more preferred 1.1 to 1.3635 only in that they comprise as the active compound A the uracilpyridine of formula (I.h.339) and additionally comprise B.76 as further herbicide B.

Also especially preferred are compositions 103.1 to 103.3653, more preferred 103.1. to 103.3635, which differ from the corresponding compositions 1.1 to 1.3653, more preferred 1.1 to 1.3635, only in that they comprise as the active compound A the uracilpyridine of formula (I.h.339) and additionally comprise B.81 as further herbicide B.

Also especially preferred are compositions 104.1 to 104.3653, more preferred 104.1. to 104.3635, which differ from the corresponding compositions 1.1 to 1.3653, more preferred 1.1 to 1.3635, only in that they comprise as the active compound A the uracilpyridine of formula (I.h.339) and additionally comprise B.82 as further herbicide B.

Also especially preferred are compositions 105.1 to 105.3653, more preferred 105.1. to 105.3635, which differ from the corresponding compositions 1.1 to 1.3653, more preferred 1.1 to 1.3635, only in that they comprise as the active compound A the uracilpyridine of formula (I.h.339) and additionally comprise B.85 as further herbicide B.

Also especially preferred are compositions 106.1 to 106.3653, more preferred 106.1. to 106.3635, which differ from the corresponding compositions 1.1 to 1.3653, more preferred 1.1 to 1.3635, only in that they comprise as the active compound A the uracilpyridine of formula (I.h.339) and additionally comprise B.88 as further herbicide B.

Also especially preferred are compositions 107.1 to 107.3653, more preferred 107.1. to 107.3635, which differ from the corresponding compositions 1.1 to 1.3653, more preferred 1.1 to 1.3635, only in that they comprise as the active compound A the uracilpyridine of formula (I.h.339) and additionally comprise B.89 as further herbicide B.

Also especially preferred are compositions 108.1 to 108.3653, more preferred 108.1. to 108.3635, which differ from the corresponding compositions 1.1 to 1.3653, more preferred 1.1 to 1.3635, only in that they comprise as the active compound A the uracilpyridine of formula (I.h.339) and additionally comprise B.94 as further herbicide B.

Also especially preferred are compositions 191.1 to 109.3653, more preferred 109.1. to 109.3635, which differ from the corresponding compositions 1.1 to 1.3653, more preferred 1.1 to 1.3635, only in that they comprise as the active compound A the uracilpyridine of formula (I.h.339) and additionally comprise B.95 as further herbicide B.

Also especially preferred are compositions 110.1 to 110.3653, more preferred 110.1. to 110.3635, which differ from the corresponding compositions 1.1 to 1.3653, more preferred 1.1 to 1.3635, only in that they comprise as the active compound A the uracilpyridine of formula (I.h.339) and additionally comprise B.98 as further herbicide B.

Also especially preferred are compositions 111.1 to 111.3653, more preferred 111.1. to 111.3635, which differ from the corresponding compositions 1.1 to 1.3653, more preferred 1.1 to 1.3635, only in that they comprise as the active compound A the uracilpyridine of formula (I.h.339) and additionally comprise B.100 as further herbicide B.

Also especially preferred are compositions 112.1 to 112.3653, more preferred 112.1. to 112.3635, which differ from the corresponding compositions 1.1 to 1.3653, more preferred 1.1 to 1.3635, only in that they comprise as the active compound A the uracilpyridine of formula (I.h.339) and additionally comprise B.103 as further herbicide B.

Also especially preferred are compositions 113.1 to 113.3653, more preferred 113.1. to 113.3635, which differ from the corresponding compositions 1.1 to 1.3653, more preferred 1.1 to 1.3635, only in that they comprise as the active compound A the uracilpyridine of formula (I.h.339) and additionally comprise B.103 and B.67 as further herbicides B.

Also especially preferred are compositions 114.1 to 114.3653, more preferred 114.1. to 114.3635, which differ from the corresponding compositions 1.1 to 1.3653, more preferred 1.1 to 1.3635, only in that they comprise as the active compound A the uracilpyridine of formula (I.h.339) and additionally comprise B.103 and B.76 as further herbicides B.

Also especially preferred are compositions 115.1 to 115.3653, more preferred 115.1. to 115.3635, which differ from the corresponding compositions 1.1 to 1.3653, more preferred 1.1 to 1.3635, only in that they comprise as the active compound A the uracilpyridine of formula (I.h.339) and additionally comprise B.103 and B.82 as further herbicides B.

Also especially preferred are compositions 116.1 to 116.3653, more preferred 116.1. to 116.3635, which differ from the corresponding compositions 1.1 to 1.3653, more preferred 1.1 to 1.3635, only in that they comprise as the active compound A the uracilpyridine of formula (I.h.339) and additionally comprise B.104 as further herbicide B.

Also especially preferred are compositions 117.1 to 117.3653, more preferred 117.1. to 117.3635, which differ from the corresponding compositions 1.1 to 1.3653, more preferred 1.1 to 1.3635, only in that they comprise as the active compound A the uracilpyridine of formula (I.h.339) and additionally comprise B.104 and B.67 as further herbicides B.

Also especially preferred are compositions 118.1 to 118.3653, more preferred 118.1. to 118.3635, which differ from the corresponding compositions 1.1 to 1.3653, more preferred 1.1 to 1.3635, only in that they comprise as the active compound A the uracilpyridine of formula (I.h.339) and additionally comprise B.104 and B.76 as further herbicides B.

Also especially preferred are compositions 119.1 to 119.3653, more preferred 119.1. to 119.3635, which differ from the corresponding compositions 1.1 to 1.3653, more preferred 1.1 to 1.3635, only in that they comprise as the active compound A the uracilpyridine of formula (I.h.339) and additionally comprise B.104 and B.82 as further herbicides B.

Also especially preferred are compositions 120.1 to 120.3653, more preferred 120.1. to 120.3635, which differ from the corresponding compositions 1.1 to 1.3653, more preferred 1.1 to 1.3635, only in that they comprise as the active compound A the uracilpyridine of formula (I.h.339) and additionally comprise B.106 as further herbicide B.

Also especially preferred are compositions 121.1 to 121.3653, more preferred 121.1. to 121.3635, which differ from the corresponding compositions 1.1 to 1.3653, more preferred 1.1 to 1.3635, only in that they comprise as the active compound A the uracilpyridine of formula (I.h.339) and additionally comprise B.107 as further herbicide B.

Also especially preferred are compositions 122.1 to 122.3653, more preferred 122.1. to 122.3635, which differ from the corresponding compositions 1.1 to 1.3653, more preferred 1.1 to 1.3635, only in that they comprise as the active compound A the uracilpyridine of formula (I.h.339) and additionally comprise B. 107 and B.67 as further herbicides B.

Also especially preferred are compositions 123.1 to 123.3653, more preferred 123.1. to 123.3635, which differ from the corresponding compositions 1.1 to 1.3653, more preferred 1.1 to 1.3635, only in that they comprise as the active compound A the uracilpyridine of formula (I.h.339) and additionally comprise B. 107 and B.76 as further herbicides B.

Also especially preferred are compositions 124.1 to 124.3653, more preferred 124.1. to 124.3635, which differ from the corresponding compositions 1.1 to 1.3653, more preferred 1.1 to 1.3635, only in that they comprise as the active compound A the uracilpyridine of formula (I.h.339) and additionally comprise B. 107 and B.82 as further herbicides B.

Also especially preferred are compositions 125.1 to 125.3653, more preferred 125.1. to 125.3635, which differ from the corresponding compositions 1.1 to 1.3653, more preferred 1.1 to 1.3635, only in that they comprise as the active compound A the uracilpyridine of formula (I.h.339) and additionally comprise B.109 as further herbicide B.

Also especially preferred are compositions 126.1 to 126.3653, more preferred 126.1. to 126.3635, which differ from the corresponding compositions 1.1 to 1.3653, more preferred 1.1 to 1.3635, only in that they comprise as the active compound A the uracilpyridine of formula (I.h.339) and additionally comprise B.111 as further herbicide B.

Also especially preferred are compositions 127.1 to 127.3653, more preferred 127.1. to 127.3635, which differ from the corresponding compositions 1.1 to 1.3653, more preferred 1.1 to 1.3635, only in that they comprise as the active compound A the uracilpyridine of formula (I.h.339) and additionally comprise B.111 and B.67 as further herbicides B.

Also especially preferred are compositions 128.1 to 128.3653, more preferred 128.1. to 128.3635, which differ from the corresponding compositions 1.1 to 1.3653, more preferred 1.1 to 1.3635, only in that they comprise as the active compound A the uracilpyridine of formula (I.h.339) and additionally comprise B.111 and B.76 as further herbicides B.

Also especially preferred are compositions 129.1 to 129.3653, more preferred 129.1. to 129.3635, which differ from the corresponding compositions 1.1 to 1.3653, more preferred 1.1 to 1.3635, only in that they comprise as the active compound A the uracilpyridine of formula (I.h.339) and additionally comprise B.111 and B.82 as further herbicides B.

Also especially preferred are compositions 130.1 to 130.3653, more preferred 130.1. to 130.3635, which differ from the corresponding compositions 1.1 to 1.3653, more preferred 1.1 to 1.3635, only in that they comprise as the active compound A the uracilpyridine of formula (I.h.339) and additionally comprise B. 116 as further herbicide B.

Also especially preferred are compositions 131.1 to 131.3653, more preferred 131.1. to 131.3635, which differ from the corresponding compositions 1.1 to 1.3653, more preferred 1.1 to 1.3635, only in that they comprise as the active compound A the uracilpyridine of formula (I.h.339) and additionally comprise B.116 and B.67 as further herbicides B.

Also especially preferred are compositions 132.1 to 132.3653, more preferred 132.1. to 132.3635, which differ from the corresponding compositions 1.1 to 1.3653, more preferred 1.1 to 1.3635, only in that they comprise as the active compound A the uracilpyridine of formula (I.h.339) and additionally comprise B.116 and B.94 as further herbicides B.

Also especially preferred are compositions 133.1 to 133.3653, more preferred 133.1. to 133.3635, which differ from the corresponding compositions 1.1 to 1.3653, more preferred 1.1 to 1.3635, only in that they comprise as the active compound A the uracilpyridine of formula (I.h.339) and additionally comprise B.116 and B.103 as further herbicides B.

Also especially preferred are compositions 134.1 to 134.3653, more preferred 134.1. to 134.3635, which differ from the corresponding compositions 1.1 to 1.3653, more preferred 1.1 to 1.3635, only in that they comprise as the active compound A the uracilpyridine of formula (I.h.339) and additionally comprise B.116 and B.128 as further herbicides B.

Also especially preferred are compositions 135.1 to 135.3653, more preferred 135.1. to 135.3635, which differ from the corresponding compositions 1.1 to 1.3653, more preferred 1.1 to 1.3635, only in that they comprise as the active compound A the uracilpyridine of formula (I.h.339) and additionally comprise B.116 and B.104 as further herbicides B.

Also especially preferred are compositions 136.1 to 136.3653, more preferred 136.1. to 136.3635, which differ from the corresponding compositions 1.1 to 1.3653, more preferred 1.1 to 1.3635, only in that they comprise as the active compound A the uracilpyridine of formula (I.h.339) and additionally comprise B.116 and B.107 as further herbicides B.

Also especially preferred are compositions 137.1 to 137.3653, more preferred 137.1. to 137.3635, which differ from the corresponding compositions 1.1 to 1.3653, more preferred 1.1 to 1.3635, only in that they comprise as the active compound A the uracilpyridine of formula (I.h.339) and additionally comprise B.116 and B.111 as further herbicides B.

Also especially preferred are compositions 138.1 to 138.3653, more preferred 138.1. to 138.3635, which differ from the corresponding compositions 1.1 to 1.3653, more preferred 1.1 to 1.3635, only in that they comprise as the active compound A the uracilpyridine of formula (I.h.339) and additionally comprise B.122 as further herbicide B.

Also especially preferred are compositions 139.1 to 139.3653, more preferred 139.1. to 139.3635, which differ from the corresponding compositions 1.1 to 1.3653, more preferred 1.1 to 1.3635, only in that they comprise as the active compound A the uracilpyridine of formula (I.h.339) and additionally comprise B.126 as further herbicide B.

Also especially preferred are compositions 140.1 to 140.3653, more preferred 140.1. to 140.3635, which differ from the corresponding compositions 1.1 to 1.3653, more preferred 1.1 to 1.3635, only in that they comprise as the active compound A the uracilpyridine of formula (I.h.339) and additionally comprise B.128 as further herbicide B.

Also especially preferred are compositions 141.1 to 141.3653, more preferred 141.1. to 141.3635, which differ from the corresponding compositions 1.1 to 1.3653, more preferred 1.1 to 1.3635, only in that they comprise as the active compound A the uracilpyridine of formula (I.h.339) and additionally comprise B.131 as further herbicide B.

Also especially preferred are compositions 142.1 to 142.3653, more preferred 142.1. to 142.3635, which differ from the corresponding compositions 1.1 to 1.3653, more preferred 1.1 to 1.3635, only in that they comprise as the active compound A the uracilpyridine of formula (I.h.339) and additionally comprise B.132 as further herbicide B.

Also especially preferred are compositions 143.1 to 143.3653, more preferred 143.1. to 143.3635, which differ from the corresponding compositions 1.1 to 1.3653, more preferred 1.1 to 1.3635, only in that they comprise as the active compound A the uracilpyridine of formula (I.h.339) and additionally comprise B.133 as further herbicide B.

Also especially preferred are compositions 144.1 to 144.3653, more preferred 144.1. to 144.3635, which differ from the corresponding compositions 1.1 to 1.3653, more preferred 1.1 to 1.3635, only in that they comprise as the active compound A the uracilpyridine of formula (I.h.339) and additionally comprise B.135 as further herbicide B.

Also especially preferred are compositions 145.1 to 145.3653, more preferred 145.1. to 145.3635, which differ from the corresponding compositions 1.1 to 1.3653, more preferred 1.1 to 1.3635, only in that they comprise as the active compound A the uracilpyridine of formula (I.h.339) and additionally comprise B.137 as further herbicide B.

Also especially preferred are compositions 146.1 to 146.3653, more preferred 146.1. to 146.3635, which differ from the corresponding compositions 1.1 to 1.3653, more preferred 1.1 to 1.3635, only in that they comprise as the active compound A the uracilpyridine of formula (I.h.339) and additionally comprise B.138 as further herbicide B.

Also especially preferred are compositions 147.1 to 147.3653, more preferred 147.1. to 147.3635, which differ from the corresponding compositions 1.1 to 1.3653, more preferred 1.1 to 1.3635, only in that they comprise as the active compound A the uracilpyridine of formula (I.h.339) and additionally comprise B.140 as further herbicide B.

Also especially preferred are compositions 148.1 to 148.3653, more preferred 148.1. to 148.3635, which differ from the corresponding compositions 1.1 to 1.3653, more preferred 1.1 to 1.3635, only in that they comprise as the active compound A the uracilpyridine of formula (I.h.339) and additionally comprise B.145 as further herbicide B.

Also especially preferred are compositions 149.1 to 149.3653, more preferred 149.1. to 149.3635, which differ from the corresponding compositions 1.1 to 1.3653, more preferred 1.1 to 1.3635, only in that they comprise as the active compound A the uracilpyridine of formula (I.h.339) and additionally comprise B.153 as further herbicide B.

Also especially preferred are compositions 150.1 to 150.3653, more preferred 150.1. to 150.3635, which differ from the corresponding compositions 1.1 to 1.3653, more preferred 1.1 to 1.3635, only in that they comprise as the active compound A the uracilpyridine of formula (I.h.339) and additionally comprise B.156 as further herbicide B.

Also especially preferred are compositions 151.1 to 151.3653, more preferred 151.1. to 151.3635, which differ from the corresponding compositions 1.1 to 1.3653, more preferred 1.1 to 1.3635, only in that they comprise as the active compound A the uracilpyridine of formula (I.h.339) and additionally comprise B.171 as further herbicide B.

Also especially preferred are compositions 152.1 to 152.3653, more preferred 152.1. to 152.3635, which differ from the corresponding compositions 1.1 to 1.3653, more preferred 1.1 to 1.3635, only in that they comprise as the active compound A the uracilpyridine of formula (I.h.339) and additionally comprise B.174 as further herbicide B.

It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

It is recognized that the polynucleotide molecules and polypeptides of the invention encompass polypeptides comprising an amino acid sequence that is sufficiently identical to the amino acid sequences set forth in SEQ ID Nos: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 577, 579, 581, 583, 585, 587, 589, 591, 593, 595, 597, 599, 601, 603, 605, 607, 609, 611, 613, 615, 617, 619, 621, 623, 625, 627, or 637. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity.

Generally, "sequence identity" refers to the extent to which two optimally aligned DNA or amino acid sequences are invariant throughout a window of alignment of components, e.g., nucleotides or amino acids. An "identity fraction" for aligned segments of a test sequence and a reference sequence is the number of identical components that are shared by the two aligned sequences divided by the total number of components in reference sequence segment, i.e., the entire reference sequence or a smaller defined part of the reference sequence. "Percent identity" is the identity fraction times 100. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG. Wisconsin Package. (Accelrys Inc. Burlington, Mass.)

Polynucleotides and Oligonucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. That means other nucleic acid molecules are present in an amount less than 5% based on weight of the amount of the desired nucleic acid, preferably less than 2% by weight, more preferably less than 1% by weight, most preferably less than 0.5% by weight. Preferably, an "isolated" nucleic acid is free of some of the sequences that naturally flank the nucleic acid (i.e., sequences located at the 5' and 3' ends of the nucleic acid) in the genomic DNA of the organism from which the nucleic acid is derived. For example, in various embodiments, the isolated herbicide resistance and/or tolerance related protein encoding nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized. Preferably, the isolated polynucleotide is at least 60% free, preferably at least 75% free, and most preferably at least 90% free from other components with which they are naturally associated. As the skilled addressee would be aware, an isolated polynucleotide can be an exogenous polynucleotide present in, for example, a transgenic organism which does not naturally comprise the polynucleotide. Furthermore, the terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

The term "mutated PPO nucleic acid" refers to a PPO nucleic acid having a sequence that is mutated from a wild-type PPO nucleic acid, such as e.g. SEQ ID NO: 118, 119, 120, 121, 122, 123, 124, 125, 126, 127, 128, 624, 626, or 650, or homologues, paralogues and and orthologues thereof; and that confers increased uracilpyridine herbicide tolerance to a plant in which it is expressed. Furthermore, the term "mutated protoporphyrinogen oxidase (mutated PPO)" refers to the replacement of an amino acid of the wild-type primary sequences SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, or a variant, a derivative, a homologue, an orthologue, or paralogue thereof, with another amino acid. The expression "mutated amino acid" will be used below to designate the amino acid which is replaced by another amino acid, thereby designating the site of the mutation in the primary sequence of the protein.

In a preferred embodiment, the PPO nucleotide sequence encoding a mutated PPO comprises the sequence of SEQ ID NO: 118, 119, 120, 121, 122, 123, 124, 125, 126, 127, 128, 624, 626, or 650, or a variant or derivative thereof.

Furthermore, it will be understood by the person skilled in the art that the PPO nucleotide sequences encompasse homologues, paralogues and and orthologues of SEQ ID NO: 118, 119, 120, 121, 122, 123, 124, 125, 126, 127, 128, 624, 626, or 650, as defined hereinafter.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein, e.g. the mutated PPO according to the present invention as disclosed herein.

Generally, nucleotide sequence variants of the invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence encoding a polypeptide of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, 637, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, or 565.

The % identity of a polynucleotide is determined by GAP (Needleman and Wunsch, 1970) analysis (GCG program) with a gap creation penalty=5, and a gap extension penalty=0.3. Unless stated otherwise, the query sequence is at least nucleotides in length, and the GAP analysis aligns the two sequences over a region of at least nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

Polypeptides

By "substantially purified polypeptide" or "purified" a polypeptide is meant that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated. As the skilled addressee will appreciate, the purified polypeptide can be a recombinantly produced polypeptide. The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least amino acids in length, and the GAP analysis aligns the two sequences over a region of at least amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

With regard to a defined polypeptide, it will be appreciated that % identity figures higher than those provided above will encompass preferred embodiments. Thus, where applicable, in light of the minimum % identity figures, it is preferred that the PPO polypeptide of the invention comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, 637, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, or 565.

By "variant" polypeptide is intended a polypeptide derived from the protein of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, 637, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, or 565, by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

"Derivatives" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag·100 epitope, c-myc epitope, FLAG®-epitope, IacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds).

TABLE 1

Examples of conserved amino acid substitutions

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; He |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, OH), Quick-Change Site Directed mutagenesis (Stratagene, San Diego, CA), PCR-mediated site-directed mutagenesis or other site-directed mutagenesis protocols.

"Derivatives" further include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

"Orthologues" and "paralogues" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

It is well-known in the art that paralogues and orthologues may share distinct domains harboring suitable amino acid residues at given sites, such as binding pockets for particular substrates or binding motifs for interaction with other proteins.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif" or "consensus sequence" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain). Preferred motifs which are contained in the sequences of the PPO polypeptides according to the present invention are SQ[N/K/H]KRYI, TLGTLFSS, [F/Y]TTF[V/I]GG.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The inventors of the present invention have found that by substituting one or more of the key amino acid residues, employing e.g. one of the above described methods to mutate the encoding nucleic acids, the uracilpyridine herbicide tolerance or resistance could be remarkably increased as compared to the activity of the wild type PPO enzymes with SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637. Preferred substitutions of mutated PPO are those that increase the herbicide tolerance of the plant, but leave the biological activity of the oxidase activity substantially unaffected.

Accordingly, in another object of the present invention the key amino acid residues of a PPO enzyme comprising SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, is substituted by any other amino acid.

In one embodiment, the key amino acid residues of a PPO enzyme, a variant, derivative, orthologue, paralogue or homologue thereof, is substituted by a conserved amino acid as depicted in Table 1.

It will be understood by the person skilled in the art that amino acids located in a close proximity to the positions of amino acids mentioned below may also be substituted. Thus, in another embodiment the variant of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof comprises a mutated PPO, wherein an amino acid ±3, ±2 or ±1 amino acid positions from a key amino acid is substituted by any other amino acid.

Based on techniques well-known in the art, a highly characteristic sequence pattern can be developed, by means of which further of mutated PPO candidates with the desired activity may be searched.

Searching for further mutated PPO candidates by applying a suitable sequence pattern would also be encompassed by the present invention. It will be understood by a skilled reader that the present sequence pattern is not limited by the exact distances between two adjacent amino acid residues of said pattern. Each of the distances between two neighbours in the above patterns may, for example, vary independently of each other by up to ±10, ±5, ±3, ±2 or ±1 amino acid positions without substantially affecting the desired activity.

Furthermore, by applying the method of site directed mutagenesis, in particular saturation mutagenes (see e.g. Schenk et al., Biospektrum 03/2006, pages 277-279), the inventors of the present invention have identified and generated specific amino acid subsitutions and combinations thereof, which—when introduced into a plant by transforming and expressing the respective mutated PPO encoding nucleic acid—confer increased herbicide resistance or tolerance to a uracilpyridine herbicide to said plant.

Thus, in a particularly preferred embodiment, the variant or derivative of the mutated PPO refers to a polypeptide comprsining SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, or 637, comprising a single amino acid substitution at positions depicted in the following Table 2a..

TABLE 2a-1

Single amino acid substitutions within SEQ ID NO: 1, 2, 3, 4, 5, 6, 7, 8, 9, 10, 11, 12, 13, 14, 15, 16, 17, 18, 19, 20, 21, TABLE 2a-1-continued Single amino acid substitutions within SEQ ID NO: 1, 2, 3, 4, 5, 6, 7, 8, 9,
10, 11, 12, 13, 14, 15, 16, 17, 18, 19, 20, 21, 22, 23, 24, 25, 26, 27, 28,
29, 30, 31, 32, 33, 34, 35, 36, 37, 38, 39, 40, 41, 42, 43, 44, 45, 46, 47,
48, 49, 50, 51, 52, 53, 54, 55, 56, 57, 58, 59, 60, 61, 62, 63, 64, 65, 66,
67, 68, 69, 70, 71, 72, 73, 74, 75, 76, 77, 78, 79, 80, 81, 82, 83, 84, 85,
86, 87, 88, 89, 90, 91, 92, 93, 94, 95, 96, 97, 98, 99, 100, 101, 102, 103,
104, 105, 106, 107, 108, 109, 110, 111, 112, 113, 114, 115, 116, 117, or 637

| SEQ ID | Organism | Mutated site 1 | Mutated site 2 | Mutated site 3 | Mutated site 4 | Mutated site 5 |
|---|---|---|---|---|---|---|
| 54 | Zea mays | — | — | — | L69 | F92 |
| 55 | Rhodothermus marinus | R87 | A162 | G163 | L330 | F353 |
| 56 | Caldithrix abyssi | R86 | A160 | G161 | L329 | F352 |
| 57 | Opitutus terrae PB90-1 | R103 | A178 | G179 | L345 | M368 |
| 58 | Verrucomicrobia bacterium | R91 | A166 | G167 | L332 | Y355 |
| 59 | Ignavibacterium album | R88 | A163 | G164 | L332 | F355 |
| 60 | Coraliomargarita sp. CAG: 312 | R88 | G163 | A164 | L331 | Y354 |
| 61 | Salisaeta longa | R88 | A163 | G164 | L329 | F352 |
| 62 | Ambrosia artemisiifolia | R98 | G175 | G176 | — | — |
| 63 | Melioribacter roseus P3M-2 | R88 | A163 | G164 | L333 | F356 |
| 64 | Halothiobacillus neapolitanus c2 | R97 | A170 | G171 | L343 | F366 |
| 65 | Chondrus crispus | Y98 | S176 | G177 | L352 | Y376 |
| 66 | Rubritalea marina | R88 | A163 | G164 | L339 | M362 |
| 67 | Acidobacteria bacterium | R88 | A161 | G162 | L330 | F353 |
| 68 | Coraliomargarita akajimensis DSM 45221 | R88 | A163 | G164 | L323 | F346 |
| 69 | Oscillochloris trichoides DG6 | R90 | S164 | G165 | L340 | L363 |
| 70 | Opitutaceae bacterium TAV1 | R86 | A161 | G162 | L352 | L375 |
| 71 | Amborella trichopoda | R87 | A173 | A174 | L230 | — |
| 72 | Opitutaceae bacterium TAV5 | R105 | A180 | G181 | L368 | L391 |
| 73 | Chloroflexus sp. Y-400-fl | R91 | A166 | G167 | L335 | L358 |
| 74 | Leptospirillum sp. Group II '5-way CG' | R92 | A167 | S168 | L335 | F358 |
| 75 | Leptospirillum ferriphilum ML-04 | R92 | A167 | S168 | L335 | F358 |
| 76 | Verrucomicrobia bacterium SCGC AAA300-O17 | R89 | A165 | A166 | L334 | Y357 |
| 77 | Chloroflexus aggregans DSM 9485 | R92 | A167 | G168 | L336 | L359 |
| 78 | Desulfurobacterium thermolithotrophum | R86 | A161 | G162 | L333 | M356 |
| 79 | Desulfurobacterium sp. TC5-1 | R90 | A165 | G166 | L332 | M355 |
| 80 | Arthrospira platensis C1 | R93 | A176 | G177 | L352 | Y375 |
| 81 | Leptospirillum sp. Group II 'C75' | R92 | A167 | S168 | L335 | F358 |
| 82 | Verrucomicrobiae bacterium DG1235 | R87 | A164 | G165 | L332 | M355 |
| 83 | Verrucomicrobia bacterium SCGC AAA300-K03 | R89 | A165 | A166 | L334 | F357 |
| 84 | Synechococcus sp. JA-3-3Ab | R101 | A177 | G178 | L350 | F373 |
| 85 | Hymenobacter norwichensis | R86 | A161 | G162 | A321 | F344 |
| 86 | Pontibacter sp. BAB1700 | R85 | G159 | G160 | S319 | Y342 |
| 87 | Leptospirillum ferrodiazotrophum | R92 | A172 | S173 | L339 | F362 |
| 88 | Prevotella histicola F0411 | C89 | A164 | G165 | L328 | F351 |
| 89 | Flexithrix dorotheae | R84 | A158 | G159 | A313 | F336 |
| 90 | Geobacter metallireducens GS-15 | R93 | A168 | G169 | L342 | M365 |
| 91 | Synechococcus sp. JA-2-3B'a(2-13) | R93 | A169 | G170 | L362 | F385 |
| 92 | Crinalium epipsammum PCC 9333 | R85 | A168 | G169 | L344 | F367 |
| 93 | Planctomyces maris | A99 | T187 | S188 | F358 | F381 |

TABLE 2a-1-continued

Single amino acid substitutions within SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, or 637

| SEQ ID | Organism | Mutated site 1 | Mutated site 2 | Mutated site 3 | Mutated site 4 | Mutated site 5 |
| --- | --- | --- | --- | --- | --- | --- |
| 94 | Geobacter uraniireducens Rf4 | R93 | A170 | G171 | L344 | M367 |
| 95 | Acidithiobacillus ferrivorans | R87 | A162 | G163 | L323 | F346 |
| 96 | Prevotella melaninogenica | C88 | A163 | G164 | L327 | F350 |
| 97 | Thermovibrio ammonificans | R86 | A160 | G161 | L333 | M356 |
| 98 | Brassica_rapa | R143 | A219 | G220 | L402 | Y425 |
| 99 | Brassica_rapa | R112 | A195 | A196 | L384 | F407 |
| 100 | Gossypium | R146 | A222 | G223 | L405 | Y428 |
| 101 | Gossypium | R98 | A180 | G181 | L370 | F393 |
| 102 | Conyza_canadensis | R142 | A218 | G219 | L401 | Y424 |
| 103 | Conyza_canadensis | R102 | G179 | G180 | L365 | F388 |
| 104 | Kochia_scobaria | R172 | A248 | G249 | L431 | F454 |
| 105 | Lolium_rigidum | R138 | A214 | G215 | L397 | Y420 |
| 106 | Lolium_rigidum | R97 | A182 | G183 | L377 | F400 |
| 107 | Gossypium hirsutum PPO1 | R146 | A222 | G223 | L405 | Y428 |
| 108 | Beta vulgaris PPO1 | R167 | A243 | G244 | L426 | Y449 |
| 109 | Hordeum vulgare PPO1 | R137 | A213 | G214 | L396 | Y419 |
| 110 | Hordeum vulgare PPO2 | R142 | A227 | G228 | L422 | F445 |
| 111 | Triticum aestivum PPO1 | R138 | A214 | G215 | L397 | Y420 |
| 112 | Solarium lycopersicum PPO2 | R95 | G175 | G176 | L366 | F389 |
| 113 | Triticum aestivum PPO1_v2 | R153 | A229 | G230 | L412 | Y435 |
| 114 | Gossypium hirsutum PPO1_v2 | R146 | A222 | G223 | L405 | Y428 |
| 115 | Gossypium hirsutum PPO2 | R98 | A180 | G181 | L370 | F393 |
| 116 | Beta vulgaris PPO1_v2 | R167 | A243 | G244 | L426 | Y449 |
| 117 | Brassica napus_PPO2 | R99 | A182 | A183 | L371 | F394 |
| 637 | Oryza sativa_PPO2 | R139 | | G225 | L419 | F442 |

TABLE 2a-2

| | Additional single amino acid substitutions within reference to SEQ ID NO 1, or 637 | | |
| --- | --- | --- | --- |
| SEQ ID | Organism | Mutated site 6 | Mutated site 7 |
| 1 | Amaranthus tuberculatus | G398 | L400 |
| 637 | Oryza sativa_PPO2 | G420 | L422 |

In a further particularly preferred embodiment, the variant or derivative of the mutated PPO refers to SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, or 637, comprising a single amino acid substitutions at the positions depicted in the following Table 2b.

It should be noted that Mutated site 1 of Table 2a) corresponds to Pos 1 of Table 2b); Mutated site 2 of Table 2a) corresponds to Pos 16 of Table 2b); Mutated site 3 of Table 2a) corresponds to Pos 17 of Table 2b); Mutated site 4 of Table 2a) corresponds to Pos 38 of Table 2b); Mutated site 5 of Table 2a) corresponds to Pos 42 of Table 2b).

TABLE 2b

| ID | Pos 1 | Pos 2 | Pos 3 | Pos 4 | Pos 5 | Pos 6 | Pos 7 | Pos 8 | Pos 9 | Pos 10 |
| --- | --- | --- | --- | --- | --- | --- | --- | --- | --- | --- |
| 1 | R128 | Y129 | A131 | S149 | I151 | A154 | P164 | K169 | E182 | S183 |
| 2 | R128 | Y129 | A131 | S149 | I151 | A154 | P164 | K169 | E182 | S183 |
| 3 | R128 | Y129 | A131 | S149 | I151 | A154 | P164 | K169 | E182 | S183 |
| 4 | R128 | Y129 | A131 | S149 | I151 | A154 | P164 | K169 | E182 | S183 |
| 5 | R128 | Y129 | A131 | S149 | I151 | A154 | P164 | K169 | E182 | S183 |
| 6 | R98 | Y99 | A101 | S119 | I121 | A124 | P134 | K139 | E152 | S153 |
| 7 | R127 | Y128 | A130 | S148 | I150 | A153 | P163 | K168 | E181 | S182 |
| 8 | R100 | Y101 | V103 | S121 | I123 | A126 | P136 | K141 | E154 | S155 |
| 9 | R99 | Y100 | V102 | S120 | I122 | A125 | P135 | K140 | E153 | S154 |

TABLE 2b-continued

| | | | | | | | | | | |
|---|---|---|---|---|---|---|---|---|---|---|
| 10 | R98 | Y99 | V101 | S119 | I121 | A124 | P134 | K139 | E152 | S153 |
| 11 | R98 | Y99 | V101 | S119 | L121 | A124 | P134 | R139 | E152 | S153 |
| 12 | R96 | Y97 | V99 | S117 | F119 | A122 | P132 | D137 | E147 | S148 |
| 13 | R98 | Y99 | V101 | S119 | L121 | A124 | P134 | R139 | E152 | S153 |
| 14 | R98 | Y99 | A101 | S119 | F121 | T124 | P134 | K139 | E149 | S150 |
| 15 | R98 | Y99 | V101 | S119 | F121 | A124 | P134 | K139 | E152 | S153 |
| 16 | R98 | Y99 | V101 | S119 | F121 | A124 | P134 | K139 | E152 | S153 |
| 17 | R98 | Y99 | V101 | S119 | L121 | A124 | P134 | R139 | E152 | S153 |
| 18 | R98 | Y99 | V101 | S119 | F121 | A124 | P134 | K139 | E152 | S153 |
| 19 | R93 | Y94 | V96 | S114 | F116 | A119 | P129 | K134 | E147 | S148 |
| 20 | R98 | Y99 | A101 | S119 | F121 | T124 | P134 | N139 | E150 | S151 |
| 21 | R95 | Y96 | A98 | S116 | F118 | T121 | P131 | N136 | E147 | S148 |
| 22 | R101 | Y102 | V104 | S122 | V124 | T127 | P137 | K142 | E154 | S155 |
| 23 | R103 | Y104 | V106 | S124 | V126 | T129 | P139 | K144 | E158 | S159 |
| 24 | R101 | Y102 | V104 | S122 | V124 | T127 | P137 | K142 | E154 | S155 |
| 25 | R147 | Y148 | V150 | S168 | V170 | T173 | P183 | K188 | E200 | S201 |
| 26 | R74 | Y75 | V77 | S95 | F97 | T100 | P110 | K115 | E123 | S124 |
| 27 | R128 | Y129 | V131 | S149 | V151 | T154 | P164 | K169 | E185 | S186 |
| 28 | R130 | Y131 | V133 | S151 | V153 | T156 | P166 | K171 | E187 | S188 |
| 29 | R101 | Y102 | V104 | — | — | — | — | — | E124 | S125 |
| 30 | R130 | Y131 | V133 | S151 | V153 | T156 | P166 | K171 | E187 | S188 |
| 31 | R130 | Y131 | V133 | S151 | V153 | T156 | P166 | K171 | E187 | S188 |
| 32 | R105 | Y106 | V108 | S126 | L128 | T131 | P141 | R146 | E160 | S161 |
| 33 | R150 | F151 | L153 | F171 | L173 | I176 | A186 | P191 | E201 | E202 |
| 34 | R100 | Y101 | V103 | S121 | F123 | A126 | P136 | K141 | E154 | S155 |
| 35 | R165 | Y166 | V168 | S186 | V188 | T191 | P201 | K206 | E220 | S221 |
| 36 | R134 | Y135 | V137 | S155 | V157 | T160 | P170 | K175 | E191 | S192 |
| 37 | R95 | Y96 | V98 | S116 | V118 | T121 | P131 | K136 | E152 | S153 |
| 38 | R100 | Y101 | V103 | S121 | T123 | A126 | P136 | H141 | E158 | S159 |
| 39 | R98 | Y99 | A101 | S119 | F121 | T124 | P134 | N139 | E150 | S151 |
| 40 | R139 | Y140 | V142 | S160 | V162 | T165 | P175 | K180 | E196 | S197 |
| 41 | R139 | Y140 | V142 | S160 | V162 | T165 | P175 | K180 | E196 | S197 |
| 42 | R96 | Y97 | V99 | S117 | V119 | T122 | P132 | K137 | E151 | S152 |
| 43 | R97 | Y98 | V100 | T118 | L120 | A123 | P133 | R138 | E147 | S148 |
| 44 | R97 | Y98 | V100 | T118 | L120 | A123 | P133 | R138 | E147 | S148 |
| 45 | R128 | Y129 | A131 | S149 | I151 | A154 | P164 | K169 | E182 | S183 |
| 46 | R128 | Y129 | A131 | S149 | I151 | A154 | P164 | K169 | E182 | S183 |
| 47 | — | — | — | S3 | V5 | T8 | P18 | K23 | E39 | S40 |
| 48 | R30 | Y31 | V33 | — | — | — | P47 | K52 | E68 | S69 |
| 49 | R89 | Y90 | V92 | S110 | I112 | S115 | P125 | Q130 | E140 | S141 |
| 50 | — | — | — | — | — | — | — | — | — | — |
| 51 | R87 | F88 | V90 | T108 | L110 | P113 | P123 | H126 | A137 | K138 |
| 52 | R87 | Y88 | V90 | T108 | L110 | T113 | P123 | G126 | A136 | R137 |
| 53 | R87 | Y88 | V90 | T108 | L110 | T113 | P123 | G126 | A136 | R137 |
| 54 | — | — | — | — | — | — | — | — | — | — |
| 55 | R87 | F88 | V90 | T108 | L110 | P113 | P123 | H126 | A137 | K138 |
| 56 | R86 | Y87 | V89 | T107 | L109 | W112 | P122 | P125 | A135 | D136 |
| 57 | R103 | Y104 | V106 | S124 | L126 | P129 | L139 | R142 | A153 | E154 |
| 58 | R91 | Y92 | I94 | T112 | L114 | L117 | P127 | A130 | A141 | A142 |
| 59 | R88 | Y89 | L91 | T109 | L111 | A114 | P124 | G127 | A138 | E139 |
| 60 | R88 | F89 | A91 | T109 | L111 | F114 | P124 | K127 | A138 | D139 |
| 61 | R88 | F89 | V91 | T109 | L111 | T114 | P124 | A127 | A138 | S139 |
| 62 | R98 | Y99 | V101 | S119 | F121 | T124 | P134 | K139 | E147 | S148 |
| 63 | R88 | Y89 | L91 | T109 | L111 | S114 | P124 | S127 | A138 | E139 |
| 64 | R97 | F98 | A100 | S118 | L120 | M123 | A133 | K136 | A145 | E146 |
| 65 | Y98 | Y99 | M101 | T119 | L121 | W124 | P134 | L139 | S149 | V150 |
| 66 | R88 | F89 | I91 | S109 | I111 | L114 | P124 | K127 | A138 | D139 |
| 67 | R88 | Y89 | V91 | S109 | L111 | W114 | P124 | G127 | A136 | D137 |
| 68 | R88 | Y89 | V91 | T109 | L111 | I114 | P124 | K127 | A138 | D139 |
| 69 | R90 | Y91 | L93 | M111 | H113 | M116 | P126 | P129 | A139 | S140 |
| 70 | R86 | F87 | V89 | T107 | L109 | L112 | L122 | R125 | G136 | E137 |
| 71 | R87 | F88 | A90 | S108 | L110 | P113 | P123 | S128 | E145 | S146 |
| 72 | R105 | F106 | V108 | T126 | L128 | T131 | P141 | L144 | G155 | E156 |
| 73 | R91 | F92 | L94 | T112 | L114 | W117 | P127 | N130 | A141 | A142 |
| 74 | R92 | Y93 | V95 | T113 | L115 | W118 | W128 | P131 | S142 | H143 |
| 75 | R92 | Y93 | V95 | T113 | L115 | W118 | W128 | P131 | S142 | H143 |
| 76 | R89 | F90 | I92 | S110 | F112 | P115 | P125 | G128 | A140 | E141 |
| 77 | R92 | Y93 | L95 | T113 | L115 | W118 | P128 | N131 | A142 | A143 |
| 78 | R86 | F87 | Y89 | S107 | L109 | W112 | F122 | P125 | S136 | E137 |
| 79 | R90 | F91 | F93 | S111 | V113 | F116 | Y126 | P129 | S140 | S141 |
| 80 | R93 | Y94 | V96 | S114 | L116 | A119 | A129 | P134 | T151 | Q152 |
| 81 | R92 | Y93 | V95 | T113 | L115 | W118 | W128 | P131 | S142 | H143 |
| 82 | R87 | Y88 | V90 | T108 | L110 | L113 | P123 | K126 | A139 | S140 |
| 83 | R89 | F90 | I92 | S110 | F112 | P115 | P125 | G128 | A140 | E141 |
| 84 | R101 | Y102 | V104 | S122 | L124 | V127 | L137 | P142 | R152 | Q153 |
| 85 | R86 | Y87 | L89 | N107 | F109 | W112 | L122 | A126 | D136 | A137 |
| 86 | R85 | Y86 | L88 | N106 | L108 | N111 | R121 | A126 | S134 | D135 |
| 87 | R92 | F93 | L95 | T113 | I115 | L118 | P128 | P131 | A147 | D148 |
| 88 | C89 | R90 | I92 | T111 | L113 | L116 | P126 | R129 | G139 | A140 |
| 89 | R84 | Y85 | F87 | N105 | F107 | W110 | L120 | T125 | A133 | D134 |

TABLE 2b-continued

| | Pos 2 | Pos 3 | Pos 4 | Pos 5 | Pos 6 | Pos 7 | Pos 8 | Pos 9 | Pos 10 |
|---|---|---|---|---|---|---|---|---|---|
| 90 | R93 | F94 | Y96 | S114 | L116 | W119 | P129 | S132 | A143 | S144 |
| 91 | R93 | Y94 | Y96 | S114 | L116 | V119 | L129 | A134 | R144 | Q145 |
| 92 | R85 | F86 | Y88 | S106 | L108 | L111 | A121 | P126 | A143 | Q144 |
| 93 | A99 | L100 | L102 | T128 | L130 | P133 | Y143 | P146 | A162 | Q163 |
| 94 | R93 | F94 | Y96 | S114 | L116 | W119 | P129 | A134 | A145 | A146 |
| 95 | R87 | Y88 | L90 | G107 | L109 | W112 | P122 | S125 | A137 | D138 |
| 96 | C88 | R89 | I91 | T110 | L112 | L115 | P125 | K128 | G138 | S139 |
| 97 | R86 | F87 | Y89 | S107 | L109 | W112 | P122 | P125 | A135 | E136 |
| 98 | R143 | F144 | L146 | F164 | L166 | I169 | A179 | P184 | E191 | S192 |
| 99 | R112 | Y113 | V115 | S133 | V135 | T138 | P148 | K153 | E167 | S168 |
| 100 | R146 | F147 | L149 | F167 | L169 | I172 | A182 | P187 | E194 | S195 |
| 101 | R98 | Y99 | V101 | S119 | I121 | A124 | P134 | K139 | E152 | S153 |
| 102 | R142 | F143 | L145 | F163 | L165 | L168 | A178 | P183 | E190 | S191 |
| 103 | R102 | Y103 | V105 | S123 | L125 | T128 | P138 | K143 | E151 | S152 |
| 104 | R172 | F173 | L175 | F193 | L195 | F198 | A208 | P213 | E220 | S221 |
| 105 | R138 | F139 | L141 | F159 | L161 | I164 | A174 | P179 | E186 | S187 |
| 106 | R97 | Y98 | V100 | S118 | L120 | T123 | P133 | K138 | E154 | S155 |
| 107 | R146 | F147 | L149 | F167 | L169 | I172 | A182 | P187 | E194 | S195 |
| 108 | R167 | F168 | L170 | F188 | L190 | I193 | A203 | P208 | E215 | S216 |
| 109 | R137 | F138 | L140 | F158 | L160 | V163 | A173 | P178 | E185 | S186 |
| 110 | R142 | Y143 | V145 | S163 | V165 | T168 | P178 | K183 | E199 | S200 |
| 111 | R138 | F139 | L141 | F159 | L161 | I164 | A174 | P179 | E186 | S187 |
| 112 | R95 | Y96 | A98 | S116 | F118 | T121 | P131 | N136 | E147 | S148 |
| 113 | R153 | F154 | L156 | F174 | L176 | I179 | A189 | P194 | E201 | S202 |
| 114 | R146 | F147 | L149 | F167 | L169 | I172 | A182 | P187 | E194 | S195 |
| 115 | R98 | Y99 | M101 | S119 | I121 | A124 | P134 | N139 | E152 | S153 |
| 116 | R167 | F168 | L170 | F188 | L190 | I193 | A203 | P208 | E215 | S216 |
| 117 | R99 | Y100 | V102 | S120 | V122 | T125 | P135 | N141 | E154 | S155 |

| ID | Pos 11 | Pos 12 | Pos 13 | Pos 14 | Pos 15 | Pos 16 | Pos 17 | Pos 18 | Pos 19 | Pos 20 |
|---|---|---|---|---|---|---|---|---|---|---|
| 1 | E189 | F196 | D202 | C209 | G210 | G211 | L216 | M218 | H219 | H220 |
| 2 | E189 | F196 | D202 | C209 | G210 | G211 | L216 | M218 | H219 | H220 |
| 3 | E189 | F196 | D202 | C209 | G210 | — | L215 | M217 | H218 | H219 |
| 4 | E189 | F196 | D202 | C209 | G210 | — | L215 | M217 | Y218 | H219 |
| 5 | E189 | F196 | D202 | C209 | G210 | G211 | L216 | V218 | H219 | H220 |
| 6 | E159 | F166 | D172 | C179 | G180 | G181 | L186 | M188 | H189 | H190 |
| 7 | E188 | F195 | D201 | S208 | G209 | G210 | L215 | M217 | R218 | H219 |
| 8 | Q161 | V168 | D174 | S181 | G182 | G183 | L188 | M190 | H191 | H192 |
| 9 | Q160 | V167 | D173 | S180 | A181 | G182 | L187 | V189 | C190 | H191 |
| 10 | Q159 | V166 | D172 | S179 | A180 | A181 | L186 | M188 | R189 | H190 |
| 11 | E159 | V166 | D172 | S179 | A180 | A181 | L186 | M188 | R189 | H190 |
| 12 | Q154 | V161 | D167 | S174 | A175 | G176 | L181 | M183 | R184 | H185 |
| 13 | E159 | V166 | D172 | S179 | A180 | A181 | L186 | I188 | R189 | H190 |
| 14 | Q156 | V163 | D169 | S176 | A177 | G178 | L183 | M185 | P186 | H187 |
| 15 | Q159 | V166 | D172 | S179 | A180 | A181 | L186 | M188 | R189 | H190 |
| 16 | Q159 | V166 | D172 | S179 | A180 | A181 | L186 | M188 | R189 | H190 |
| 17 | E159 | V166 | D172 | S179 | A180 | A181 | L186 | M188 | R189 | H190 |
| 18 | Q159 | V166 | D172 | S179 | A180 | A181 | L186 | M188 | S189 | H190 |
| 19 | Q154 | V161 | D167 | S174 | A175 | G176 | L181 | M183 | S184 | H185 |
| 20 | Q157 | V164 | D170 | C177 | G178 | G179 | L184 | M186 | H187 | H188 |
| 21 | Q154 | V161 | D167 | C174 | G175 | G176 | L181 | M183 | H184 | L185 |
| 22 | Q161 | V168 | D174 | S181 | A182 | A183 | L188 | M190 | K191 | H192 |
| 23 | Q165 | V172 | D178 | S185 | A186 | A187 | L192 | M194 | K195 | H196 |
| 24 | Q161 | V168 | D174 | S181 | A182 | A183 | L188 | M190 | K191 | H192 |
| 25 | Q207 | V214 | D220 | S227 | A228 | A229 | L234 | M236 | K237 | H238 |
| 26 | Q130 | V137 | D143 | S150 | G151 | G152 | L157 | M159 | R160 | H161 |
| 27 | E192 | V199 | D205 | S212 | A213 | G214 | L219 | I221 | R222 | H223 |
| 28 | E194 | V201 | D207 | S214 | A215 | G216 | L221 | I223 | C224 | H225 |
| 29 | Q131 | V138 | D144 | S151 | A152 | A153 | L158 | M160 | K161 | H162 |
| 30 | E194 | V201 | D207 | S214 | A215 | G216 | L221 | I223 | R224 | H225 |
| 31 | E194 | V201 | D207 | S214 | A215 | G216 | L221 | I223 | R224 | H225 |
| 32 | Q167 | V174 | D180 | S187 | G188 | G189 | L194 | M196 | P197 | H198 |
| 33 | — | V212 | E218 | Y225 | A226 | G227 | L232 | M234 | K235 | A236 |
| 34 | Q161 | V168 | D174 | S181 | A182 | G183 | L188 | A190 | R191 | H192 |
| 35 | R227 | V234 | D240 | S247 | A248 | A249 | L254 | M277 | K278 | Y279 |
| 36 | E198 | V205 | D211 | S218 | A219 | G220 | L225 | I227 | R228 | H229 |
| 37 | C158 | V165 | D171 | S178 | G179 | G180 | L185 | I187 | R188 | H189 |
| 38 | R165 | V172 | D178 | A185 | G186 | A187 | L192 | I194 | R195 | H196 |
| 39 | Q157 | V164 | D170 | C177 | G178 | G179 | L184 | M186 | H187 | L188 |
| 40 | C213 | V220 | D229 | S233 | G234 | G235 | L240 | I242 | R243 | H244 |
| 41 | C213 | V220 | D229 | S233 | G234 | G235 | L240 | I242 | R243 | H244 |
| 42 | Q158 | V165 | D171 | S178 | A179 | A180 | L185 | M187 | K188 | H189 |
| 43 | E154 | I161 | D167 | S174 | G175 | G176 | I181 | I183 | R184 | H185 |
| 44 | E154 | I161 | D167 | S174 | G175 | S176 | I181 | I183 | R184 | H185 |
| 45 | E189 | F196 | D202 | C209 | G210 | G211 | L216 | M218 | H219 | H220 |
| 46 | E189 | F196 | D202 | C209 | G210 | — | L215 | M217 | H218 | H219 |
| 47 | E46 | V53 | D59 | S66 | A67 | G68 | L73 | I75 | R76 | H77 |
| 48 | E75 | V82 | D88 | S95 | A96 | G97 | L102 | I104 | R105 | H106 |

TABLE 2b-continued

| | | | | | | | | | |
|---|---|---|---|---|---|---|---|---|---|
| 49 | Q147 | V154 | D160 | S167 | G168 | G169 | L174 | M176 | R177 | H178 |
| 50 | — | — | — | — | — | — | — | — | — | — |
| 51 | — | V148 | E154 | F161 | A162 | G163 | L168 | V170 | R171 | Y172 |
| 52 | — | V147 | A153 | F160 | A161 | G162 | L167 | V169 | Q170 | H171 |
| 53 | — | V147 | A153 | F160 | A161 | G162 | L167 | V169 | Q170 | H171 |
| 54 | — | — | — | — | — | — | — | — | — | — |
| 55 | — | V148 | E154 | F161 | A162 | G163 | L168 | V170 | R171 | Y172 |
| 56 | — | F146 | N152 | Y159 | A160 | G161 | L166 | A168 | P169 | A170 |
| 57 | — | F164 | N170 | Y177 | A178 | G179 | L184 | A186 | R187 | Q188 |
| 58 | — | F152 | N158 | Y165 | A166 | G167 | L172 | V174 | Q175 | H176 |
| 59 | — | F149 | N155 | Y162 | A163 | G164 | L169 | V171 | K172 | S173 |
| 60 | — | V149 | N155 | Y162 | G163 | A164 | L169 | I171 | K172 | H173 |
| 61 | — | V149 | D155 | F162 | A163 | G164 | L169 | L171 | K172 | H173 |
| 62 | Q154 | V161 | D167 | S174 | G175 | G176 | — | — | — | — |
| 63 | — | F149 | D155 | F162 | A163 | G164 | L169 | V171 | K172 | S173 |
| 64 | — | F156 | D162 | Y169 | A170 | G171 | L176 | V178 | Q179 | A180 |
| 65 | Q155 | V162 | D168 | Y175 | S176 | G177 | L182 | M184 | K185 | H186 |
| 66 | — | P149 | N155 | Y162 | A163 | G164 | L169 | V171 | E172 | H173 |
| 67 | — | F147 | N153 | Y160 | A161 | G162 | L167 | V169 | R170 | F171 |
| 68 | — | L149 | N155 | Y162 | A163 | G164 | L169 | L171 | R172 | Y173 |
| 69 | — | V150 | D156 | Y163 | S164 | G165 | M170 | I172 | K173 | A174 |
| 70 | — | L147 | D153 | Y160 | A161 | G162 | L167 | A169 | R170 | Y171 |
| 71 | Q152 | V159 | D165 | S172 | A173 | A174 | L179 | — | — | — |
| 72 | — | L166 | D172 | Y179 | A180 | G181 | L186 | A188 | R189 | Y190 |
| 73 | — | A152 | D158 | Y165 | A166 | G167 | L172 | T174 | A175 | A176 |
| 74 | — | A153 | D159 | Y166 | A167 | S168 | L173 | V175 | E176 | A177 |
| 75 | — | A153 | D159 | Y166 | A167 | S168 | L173 | V175 | E176 | A177 |
| 76 | — | V151 | N157 | Y164 | A165 | A166 | L171 | L173 | K174 | Y175 |
| 77 | — | A153 | D159 | Y166 | A167 | S168 | L173 | A175 | A176 | A177 |
| 78 | — | A147 | D153 | F160 | A161 | G162 | L167 | L169 | K170 | A171 |
| 79 | — | A151 | D157 | F164 | A165 | G166 | L171 | V173 | K174 | A175 |
| 80 | — | V162 | Q168 | Y175 | A176 | G177 | L182 | V184 | R185 | S186 |
| 81 | — | A153 | D159 | Y166 | A167 | S168 | L173 | V175 | E176 | A177 |
| 82 | — | F150 | D156 | Y163 | A164 | G165 | L170 | L172 | E173 | H174 |
| 83 | — | V151 | N157 | Y164 | A165 | A166 | L171 | L173 | K174 | Y175 |
| 84 | — | V163 | E169 | Y176 | A177 | G178 | L183 | A185 | V186 | A187 |
| 85 | — | I147 | N153 | Y160 | A161 | G162 | L167 | I169 | H170 | K171 |
| 86 | — | Q145 | A151 | Y158 | G159 | G160 | L165 | V167 | N168 | K169 |
| 87 | — | F158 | D164 | Y171 | A172 | S173 | L178 | M180 | A181 | D182 |
| 88 | — | F150 | D156 | Y163 | A164 | G165 | L170 | T172 | R173 | L174 |
| 89 | — | I144 | N150 | Y157 | A158 | G159 | L164 | M166 | E167 | K168 |
| 90 | — | A154 | S160 | F167 | A168 | G169 | M174 | L176 | R177 | S178 |
| 91 | — | V155 | E161 | Y168 | A169 | G170 | L175 | A177 | L178 | A179 |
| 92 | — | V154 | A160 | Y167 | A168 | G169 | L174 | A176 | R177 | S178 |
| 93 | — | A173 | Q179 | Y186 | T187 | S188 | L193 | L195 | R196 | A197 |
| 94 | — | A156 | A162 | F169 | A170 | G171 | M176 | L178 | V179 | S180 |
| 95 | — | A148 | D154 | F161 | A162 | G163 | L168 | V170 | Q171 | A172 |
| 96 | — | F149 | D155 | Y162 | A163 | G164 | L169 | T171 | R172 | L173 |
| 97 | — | A146 | D152 | F159 | A160 | G161 | M166 | L168 | K169 | A170 |
| 98 | R198 | V205 | E211 | Y218 | A219 | G220 | L225 | M227 | K228 | A229 |
| 99 | Q174 | V181 | D187 | S194 | A195 | A196 | L201 | M203 | K204 | H205 |
| 100 | R201 | V208 | E214 | Y221 | A222 | G223 | L228 | M230 | K231 | A232 |
| 101 | Q159 | V166 | D172 | S179 | A180 | G181 | L186 | M188 | C189 | H190 |
| 102 | R197 | V204 | E210 | Y217 | A218 | G219 | L224 | M226 | K227 | A228 |
| 103 | Q158 | V165 | N171 | S178 | G179 | G180 | L185 | M187 | R188 | Y189 |
| 104 | R227 | V234 | E240 | Y247 | A248 | G249 | L254 | M256 | K257 | A258 |
| 105 | R193 | V200 | E206 | Y213 | A214 | G215 | L220 | M222 | R223 | A224 |
| 106 | E161 | V168 | D174 | S181 | A182 | G183 | L188 | I190 | R191 | H192 |
| 107 | R201 | V208 | E214 | Y221 | A222 | G223 | L228 | M230 | K231 | A232 |
| 108 | R222 | V229 | E235 | Y242 | A243 | G244 | L249 | M251 | K252 | A253 |
| 109 | R192 | V199 | E205 | Y212 | A213 | G214 | L219 | M221 | K222 | A223 |
| 110 | E206 | V213 | D219 | S226 | A227 | G228 | L233 | I235 | R236 | H237 |
| 111 | R193 | V200 | E206 | Y213 | A214 | G215 | L220 | M222 | K223 | A224 |
| 112 | Q154 | V161 | D167 | C174 | G175 | G176 | L181 | M183 | H184 | L185 |
| 113 | R208 | V215 | E221 | Y228 | A229 | G230 | L235 | M237 | K238 | A239 |
| 114 | R201 | V208 | E214 | Y221 | A222 | G223 | L228 | M230 | K231 | A232 |
| 115 | Q159 | V166 | D172 | S179 | A180 | G181 | L186 | M188 | C189 | H190 |
| 116 | R222 | V229 | E235 | Y242 | A243 | G244 | L249 | M251 | K252 | A253 |
| 117 | Q161 | V168 | D174 | S181 | A182 | A183 | L188 | M190 | K191 | H192 |

| ID | Pos 21 | Pos 22 | Pos 23 | Pos 24 | Pos 25 | Pos 26 | Pos 27 | Pos 28 | Pos 29 | Pos 30 |
|---|---|---|---|---|---|---|---|---|---|---|
| 1 | N227 | S234 | S246 | K259 | P260 | R261 | L295 | Q301 | G308 | S324 |
| 2 | N227 | S234 | S246 | K259 | P260 | R261 | L295 | Q301 | G308 | S324 |
| 3 | N226 | S233 | S245 | K258 | P259 | R260 | L294 | Q300 | G307 | S323 |
| 4 | N226 | S233 | S245 | K258 | P259 | R260 | L294 | Q300 | G307 | S323 |
| 5 | N227 | S234 | S246 | K260 | P261 | R262 | L296 | Q302 | G309 | S325 |
| 6 | N197 | S204 | S216 | K230 | P231 | R232 | L266 | Q272 | G279 | S295 |
| 7 | N226 | S233 | S245 | K259 | P260 | R261 | L295 | H301 | E308 | P324 |

TABLE 2b-continued

| | | | | | | | | | | |
|---|---|---|---|---|---|---|---|---|---|---|
| 8 | N199 | S206 | A218 | K232 | K234 | R235 | L269 | H275 | E282 | S300 |
| 9 | N198 | S205 | T217 | K231 | K233 | Q234 | F268 | P274 | E281 | S299 |
| 10 | D197 | S204 | A216 | K229 | K231 | P232 | L266 | H272 | E279 | S297 |
| 11 | N197 | S204 | A216 | K230 | K232 | H233 | L267 | H273 | Q280 | D294 |
| 12 | N192 | S199 | A211 | K225 | K227 | R228 | L262 | Q268 | E275 | S293 |
| 13 | N197 | S204 | G216 | K230 | K232 | H233 | L267 | H273 | Q280 | D294 |
| 14 | N194 | S201 | S213 | K227 | K229 | R230 | L264 | H270 | E277 | S295 |
| 15 | N197 | S204 | A216 | K230 | H232 | R233 | L267 | H273 | E280 | S297 |
| 16 | N197 | S204 | A216 | K230 | H232 | R233 | L267 | H273 | E280 | S297 |
| 17 | N197 | S204 | G216 | K230 | K232 | H233 | L267 | H273 | E280 | D294 |
| 18 | N197 | S204 | T216 | K230 | K232 | P233 | L267 | — | Q279 | I295 |
| 19 | N192 | S199 | T211 | K225 | Q227 | P228 | L262 | — | Q274 | I290 |
| 20 | N195 | S202 | P214 | N228 | K230 | R231 | L265 | C271 | D278 | S296 |
| 21 | N192 | S199 | P211 | N225 | K227 | R228 | L262 | C268 | D275 | S293 |
| 22 | N199 | S206 | A218 | T232 | K234 | G235 | L269 | — | E280 | H298 |
| 23 | N203 | S210 | A222 | T236 | R238 | G239 | L273 | — | E284 | H302 |
| 24 | N199 | S203 | A215 | T229 | K231 | G232 | L266 | — | E277 | H295 |
| 25 | N245 | S249 | A261 | T275 | K277 | G278 | L312 | — | E323 | H341 |
| 26 | D168 | S175 | S187 | N197 | K199 | R200 | L234 | C240 | G246 | S263 |
| 27 | N230 | S237 | A249 | K263 | R265 | N266 | L300 | F306 | G313 | T334 |
| 28 | N232 | S239 | A251 | K265 | R267 | N268 | L302 | L308 | G315 | T336 |
| 29 | N169 | S176 | A188 | T202 | K204 | G205 | L239 | — | E250 | H268 |
| 30 | N232 | S239 | A251 | K265 | R267 | N268 | L302 | F308 | G315 | T336 |
| 31 | N232 | S239 | A251 | K265 | R267 | N268 | L302 | F308 | G315 | T336 |
| 32 | N205 | S212 | D224 | K238 | R240 | — | L274 | H280 | D287 | F308 |
| 33 | K243 | S250 | R262 | P275 | P277 | K278 | G312 | N318 | Y325 | N335 |
| 34 | N199 | S206 | A218 | K232 | K234 | R235 | L269 | Y275 | E282 | S300 |
| 35 | N286 | S293 | A305 | — | — | — | L331 | — | E342 | H360 |
| 36 | D236 | S243 | A255 | K269 | R271 | N272 | L306 | C312 | D319 | L340 |
| 37 | N196 | S203 | T215 | K229 | R231 | N232 | L266 | C272 | G279 | S300 |
| 38 | D203 | S210 | R222 | Q236 | K237 | R238 | L272 | L278 | N285 | S306 |
| 39 | N195 | S202 | P214 | N228 | K230 | R231 | L265 | C271 | D278 | S296 |
| 40 | N251 | S258 | T270 | K284 | R286 | N287 | L321 | C327 | G334 | S355 |
| 41 | N251 | S258 | T270 | K284 | R286 | N287 | L321 | C327 | G334 | S355 |
| 42 | N196 | S203 | A215 | T229 | K231 | G232 | L266 | — | E277 | H295 |
| 43 | S192 | S199 | K211 | T233 | P235 | R236 | T270 | Q276 | Q283 | T303 |
| 44 | S192 | S199 | K211 | T233 | P235 | R236 | T270 | Q276 | Q283 | T303 |
| 45 | N227 | — | — | — | — | — | — | — | — | — |
| 46 | N226 | — | — | — | — | — | — | — | — | — |
| 47 | N84 | S91 | A103 | K117 | R119 | N120 | L154 | F160 | G167 | T188 |
| 48 | N113 | S120 | A132 | K146 | R148 | S149 | L183 | C189 | D196 | S217 |
| 49 | N185 | S192 | A204 | N218 | R220 | R221 | L255 | N261 | D268 | S287 |
| 50 | — | — | S3 | K17 | K19 | H20 | L54 | D60 | S67 | S88 |
| 51 | E179 | S186 | — | — | A203 | P204 | L238 | — | P247 | F262 |
| 52 | A178 | S185 | — | — | D204 | T205 | H238 | — | W247 | S262 |
| 53 | A178 | S185 | — | — | D204 | T205 | H238 | — | W247 | S262 |
| 54 | — | — | — | — | — | — | — | — | — | — |
| 55 | E179 | S186 | — | — | A203 | P204 | L238 | — | P247 | F262 |
| 56 | N177 | S184 | R196 | — | K204 | D205 | R238 | — | — | F261 |
| 57 | E195 | S202 | R214 | — | E219 | P220 | D254 | — | K261 | S276 |
| 58 | A183 | S190 | R202 | — | K210 | D211 | E244 | — | — | S263 |
| 59 | A180 | G187 | R199 | — | K207 | Q208 | I241 | — | — | V264 |
| 60 | N180 | S187 | — | G203 | F205 | F206 | I239 | S243 | — | — |
| 61 | E180 | S187 | G199 | — | A207 | T208 | T241 | — | T250 | — |
| 62 | — | — | — | — | — | — | — | — | — | — |
| 63 | R180 | G187 | R199 | — | K207 | Q208 | L241 | — | Q250 | T265 |
| 64 | A187 | S194 | A206 | — | — | A217 | D250 | I256 | G263 | H275 |
| 65 | R193 | S200 | T212 | T222 | K224 | E225 | T259 | T265 | G272 | — |
| 66 | Q180 | S187 | Q199 | H207 | L209 | Q210 | G244 | R250 | — | S270 |
| 67 | A178 | G185 | R197 | — | K205 | I206 | L239 | — | — | R262 |
| 68 | A180 | G187 | — | G204 | K206 | A207 | E240 | Q244 | — | — |
| 69 | E181 | S188 | K200 | G212 | K214 | M215 | T249 | — | G257 | E272 |
| 70 | E178 | S185 | R197 | P209 | P211 | P212 | V246 | V252 | A257 | R283 |
| 71 | — | — | — | — | — | — | T184 | C190 | L197 | — |
| 72 | E197 | S204 | R216 | P228 | P230 | P231 | V265 | V271 | A276 | R299 |
| 73 | E183 | S190 | K202 | — | K209 | M210 | V244 | — | W252 | I267 |
| 74 | R184 | G191 | R203 | G209 | S211 | P212 | V243 | — | G252 | T267 |
| 75 | R184 | G191 | R203 | G209 | S211 | P212 | V243 | — | G252 | T267 |
| 76 | D182 | S189 | — | E203 | I205 | S206 | K239 | K244 | — | V264 |
| 77 | E184 | S191 | K203 | — | K210 | M211 | V245 | — | Y253 | T268 |
| 78 | Y178 | G185 | A197 | P206 | G208 | P207 | I241 | — | I250 | T265 |
| 79 | H182 | S189 | K201 | T205 | G207 | P208 | V240 | — | K249 | S264 |
| 80 | A193 | G200 | K212 | P224 | T226 | R227 | R261 | H267 | F274 | E284 |
| 81 | R184 | G191 | R203 | G209 | A211 | P212 | V243 | — | G252 | T267 |
| 82 | G181 | S188 | — | G204 | A206 | Y207 | V240 | R244 | — | F263 |
| 83 | D182 | S189 | — | E203 | I205 | S206 | K239 | K244 | — | V264 |
| 84 | G194 | S201 | — | P223 | P225 | K226 | Q260 | G265 | F272 | A282 |
| 85 | A178 | S185 | A197 | — | — | G198 | L232 | G238 | S245 | S253 |
| 86 | E176 | S183 | G195 | — | — | V196 | F229 | G235 | A242 | E251 |
| 87 | Q189 | S196 | Q207 | P213 | F215 | A216 | V247 | — | G256 | R271 |

TABLE 2b-continued

| | | | | | | | | | | |
|---|---|---|---|---|---|---|---|---|---|---|
| 88 | N181 | S188 | P200 | — | R207 | A208 | L242 | G248 | K250 | I261 |
| 89 | E175 | S182 | T194 | — | — | Q195 | E227 | G233 | — | K245 |
| 90 | E185 | S192 | K204 | A217 | G219 | P220 | V253 | — | — | D274 |
| 91 | G186 | S193 | R205 | P226 | P228 | K229 | H263 | E268 | F275 | A294 |
| 92 | Q185 | G192 | R204 | P216 | V218 | R219 | E253 | N259 | F266 | E276 |
| 93 | D204 | S211 | T223 | T229 | A231 | R232 | V266 | — | G275 | H290 |
| 94 | E187 | G194 | K206 | A219 | G221 | P222 | V255 | — | — | D276 |
| 95 | A179 | S186 | A194 | — | — | — | E236 | — | S244 | Q255 |
| 96 | D180 | S187 | P199 | — | R206 | A207 | L241 | G247 | K249 | I260 |
| 97 | R177 | G184 | A196 | P206 | G208 | P209 | V241 | — | K250 | E265 |
| 98 | K236 | S243 | A254 | K269 | P270 | K271 | S304 | — | G312 | — |
| 99 | N212 | S219 | A231 | K246 | K247 | G248 | L282 | T288 | E293 | H311 |
| 100 | K239 | S246 | E257 | K272 | P273 | K274 | S307 | — | G315 | — |
| 101 | D197 | S204 | A216 | R230 | K231 | A232 | L266 | H272 | E279 | S297 |
| 102 | K235 | S242 | A253 | T268 | P269 | K270 | V303 | — | R311 | — |
| 103 | D196 | S203 | S215 | S226 | K227 | R228 | L262 | C268 | G274 | P292 |
| 104 | V265 | N272 | E283 | K298 | P299 | K300 | A333 | — | G341 | — |
| 105 | R231 | S238 | D249 | T264 | P265 | K266 | T299 | — | Q307 | — |
| 106 | N199 | S206 | A218 | G233 | R234 | N235 | L269 | C275 | N282 | P303 |
| 107 | K239 | S246 | R258 | K272 | P273 | K274 | S307 | G313 | T320 | S334 |
| 108 | K260 | S267 | R279 | K293 | P294 | K295 | S328 | L334 | T341 | S355 |
| 109 | R230 | S237 | K249 | A263 | P264 | K265 | T298 | D304 | G311 | S325 |
| 110 | N244 | S251 | A263 | G278 | R279 | N280 | L314 | C320 | D327 | S348 |
| 111 | R231 | S238 | K250 | A264 | P265 | K266 | T299 | D305 | G312 | S326 |
| 112 | N192 | S199 | P211 | K226 | K227 | R228 | L262 | C268 | D275 | S293 |
| 113 | R246 | S253 | K265 | A279 | P280 | K281 | T314 | D320 | G327 | S341 |
| 114 | K239 | S246 | R258 | K272 | P273 | K274 | S307 | G313 | T320 | S334 |
| 115 | D197 | S204 | A216 | R230 | K231 | A232 | L266 | H272 | E279 | S297 |
| 116 | K260 | S267 | R279 | K293 | P294 | K295 | S328 | L334 | T341 | S355 |
| 117 | N199 | S206 | A218 | K233 | K234 | G235 | L269 | A275 | E280 | H298 |

| ID | Pos 31 | Pos 32 | Pos 33 | Pos 34 | Pos 35 | Pos 36 | Pos 37 | Pos 38 | Pos 39 | Pos 40 |
|---|---|---|---|---|---|---|---|---|---|---|
| 1 | R335 | G346 | F349 | L351 | D352 | T358 | L384 | L397 | F417 | T418 |
| 2 | R335 | G346 | F349 | L351 | D352 | T358 | L384 | L397 | F417 | T418 |
| 3 | R334 | G345 | F348 | L350 | D351 | T357 | L383 | L396 | F416 | T417 |
| 4 | R334 | G345 | F348 | L350 | D351 | T357 | L383 | L396 | F416 | T417 |
| 5 | R336 | G347 | F350 | L352 | D353 | T359 | L385 | L398 | F418 | T419 |
| 6 | R306 | G317 | F320 | L322 | D323 | S329 | L355 | L368 | F388 | T389 |
| 7 | N335 | E346 | F349 | L351 | D352 | S358 | L384 | L397 | Y417 | T418 |
| 8 | C311 | G322 | F325 | L327 | D328 | S334 | L360 | L373 | Y393 | T394 |
| 9 | C310 | R321 | F324 | L326 | N327 | S333 | L359 | L372 | Y392 | T393 |
| 10 | C308 | G319 | F322 | L324 | N325 | S331 | L357 | L370 | Y390 | T391 |
| 11 | Y305 | G316 | F319 | L321 | N322 | S328 | L354 | L367 | Y387 | T388 |
| 12 | C304 | G315 | F318 | L320 | D321 | V327 | L353 | L366 | Y386 | T387 |
| 13 | G305 | G316 | F319 | L321 | N322 | T328 | L354 | L367 | Y387 | T388 |
| 14 | C306 | G317 | F320 | L322 | D323 | N329 | L355 | L368 | Y388 | T389 |
| 15 | C308 | G319 | F322 | L324 | D325 | I331 | L357 | L370 | Y390 | T391 |
| 16 | C308 | G319 | F322 | L324 | D325 | I331 | L357 | L370 | Y390 | T391 |
| 17 | G305 | G316 | F319 | L321 | N322 | T328 | L354 | L367 | Y387 | T388 |
| 18 | C306 | G317 | F320 | L322 | N323 | A329 | L355 | L368 | Y388 | T389 |
| 19 | C301 | G312 | F315 | L317 | N318 | A324 | L350 | L363 | Y383 | T384 |
| 20 | C307 | G318 | F321 | L323 | N324 | D330 | L356 | L369 | Y389 | T390 |
| 21 | C304 | G315 | F318 | L320 | N321 | D327 | L353 | L366 | Y386 | T387 |
| 22 | C309 | G320 | F323 | L325 | N326 | N332 | L358 | L371 | Y391 | T392 |
| 23 | C313 | G324 | F327 | L329 | N330 | N336 | L362 | L375 | Y395 | T396 |
| 24 | C302 | G313 | F316 | L318 | N319 | N325 | L351 | L364 | Y384 | T385 |
| 25 | C348 | G359 | F362 | L364 | N365 | N371 | L397 | L410 | Y430 | T431 |
| 26 | N274 | G285 | F288 | L290 | N291 | S297 | L323 | L336 | Y356 | T357 |
| 27 | S345 | G356 | F359 | L361 | D362 | N368 | L394 | L408 | Y428 | T429 |
| 28 | S347 | G358 | F361 | L363 | D364 | D370 | L396 | L410 | Y430 | T431 |
| 29 | C279 | G290 | F293 | L295 | N296 | N302 | L328 | L341 | Y361 | T362 |
| 30 | S347 | G358 | V361 | L363 | D364 | D370 | L396 | L410 | Y430 | T431 |
| 31 | S347 | G358 | V361 | L363 | D364 | D370 | L396 | L410 | Y430 | T431 |
| 32 | G319 | G330 | F333 | L335 | D336 | T342 | L368 | L381 | Y401 | T402 |
| 33 | Y346 | — | N357 | A359 | A360 | Y367 | L399 | L409 | Y429 | T430 |
| 34 | C311 | R322 | F325 | L327 | D328 | S334 | L360 | L373 | Y393 | T394 |
| 35 | C371 | G382 | F385 | L387 | N388 | K394 | L420 | L433 | Y453 | T454 |
| 36 | S351 | G362 | F365 | L367 | D368 | D374 | L400 | L414 | F434 | T435 |
| 37 | S311 | G322 | F325 | L327 | D328 | D334 | L360 | L374 | Y394 | T395 |
| 38 | — | — | — | — | — | T315 | L341 | L354 | F374 | T375 |
| 39 | C307 | G318 | F321 | L323 | N324 | D330 | L356 | L369 | Y389 | T390 |
| 40 | S366 | G377 | F380 | L382 | D383 | D389 | L415 | L429 | Y449 | T450 |
| 41 | S366 | G377 | F380 | L382 | D383 | D389 | L415 | L429 | Y449 | T450 |
| 42 | C306 | G317 | F320 | L322 | N323 | K329 | L355 | L368 | Y388 | T389 |
| 43 | D314 | G325 | Y328 | L330 | D331 | I337 | L363 | L377 | F397 | T398 |
| 44 | D314 | G325 | Y328 | L330 | D331 | I337 | L363 | L377 | F397 | T398 |
| 45 | — | — | — | — | — | — | — | — | — | — |
| 46 | — | — | — | — | — | — | — | — | — | — |

TABLE 2b-continued

| | | | | | | | | | | |
|---|---|---|---|---|---|---|---|---|---|---|
| 47 | S199 | G210 | V213 | L215 | D216 | D222 | L248 | L262 | Y282 | T283 |
| 48 | S228 | G239 | F242 | L244 | D245 | D251 | L277 | L291 | F311 | T312 |
| 49 | S298 | — | — | — | — | — | — | — | — | — |
| 50 | R99 | G110 | Y113 | L115 | D116 | M122 | L148 | L161 | Y181 | T182 |
| 51 | H273 | P282 | D285 | — | R286 | E293 | L319 | L330 | L350 | T351 |
| 52 | H273 | T282 | D285 | — | L286 | T293 | L319 | L330 | L350 | T351 |
| 53 | H273 | T282 | D285 | — | L286 | T293 | L319 | L330 | L350 | T351 |
| 54 | S6 | G17 | V20 | L22 | D23 | D29 | L55 | L69 | Y89 | T90 |
| 55 | H273 | P282 | D285 | — | R286 | E293 | L319 | L330 | L350 | T351 |
| 56 | Y272 | S280 | K283 | R285 | A286 | L293 | L319 | L329 | F349 | T350 |
| 57 | P287 | T296 | E299 | P301 | L302 | E309 | L335 | L345 | L365 | T366 |
| 58 | H274 | D283 | D286 | D288 | M289 | I296 | L322 | L332 | L352 | S353 |
| 59 | Y275 | K283 | K286 | F288 | K289 | Y296 | L322 | L332 | F352 | T353 |
| 60 | P273 | M283 | A286 | L288 | A289 | Q295 | L321 | L331 | L351 | T352 |
| 61 | H272 | P281 | D284 | — | T285 | P292 | L318 | L329 | L349 | T350 |
| 62 | — | — | — | — | — | — | — | — | — | — |
| 63 | Y276 | E284 | Q287 | L289 | A290 | Y297 | L323 | L333 | F353 | T354 |
| 64 | H286 | — | G297 | L299 | A300 | E307 | L333 | L343 | L363 | S364 |
| 65 | H292 | A303 | K306 | F308 | K309 | K316 | L342 | L352 | L373 | T374 |
| 66 | H281 | E290 | L293 | S295 | L296 | D303 | L329 | L339 | I359 | N360 |
| 67 | Y273 | R281 | P284 | A286 | A287 | V294 | L320 | L330 | L350 | T351 |
| 68 | H270 | — | E278 | P280 | I281 | D287 | L313 | L323 | L343 | T344 |
| 69 | Y283 | — | P294 | A296 | A297 | R304 | L330 | L340 | T360 | I361 |
| 70 | E294 | A303 | E306 | P308 | L309 | E316 | L342 | L352 | L372 | T373 |
| 71 | S213 | — | — | — | — | — | — | L230 | — | — |
| 72 | E310 | A319 | E322 | P324 | L325 | E332 | L358 | L368 | L388 | T389 |
| 73 | F278 | — | Q289 | A291 | A292 | P299 | L325 | L335 | T355 | T356 |
| 74 | P278 | — | D289 | P291 | S292 | P299 | L325 | L335 | L355 | T356 |
| 75 | P278 | — | D289 | P291 | S292 | P299 | L325 | L335 | L355 | T356 |
| 76 | H275 | I285 | S288 | L290 | L291 | Y298 | L324 | L334 | L354 | T355 |
| 77 | Y279 | — | P290 | A292 | A293 | P300 | L326 | L336 | T356 | I357 |
| 78 | Y276 | — | L287 | L289 | S290 | E297 | L323 | L333 | I353 | R354 |
| 79 | Y275 | — | E286 | L288 | A289 | E297 | L322 | L332 | L352 | R353 |
| 80 | H295 | — | S306 | I308 | A309 | P316 | L342 | L352 | L372 | S373 |
| 81 | P278 | — | E289 | P291 | S292 | P299 | L325 | L335 | L355 | T356 |
| 82 | H274 | E283 | A286 | P288 | L289 | E296 | L322 | L332 | L352 | T353 |
| 83 | H275 | I285 | S288 | L290 | L291 | Y298 | L324 | L334 | L354 | T355 |
| 84 | Y293 | — | P304 | A306 | S307 | L314 | L340 | L350 | F370 | T371 |
| 85 | F264 | — | P275 | A277 | A278 | H285 | L311 | A321 | F341 | T342 |
| 86 | H262 | — | P273 | M275 | S276 | N283 | L309 | S319 | I339 | T340 |
| 87 | A282 | — | P293 | I295 | P296 | P303 | L329 | L339 | L359 | T360 |
| 88 | Y272 | — | K283 | Q285 | L286 | Y293 | L318 | L328 | Y348 | A349 |
| 89 | Y256 | — | P267 | S269 | A270 | N277 | L303 | A313 | I333 | T334 |
| 90 | H285 | — | A296 | M298 | A299 | P306 | L332 | L342 | L362 | R363 |
| 91 | Y305 | — | P316 | A318 | S319 | P326 | L352 | L362 | L382 | I383 |
| 92 | Y287 | — | P298 | A300 | S301 | P308 | L334 | L344 | L364 | T365 |
| 93 | P301 | — | P312 | L314 | S315 | E322 | V348 | F358 | L378 | R379 |
| 94 | Y287 | — | G298 | M300 | S301 | P308 | L334 | L344 | L364 | R365 |
| 95 | G266 | — | A277 | L279 | A280 | P287 | L313 | L323 | L343 | T344 |
| 96 | Y271 | — | K282 | Q284 | L285 | E292 | L317 | L327 | Y347 | A348 |
| 97 | Y276 | — | R287 | L289 | S290 | E297 | L323 | L333 | I353 | R354 |
| 98 | — | L348 | S351 | A353 | E354 | Y360 | L386 | L402 | L422 | L423 |
| 99 | C322 | G333 | F336 | L338 | N339 | K345 | L371 | L384 | Y404 | T405 |
| 100 | — | L351 | A354 | A356 | D357 | Y363 | L389 | L405 | L425 | L426 |
| 101 | C308 | G319 | F322 | L324 | N325 | S331 | L357 | L370 | Y390 | T391 |
| 102 | — | L347 | E350 | A352 | D353 | Y359 | L385 | L401 | L421 | L422 |
| 103 | G303 | G314 | F317 | L319 | N320 | S326 | L352 | L365 | Y385 | T386 |
| 104 | — | F377 | A380 | A382 | D383 | H389 | L415 | L431 | I451 | L452 |
| 105 | — | L343 | D346 | A348 | D349 | Y355 | L381 | L397 | L417 | L418 |
| 106 | S314 | G325 | F328 | L330 | D331 | D337 | L363 | L377 | F397 | T398 |
| 107 | S345 | A356 | L359 | Q361 | F362 | A368 | L395 | L405 | L425 | L426 |
| 108 | S366 | A377 | L380 | K382 | F383 | A389 | L416 | L426 | I446 | L447 |
| 109 | S336 | A347 | L350 | K352 | F353 | A359 | L386 | L396 | L416 | L417 |
| 110 | S359 | G370 | F373 | L375 | D376 | D382 | L408 | L422 | F442 | T443 |
| 111 | S337 | A348 | L351 | K353 | F354 | A360 | L387 | L397 | L417 | L418 |
| 112 | C304 | G315 | F318 | L320 | N321 | D327 | L353 | L366 | Y386 | T387 |
| 113 | S352 | A363 | L366 | K368 | F369 | A375 | L402 | L412 | L432 | L433 |
| 114 | S345 | A356 | L359 | Q361 | F362 | A368 | L395 | L405 | L425 | L426 |
| 115 | C308 | G319 | F322 | L324 | N325 | S331 | L357 | L370 | Y390 | T391 |
| 116 | S366 | A377 | L380 | K382 | F383 | A389 | L416 | L426 | I446 | L447 |
| 117 | C309 | G320 | F323 | L325 | N326 | K332 | L358 | L371 | Y391 | T392 |

| Pos ID | Pos 41 | Pos 42 | Pos 43 | Pos 44 | Pos 45 | Pos 46 | Pos 47 | Pos 48 | Pos 49 | Pos 50 | Pos 51 | Pos 52 | Pos 53 | Pos 54 | Pos 55 | Pos 56 |
|---|---|---|---|---|---|---|---|---|---|---|---|---|---|---|---|---|
| 1 | T419 | F420 | A432 | T434 | K438 | L449 | T451 | F462 | Y470 | S476 | V477 | D482 | Y493 | K498 | E515 | K528 |
| 2 | T419 | F420 | A432 | T434 | K438 | L449 | T451 | F462 | Y470 | S476 | V477 | D482 | Y493 | K498 | E515 | K528 |
| 3 | T418 | F419 | A431 | T433 | K437 | L448 | T450 | F461 | Y469 | C475 | V476 | D481 | Y492 | K497 | E514 | K527 |
| 4 | T418 | F419 | A431 | T433 | K437 | L448 | T450 | F461 | Y469 | S475 | V476 | D481 | Y492 | K497 | E514 | K527 |
| 5 | T420 | F421 | A433 | T435 | K439 | L450 | T452 | F463 | Y471 | S477 | V478 | D483 | Y494 | K499 | E516 | K529 |

TABLE 2b-continued

| | | | | | | | | | | | | | | | |
|---|---|---|---|---|---|---|---|---|---|---|---|---|---|---|---|
| 6 | T390 | F391 | A403 | T405 | K409 | L420 | T422 | F433 | Y441 | S447 | V448 | D453 | Y464 | K469 | E486 | K499 |
| 7 | T419 | F420 | A432 | T434 | K438 | L449 | T451 | Y462 | Y470 | S476 | V477 | E482 | Y493 | K498 | E515 | K525 |
| 8 | T395 | F396 | A408 | T410 | K414 | L425 | A427 | Y438 | F446 | S452 | V453 | D458 | Y469 | K474 | D491 | K504 |
| 9 | T394 | F395 | A407 | T409 | K413 | L424 | A426 | Y437 | Y445 | S451 | V452 | D457 | Y468 | K473 | D490 | K503 |
| 10 | T392 | F393 | A405 | T407 | K411 | L422 | V424 | Y435 | Y443 | S449 | V450 | E455 | Y466 | K471 | D488 | K500 |
| 11 | T389 | F390 | A402 | T404 | R408 | L419 | A421 | Y432 | Y440 | S446 | V447 | D452 | F463 | K468 | D485 | T498 |
| 12 | T388 | F389 | A401 | T403 | K407 | L418 | A420 | Y431 | Y439 | S445 | V446 | E451 | Y462 | R467 | E484 | K497 |
| 13 | T389 | F390 | A402 | T404 | T408 | L419 | A421 | F432 | Y440 | S446 | V447 | D452 | Y463 | R468 | D485 | S498 |
| 14 | T390 | F391 | A403 | K405 | K409 | L420 | A422 | Y433 | Y441 | S447 | V448 | E453 | Y464 | K469 | D486 | K499 |
| 15 | T392 | F393 | A405 | T407 | K411 | L422 | V424 | F435 | Y443 | S449 | V450 | E455 | Y466 | K471 | E488 | K501 |
| 16 | T392 | F393 | A405 | T407 | K411 | L422 | V424 | F435 | Y443 | S449 | V450 | E455 | Y466 | K471 | E488 | K501 |
| 17 | T389 | F390 | A402 | T404 | T408 | L419 | A421 | Y432 | Y440 | L446 | V447 | D452 | Y463 | R468 | D485 | T498 |
| 18 | T390 | F391 | S403 | T405 | K409 | L420 | V422 | Y433 | Y441 | S447 | V448 | E453 | Y464 | K469 | D486 | S499 |
| 19 | T385 | F386 | S398 | T400 | K404 | L415 | V417 | Y428 | Y436 | S442 | V443 | E448 | Y459 | R464 | D481 | S494 |
| 20 | T391 | F392 | A404 | R406 | K410 | L421 | A423 | Y434 | Y442 | S448 | V449 | D454 | Y465 | R470 | D487 | S500 |
| 21 | T388 | F389 | A401 | R403 | K407 | L418 | A420 | C431 | Y439 | S445 | V446 | D451 | Y462 | K467 | D484 | T497 |
| 22 | T393 | F394 | A406 | T408 | K412 | L423 | V425 | Y436 | Y444 | S450 | V451 | D456 | Y467 | R472 | D489 | K502 |
| 23 | T397 | F398 | A410 | T412 | K416 | L427 | V429 | Y440 | Y448 | S454 | V455 | D460 | Y471 | R476 | D493 | K506 |
| 24 | T386 | F387 | A399 | T401 | K405 | L416 | V418 | Y429 | Y437 | S443 | V444 | D449 | Y460 | R465 | D482 | K495 |
| 25 | T432 | F433 | A445 | T447 | K451 | L462 | V464 | Y475 | Y483 | S489 | V490 | D495 | Y506 | R511 | D528 | K541 |
| 26 | T358 | F359 | A371 | R373 | L377 | L388 | T390 | Y401 | Y409 | S415 | V416 | E421 | Y432 | K437 | E454 | K467 |
| 27 | T430 | F431 | A443 | T445 | K449 | L460 | Y462 | Y473 | Y481 | S487 | V488 | E493 | Y504 | K509 | E526 | N539 |
| 28 | T432 | F433 | A445 | T447 | K451 | L462 | V464 | Y475 | Y483 | S489 | V490 | E495 | Y506 | K511 | D528 | N541 |
| 29 | T363 | F364 | A376 | T378 | K382 | L393 | V395 | Y406 | Y414 | S420 | V421 | D426 | Y437 | R442 | D459 | K472 |
| 30 | T432 | F433 | A445 | T447 | K451 | L462 | V464 | Y475 | Y483 | S489 | V490 | E495 | Y506 | K511 | D528 | N541 |
| 31 | T432 | F433 | A445 | T447 | K451 | L462 | V464 | Y475 | Y483 | S489 | V490 | E495 | Y506 | K511 | D528 | N541 |
| 32 | T403 | F404 | A416 | F418 | K422 | L433 | V435 | Y446 | Y454 | L460 | V461 | D466 | Y477 | R482 | D499 | — |
| 33 | N431 | Y432 | K444 | E446 | V450 | L461 | K463 | V476 | F484 | D490 | L491 | T496 | L509 | V514 | A531 | F544 |
| 34 | T395 | F396 | — | — | L402 | C404 | Y408 | Y416 | L422 | V423 | E428 | Y439 | R444 | D461 | K474 | |
| 35 | T455 | F456 | A468 | T470 | K474 | L485 | V487 | Y498 | Y506 | S512 | V513 | D518 | Y529 | R534 | D551 | K564 |
| 36 | T436 | F437 | A449 | T451 | K455 | L466 | V468 | H479 | Y487 | L493 | A494 | G499 | Y510 | K515 | D532 | A543 |
| 37 | S396 | F397 | A409 | T411 | K415 | L426 | V428 | H439 | Y447 | L453 | V454 | A459 | Y470 | K475 | D492 | D505 |
| 38 | T376 | F377 | S389 | L391 | Q395 | L406 | V408 | Y419 | Y427 | S433 | V434 | D439 | F450 | R455 | D472 | T485 |
| 39 | T391 | F392 | A404 | | | | | | | | | | | | | |
| 40 | S451 | F452 | A464 | T466 | K470 | L481 | V483 | H494 | Y502 | L508 | V509 | A514 | Y525 | — | K537 | — |
| 41 | S451 | F452 | A464 | T466 | K470 | L481 | V483 | H494 | Y502 | L508 | V509 | A514 | Y525 | — | K537 | — |
| 42 | T390 | F391 | A403 | T405 | | | | | | | | | | | | |
| 43 | T399 | F400 | R412 | K414 | L418 | I429 | V431 | Y442 | Y450 | N456 | V457 | Q462 | Y473 | R478 | E495 | K508 |
| 44 | T399 | F400 | R412 | K414 | L418 | I429 | V431 | Y442 | Y450 | N456 | V457 | Q462 | Y473 | R478 | E495 | K508 |
| 45 | — | — | — | — | — | — | — | — | — | — | — | — | — | — | — | — |
| 46 | — | — | — | — | — | — | — | — | — | — | — | — | — | — | — | — |
| 47 | T284 | F285 | A297 | T299 | K303 | L314 | V316 | Y327 | Y335 | S341 | V342 | E347 | Y358 | K363 | D380 | N393 |
| 48 | T313 | F314 | A326 | T328 | K332 | L343 | V345 | H356 | Y364 | S370 | A371 | G376 | — | K383 | D400 | V413 |
| 49 | — | — | — | — | — | — | — | — | — | — | — | — | — | — | — | — |
| 50 | T183 | F184 | A196 | L198 | R202 | L213 | V215 | Y226 | Y234 | M240 | V241 | E246 | Y257 | S262 | — | — |
| 51 | T352 | F353 | L365 | E367 | E371 | L382 | I384 | R395 | Y403 | A409 | V410 | H415 | L426 | M431 | R448 | G461 |
| 52 | T352 | F353 | S365 | A367 | Q371 | L382 | V384 | H395 | Y403 | T409 | V410 | D415 | F426 | R431 | — | A458 |
| 53 | T352 | F353 | S365 | A367 | Q371 | L382 | V384 | H395 | Y403 | T409 | V410 | D415 | F426 | R431 | — | T458 |
| 54 | T91 | F92 | A104 | T106 | K110 | L121 | V123 | Y134 | Y142 | S148 | V149 | E154 | Y165 | K170 | D187 | N200 |
| 55 | T352 | F353 | L365 | E367 | E371 | L382 | I384 | R395 | Y403 | A409 | V410 | H415 | L426 | M431 | R448 | G461 |
| 56 | T351 | F352 | K364 | D366 | K370 | V381 | L383 | R394 | Y402 | K408 | I409 | D414 | F425 | R430 | E447 | — |
| 57 | V367 | M368 | L380 | A382 | L386 | L397 | V399 | F410 | Y418 | H424 | F425 | A430 | M441 | R446 | E463 | — |
| 58 | T354 | Y355 | L367 | D369 | D373 | L384 | V386 | V397 | Y405 | K411 | I412 | N417 | F428 | R433 | Q450 | — |
| 59 | L354 | F355 | E367 | R369 | L373 | M384 | I386 | F397 | Y405 | H412 | D417 | I428 | R433 | N450 | — | — |
| 60 | N353 | Y354 | L366 | R368 | R372 | L383 | V385 | F396 | Y404 | E410 | Y411 | D416 | L427 | R432 | A449 | — |
| 61 | T351 | F352 | A364 | D366 | R370 | L381 | V383 | A394 | Y402 | A408 | A409 | E414 | F425 | R430 | R447 | V460 |
| 62 | — | — | — | — | — | — | — | — | — | — | — | — | — | — | — | — |
| 63 | L355 | F356 | M368 | K370 | I374 | L385 | I387 | L398 | Y406 | E412 | H413 | E418 | L429 | R434 | K451 | — |
| 64 | A365 | F366 | G378 | D380 | L384 | L395 | I397 | R408 | Y416 | E422 | L423 | S428 | L439 | R444 | E461 | — |
| 65 | V375 | Y376 | R388 | A390 | V394 | L405 | V407 | T418 | Y426 | E432 | S433 | A438 | F449 | R454 | E471 | — |
| 66 | V361 | M362 | L374 | E376 | R380 | L391 | V393 | H404 | L412 | I418 | V419 | I424 | L435 | R440 | E457 | — |
| 67 | T352 | F353 | R365 | N367 | I371 | L382 | L384 | R395 | Y403 | E409 | I410 | D415 | F426 | R431 | E448 | — |
| 68 | V345 | F346 | P358 | T360 | L364 | L375 | I377 | H388 | Y396 | K402 | V403 | T408 | L419 | R424 | N441 | — |
| 69 | N362 | L363 | Q375 | D377 | I381 | I392 | A394 | R405 | Y413 | E419 | A420 | E425 | L436 | R441 | E458 | A471 |
| 70 | V374 | L375 | M387 | L389 | M393 | L404 | V406 | V417 | Y425 | R431 | F432 | E437 | V448 | R453 | R470 | — |
| 71 | — | — | — | — | — | — | — | — | — | — | — | — | — | — | — | — |
| 72 | V390 | L391 | M403 | L405 | M409 | L420 | V422 | V433 | Y441 | R447 | F448 | E453 | V464 | R469 | R486 | — |
| 73 | T357 | L358 | R370 | D372 | I376 | L387 | I389 | R400 | Y408 | E414 | R415 | V420 | F431 | R436 | E453 | A466 |
| 74 | V357 | F358 | A370 | D372 | E376 | L387 | V389 | R400 | L408 | E414 | T415 | R420 | L429 | L434 | E451 | — |
| 75 | V357 | F358 | A370 | D372 | E376 | L387 | V389 | R400 | L408 | E414 | T415 | R420 | L429 | L434 | E451 | — |
| 76 | T356 | Y357 | F369 | Q371 | L375 | L386 | I388 | L399 | P407 | D413 | R414 | S419 | I430 | I435 | — | — |
| 77 | T358 | F359 | Q371 | E373 | I377 | L388 | I390 | R401 | Y409 | E415 | R416 | E421 | L432 | R437 | E454 | A467 |
| 78 | V355 | M356 | F368 | D370 | V374 | M385 | I387 | K398 | Y406 | E412 | R413 | F418 | L429 | Y434 | R451 | — |
| 79 | A354 | M355 | A367 | E369 | A373 | M384 | I386 | K397 | Y405 | E411 | K412 | F417 | L428 | Y433 | E450 | — |
| 80 | N374 | Y375 | M387 | D389 | V393 | L404 | A406 | L418 | M432 | N432 | E438 | L449 | I454 | S471 | N484 | |
| 81 | V357 | F358 | T370 | D372 | E376 | L387 | V389 | R400 | F408 | E414 | T415 | R420 | L429 | L434 | E451 | — |
| 82 | V354 | M355 | F367 | Q369 | L373 | L384 | L386 | S397 | Y405 | P411 | W412 | K417 | F428 | V433 | E450 | — |
| 83 | T356 | F357 | F369 | Q371 | L375 | L386 | I388 | L399 | P407 | D413 | R414 | S419 | I430 | I435 | — | — |
| 84 | S372 | F373 | F394 | P396 | A400 | L411 | T413 | L425 | Y433 | Q439 | R440 | Q445 | V457 | L462 | Q479 | — |
| 85 | T343 | F344 | Q356 | E358 | K362 | — | D374 | L387 | Y395 | — | R398 | H403 | S416 | R421 | D438 | — |

TABLE 2b-continued

| 86 | S341 | Y342 | F354 | E356 | L360 | — | Q372 | L385 | F393 | — | Y396 | H401 | I414 | Y419 | A436 | — |
|---|---|---|---|---|---|---|---|---|---|---|---|---|---|---|---|---|
| 87 | V361 | F362 | A374 | D376 | L380 | L391 | V393 | R404 | S412 | E418 | R419 | E424 | L433 | L438 | E455 | — |
| 88 | F350 | F351 | K363 | D365 | R369 | L380 | Y382 | R395 | Y403 | S409 | R410 | D415 | I426 | K431 | E448 | — |
| 89 | S335 | F336 | F348 | D350 | K354 | — | K366 | R378 | Y386 | — | D389 | H394 | V407 | E412 | E429 | — |
| 90 | S364 | M365 | F377 | D379 | M383 | M394 | I396 | R407 | Y415 | K421 | R422 | Q427 | L438 | Y443 | D460 | — |
| 91 | S384 | F385 | F406 | P408 | A412 | L423 | T425 | L437 | Y445 | Q451 | R452 | Q457 | V469 | L474 | Q491 | — |
| 92 | N366 | F367 | F379 | N381 | V385 | L396 | K398 | L410 | Y418 | L424 | R425 | N430 | L441 | T446 | P463 | — |
| 93 | T380 | F381 | H393 | D395 | N399 | L410 | V412 | Q437 | L438 | — | E443 | L454 | Y459 | E476 | — |  |
| 94 | S366 | M367 | F379 | D381 | V385 | M396 | I398 | R409 | Y417 | R423 | R424 | E429 | L440 | Y445 | D462 | — |
| 95 | A345 | F346 | R357 | D359 | L363 | L374 | I376 | T387 | Y395 | D401 | R402 | D407 | F418 | R423 | Q440 | — |
| 96 | C349 | F350 | K362 | D364 | I368 | L379 | Y381 | R394 | Y402 | A408 | R409 | D414 | I425 | K430 | E447 | — |
| 97 | V355 | M356 | K368 | E370 | T374 | M385 | I387 | R398 | Y406 | E412 | K413 | F418 | F429 | Y434 | E451 | — |
| 98 | N424 | Y425 | K437 | E439 | V443 | L454 | S458 | V469 | F477 | D483 | L484 | K489 | L502 | V507 | T524 | — |
| 99 | T406 | F407 | A419 | T421 | K425 | L436 | I438 | Y449 | Y457 | S463 | V464 | D469 | Y480 | R485 | D502 | N515 |
| 100 | N427 | Y428 | K440 | E442 | V446 | L457 | N461 | V472 | F480 | D486 | L487 | K492 | L505 | V510 | A527 | — |
| 101 | T392 | F393 | A405 | T407 | K411 | L422 | V424 | Y435 | Y443 | S449 | V450 | E455 | Y466 | K471 | D488 | K500 |
| 102 | N423 | Y424 | K436 | E438 | V442 | L453 | K457 | V468 | F476 | D482 | I483 | K488 | L501 | V506 | A523 | — |
| 103 | T387 | F388 | A400 | R402 | K406 | L417 | A419 | Y430 | Y438 | L444 | V445 | E450 | Y461 | K466 | E483 | K496 |
| 104 | S453 | F454 | K466 | Q468 | A472 | L483 | S487 | V498 | F506 | D512 | L513 | K518 | L531 | V536 | A553 | — |
| 105 | N419 | Y420 | K432 | E434 | V438 | L449 | T453 | V464 | F472 | D478 | R479 | K484 | L497 | V502 | S519 | — |
| 106 | T399 | F400 | A412 | T414 | K418 | L429 | V431 | H442 | Y450 | S456 | V457 | G462 | Y473 | K478 | D495 | D508 |
| 107 | N427 | Y428 | K440 | E442 | V446 | L457 | N461 | V472 | F480 | D486 | L487 | K492 | L505 | V510 | A527 | — |
| 108 | S448 | Y449 | K461 | K463 | A467 | L478 | D482 | V493 | F501 | D507 | L508 | K513 | L526 | V531 | A548 | — |
| 109 | N418 | Y419 | K431 | E433 | V437 | L448 | R452 | V463 | F471 | D477 | R478 | K483 | L496 | V501 | S518 | — |
| 110 | T444 | F445 | A457 | T459 | K463 | L474 | V476 | H487 | Y495 | L501 | A502 | G507 | Y518 | K523 | D540 | G549 |
| 111 | N419 | Y420 | K432 | E434 | V438 | L449 | R453 | V464 | F472 | D478 | R479 | K484 | L497 | V502 | S519 | — |
| 112 | T388 | F389 | A401 | R403 | K407 | L418 | A420 | C431 | Y439 | S445 | V446 | D451 | Y462 | K467 | D484 | S494 |
| 113 | N434 | Y435 | K447 | E449 | V453 | L464 | R468 | V479 | F487 | D493 | R494 | K499 | L512 | V517 | S534 | — |
| 114 | N427 | Y428 | K440 | E442 | V446 | L457 | N461 | V472 | F480 | D486 | L487 | K492 | L505 | V510 | A527 | — |
| 115 | T392 | F393 | A405 | T407 | K411 | L422 | V424 | Y435 | Y443 | S449 | V450 | E455 | Y466 | K471 | D488 | S497 |
| 116 | S448 | Y449 | K461 | K463 | A467 | L478 | D482 | V493 | F501 | D507 | L508 | K513 | L526 | V531 | A548 | — |
| 117 | T393 | F394 | A406 | T408 | K412 | L423 | V425 | Y436 | Y444 | S450 | V451 | D456 | Y467 | R472 | D489 | K502 |

Assays to test for the functionality of such mutants are readily available in the art, and respectively, described in the Example section of the present invention.

In a preferred embodiment, the mutated PPO refers to a polypeptide of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, in which the amino acid sequence differs at Mutated site 1 (which corresponds to Arg128 of SEQ ID NO: 1) according to Table 2a, and/or at Mutated site 5 (which corresponds to Phe420 of SEQ ID NO: 1) according to Table 2a.

Examples of differences at these amino acid positions include, but are not limited to, one or more of the following:

the amino acid at Mutated site 1 is other than Arginine (or Tryosine, or Cysteine; as the case may be according to Table 2a);

the amino acid at Mutated site 5 is other than Phenylalanine (or Methionine, or Tyrosine, or Leucine, as the case may be according to Table 2a), In particularly preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 (which corresponds to Arg128 of SEQ ID NO: 1) is Leu, Ala, Val, Ile, Met, Tyr, Gly, Asn, Cys, Phe, Ser, Thr, Gln, or His, and the amino acid at Mutated site 5 (which corresponds to Phe420 of SEQ ID NO: 1) is Ala, Leu, Val, Ile, or Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Leu, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Leu, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Leu, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Leu, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Leu, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ala, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ala, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ala, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ala, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ala, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Val, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Val, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Val, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Val, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Val, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ile, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ile, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ile, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ile, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ile, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Met, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Met, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Met, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Met, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Met, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Tyr, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Tyr, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Tyr, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Tyr, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Tyr, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Gly, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Gly, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Gly, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Gly, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Gly, and the amino acid at Mutated site 5 is Met. In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Asn, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Asn, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Asn, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Asn, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Asn, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Cys, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Cys, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Cys, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Cys, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Cys, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Phe, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Phe, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Phe, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Phe, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Phe, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ser, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ser, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ser, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ser, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Ser, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Thr, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Thr, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Thr, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Thr, and the amino acid at Mutated site 5 is Ile. In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Thr, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Gln, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Gln, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Gln, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 1 is Gln, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 1 is Gln, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 1 is His, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 1 is His, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 1 is His, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 1 is His, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 1 is His, and the amino acid at Mutated site 5 is Met.

In another preferred embodiment, the mutated PPO refers to a polypeptide of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, or 117, in which the amino acid sequence differs at Mutated site 4 (which corresponds to Leu397 of SEQ ID NO: 1) according to Table 2a, and/or at Mutated site 5 (which corresponds to Phe420 of SEQ ID NO: 1) according to Table 2a.

Examples of differences at these amino acid positions include, but are not limited to, one or more of the following:
the amino acid at Mutated site 4 is other than Leucine (or Alanine, or Serine, or Phenylalanine, as the case may be according to Table 2a);
the amino acid at Mutated site 5 is other than Phenylalanine (or Methionine, or Tyrosine, or Leucine, as the case may be according to Table 2a), In particularly preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 (which corresponds to Leu397 of SEQ ID NO: 1) is Ala, Arg, Val, Ile, Met, His, Lys, Asp, Glu, Ser, Thr, Asn, Gln, Cys, Gly, Pro, Phe, Tyr, or Trp, and the amino acid at Mutated site 5 (which corresponds to Phe420 of SEQ ID NO: 1) is Ala, Leu, Val, Ile, Met, His, Lys, Asp, Glu, Ser, Thr, Asn, Gln, Cys, Gly, Pro, Arg, Tyr, or Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which: the amino acid at Mutated site 4 is Ala, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ala, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Ala, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Arg, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Arg, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Arg, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Arg, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Arg, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Arg, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Arg, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Arg, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Arg, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Arg, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Arg, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Arg, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Arg, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Arg, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Arg, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Arg, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Arg, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Arg, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Arg, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Val, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Val, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Val, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Val, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Val, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Val, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Val, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Val, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Val, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Val, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which: the amino acid at Mutated site 4 is Val, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Val, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Val, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Val, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Val, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Val, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Val, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Val, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Val, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ile, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Met, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is His, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is His, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is His, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is His, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Lys, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Lys, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Lys, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Lys, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Lys, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Lys, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Lys, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Lys, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Lys, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Lys, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Lys, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Lys, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Lys, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Lys, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Lys, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Lys, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Lys, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Lys, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Lys, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asp, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Glu, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Ser, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Thr, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asn, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asn, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asn, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asn, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asn, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asn, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asn, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asn, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asn, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asn, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asn, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Asn, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which: the amino acid at Mutated site 4 is Asn, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Asn, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Asn, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Asn, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Asn, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Asn, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Asn, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Gln, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Gln, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Gln, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gln, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Cys, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Cys, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Cys, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Cys, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Cys, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Cys, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Cys, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Cys, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Cys, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which: the amino acid at Mutated site 4 is Cys, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which: the amino acid at Mutated site 4 is Cys, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Cys, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Cys, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Cys, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Cys, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Cys, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Cys, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Cys, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Cys, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Gly, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Pro, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Phe, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Tyr, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Tyr, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Tyr, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Tyr, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Tyr, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Trp, and the amino acid at Mutated site 5 is Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Trp, and the amino acid at Mutated site 5 is Leu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Trp, and the amino acid at Mutated site 5 is Val.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Trp, and the amino acid at Mutated site 5 is Ile.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Trp, and the amino acid at Mutated site 5 is Met.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Trp, and the amino acid at Mutated site 5 is His.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Trp, and the amino acid at Mutated site 5 is Lys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Trp, and the amino acid at Mutated site 5 is Asp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Trp, and the amino acid at Mutated site 5 is Glu.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Trp, and the amino acid at Mutated site 5 is Ser.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Trp, and the amino acid at Mutated site 5 is Thr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Trp, and the amino acid at Mutated site 5 is Asn.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Trp, and the amino acid at Mutated site 5 is Gln.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:

the amino acid at Mutated site 4 is Trp, and the amino acid at Mutated site 5 is Cys.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Trp, and the amino acid at Mutated site 5 is Gly.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Trp, and the amino acid at Mutated site 5 is Pro.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Trp, and the amino acid at Mutated site 5 is Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which: the amino acid at Mutated site 4 is Trp, and the amino acid at Mutated site 5 is Tyr.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 4 is Trp, and the amino acid at Mutated site 5 is Trp.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 3 is other than Gly, is preferably Arg.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 6 is other than Gly, is preferably Ala.

In another preferred embodiment, the mutated PPO comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, a variant, derivative, orthologue, paralogue or homologue thereof, in which:
the amino acid at Mutated site 7 is other than Leu, is preferably Phe.

It will be within the knowledge of the skilled artisan to identify conserved regions and motifs shared between the homologues, orthologues and paralogues of PPO polypeptides comprising SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637. Having identified such conserved regions that may represent suitable binding motifs, amino acids corresponding to the amino acids listed in Table 2a and 2b can be chosen to be substituted by any other amino acid, preferably by the amino acids listed under mutated sites 1, 2, 3, 4, or 5.

Accordingly, preferred motifs shared between the homologues, orthologues and paralogues of PPO polypeptides described above are Motif 1: SQ[N/K/H]KRYI, wherein the Arg at position 5 within said motif is substituted by Leu, Ala, Val, Ile, Met, Tyr, Gly, Asn, Cys, Phe, Ser, Thr, Gln, or His; Motif 2: TLGTLFSS, wherein the Leu at position 2 within said motif is substituted by Ala, Arg, Val, Ile, Met, His, Lys, Asp, Glu, Ser, Thr, Asn, Gln, Cys, Gly, Pro, Phe, Tyr, or Trp; and/or wherein the Gly at position 3 within said motif is substituted by Ala, Arg, Val, Ile, Met, His, Lys, Asp, Glu, Ser, Thr, Asn, Gln, Cys, Leu, Pro, Phe, Tyr, or Trp; and/or wherein the Leu at position 5 within said motif is substituted by Ala, Arg, Val, Ile, Met, His, Lys, Asp, Glu, Ser, Thr, Asn, Gln, Cys, Gly, Pro, Phe, Tyr, or Trp; Motif 3: [F/Y]TTF[V/I]GG, wherein the Phe at position 4 within said motif is substituted by Ala, Leu, Val, Ile, Met, His, Lys, Asp, Glu, Ser, Thr, Asn, Gln, Cys, Gly, Pro, Arg, Tyr, or Trp.

Further examples of such homologues, orthologues and paralogues are PPO polypeptides comprising the amino acid sequence of SEQ ID NO: 577, 579, 581, 583, 585, 587, 589, 591, 593, 595, 597, 599, 601, 603, 605, 607, 609, 611, 613, 615, 617, 619, 621, 623, 625, 627, or 637.

In addition, the present invention refers to a method for identifying a uracilpyridine herbicide by using a herbicide tolerant PPO polypeptide as defined SUPRA.

Said method comprises the steps of:
a) generating a transgenic cell or plant comprising a nucleic acid encoding a mutated PPO, wherein the mutated PPO is expressed;
b) applying a uracilpyridine herbicide to the transgenic cell or plant of a) and to a control cell or plant of the same variety;
c) determining the growth or the viability of the transgenic cell or plant and the control cell or plant after application of said uracilpyridine herbicide, and
d) selecting "uracilpyridine herbicides" which confer reduced growth to the control cell or plant as compared to the growth of the transgenic cell or plant.

By "control cell" or "similar, wild-type, plant, plant tissue, plant cell or host cell" is intended a plant, plant tissue, plant cell, or host cell, respectively, that lacks the herbicide-resistance characteristics and/or particular polynucleotide of the invention that are disclosed herein. The use of the term "wild-type" is not, therefore, intended to imply that a plant, plant tissue, plant cell, or other host cell lacks recombinant DNA in its genome, and/or does not possess herbicide-resistant characteristics that are different from those disclosed herein.

Another object refers to a method of identifying a nucleotide sequence encoding a mutated PPO which is resistant or tolerant to a uracilpyridine herbicide, the method comprising:
a) generating a library of mutated PPO-encoding nucleic acids,
b) screening a population of the resulting mutated PPO-encoding nucleic acids by expressing each of said nucleic acids in a cell or plant and treating said cell or plant with a uracilpyridine herbicide,
c) comparing the uracilpyridine herbicide-tolerance levels provided by said population of mutated PPO encoding nucleic acids with the uracilpyridine herbicide-tolerance level provided by a control PPO-encoding nucleic acid,
d) selecting at least one mutated PPO-encoding nucleic acid that provides a significantly increased level of tolerance to a uracilpyridine herbicide as compared to that provided by the control PPO-encoding nucleic acid.

In a preferred embodiment, the mutated PPO-encoding nucleic acid selected in step d) provides at least 2-fold as much resistance or tolerance of a cell or plant to a uracilpyridine herbicide as compared to that provided by the control PPO-encoding nucleic acid.

In a further preferred embodiment, the mutated PPO-encoding nucleic acid selected in step d) provides at least 2-fold, at least 5-fold, at least 10-fold, at least 20-fold, at least 50-fold, at least 100-fold, at least 500-fold, as much resistance or tolerance of a cell or plant to a uracilpyridine herbicide as compared to that provided by the control PPO-encoding nucleic acid.

The resistance or tolerance can be determined by generating a transgenic plant or host cell, preferably a plant cell, comprising a nucleic acid sequence of the library of step a) and comparing said transgenic plant with a control plant or host cell, preferably a plant cell.

Another object refers to a method of identifying a plant or algae containing a nucleic acid comprising a nucleotide sequence encoding a wild-type or mutated PPO which is resistant or tolerant to a uracilpyridine herbicide, the method comprising:
a) identifying an effective amount of a uracilpyridine herbicide in a culture of plant cells or green algae that leads to death of said cells.
b) treating said plant cells or green algae with a mutagenizing agent,
c) contacting said mutagenized cells population with an effective amount of uracilpyridine herbicide, identified in a),
d) selecting at least one cell surviving these test conditions,
e) PCR-amplification and sequencing of PPO genes from cells selected in d) and comparing such sequences to wild-type PPO gene sequences, respectively.

In a preferred embodiment, said mutagenizing agent is ethylmethanesulfonate (EMS). Many methods well known to the skilled artisan are available for obtaining suitable candidate nucleic acids for identifying a nucleotide sequence encoding a mutated PPO from a variety of different potential source organisms including microbes, plants, fungi, algae, mixed cultures etc. as well as environmental sources of DNA such as soil. These methods include inter alia the preparation of cDNA or genomic DNA libraries, the use of suitably degenerate oligonucleotide primers, the use of probes based upon known sequences or complementation assays (for example, for growth upon tyrosine) as well as the use of mutagenesis and shuffling in order to provide recombined or shuffled mutated PPO-encoding sequences.

Nucleic acids comprising candidate and control PPO encoding sequences can be expressed in yeast, in a bacterial host strain, in an alga or in a higher plant such as tobacco or *Arabidopsis* and the relative levels of inherent tolerance of the PPO encoding sequences screened according to a visible indicator phenotype of the transformed strain or plant in the presence of different concentrations of the selected uracilpyridine herbicide. Dose responses and relative shifts in dose responses associated with these indicator phenotypes (formation of brown color, growth inhibition, herbicidal effect etc) are conveniently expressed in terms, for example, of GR50 (concentration for 50% reduction of growth) or MIC (minimum inhibitory concentration) values where increases in values correspond to increases in inherent tolerance of the expressed PPO. For example, in a relatively rapid assay system based upon transformation of a bacterium such as E. coli, each mutated PPO encoding sequence may be expressed, for example, as a DNA sequence under expression control of a controllable promoter such as the lacZ promoter and taking suitable account, for example by the use of synthetic DNA, of such issues as codon usage in order to obtain as comparable a level of expression as possible of different PPO sequences. Such strains expressing nucleic acids comprising alternative candidate PPO sequences may be plated out on different concentrations of the selected uracilpyridine herbicide in, optionally, a tyrosine supplemented medium and the relative levels of inherent tolerance of the expressed PPO enzymes estimated on the basis of the extent and MIC for inhibition of the formation of the brown, ochronotic pigment.

In another embodiment, candidate nucleic acids are transformed into plant material to generate a transgenic plant, regenerated into morphologically normal fertile plants which are then measured for differential tolerance to selected uracilpyridine herbicides as described in the Example section hereinafter. Many suitable methods for transformation using suitable selection markers such as kanamycin, binary vectors such as from *Agrobacterium* and plant regeneration as, for example, from tobacco leaf discs are well known in the art. Optionally, a control population of plants is likewise transformed with a nucleic acid expressing the control PPO. Alternatively, an untransformed dicot plant such as *Arabidopsis* or Tobacco can be used as a control since this, in any case, expresses its own endogenous PPO. The average, and distribution, of herbicide tolerance levels of a range of primary plant transformation events or their progeny to uracilpyridine herbicides described supra are evaluated in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed PPO. Herbicides can suitably be applied pre-emergence or post-emergence.

In another embodiment, the invention refers to a plant cell transformed by a nucleic acid encoding a herbicide tolerant PPO polypeptide disclosed herein or to a plant cell which has been mutated to obtain a plant expressing a nucleic acid encoding a mutated PPO polypeptide according to the present invention, wherein expression of the nucleic acid in the plant cell results in increased resistance or tolerance to a uracilpyridine herbicide as compared to a wild type variety of the plant cell.

The term "expression/expressing" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

To obtain the desired effect, i.e. plants that are tolerant or resistant to the uracilpyridine herbicide derivative herbicide of the present invention, it will be understood that the at least one nucleic acid is "over-expressed" by methods and means known to the person skilled in the art.

The term "increased expression" or "overexpression" as used herein means any form of expression that is additional to the original wild-type expression level. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-5 intron 1, 2, and 6, the Bronze-1 intron are known in the art. For general information see: The Maize Handbook, Chapter 116, Freeling and Walbot, Eds., Springer, N.Y. (1994)

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transforrmation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 Al, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Hofgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, Si and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229). The genetically modified plant cells can be regenerated via all methods with which the skilled worker is familiar. Suitable methods can be found in the abovementioned publications by S. D. Kung and R. Wu, Potrykus or Hofgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the wild-type or mutated PPO nucleic acid comprises a polynucleotide sequence selected from the group consisting of: a) a polynucleotide encoding a polypeptide as shown in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, or a variant or derivative thereof; b) a polynucleotide comprising at least 60 consecutive nucleotides of any of a); and c) a polynucleotide complementary to the polynucleotide of any of a) through b).

Preferably, the expression of the nucleic acid in the plant results in the plant's increased resistance to uracilpyridine herbicide as compared to a wild type variety of the plant.

In another embodiment, the invention refers to a plant, preferably a transgenic plant, comprising a plant cell according to the present invention, wherein expression of the nucleic acid in the plant results in the plant's increased resistance to uracilpyridine herbicide as compared to a wild type variety of the plant.

The plants described herein can be either transgenic crop plants or non-transgenic plants.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or (b) genetic control sequence(s) which is operably linked with the nucleic acid sequence according to the invention, for example a promoter, or (c) a) and b)

are not located in their natural genetic environment or have been modified by recombinant methods, it being possible for the modification to take the form of, for example, a substitution, addition, deletion, inversion or insertion of one or more nucleotide residues in order to allow for the expression of the mutated PPO of the present invention. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein. Furthermore, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

Plants containing mutations arising due to non-spontaneous mutagenesis and selective breeding are referred to herein as non-transgenic plants and are included in the present invention. In embodiments wherein the plant is transgenic and comprises multiple mutated PPO nucleic acids, the nucleic acids can be derived from different genomes or from the same genome. Alternatively, in embodiments wherein the plant is non-transgenic and comprises multiple mutated PPO nucleic acids, the nucleic acids are located on different genomes or on the same genome.

As used herein, "mutagenized" refers to an organism or DNA thereof having alteration(s) in the biomolecular sequence of its native genetic material as compared to the sequence of the genetic material of a corresponding wild-type organism or DNA, wherein the alteration(s) in genetic material were induced and/or selected by human action. Methods of inducing mutations can induce mutations in random positions in the genetic material or can induce mutations in specific locations in the genetic material (i.e., can be directed mutagenesis techniques), such as by use of a genoplasty technique.

In certain embodiments, the present invention involves herbidicide-resistant plants that are produced by mutation breeding. Such plants comprise a polynucleotide encoding a mutated PPO and are tolerant to one or more uracilpyridine herbicides. Such methods can involve, for example, exposing the plants or seeds to a mutagen, particularly a chemical mutagen such as, for example, ethyl methanesulfonate (EMS) and selecting for plants that have enhanced tolerance to at least one or more uracilpyridine herbicide.

However, the present invention is not limited to herbicide-tolerant plants that are produced by a mutagenesis method involving the chemical mutagen EMS. Any mutagenesis method known in the art may be used to produce the herbicide-resistant plants of the present invention. Such mutagenesis methods can involve, for example, the use of any one or more of the following mutagens: radiation, such as X-rays, Gamma rays (e.g., cobalt 60 or cesium 137), neutrons, (e.g., product of nuclear fission by uranium 235 in an atomic reactor), Beta radiation (e.g., emitted from radioisotopes such as phosphorus 32 or carbon 14), and ultraviolet radiation (preferably from 2500 to 2900 nm), and chemical mutagens such as base analogues (e.g., 5-bromo-uracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Herbicide-resistant plants can also be produced by using tissue culture methods to select for plant cells comprising herbicide-resistance mutations and then regenerating herbicide-resistant plants therefrom. See, for example, U.S. Pat. Nos. 5,773,702 and 5,859,348, both of which are herein incorporated in their entirety by reference. Further details of mutation breeding can be found in "Principals of Cultivar Development" Fehr, 1993 Macmillan Publishing Company the disclosure of which is incorporated herein by reference Alternatively, herbicide-resistant plants according to the present invention can also be produced by using genome editing methods to select for plant cells comprising herbicide-resistance mutations and then regenerating herbicide-resistant plants therefrom. "Genome Editing" refers to a type of genetic engineering in which DNA is inserted, deleted or replaced in the genome of an organism using engineered nucleases. These nucleases are known to the skilled artisan to create site-specific double-strand breaks at desired locations in the genome. The induced double-strand breaks are repaired through nonhomologous end-joining or homologous recombination, resulting in targeted mutations. Known in the art are currently four families of engineered nucleases which can be used for the purposes of the present invention: meganucleases, zinc finger nucleases (ZFNs), transcription activator-like effector-based nucleases (TALEN), and the CRISPR-Cas system. -For references, see, for example, Esvelt, K M. and Wang, H H. (2013) "*Genome-scale engineering for systems and synthetic biology*", *Mol Syst Biol.* 9 (1): 641; Tan, WS. et al., (2012) "*Precision editing of large animal genomes*", *Adv Genet.* 80: 37-97; Puchta, H. and Fauser, F. (2013) "*Gene targeting in plants: 25 years later*", *Int. J. Dev. Biol.* 57: 629-637; Boglioli, Elsy and Richard, Magali "*Rewriting the book of life: a new era in precision genome editing*", Boston Consulting Group, Retrieved Nov. 30, 2015; Method of the Year 2011. Nat Meth 9 (1), 1-1.

Consequently, in another embodiment, the invention refers to a non-transgenic plant, comprising a plant cell according to the present invention, wherein expression of the nucleic acid encoding a mutated PPO in the plant results in the plant's increased resistance to uracilpyridine herbicide as compared to a wild type variety of the plant.

In addition to the definition above, the term "plant" is intended to encompass crop plants at any stage of maturity or development, as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts, and the like.

The plant of the present invention comprises at least one mutated PPO nucleic acid or over-expressed wild-type PPO nucleic acid, and has increased tolerance to a uracilpyridine herbicide as compared to a wild-type variety of the plant. It is possible for the plants of the present invention to have multiple wild-type or mutated PPO nucleic acids from different genomes since these plants can contain more than one genome. For example, a plant contains two genomes, usually referred to as the A and B genomes. Because PPO is a required metabolic enzyme, it is assumed that each genome has at least one gene coding for the PPO enzyme (i.e. at least one PPO gene). As used herein, the term "PPO gene locus" refers to the position of an PPO gene on a genome, and the terms "PPO gene" and "PPO nucleic acid" refer to a nucleic acid encoding the PPO enzyme. The PPO nucleic acid on each genome differs in its nucleotide sequence from an PPO nucleic acid on another genome. One of skill in the art can determine the genome of origin of each PPO nucleic acid through genetic crossing and/or either sequencing methods or exonuclease digestion methods known to those of skill in the art.

The present invention includes plants comprising one, two, three, or more mutated PPO alleles, wherein the plant has increased tolerance to a uracilpyridine herbicide as compared to a wild-type variety of the plant. The mutated PPO alleles can comprise a nucleotide sequence selected from the group consisting of a polynucleotide encoding a polypeptide as defined in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, or a variant or derivative, homologue, orthologue, paralogue thereof, a polynucleotide comprising at least 60 consecutive nucleotides of any of the aforementioned polynucleotides; and a polynucleotide complementary to any of the aforementioned polynucleotides.

In a particularly preferred embodiment, the mutagenized plant refers to a rice plant of the species *Oryza sativa* which comprises a mutated PPO allele which comprises a polynucleotide encoding a polypeptide as defined in SEQ ID NO: 628, 629, 630, 631, 632, 633, 634, 635, or 636.

Preferably, the polynucleotide comprises a nucleic acid sequence as defined in SEQ ID NO: 638, 639, 640, 641, 642, 643, 644, 645, 646, 647, 648, or 649.

Said mutated rice lines were deposited under the terms of the Budapest Treaty on Nov. 8, 2017, and have been assigned the NCIMB accession numbers 42873, 42876, 42878, 42871, 42874, 42875, 42870, 42877, and 42872.

"Alleles" or "allelic variants" are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms The term "variety" refers to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. The terms "breeding line" or "line" refer to a group of plants within a cultivar defined by the sharing of a common set of characteristics or traits accepted by those skilled in the art as sufficient to distinguish one breeding line or line from another breeding line or line. There is no implication in either term that all plants of any given breeding line or line will be genetically identical at either the whole gene or molecular level or that any given plant will be homozygous at all loci. A breeding line or line is considered "true breeding" for a particular trait if, when the true-breeding line or breeding line is self-pollinated, all of the progeny contain the trait. In the present invention, the trait arises from a mutation in a PPO gene of the plant or seed.

In some embodiments, traditional plant breeding is employed whereby the uracilpyridine herbicides-tolerant trait is introduced in the progeny plant resulting therefrom. In one embodiment, the present invention provides a method for producing a uracilpyridine herbicides-tolerant progeny plant, the method comprising: crossing a parent plant with a uracilpyridine herbicides-tolerant plant to introduce the uracilpyridine herbicides-tolerance characteristics of the uracilpyridine herbicides-tolerant plant into the germplasm of the progeny plant, wherein the progeny plant has increased tolerance to the uracilpyridine herbicides relative to the parent plant. In other embodiments, the method further comprises the step of introgressing the uracilpyridine herbicides-tolerance characteristics through traditional plant breeding techniques to obtain a descendent plant having the uracilpyridine herbicides-tolerance characteristics.

The herbicide-resistant plants of the invention that comprise polynucleotides encoding mutated PPO polypeptides also find use in methods for increasing the herbicide-resistance of a plant through conventional plant breeding involving sexual reproduction. The methods comprise crossing a first plant that is a herbicide-resistant plant of the invention to a second plant that may or may not be resistant to the same herbicide or herbicides as the first plant or may be resistant to different herbicide or herbicides than the first plant. The second plant can be any plant that is capable of producing viable progeny plants (i.e., seeds) when crossed with the first plant. Typically, but not necessarily, the first and second plants are of the same species. The methods can optionally involve selecting for progeny plants that comprise the mutated PPO polypeptides of the first plant and the herbicide resistance characteristics of the second plant. The progeny plants produced by this method of the present invention have increased resistance to a herbicide when compared to either the first or second plant or both. When the first and second plants are resistant to different herbicides, the progeny plants will have the combined herbicide tolerance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The present invention also provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

In other aspects, plants of the invention include those plants which, in addition to being tolerant to uracilpyridine herbicides, have been subjected to further genetic modifications by breeding, mutagenesis or genetic engineering, e.g. have been rendered tolerant to applications of specific other classes of herbicides, such as AHAS inhibitors; auxinic herbicides; bleaching herbicides such as hydroxyphenylpyruvate dioxygenase (HPPD) inhibitors or phytoene desaturase (PDS) inhibitors; EPSPS inhibitors such as glyphosate; glutamine synthetase (GS) inhibitors such as glufosinate; lipid biosynthesis inhibitors such as acetyl CoA carboxylase (ACCase) inhibitors; or oxynil (i.e. bromoxynil or ioxynil) herbicides as a result of conventional methods of breeding or genetic engineering, Thus, uracilpyridine herbicides-tolerant plants of the invention can be made resistant to multiple classes of herbicides through multiple genetic modifications, such as resistance to both glyphosate and glufosinate or to both glyphosate and a herbicide from another class such as HPPD inhibitors, AHAS inhibitors, or ACCase inhibitors. These herbicide resistance technologies are, for example, described in Pest Management Science (at volume, year, page): 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. For example, uracilpyridine herbicides-tolerant plants of the invention, in some embodiments, may be tolerant to ACCase inhibitors, such as "dims" (e.g., cycloxydim, sethoxydim, clethodim, or tepraloxydim), "fops" (e.g., clodinafop, diclofop, fluazifop, haloxyfop, or quizalofop), and "dens" (such as pinoxaden); to auxinic herbicides, such as dicamba; to EPSPS inhibitors, such as glyphosate; to other PPO inhibitors; and to GS inhibitors, such as glufosinate.

In addition to these classes of inhibitors, uracilpyridine herbicides-tolerant plants of the invention may also be tolerant to herbicides having other modes of action, for example, chlorophyll/carotenoid pigment inhibitors, cell membrane disrupters, photosynthesis inhibitors, cell division inhibitors, root inhibitors, shoot inhibitors, and combinations thereof.

Such tolerance traits may be expressed, e.g.: as mutant or wildtype PPO proteins, as mutant AHASL proteins, mutant ACCase proteins, mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or CYP450s proteins having an herbicide-degrading activity.

uracilpyridine herbicides-tolerant plants hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, in other embodiments, uracilpyridine herbicides-tolerant plants are also covered which are, by the use of recombinant DNA techniques and/or by breeding and/or otherwise selected for such characteristics, rendered able to synthesize one or more insecticidal proteins, especially those known from the bacterial genus *Bacillus*, particularly from *Bacillus thuringiensis*, such as [delta]-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such streptomycete toxins; plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (*Coleoptera*), two-winged insects (*Diptera*), and moths (*Lepidoptera*) and to nematodes (*Nematoda*).

In some embodiments, expression of one or more protein toxins (e.g., insecticidal proteins) in the uracilpyridine herbicides-tolerant plants is effective for controlling organisms that include, for example, members of the classes and orders: *Coleoptera* such as the American bean weevil *Acanthoscelides obtectus*; the leaf beetle *Agelastica alni*; click beetles (*Agriotes lineatus, Agriotes obscurus, Agriotes bicolor*); the grain beetle *Ahasverus advena*; the summer schafer *Amphimallon solstitialis*; the furniture beetle *Anobium punctatum; Anthonomus* spp. (weevils); the Pygmy mangold beetle *Atomaria linearis*; carpet beetles (*Anthrenus* spp., *Attagenus* spp.); the cowpea weevil *Callosobruchus maculates*; the fried fruit beetle *Carpophilus hemipterus*; the cabbage seedpod weevil *Ceutorhynchus assimilis*; the rape winter stem weevil *Ceutorhynchus picitarsis*; the wireworms *Conoderus vespertinus* and *Conoderus falli*; the banana weevil *Cosmopolites sordidus*; the New Zealand grass grub *Costelytra zealandica*; the June beetle *Cotinis nitida*; the sunflower stem weevil *Cylindrocopturus adspersus*; the larder beetle *Dermestes lardarius*; the corn rootworms *Diabrotica virgifera, Diabrotica virgifera*, and *Diabrotica barberi*; the Mexican bean beetle *Epilachna varivestis*; the old house borer *Hylotropes bajulus*; the lucerne weevil *Hypera postica*; the shiny spider beetle *Gibbium psylloides*; the cigarette beetle *Lasioderma serricorne*; the Colorado potato beetle *Leptinotarsa decemlineata*; Lyctus beetles {*Lyctus* spp., the pollen beetle *Meligethes aeneus*; the common cockshafer *Melolontha melolontha*; the American spider beetle *Mezium americanum*; the golden spider beetle *Niptus hololeuc s*; the grain beetles *Oryzaephilus surinamensis* and *Oryzaephilus Mercator*; the black vine weevil *Otiorhynchus sulcatus*; the mustard beetle *Phaedon cochleariae*, the crucifer flea beetle *Phyllotreta cruciferae*; the striped flea beetle *Phyllotreta striolata*; the cabbage steam flea beetle *Psylliodes chrysocephala; Ptinus* spp. (spider beetles); the lesser grain borer *Rhizopertha dominica*; the pea and been weevil *Sitona lineatus*; the rice and granary beetles *Sitophilus oryzae* and *Sitophilus granaries*; the red sunflower seed weevil *Smicro-* nyx fulvus; the drugstore beetle *Stegobium paniceum*; the yellow mealworm beetle *Tenebrio molitor*, the flour beetles *Tribolium castaneum* and *Tribolium confusum*; warehouse and cabinet beetles (*Trogoderma* spp.); the sunflower beetle *Zygogramma exclamationis; Dermaptera* (earwigs) such as the European earwig *Forficula auricularia* and the striped earwig *Labidura riparia; Dictyoptera* such as the oriental cockroach *Blatta orientalis*; the greenhouse millipede *Oxidus gracilis*; the beet fly *Pegomyia betae*; the frit fly *Oscinella frit*; fruitflies (*Dacus* spp., *Drosophila* spp.); *Isoptera* (termites) including species from the familes Hodotermitidae, Kalotermitidae, Mastotermitidae, Rhinotermitidae, Serritermitidae, Termitidae, Termopsidae; the tarnished plant bug *Lygus lineolaris*; the black bean aphid *Aphis fabae*; the cotton or melon aphid *Aphis gossypii*; the green apple aphid *Aphis pomi*; the citrus spiny whitefly *Aleurocanthus spiniferus*; the sweet potato whitefly *Bemesia tabaci*; the cabbage aphid *Brevicoryne brassicae*; the pear psylla *Cacopsylla pyricola*; the currant aphid *Cryptomyzus ribis*; the grape phylloxera *Daktulosphaira vitifoliae*; the citrus psylla *Diaphorina citri*; the potato leafhopper *Empoasca fabae*; the bean leafhopper *Empoasca Solana*; the vine leafhopper *Empoasca vitis*; the woolly aphid *Eriosoma lanigerum*; the European fruit scale *Eulecanium corni*; the mealy plum aphid *Hyalopterus arundinis*; the small brown planthopper *Laodelphax striatellus*; the potato aphid *Macrosiphum euphorbiae*; the green peach aphid *Myzus persicae*; the green rice leafhopper *Nephotettix cinticeps*; the brown planthopper *Nilaparvata lugens*; the hop aphid *Phorodon humuli*; the bird-cherry aphid *Rhopalosiphum padi*; the grain aphid *Sitobion avenae; Lepidoptera* such as *Adoxophyes orana* (summer fruit tortrix moth); *Archips podana* (fruit tree tortrix moth); *Bucculatrix pyrivorella* (pear leafminer); *Bucculatrix thurberiella* (cotton leaf perforator); *Bupalus piniarius* (pine looper); *Carpocapsa pomonella* (codling moth); *Chilo suppressalis* (striped rice borer); *Choristoneura fumiferana* (eastern spruce budworm); *Cochylis hospes* (banded sunflower moth); *Diatraea grandiosella* (southwestern corn borer); *Eupoecilia ambiguella* (European grape berry moth); *Helicoverpa armigera* (cotton bollworm); *Helicoverpa zea* (cotton bollworm); *Heliothis vires cens* (tobacco budworm), *Homeosoma electellum* (sunflower moth); *Homona magnanima* (oriental tea tree tortrix moth); *Lithocolletis blancardella* (spotted tentiform leafminer); *Lymantria dispar* (gypsy moth); *Malacosoma neustria* (tent caterpillar); *Mamestra brassicae* (cabbage armyworm); *Mamestra configurata* (Bertha armyworm); *Operophtera brumata* (winter moth); *Ostrinia nubilalis* (European corn borer), *Panolis flammea* (pine beauty moth), *Phyllocnistis citrella* (citrus leafminer); *Pieris brassicae* (cabbage white butterfly); *Rachiplusia ni* (soybean looper); *Spodoptera exigua* (beet armywonn); *Spodoptera littoralis* (cotton leafworm); *Sylepta derogata* (cotton leaf roller); *Trichoplusia ni* (cabbage looper); *Orthoptera* such as the common cricket *Acheta domesticus*, tree locusts (*Anacridium* spp.), the migratory locust *Locusta migratoria*, the twostriped grasshopper *Melanoplus bivittatus*, the differential grasshopper *Melanoplus differentialis*, the redlegged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus abbreviatus*, the southern mole cricket *Scapteriscus borellii*, the tawny mole cricket *Scapteriscus vicinus*, and the desert locust *Schistocerca gregaria; Symphyla* such as the garden symphylan *Scutigerella immaculata; Thysanoptera* such as the tobacco thrips *Frankliniella fusca*, the flower thrips *Frankliniella intonsa*, the western flower thrips *Frankliniella occidentalism* the cotton bud thrips *Frankliniella schultzei*, the banded greenhouse thrips *Hercinothrips femoralis*, the soybean thrips *Neohydatothrips variabilis*, Kelly's citrus thrips *Pezothrips kellyanus*, the avocado thrips *Scirtothrips perseae*, the melon thrips *Thrips palmi*, and the onion thrips *Thrips tabaci*; and the like, and combinations comprising one or more of the foregoing organisms.

In some embodiments, expression of one or more protein toxins (e.g., insecticidal proteins) in the uracilpyridine herbicides-tolerant plants is effective for controlling flea beetles, i.e. members of the flea beetle tribe of family Chrysomelidae, preferably against *Phyllotreta* spp., such as *Phyllotreta cruciferae* and/or *Phyllotreta triolata*. In other embodiments, expression of one or more protein toxins {e.g., insecticidal proteins) in the uracilpyridine herbicides—tolerant plants is effective for controlling cabbage seed pod weevil, the Bertha armyworm, Lygus bugs, or the diamondback moth. Furthermore, in one embodiment, uracilpyridine herbicides-tolerant plants are also covered which are, e.g. by the use of recombinant DNA techniques and/or by breeding and/or otherwise selected for such traits, rendered able to synthesize one or more proteins to increase the resistance or tolerance of those plants to bacterial, viral or fungal pathogens. The methods for producing such genetically modified plants are generally known to the person skilled in the art.

Furthermore, in another embodiment, uracilpyridine herbicides-tolerant plants are also covered which are, e.g. by the use of recombinant DNA techniques and/or by breeding and/or otherwise selected for such traits, rendered able to synthesize one or more proteins to increase the productivity (e.g. oil content), tolerance to drought, salinity or other growth-limiting environmental factors or tolerance to pests and fungal, bacterial or viral pathogens of those plants.

Furthermore, in other embodiments, uracilpyridine herbicides-tolerant plants are also covered which are, e.g. by the use of recombinant DNA techniques and/or by breeding and/or otherwise selected for such traits, altered to contain a modified amount of one or more substances or new substances, for example, to improve human or animal nutrition, e.g. oil crops that produce health-promoting long-chain omega-3 fatty acids or unsaturated omega-9 fatty acids (e.g. Nexera(R) rape, Dow Agro Sciences, Canada).

Furthermore, in some embodiments, uracilpyridine herbicides-tolerant plants are also covered which are, e.g. by the use of recombinant DNA techniques and/or by breeding and/or otherwise selected for such traits, altered to contain increased amounts of vitamins and/or minerals, and/or improved profiles of nutraceutical compounds.

In one embodiment, uracilpyridine herbicides-tolerant plants of the present invention, relative to a wild-type plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate (glucobrassicin), I-methoxy-3-indolylmethyl-glucosinolate (neoglucobrassicin)); phenolics (e.g., flavonoids (e.g., quercetin, kaempferol), hydroxycinnamoyl derivatives (e.g., 1,2, 2'-trisinapoylgentiobiose, 1,2-diferuloylgentiobiose, I,2'-disinapoyl-2-feruloylgentiobiose, 3-O-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, uracilpyridine herbicides-tolerant plants of the present invention, relative to a wild-type plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavans/tannins (such as the procyanidins comprising coumarin, proanthocyanidins, catechins, and anthocyanins); flavones; phytoestrogens such as coumestans, lignans, resveratrol, isoflavones e.g. genistein, daidzein, and glycitein; resorcyclic acid lactones; organosulphur compounds; phytosterols; terpenoids such as carnosol, rosmarinic acid, glycyrrhizin and saponins; chlorophyll; chlorphyll in, sugars, anthocyanins, and vanilla. In other embodiments, uracilpyridine herbicides-tolerant plants of the present invention, relative to a wild-type plant, comprise an increased amount of, or an improved profile of, a compound selected from the group consisting of: vincristine, vinblastine, taxanes (e.g., taxol (paclitaxel), baccatin III, 10-desacetylbaccatin III, 10-desacetyl taxol, xylosyl taxol, 7-epitaxol, 7-epibaccatin III, 10-desacetylcephalomannine, 7-epicephalomannine, taxotere, cephalomannine, xylosyl cephalomannine, taxagifine, 8-benxoyloxy taxagifine, 9-acetyloxy taxusin, 9-hydroxy taxusin, taiwanxam, taxane Ia, taxane Ib, taxane Ic, taxane Id, GMP paclitaxel, 9-dihydro 13-acetylbaccatin III, 10-desacetyl-7-epitaxol, tetrahydrocannabinol (THC), cannabidiol (CBD), genistein, diadzein, codeine, morphine, quinine, shikonin, ajmalacine, serpentine, and the like.

It is to be understood that the plant of the present invention can comprise a wild type PPO nucleic acid in addition to a mutated PPO nucleic acid. It is contemplated that the uracilpyridine herbicide tolerant lines may contain a mutation in only one of multiple PPO isoenzymes. Therefore, the present invention includes a plant comprising one or more mutated PPO nucleic acids in addition to one or more wild type PPO nucleic acids.

In another embodiment, the invention refers to a seed produced by a transgenic plant comprising a plant cell of the present invention, wherein the seed is true breeding for an increased resistance to a uracilpyridine herbicide as compared to a wild type variety of the seed.

In another embodiment, the invention refers to a method of producing a transgenic plant cell with an increased resistance to a uracilpyridine herbicide as compared to a wild type variety of the plant cell comprising, transforming the plant cell with an expression cassette comprising a mutated PPO nucleic acid.

In another embodiment, the invention refers to a method of producing a transgenic plant comprising, (a) transforming a plant cell with an expression cassette comprising a mutated PPO nucleic acid, and (b) generating a plant with an increased resistance to uracilpyridine herbicide from the plant cell.

Consequently, mutated PPO nucleic acids of the invention are provided in expression cassettes for expression in the plant of interest. The cassette will include regulatory sequences operably linked to a mutated PPO nucleic acid sequence of the invention. The term "regulatory element" as used herein refers to a polynucleotide that is capable of regulating the transcription of an operably linked polynucleotide. It includes, but not limited to, promoters, enhancers, introns, 5' UTRs, and 3' UTRs. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

In a preferred embodiment, the expression cassette comprises the sequence of SEQ ID NO: 240, 241, 242, 243, 244, 245, 246, 247, 248, 249, 250, 251, 252, 253, 254, 255, 256, 257, 258, 259, 260, 261, 262, or 264.

Such an expression cassette is provided with a plurality of restriction sites for insertion of the mutated PPO nucleic acid sequence to be under the transcriptional regulation of the regulatory regions. The expression cassette may additionally contain selectable marker genes.

The expression cassette of the present invention will include in the 5'-3' direction of transcription, a transcriptional and translational initiation region (i.e., a promoter), a mutated PPO encoding nucleic acid sequence of the invention, and a transcriptional and translational termination region (i.e., termination region) functional in plants. The promoter may be native or analogous, or foreign or heterologous, to the plant host and/or to the mutated PPO nucleic acid sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the mutated PPO nucleic acid sequence of the invention, it is intended that the promoter is not the native or naturally occurring promoter for the operably linked mutated PPO nucleic acid sequence of the invention. As used herein, a chimeric gene comprises a coding sequence operably linked to a transcription initiation region that is heterologous to the coding sequence.

While it may be preferable to express the mutated PPO nucleic acids of the invention using heterologous promoters, the native promoter sequences may be used. Such constructs would change expression levels of the mutated PPO protein in the plant or plant cell. Thus, the phenotype of the plant or plant cell is altered.

The termination region may be native with the transcriptional initiation region, may be native with the operably linked mutated PPO sequence of interest, may be native with the plant host, or may be derived from another source (i.e., foreign or heterologous to the promoter, the mutated PPO nucleic acid sequence of interest, the plant host, or any combination thereof). Convenient termination regions are available from the Ti-plasmid of *A. tumefaciens*, such as the octopine synthase and nopaline synthase termination regions. See also Guerineau et al. (1991) Mol. Gen. Genet. 262: 141-144; Proudfoot (1991) Cell 64:671-674; Sanfacon et al. (1991) Genes Dev. 5: 141-149; Mogen et al. (1990) Plant Cell 2: 1261-1272; Munroe et al. (1990) Gene 91: 151-158; Ballas t al. 1989) Nucleic Acids Res. 17:7891-7903; and Joshi et al. (1987) Nucleic Acid Res. 15:9627-9639. Where appropriate, the gene(s) may be optimized for increased expression in the transformed plant. That is, the genes can be synthesized using plant-preferred codons for improved expression. See, for example, Campbell and Gowri (1990) Plant Physiol. 92: 1-11 for a discussion of host-preferred codon usage. Methods are available in the art for synthesizing plant-preferred genes. See, for example, U.S. Patent Nos. 5,380,831, and 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. Nucleotide sequences for enhancing gene expression can also be used in the plant expression vectors. These include the introns of the maize Adhl, intronl gene (Callis et al. Genes and Development 1: 1183-1200, 1987), and leader sequences, (W-sequence) from the Tobacco Mosaic virus (TMV), Maize Chlorotic Mottle Virus and Alfalfa Mosaic Virus (Gallie et al. Nucleic Acid Res. 15:8693-8711, 1987 and Skuzeski et al. Plant Mol. Biol. 15:65-79, 1990). The first intron from the shrunken-1 locus of maize, has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize mutated PPO gene expression, the plant expression vectors of the invention may also contain DNA sequences containing matrix attachment regions (MARs). Plant cells transformed with such modified expression systems, then, may exhibit overexpression or constitutive expression of a nucleotide sequence of the invention.

The expression cassettes of the present invention may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. ScL USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and trans versions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2: 163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced mutated PPO expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) Plant J. 12(2):255-265; Kawamata et al. (1997) Plant Cell Physiol. 38(7):792-803; Hansen et al. (1997) Mol. Gen Genet. 254(3):337-343; Russell et al. (1997) Transgenic Res. 6(2): 157-168; Rinehart et al. (1996) Plant Physiol. 112(3): 1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20: 181-196; Orozco et al. (1993) Plant Mol Biol. 23(6): 1129-1138; Matsuoka e/[alpha]/. (1993) Proc Natl. Acad. Sci. USA 90(20):9586-9590; and Guevara-Garcia et al. (1993) Plant J. 4(3):495-505. Such promoters can be modified, if necessary, for weak expression. In one embodiment, the nucleic acids of interest are targeted to the chloroplast for expression. In this manner, where the nucleic acid of interest is not directly inserted into the chloroplast, the expression cassette will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the mutated PPO nucleic acid of the invention such that the two sequences are contiguous and in the same reading frame. See, for example, Von Heijne et al. (1991) Plant Mol. Biol. Rep. 9: 104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481. While the mutated PPO proteins of the invention include a native chloroplast transit peptide, any chloroplast transit peptide known in the art can be fused to the amino acid sequence of a mature mutated PPO protein of the invention by operably linking a choloroplast-targeting sequence to the 5'-end of a nucleotide sequence encoding a mature mutated PPO protein of the invention. Chloroplast targeting sequences are known in the art and include the chloroplast small subunit of ribulose-1, 5-bisphosphate carboxylase (Rubisco) (de Castro Silva Filho et al. (1996) Plant Mol. Biol. 30:769-780; Schnell et al. (1991) J. Biol. Chem. 266(5):3335-3342); 5-(enolpyruvyl)shikimate-3-phosphate synthase (EPSPS) (Archer et al. (1990) J. Bioenerg. Biomemb. 22(6):789-810); tryptophan synthase (Zhao et al. (1995) J. Biol. Chem.

270(11):6081-6087); plastocyanin(Lawrence et al. (1997) J. Biol. Chem. 272(33):20357-20363); chorismate synthase (Schmidt et al. (1993) J. Biol. Chem. 268(36):27447-27457); and the light harvesting chlorophyll a/b binding protein (LHBP) (Lamppa et al. (1988) J. Biol. Chem. 263: 14996-14999). See also Von Heijne et al. (1991) Plant Mol. Biol. Rep. 9: 104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196: 1414-1421; and Shah et al. (1986) Science 233:478-481.

In a preferred embodiment, the transit peptide comprises the amino acid sequence of SEQ ID NO: 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226.

Preferred expression cassettes comprise a transit peptide from *Amaranthus* PPO-2 fused to PPO or PPO like polypeptides, such as chimeric expression cassettes having the SEQ ID NO: 240, 241, 242, 243, 244, 245, 246, 247, 248, 249, 250, 251, 252, 253, 254, 255, 256, 257, 258, 259, 260, 261, 262, or 264

Methods for transformation of chloroplasts are known in the art. See, for example, Svab et al. (1990) Proc. Natl. Acad. ScL USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305. The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

In a preferred embodiment, the mutated PPO nucleic acid comprises a polynucleotide sequence selected from the group consisting of: a) a polynucleotide encoding a polypeptide as shown in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, or a variant or derivative thereof; b) a polynucleotide comprising at least 60 consecutive nucleotides of any of a); and c) a polynucleotide complementary to the polynucleotide of any of a) through b)

Preferably, the expression cassette of the present invention further comprises a transcription initiation regulatory region and a translation initiation regulatory region that are functional in the plant.

While the polynucleotides of the invention find use as selectable marker genes for plant transformation, the expression cassettes of the invention can include another selectable marker gene for the selection of transformed cells. Selectable marker genes, including those of the present invention, are utilized for the selection of transformed cells or tissues. Marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christophers on et al (1992) Proc. Natl. Acad. ScL USA 89:6314-6318; Yao et al. (1992) Cell 71:63-72; Reznikoff (1992) Mol Microbiol 6:2419-2422; Barkley et al (1980) in The Operon, pp. 177-220; Hu et al (1987) Cell 48:555-566; Brown et al (1987) Cell 49:603-612; Figge et al (1988) Cell 52:713-722; Deuschle et al (1989) Proc. Natl Acad. AcL USA 86:5400-5404; Fuerst et al (1989) Proc. Natl. Acad. ScL USA 86:2549-2553; Deuschle et al (1990) Science 248:480-483; Gossen (1993) Ph.D. Thesis, University of Heidelberg; Reines et al (1993) Proc. Natl Acad. ScL USA 90: 1917-1921; Labow et al (1990) Mol Cell Biol 10:3343-3356; Zambretti et al (1992) Proc. Natl Acad. ScL USA 89:3952-3956; Bairn et al (1991) Proc. Natl Acad. ScL USA 88:5072-5076; Wyborski et al (1991) Nucleic Acids Res. 19:4647-4653; Hillenand-Wissman (1989) Topics Mol Struc. Biol 10: 143-162; Degenkolb et al (1991) Antimicrob. Agents Chemother. 35: 1591-1595; Kleinschnidt et al (1988) Biochemistry 27: 1094-1104; Bonin (1993) Ph.D. Thesis, University of Heidelberg; Gossen et al (1992) Proc. Natl Acad. ScL USA 89:5547-5551; Oliva et al (1992) Antimicrob. Agents Chemother. 36:913-919; Hlavka et al (1985) Handbook of Experimental Pharmacology, Vol. 78 (Springer-Verlag, Berlin); Gill et al (1988) Nature 334:721-724. Such disclosures are herein incorporated by reference. The above list of selectable marker genes is not meant to be limiting. Any selectable marker gene can be used in the present invention.

The invention further provides an isolated recombinant expression vector comprising the expression cassette containing a mutated PPO nucleic acid as described above, wherein expression of the vector in a host cell results in increased tolerance to a uracilpyridine herbicide as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., mutated PPO polypeptides, fusion polypeptides, etc.).

In a preferred embodiment of the present invention, the mutated PPO polypeptides are expressed in plants and plants cells such as unicellular plant cells (such as algae) (See Falciatore et al., 1999, Marine Biotechnology 1(3):239-251 and references therein) and plant cells from higher plants (e.g., the spermatophytes, such as crop plants). A mutated PPO polynucleotide may be "introduced" into a plant cell by any means, including transfection, transformation or transduction, electroporation, particle bombardment, agroinfection, biolistics, and the like.

Suitable methods for transforming or transfecting host cells including plant cells can be found in Sambrook et al. (Molecular Cloning: A Laboratory Manual. 2nd, ed., Cold Spring Harbor Laboratory, Cold Spring Harbor Laboratory Press, Cold Spring Harbor, NY, 1989) and other laboratory manuals such as Methods in Molecular Biology, 1995, Vol. 44, Agrobacterium protocols, ed: Gartland and Davey, Humana Press, Totowa, New Jersey. As increased tolerance to uracilpyridine herbicides is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses, and forage crops, these crop plants are also preferred target plants for a genetic engineering as one further embodiment of the present invention. In a preferred embodiment, the plant is a crop plant. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of a mutated PPO polynucleotide into a plant is achieved by Agrobacterium mediated gene transfer. One transformation method known to those of skill in the art is the dipping of a flowering plant into an Agrobacteria solution, wherein the Agrobacteria contains the mutated PPO nucleic acid, followed by breeding of the transformed gametes. Agrobacterium mediated plant transformation can be performed using for example the GV3101 (pMP90) (Koncz and Schell, 1986, Mol. Gen. Genet. 204:383-396) or LBA4404 (Clontech) Agrobacterium tumefaciens strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, 2nd Ed. -Dordrecht: Kluwer Academic Publ., 1995.-in Sect., Ringbuc Zentrale Signatur: BT11-P ISBN 0-7923-2731-4; Glick, Bernard R. and Thompson, John E., Methods in Plant Molecular Biology and Biotechnology, Boca Raton: CR$^c$ Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for Agrobacterium and plant selection depends on the binary vector and the Agrobacterium strain used for transformation. Rapeseed selection is normally performed using kanamycin as selectable plant marker. Agrobacterium mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced mutated PPO polynucleotide may be maintained in the plant cell stably if it is incorporated into a non-chromosomal autonomous replicon or integrated into the plant chromosomes. Alternatively, the introduced mutated PPO polynucleotide may be present on an extra-chromosomal non-replicating vector and be transiently expressed or transiently active. In one embodiment, a homologous recombinant microorganism can be created wherein the mutated PPO polynucleotide is integrated into a chromosome, a vector is prepared which contains at least a portion of an PPO gene into which a deletion, addition, or substitution has been introduced to thereby alter, e.g., functionally disrupt, the endogenous PPO gene and to create a mutated PPO gene. To create a point mutation via homologous recombination, DNA-RNA hybrids can be used in a technique known as chimeraplasty (Cole-Strauss et al., 1999, Nucleic Acids Research 27(5):1323-1330 and Kmiec, 1999, Gene therapy American Scientist 87(3):240-247). Other homologous recombination procedures in Triticum species are also well known in the art and are contemplated for use herein.

In the homologous recombination vector, the mutated PPO gene can be flanked at its 5' and 3' ends by an additional nucleic acid molecule of the PPO gene to allow for homologous recombination to occur between the exogenous mutated PPO gene carried by the vector and an endogenous PPO gene, in a microorganism or plant. The additional flanking PPO nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987, Cell 51:503 for a description of homologous recombination vectors or Strepp et al., 1998, PNAS, 95(8):4368-4373 for cDNA based recombination in Physcomitrella patens). However, since the mutated PPO gene normally differs from the PPO gene at very few amino acids, a flanking sequence is not always necessary. The homologous recombination vector is introduced into a microorganism or plant cell (e.g., via polyethylene glycol mediated DNA), and cells in which the introduced mutated PPO gene has homologously recombined with the endogenous PPO gene are selected using art-known techniques.

In another embodiment, recombinant microorganisms can be produced that contain selected systems that allow for regulated expression of the introduced gene. For example, inclusion of a mutated PPO gene on a vector placing it under control of the lac operon permits expression of the mutated PPO gene only in the presence of IPTG. Such regulatory systems are well known in the art.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a mutated PPO polynucleotide can be expressed in bacterial cells such as C. glutamicum, insect cells, fungal cells, or mammalian cells (such as Chinese hamster ovary cells (CHO) or COS cells), algae, ciliates, plant cells, fungi or other microorganisms like C. glutamicum. Other suitable host cells are known to those skilled in the art.

A host cell of the invention, such as a prokaryotic or eukaryotic host cell in culture, can be used to produce (i.e., express) a mutated PPO polynucleotide. Accordingly, the invention further provides methods for producing mutated PPO polypeptides using the host cells of the invention. In one embodiment, the method comprises culturing the host cell of invention (into which a recombinant expression vector encoding a mutated PPO polypeptide has been introduced, or into which genome has been introduced a gene encoding a wild-type or mutated PPO polypeptide) in a suitable medium until mutated PPO polypeptide is produced. In another embodiment, the method further comprises isolating mutated PPO polypeptides from the medium or the host cell. Another aspect of the invention pertains to isolated mutated PPO polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of mutated PPO polypeptide in which the polypeptide is separated from some of the cellular components of the cells in which it is naturally or recombinantly produced. In one embodiment, the language "substantially free of cellular material" includes preparations of a mutated PPO polypeptide having less than about 30% (by dry weight) of non-mutated PPO material (also referred to herein as a "contaminating polypeptide"), more preferably less than about 20% of non-mutated PPO material, still more preferably less than about 10% of non-mutated PPO material, and most preferably less than about 5% non-mutated PPO material.

When the mutated PPO polypeptide, or biologically active portion thereof, is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of mutated PPO polypeptide in which the polypeptide is separated from chemical precursors or other chemicals that are involved in the synthesis of the polypeptide. In one embodiment, the language "substantially free of chemical precursors or other chemicals" includes preparations of a mutated PPO polypeptide having less than about 30% (by dry weight) of chemical precursors or non-mutated PPO chemicals, more preferably less than about 20% chemical precursors or non-mutated PPO chemicals, still more preferably less than about 10% chemical precursors or non-mutated PPO chemicals, and most preferably less than about 5% chemical precursors or non-mutated PPO chemicals. In preferred embodiments, isolated polypeptides, or biologically active portions thereof, lack contaminating polypeptides from the same organism from which the mutated PPO polypeptide is derived. Typically, such polypeptides are produced by recombinant expression of, for example, a mutated PPO polypeptide in plants other than, or in microorganisms such as C. glutamicum, ciliates, algae, or fungi.

In other aspects, a method for treating a plant of the present invention is provided.

In some embodiments, the method comprises contacting the plant with an agronomically acceptable composition.

In another aspect, the present invention provides a method for preparing a descendent seed. The method comprises planting a seed of or capable of producing a plant of the present invention. In one embodiment, the method further comprises growing a descendent plant from the seed; and harvesting a descendant seed from the descendent plant. In other embodiments, the method further comprises applying a uracilpyridine herbicides herbicidal composition to the descendent plant.

In another embodiment, the invention refers to harvestable parts of the transgenic plant according to the present invention. Preferably, the harvestable parts comprise the PPO nucleic acid or PPO protein of the present invention. The harvestable parts may be seeds, roots, leaves and/or flowers comprising the PPO nucleic acid or PPO protein or parts thereof. Preferred parts of soy plants are soy beans comprising the PPO nucleic acid or PRO protein.

In another embodiment, the invention refers to products derived from a plant according to the present invention, parts thereof or harvestable parts thereof. A preferred plant product is fodder, seed meal, oil, or seed-treatment-coated seeds. Preferably, the meal and/or oil comprises the mutated PPO nucleic acids or PRO proteins of the present invention.

In another embodiment, the invention refers to a method for the production of a product, which method comprises
  a) growing the plants of the invention or obtainable by the methods of invention and
  b) producing said product from or by the plants of the invention and/or parts, e.g. seeds, of these plants.

In a further embodiment the method comprises the steps
  a) growing the plants of the invention,
  b) removing the harvestable parts as defined above from the plants and
  c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

As described above, the present invention teaches compositions and methods for increasing the PPO-inhibiting tolerance of a crop plant or seed as compared to a wild-type variety of the plant or seed. In a preferred embodiment, the PPO-inhibiting tolerance of a crop plant or seed is increased such that the plant or seed can withstand a uracilpyridine herbicide application of preferably approximately 1-1000 g ai ha$^{-1}$, more preferably 1-200 g ai ha$^{-1}$, even more preferably 5-150 g ai ha$^{-1}$, and most preferably 10-100 g ai ha$^{-1}$. As used herein, to "withstand" a uracilpyridine herbicide application means that the plant is either not killed or only moderately injured by such application. It will be understood by the person skilled in the art that the application rates may vary, depending on the environmental conditions such as temperature or humidity, and depending on the chosen kind of herbicide (active ingredient ai).

Furthermore, the present invention provides methods that involve the use of at least one uracilpyridine herbicide, optionally in combination with one or more herbicidal compounds B, and, optionally, a safener C, as described in detail supra.

In these methods, the uracilpyridine herbicide can be applied by any method known in the art including, but not limited to, seed treatment, soil treatment, and foliar treatment. Prior to application, the uracilpyridine herbicide can be converted into the customary formulations, for example solutions, emulsions, suspensions, dusts, powders, pastes and granules. The use form depends on the particular intended purpose; in each case, it should ensure a fine and even distribution of the compound according to the invention.

By providing plants having increased tolerance to uracilpyridine herbicide, a wide variety of formulations can be employed for protecting plants from weeds, so as to enhance plant growth and reduce competition for nutrients. A uracilpyridine herbicide can be used by itself for pre-emergence, post-emergence, pre-planting, and at-planting control of weeds in areas surrounding the crop plants described herein, or a uracilpyridine herbicide formulation can be used that contains other additives. The uracilpyridine herbicide can also be used as a seed treatment. Additives found in a uracilpyridine herbicide formulation include other herbicides, detergents, adjuvants, spreading agents, sticking agents, stabilizing agents, or the like. The uracilpyridine herbicide formulation can be a wet or dry preparation and can include, but is not limited to, flowable powders, emulsifiable concentrates, and liquid concentrates. The uracilpyridine herbicide and herbicide formulations can be applied in accordance with conventional methods, for example, by spraying, irrigation, dusting, or the like.

Suitable formulations are described in detail in PCT/EP2009/063387 and PCT/EP2009/063386, which are incorporated herein by reference.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Legend to the Uracilpyridines according to the present invention which were used in the following examples:

| | |
|---|---|
| Uracilpyridine 1 | ethyl 2-[[3-[2-chloro-4-fluoro-5-[3-methyl-2,6-dioxo-4-(trifluoromethyl)pyrimiclin-1-yl]phenoxy]-2-pyridyl]oxy]acetate |
| Uracilpyridine 2 | ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate |
| Uracilpyridine 3 | 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetic acid |
| Uracilpyridine 4 | ethyl 2-[2-[[3-chloro-5-fluoro-6-[3-methyl-2,6-dioxo-4-(trifluoromethyl)pyrimidin-1-yl]-2-pyridyl]oxy]phenoxy]acetate |
| Uracilpyridine 5 | 2-[2-[[3-chloro-5-fluoro-6-[3-methyl-2,6-dioxo-4-(trifluoromethyl)pyrimidin-1-yl]-2-pyridyl]oxy]phenoxy]acetic acid |
| Uracilpyridine 6 | ethyl 2-[2-[[3-bromo-6-[3-methyl-2,6-dioxo-4-(trifluoromethyl)pyrimidin-1-yl]-2-pyridyl]oxy]phenoxy]acetate |
| Uracilpyridine 7 | ethyl 2-[2-[[3-chloro-5-fluoro-6-[3-methyl-2,6-dioxo-4-(trifluoromethyl)pyrimidin-1-yl]-2-pyridyl]oxy]-4-fluoro-phenoxy]acetate |
| Uracilpyridine 8 | ethyl 2-[2-[[3,5-difluoro-6-[3-methyl-2,6-dioxo-4-(trifluoromethyl)pyrimidin-1-yl]-2-pyridyl]oxy]phenoxy]acetate |
| Uracilpyridine 9 | 2-[2-[[3,5-difluoro-6-[3-methyl-2,6-dioxo-4-(trifluoromethyl)pyrimidin-1-yl]-2-pyridyl]oxy]phenoxy]acetic acid |

| | |
|---|---|
| Uracilpyridine 10 | 2-[2-[[3-chloro-5-fluoro-6-[3-methyl-2,6-dioxo-4-(trifluoromethyl)pyrimidin-1-yl]-2-pyridyl]oxy]phenoxy]-N-methylsulfonyl-acetamide |
| Uracilpyridine 11 | ethyl 2-[[3-[[3-chloro-6-[3,5-dimethyl-2,6-dioxo-4-(trifluoromethyl)pyrimidin-1-yl]-5-fluoro-2-pyridyl]oxy]-2-pyridyl]oxy]acetate |
| Uracilpyridine 12 | ethyl 2-[2-[[3-chloro-6-[3,5-dimethyl-2,6-dioxo-4-(trifluoromethyl)pyrimidin-1-yl]-5-fluoro-2-pyridyl]oxy]phenoxy]acetate |
| Uracilpyridine 13 | allyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate |
| Uracilpyridine 14 | prop-2-ynyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate |
| Uracilpyridine 15 | cyclopropylmethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate |
| Uracilpyridine 16 | 2,2-difluoroethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate |
| Uracilpyridine 17 | isobutyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate |
| Uracilpyridine 18 | (2-ethoxy-2-oxo-ethyl) 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate |
| Uracilpyridine 19 | 2-methoxyethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate |
| Uracilpyridine 20 | 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]-N-methylsulfonyl-acetamide |
| Uracilpyridine 21 | methyl 2-[2-[[3-chloro-5-fluoro-6-[3-methyl-2,6-dioxo-4-(trifluoromethyl)pyrimidin-1-yl]-2-pyridyl]oxy]phenoxy]acetate |
| Uracilpyridine 22 | ethyl 2-[2-[[3-bromo-5-fluoro-6-[3-methyl-2,6-dioxo-4-(trifluoromethyl)pyrimidin-1-yl]-2-pyridyl]oxy]phenoxy]acetate |

Example 1: Site-Directed Mutagenesis PPO

All nucleic acid coding sequence and all single and double mutants encoding a herbicide tolerant PPO polypeptides are synthesized and cloned by Geneart (Geneart AG, Regensburg, Germany). Rational design mutants are synthesized by Geneart. Random PPO gene libraries are synthesized by Geneart. Plasmids are isolated from *E. coli* TOP10 by performing a plasmid minpreparation and confirmed by DNA sequencing.

Example 2: Expression and Purification of Recombinant Wildtype and Mutant PPO (Taken from: Franck E. Dayan, Pankaj R. Daga, Stephen O. Duke, Ryan M. Lee, Patrick J. Tranel, Robert J. Doerksen. Biochemical and structural consequences of a glycine deletion in the α-8 helix of protoporphyrinogen oxidase. Biochimica et Biophysica Acta 1804 (2010), 1548-56) Clones in pRSET vector are transformed into BL21 (DE3)-pLysS strain of *E. coli*. Cells are grown in 250 mL of LB with 100 µgmL-1 of carbenicillin, shaking overnight at 37° C. Cultures are diluted in 1 L of LB with antibiotic and grown at 37° C. shaking for 2 h, induced with 1 mM IPTG and grown at 25° C. shaking for 5 more hours. The cells are harvested by centrifugation at 1600×g, washed with 0.09% NaCl, and stored at −80° C. Cells are lysed using a French press at 140 MPa in 50 mM sodium phosphate pH 7.5, 1 M NaCl, 5 mM imidazole, 5% glycerol, and 1 µg mL-1 leupeptin. Following lysis, 0.5 U of benzonase (Novagen, EMD Chemicals, Inc., Gibbstown, NJ) and PMSF (final concentration of 1 mM) are added. Cell debris is removed by centrifugation at 3000×g. His-tagged PPO proteins are purified on a nickel activated Hitrap Chelating HP column (GE Healthcare Bio-Sciences Corp., Piscataway, NJ) equilibrated with mM sodium phosphate pH 8.0, 50 mM NaCl, 5 mM imidazole, 5 mM MgCl2, 0.1 mM EDTA, and 17% glycerol. PPO is eluted with 250 mM imidazole. The active protein is desalted on a PD-column (GE Healthcare Bio-Sciences Corp., Piscataway, NJ) equilibrated with a 20 mM sodium phosphate buffer, pH 7.5, 5 mM MgCl2, 1 mM EDTA and 17% glycerol. Each litre of culture provided approximately 10 mg of pure PPO, which is stored at −20° C. until being used in assays.

Example 3: PPO Enzyme Assay (Non-Recombinant)

PPO protein (EC 1.3.3.4) is extracted from coleoptiles or shoots (150 g fresh weight) of dark-grown corn, black nightshade, morning glory, and velvetleaf seedlings as described previously (Grossmann et al. 2010). Before harvesting, the seedlings are allowed to green for 2 hours in the light in order to achieve the highest specific enzyme activities in the thylakoid fractions at low chlorophyll concentrations. At high chlorophyll concentrations significant quenching of fluorescence occurs, which limits the amount of green thylakoids that can be used in the test. Plant materials are homogenized in the cold with a Braun blender using a fresh-weight-to-volume ratio of 1:4. Homogenization buffer consisted of tris(hydroxymethyl)aminomethane (Tris)-HCl (50 mM; pH 7.3), sucrose (0.5 M), magnesium chloride (1 mM), ethylenediaminetetraacetic acid (EDTA) (1 mM) and bovine serum albumin (2 g $L^{-1}$). After filtration through four layers of Miracloth, crude plastid preparations are obtained after centrifugation at 10 000×g for 5 min and resuspension in homogenization buffer before centrifugation at 150×g for 2 min to remove crude cell debris. The supernatant is centrifuged at 4000×g for min and the pellet fraction is resuspended in 1 ml of a buffer containing Tris-HCl (50 mM; pH 7.3), EDTA (2 mM), leupeptin (2 µM), pepstatin (2 µM) and glycerol (200 ml $L^{-1}$) and stored at −80° C. until use. Protein is determined in the enzyme extract with bovine serum albumin as a standard. PPO activity is assayed fluorometrically by monitoring the rate of Proto formation from chemically reduced protoporphyrinogen IX under initial velocity conditions. The assay mixture consisted of Tris-HCl (100 mM; pH 7.3), EDTA (1 mM), dithiothreitol (5 mM), Tween 80 (0.085%), protoporphyrinogen IX (2 µM), and 40 µg extracted protein in a total volume of 200 µl. The reaction is initiated by addition of substrate protoporphyrinogen IX at 22° C. The uracilpyridines disclosed SUPRA, and photosynthesis inhibitor diuron as negative control are prepared in dimethyl sulfoxide (DMSO) solution (0.1 mM concentration of DMSO in the assay) and added to the assay mixture in concentrations of 0.005 pM to 5 µM before incubation. Fluorescence is monitored directly from the assay mixture using a POLARstar Optima/Galaxy (BMG) with excitation at 405 nm and emission monitored at 630 nm. Non-enzymatic activity in the presence of heat-inactivated extract is negligible. Inhibition of enzyme activity induced by the herbicide is expressed as percentage inhibition relative to untreated controls. Molar concentrations of compound required for 50% enzyme inhibition ($IC_{50}$ values) are calculated by fitting the values to the dose-response equation using non-linear regression analysis.

Example 4: PPO Enzyme Assay (Recombinant)

Proto is purchased from Sigma-Aldrich (Milwaukee, WI). Protogen is prepared according to Jacobs and Jacobs (N. J. Jacobs, J. M. Jacobs, Assay for enzymatic protoporphyrinogen oxidation, a late step in heme synthesis, Enzyme 28 (1982) 206-219). Assays are conducted in 100 mM sodium phosphate pH 7.4 with 0.1 mM EDTA, 0.1% Tween 20, 5 µM FAD, and 500 mM imidazole. Dose-response curves with the uracilpyridines disclosed SUPRA, and photosynthesis inhibitor diuron as negative control, and MC-15608 are obtained in the presence of 150 µM Protogen. The excitation and emission bandwidths are set at 1.5 and 30 nm, respectively. AH assays are made in duplicates or triplicates and measured using a POLARstar Optima/Galaxy (BMG) with excitation at 405 nm and emission monitored at 630 nm. Molar concentrations of compound required for 50% enzyme inhibition ($IC_{50}$ values) are calculated by fitting the values to the dose-response equation using non-linear regression analysis. The results are shown in Table x.

TABLE X

| Compound | Variant PPO Enzyme and IC50 (M) Based on SEQ ID NO: 1 (Amaranthus PPO2) | | Wild Type PPO Enzyme IC50 (M) | Tolerance Factor (R/S) |
|---|---|---|---|---|
| Uracilpyridine 1 | R128A, F420V | 2.80E−07 | 1.77E−10 | 1579 |
| Uracilpyridine 1 | R128A, F420V | 1.62E−07 | 1.77E−10 | 915 |
| Uracilpyridine 1 | R128A, F420M | 6.16E−08 | 1.77E−10 | 347 |
| Uracilpyridine 1 | L397Q, F420V | 2.26E−06 | 1.77E−10 | 12739 |
| Uracilpyridine 1 | L397Q, F420M | 4.29E−07 | 1.77E−10 | 2418 |
| Uracilpyridine 1 | L397Q | 2.38E−09 | 1.77E−10 | 13 |
| Uracilpyridine 1 | F420V | 6.64E−08 | 1.77E−10 | 374 |
| Uracilpyridine 1 | F420M | 3.81E−08 | 1.77E−10 | 215 |
| Uracilpyridine 1 | F420M | 4.69E−08 | 1.77E−10 | 265 |
| Uracilpyridine 4 | R128A, F420V | 2.97E−07 | 1.73E−10 | 1718 |
| Uracilpyridine 4 | R128A, F420M | 6.94E−08 | 1.73E−10 | 401 |
| Uracilpyridine 4 | F420M | 9.44E−09 | 1.73E−10 | 55 |
| Uracilpyridine 2 | R128A, F420V | 1.49E−07 | 1.87E−10 | 796 |
| Uracilpyridine 2 | R128A, F420V | 2.07E−07 | 1.87E−10 | 1105 |
| Uracilpyridine 2 | R128A, F420M | 9.74E−08 | 1.87E−10 | 521 |
| Uracilpyridine 2 | L397Q, F420V | 2.56E−06 | 1.87E−10 | 13678 |
| Uracilpyridine 2 | L397Q, F420M | 9.05E−07 | 1.87E−10 | 4843 |
| Uracilpyridine 2 | L397Q | 1.29E−09 | 1.87E−10 | 7 |
| Uracilpyridine 2 | F420V | 1.06E−07 | 1.87E−10 | 567 |
| Uracilpyridine 2 | F420M | 4.57E−08 | 1.87E−10 | 244 |
| Uracilpyridine 2 | F420M | 7.76E−08 | 1.87E−10 | 415 |
| Uracilpyridine 8 | R128A, F420V | 2.25E−06 | 4.96E−10 | 4531 |
| Uracilpyridine 8 | F420M | 6.91E−08 | 4.96E−10 | 139 |
| Uracilpyridine 10 | R128A, F420M | 1.67E−06 | 2.12E−10 | 7879 |
| Uracilpyridine 10 | L397E, F420M | 6.51E−06 | 2.12E−10 | 30714 |
| Uracilpyridine 12 | R128A, F420M | 1.14E−07 | 2.12E−10 | 536 |
| Uracilpyridine 13 | R128A, F420M | 9.18E−08 | 2.18E−10 | 421 |
| Uracilpyridine 14 | R128A, F420M | 1.58E−07 | 2.34E−10 | 675 |
| Uracilpyridine 19 | R128A, F420M | 1.25E−07 | 2.48E−10 | 503 |
| Uracilpyridine 15 | R128A, F420M | 4.29E−08 | 2.20E−10 | 195 |
| Uracilpyridine 16 | R128A, F420M | 8.90E−08 | 1.75E−10 | 508 |
| Uracilpyridine 17 | R128A, F420M | 4.61E−08 | 1.13E−10 | 406 |
| Uracilpyridine 18 | R128A, F420M | 1.16E−07 | 1.54E−10 | 753 |

Example 5: Engineering PPO-derivative Herbicide Tolerant Plants having Wildtype or Mutated PPO Sequences PPO-derivative herbicide tolerant soybean (*Glyceine max*), plants are produced by a method as described by Olhoft et al. (US patent 2009/0049567). For transformation of soybean or *Arabidopsis thaliana*, Wildtype or Mutated PPO sequences encoding herbicide tolerant PPO polypeptides are cloned with standard cloning techniques as described in Sambrook et al. (Molecular cloning (2001) Cold Spring Harbor Laboratory Press) in a binary vector containing resistance marker gene cassette (AHAS) and mutated PPO sequence (marked as GOI) in between ubiquitin promoter (PcUbi) and nopaline synthase terminator (NOS) sequence. For corn transformation, Wildtype or Mutated PPO sequences are cloned with standard cloning techniques as described in Sambrook et al. (Molecular cloning (2001) Cold Spring Harbor Laboratory Press) in a binary vector containing resistance marker gene cassette (AHAS) and mutated PPO sequence (marked as GOI) in between corn ubiquitin promoter (ZmUbi) and nopaline synthase terminator (NOS) sequence. Binary plasmids are introduced to *Agrobacterium tumefaciens* for plant transformation. Plasmid constructs are introduced into soybean's axillary meristem cells at the primary node of seedling explants via *Agrobacterium*-mediated transformation. After inoculation and co-cultivation with *Agrobacteria*, the explants are transferred to shoot introduction media without selection for one week. The explants are subsequently transferred to a shoot induction medium with 1-3 µM imazapyr (Arsenal) for 3 weeks to select for transformed cells. Explants with healthy callus/shoot pads at the primary node are then transferred to shoot elongation medium containing 1-3 µM imazapyr until a shoot elongated or the explant died. Transgenic plantlets are rooted, subjected to TaqMan analysis for the presence of the transgene, transferred to soil and grown to maturity in greenhouse. Plant transformation vector constructs containing mutated PPO sequences are introduced into maize immature embryos via Agrobacterium-mediated transformation according to the procedure outlined in Peng et al. (WO2006/136596).

Transformed cells are selected in selection media supplemented with 0.5-1.5 µM imazethapyr for 3-4 weeks. Transgenic plantlets are regenerated on plant regeneration media and rooted afterwards. Transgenic plantlets are subjected to TaqMan analysis for the presence of the transgene before being transplanted to potting mixture and grown to maturity in greenhouse. Arabidopsis thaliana are transformed with wildtype or mutated PPO sequences by floral dip method as decribed by McElver and Singh (WO 2008/124495). Transgenic Arabidopsis plants are subjected to TaqMan analysis for analysis of the number of integration loci. Transformation of Oryza sativa (rice) are done by protoplast transformation as decribed by Peng et al. (U.S. Pat. No. 6,653,529) T0 or T1 transgenic plants of soybean, corn, and rice containing mutated PPO sequences are tested for improved tolerance to PPO-derived herbicides in greenhouse studies and mini-plot studies with the uracilpyridines disclosed SUPRA, and photosynthesis inhibitor diuron as negative control.

Example 6: Tissue Culture Conditions

An in vitro tissue culture mutagenesis assay has been developed to isolate and characterize plant tissue (e.g., maize, rice tissue) that is tolerant to protoporphyrinogen oxidase inhibiting herbicides, e.g. the uracilpyridines disclosed SUPRA, and photosynthesis inhibitor diuron as negative control). The assay utilizes the somaclonal variation that is found in in vitro tissue culture. Spontaneous mutations derived from somaclonal variation can be enhanced by treatment with a chemical mutagen (e.g. Ethyl methanesulfonate, N-ethyl-N-nitrosourea, N-Nitroso-N-methylurea) and subsequent selection in a stepwise manner, on increasing concentrations of herbicide.

The present invention provides tissue culture conditions for encouraging growth of friable, embryogenic maize or rice callus that is regenerable. Calli are initiated from rice cultivar Indica (Indica I). Seeds are surface sterilized in 70% ethanol for approximately I min followed by 20% commercial Clorox bleach for minutes. Seeds are rinsed with sterile water and plated on R001M media. The ingredient lists for the media tested are presented in Table y.

TABLE y

| Ingredients | Supplier | R001M | R025M | R026M | R327M | R008S |
|---|---|---|---|---|---|---|
| N6 Salts | Phytotech | 4 g/L | 4 g/L | 4.3 g/L | 4.3 g/L | 3.25 g/L |
| N6 vitamins | Phytotech | 1X | 1X | 1X | 1X | |
| Maltose | VWR | 30 g/L | 30 g/L | 30 g/L | 30 g/L | |
| Casamino Acid | BD | 0.3 g/L | 0.3 g/L | 2 g/L | | |
| Proline | Sigma | 2.9 g/L | 0.5 g/L | | | |
| 2,4-D | ICN | 2 mg/L | | | | |
| MES | Sigma | 0.5 g/L | 0.5 g/L | 0.5 g/L | 0.5 g/L | 0.5 g/L |
| MS Salts | Phytotech | | | | | |
| MS Vitamins | Phytotech | | | | | |
| Sorbitol | Sigma | | | | 30 g/L | |
| Sucrose | Sigma | | | | | 20 g/L |
| Nicotinic Acid | Sigma | | | | | 0.5 mg/L |
| Pyridoxine HCL | Sigma | | | | | 0.5 mg/L |
| Thiamine HCL | Sigma | | | | | 1 mg/L |
| Myo-inositol | Sigma | | | | | 0.1 g/L |

R001M callus induction media is selected after testing numerous variations. Cultures are kept in the dark at 30° C. Embryogenic callus is subcultured to fresh media after 10-14 days.

Example 7: Selection of Herbicide-Tolerant Calli

Once tissue culture conditions are determined, further establishment of selection conditions are established through the analysis of tissue survival in kill curves with saflufenacil, trifludimoxazin, sulfentrazone, and the uracilpyridines disclosed SUPRA, and photosynthesis inhibitor diuron as negative control. Careful consideration of accumulation of the herbicide in the tissue, as well as its persistence and stability in the cells and the culture media is performed. Through these experiments, a sub-lethal dose has been established for the initial selection of mutated material. After the establishment of the starting dose of uracilpyridines disclosed SUPRA, and photosynthesis inhibitor diuron as negative control in selection media, the tissues are selected in a step-wise fashion by increasing the concentration of the PPO inhibitor with each transfer until cells are recovered that grew vigorously in the presence of toxic doses. The resulting calli are further subcultured every 3-4 weeks to R001M with selective agent. Over 26,000 calli are subjected to selection for 4-5 subcultures until the selective pressure is above toxic levels as determined by kill curves and observations of continued culture. Alternatively, liquid cultures initiated from calli in MS711R with slow shaking and weekly subcultures. Once liquid cultures are established, selection agent is added directly to the flask at each subculture. Following 2-4 rounds of liquid selection, cultures are transferred to filters on solid R001M media for further growth.

Example 8: Regeneration of Plants

Tolerant tissue, e.g. rice tissue, is regenerated and characterized molecularly for PPO gene, e.g. Oryza sative PPO2 sequence mutations and/or biochemically for altered PPO activity in the presence of the selective agent. In addition, genes involved directly and/or indirectly in tetrapyrrole biosynthesis and/or metabolism pathways are also sequenced to characterize mutations. Finally, enzymes that change the fate (e.g. metabolism, translocation, transportation) are also sequence to characterized mutations. Following herbicide selection, calli are regenerated using a media regime of R025M for 10-14 days, R026M for ca. 2 weeks, R327M until well formed shoots are developed, and ROO8S until shoots are well rooted for transfer to the greenhouse. Regeneration is carried out in the light. No selection agent is included during regeneration. Once strong roots are established, M0 regenerants are transplant to the greenhouse in square or round pots. Transplants are maintained under a clear plastic cup until they are adapted to greenhouse conditions. The greenhouse is set to a day/night cycle of 27° C./21° C. (80° F./70° F.) with 600 W high pressure sodium lights supplementing light to maintain a 14 hour day length. Plants are watered according to need, depending in the weather and fertilized daily.

Example 9: Sequence Analysis

Leaf tissue is collected from clonal plants separated for transplanting and analyzed as individuals. Genomic DNA is extracted using a Chloropure Nucleic acid extraction kit (Agencourt, U.S. Pat. Nos. 5,898,071; 5,705,628; 6,534,262) as directed by the manufacturer. Isolated DNA is PCR amplified using the appropriate forward and reverse primer.

PCR amplification is performed using LongAmp HotStart Taq DNA Polymerase Mix (New England Biolabs) using thermocycling program as follows: 94° C. for sec, followed by cycles (94° C., sec; 54° C., sec; 65° C., 300 sec), min at 65° C. PCR products are verified for concentration and fragment size via agarose gel electrophoresis. Dephosphorylated PCR products are analyzed by direct sequence using the PCR primers (Genewiz or GenScript). Chromatogram trace files (.scf) are analyzed for mutation relative to the wild-type gene using Sequencher (Gene Codes) or Vector NTI Advance 10™ (Invitrogen). Based on sequence information, mutations are identified in several individuals. Sequence analysis is performed on the representative chromatograms and corresponding alignment with default settings and edited to call secondary peaks.

Example 10: Demonstration of Herbicide-Tolerance

T0 or T1 transgenic plant of soybean, corn, Canola varieties and rice containing PPO1 and or PPO2 sequences are tested for improved tolerance to herbicides in greenhouse studies and mini-plot studies with the uracilpyridines disclosed SUPRA, and photosynthesis inhibitor diuron as negative control. For the pre-emergence treatment, the herbicides are applied directly after sowing by means of finely distributing nozzles. The containers are irrigated gently to promote germination and growth and subsequently covered with transparent plastic hoods until the plants have rooted. This cover causes uniform germination of the test plants, unless this has been impaired by the herbicides. For post emergence treatment, the test plants are first grown to a height of 3 to 15 cm, depending on the plant habit, and only then treated with the herbicides. For this purpose, the test plants are either sown directly, and grown in the same containers or they are first grown separately and transplanted into the test containers a few days prior to treatment.

For testing of T0 plants, cuttings can be used. In the case of soybean plants, an optimal shoot for cutting is about 7.5 to 10 cm tall, with at least two nodes present. Each cutting is taken from the original transformant (mother plant) and dipped into rooting hormone powder (indole-3-butyric acid, IBA). The cutting is then placed in oasis wedges inside a bio-dome. Wild type cuttings are also taken simultaneously to serve as controls. The cuttings are kept in the bio-dome for 5-7 days and then transplanted to pots and then acclimated in the growth chamber for two more days. Subsequently, the cuttings are transferred to the greenhouse, acclimated for approximately 4 days, and then subjected to spray tests as indicated. Depending on the species, the plants are kept at 10-25° C. or 20-35° C. The test period extends over 3 weeks. During this time, the plants are tended and their response to the individual treatments is evaluated. Herbicide injury evaluations are taken at 2 and 3 weeks after treatment. Plant injury is rated on a scale of 0% to 100%, 0% being no injury and 100% being complete death.

Transgenic *Arabidopsis thaliana* plants are assayed for improved tolerance to the uracilpyridines disclosed SUPRA, in 48-well plates. Therefore, T2 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) *Physiologia Plantarum* 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 µmol Phot*$m^{-2}$*$s^{-1}$ with 14:10 h light:dark photoperiod. Growth inhibition is evaluated seven to ten days after seeding in comparison to wild type plants. The results are shown in Table i)

| Compound | Gene Species Source | Construct Name | Tolerance Factor* |
|---|---|---|---|
| Uracilpyridine 1 | *Amaranthus tuberculatus* | AMATU_PPO2_WT | 6 |
| Uracilpyridine 1 | *Amaranthus tuberculatus* | AMATU_PPO2_F420M | 110 |
| Uracilpyridine 1 | *Amaranthus tuberculatus* | AMATU_PPO2_L397D | 50 |
| Uracilpyridine 1 | *Amaranthus tuberculatus* | AMATU_PPO2_L397D_F420V | 41 |
| Uracilpyridine 1 | *Amaranthus tuberculatus* | AMATU_PPO2_R128A_F420M | 50 |
| Uracilpyridine 1 | *Amaranthus tuberculatus* | AMATU_PPO2_R128A_F420V | 75 |
| Uracilpyridine 1 | *Arabidopsis thaliana* | ARBTH_PPO1_WT | 50 |
| Uracilpyridine 1 | *Arabidopsis thaliana* | ARBTH_PPO1_S305L_Y426M | 250 |
| Uracilpyridine 3 | *Escherichia coli* | AMATU_PPO2_TP_hemG | 1600 |
| Uracilpyridine 9 | *Escherichia coli* | AMATU_PPO2_TP_hemG | 1600 |
| Uracilpyridine 4 | *Escherichia coli* | AMATU_PPO2_TP_hemG | 810000 |

-continued

| Compound | Gene Species Source | Construct Name | Tolerance Factor* |
|---|---|---|---|
| Uracilpyridine 5 | *Escherichia coli* | AMATU_PPO2_TP_hemG | 1400 |
| Uracilpyridine 2 | *Escherichia coli* | AMATU_PPO2_TP_hemG | 6400 |
| Uracilpyridine 8 | *Escherichia coli* | AMATU_PPO2_TP_hemG | 8202 |

Transgenic T2 *Arabidopsis* plants harboring PPO inhibitor tolerance trait in lab based germination assay.

Additionally, transgenic T2 *Arabidopsis* plants are tested for improved tolerance to herbicides in greenhouse studies with the uracilpyridines as disclosed SUPRA, and photosynthesis inhibitor diuron as negative control. Results are shown in table ii), table iii), and FIG. 1.

Table ii): Transgenic T2 *Arabidopsis* plants, sprayed post in the greenhouse with the indicated amount of PPO inhibitor+1% (v/v) MSO. Evaluation performed 14 Days After Treatment (DAT) and is shown as injury (%) relative to non-transgenic treated plants.

TABLE ii

| Compound | g ai/ha | ARBTH WT MC24 - non-transgenic / | ARBTH_PPO1_WT Q | AMATU_PPO2_WT Q | ALOMY_PPO2_TP_AMATU_PPO2_R128M_F420I R | AMATU_PPO2_R128M_F420I K | AMATU_PPO2_R128A_F420M Q | AMATU_PPO2_TP_hemG R | AMATU_PPO2_TP_hemG R |
|---|---|---|---|---|---|---|---|---|---|
| Uracilpyridine 2 | 200 | 100 | | | 75 | 70 | 65 | 35 | 30 |
| | 100 | 100 | | | 45 | 58 | 15 | 40 | 33 |
| | 80 | 100 | | | | | | | |
| | 50 | 100 | | | 45 | 18 | 10 | 55 | 28 |
| | 30 | 100 | 100 | 100 | | | | | |
| | 10 | 100 | 100 | 100 | | | | | |
| | 5 | 100 | 100 | 100 | | | | | |
| | 1 | 100 | 15 | 23 | | | | | |
| Uracilpyridine 3 | 80 | 100 | | | | | | | |
| | 30 | 100 | 100 | 100 | | | | | |
| | 10 | 100 | 98 | 100 | | | | | |
| | 5 | 100 | 83 | 80 | | | | | |
| | 1 | 88 | 10 | 48 | | | | | |
| Uracilpyridine 4 | 200 | 100 | | | 80 | 73 | 60 | 65 | |
| | 100 | 100 | | | 60 | 58 | 60 | 38 | |
| | 80 | 100 | | | | | | | |
| | 50 | 100 | | | 40 | 30 | 55 | 30 | |
| | 30 | 100 | 100 | 100 | | | | | |
| | 10 | 100 | 100 | 100 | | | | | |
| | 5 | 100 | 99 | 88 | | | | | |
| | 1 | 100 | 33 | 25 | | | | | |
| Uracilpyridine 5 | 80 | 100 | | | | | | | |
| | 30 | 100 | 100 | 100 | | | | | |
| | 10 | 100 | 99 | 100 | | | | | |
| | 5 | 100 | 90 | 90 | | | | | |
| | 1 | 100 | 45 | 28 | | | | | |
| Uracilpyridine 1 | 200 | 100 | | | 84 | 75 | 75 | 53 | |
| | 100 | 100 | | | 92 | 73 | 60 | 63 | |
| | 50 | 100 | | | 60 | 60 | 55 | 60 | |
| Uracilpyridine 10 | 200 | | | | | | | | |
| | 100 | | | | | | | | |
| | 50 | | | | | | | | |
| Uracilpyridine 6 | 200 | | | | | | | | |
| | 100 | | | | | | | | |
| | 50 | | | | | | | | |
| Uracilpyridine 7 | 200 | | | | | | | | |
| | 100 | | | | | | | | |
| | 50 | | | | | | | | |
| Uracilpyridine 8 | 80 | 100 | | | | | | | |
| | 30 | 100 | 100 | 100 | | | | | |
| | 10 | 100 | 55 | 100 | | | | | |
| | 5 | 100 | 30 | 55 | | | | | |
| | 1 | 88 | 10 | 10 | | | | | |
| Uracilpyridine 9 | 80 | 100 | | | | | | | |
| | 30 | 100 | 98 | 100 | | | | | |
| | 10 | 100 | 70 | 100 | | | | | |
| | 5 | 100 | 50 | 68 | | | | | |
| | 1 | 85 | 10 | 38 | | | | | |
| Uracilpyridine 10 | 80 | 100 | | | | | | | |
| | 30 | 100 | 100 | 100 | | | | | |
| | 10 | 100 | 100 | 100 | | | | | |

TABLE ii-continued

| | | 5 | 100 | 98 | 100 | | | |
| | | 1 | 100 | 50 | 58 | | | |

| Compound | g ai/ha | ALOMY_PPO2_R137L_F438V F | ALOMY_PPO2_R137L_F438V G | AMATU_PPO2_R128A_F420V A | AMATU_PPO2_R128A_F420V D | AMATU_PPO2_L397E_F420V D | AMATU_PPO2_L397E_F420V L | ARBTH_PPO1_S305L_Y426M O |
|---|---|---|---|---|---|---|---|---|
| Uracilpyridine 2 | 200 | 23 | 20 | | | | | |
| | 100 | 18 | 10 | | | | | |
| | 80 | | | | | | | 45 |
| | 50 | 18 | 0 | | | | | |
| | 30 | | | | | | | 33 |
| | 100 | | | | | | | 0 |
| | 50 | | | | | | | 0 |
| | 1 | | | | | | | |
| Uracilpyridine 3 | 80 | | | | | | | 13 |
| | 30 | | | | | | | 49 |
| | 10 | | | | | | | 0 |
| | 5 | | | | | | | 0 |
| | 1 | | | | | | | |
| Uracilpyridine 4 | 200 | 20 | 8 | | | | | |
| | 100 | 20 | 15 | | | | | |
| | 80 | | | | | | | 95 |
| | 50 | 8 | 8 | | | | | |
| | 30 | | | | | | | 0 |
| | 10 | | | | | | | 0 |
| | 5 | | | | | | | 0 |
| | 1 | | | | | | | |
| Uracilpyridine 5 | 80 | | | | | | | 73 |
| | 30 | | | | | | | 68 |
| | 10 | | | | | | | 0 |
| | 5 | | | | | | | 0 |
| | 1 | | | | | | | |
| Uracilpyridine 1 | 200 | 65 | 28 | | | | | |
| | 100 | 33 | 75 | | | | | |
| | 50 | 20 | 5 | | | | | |
| Uracilpyridine 10 | 200 | 10 | 5 | 68 | 88 | 13 | 20 | |
| | 100 | 8 | 0 | 53 | 78 | 5 | 53 | |
| | 50 | 0 | 0 | 38 | 30 | 0 | 8 | |
| Uracilpyridine 6 | 200 | 18 | 0 | 30 | 28 | 8 | 15 | |
| | 100 | 0 | 0 | 43 | 38 | 0 | 0 | |
| | 50 | 0 | 0 | 0 | 0 | 0 | 0 | |
| Uracilpyridine 7 | 200 | 13 | 8 | 70 | 75 | 10 | 33 | |
| | 100 | 18 | 0 | 50 | 65 | 0 | 0 | |
| | 50 | 0 | 0 | 13 | 33 | 0 | 0 | |
| Uracilpyridine 8 | 80 | | | | | | | 0 |
| | 30 | | | | | | | 0 |
| | 10 | | | | | | | 0 |
| | 5 | | | | | | | 0 |
| | 1 | | | | | | | |
| Uracilpyridine 9 | 80 | | | | | | | 0 |
| | 30 | | | | | | | 0 |
| | 10 | | | | | | | 0 |
| | 5 | | | | | | | 0 |
| | 1 | | | | | | | |
| Uracilpyridine 10 | 80 | | | | | | | 99 |
| | 30 | | | | | | | 99 |
| | 10 | | | | | | | 8 |
| | 5 | | | | | | | 10 |
| | 1 | | | | | | | |

TABLE iii

Transgenic T2 Arabidopsis plants, sprayed post in the greenhouse with the indicated amount of PPO inhibitor + 1% (v/v) MSO. Evaluation performed 14 Days After Treatment (DAT) and is shown as injury (%) relative to non-transgenic treated plants.

| Compound | g ai/ha | ARBTH WT MC 24 (non-transgenic) | ALOMY_PPO2_R137L_F438M | ALOMY_PPO2_R137L_F438M | ALOMY_PPO2_R137L_F438M | ALOMY_PPO2_R137L_F438M | ALOMY_PPO2_R137L_F438V | ALOMY_PPO2_R137L_F438V | ALOMY_PPO2_R137L_F438V | ALOMY_PPO2_R137L_F438V |
|---|---|---|---|---|---|---|---|---|---|---|
| Uracil-pyridine 2 | 100 | 100 | 0 | 0 | 0 | 0 | 0 | 0 | 0 | 0 |
| | 50 | 100 | 0 | 0 | 0 | 0 | 0 | 0 | 0 | 0 |

TABLE iii-continued

Transgenic T2 Arabidopsis plants, sprayed post in the greenhouse with the indicated amount of PPO inhibitor + 1% (v/v) MSO. Evaluation performed 14 Days After Treatment (DAT) and is shown as injury (%) relative to non-transgenic treated plants.

| Compound | g ai/ ha | | | | | | | | | |
|---|---|---|---|---|---|---|---|---|---|---|
| Uracil-pyridine 4 | 100 | 100 | 0 | 0 | 0 | 0 | 0 | 10 | 10 | 10 |
|  | 50 | 100 | 0 | 0 | 0 | 0 | 10 | 0 | 0 | 0 |
| Uracil-pyridine 1 | 100 | 100 | 20 | 0 | 0 | 0 | 0 | 25 | 35 | 40 |
|  | 50 | 100 | 0 | 0 | 0 | 0 | 5 | 50 | 15 | 0 |

| Compound | g ai/ ha | AMATU_ PPO2_ L397E_ F420V | AMATU_ PPO2_ L397E_ F420V | AMATU_ PPO2_ L397E_ F420V | AMATU_ PPO2_ L397E_ F420V | AMATU_ PPO2_ L397E_ F420M | AMATU_ PPO2_ L397E_ F420M | AMATU_ PPO2_ L397E_ F420M | AMATU_ PPO2_ L397E_ F420M | AMATU_ PPO2_ L397Q_ F420V |
|---|---|---|---|---|---|---|---|---|---|---|
| Uracil-pyridine 2 | 100 | 0 | 0 | 0 | 0 | 10 | 35 | 0 | 20 | 80 |
|  | 50 | 0 | 0 | 0 | 15 | 0 | 0 | 0 | 0 | 45 |
| Uracil-pyridine 4 | 100 | 0 | 30 | 0 | 0 | 15 | 35 | 60 | 20 | 80 |
|  | 50 | 0 | 10 | 0 | 10 | 0 | 25 | 0 | 0 | 60 |
| Uracil-pyridine 1 | 100 | 0 | 35 | 55 | 0 | 15 | 30 | 60 | 55 | 85 |
|  | 50 | 0 | 10 | 0 | 35 | 0 | 10 | 15 | 40 | 40 |

| Compound | g ai/ ha | ARBTH WT MC 24 (non-transgenic) | AMATU_ PPO2_ L397Q_ F420V | AMATU_ PPO2_ R128A_ F420L | AMATU_ PPO2_ R128A_ F420L | AMATU_ PPO2_ R128A_ F420L | AMATU_ PPO2_ R128A_ F420L | AMATU_ PPO2_ R128A_ F420I | AMATU_ PPO2_ R128A_ F420I | AMATU_ PPO2_ R128A_ F420I |
|---|---|---|---|---|---|---|---|---|---|---|
| Uracil-pyridine 2 | 100 | 100 | 65 | 60 | 35 | 15 | 30 | 65 | 65 | 65 |
|  | 50 | 100 | 0 | 0 | 0 | 0 | 15 | 0 | 45 | 65 |
| Uracil-pyridine 4 | 100 | 100 | — | 10 | 65 | 20 | 20 | 65 | 50 | 55 |
|  | 50 | 100 | — | 0 | 10 | 0 | 0 | 0 | 50 | 40 |
| Uracil-pyridine 1 | 100 | 100 | 65 | 60 | 90 | 95 | 80 | 65 | 80 | 95 |
|  | 50 | 100 | 75 | 65 | 75 | 5 | 75 | 70 | 75 | 60 |

| Compound | g ai/ ha | AMATU_ PPO2_ R128A_ F420I | AMATU_ PPO2_ R128A_ F420M | AMATU_ PPO2_ R128A_ F420M | AMATU_ PPO2_ R128A_ F420M | AMATU_ PPO2_ R128A_ F420M | AMATU_ PPO2_ R128A_ F420M | AMATU_ PPO2_ R128A_ F420V | AMATU_ PPO2_ R128A_ F420V | AMATU_ PPO2_ R128A_ F420V |
|---|---|---|---|---|---|---|---|---|---|---|
| Uracil-pyridine 2 | 100 | 30 | 0 | 65 | 30 | 0 | 85 | 70 | 25 | 65 |
|  | 50 | 0 | 0 | 0 | 30 | 0 | 0 | 0 | 20 | 0 |
| Uracil-pyridine 4 | 100 | 65 | 25 | 65 | 40 | 45 | 15 | 75 | 25 | 40 |
|  | 50 | 50 | 0 | 15 | 25 | 30 | 75 | 70 | 60 | 75 |
| Uracil-pyridine 1 | 100 | 60 | 35 | 80 | 65 | 65 | 95 | 98 | 95 | 80 |
|  | 50 | 60 | 55 | 65 | 25 | 40 | 90 | 55 | 65 | 95 |

Example 11: Demonstration of Herbicide Tolerance in Mutagenized Non-Transgenic Rice Selected mutants are transferred to pots and grown in the greenhouse for seed production. The resulting M1 progeny are screened for the presence and zygosity of tolerance conferring mutations in the OsPPO2 gene, e.g. mutated OsPPO2 polypeptides as shown in SEQ ID Nos: 628, 629, 630, 631, 632, 633, 634, 635, 636, or 637. M1 plants containing a homozygous in the OsPPO2 gene are kept for seed production to generate a stable, homozygous, herbicide tolerant line. Homozygous lines ca. 2 weeks old are sprayed using a track sprayer with uracilpyridine 2 or uracilpyridine 4 supplemented with 0.1% methylated seed oil. Once sprayed, plants are kept on drought conditions for 24 hours before being watered and fertilized again. Sprayed plants are photographed and rated for herbicide injury at 3 days and 7 days treatment. The results are shown in FIGS. 1 to 4.

Example 12: Herbicide Selection using Tissue Culture

Media is selected for use and kill curves developed as specified above. For selection, different techniques are utilized. Either a step wise selection is applied, or an immediate lethal level of herbicide is applied. In either case, all of the calli are transferred for each new round of selection. Selection is 4-5 cycles of culture with 3-5 weeks for each cycle. Cali are placed onto nylon membranes to facilitate transfer (200 micron pore sheets, Biodesign, Saco, Maine). Membranes are cut to fit 100×°mm Petri dishes and are autoclaved prior to use 25-35 calli (average weight/calli being 22 mg) are utilized in every plate. In addition, one set of calli are subjected to selection in liquid culture media with weekly subcultures followed by further selection on semisolid media. Mutant lines are selected using the uracilpyridines as disclosed SUPRA, and photosynthesis inhibitor diuron as negative control. Efficiencies of obtaining mutants is high either based on a percentage of calli that gave rise to a regenerable, mutant line or the number of lines as determined by the gram of tissue utilized.

Example 13: Maize Whole Plant Transformation and PPO Inhibitor Tolerance Testing Immature embryos are transformed according to the procedure outlined in Peng et al. (WO2006/136596). Plants are tested for the presence of the T-DNA by Taqman analysis with the target being the nos terminator which is present in all constructs. Healthy looking plants are sent to the greenhouse for hardening and subsequent spray testing. The plants are individually transplanted into MetroMix 360 soil in 4" pots. Once in the greenhouse (day/night cycle of 27° C./21° C. with 14 hour day length supported by 600 W high pressure sodium lights), they are allowed to grow for 14 days. T0 or T1 plants are sprayed with a treatment of the uracilpyridines as disclosed SUPRA and photosynthesis inhibitor diuron as negative control. Herbicide injury evaluations are taken at 7, 14 and 21 days after treatment. Herbicide injury evaluations are taken 2, 7, 14 and 21 days post-spray to look for injury to new growth points and overall plant health. The top survivors are transplanted into gallon pots filled with MetroMix 360 for seed production.

Transgenic T2 Corn plants harbouring PPO inhibitor tolerance trait, were sprayed post with the indicated amount of uracilpyridine+1% (v/v) MSO. Evaluation performed 14 Days After Treatment (DAT) and shown as injury (0-9) relative to non-transgenic treated plants.

Injury Scale: 0-9, 0=no injury, 9=maximum injury. Note: segregating lines. The results are shown in the following Table and in FIGS. 7 and 8.

| Compound | Rate (g/ha) | Corn Trial | | | |
| --- | --- | --- | --- | --- | --- |
| | | R128A, F420I Event 1 | R128A, F420L Event 2 | R128A, F420L Event 3 | J553 non transgenic |
| Check | | 0 | 0 | 1 | 5 |
| | | 1 | 1 | 1 | 6 |
| | | 1 | 2 | 0 | 6 |
| 1% MSO | | 0 | 0 | 0 | 1 |
| | | 1 | 0 | 0 | 2 |
| | | 1 | 1 | 1 | 1 |
| Uracilpyridine 2 | 25 | 1 | 0 | 1 | 9 |
| | | 0 | 1 | 0 | 9 |
| | | 1 | 0 | 0 | 9 |
| Uracilpyridine 2 | 50 | 0 | 1 | 0 | 9 |
| | | 1 | 1 | 0 | 9 |
| | | 0 | 1 | 1 | 9 |
| Uracilpyridine 2 | 100 | 1 | 1 | 0 | 9 |
| | | 0 | 1 | 1 | 9 |
| | | 1 | 1 | 1 | 9 |
| Uracilpyridine 4 | 25 | 0 | 0 | 0 | 9 |
| | | 0 | 0 | 1 | 7 |
| | | 0 | 0 | 0 | 7 |
| Uracilpyridine 4 | 50 | 0 | 1 | 1 | 9 |
| | | 1 | 0 | 0 | 7 |
| | | 0 | 1 | 0 | 9 |
| Uracilpyridine 4 | 100 | 1 | 0 | 1 | 9 |
| | | 0 | 1 | 0 | 9 |
| | | 0 | 1 | 0 | 9 |

Transgenic T3 Maize plants harboring a PPO inhibitor tolerance trait sprayed post in the field at the V3 leaf stage with 100 g/ha of PPO inh. 2+1% (v/v) MSO. Evaluation performed 2 and 12 Days After Treatment (DAT) and is shown as injury (%) relative to non-transgenic treated plants. Pictures taken 2 DAT.

| DAT | Plant Injury (%) | | |
| --- | --- | --- | --- |
| | J553/TR5753 Non-transgenic | AMATU_PPO2_R128A_F420L | AMATU_PPO2_R128A_F420I |
| 2 | 95 | 0 | 0 |
| 12 | 100 | 0 | 0 |

Example 14: Soybean Transformation and PPO Inhibitor Tolerance Testing

Soybean cv Jake is transformed as previously described by Siminszky et al., Phytochem Rev. 5:445-458 (2006). After regeneration, transformants are transplanted to soil in small pots, placed in growth chambers (16 hr day/8 hr night; 25° C. day/23° C. night; 65% relative humidity; 130-150 microE m-2 s-1) and subsequently tested for the presence of the T-DNA via Taqman analysis. After a few weeks, healthy, transgenic positive, single copy events are transplanted to larger pots and allowed to grow in the growth chamber. An optimal shoot for cutting is about 3-4 inches tall, with at least two nodes present. Each cutting is taken from the original transformant (mother plant) and dipped into rooting hormone powder (indole-3-butyric acid, IBA). The cutting is then placed in oasis wedges inside a bio-dome. The mother plant is taken to maturity in the greenhouse and harvested for seed. Wild type cuttings are also taken simultaneously to serve as negative controls. The cuttings are kept in the bio-dome for 5-7 days and then transplanted to 3 inch pots and then acclimated in the growth chamber for two more days. Subsequently, the cuttings are transferred to the greenhouse, acclimated for approximately 4 days prior to spray. T0 or 2-week old T1 plants are sprayed with a treatment of the uracilpyridines as disclosed SUPRA and photosynthesis inhibitor diuron as negative control. Herbicide injury evaluations are taken at 2, 7, 14 and 21 days after treatment.

Transgenic T2 or T3 Soybean plants harbouring PPO inhibitor tolerance trait, were sprayed post in the greenhouse with the indicated amount of uracilpyridine+1% (v/v) MSO. Evaluation performed 7 Days After Treatment (DAT) and shown as injury (0-9) relative to non-transgenic treated plants. Injury Scale: 0-9, 0=no imjury, 9=maximum injury. Note: segregating lines.

| Compound | Rate (g/ha) | R128A, F420L Event 1 | R128A, F420I Event 2 | L397E, F420V Event 3 | L397E, F420M Event 4 | L397Q, F420M Event 5 | Jake non transgenic |
|---|---|---|---|---|---|---|---|
| Uracilpyridine 1 | 25 | 1 | 1 | 2 | 1 | 1 | 9 |
|  |  | 1 | 1 | 1 | 2 | 2 | 9 |
|  |  | 1 | * | 1 | 1 | 2 | 9 |
|  |  | 1 | 9 | 1 | 1 | 1 | 9 |
| Uracilpyridine 1 | 50 | 1 | 1 | 9 | 2 | 1 | 9 |
|  |  | 1 | * | 1 | 0 | 2 | 9 |
|  |  | 1 | * | 1 | 1 | 1 | 9 |
|  |  | 1 | 3 | 2 | 1 | 2 | 9 |
| Uracilpyridine 1 | 100 | 1 | 1 | 1 | 1 | 3 | 9 |
|  |  | 1 | 2 | 1 | 2 | 2 | 9 |
|  |  | 1 | * | 9 | * | * | 9 |
|  |  | 4 | 1 | 9 | 1 | 3 | 9 |
| Uracilpyridine 1 | 200 | 1 | 1 | 9 | 4 | 3 | 9 |
|  |  | 1 | 1 | 2 | 1 | 3 | 9 |
|  |  | 1 | 1 | 9 | 2 | * | 9 |
|  |  | 1 | 1 | 1 | 2 | 4 | 9 |
|  | 1% MSO | 1 | * | 1 | 1 | 1 | 3 |
|  |  | 1 | * | 2 | 1 | 2 | 2 |
|  |  | 1 | 1 | 1 | 2 | 2 | 2 |
|  |  | 2 | * | 1 | 1 | 1 | 3 |
|  | Check | 1 | * | 0 | 1 | 0 | 1 |
|  |  | 0 | 0 | 1 | 1 | 2 | 0 |
|  |  | 0 | * | * | 1 | * | 1 |
|  |  | 1 | * | 2 | 1 | * | 1 |

Transgenic T2 or T3 Soybean plants harbouring PPO inhibitor tolerance trait, were sprayed post with the indicated amount of uracilpyridine+1% (v/v) MSO. Evaluation performed 14 Days After Treatment (DAT) and shown as injury (0-9) relative to non-transgenic treated plants. Injury Scale: 0-9, 0=no injury, 9=maximum injury. Note: segregating lines. The results are shown in the following Table and in FIGS. 7 and 8.

| Compound | Rate (g/ha) | L397E, F420V Event 1 | L397E, F420M Event 2 | L397Q, F420M Event 3 | Jake non transgenic |
|---|---|---|---|---|---|
| Check |  | 0 | 9 | 9 | 9 |
|  |  | 0 | 0 | 2 | 9 |
|  |  | 0 | 2 | 1 | 9 |
| 1% MSO |  | 0 | 0 | 0 | 1 |
|  |  | 0 | 0 | 0 | 1 |
|  |  | 0 | 0 | 0 | 1 |
| Uracilpyridine 2 | 25 | 0 | 0 | 0 | 9 |
|  |  | 0 | 0 | 9 | 9 |
|  |  | 0 | 0 | 3 | 9 |
| Uracilpyridine 2 | 50 | 0 | 0 | 3 | 9 |
|  |  | 0 | 0 | 9 | 9 |
|  |  | 0 | 0 | 1 | 9 |

-continued

| Compound | Rate (g/ha) | L397E, F420V Event 1 | L397E, F420M Event 2 | L397Q, F420M Event 3 | Jake non transgenic |
|---|---|---|---|---|---|
| Uracilpyridine 2 | 100 | 0 | 0 | 1 | 9 |
|  |  | 0 | 0 | 3 | 9 |
|  |  | 0 | 0 | 2 | 9 |
| Uracilpyridine 4 | 25 | 0 | 0 | 1 | 9 |
|  |  | 0 | 0 | 9 | 9 |
|  |  | 0 | 0 | 0 | 9 |
| Uracilpyridine 4 | 50 | 0 | 0 | 9 | 9 |
|  |  | 0 | 0 | 9 | 9 |
|  |  | 0 | 0 | 3 | 9 |
| Uracilpyridine 4 | 100 | 0 | 0 | 3 | 9 |
|  |  | 0 | 0 | 4 | 9 |
|  |  | 0 | 1 | 3 | 9 |

Transgenic T4 Soybean plants harbouring PPO inhibitor tolerance trait, were sprayed post with the indicated amount of uracilpyridine+1% (v/v) MSO. Evaluation performed 7 Days After Treatment (DAT) and shown as injury (0-9) relative to non-transgenic treated plants. Injury Scale: 0-9, 0=no imjury, 9=maximum injury. Asterisks indicates plants that did not germinate. Results are also shown in FIGS. 9 through 12.

| Compound | Rate (g/ha) | R128A + F420L Event 1 | R128A + F420I Event 2 | L397E + F420V Event 3 | L397E + F420M Event 4 | L397Q + F420M Event 5 | Jake non-transgenic |
|---|---|---|---|---|---|---|---|
| Uracilpyridine 10 | 25 | 0 | 1 | 1 | 0 | 3 | 9 |
|  |  | 1 | 0 | 1 | 1 | * | 9 |
|  |  | 0 | 2 | 0 | 0 | 3 | 9 |
|  |  | 0 | 1 | 0 | 0 | 5 | 9 |
|  |  | 1 | 1 | * | 0 | * | * |
|  |  | 0 | 1 | * | 0 | 3 | 9 |
| Uracilpyridine 10 | 50 | 1 | 1 | * | 0 | 4 | 9 |
|  |  | 1 | 2 | 1 | 1 | 4 | 9 |
|  |  | 0 | 1 | * | 0 | 4 | 9 |
|  |  | 1 | 2 | * | 0 | 4 | 9 |
|  |  | 0 | 2 | 0 | 0 | 4 | 9 |
|  |  | 1 | 2 | 1 | 1 | 4 | 9 |

-continued

| Compound | Rate (g/ha) | R128A + F420L Event 1 | R128A + F420I Event 2 | L397E + F420V Event 3 | L397E + F420M Event 4 | L397Q + F420M Event 5 | Jake non-transgenic |
|---|---|---|---|---|---|---|---|
| Uracilpyridine 10 | 100 | 2 | 2 | * | 1 | * | 9 |
|  |  | 1 | 2 | 0 | 2 | 4 | 9 |
|  |  | 2 | 2 | 0 | 1 | * | 9 |
|  |  | 2 | 3 | 0 | 1 | 5 | 9 |
|  |  | 2 | 3 | 1 | 0 | 5 | 9 |
|  |  | 2 | 3 | * | 1 | * | 9 |
| Uracilpyridine 20 | 25 | 2 | 2 | 0 | 0 | 4 | 9 |
|  |  | 0 | 2 | 1 | 0 | 3 | 9 |
|  |  | 1 | 2 | 0 | 1 | * | 9 |
|  |  | 0 | 2 | * | 0 | 3 | 9 |
|  |  | 1 | 2 | 0 | 0 | * | 9 |
|  |  | 2 | 1 | * | 0 | 3 | 9 |
| Uracilpyridine 20 | 50 | 3 | 3 | 0 | 0 | * | 9 |
|  |  | 3 | 3 | 0 | 1 | * | 9 |
|  |  | 2 | 3 | 0 | 0 | 3 | 9 |
|  |  | 1 | 2 | 1 | 1 | 4 | 9 |
|  |  | 2 | 3 | 1 | 0 | 4 | 9 |
|  |  | 2 | 3 | 0 | 0 | 4 | 9 |
| Uracilpyridine 20 | 100 | 3 | 4 | * | 0 | * | 9 |
|  |  | 4 | 4 | 0 | 0 | 4 | 9 |
|  |  | 5 | 4 | 0 | 1 | * | 9 |
|  |  | 5 | 4 | * | 1 | 4 | 9 |
|  |  | 5 | 4 | 0 | 1 | 7 | 9 |
|  |  | * | 4 | 2 | 1 | * | 9 |
| Uracilpyridine 21 | 25 | 0 | 0 | 0 | 0 | 3 | 9 |
|  |  | 1 | 1 | 0 | 0 | 2 | 9 |
|  |  | 1 | 1 | * | 0 | 2 | 9 |
|  |  | 1 | 1 | 0 | 0 | 3 | 9 |
|  |  | 1 | 1 | * | 0 | * | 9 |
|  |  | 1 | 1 | * | 1 | 2 | 9 |
| Uracilpyridine 21 | 50 | 1 | 2 | 0 | 0 | 3 | 9 |
|  |  | 2 | 2 | * | 0 | * | 9 |
|  |  | 1 | 1 | 0 | 0 | 3 | 9 |
|  |  | 1 | 2 | 0 | 0 | 3 | 9 |
|  |  | 2 | 2 | 0 | 1 | 3 | 9 |
|  |  | 1 | 2 | 0 | 1 | * | 9 |
| Uracilpyridine 21 | 100 | 2 | 3 | * | 0 | 3 | 9 |
|  |  | 1 | 3 | * | 0 | 3 | 9 |
|  |  | 4 | 2 | 0 | 0 | * | 9 |
|  |  | 2 | 3 | 2 | 0 | 3 | 9 |
|  |  | 2 | 2 | 0 | 0 | 3 | 9 |
|  |  | 2 | 3 | 0 | 1 | * | 9 |
| Uracilpyridine 22 | 25 | 0 | 1 | * | 1 | * | 9 |
|  |  | 0 | 0 | 0 | 0 | 1 | 9 |
|  |  | 0 | 0 | 0 | 0 | * | 9 |
|  |  | 1 | 1 | 0 | 0 | 1 | 9 |
|  |  | 0 | 2 | 0 | 0 | 2 | 9 |
|  |  | 1 | 1 | 1 | 1 | 1 | 9 |
| Uracilpyridine 22 | 50 | 1 | 0 | 0 | 1 | 3 | 9 |
|  |  | 1 | 0 | 0 | 0 | 3 | 9 |
|  |  | 1 | 3 | 0 | 2 | 3 | 9 |
|  |  | 1 | 2 | 0 | 1 | 2 | 9 |
|  |  | 2 | 2 | * | 0 | * | 9 |
|  |  | 1 | 2 | * | 1 | 1 | 9 |
| Uracilpyridine 22 | 100 | 1 | 2 | * | 0 | * | 9 |
|  |  | 1 | 3 | 0 | 0 | 4 | 9 |
|  |  | 1 | 1 | 1 | 0 | 4 | 9 |
|  |  | 1 | 2 | 0 | 1 | * | 9 |
|  |  | 2 | 2 | 0 | 1 | 4 | 9 |
|  |  | 2 | 3 | 1 | 0 | 4 | 9 |

Transgenic T3 Soybean plants harboring a PPO inhibitor tolerance trait, sprayed post in the field at the V3 leaf stage with 100 g/ha of PPO inh. 2+1% (v/v) MSO. Evaluation performed 2 and 12 Days After Treatment (DAT) and is shown as injury (%) relative to non-transgenic treated plants. Pictures taken 2 DAT.

| | Plant Injury (%) | | | | | |
|---|---|---|---|---|---|---|
| EXP | Jake Non-transgenic | AMATU_PPO2_R128A, F420I | AMATU_PPO2_L397E, F420V | AMATU_PPO2_L397E, F420M | AMATU_PPO2_L397Q, F420M | DAT |
| PPO Inh. 2 | 92 | 10 | 0 | 5 | 5 | 2 |

| EXP | Jake Non-transgenic | AMATU_PPO2_R128A, F420I | AMATU_PPO2_L397E, F420V | AMATU_PPO2_L397E, F420M | AMATU_PPO2_L397Q, F420M | DAT |
|---|---|---|---|---|---|---|
| | | | Plant Injury (%) | | | |
| PPO Inh. 2 | 100 | 5 | 0 | 0 | 0 | 12 |

The following gives a definition of the injury scores measured above:

Score Description of Injury
0 No Injury
1 Minimal injury, only a few patches of leaf injury or chlorosis.
2 Minimal injury with slightly stronger chlorosis. Overall growth points remain undamaged.
3 Slightly stronger injury on secondary leaf tissue, but primary leaf and growth points are still undamaged.
4 Overall plant morphology is slightly different, some chlorosis and necrosis in secondary growth points and leaf tissue. Stems are intact. Regrowth is highly probable within 1 week.
5 Overall plant morphology is clearly different, some chlorosis and necrosis on a few leaves and growth points, but primary growth point is intact. Stem tissue is still green. Regrowth is highly probably within 1 week.
6 Strong injury can be seen on the new leaflet growth. Plant has a high probability to survive only through regrowth at different growth points. Most of the leaves are chlorotic/necrotic but stem tissue is still green. May have regrowth but with noticeable injured appearance.
7 Most of the active growth points are necrotic. There may be a single growth point that could survive and may be partially chlorotic or green and partially necrotic. Two leaves may still be chlorotic with some green; the rest of the plant including stem is necrotic.
8 Plant will likely die, and all growth points are necrotic. One leaf may still be chlorotic with some green. The remainder of the plant is necrotic.
9 Plant is dead.

The invention claimed is:

1. A method for controlling undesired vegetation at a plant cultivation site, the method comprising the steps of:
   a) providing, at said site, a plant that comprises at least one nucleic acid comprising a nucleotide sequence encoding a protoporphyrinogen oxidase (PPO) polypeptide which is resistant or tolerant to a PPO inhibiting herbicide; and
   b) applying to said site an effective amount of said herbicide, wherein the PPO inhibiting herbicide is a uracilpyridine selected from the group consisting of:
   ethyl 2-[[3-[2-chloro-4-fluoro-5-[3-methyl-2,6-dioxo-4-(trifluoromethyl)pyrimidin-1-yl]phenoxy]-2-pyridyl]oxy]acetate;
   ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;

2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetic acid;
ethyl 2-[2-[[3-chloro-5-fluoro-6-[3-methyl-2,6-dioxo-4-(trifluoromethyl)pyrimidin-1-yl]-2-pyridyl]oxy]phenoxy]acetate;
2-[2-[[3-chloro-5-fluoro-6-[3-methyl-2,6-dioxo-4-(trifluoromethyl)pyrimidin-1-yl]-2-pyridyl]oxy]phenoxy]acetic acid;
ethyl 2-[2-[[3-bromo-6-[3-methyl-2,6-dioxo-4-(trifluoromethyl)pyrimidin-1-yl]-2-pyridyl]oxy]phenoxy]acetate;
ethyl 2-[2-[[3-chloro-5-fluoro-6-[3-methyl-2,6-dioxo-4-(trifluoromethyl)pyrimidin-1-yl]-2-pyridyl]oxy]-4-fluoro-phenoxy]acetate;
ethyl 2-[2-[[3,5-difluoro-6-[3-methyl-2,6-dioxo-4-(trifluoromethyl)pyrimidin-1-yl]-2-pyridyl]oxy]phenoxy]acetate;
2-[2-[[3,5-difluoro-6-[3-methyl-2,6-dioxo-4-(trifluoromethyl)pyrimidin-1-yl]-2-pyridyl]oxy]phenoxy]acetic acid;
2-[2-[[3-chloro-5-fluoro-6-[3-methyl-2,6-dioxo-4-(trifluoromethyl)pyrimidin-1-yl]-2-pyridyl]oxy]phenoxy]-N-methylsulfonyl-acetamide;
ethyl 2-[[3-[[3-chloro-6-[3,5-dimethyl-2,6-dioxo-4-(trifluoromethyl)pyrimidin-1-yl]-5-fluoro-2-pyridyl]oxy]-2-pyridyl]oxy]acetate;
ethyl 2-[2-[[3-chloro-6-[3,5-dimethyl-2,6-dioxo-4-(trifluoromethyl)pyrimidin-1-yl]-5-fluoro-2-pyridyl]oxy]phenoxy]acetate;
allyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
prop-2-ynyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
cyclopropylmethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
2,2-difluoroethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate isobutyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
(2-ethoxy-2-oxo-ethyl) 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
2-methoxyethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
2-[[3-[[3-chloro-5-fluoro-6-[3-methyl-2,6-dioxo-4-(trifluoromethyl)pyrimidin-1-yl]-2-pyridyl]oxy]-2-pyridyl]oxy]-N-methylsulfonyl-acetamide;
methyl 2-[2-[[3-chloro-5-fluoro-6-[3-methyl-2,6-dioxo-4-(trifluoromethyl)pyrimidin-1-yl]-2-pyridyl]oxy]phenoxy]acetate; and
ethyl 2-[2-[[3-bromo-5-fluoro-6-[3-methyl-2,6-dioxo-4-(trifluoromethyl)pyrimidin-1-yl]-2-pyridyl]oxy]phenoxy]acetate;
wherein the effective amount of said herbicide does not kill or inhibit the growth of the herbicide-tolerant plant of a); and
wherein the herbicide resistant or tolerant PPO polypeptide comprises one or more of the following motifs 1, 2, and/or 3:

a. Motif 1: SQ[N/K/H]KRYI, wherein the Arg at position 5 within said motif is substituted by any other amino acid;
b. Motif 2: TLGTLFSS, wherein the Leu at position 2, and/or the Gly at position 3, and/or the Leu at position 5 within said motif is substituted by any other amino acid;
c. Motif 3: [F/Y]TTF[V/I]GG, wherein the Phe at position 4 within said motif is substituted by any other amino acid.

2. A method for controlling undesired vegetation at a plant cultivation site, the method comprising the steps of:
a) providing, at said site, a plant that comprises at least one nucleic acid comprising a nucleotide sequence encoding a protoporphyrinogen oxidase (PPO) polypeptide which is resistant or tolerant to a PPO inhibiting herbicide; and
b) applying to said site an effective amount of said herbicide, wherein the PPO inhibiting herbicide is a uracilpyridine selected from the group consisting of:
ethyl 2-[[3-[2-chloro-4-fluoro-5-[3-methyl-2,6-dioxo-4-(trifluoromethyl)pyrimidin-1-yl]phenoxy]-2-pyridyl]oxy]acetate;
ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetic acid;
ethyl 2-[2-[[3-chloro-5-fluoro-6-[3-methyl-2,6-dioxo-4-(trifluoromethyl)pyrimidin-1-yl]-2-pyridyl]oxy]phenoxy]acetate;
2-[2-[[3-chloro-5-fluoro-6-[3-methyl-2,6-dioxo-4-(trifluoromethyl)pyrimidin-1-yl]-2-pyridyl]oxy]phenoxy]acetic acid;
ethyl 2-[2-[[3-bromo-6-[3-methyl-2,6-dioxo-4-(trifluoromethyl)pyrimidin-1-yl]-2-pyridyl]oxy]phenoxy]acetate;
ethyl 2-[2-[[3-chloro-5-fluoro-6-[3-methyl-2,6-dioxo-4-(trifluoromethyl)pyrimidin-1-yl]-2-pyridyl]oxy]-4-fluoro-phenoxy]acetate;
ethyl 2-[2-[[3,5-difluoro-6-[3-methyl-2,6-dioxo-4-(trifluoromethyl)pyrimidin-1-yl]-2-pyridyl]oxy]phenoxy]acetate;
2-[2-[[3,5-difluoro-6-[3-methyl-2,6-dioxo-4-(trifluoromethyl)pyrimidin-1-yl]-2-pyridyl]oxy]phenoxy]acetic acid;
2-[2-[[3-chloro-5-fluoro-6-[3-methyl-2,6-dioxo-4-(trifluoromethyl)pyrimidin-1-yl]-2-pyridyl]oxy]phenoxy]-N-methylsulfonyl-acetamide;
ethyl 2-[[3-[[3-chloro-6-[3,5-dimethyl-2,6-dioxo-4-(trifluoromethyl)pyrimidin-1-yl]-5-fluoro-2-pyridyl]oxy]-2-pyridyl]oxy]acetate;
ethyl 2-[2-[[3-chloro-6-[3,5-dimethyl-2,6-dioxo-4-(trifluoromethyl)pyrimidin-1-yl]-5-fluoro-2-pyridyl]oxy]phenoxy]acetate;
allyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
prop-2-ynyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
cyclopropylmethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;

2,2-difluoroethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate isobutyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;

(2-ethoxy-2-oxo-ethyl) 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;

2-methoxyethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;

2-[[3-[[3-chloro-5-fluoro-6-[3-methyl-2,6-dioxo-4-(trifluoromethyl)pyrimidin-1-yl]-2-pyridyl]oxy]-2-pyridyl]oxy]-N-methylsulfonyl-acetamide;

methyl 2-[2-[[3-chloro-5-fluoro-6-[3-methyl-2,6-dioxo-4-(trifluoromethyl)pyrimidin-1-yl]-2-pyridyl]oxy]phenoxy]acetate; and ethyl 2-[2-[[3-bromo-5-fluoro-6-[3-methyl-2,6-dioxo-4-(trifluoromethyl)pyrimidin-1-yl]-2-pyridyl]oxy]phenoxy]acetate;

wherein the effective amount of said herbicide does not kill or inhibit the growth of the herbicide-tolerant plant of a); and wherein the herbicide resistant or tolerant PPO polypeptide comprises a variant of the amino acid sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 577, 579, 581, 583, 585, 587, 589, 591, 593, 595, 597, 599, 601, 603, 605, 607, 609, 611, 613, 615, 617, 619, 621, 623, 625, 627, or 637, which variant comprises one or more of the following substitutions:

a. the amino acid corresponding to Arg128 of SEQ ID NO: 1 is substituted by any other amino acid
b. The amino acid corresponding to Gly211 of SEQ ID NO: 1 is substituted by any other amino acid
c. the amino acid corresponding to Leu397 of SEQ ID NO: 1 is substituted by any other amino acid
d. the amino acid corresponding to Gly398 of SEQ ID NO: 1 is substituted by any other amino acid
e. the amino acid corresponding to Leu400 of SEQ ID NO: 1 is substituted by any other amino acid
f. the amino acid corresponding to Phe420 of SEQ ID NO: 1 is substituted by by any other amino acid.

3. A method for controlling undesired vegetation at a plant cultivation site, the method comprising the steps of:

a) providing, at said site, a plant that comprises at least one nucleic acid comprising a nucleotide sequence encoding a protoporphyrinogen oxidase (PPO) polypeptide which is resistant or tolerant to a PPO inhibiting herbicide; and b) applying to said site an effective amount of said herbicide, wherein the PPO inhibiting herbicide is a uracilpyridine selected from the group consisting of:

ethyl 2-[[3-[2-chloro-4-fluoro-5-[3-methyl-2,6-dioxo-4-(trifluoromethyl)pyrimidin-1-yl]phenoxy]-2-pyridyl]oxy]acetate;

ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;

2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetic acid;

ethyl 2-[2-[[3-chloro-5-fluoro-6-[3-methyl-2,6-dioxo-4-(trifluoromethyl)pyrimidin-1-yl]-2-pyridyl]oxy]phenoxy]acetate;

2-[2-[[3-chloro-5-fluoro-6-[3-methyl-2,6-dioxo-4-(trifluoromethyl)pyrimidin-1-yl]-2-pyridyl]oxy]phenoxy]acetic acid;

ethyl 2-[2-[[3-bromo-6-[3-methyl-2,6-dioxo-4-(trifluoromethyl)pyrimidin-1-yl]-2-pyridyl]oxy]phenoxy]acetate;

ethyl 2-[2-[[3-chloro-5-fluoro-6-[3-methyl-2,6-dioxo-4-(trifluoromethyl)pyrimidin-1-yl]-2-pyridyl]oxy]-4-fluoro-phenoxy]acetate;

ethyl 2-[2-[[3,5-difluoro-6-[3-methyl-2,6-dioxo-4-(trifluoromethyl)pyrimidin-1-yl]-2-pyridyl]oxy]phenoxy]acetate;

2-[2-[[3,5-difluoro-6-[3-methyl-2,6-dioxo-4-(trifluoromethyl)pyrimidin-1-yl]-2-pyridyl]oxy]phenoxy]acetic acid;

2-[2-[[3-chloro-5-fluoro-6-[3-methyl-2,6-dioxo-4-(trifluoromethyl)pyrimidin-1-yl]-2-pyridyl]oxy]phenoxy]-N-methylsulfonyl-acetamide;

ethyl 2-[[3-[[3-chloro-6-[3,5-dimethyl-2,6-dioxo-4-(trifluoromethyl)pyrimidin-1-yl]-5-fluoro-2-pyridyl]oxy]-2-pyridyl]oxy]acetate;

ethyl 2-[2-[[3-chloro-6-[3,5-dimethyl-2,6-dioxo-4-(trifluoromethyl)pyrimidin-1-yl]-5-fluoro-2-pyridyl]oxy]phenoxy]acetate;

allyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;

prop-2-ynyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;

cyclopropylmethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;

2,2-difluoroethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate isobutyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;

(2-ethoxy-2-oxo-ethyl) 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;

2-methoxyethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;

2-[[3-[[3-chloro-5-fluoro-6-[3-methyl-2,6-dioxo-4-(trifluoromethyl)pyrimidin-1-yl]-2-pyridyl]oxy]-2-pyridyl]oxy]-N-methylsulfonyl-acetamide;

methyl 2-[2-[[3-chloro-5-fluoro-6-[3-methyl-2,6-dioxo-4-(trifluoromethyl)pyrimidin-1-yl]-2-pyridyl]oxy]phenoxy]acetate; and ethyl 2-[2-[[3-bromo-5-fluoro-6-[3-methyl-2,6-dioxo-4-(trifluoromethyl)pyrimidin-1-yl]-2-pyridyl]oxy]phenoxy]acetate;

wherein the effective amount of said herbicide does not kill or inhibit the growth of the herbicide-tolerant plant of a); and wherein the herbicide resistant or tolerant PPO polypeptide comprises the amino acid sequence of SEQ ID NO: 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, or a variant thereof.

4. A method for controlling undesired vegetation at a plant cultivation site, the method comprising the steps of:
  a) providing, at said site, a plant that comprises at least one nucleic acid comprising a nucleotide sequence encoding a protoporphyrinogen oxidase (PPO) polypeptide which is resistant or tolerant to a PPO inhibiting herbicide; and
  b) applying to said site an effective amount of said herbicide, wherein the PPO inhibiting herbicide is a uracilpyridine selected from the group consisting of:
    ethyl 2-[[3-[2-chloro-4-fluoro-5-[3-methyl-2,6-dioxo-4-(trifluoromethyl)pyrimidin-1-yl]phenoxy]-2-pyridyl]oxy]acetate;
    ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
    2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetic acid;
    ethyl 2-[2-[[3-chloro-5-fluoro-6-[3-methyl-2,6-dioxo-4-(trifluoromethyl)pyrimidin-1-yl]-2-pyridyl]oxy]phenoxy]acetate;
    2-[2-[[3-chloro-5-fluoro-6-[3-methyl-2,6-dioxo-4-(trifluoromethyl)pyrimidin-1-yl]-2-pyridyl]oxy]phenoxy]acetic acid;
    ethyl 2-[2-[[3-bromo-6-[3-methyl-2,6-dioxo-4-(trifluoromethyl)pyrimidin-1-yl]-2-pyridyl]oxy]phenoxy]acetate;
    ethyl 2-[2-[[3-chloro-5-fluoro-6-[3-methyl-2,6-dioxo-4-(trifluoromethyl)pyrimidin-1-yl]-2-pyridyl]oxy]-4-fluoro-phenoxy]acetate;
    ethyl 2-[2-[[3,5-difluoro-6-[3-methyl-2,6-dioxo-4-(trifluoromethyl)pyrimidin-1-yl]-2-pyridyl]oxy]phenoxy]acetate;
    2-[2-[[3,5-difluoro-6-[3-methyl-2,6-dioxo-4-(trifluoromethyl)pyrimidin-1-yl]-2-pyridyl]oxy]phenoxy]acetic acid;
    2-[2-[[3-chloro-5-fluoro-6-[3-methyl-2,6-dioxo-4-(trifluoromethyl)pyrimidin-1-yl]-2-pyridyl]oxy]phenoxy]-N-methylsulfonyl-acetamide;
    ethyl 2-[[3-[[3-chloro-6-[3,5-dimethyl-2,6-dioxo-4-(trifluoromethyl)pyrimidin-1-yl]-5-fluoro-2-pyridyl]oxy]-2-pyridyl]oxy]acetate;
    ethyl 2-[2-[[3-chloro-6-[3,5-dimethyl-2,6-dioxo-4-(trifluoromethyl)pyrimidin-1-yl]-5-fluoro-2-pyridyl]oxy]phenoxy]acetate;
    allyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
    prop-2-ynyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
    cyclopropylmethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
    2,2-difluoroethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate isobutyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
    (2-ethoxy-2-oxo-ethyl) 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
    2-methoxyethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate;
    2-[[3-[[3-chloro-5-fluoro-6-[3-methyl-2,6-dioxo-4-(trifluoromethyl)pyrimidin-1-yl]-2-pyridyl]oxy]-2-pyridyl]oxy]-N-methylsulfonyl-acetamide;
    methyl 2-[2-[[3-chloro-5-fluoro-6-[3-methyl-2,6-dioxo-4-(trifluoromethyl)pyrimidin-1-yl]-2-pyridyl]oxy]phenoxy]acetate; and
    ethyl 2-[2-[[3-bromo-5-fluoro-6-[3-methyl-2,6-dioxo-4-(trifluoromethyl)pyrimidin-1-yl]-2-pyridyl]oxy]phenoxy]acetate;
  wherein the effective amount of said herbicide does not kill or inhibit the growth of the herbicide-tolerant plant of a); and
  wherein the herbicide resistant or tolerant PPO polypeptide comprises the amino acid sequence of SEQ ID NO: 240, 241, 242, 243, 244, 245, 246, 247, 248, 249, 250, 251, 252, 253, 254, 255, 256, 257, 258, 259, 260, 261, or 262.

5. The method according to claim 1, wherein the plant comprises at least one additional heterologous nucleic acid comprising a nucleotide sequence encoding a herbicide tolerance enzyme.

6. The method according to claim 1, wherein the uracilpyridine is applied in conjunction with one or more additional herbicides.

7. The method according to claim 2, wherein the plant comprises at least one additional heterologous nucleic acid comprising a nucleotide sequence encoding a herbicide tolerance enzyme.

8. The method according to claim 2, wherein the uracilpyridine is applied in conjunction with one or more additional herbicides.

9. The method according to claim 3, wherein the plant comprises at least one additional heterologous nucleic acid comprising a nucleotide sequence encoding a herbicide tolerance enzyme.

10. The method according to claim 3, wherein the uracilpyridine is applied in conjunction with one or more additional herbicides.

11. The method according to claim 4, wherein the plant comprises at least one additional heterologous nucleic acid comprising a nucleotide sequence encoding a herbicide tolerance enzyme.

12. The method according to claim 4, wherein the uracil-pyridine is applied in conjunction with one or more additional herbicides.

13. The method according to claim 1, wherein the uracil-pyridine is ethyl 2-[2-[[3-chloro-5-fluoro-6-[3-methyl-2,6-dioxo-4-(trifluoromethyl)pyrimidin-1-yl]-2-pyridyl]oxy]phenoxy]acetate.

14. The method according to claim 2, wherein the uracil-pyridine is ethyl 2-[2-[[3-chloro-5-fluoro-6-[3-methyl-2,6-dioxo-4-(trifluoromethyl)pyrimidin-1-yl]-2-pyridyl]oxy]phenoxy]acetate.

15. The method according to claim 3, wherein the uracil-pyridine is ethyl 2-[2-[[3-chloro-5-fluoro-6-[3-methyl-2,6-dioxo-4-(trifluoromethyl)pyrimidin-1-yl]-2-pyridyl]oxy]phenoxy]acetate.

16. The method according to claim 4, wherein the uracil-pyridine is ethyl 2-[2-[[3-chloro-5-fluoro-6-[3-methyl-2,6-dioxo-4-(trifluoromethyl)pyrimidin-1-yl]-2-pyridyl]oxy]phenoxy]acetate.

17. The method according to claim 1, wherein the uracil-pyridine is 2-[2-[[3-chloro-5-fluoro-6-[3-methyl-2,6-dioxo-4-(trifluoromethyl)pyrimidin-1-yl]-2-pyridyl]oxy]phenoxy]acetic acid.

18. The method according to claim 2, wherein the uracil-pyridine is 2-[2-[[3-chloro-5-fluoro-6-[3-methyl-2,6-dioxo-4-(trifluoromethyl)pyrimidin-1-yl]-2-pyridyl]oxy]phenoxy]acetic acid.

19. The method according to claim 3, wherein the uracil-pyridine is 2-[2-[[3-chloro-5-fluoro-6-[3-methyl-2,6-dioxo-4-(trifluoromethyl)pyrimidin-1-yl]-2-pyridyl]oxy]phenoxy]acetic acid.

20. The method according to claim 4, wherein the uracil-pyridine is 2-[2-[[3-chloro-5-fluoro-6-[3-methyl-2,6-dioxo-4-(trifluoromethyl)pyrimidin-1-yl]-2-pyridyl]oxy]phenoxy]acetic acid.

\* \* \* \* \*

```
                          SEQUENCE LISTING

Sequence total quantity: 650
SEQ ID NO: 1              moltype = AA  length = 534
FEATURE                   Location/Qualifiers
source                    1..534
                          mol_type = protein
                          organism = Amaranthus sp.
SEQUENCE: 1
MVIQSITHLS PNLALPSPLS VSTKNYPVAV MGNISEREEP TSAKRVAVVG AGVSGLAAAY   60
KLKSHGLSVT LFEADSRAGG KLKTVKKDGF IWDEGANTMT ESEAEVSSLI DDLGLREKQQ  120
LPISQNKRYI ARDGLPVLLP SNPAALLTSN ILSAKSKLQI MLEPFLWRKH NATELSDEHV  180
QESVGEFFER HFGKEFVDYV IDPFVAGTCG GDPQSLSMHH TFPEVWNIEK RFGSVFAGLI  240
QSTLLSKKEK GGENASIKKP RVRGSFSFQG GMQTLVDTMC KQLGEDELKL QCEVLSLSYN  300
QKGIPSLGNW SVSSMSNNTS EDQSYDAVVV TAPIRNVKEM KIMKFGNPFS LDFIPEVTYV  360
PLSVMITAFK KDKVKRPLEG FGVLIPSKEQ HNGLKTLGTL FSSMMFPDRA PSDMCLFTTF  420
VGGSRNRKLA NASTDELKQI VSSDLQQLLG TEDEPSFVNH LFWSNAFPLY GHNYDSVLRA  480
IDKMEKDLPG FFYAGNHKGG LSVGKAMASG CKAAELVISY LDSHIYVKMD EKTA        534

SEQ ID NO: 2              moltype = AA  length = 534
FEATURE                   Location/Qualifiers
source                    1..534
                          mol_type = protein
                          organism = Amaranthus sp.
SEQUENCE: 2
MVIQSITHLS PNLALPSPLS VSTKNYPVAV MGNISEREEP TSAKRVAVVG AGVSGLAAAY   60
KLKSHGLSVT LFEADSRAGG KLKTVKKDGF IWDEGANTMT ESEAEVSSLI DDLGLREKQQ  120
LPISQNKRYI ARAGLPVLLP SNPAALLTSN ILSAKSKLQI MLEPFLWRKH NATELSDEHV  180
QESVGEFFER HFGKEFVDYV IDPFVAGTCG GDPQSLSMHH TFPEVWNIEK RFGSVFAGLI  240
QSTLLSKKEK GGENASIKKP RVRGSFSFQG GMQTLVDTMC KQLGEDELKL QCEVLSLSYN  300
QKGIPSLGNW SVSSMSNNTS EDQSYDAVVV TAPIRNVKEM KIMKFGNPFS LDFIPEVTYV  360
PLSVMITAFK KDKVKRPLEG FGVLIPSKEQ HNGLKTLGTL FSSMMFPDRA PSDMCLFTTF  420
VGGSRNRKLA NASTDELKQI VSSDLQQLLG TEDEPSFVNH LFWSNAFPLY GHNYDSVLRA  480
IDKMEKDLPG FFYAGNHKGG LSVGKAMASG CKAAELVISY LDSHIYVKMD EKTA        534

SEQ ID NO: 3              moltype = AA  length = 533
FEATURE                   Location/Qualifiers
source                    1..533
                          mol_type = protein
                          organism = Amaranthus sp.
SEQUENCE: 3
MVIQSITHLS PNLALPSPLS VSTKNYPVAV MGNISEREEP TSAKRVAVVG AGVSGLAAAY   60
KLKSHGLSVT LFEADSRAGG KLKTVKKDGF IWDEGANTMT ESEAEVSSLI DDLGLREKQQ  120
LPISQNKRYI ARDGLPVLLP SNPAALLTSN ILSAKSKLQI MLEPFLWRKH NATELSDEHV  180
QESVGEFFER HFGKEFVDYV IDPFVAGTCG DPQSLSMHHT FPEVWNIEKR FGSVFAGLIQ  240
STLLSKKEKG GENASIKKPR VRGSFSFQGG MQTLVDTMCK QLGEDELKLQ CEVLSLSYNQ  300
```

```
KGIPSLGNWS VSSMSNNTSE DQSYDAVVVT APIRNVKEMK IMKFGNPFSL DFIPEVTYVP    360
LSVMITAFKK DKVKRPLEGF GVLIPSKEQH NGLKTLGTLF SSMMFPDRAP SDMCLFTTFV    420
GGSRNRKLAN ASTDELKQIV SSDLQQLLGT EDEPSFVNHL FWSNAFPLYG HNYDCVLRAI    480
DKMEKDLPGF FYAGNHKGGL SVGKAMASGC KAAELVISYL DSHIYVKMDE KTA          533

SEQ ID NO: 4             moltype = AA  length = 533
FEATURE                  Location/Qualifiers
source                   1..533
                         mol_type = protein
                         organism = Amaranthus sp.
SEQUENCE: 4
MVIQSITHLS PNLALPSPLS VSTKNYPVAV MGNISEREEP TSAKRVAVVG AGVSGLAAAY     60
KLKSHGLSVT LFEANSRAGG KLKTVKKDGF IWDEGANTMT ESEAEVSSLI DDLGLREKQQ    120
LPISQNKRYI ARDGLPVLLP SNPAALLTSN ILSAKSKLQI MLEPFLWRKH NATELSDEHV    180
QESVGEFFER HFGKEFVDYV IDPFVAGTCG DPQSLSMYHT FPEVWNIEKR FGSVFAGLIQ    240
STLLSKKEKG GENASIKKPR VRGSFSFQGG MQTLVDTMCK QLGEDELKLQ CEVLSLSYNQ    300
KGIPSLGNWS VSSMSNNTSE DQSYDAVVVT APIRNVKEMK IMKFGNPFSL DFIPEVTYVP    360
LSVMITAFKK DKVKRPLEGF GVLIPSKEQH NGLKTLGTLF SSMMFPDRAP SDMCLFTTFV    420
GGSRNRKLAN ASTDELKQIV SSDLQQLLGT EDEPSFVNHL FWSNAFPLYG HNYDSVLRAI    480
DKMEKDLPGF FYAGNHKGGL SVGKAMASGC KAAELVISYL DSHIYVKMDE KTA          533

SEQ ID NO: 5             moltype = AA  length = 535
FEATURE                  Location/Qualifiers
source                   1..535
                         mol_type = protein
                         organism = Amaranthus sp.
SEQUENCE: 5
MVIQSITHLS PKLALPSPLS VSTKNYPVAV MGNISEREEP TSAKRVAVVG AGVSGLAAAY     60
KLKSHGLNVT LFEADSRAGG KLKTVKKDGF IWDEGANTMT ESEAEVSSLI DDLGLREKQQ    120
LPISQNKRYI ARDGLPVLLP SNPAALLSSN ILSAKSKLQI MLEPFLWRKR NATELSDEHV    180
QESVGEFFER HFGKEFVDYV IDPFVAGTCG GDPQSLSVHH TFPDVWNVEK RFGSVFAGLI    240
QSTLLSKKEK GGGENASIKK PRVRGSFSPH GGMQTLVDTM CKQIGEDELK LQCEVLSLSY    300
NQKGIPSLGN WSVSSMSNNT SEDQSYDAVV VTAPIRNVKE MKIMKFGNPF SLDFIPEVTY    360
VPLSVMITAF KKDKVKRPLE GFGVLIPSKE QHNGLKTLGT LFSSMMFPDR APSDMCLFTT    420
FVGGSRNRKL AKASTDELKQ IVSSDLQQLL GTEDEPSFVN HLFWSNAFPL YGHNYDSVLR    480
AIDKMEKDLP GFFYAGNHKG GLSVGKAMAS GCKAAELVIS YLDSHLYVKM NEKTA         535

SEQ ID NO: 6             moltype = AA  length = 505
FEATURE                  Location/Qualifiers
source                   1..505
                         mol_type = protein
                         organism = Amaranthus sp.
SEQUENCE: 6
MGNISERDEP TSAKRVAVVG AGVSGLAAAY KLKSHGLNVT LFEADSRAGG KLKTVKKDGF     60
IWDEGANTMT ESEAEVSSLI DDLGLREKQQ LPISQNKRYI ARDGLPVLLP SNPAALLTSN    120
ILSAKSKLQI MLEPFFWRKH NATELSDEHV QESVGEFFER HFGKEFVDYV IDPFVAGTCG    180
GDPQSLSMHH TFPEVWNIEK RFGSVFAGLI QSTLLSKKEK GGGNASIKK PRVRGSFSFH     240
GGMQTLVDTI CKQLGEDELK LQCEVLSLSY NQKGIPSLGN WSVSSMSNNT SEDQSYDAVV    300
VTAPIRNVKE MKIMKFGNPF SLDFIPEVSY VPLSVMITAF KKDKVKRPLE GFGVLIPSKE    360
QHNGLKTLGT LFSSMMFPDR APSDMCLFTT FVGGSRNRKL ANASTDELKQ IVSSDLQQLL    420
GTEDEPSFVN HLFWSNAFPL YGHNYDSVLR AIDKMEKDLP GFFYAGNHKG GLSVGKAMAS    480
GCKAAELVIS YLDSHIYVKM DEKTA                                         505

SEQ ID NO: 7             moltype = AA  length = 531
FEATURE                  Location/Qualifiers
source                   1..531
                         mol_type = protein
                         organism = Spinacia sp.
SEQUENCE: 7
MVILPVSQLS TNLGLSLVSP TKNNPVMGNV SERNQVNQPI SAKRVAVVGA GVSGLAAAYK     60
LKSNGLNVTL FEADSRAGGK LKTVVKDGLI WDEGANTMTE SDEEVTSLFD DLGIREKLQL    120
PISQNKRYIA RDGLPVLLPS NPVALLKSNI LSAKSKLQIM LEPFLWKKHN GAKVSDENAQ    180
ESVGEFFERH FGKEFVDYLI DPFVAGTSGG DPQSLSMRHA FPELWNIENR FGSVISGFIN    240
SKLSSKKEKG GEKQSSNKKP RVRGSFSFQG GMQTLVDTIC KEFGEDELKL QSEVLSLSYS    300
HNGSLTSENW SVSSMSNSTI QDQPYDAVVV TAPINNVKEL KIMKVENPFS LDFIPEVSCL    360
PLSVIITTFK KTNVKRPLEG FGVLVPSNEQ HNGLKTLGTL FSSMMFPDRA PSDVYLTTTF    420
VGGSRNRELA KASTDELKQI VSSDLQQLLG TEGEPTFVNH FYWSKAFPLY GRNYDSVLRA    480
IEKMERDLPG LFYAGNHKGG LSVGKSIASG YKAAELAISY LESNKMTEET I             531

SEQ ID NO: 8             moltype = AA  length = 508
FEATURE                  Location/Qualifiers
source                   1..508
                         mol_type = protein
                         organism = Vicia sp.
SEQUENCE: 8
MAEKSDAQSH YNGSGKRVAV VGAGVSGLAA AYKLKLHGVN ITLYEAEERA GGKLRSVSQH     60
GLVWDEGANT MTESEIEVGS LLDNLRLREK QQFPISQNKR YIVRNGMPVL LPSNPIALIK    120
SNILSAKSKF QIILEPFLWK KSDLSKVSDD HMKESVGGFF QRHFGKEVVD YLIDPFVAGT    180
SGGDPESLSM HHTFPELWNL EKRFGSIIAG AVLSKLSAKR EKRGETKGSS EKKKRQRGSF    240
```

```
SFQGGMQTLT DTLCKELGKD KLRLKSKVLS LSYSHGEKSA LENWSVAYAS NPGKQSKDLS   300
FDAVIMTAPL CNVREMKIMK KGNPFLLDFL PEVSYLPLSV IITTFKKENV KRPLEGFGVL   360
VPSKEQQNGL KTLGTLFSSM MFPDRAPNDL YLYTTFIGGS RNRELAKAST DELKQIVTSD   420
LRQLLGAEGE PTFVNHFYWS KAFPLFGHNY DSVLEAIDKM EKDLPGFFYA GNHKGGLSVG   480
KAIASGCKAA DLVISYLNSS SDGKMFKE                                      508

SEQ ID NO: 9              moltype = AA   length = 511
FEATURE                   Location/Qualifiers
source                    1..511
                          mol_type = protein
                          organism = Ricinus sp.
SEQUENCE: 9
MSSVIKEDRN PSHVKRVAVV GAGVSGLAAA YKLKSHGLKV TVFEAEERAG GKLRSVNHDG   60
LIWDEGANTM TESEMEVKSL IGNLGIREKQ QFPISQNKRY IVRNGKPILI PTNPIALITS   120
NILSAQSKFQ IILEPFLWKK RESSETHNAY TEESVGEFFQ RHFGKEVVDY LIDPFVAGTS   180
AGDPESLSVC HSFPELWNLE KRFGSIIAGV VQAKLSTKRG KSQETKGSSV KKKQQRGSFS   240
FFGGMQTLTD TLCKALAKDE LRLESKVFSL SYNPDSKSAV ENWSLSYAFK GAKHLQNSSY   300
DAIVMTAPLC NVKEMKITKN RNIFSLNFLP EVSYMPLSVV ITTFKKDNVK SPLEGFGVLV   360
PSKEQQNGLK TLGTLFSSMM FPDRAPNDLY LYTTFVGGSR NKELAKASTD DLKQIVTSDL   420
RQLLGAEGEP TFVNHFYWSK AFPLYGRNYD AVLEAIDTME KDLPGFFYAG NHKGGLSVGK   480
AIASGCKAAD LVISYLESSS DDKMLKEGPS N                                  511

SEQ ID NO: 10             moltype = AA   length = 504
FEATURE                   Location/Qualifiers
source                    1..504
                          mol_type = protein
                          organism = Theobroma sp.
SEQUENCE: 10
MAAAKNKDKQ TSAKRVAVVG AGVSGLAAAY KLKSHGLNVT MFEAEGRAGG KLRSVSQEGL   60
IWDEGANTMT ESEIEVRSLF DDLGIRDKQQ VPIAQKKRYI VRNGVPVLIP SNPIALITSN   120
ILSAKSKFQI ILEPFLWKKS DASKVSDAYN LESVGGFFQR HFGQEVVDYL IDPFVAGTSA   180
GDPESLSMRH SFPELWDLEK RFGSIIVGAV KSKLSAKREN RGERKTSEKR KPLPGPFSFQ   240
GGMQTLTDML CKDLSKDELK LKSKVLSLSY SHDGKSTLEN WSLSYASDRD KRSQGSSFDA   300
VVMTAPLCNV KEMKIMKGGK LFPLNFIPQV SYMPLSVIIT TFKKENVKKP LEGFGVLVPS   360
KEQQNGLKTL GTLFSSIMFP DRAPNNLYLY TTFVGGSRNK ELAKASTDEL KHIVTSDLRQ   420
LLGVEGEPTF LNHFYWSKAF PLYGRNYASV LKAIEKMETD LPGFFYAGNH KGGLSVGKAI   480
ASGCKAADLV ISYLESSHQK LLKD                                          504

SEQ ID NO: 11             moltype = AA   length = 502
FEATURE                   Location/Qualifiers
source                    1..502
                          mol_type = protein
                          organism = Glycine sp.
SEQUENCE: 11
MASSATDDNP RSVKRVAVVG AGVSGLAAAY KLKSHGLDVT VFEAEGRAGG RLRSVSQDGL   60
IWDEGANTMT ESEIEVKGLI DALGLQEKQQ FPISQHKRYI VKNGAPLLVP TNPAALLKSK   120
LLSAQSKIHL IFEPFMWKRS DPSNVCDENS VESVGRFFER HFGKEVVDYL IDPFVAGTSA   180
ADPESLSMRH SFPELWNLEK RFGSIIAGAL QSKLFAKREK TGENRTALRK NKHKRGSFSF   240
QGGMQTLTDT LCKELGKDDL KLNEKVLTLA YGHDGSSSSQ NWSITSASNQ STQDVDAVIM   300
TAPLYNVKDI KITKRGTPFP LNFLPEVSYV PISVMITTFK KENVKRPLEG FGVLVPSKEQ   360
KNGLKTLGTL FSSMMFPDRA PSDLYLYTTF IGGTQNRELA QASTDELRKI VTSDLRKLLG   420
AEGEPTFVNH FYWSKGFPLY GRNYGSVLQA IDKIEKDLPG FFFAGNYKGG LSVGKAIASG   480
CKAADLVISY LNSASDNTVP DK                                            502

SEQ ID NO: 12             moltype = AA   length = 502
FEATURE                   Location/Qualifiers
source                    1..502
                          mol_type = protein
                          organism = Prunus sp.
SEQUENCE: 12
MTSLTTKEGS VKRVAVVGAG VSGLAAAYKL KSHGFDVTVF EAEGRAGGKL RSVSHDGLIW   60
DEGANTMTES EKEVQTLLDD LGIREKQQFP ISQNKRYIVR NGSPVLIPTN PIALIKSNFL   120
SAQSKLQIIL EPYLWKDKRV SDDHTEESVG GFFQRHFGEE VVDLIDPFV AGTSAGDPES   180
LSMRHSFPDI WNIEKRFGSV ISGAIKSKLS ASKGKSGETK GSVEKGKRQR GSFSPHGGMQ   240
TLTDILCNQL EKDELKLNSK VLSLSYRQGG NSASENWSVS RVADDDKHSQ SLSVDALIMT   300
APLCNVKEMK ITKRGTRFPL DFIPEVVYMP LSVIITTFKK ENVKRPLEGF GVLVPSKEQK   360
NGLKTLGTLF SSMMFPDRAP SDLYLYTTFV GGSRNKELAK ASTDELKQIV TSDIRHLLGA   420
EGEPTFVNHF YWSNAFPLYG RDYDSVIEAI ENMEKNLPGF FYAGNHRGGL SVGKSIASGC   480
KAAELVISYL ESPSDEKTRH KG                                            502

SEQ ID NO: 13             moltype = AA   length = 499
FEATURE                   Location/Qualifiers
source                    1..499
                          mol_type = protein
                          organism = Medicago sp.
SEQUENCE: 13
MASSAKDDNP RSVKRVAVVG AGVSGLAAAY KLKSHGLDVT VFEAEGRAGG RLRTVSRDGL   60
VWDEGANTMT ENEIEVKGLI DALGLHEKQQ YPLSQHKRYI VKNGTPVLVP ANPAALLKSK   120
LLSAQSKIQV IFEPFMWKRS DSSAVRDENS EESVSRFFER HFGKEVVDYL IDPFVGGTSA   180
```

```
AGPESLSIRH SFPELWNLEK RFGSIIAGAL QSSVFGKKDK AGETKDVPRK NKHQRGSFSF   240
QGGMQTLTDT LCKELGKDDI KLNAKVLTLA YSHDGSSPSQ NWSITCTSNR KAQDVDAVIM   300
TAPLGNVRDI QIKKKGNPFP LNFLPEVTYL PLSVLITTFK KENVKRPLEG FGVLVPSKEQ   360
QNGFKTLGTL FSSMMFPDRA PSDMHLYTTF IGGTRNRELA QASTDELTKI VTSDLRKLLG   420
AEGEPAFVNH FFWSKGFPLY GHNYGSVLEA IDKMEKDLPG FFYAGNHRGG LSVGRAIASG   480
CKAADLVISY LNNASDNSV                                                499

SEQ ID NO: 14            moltype = AA  length = 506
FEATURE                  Location/Qualifiers
source                   1..506
                         mol_type = protein
                         organism = Fragaria sp.
SEQUENCE: 14
MASPSQPHNH RSVKKVAVVG AGVSGLAAAY KLKSHGFDVT VLEAEGRAGG KLRSVSYNGL    60
IWDEGANTMT EAETEVQTLL DSLGLRDKQQ FPISQNKRYV ARNGMPVLLP TNPIELIKSN   120
FLSTKSKFQI LLEPYLWKKK VSDDHTQES VAGFFQRHFG KEVVDYLIDP FVAGTSAGDP   180
ESLSMPHSFP ELWNIEKRYG SVITGTIRSK VSSRKEKRGD TKGSVEKGKR QRGSFSFQGG   240
MQTLTLTDTLCK QLGKHELKLN SKVLSLSYSH DGSSTSENWS LSCVANDDKH SQSSSVDAII   300
MTAPLCSIKE MKITRRGTIF PLDFLPEVNY MPLSVLITSF KKENIKRPLE GFGVLVPSKE   360
QENGLKTLGT LFSSMMFPDR APSDQYLYTT FVGGSRNKEL AKASKDELKQ IVTSDIRQLL   420
GAEGEPTFVN HYYWSKAFPL YGHNYDSVIE AIEKMEKNLP GLFYAGNHRG GLSVGKAIAS   480
GCKAADLVIS YLESSSDGKI LQQGSS                                        506

SEQ ID NO: 15            moltype = AA  length = 509
FEATURE                  Location/Qualifiers
source                   1..509
                         mol_type = protein
                         organism = Citrus sp.
SEQUENCE: 15
MASAPGEDNQ RSAKRVAVVG AGVSGLAAAY KLKSNGVNVM VFEADERAGG KLRSISKDGL    60
IWDEGANTMT ESEMEVKGLL DDLGIREKQQ FPISQYKRYV VRNGVPFLIP TNPIALITSN   120
FLSAQSKFQI ILEPFLWKKS DSAKVSAEDA KESVGGFFQR HFGREVVDFL IDPFVAGTSA   180
ADPESLVMRH SFPELWNLEK RYGSVIAGAI KSKFSARKEK SAEAKGSSEK KHRQRGSFSF   240
LGGMQTLTDA LCKALGKDEV CLKSKVLSLS YSHDGKSALE NWSLSSSNQD KQSQGLSFDA   300
VIMTASLCNV KEMKITKGGN LFPLDFLPEV IYMPLSVFIT AFKKENVGKP LQGFGVLVPS   360
KEQQNGLKTL GTLFSSMMFP DRAPKDLFLY TTFVGGSRNK ELAKASTDEL KQIVTSDLRQ   420
LLGVEGEPTF VNHFFWSKAF PLYGRDYDSV LEAIEKMEKN LPGFFYAGNH KGGLSVGKSI   480
ASGCKAAELV ISYLENSSDD KMLKEGSSK                                     509

SEQ ID NO: 16            moltype = AA  length = 509
FEATURE                  Location/Qualifiers
source                   1..509
                         mol_type = protein
                         organism = Citrus sp.
SEQUENCE: 16
MTNKWRVDFS GSAKRVAVVG AGVSGLAAAY KLKSNGVNVM VFEADERAGG KLRSISKDGL    60
IWDEGANTMT ESEMEVKGLL DDLGIREKQQ FPISQYKRYV VRNGVPFLIP TNPIALITSN   120
FLSAQSKFQI ILEPFLWKKS DSAKVSAEDA KESVGGFFQR HFGREVVDFL IDPFVAGTSA   180
ADPESLVMRH SFPELWNLEK RYGSVIAGAI KSKFSARKEK SAEAKGSSEK KHRQRGSFSF   240
LGGMQTLTDA LCKALGKDEV CLKSKVLSLS YSHDGKSALE NWSLSSSNQD KQSQGLSFDA   300
VIMTASLCNV KEMKITKGGN LFPLDFLPEV IYMPLSVFIT AFKKENVGKP LQGFGVLVPS   360
KEQQNGLKTL GTLFSSMMFP DRAPKDLFLY TTFVGGSRNK ELAKASTDEL KQIVTSDLRQ   420
LLGVEGEPTF VNHFFWSKAF PLYGRDYDSV LEAIEKMEKN LPGFFYAGNH KGGLSVGKSI   480
ASGCKAAELV ISYLENSSDD KMLKEGSSK                                     509

SEQ ID NO: 17            moltype = AA  length = 502
FEATURE                  Location/Qualifiers
source                   1..502
                         mol_type = protein
                         organism = Cicer sp.
SEQUENCE: 17
MASSAKDNNS RSVKRVAVVG AGVSGLAAAY KLKSHGLDVT VFEAEGRAGG RLRTVSRDGL    60
VWDEGANTMT ENEAEVKSLI DALGLQEKQQ YPLSQHKRYI VKNGMPLLVP ANPAALLKSK   120
LLSAQSKIRV IFEPFMWKRS DSSTVCDENS EESVSRFFER HFGKEVVDYL IDPFVGGTSA   180
ADPESLSMRH SFPELWNLEK RFGSIIGGAL QSNLFGKRDK TGETKDAPRK SKHQRGSFSF   240
QGGMQTLTDT LCKELGKDNL KLNAKVLTLA YSHNGSSPSE NWSITCASNL TTQDVDAVIM   300
TAPLGNVKDI QITKRGTPFT LNFFPEVTYL PLSVLITTFK KENVKRPLEG FGVLVPSKEE   360
QNGFKTLGTL FSSMMFPDRA PSDLHLYTTF IGGTRNRELA QASTDELKKI VTSDLRKLLG   420
AEGEPTFVNH FYWSKGFPLY GHNYGLVLEA IDKMEKGLPG FFYAGNHRGG LSVGRAIASG   480
CKAADLVISY LNNASDNTVA DK                                            502

SEQ ID NO: 18            moltype = AA  length = 502
FEATURE                  Location/Qualifiers
source                   1..502
                         mol_type = protein
                         organism = Cucumis sp.
SEQUENCE: 18
MASPAKQDRR TSRKKVAVVG AGVSGLAAAY KLKSHGFDVT VLEADERVGG KLRSVSYKGL    60
IWDEGANTMT ESEPEVQCLL DDLGLREKQQ FPISQNKRYI VRNGVPVLVP TNPIALIKSN   120
```

```
FLSAKSKFQI ILEPFLWKKY DSSKVSDDGT DESVGGFFQR HFGQEVVDYL IDPIVAGTSA   180
GDPDSLSMSH SFPELWNIEK RFGSIFAGLV LSKLSTKKES GGVRNGTTGK SKPRRGSFSF   240
QNGMQTLTDT LSKELGEGVL KLRSEVLSLS YNAGKYASQN WSLIYSKDKN SKDLIADAVI   300
MTAPVCSVRE MKFMKGGIPF SLNFLPEVAY MPLSVMITTF RKESVKRPLE GFGVLVPSSE   360
QQNGLRTLGT LFSSMMFPNR ASNDEYLYTT FIGGSRNREL AKSSTDELKQ IVTTDLRQLL   420
GVEGEPTFIN HFYWSKAFPL YGRNYDSVVK AIETMEKNLP GFFYAGNHRD GLSVGKSIAS   480
GCKAADLVIS YLESSTDQSC AE                                            502

SEQ ID NO: 19             moltype = AA   length = 497
FEATURE                   Location/Qualifiers
source                    1..497
                          mol_type = protein
                          organism = Cucumis sp.
SEQUENCE: 19
MKSSQSSRKK VAVVGAGVSG LAAAYKLKSH GFDVTVLEAD ERVGGKLRSV SYKGLIWDEG   60
ANTMTESEPE VQCLLDDLGL REKQQFPISQ NKRYIVRNGV PVLVPTNPIA LIKSNFLSAK   120
SKFQIILEPF LWKKYDSSKV SDDGTDESVG GFFQRHFGQE VVDYLIDPIV AGTSAGDPDS   180
LSMSHSFPEL WNIEKRFGSI FAGLVLSKLS TKKESGGVRN GTTGKSKPRR GSFSFQNGMQ   240
TLTDTLSKEL GEGVLKLRSE VLSLSYNAGK YASQNWSLIY SKDKNSKDLI ADAVIMTAPV   300
CSVREMKFMK GGIPFSLNFL PEVAYMPLSV MITTFRKESV KRPLEGFGVL VPSSEQQNGL   360
RTLGTLFSSM MFPNRASNDE YLYTTFIGGS RNRELAKSST DELKQIVTTD LRQLLGVEGE   420
PTFINHFYWS KAFPLYGRNY DSVVKAIETM EKNLPGFFYA GNHRDGLSVG KSIASGCKAA   480
DLVISYLESS TDQSCAE                                                  497

SEQ ID NO: 20             moltype = AA   length = 504
FEATURE                   Location/Qualifiers
source                    1..504
                          mol_type = protein
                          organism = Nicotiana sp.
SEQUENCE: 20
MAPSAGEDKH SSAKRVAVIG AGVSGLAAAY KLKIHGLNVT VFEAEGKAGG KLRSVSQDGL   60
IWDEGANTMT ESEGDVTFLI DSLGLREKQQ FPLSQNKRYI ARNGTPVLLP SNPIDLIKSN   120
FLSTGSKLQM LLEPILWKNK KLSQVSDSHE SVSGFFQRHF GKEVVDYLID PFVAGTCGGD   180
PDSLSMHHSF PELWNLEKRF GSVILGAIRS KLSPKNEKKQ GPPKTSANKK RQRGSFSFLG   240
GMQTLTDAIC KDLREDELRL NSRVLELSCS CTEDSAIDSW SIISASPHKR QSEEESFDAV   300
IMTAPLCDVK SMKIAKRGNP FLLNFIPEVD YVPLSVVITT FKRENVKYPL EGFGVLVPSK   360
EQQHGLKTLG TLFSSMMFPD RAPNNVYLYT TFVGGSRNRE LAKASRTELK EIVTSDLKQL   420
LGAEGEPTYV NHLYWSKAFP LYGHNYDSVL DAIDKMEKNL PGLFYAGNHR GGLSVGKALS   480
SGCNAADLVI SYLESVSTDS KRHC                                          504

SEQ ID NO: 21             moltype = AA   length = 501
FEATURE                   Location/Qualifiers
source                    1..501
                          mol_type = protein
                          organism = Solanum sp.
SEQUENCE: 21
MAPSAGEDKQ KRVAVIGAGV SGLAAAYKLK VHGLNVTVFE AEGRAGGKLR SLSQDGLIWD   60
EGANTMTESE GDVTFLLDSL GLREKQQFPL SQNKRYIARN GTPTLIPSNP FDLFKSNFLS   120
TGSKLQMLFE PLLWKNKKLT KVSDKHESVS GFFQRHFGKE VVDYLIDPFV AGTCGGDPDS   180
LSMHLSFPDL WNLEKRFGSV IVGAIQSKLS PIKEKKQGPP RTSINKKRQR GSFSFLGGMQ   240
TLTDAICKNL KEDELRLNSR VLELSCSCSG DSAIDSWSIF SASPHKRQAE EESFDAVIMT   300
APLCDVKSMK IAKRGNPFLL NFIPEVDYVP LSVVITTFKK ESVKHPLEGF GVLVPSQEQK   360
HGLKTLGTLF SSMMFPDRAP NNVYLYTTFV GGSRNRELAK ASRTELKEIV TSDLKQLLGA   420
EGEPTYVNHL CWSKAFPLYG HNYDSVLDAI DKMEKSLPGL FYAGNHKGGL SVGKALSSGC   480
NAADLVISYL EAVSADTKNH S                                             501

SEQ ID NO: 22             moltype = AA   length = 508
FEATURE                   Location/Qualifiers
source                    1..508
                          mol_type = protein
                          organism = Arabidopsis sp.
SEQUENCE: 22
MASGAVADHQ IEAVSGKRVA VVGAGVSGLA AAYKLKSRGL NVTVFEADGR VGGKLRSVMQ   60
NGLIWDEGAN TMTEAEPEVG SLLDDLGLRE KQQFPISQKK RYIVRNGVPV MLPTNPIELV   120
TSSVLSTQSK FQILLEPFLW KKKSSKVSDA SAEESVSEFF QRHFGQEVVD YLIDPFVGGT   180
SAADPDSLSM KHSFPDLWNV EKSFGSIIVG AIRTKFAAKG GKSRDTKSSP GTKKGSRGSF   240
SFKGGMQILP DTLCKSLSHD EINLDSKVLS LSYNSGSRQE NWSLSCVSHN ETQRQNPHYD   300
AVIMTAPLCN VKEMKVMKGG QPFQLNFLPE INYMPLSVVL TTPFTKEKVR PLEGFGVLIP   360
SKEQKHGFKT LGTLFSSMMF PDRSPSDVHL YTTFIGGSRN QELAKASTDE LKQVVTSDLQ   420
RLLGVEGEPV SVNHYYWRKA FPLYDSSYDS VMEAIDKMEN DLPGFFYAGN HRGGLSVGKS   480
IASGCKAADL VISYLESCSN DKKPNDSL                                      508

SEQ ID NO: 23             moltype = AA   length = 512
FEATURE                   Location/Qualifiers
source                    1..512
                          mol_type = protein
                          organism = Arabidopsis sp.
SEQUENCE: 23
MESGAVGDHD TKFESISGKR VAVVGAGVSG LAAAYKLKSR GLNVTVFEAD ERAGGKLTSV   60
```

```
MQNGLIWDQG ANTMTEAEPE VGSLLDDLGL RDKQQFPISQ KKRYIVRNGL PMMLPTNPIE    120
LVTSSVLSTQ AKIQILLEPF LWKKNDSSSK VSDASAEESV SGFFQRHFGQ EVVDYLIDPF    180
VGGTSAADPD SLSMKHSFPD LWNVEKSFGS IIVGAIRTKL AAKGGKSGEA KSSPGTKRGS    240
RRSFSFKGGM QILPDMLCKS LSHDEINLDS KVLSLSYNSG SRQENWSLSC VSHNETQRQN    300
LHYDAVVMTA PLCNVKEMKV TKGGQPFLLN FLPEINYMPL SVLITTFTKE KVKRPLEGFG    360
VLIPSKEKKH GFKTLGTLFS SMMFPDRCPS DLHYTTFIG GSRNQELAKA STDELKQVVT    420
SDLQRLLGVE GEPVSVNHYY WRKAFPLYDS SYGSVMEAID KMEKDLPGFF YAGNHRGGLS    480
IGKSIASGCK AADLVISYLE SCSNDKKPDE SL                                 512

SEQ ID NO: 24           moltype = AA  length = 501
FEATURE                 Location/Qualifiers
source                  1..501
                        mol_type = protein
                        organism = Arabidopsis sp.
SEQUENCE: 24
MASGAVADHQ IEAVSGKRVA VVGAGVSGLA AAYKLKSRGL NVTVFEADGR VGGKLRSVMQ     60
NGLIWDEGAN TMTEAEPEVG SLLDDLGLRE KQQFPISQKK RYIVRNGVPV MLPTNPIELV    120
TSSVLSTQSK FQILLEPFLW KKKSSKVSDA SAEESVSEFF QRHFGQEVVD YLIDPFVGGT    180
SAADPDSLSM KHSFPDLWNS FGSIIVGAIR TKFAAKGGKS RDTKSSPGTK KGSRGSFSFK    240
GGMQILPDTL CKSLSHDEIN LDSKVLSLSY NSGSRQENWS LSCVSHNETQ RQNPHYDAAP    300
LCNVKEMKVM KGGQPFQLNF LPEINYMPLS VLITTFTKEK VKRPLEGFGV LIPSKEQKHG    360
FKTLGTLFSS MMFPDRSPSD VHLYTTFIGG SRNQELAKAS TDELKQVVTS DLQRLLGVEG    420
EPVSVNHYYW RKAFPLYDSS YDSVMEAIDK MENDLPGFFY AGNHRGGLSV GKSIASGCKA    480
ADLVISYLES CSNDKKPNDS L                                             501

SEQ ID NO: 25           moltype = AA  length = 547
FEATURE                 Location/Qualifiers
source                  1..547
                        mol_type = protein
                        organism = Arabidopsis sp.
SEQUENCE: 25
MGLIKNGTLY CRFGISWNFA AVFFSTYFRH CFRLVRDFDS ELLQIAMASG AVADHQIEAV     60
SGKRVAVVGA GVSGLAAAYK LKSRGLNVTV FEADGRVGGK LRSVMQNGLI WDEGANTMTE    120
AEPEVGSLLD DLGLREKQQF PISQKKRYIV RNGVPVMLTN NPIELVTSSV LSTQSKFQIL    180
LEPFLWKKKS SKVSDASAEE SVSEFFQRHF GQEVVDYLID PFVGGTSAAD PDSLSMKHSF    240
PDLWNSFGSI IVGAIRTKFA AKGGKSRDTK SSPGTKKGSR GSFSFKGGMQ ILPDTLCKSL    300
SHDEINLDSK VLSLSYNSGS RQENWSLSCV SHNETQRQNP HYDAAPLCNV KEMKVMGGQ     360
PFQLNFLPEI NYMPLSVLIT TFTKEKVKRP LEGFGVLIPS KEQKHGFKTL GTLFSSMMFP    420
DRSPSDVHLY TTFIGGSRNQ ELAKASTDEL KQVVTSDLQR LLGVEGEPVS VNHYYWRKAF    480
PLYDSSYDSV MEAIDKMEND LPGFFYAGNH RGGLSVGKSI ASGCKAADLV ISYLESCSND    540
KKPNDSL                                                             547

SEQ ID NO: 26           moltype = AA  length = 467
FEATURE                 Location/Qualifiers
source                  1..467
                        mol_type = protein
                        organism = Ambrosia sp.
SEQUENCE: 26
GCAAAYKLKL HGLNVTVFEA DERVGGKLRS VSQDGLIWDE GANTMTESEA DVSSLIDDLG     60
LRDKQQFPIS QHKRYIVRNG KPVLIPSNPI ALIRSSFLST QSKVQILLEP FLWKKTKSSD    120
EPESGFFQ RHFGKEVVEY LIDPVVAGTS GGDPESLSMR HAFPELWDLE RRFGSIISGA      180
FQSMVSSRGG KRKPSGNSKR RRGSFSFFGG MQTLTDALSK EIGPHEINLQ SKVLEMSYSC    240
DDDNAVGNWSI YCAPDQNKQF QQSFDAVIMT APLNNLKEMK ITKTGSPLLL NFIPEVSYLP    300
ISVIISTFKK ENVKQPLEGF GVLVPAKEQE NGLRTLGTLF SSMMFPDRAS EDVYLTTFV    360
GGSRNKELAK ASRDELKQIV TSDLRQLLGT EGEPKFLTHY YWSKAFPLYG RDYGSVIEAI    420
EKMEKELPGY FYAGNHKGGL SVGKAISSGC KAAESVIAYL DSYSNQK                 467

SEQ ID NO: 27           moltype = AA  length = 542
FEATURE                 Location/Qualifiers
source                  1..542
                        mol_type = protein
                        organism = Setaria sp.
SEQUENCE: 27
MLSSSTTTAS PASSHPYRPA YPRASLRPVL AMAGSDDPRA APARSVAVIG AGVSGLAAAY     60
RLRKSGVNVT VFEAADRAGG KIRTNSEAGF LWDEGANTMT EGELEVSRLI DDLGLQDRQQ    120
YPNSQHKRYI VKDGAPALIP ADPISLMKSS VLSTKSKLAL FLEPFLYKKS NTRNSGKVSD    180
EHLSESVGSF FERHFGREVV DYLIDPFVAG TSAGDPESLS IRHAFPALWN LERKYHSIIV    240
GAILSLTAK GDPVKTGSDL SGKRRNRRAS FSPHGGMQSL INALHNEVGD DNVKLGTEVL    300
SLACTFDGLP STGGWSISVD SKDAGSKDLA KNQTFDAVIM TAPLSNVQRM KFRKGGAPFV    360
LDFPLPKVNYL PLSLMVTAFK KEDVKKPLEG FGVLIPYKEQ QKHGLKTLGT LFSSMMFPDR    420
APDDQYLYTT FVGGSHNRDL AGAPTSILKQ LVTSDLKKLL GVEGOPTFVK HIYWRNAFPL    480
YGRDYGSVLD AIEKMEKNLP GFFYAGNNKD GLAVGNVIAS GSKAAELAIS YLESQTKHNN    540
SH                                                                  542

SEQ ID NO: 28           moltype = AA  length = 544
FEATURE                 Location/Qualifiers
source                  1..544
                        mol_type = protein
                        organism = Sorghum sp.
```

```
SEQUENCE: 28
MLARTATVSS TSSHSHPYRP TSARSLRLRP VLAMAGSDDS RAAPARSVAV VGAGVSGLVA    60
AYRLRKSGVN VTVFEAADRA GGKIRTNSEG GFLWDEGANT MTEGELEASR LIDDLGLQDK   120
QQYPNSQHKR YIVKDGAPAL IPSDPISLMK SSVLSTKSKI ALFFEPFLYK KANTRNPGKV   180
SDEHLSESVG SFFERHFGRE VVDYLIDPFV AGTSAGDPES LSICHAFPAL WNLERKYGSV   240
VVGAILSKLT AKGDPVKTRR DSSAKRRNRR VSFSFHGGMQ SLINALHNEV GDDNVKLGTE   300
VLSLACTLDG APAPGGWSIS DDSKDASGKD LAKNQTFDAV IMTAPLSNVQ RMKFTKGGAP   360
FVLDFLPKVD YLPLSLMVTA FKKEDVKKPL EGFGVLIPYK EQQKHGLKTL GTLFSSMMFP   420
DRAPDDQYLY TTFVGGSHNR DLAGAPTSIL KQLVTSDLKK LLGVQGQPTF VKHIYWGNAF   480
PLYGHDYNSV LEAIEKMEKN LPGFFYAGNN KDGLAVGSVI ASGSKAADLA ISYLESHTKH   540
NNLH                                                                544

SEQ ID NO: 29           moltype = AA   length = 477
FEATURE                 Location/Qualifiers
source                  1..477
                        mol_type = protein
                        organism = Arabidopsis sp.
SEQUENCE: 29
MASGAVADHQ IEAVSGKRVA VVGAGVSGLA AAYKLKSRGL NVTVFEADGR VGGKLRSVMQ    60
NGLIWDEGAN TMTEAEPEVG SLLDDLGLRE KQQFPISQKK RYIVRNGVPV MKKSSKVSDA   120
SAEESVSEFF QRHFGQEVVD YLIDPFVGGT SAADPDSLSM KHSFPDLWNV EKSFGSIIVG   180
AIRTKFAAKG GKSRDTKSSP GTKKGSRGSF SFKGGMQILP DTLCKSLSHD EINLDSKVLS   240
LSYNSGSRQE NWSLSCVSHN ETQRQNPHYD AVIMTAPLCN VKEMKVMKGG QPFQLNFLPE   300
INYMPLSVLI TTFTKEKVKR PLEGFGVLIP SKEQKHGFKT LGTLFSSMMF PDRSPSDVHL   360
YTTFIGGSRN QELAKASTDE LKQVVTSDLQ RLLGVEGEPV SVNHYYWRKA FPLYDSSYDS   420
VMEAIDKMEN DLPGFFYAGN HRGGLSVGKS IASGCKAADL VISYLESCSN DKKPNDS      477

SEQ ID NO: 30           moltype = AA   length = 544
FEATURE                 Location/Qualifiers
source                  1..544
                        mol_type = protein
                        organism = Zea sp.
SEQUENCE: 30
MLALTASASS ASSHPYRHAS AHTRRPRLRA VLAMAGSDDP RAAPARSVAV VGAGVSGLAA    60
AYRLRQSGVN VTVFEAADRA GGKIRTNSEG GFVWDEGANT MTEGEWEASR LIDDLGLQDK   120
QQYPNSQHKR YIVKDGAPAL IPSDPISLMK SSVLSTKSKI ALFFEPFLYK KANTRNSGKV   180
SEEHLSESVG SFCERHFGRE VVDYFVDPFV AGTSAGDPES LSIRHAFPAL WNLERKYGSV   240
IVGAILSKLA AKGDPVKTRH DSSGKRRNRR VSFSFHGGMQ SLINALHNEV GDDNVKLGTE   300
VLSLACTFDG VPALGRWSIS VDSKDSGDKD LASNQTFDAV IMTAPLSNVR RMKFTKGGAP   360
VVLDFLPKMD YLPLSLMVTA FKKDDVKKPL EGFGVLIPYK EQQKHGLKTL GTLFSSMMFP   420
DRAPDDQYLY TTFVGGSHNR DLAGAPTSIL KQLVTSDLKK LLGVEGQPTF VKHVYWGNAF   480
PLYGHDYSSV LEAIEKMEKN LPGFFYAGNN KDGLAVGSVI ASGSKAADLA ISYLESHTKH   540
NNSH                                                                544

SEQ ID NO: 31           moltype = AA   length = 544
FEATURE                 Location/Qualifiers
source                  1..544
                        mol_type = protein
                        organism = Zea sp.
SEQUENCE: 31
MLALTASASS ASSHPYRHAS AHTRRPRLRA VLAMAGSDDP RAAPARSVAV VGAGVSGLAA    60
AYRLRQSGVN VTVFEAADRA GGKIRTNSEG GFVWDEGANT MTEGEWEASR LIDDLGLQDK   120
QQYPNSQHKR YIVKDGAPAL IPSDPISLMK SSVLSTKSKI ALFFEPFLYK KANTRNSGKV   180
SEEHLSESVG SFCERHFGRE VVDYFVDPFV AGTSAGDPES LSIRHAFPAL WNLERKYGSV   240
IVGAILSKLA AKGDPVKTRH DSSGKRRNRR VSFSFHGGMQ SLINALHNEV GDDNVKLGTE   300
VLSLACTFDG VPALGRWSIS VDSKDSGDKD LASNQTFDAV IMTAPLSNVR RMKFTKGGAP   360
VVLDFLPKMD YLPLSLMVTA FKKDDVKKPL EGFGVLIPYK EQQKHGLKTL GTLFSSMMFP   420
DRAPDDQYLY TTFVGGSHNR DLAGAPTSIL KQLVTSDLKK LLGVEGQPTF VKHVYWGNAF   480
PLYGHDYSSV LEAIEKMEKN LPGFFYAGNS KDGLAVGSVI ASGSKAADLA ISYLESHTKH   540
NNSH                                                                544

SEQ ID NO: 32           moltype = AA   length = 509
FEATURE                 Location/Qualifiers
source                  1..509
                        mol_type = protein
                        organism = Lemna perpusilla
SEQUENCE: 32
MEADAGKGSA GGAQILSHDS VRSVAVIGGG ISGLAAAYKL KSNGFRAVVF EAEGKAGGKI    60
RSGSQEGLIW DEGANTMAES VEAGELFDDV GIREKQQYPL SQSKRYVVRN GVPVMIPSDP   120
ISLIKSNLLS TKAKFRMFLE PFFSYRRVKP SKVSDEKLSE SVGEFFQRHF GKEVVDYLID   180
PPVAGTSGGD PESLSMPHAF PEIWNLQEKY GSVILGAIQS KFLDKRKGDR TERATVKKRR   240
PRGSFSFHGG MQTLIDVLCA KVGEENLELN SKVLSLACGH EGDPSFDSWS ISVASNNGSQ   300
KDLLTKSFFD AVIMTAPLGN VEDMKFTKKG SPFALDFLPQ VTYLPLSVLI TSFKRENVKR   360
PLEGFGVLVP SKEQEGGFKT LGTLFSSAMF PDRAPSDQYL YTTFIGGSRN RDLAGASLEE   420
LKQIVLSDLH KLLGVVGEPS FIKHVYWSKA FPLYGRDYGL VMEAIDRMER NLPGFYYAGN   480
HRDGLSVGKA IASGFRAADL AISYINSSV                                     509

SEQ ID NO: 33           moltype = AA   length = 544
FEATURE                 Location/Qualifiers
```

```
                                source          1..544
                                                mol_type = protein
                                                organism = Lemna perpusilla
SEQUENCE: 33
MASSAAISPL HFSPAPPRRR ELSHRCRVRC SIAGKPPATA ANDSSATSVT GGEPVRRLRA      60
DCVIVGAGIS GLCTAQALTV RPAAGRSSAP DVLVTEARDR VGGNITTVER DGYLWEEGPN     120
SFQPSDAVLT MAVDSGLKDD LVLGDPDAPR FVLWKGKLRP VPAKPTDLPF FDLMSIGGKI     180
RAGFGALGLR PSPPSREESV EEFVRRNLGD EVFERLIEPF CSGVYAGDPS KLSMKAAFGK     240
VWKLEQTGGS IIGGTFKAIQ ERSKNPKPPR DPRLPTPKGQ TVGSFSKGLA MLPNAIASRL     300
GDKVKLSWKL SGIKKSENGG YALTYDTPEG LTSVNADCVV LTIPSYVAGD LLRPLSNEAA     360
DALTKFYYPP VAAVTISYPS DSIRSECLID GQLKGFGQLH PRSQGVETLG TIYSSSLFPN     420
RAPPGRVLLL NYIGGSTNTA IVSKTESELV EAVDRDLRKM LVKVNAADPA VQGVRVWPRA     480
IPQFLIGHTD LLDAATRSLD RAGYGGLILG GNYAVGVALG RCIEGAYDTA AKVNSFLSKY     540
ARSF                                                                 544

SEQ ID NO: 34                   moltype = AA  length = 482
FEATURE                         Location/Qualifiers
source                          1..482
                                mol_type = protein
                                organism = Populus sp.
SEQUENCE: 34
MTAAAKDDDF GSKQSKNVAV IGAGVSGLAA AYKLKSNGVK VTVFEAEGRA GGKLRSVSHH      60
DLVWDEGANT MTESEVEVKS LLDDLGLREK QQFPIAQNKR YIVRNGMPVL IPTNPVALIK     120
SNFLSAQSKL QIILEPFLWK KNESSKVSDA DIQESVGEFF QRHFGKEVVD YLIDPFVAGT     180
SAGDPESLSA RHNFPDLWNL EKRFGSIIAG AVKAKLSAKK EKNGEKKGSS EKKKRQHGSF     240
SFLGGMQTLT DTLCTELGKD GVKLESKVLS LSYSYDGKSY FENWVSVSAS KGGKHAQASS     300
YDAVIMTAPL CNVKEININK GRNRFSLDFL PQMSYMPLSV IITTFKKEDV KRPLEGFGVL     360
VPSKEQQNGL KTLGTLFSSM MFPDRAPKDS YLYTTFVAST VLDCSHYYWS KAFPLYGKNY     420
DLVLEGIERM EKNLPGFFYA GNHRGGLSVG KAIASGCKAA DLVISHLNSS ADDKMLKKGS     480
QS                                                                   482

SEQ ID NO: 35                   moltype = AA  length = 569
FEATURE                         Location/Qualifiers
source                          1..569
                                mol_type = protein
                                organism = Capsella sp.
SEQUENCE: 35
MHDAGDSHDP FEIHKHVDVE LKSGLDAKTL NKGPLDKRLK IIGPEELKTR FDAELSWLLL      60
ITMASAKVAD NDTKFEAVSG RRVAVVGGGV SGLAAAYKLK SKGLNVTVFE ADGRAGGKLR     120
SVMHNGLIWD EGANTMTEAE PEVGTLLDDL GLREKQQFPI SQKKRYIVRN GVPVMIPTNP     180
IDLVTSTVLS TQSKFEILLE PFLWKKNDLS SKVSDASAAE SVSGFFRRHF GQEVVDYLID     240
PFVGGTSAAD PDSLSIVFVY CLILLILISL PTIHDQMKHS FPDLWNVEKS FGSVIVGAIR     300
TKLAAKGVQI LPDMLCKGLS HDELNLDSKV LSLSYNSGSR QENWSLSCVS HNEMQRQNLH     360
YDAVIMTAPL CNVKEMDVMK GGQPFQLNFL PEIKYMPLSV IITTFTKEKV KRPLEGFGVL     420
IPSKEQHGF KTLGTLFSSM MFPDRCPSDL HLYTTFIGGS RNQELAKAST DELKQVVTSD     480
LQRLLGEGE PEFVNHYYWR KAFPLYDSSY DSVMEAIDKM EKDLPGFFYA GNHRGGLSVG     540
KSIASGCKAA DLVISYLESC SNDKKPEDS                                      569

SEQ ID NO: 36                   moltype = AA  length = 544
FEATURE                         Location/Qualifiers
source                          1..544
                                mol_type = protein
                                organism = Brachypodium sp.
SEQUENCE: 36
MLTSATASPS ASTRFSSTCR PCRSDSVPAR RPRPVLAMAA SDDPRAAPAR SVAVVGAGVS      60
GLVAAHRLRK SGVRVTVFEA DDRAGGKIRT NSDSGFLWDE GANTMTESAL EASRLIDDLG     120
LQDKQQYPNS QHKRYTVKDG APTLIPSDPI ALMKSTVLST KSKFKLFLEP FLYEKSHTRN     180
SQKVSDNHLS ESVGSFFERH FGKEVVDYLI DPFVAGTSAG DPESLSIRHA FPGLWDLEKK     240
YGSIIVGAIL SKLTAKGDST KKADTSSGKG RNKQASFSFH GGMQTLVEGL HKDVGDGNVK     300
LGTQVLSLAC SCDRLSASDG WSISVNSKDA SSKLAAKNQL FDAVIMTAPL SNVQRMKFTK     360
GGVPFVLDFL PKVDYLPLSL MVTAFRKEDV KRPLEGFGVL IPYKEQQKYG LKTLGTLFSS     420
MMFPDRAPND QHLFTTFVGG SHNRDLAAAP TAILKQLVTS DLRKLLGVEG QPTFVKHVHW     480
KNAFPLYGHD YDLALEAIGK MENELPGFFY AGNNKDGLAV GNVIASGSKT ADLVISYLES     540
HQAR                                                                 544

SEQ ID NO: 37                   moltype = AA  length = 506
FEATURE                         Location/Qualifiers
source                          1..506
                                mol_type = protein
                                organism = Oryza sp.
SEQUENCE: 37
MAASDDPRGG RSVAVVGAGV SGLAAAYRLR KRGVQVTVFE AADRAGGKIR TNSEGGFIWD      60
EGANTMTESE LEASRLIDDL GLQGKQQYPN SQHKRYIVKD GAPTLIPSDP IALMKSTVLS     120
TKSKLKLFLE PFLYEKSSRR TSGKVSDEHL SESVIFLCIC RDNQVVDYLI DPFVAGTSGG     180
DPESLSIRHA FPALWNLENK YGSVIAGAIL SKLSTKGDSV KTGGASPKGK RNKRVSFSFH     240
GGMQSLIDAL HNEVGDGNVK LGTEVLSLAC CCDGVSSSGG WSISVDSKDA KGKDLRKNQS     300
FDAVIMTAPL SNVQRMKFTK GGVPFVLDFL PKVDYLPLSL MVTAFKKEDV KKPLEGFGAL     360
IPYKEQQKHG LKTLGTLFSS MMFPDRAPND QYLYTSFIGG SHNRDLAGAP TAILKQLVTS     420
DLRKLLGVEG QPTFVKHVHW RNAFPLYGQN YDLVLEAIAK MENNLPGFFY AGNNKDGLAV     480
```

```
GNVIASGSKA ADLVISYLES CTDQDN                                             506

SEQ ID NO: 38           moltype = AA  length = 494
FEATURE                 Location/Qualifiers
source                  1..494
                        mol_type = protein
                        organism = Picea sp.
SEQUENCE: 38
MAEHIHTDQN DKRPLKSVAV VGAGISGLAA AYRLKSQGLA VTIFEADGTT GGKIKSFAQN         60
GLIWEKGANT MTETEPEVGK LIDDLGIRGK QQFPIMQSKR YIVRDGKPQL LPSNPVAFIG        120
SKTLSAQAKL NIFLEPILWK HKNSKEKTPN SPDIYQEESV GDFFRRHFGQ EVVDYIVDPF        180
VAGTAGADAE SLSIRHMFPE IWDLEERFGS IITGAIKSSW SRKKAQRDAK HVTHGQKRQR        240
GSFSFMGGLQ TLTNALSKKL GEESLRMHCS VLSLSCNLQG NPPHNNWSVC YARNDASYKE        300
PLKEQSFDAV VMTVTYLPMS IIITTFKKQD VKHPLEGFGI LVPSKEEKNG FQTLGTLFSS        360
NMFPDRAPTD QYLFTTFIGG NRNRKLAKSQ LKDLQEVAVN DLNKILGVGS DPLSVKHIYW        420
NEAFPLYSLD YNSVVAAIDK LGKSLPGIYF AGNYRGGLSV GKALTSGFKA ADLAISDFNS        480
KGLCTMIGTD HEVK                                                         494

SEQ ID NO: 39           moltype = AA  length = 404
FEATURE                 Location/Qualifiers
source                  1..404
                        mol_type = protein
                        organism = Solanum sp.
SEQUENCE: 39
MAPSAGEDKQ NCPKRVAVIG AGVSGLAAAY KLKIHGLNVT VFEAEGRAGG KLRSLSQDGL         60
IWDEGANTMT ESEGDVTFLL DSLGLREKQQ FPLSQNKRYI ARNGTPTLIP SNPIDLIKSN        120
FLSTGSKLQM LFEPLLWKNN KLTKVSDEHE SVSGFFQRHF GKEVVDYLID PFVAGTCGGD        180
PDSLSMHLSF PELWNLEKRF GSVIVGAIRS KLSPIKEKKQ GPPKTSVNKK RQRGSFSFLG        240
GMQTLTDAIC KDLKEDELRL NSRVLELSCS CSGDSAIDSW SIFSASPHKR QAEEESFDAV        300
IMTAPLCDVK SMKIAKRGNP FLLNFIPEVD YVPLSVVITT FKKESVKHPL EGFGVLVPSQ        360
EQKHGLKTLG TLFSSMMFPD RAPNNVYLYT TFVGGSRNRE LAKA                         404

SEQ ID NO: 40           moltype = AA  length = 549
FEATURE                 Location/Qualifiers
source                  1..549
                        mol_type = protein
                        organism = Oryza sp.
SEQUENCE: 40
MLSPATTFSS SSSSSSPSRA HARAPTRFAV AASARAARFR PARAMAASDD PRGGRSVAVV         60
GAGVSGLAAA YRLRKRGVQV TVFEAADRAG GKIRTNSEGG FIWDEGANTM TESELEASRL        120
IDDLGLQGKQ QYPNSQHKRY IVKDGAPTLI PSDPIALMKS TVLSTKSKLK LFLEPFLYEK        180
SSRRTSGKVS DEHLSESMFS DQREYICSVI FLCICRDNQV VDYLIDPFVA GTSGGDPESL        240
SIRHAFPALW NLENKYGSVI AGAILSKLST KGDSVKTGGA SPGKGRNKRV SFSFHGGMQS        300
LIDALHNEVG DGNVKLGTEV LSLACCCDGV SSSSGGWSISV DSKDAKGKDL RKNQSFDAVI        360
MTAPLSNVQR MKFTKGGVPF VLDFLPKVDY LPLSLMVTAF KKEDVKKPLE GFGALIPYKE        420
QQKHGLKTLG TLFSSMMFPD RAPNDQYLYT SFIGGSHNRD LAGAPTAILK QLVTSDLRKL        480
LGVEGQPTFV KHVHWRNAFP LYGQNYDLVL EAIAKMENNL PGFFYAGKSM KAPLLYKRNL        540
RYLKHIPVD                                                               549

SEQ ID NO: 41           moltype = AA  length = 549
FEATURE                 Location/Qualifiers
source                  1..549
                        mol_type = protein
                        organism = Oryza sp.
SEQUENCE: 41
MLSPATTFSS SSSSSSPSRA HARAPTRFAV AASARAARFR PARAMAASDD PRGGRSVAVV         60
GAGVSGLAAA YRLRKRGVQV TVFEAADRAG GKIRTNSEGG FIWDEGANTM TESELEASRL        120
IDDLGLQGKQ QYPNSQHKRY IVKDGAPTLI PSDPIALMKS TVLSTKSKLK LFLEPFLYEK        180
SSRRTSGKVS DEHLSESMFS DQREYICSVI FLCICRDNQV VDYLIDPFVA GTSGGDPESL        240
SIRHAFPALW NLENKYGSVI AGAILSKLST KGDSVKTGGA SPGKGRDKRV SFSFHGGMQS        300
LIDALHNEVG DGNVKLGTEV LSLACCCDGV SSSSGGWSISV DSKDAKGKDL RKNQSFDAVI        360
MTAPLSNVQR MKFTKGGVPF VLDFLPKVDY LPLSLMVTAF KKEDVKKPLE GFGALIPYKE        420
QQKHGLKTLG TLFSSMMFPD RAPNDQYLYT SFIGGSHNRD LAGAPTAILK QLVTSDLRKL        480
LGVEGQPTFV KHVHWRNAFP LYGQNYDLVL EAIAKMENNL PGFFYAGKSM KAPLLYKRNL        540
RYLKHIPVD                                                               549

SEQ ID NO: 42           moltype = AA  length = 405
FEATURE                 Location/Qualifiers
source                  1..405
                        mol_type = protein
                        organism = Eutrema sp.
SEQUENCE: 42
MAPDAVADHD KKFEALSGKR VAVVGAGVRL KSRGLNVTVF EADGRAGGKL RSVMHKGLIW         60
DEGANTMTEA EPEVGSLLDD LGLREKQQFP ISQKKRYIVR NGLPVMIPTN PIALVTSSVL        120
STHSKFQILL EPFLWKKNDS SSKVSDASTV ESVSGFFQRH FGQEVVDYLI DPFVGGTSAA        180
DPDSLSMKHT FPDLWNIEKS FGSIIVGAIR TKFAAKGGKS GETRTSPGTK KGSRGSFSFK        240
GGMQILPDML CKDLSHDELN LDSKVLSLSY NSGSRQENWS LSCVSHNETL RQNLHYDAVV        300
MTAPLCNVKE MKVVGGQPF QLNFIPEIKY MPLSVIITTF TKEKVKRPLE GFGVLIPSKE        360
EKHGFKTLGT LFSSMMFPDR CPSDLHLYTT FVGGSRNQEL AKAST                        405
```

```
SEQ ID NO: 43           moltype = AA  length = 520
FEATURE                 Location/Qualifiers
source                  1..520
                        mol_type = protein
                        organism = Selaginella sp.
SEQUENCE: 43
MAMAEGETAP VLGSVAVVGA GASGLAAAYR LRAAGVSVTV YEAENSIGGK LKSVSENGFI    60
WEKGPNTMTE NDPSISRMFD DLHLRDKQQF PVEQKKRYIV RNASPTMLPS NPLGFITTGL   120
FSAQAKLKLL TEPFSWKRTK AESNEDESVG AFMERHFGDE IVDYAVDPFV AGTSGSDPSS   180
ISIRHSFPEL WSLEKNYGSL FVGAIKSGFS KKKKQKLRPV EFEDEDSDFP ARTRPRRGGS   240
FSFVGGMQTL ANELVSRIGK EKFKLNTFVT GLACNQQGNP SRQSWTVTGL ETSGKRSKRS   300
DKTFDAVIMT APVDDVRAMK VVKDGKPYAL DYLPTVIYEP MSVLITMFNK DSVKRALPGF   360
GVLVPSKEQQ ANGFQTLGTL FSSFMFPDRA PEDQLLFTTF IGGSRNTLLA SRSKEELLDI   420
TLKDLSRLIG VEGQPTAIRH VYWEKAFPRY SIGYDNVLHS IQKLESDLPG LFYAGNHRGG   480
LAVGKTIVSG LDAAEQVLQY LQGSGGKKVF TMASLEQPVS                        520

SEQ ID NO: 44           moltype = AA  length = 514
FEATURE                 Location/Qualifiers
source                  1..514
                        mol_type = protein
                        organism = Selaginella sp.
SEQUENCE: 44
MAMAEGETVP VLGSVAVVGA GASGLAAAYR LRAAGVSVTV YEAENSIGGK LKSVSENGFI    60
WEKGPNTMTE NDPSISRMFD DLHLRDKQQF PVEQKKRYIV RNASPTMLPS NPLGFITTGL   120
FSAQAKLKLL TEPFSWKRTK AESNEDESVG AFMERHFGDE IVDYAVDPFV AGTSGSDPSS   180
ISIRHSFPEL WSLEKNYGSL FVGAIKSGFS KKKKQKLRPV EFEDEDSDFP ARTRPRRGGS   240
FSFVGGMQTL ANELVSRIGK EKFKLNTFVT GLACNQQGNP SRQSWTVTGL ETSGKRSKRS   300
DKTFDAVIMT APVDDVRTMK VVKDGKPYAL DYLPTVIYEP MSVLITMFNK DSVKRALPGF   360
GVLVPSKEQQ ANGFQTLGTL FSSFMFPDRA PEDQLLFTTF IGGSRNTLLA SRSKEELLDV   420
TLKDLSRLIG VEGQPTAMRH VYWEKAFPRY SIGYDNVLNS IQKLESDLPG LFYAGNHRGG   480
LAVGKTIVSG LDAAEQVLQY LQGSGGKKVF TMAS                              514

SEQ ID NO: 45           moltype = AA  length = 230
FEATURE                 Location/Qualifiers
source                  1..230
                        mol_type = protein
                        organism = Amaranthus sp.
SEQUENCE: 45
MVIQSITHLS PNLALPSPLS VSTKNYPVAV MGNISEREEP TSAKRVAVVG AGVSGLAAAY    60
KLKSHGLSVT LFEADSRAGG KLKTVKKDGF IWDEGANTMT ESEAEVSSLI DDLGLREKQQ   120
LPISQNKRYI ARDGLPVLLP SNPAALLTSN ILSAKSKLQI MLEPFLWRKH NATELSDEHV   180
QESVGEFFER HFGKEFVDYV IDPFVAGTCG GDPQSLSMHH TFPEVWNIEK             230

SEQ ID NO: 46           moltype = AA  length = 229
FEATURE                 Location/Qualifiers
source                  1..229
                        mol_type = protein
                        organism = Amaranthus sp.
SEQUENCE: 46
MVIQSITHLS PNLALPSPLS VSTKNYPVAV MGNISEREEP TSAKRVAVVG AGVSGLAAAY    60
KLKSHGLSVT LFEADSRAGG KLKTVKKDGF IWDEGANTMT ESEAEVSSLI DDLGLREKQQ   120
LPISQNKRYI ARDGLPVLLP SNPAALLTSN ILSAKSKLQI MLEPFLWRKH NATELSDEHV   180
QESVGEFFER HFGKEFVDYV IDPFVAGTCG DPQSLSMHHT FPEVWNIEK               229

SEQ ID NO: 47           moltype = AA  length = 396
FEATURE                 Location/Qualifiers
source                  1..396
                        mol_type = protein
                        organism = Zea sp.
SEQUENCE: 47
MKSSVLSTKS KIALFFEPFL YKKANTRNSG KVSEEHLSES VGSFCERHFG REVVDYFVDP    60
FVAGTSAGDP ESLSIRHAFP ALWNLERKYG SVIVGAILSK LAAKGDPVKT RHDSSGKRRN   120
RRVSFSFHGG MQSLINALHN EVGDDNVKLG TEVLSLACTF DGVPALGRWS ISVDSKDSGD   180
KDLASNQTFD AVIMTAPLSN VRRMKFTKGG APVVLDFLPK MDYLPLSLMV TAFKKDDVKK   240
PLEGFGVLIP YKEQQKHGLK TLGTLFSSMM FPDRAPDDQY LYTTFVGGSH NRDLAGAPTS   300
ILKQLVTSDL KKLLGVEGQP TFVKHVYWGN AFPLYGHDYS SVLEAIEKME KNLPGFFYAG   360
NNKDGLAVGS VIASGSKAAD LAISYLESHT KHNNSH                            396

SEQ ID NO: 48           moltype = AA  length = 414
FEATURE                 Location/Qualifiers
source                  1..414
                        mol_type = protein
                        organism = Aegilops sp.
SEQUENCE: 48
MTESALEASR LIDDLGLEDR LQYPNSQHKR YTVKDGAPAL FKLFLEPFLY EKSSTRNSKK    60
VSDEHLRESV GSFFERHFGR EVVDYLIDPF VAGTSAGDPE SLSIRHAFPG LWNLEKKYGS   120
LIVGAILSKL TAKGDSSKKG GASSGKGRSK RASFSFHGGM QTLVDALHKE VGDSNVKLGT   180
QVLSLACNCD ELSASDGWSI FVDSKDASSK ELAKNQSFDA VIMTAPLSNV QRMRFTKGGA   240
```

```
PFVLDFLPKV   DYLPLSLMVT   AFKKEDVKRP   LEGFGVLIPF   KEQQKHGLKT   LGTLFSSMMF    300
PDRAPNDQYL   FTTFIGGSHN   RDLAGAPTAI   LKQFVTSDLT   KLLGVVGQPT   FVKHIHWRNA    360
FPLYGHDYDS   ALEAIGKMER   NNKDGLAVGN   VIASGSNTAD   LVISYLESGI   KQVS          414

SEQ ID NO: 49            moltype = AA   length = 304
FEATURE                  Location/Qualifiers
source                   1..304
                         mol_type = protein
                         organism = Genlisea sp.
SEQUENCE: 49
GPPAKNVAVI   GAGVSGLSAA   YKLKLNGLNV   TVFEADGRAG   GKIRTSSQDS   LIWDEGANTM    60
TESEEEVGFL   LDNLGLREKQ   QFPLSQQKRY   VVKNGKPALL   PSNPFALIAS   NILSSSSKLQ    120
IFLEPFLWKQ   RNSEETQAEE   SVGGFFQRHF   GKEVVDYLVD   PFVAGTSGGD   PESLSMRHAF    180
PDLWNLEKRF   GSVMSGAVLS   KLSAGRGASE   KNKGSSTNER   RKRKSFSFIG   GMQTLTDALS    240
NEIGENELKL   RSKVLGLSSN   NVKSSKVDSW   SISYASSDGK   SVSLDTGFDA   VIMTAPLSDV    300
KQMK                                                                          304

SEQ ID NO: 50            moltype = AA   length = 265
FEATURE                  Location/Qualifiers
source                   1..265
                         mol_type = protein
                         organism = Amborella sp.
SEQUENCE: 50
MSSKGEEKGK   HEATRRKPKH   QRGSFSFQGG   LQTLTDKLAE   ELGNENVKLH   SKVLSLSYGD    60
GNGDSFSNWS   VSYIKNQSDQ   RKLLLKQSFD   AVVMTAPIRN   MQEMQISKCG   KPYMLDFLPN    120
VMYLPLSIIV   TTFKKENVKL   PLEGFGVLVP   SKEQGSGLRT   LGTLFSSMMF   PDRAPKDQYL    180
YTTFVGGSRN   RNLASASLDE   LREVVTCDLK   KLLGVVGAPT   FVRHVYWGDA   FPLYGHNYDM    240
VLKAIEKMEQ   NLPGFFYAGK   FSLWC                                               265

SEQ ID NO: 51            moltype = AA   length = 469
FEATURE                  Location/Qualifiers
source                   1..469
                         mol_type = protein
                         organism = Rhodothermus sp.
SEQUENCE: 51
MASVGIIGAG   IAGLTAAYEL   HRRGLEVTVF   EATDRIGGFI   QSERIDGFLV   ELGPQTLQRT    60
SGDFEELLRQ   VDLEDACIPA   RPVAANRFIV   RGGQPIPLPR   SPRELLRTPL   LSPRARLRLL    120
AEPFIHRAHR   STEESVAKFT   RRRLGPEVLD   YLVEPFVAGI   FAGDPEQLSR   RYAFPKLFEL    180
EQQYGSLFWG   LIRDRMKQRY   HPAPRRSMFS   FVEGLHMLPR   ALAERLPAHA   IVRNAEVLAI    240
RWDEKNPWTL   TFRQHGRAST   RFFDIIVCAV   PLHRLAQLRI   HPPVDRRPLS   TVEHPPIALV    300
ALGFRREQVA   HPLDGFGMLV   PAVERDFQIL   GTLFSSSLFP   DRAPEGHVLL   TTFVGGMRHP    360
ELALLPEDRL   EALVLQDLRR   LLGISGAPVF   RHVWRWERSI   PQYRLGYDAV   LACVHDVEMS    420
RSGLFLAGNY   MEGISVIDAL   HTGLKAARAI   IQHLREEAAG   GLAKLVLGD                  469

SEQ ID NO: 52            moltype = AA   length = 461
FEATURE                  Location/Qualifiers
source                   1..461
                         mol_type = protein
                         organism = Salinibacter sp.
SEQUENCE: 52
MPNVGIIGAG   ISGLAAAYRL   QEHGHSVRLL   EASGHTGGVI   RSESSEGFLV   EHGPNSIRAG    60
AAGLETLIDA   LDLHEDRVWA   NDAADTRYVV   RDGRPTPLPR   SVGSFLTTDL   FSTRAKLRLL    120
AEPFIGRAAA   EEEESVARFTE  RRLGPEVLNY   AVAPFVGGVF   AGRPDDLSVQ   HAFRRLAALE    180
EESGSLLLGA   IRRALTSDDG   APPDTPSGLF   SFRNGLQTLP   NALADTLGDR   IRLNAPVHAL    240
AHDGTAWRVT   VSPPDAPAHT   RSFDALVCTV   PLHRLAAMEI   DTPVDLAPLG   EVTYPPLSVL    300
ALGYGRDAID   HALDGFGMLV   PPVEDTLDVL   GTIFSSTLFP   GRAPEGHVLL   TTFVGGARAP    360
HHATSDAAAL   QARVARDLDS   LLGVDASPVF   RRLVHWPHAI   PQYELGYGTV   KDTFDALEAA    420
HPHLAFAGNY   RAGVSVGDAL   TSGLEAADRL   LETDERAAQP   H                         461

SEQ ID NO: 53            moltype = AA   length = 461
FEATURE                  Location/Qualifiers
source                   1..461
                         mol_type = protein
                         organism = Salinibacter sp.
SEQUENCE: 53
MPNVGIIGAG   ISGLAAAYRL   QEHGHSVRVL   EASGHTGGVI   RSESSEGFLV   EHGPNSIRAG    60
AAGLETLIDA   LDLHEDRVWA   NDAADTRYVV   RDGRPTPLPR   SVGSFLTTDL   FSTRAKLRLL    120
AEPFIGRAAA   EDESVARFTE   RRLGPEVLNY   AVAPFVGGVF   AGRPDDLSVQ   HAFRRLAALE    180
EESGSLLLGA   IRRALTSDDG   APPDTPSGLF   SFRNGLQTLP   NALADTLGDR   IRLNAPVHAL    240
THDGTAWRVT   VSPPDAPAHT   RSFDALVCTV   PLHRLAAMEI   DTPVDLAPLG   EVTYPPLSVL    300
ALGYERDAID   HALDGFGMLV   PPVEDTLDVL   GTIFSSTLFP   GRAPEGHVLL   TTFVGGARAP    360
HHATSDAAAL   QARVARDLDS   LLGVDASPVF   RRLVHWPHAI   PQYELGYGTV   KDTFDALEAA    420
HPHLAFAGNY   RAGVSVGDAL   TSGLEAADRL   LETDERATQP   H                         461

SEQ ID NO: 54            moltype = AA   length = 203
FEATURE                  Location/Qualifiers
source                   1..203
                         mol_type = protein
                         organism = Zea sp.
```

```
SEQUENCE: 54
MTAPLSNVRR MKFTKGGAPV VLDFLPKMDY LPLSLMVTAF KKDDVKKPLE GFGVLIPYKE    60
QQKHGLKTLG TLFSSMMFPD RAPDDQYLYT TFVGGSHNRD LAGAPTSILK QLVTSDLKKL   120
LGVEGQPTFV KHVYWGNAFP LYGHDYSSVL EAIEKMEKNL PGFFYAGNNK DGLAVGSVIA   180
SGSKAADLAI SYLESHTKHN NSH                                          203

SEQ ID NO: 55            moltype = AA  length = 469
FEATURE                  Location/Qualifiers
source                   1..469
                         mol_type = protein
                         organism = Rhodothermus sp.
SEQUENCE: 55
MASVGIIGAG IAGLAAAYEL HRRGLEVTVF EATDRIGGFI QSERIDGFLV EHGPQTLQRT    60
SGDFEELLRQ VDLEDACITA RPIAANRFIV RGGRPIPLPR SPRELLRTPL LSPRARLRLL   120
AEPFIHRAHR STEESVAKFA RRRLGPEVLD YLVEPFVAGI FAGDPEQLSV RYAFPKLFEL   180
EQQYGSLFWG LIRDRMKQRY HPAPRRSMFS FVEGLHMLPR ALADRLPAHA IVRNAEVLAI   240
RWDEKNPWTL TFRQHGRAST RFFDIIVCAV PLHRLAQLRI HPPVDRRPLS TVEHPPIALV   300
ALGFRREQVA HPLDGFGMLV PAVERDFQIL GTLFSSSLFP DRAPEGHVLL TTFVGGMRHP   360
ELALLPEDRL EALVLQDLRR LLGISGAPVF RHVWRWERSI PQYRLGYDAV LACVHDVEMS   420
RSGLFLAGNY MEGISVIDAL HTGLKAARAI IQHLREEAAG GLAKLVLGD               469

SEQ ID NO: 56            moltype = AA  length = 453
FEATURE                  Location/Qualifiers
source                   1..453
                         mol_type = protein
                         organism = Caldithrix sp.
SEQUENCE: 56
MTVAVIGAGI SGLTTAYYLK QQGVDVQVFE KNNYIGGSVI TEKKDGFLID LGPNSTLETS    60
QVLRQLIDQI GLQSQKVYAS DVSNKRYVVR DGLLHALPLS PPAFIKTKLF SWKAKLQLLK   120
EPFLPKVEVD DISLADYVRY RLGDEFLDYA INPFVAGVVG GDPEQLSAPA AFPKLYNLEQ   180
NYGSFIKGAI KGKRERKKRQ EVAKDRAKMF SFDLDGMQVFP QALARQLGEV IHLNCEVREV   240
IPHGKGPKVV LEQDSGEQEC FFERVVISVP TYVQAKILNS ILKERAALLA DVLHPPIAVV   300
FMGFKRDDVA HALDGFGFLL PAKEKKQILG SIFSSTIFPQ RAPQGKVAFT TFVGGMRNPD   360
NALKDDEEIK ELVLKDLNDL VGLHGQPVLT RIRRWPRAIP QYTLGYKKIQ ALFDELEQEF   420
SGLFFAGNFR RGISVGDSVL SAFETSEKML KEK                                453

SEQ ID NO: 57            moltype = AA  length = 467
FEATURE                  Location/Qualifiers
source                   1..467
                         mol_type = protein
                         organism = Opitutus sp.
SEQUENCE: 57
MSTSPFNPSA TASGRPPKTF AVLGAGITGL TAAHRLTQLG HKVRVFEQSD RVGGSIKTEE    60
VDGWLIEGGP NTLLSGELAV DKLIDELGLN GERIAADPAA KNRYIVRRGR ALAAPMSPPS   120
FFASSLFSPV AKFKLLAELF ARRRVRTTDV SLAEFVESHF GREFVDYALN PFVGGVYAGD   180
PEKLSARQSF PKLWEIEQTH GSLIRGQIAA AKARKARGEP RPGIFSFKHG LHVLPEALAA   240
RLPAGAITLG ASLDAIVPGD KWNVVWHDDV ATHTQSFDSV VVALPAPALA RLQIGTLGEK   300
PLAALALIEH PPVSSLFLGF RREQVAHPLD GFGVLVPAVE KRSVLGVLFS SSLFPGRAPL   360
GHVALTVMVG GTRQPQLASL PADQLLAAVR PDLTQLLGVS GDPVFRHNF WPRAIPQYNL    420
GHEHFIAALA AGERFHPGLF MGGQARDGIA VPACIAAGEK LAERAGQ                 467

SEQ ID NO: 58            moltype = AA  length = 455
FEATURE                  Location/Qualifiers
source                   1..455
                         mol_type = protein
                         organism = Verrucomicrobia sp.
SEQUENCE: 58
MGNPNKTIAI LGGGITGLTA AYELLKLGHK PTVFESSSRI GGAIETIRQN DFLAECGPNT    60
LLETSPRISA LISDLGLDSR KRYANPSMKN RYIIKGGKPV PMPLSPGQFV TTKLFSLGAK   120
LNLIKEPFIA PCPSETEESL AAFVRRLGQ EFLDYAINPF VAGVYAGDPS KLSVQHAFPK    180
LYALEQQYGS MIKGQFFGAR ERKKRGTVSK DKAKLVSFDQ GLEVLVDDLG QKIEDTINIS   240
TVIESVEKAE EKWVVQGRKI RESFDAVITA IPTHRMTKMT FRDESDLDMS ILRDIIYPPV   300
SSVVMGFRRD QIQHSLEGFG MLVPKVERKN ILGTIFSSSL FENRAPEGYV TLSTYIGGMR   360
QPDHALLDDQ EMDRLILKDL EALLGVRGEP AFINRRVWKK AIPQYTVGYG KILDRFNELE   420
AAHSGLFFAG HYRNGISLGD SILAGLDVAQ RINQQ                              455

SEQ ID NO: 59            moltype = AA  length = 462
FEATURE                  Location/Qualifiers
source                   1..462
                         mol_type = protein
                         organism = Ignavibacterium sp.
SEQUENCE: 59
MTKTIVVIGA GISGLTTAYL LSKRGFNIRI LERKSEVGGS IESIKENGFL FDRGPNSALE    60
TTPLISQLVE ELNLKDELLY ANKAANKRYI LRNNELHALP MSPPALIKTK LFSAKAKLRL   120
LTEPFIGRSE DGYYQSLAEF VRRRLGQEFL DYAINPFVAG VYAGKPEELS VKSAFPKLYA   180
LEEKFGGLII GTIRSIRERK KRAEKSKQSA RMLSFKSGMI SLPKAIANYF ADKLILSAEV   240
ISVDKTAEGF IVSYRHSGID EAIVCDAVLS TVPSYVAGNL FSKFDKKFKV HSDEIYYPPV   300
LVYFLAYEKK NIGQTLDGFG FLIPEKENKS FLGALWSSVI FPYRADNNFA TFTLFIGGSR   360
YPDFVKEDRN KLLEKVRKEF EQLMKIKSDP VFSAYRFWEK AIPQYNIGYI EHERFFDEFE   420
```

```
KQNPGLFISG NFRGGISVGD CIKNAELVAN KICVQFTMHN VQ              462

SEQ ID NO: 60           moltype = AA  length = 457
FEATURE                 Location/Qualifiers
source                  1..457
                        mol_type = protein
                        organism = Coraliomargarita sp.
SEQUENCE: 60
MEKKAIVIGA GISGLCAAIE LKKSGFNVTV VEKRERAGGV IGTTARDGFR AESGSNTVMV  60
NSQKTLDFLM EIGLKDKIVN SSPAAKKRFF ARYGKPQAVP MGPLQLLTTR LFSFAGKLRM 120
LCEPFIKPPS QDSDPSVADF TAERFGREVL DYAMNPFMAG IYGADPEKLS IKHAFPPFWN 180
LAIKYGSVIK GAMKARREKM AAGNFFKPVM ISFKSGMHTL TDALAAELGD SVKCGAKVIS 240
IDSNCDGWEV SWGTETEDVC ENYDALVVAV PAPEISGLPF GGMLAAALAP LAKIQYAPVA 300
TYTMGFKRQD VSHPLDGFGV LTPKKENFSI LGSLFVSTLF DDRAPDGYIA LTNYVGGMRH 360
PEFAALERGE MRKLVLEDLK KLLGVNGEPV FEELFVWKNA IAQYNVGYQE YLDIMDDIEK 420
RIPNIALVGA YRGGVGVSSC LENGLLSAAK LAGRISD                         457

SEQ ID NO: 61           moltype = AA  length = 465
FEATURE                 Location/Qualifiers
source                  1..465
                        mol_type = protein
                        organism = Salisaeta sp.
SEQUENCE: 61
MARIGIIGAG IAGLTAAYQL QQQGHMVRVW EARGVAGGAI RSERTSDGFL VEHGPNSLRA  60
TTPIVPRLLE DLGLERARLS AAPAATKRFI VRDGTLRPLP LSPPALLTTS LLSTRAKLRL 120
LREPFVAAGA PTADETVASF VRRRLGPEVL AYAVDPHRLS LKHAFGRLYE 180
MERTHGSLLR AALHSARTGA TDDASTATDR RIFSLRDGLQ MLPHALADAL GEAIRYEAPV 240
TALRQMPDGT WTVATETDAT QVNALISTVP LHALGSIDWA PAVDTSPLQR VPYPPVRVVA 300
LGFRRADVAH PLDGFGMLVP SAEDQFQILG TLVSSTLFPG RAPAGHVLLT TFVGGMRHPT 360
LGAASDAAVR KVVLNDLQAL LGVQGAPVFE RFIAWPRAIP QYTLNHGAAV RTLEQLEDVH 420
PGLFFAGNYR DGISVGDAMA SGEDAARRVD AHLAGADRAV AATGP               465

SEQ ID NO: 62           moltype = AA  length = 179
FEATURE                 Location/Qualifiers
source                  1..179
                        mol_type = protein
                        organism = Ambrosia sp.
SEQUENCE: 62
MASPTIVDNQ KPAKRVAIVG AGVSGCAAAY KLKLHGLNVT VFEADERVGG KPRSVSQDGL  60
IWDEGANTMT ESEADASSLI DELGLRDKQQ FPISQHKRYI VRNGKPVLIP SNPIALIRSS 120
FLSTQSKVQI LLEPFLWKKT KSSDEPESVG GFFQRHFGKE VVEYLIDPVV AGTSGGDPK  179

SEQ ID NO: 63           moltype = AA  length = 451
FEATURE                 Location/Qualifiers
source                  1..451
                        mol_type = protein
                        organism = Melioribacter sp.
SEQUENCE: 63
MSKKIVVLGA GISGLSTAYW LVKKGYDVTI LETKNEPGGS MISRRLDNFL IDYGPNSGLE  60
TTPLIRKLVE EVNLSDKMIY ANAAASKRYI LKNGELIPLP MSPGSFIRTK LFSSGAKFRL 120
MAEPFVSKSD DGYYQSIAEF VRRRLGNEFL DYAIDPFVSG VFAGDPEKLS VKSAFPKLYR 180
LEEVYGGLIK GMIKGARERK QRNEESKQSA KMFSFLEGMQ SLPNAIADKL KDNIVFSAKV 240
LNVTGANDKQ WKVTYELNGN RESITADTVI STLPAYIAAG VFGELDQKLA ERLNSIYYPP 300
VMVLYLGYNK KDIKRKLDGF GFLIPSKEKK HFLGAIWSSS IFPGRSPEDM AAFTLFGGA  360
RSPQLFEMEK SDLIKKVLSE FHQIMNIKGE PVLIENKLWQ KAIPQYNLGY IEHEKYFEVF 420
EENHRGIYLR GNYRGGISVG DCIKNSELEI K                              451

SEQ ID NO: 64           moltype = AA  length = 472
FEATURE                 Location/Qualifiers
source                  1..472
                        mol_type = protein
                        organism = Halothiobacillus sp.
SEQUENCE: 64
MNTHSNASEP INCPYLVIGG GISGLATAYH LSRMGKTVTV LEATSRVGGA VGSIEEDGWL  60
RELGPNSLVQ TPEMAALMSA LDLVSEIIEA NTVAKKRFVA KNGHPVALPG SPLELLTSPL 120
FSMGDLWHLA REAWIKPVNK EETIAEFVRR RLGQGFLDWA VDPFVSGVYA GDPNRLSVQA 180
AIPKIYAFEQ ESGSLIRGGI AKMKAAKANP APVTLPAKGK LFSFKRGLQT LTDALATAIT 240
SSGRGNIQLD SAITNIQRLP EGGWSVKTVQ GKTFHTRQLI LSTPAHVSAQ LLGEVDGPLA 300
ETLAAIEYPP VTSVVMGFDR SEVAHPLDGF GLLLPSKEKK RTLGVLFSST LFPDRTPAGK 360
VLLSAFIGGR KHPEAAQGDD QELLDRVLGD LSPLLGIKGK PEFLRVKRWQ QAIPQYEIGY 420
LELQEKISQR LTALPGLSLN GNWRGGIAVG DCLNNGNKLA ERLIENTRTE ES        472

SEQ ID NO: 65           moltype = AA  length = 480
FEATURE                 Location/Qualifiers
source                  1..480
                        mol_type = protein
                        organism = Chondrus sp.
SEQUENCE: 65
MPEPVKRNVA VLGGGPAGLS AAFRLLHDLP PGLSVKVDLY EATGRLGGAV TSACDAGFCY  60
```

```
ELGPNSMNAK HPSVADLIQE KLRLKPRMLP RSPYAKRYYF MRDGKLVPLP LSPLHFATTG    120
LLSWRAKWHV VKEPFVARLQ DVRDSHMESV ASFFQRRFGR EVVDYLVDPM VAGTYSGKPA    180
DLSMKHALRK VWRLEQKHGS VIGALLRGAG KTKPDPRYKP YTGKELRASF TYDKGMEVVT    240
DALVANINDL NPRGGRLYTH GKVRTLDRDP NGAWRINGRG KYDAVISTIP THAVKSIYTN    300
MSALGKGFKK LNKSIKYAPV SVVVMGFDKS QVPHPLDGFG ALIPTVEGRQ ILGINFSSSN    360
YPQRLSDPDK VFLTVYVGGQ RNPDLPFRRA KEIVDISKKE LGHVLGVKGD PFFSRVKTWK    420
RGIPQYDPQF DESLCTMARA EKSAKGFVFG GNYRDGVGLP DALRSGILSA EKTLQYLKTL    480

SEQ ID NO: 66              moltype = AA   length = 463
FEATURE                    Location/Qualifiers
source                     1..463
                           mol_type = protein
                           organism = Rubritalea sp.
SEQUENCE: 66
MRKHIAIIGA GVSGLSTAYH LQQAGHSVVV FESSKRAGGV IQTIREDDYL CEWGPNSLMI     60
GDKRIEALLK SIGLDDEILE ANTASKKRFI IDRDRLQALP NGPFQLLGSP IFSLKAKLRL    120
LKEPWVKRHP ANSKETLADF MERRLGPEPV AKLVNPFISG IYAGDPKRLA VEHAFPKLFQ    180
LEQDYGSLIW GMIRSKKDQK NSFKSKHKLQ KRRIVSFKQG MEALPQAMAA ALDEGTLIFE    240
AKIGGISQNR NNKRWHMDWK CPNGTIGQGS FDAVILTQAS HHLNDIPLDE EVLESLSKLP    300
SIDHAPVTSM LLGFKREQIK HPLDGFGMLS TFEQKSKMLG ALFTSSLFPG RAPEGHVAIN    360
VMIGGVRRPE LCELPEPTLR ANILDELRRL LGVDGKPSFC HIHHTSKAIP QLHTDYGIVA    420
QQIIDCEREH PGLYLAGSYR NGIALPDRLL EGISLTEKIN QSL                     463

SEQ ID NO: 67              moltype = AA   length = 457
FEATURE                    Location/Qualifiers
source                     1..457
                           mol_type = protein
                           organism = Acidobacterium sp.
SEQUENCE: 67
MGVEVAIIGA GISGLSVAFF LKRAGAGVLV LEAEEDVGGT MRSRRFKGYL IELGPNSALE     60
TTPLFQELIA AAGLAGERVY ASEAARNRYI VRGGELHPLP LTPLAFLRSR LWSWKGKLRV    120
LAEPFHGRAD REESVADFAR RRVGQEFLDY AVNPFVAGIY AGDPERLSVR FAFPRLYALE    180
AQYGGLFLGM LRGARERRRR GEAPKIAARL FSFREGMGAL PRALAAALGN TVWCATRALC    240
VERAGAAFEI AFERDGRRDT LRAERVVLAT PAYAAASLLK RLAPEAARAL DRIVYPPVSA    300
VILGYPETAI GRPLDGFGPL VPEKEQRRIL GTIWNSTIFP ARAPQGFVTL TTFVGGMRQP    360
ELARRPNEEL IALVAEELTD LLRLRGEPEF AYVSRWERAI PQYELGYGEI LDALDRAERE    420
HVGLYFCANY RGGIAVGDCV MSAHATAERI LRDRARS                            457

SEQ ID NO: 68              moltype = AA   length = 441
FEATURE                    Location/Qualifiers
source                     1..441
                           mol_type = protein
                           organism = Coraliomargarita sp.
SEQUENCE: 68
MPDTCIIGAG ITGLATAWQY QRKGKDCVVL ESGPQVGGAI QSILQDGYLA EEGPNSIQLN     60
SLEIEDFLTS IPGLEAQIIE ANPAAQKRYI VRKGRLRAVP MNPLQAITTQ LWSIAGKLRV    120
LREPFIKAAP PEPDQSVADF VTRRLGKELY DYAINPLVGG IYAGKPEMLS LRYGFPKLYA    180
LEQEHGGLIR GALAKMKAAK ANKGPKAKKY ILSFKDGLQT LPQSIANNLN EPVQTGVSIE    240
SIRQIEDMWA VRWNGQVKAF KELIVTVPAH KLPGLPFEEP IRLPAIDYPP VSVISLGYPL    300
SAIKQPLDGF GALVPEREDR NILGVLFPSA VFDGRAPEGH GLLTVFVGGS RSPECSSPDT    360
DQLLKTIQPD LETLLGIQDE PSFVHHKHWP MAIPQYTLGY EKVLEAITRI EQQYIGLKLA    420
GNYRTGISLS YCLESAIAST N                                             441

SEQ ID NO: 69              moltype = AA   length = 474
FEATURE                    Location/Qualifiers
source                     1..474
                           mol_type = protein
                           organism = Oscillochloris sp.
SEQUENCE: 69
MNSYDVVVVG AGISGLSAAY TLFKRGLDVL VVEAGAEVGG VMRSIVTPEG YVLDCGPNTL     60
ASKDPRMWAE FDDLGMRDRL VVAGRAGKRR YFLKDGQPLE IPNDPIGLLR MEHVSMQAKL    120
RVLREPFIPR ATSPDESVAS FFSRRIGPEV MERMIDPFVS GVYSGDPSKM SIKATFPSLW    180
EAEQRGGSII KGFLTAGKAK KAAGEKKAKP IGPKMRSVTF NFKGGVAEWP KTIAKVLGDQ    240
RVWKNARVTT LYPESTGWTL VVERDGQVET IEAASVIMAA PAYAAADLIA ELDPAAAKGL    300
RGIRYSSMAV VNLGYRENQV TRPVNGFGVL APSCERRNFL GILSASTLFP PFAPAGRVLT    360
INLMGGEINP IRPEQSDDEL IARAIADNQA VIGANGAPEV VNLTRWPRAV AQYNFGHTEA    420
MAALENLERT RPGIYFVGSY RGGVGMPKCW RNGVNMAERV ATYLKTRSAV ASLR          474

SEQ ID NO: 70              moltype = AA   length = 474
FEATURE                    Location/Qualifiers
source                     1..474
                           mol_type = protein
                           organism = Opitutaceae sp.
SEQUENCE: 70
MPVAVIGGGI TGLTAAWRLA REGHPVRLFE ASPRPGGLIR SERDGEWLSE AGPNSLLDNK     60
PELAAALLAEL GLEDARQYAQ PAAKKRFIVR RGRPLAAPSS PVSAVTTPLL SLRGKLRIFG    120
DLFWRPRPRA EDLPLGEFAA AHFGRELADY AVDPFVSGIY AGDPQRLSAR YAFPLLWELE    180
QKHGSLIRGG IAAAKARRAT RPAGPAEKPR PPRARIFSFA EGLETIPAAL AERLPAGCVE    240
TGARVVRLVP PVARGGAWEV VWERKDEKDE KGASGVEGRL TERVAAVILA LPGEALARLE    300
```

```
IGANGEHPLA  ALAEVEYPPV  ASLFIGYRRE  QARHPLDGFG  MLAPSKENRN  LLGVLFSSTL   360
FPGRAPAGHI  ALTVLAGGVR  RPELARMELP  SLMGIVRAEL  LELLGVSGDP  VYVKHRVTPH   420
AIPQYNLGYG  RFHTVIETAE  TAHPGLLVGG  PVRDGIAVSA  CVAAGEKLAR  RVVA         474

SEQ ID NO: 71               moltype = AA  length = 239
FEATURE                     Location/Qualifiers
source                      1..239
                            mol_type = protein
                            organism = Amborella sp.
SEQUENCE: 71
STKSVAVVGG  GVSGLTTAYR  LKSHGLNVTL  YESEGTAGGR  IRSIAYGGLI  WEEGANTMTE    60
SEMEVKRLID  DLGLREKQQF  PISQNKRFIA  RNGTPVLIPS  NPLALFGSKL  LSPHSKLRVI   120
LEPLFWRSSN  RKGDISKVSD  QNLQESVGDF  FQRHFGQEVV  DYLVDPFVAG  TSAADPNSLS   180
VQVTSMSEIC  QNYLQYLGWS  QGPSSQLMTL  TLSPSSVIDQ  MLSERMVTFL  QVMLSPLLM    239

SEQ ID NO: 72               moltype = AA  length = 490
FEATURE                     Location/Qualifiers
source                      1..490
                            mol_type = protein
                            organism = Opitutaceae sp.
SEQUENCE: 72
MSASLPPPPP  PPHTHTQARL  PVAVIGGGIT  GLTAAWRLAR  EGHPVRLFEA  SPRPGGLIRS    60
ERDGEWLSEA  GPNSLLDNKP  ELAALLAELG  LEEARQYAQP  AAKKRFIVRR  GRPLAAPSSP   120
VSAVTTPLLS  LRGKLRIFGD  LFWRPRPRAE  DLPLGEFAAA  HFGRELADYA  VDPFVSGIYA   180
GDPQRLSARY  AFPLLWELEQ  KHGSLIRGGI  AAAKARRATR  PAGPAEKPRP  PRARIFSFAE   240
GLETIPAALA  ERLPAGCVET  GARVVRLVPP  VARGGAWEVV  WERKDEKGAS  GVEGRLTERV   300
AAVILALPGE  ALARLEIGAN  GEHPLAALAE  VEYPPVASLF  LGYRREQVRH  PLDGFGMLAP   360
SKENRNLLGV  LFSSTLFPGR  APAGHIALTV  LAGGVQRPEL  ARMELPSLMG  IVRAELLELL   420
GVSGDPVYVK  HRVTPHAIPQ  YNLGYGRFHT  VIEAAETAHP  GLLVGGPVRD  GIAVSACVAA   480
GEKLARRVVA                                                              490

SEQ ID NO: 73               moltype = AA  length = 474
FEATURE                     Location/Qualifiers
source                      1..474
                            mol_type = protein
                            organism = Chloroflexus sp.
SEQUENCE: 73
MMAGYDSVVI  GGGIAGLAAA  YTLHKRGYRV  LVIESTNRVG  GVIQTITTPE  GYILDCGPNT    60
VGTGDARLWQ  ELIDLGLRER  ITPAAPCSKR  RFILINGTPV  EIPTSPVGLI  TTRLLSWRGK   120
LRVLAEPFIN  RGSTDPDESV  AAFFTRRIGA  EATAHLLDPF  VAGVYAGDPQ  RLSTAAVFPS   180
LWEAAQRSGS  IVRGMLSKPK  PKTQVSEPKM  RSRTFTFRGG  LAEWPRALAQ  ALGAGNVWTE   240
RRVVKLQPRD  SWWEVTIDGV  NGPETLISRS  LIIATPAFTA  ADLIESVDQR  AAGALRGIPY   300
APVAVVHLGF  RRDQISQELS  GFGVLAPSSE  QRQFLGILWT  SSIFPHVAPT  DHVLTTTLSG   360
GAIRPELAER  SDETLIEAAI  RDHHQLLGIR  GQPIFTHVTR  WRTAIAQYTF  GHRERIATLV   420
QLEQRLPTIQ  FAGSYRDGVG  VPKTWASGVQ  AGERIAAALA  AHGTTAVSTE  TASG         474

SEQ ID NO: 74               moltype = AA  length = 462
FEATURE                     Location/Qualifiers
source                      1..462
                            mol_type = protein
                            organism = Leptospirillum sp.
SEQUENCE: 74
MAGFDCDTLV  VGGGVSGLAA  ALTLKNRGVD  VRLLESRGYL  GGAIRTVRED  GYLLEFGPNS    60
LMVRPEDAID  TVLGDPELRA  RIVPASGLSK  NRYVVKAGHL  YPVPLSPWAF  FRTPLLSWRG   120
RRDILSEWKV  PPRTGPPEET  LSHFVRRRLG  EEALDYFVDP  FVKGVYASHP  DLLSVEAAFP   180
LLVRLEREHG  GLLRGALKTF  LKRRKRPSGS  SPRGIFSFAG  GMTDLVEAMG  KRLGEDVGTN   240
VDVIKYTRLE  EGFRVALMYD  ETEYYMTSRR  LILATSAPQA  AELLEGDPDG  PSSELKSIPY   300
APVTIAYAGF  LREQVTHPLD  GFGLLCPTVE  NRKVLGVIFS  SSLFPGRAPE  GKVLLTVFVG   360
GMTGQKLAQA  FDEDLERIVL  KELTELLGVK  GAPSFFRIHR  WEKAIPQLIL  GHGETVRTIR   420
KKLPSGLRLA  GNYLDGISIA  RAFASGVRAA  EELLSEDGGT  PG                      462

SEQ ID NO: 75               moltype = AA  length = 462
FEATURE                     Location/Qualifiers
source                      1..462
                            mol_type = protein
                            organism = Leptospirillum sp.
SEQUENCE: 75
MAGFDCDTLV  VGGGVSGLAA  ALTLKNRGVD  VRLLESRGYL  GGAIRTVRED  GYLLEFGPNS    60
LMVRPEDAID  TVLGDPELRA  RIVPASGLSK  NRYVVKAGHL  YPVPLSPWAF  FRTPLLSWRG   120
RRDILSEWKV  PPRTGPPEET  LSHFVRRRLG  EEADYFVDP   FVKGVYASHP  DLLSVEAAFP   180
LLVRLEREHG  GLLRGALKTF  LKRRKRPSGS  SPRGIFSFAG  GMTDLVEAMG  KRLGEDVGTN   240
VDVIKYTRLE  EGFRVALMYD  ETEYYMTSRR  LILATSAPQA  AELLEGDPDG  PSSELKSIPY   300
APVTIAYAGF  LREQVTHPLD  GFGLLCPTVE  NRKVLGVIFS  SSLFPGRAPE  GKVLLTVFVG   360
GMTGQKLAQA  FDEDLERIVL  KELTELLGVK  GAPSFFRIHR  WEKAIPQLIL  GHRETVRTIR   420
KKLPSGLRLA  GNYLDGISIA  RAFASGVRAA  EELLSEDGGT  PG                      462

SEQ ID NO: 76               moltype = AA  length = 446
FEATURE                     Location/Qualifiers
source                      1..446
```

```
                              mol_type = protein
                              organism = Verrucomicrobia sp.
SEQUENCE: 76
MNTKKVCILG AGLSGISLGL SHENKGNQVT IFEKDLRVGG VLQSIKSEGF LMDYGANTLS    60
IRTKKTVDFL KQYEILEHAM DANQESSKRF IIRKNRIISL PQGPLSFLCS SFLSPVGKLR   120
LCLEPFIGRK KDNGSDETMA EFVERRLGRE VLDYGVNPFI GGVYAARPES LILKYAFPSL   180
HDTELTFGSI FWGMIRGGAQ PSEKISKSRL ISFREGMQEL PNRLAARMHN PPVLGCEIKK   240
IEFKDDVQWC VQGEKHDGKI QKEVFDQIIC TLPSHALDKI EWVGINSSHL LETLTRAYHP   300
PLALVFGYQ  QRQIKHPLDG FGFLVPEKER RKILGTLFSS TLFQNRAPEN SVLLTTYIGG   360
ERNPELCDLP QNEILGHAFR ENQDLLGIEG KPIFEHLKLW PKSIPIPDHT LEDRKKAAST   420
LTLENKGLQI LGAHINGAPL PNCMVL                                       446

SEQ ID NO: 77                 moltype = AA  length = 475
FEATURE                       Location/Qualifiers
source                        1..475
                              mol_type = protein
                              organism = Chloroflexus sp.
SEQUENCE: 77
MMMANYDSVV IGGGIGGLAA AYTLYKRGYR VLVIEAANRV GGVIHSITTP EGFTLDCGPN    60
TIGTNDVRLW QELIDLGLRD RIRPAARCGR RRYILINGTP IEIPSSPVGL ITTRLLSWRG   120
KLRVLGEPFV NIGTPTGEES VAAFFSRRIG HEAVAHLLDP FVAGVYAGDP NQLSAAAVFP   180
SLWEAVQRGG SIVRGMLRRP KQKTLISEPK MRSRTFSFQG GLADWPRAIA RALGTGNVWT   240
GRRAVGLRDL GTYWEVTVDG TGRLETITTR SVIIATPAYV AAELVEALDP AAASALRSIP   300
YAPVSVVHLG FRRDQLSHEL NGFGVLAPSS ERRQFLGILW ASSLFPHVAP PDRVLTITLS   360
GGAIRPEVAE QSEEALIESA IRDNQEVLGI RGQPLLTHVT RWHHAIAQYT LGHRERIATL   420
ERLEQRRPTL QLTGSYRGGI GIPKTWASGV GAGERIAAAL DAQGTTADTL EQARG        475

SEQ ID NO: 78                 moltype = AA  length = 456
FEATURE                       Location/Qualifiers
source                        1..456
                              mol_type = protein
                              organism = Desulfurobacterium sp.
SEQUENCE: 78
MKVAVIGAGI SGLSVAFYLK KGGAEVKVFE KEKTVGGKMK TIHEDGYIIE TGPNGFLDGK    60
PYTLNLVKEL GIESKLYRSS DKARKRFIYT NGRLVRLPES PIAFLASYLL SWKGKLRLVG   120
EFLVPPKKED IDESLSEFAK RRIGEEALEK LLDPMVAGIF AGDPDRLSLK AAFPAIYYLE   180
KQYGGLIKGL IAKMKEAKKS GKKSGPAGPG GVLTSFKGGV KDLIDSLSEF LGDSIETEVE   240
ILGLDRIEKG WKVKYKKENE VFEETFDAIV FSTPAYITAK LLNDLNLELS KLLSEIEYSP   300
ISVVALGFEK KGLGHDLDGF GFLVPRSEKR KILGALWDSS VFPNRAPSGK ALIRVMIGGA   360
RQPELALLPD EELVNIALKE LRRIMKIRHY PEKIKVFKHE KGIPHYTVGH AERVEKIFRL   420
ISKYPGLYLC NNAYTGVGVN DCTKAAEEVA RRILDG                            456

SEQ ID NO: 79                 moltype = AA  length = 455
FEATURE                       Location/Qualifiers
source                        1..455
                              mol_type = protein
                              organism = Desulfurobacterium sp.
SEQUENCE: 79
MKKVAVVGAG VSGLSTAFYI EKFGGDNVSV TIFEKENVPG GKMLTVQKDG FIIETGPNGF    60
LDNKPYTLDL VKDLKIEDRL YRSSDKARKR FVFVNGKLVR LPENPIAFLS SYVMSFKGKL   120
RLAAEYFIPP KKDDSDESLS SFVKRRIGKE ALEKLIDPMA AGIFAGDPDK LSVKAAFPAV   180
WHLEKKYGGL IKGLLAMKKE KKDATAGPGG VLTSFKGGVK DLIDALVANI KGEIHPGTTV   240
KKLIPENGKW KIVYEKDDEI FEESFDKVVL STPSYVAAAL VKNFDEKLAE KLYEIEYSPI   300
AVIAFGFIKK GLGHHLDGFG FLVPRSEGRK ILGVLWDSSV FPNRAPEGKA LIRAMVGGAR   360
QPHLALAGEE EIARMTYKDI KRIMKIRHRP IMTAVFKHPK GIPHYTVGHV EKVNEIFKLA   420
SNHGGLFLNS NAYRGVGVND CVYNSLKTAE MVTSE                             455

SEQ ID NO: 80                 moltype = AA  length = 484
FEATURE                       Location/Qualifiers
source                        1..484
                              mol_type = protein
                              organism = Arthrospira sp.
SEQUENCE: 80
MTNLVDSLIV GAGISGLSLA YSLNREKSVR EPLKVLVTES QNRVGGNITT GRADDFLWEE    60
GPNSFAPTPE LLGLAVDLGL KEELIFADRK LPRYVYWNLM LHPVPMNPPA LLSSELISAR   120
GKLRAALGAI GFVPPPVGAH LSQQGGEETI TQFFDRHLGS EVLERLVQPF VSGVYAGDPQ   180
QLAVRSAFSR IVAAEEAGGG LLPGFVRSRL NKKAPVSTPD PNIPKTRPGE LGSFRYGLQT   240
LPETLASKLG DRVKLNWTID RFYPTDHQTY IAEFSTPDGP QQVEARTLAL MTPAHVSARL   300
LQPLHSPIAT ALSQIPYPPV ACVVLAYPKS ALKQQLKGFG NLIPRHQGIR TLGTIWTSSL   360
FPGRAPESWQ VLSNYIGGAT DPEIGEMDDD QIVAAVHQDL RQILLAEDVP PKVLAVHLWR   420
RAIPQYTLGH QNRLNCIDAG LRSLPGLYLC SNYIDGVSVG DCVRRGQQWA SKIQSHLHDC   480
QTAN                                                               484

SEQ ID NO: 81                 moltype = AA  length = 462
FEATURE                       Location/Qualifiers
source                        1..462
                              mol_type = protein
                              organism = Leptospirillum sp.
SEQUENCE: 81
```

```
MAGFDCDTLV VGGGISGLAA ALTLKNRGVD VRLLESRGYL GGAVRTVREE GYLLEFGPNS    60
LMVRPDDAID AVLGDPELRA RIVAASGLSK NRYVVKSGNL YPVPLSPWAF IRTPLLSWRG   120
RRDILSEWKV PPRTGGPEET LSHFVRRRLG EEALDYFVDP FVKGVYASHP DLLSVEAAFP   180
LLVRLEREHG GLLRGALKTF LKRRKRPSGS APRGIFSFTG GMGDLVEAMG KRLGEDVGTN   240
VDVIKYTRLE EGFRVALMYD ETEYYMTSRR LILATSAPQA AELLEGDPEG PSGELKAIPY   300
APVTIAYAGF LREQITHPLD GFGLLCPTAE NRKVLGVIFS SSLFPGRAPD GKVLLTVFVG   360
GMTGQKLAQT FDEDLERIVL RELTELLGVK GAPAFFRIHR WEKAIPQFIL GHGETVRTIR   420
KKLPSGLRLA GNYLDGISIA RAFGSGVRAA EELLSEDGGT PG                      462

SEQ ID NO: 82           moltype = AA   length = 458
FEATURE                 Location/Qualifiers
source                  1..458
                        mol_type = protein
                        organism = Verrucomicrobia sp.
SEQUENCE: 82
MQDAIILGGG ISGLTAGYLA QKQGQDISVI EKGKIPGGPI SSFREEGYLV ERGPNSLLLP    60
DPWVETFIEE LGLRDQLQET NPIASKRYIV KNGRPEAVPS LPQAVFTPL FSLRGKFGFL   120
LEPFRKKISD RAGSRETVAS FVKRRMGLDF LDYAIDPFVS GVYAGDPNRL ILEHAFPLMR   180
GFERDSGSII RGAIKHKKKQ KREGTAYKKR SISPFKDGLGI LPQTIARKLG NRLWLGSEVV   240
AVNRVEDHWQ VTWKREGENF EGFAKNLLVC LPSHAIKRIA WSERIAAPLR SSPNLEYPAV   300
HSLALGFRRE QIAHALDGFG VLVPSKEPPT ILGALFSSSL YEGRAPDGHC LLTVMLGGIR   360
HPELAALPQD RLLELALRDL RALLGLKGDP SFYRCTSWPR AIPQYTRDFG PWRDTLKSLA   420
EEFPGLHFGG NSVDGIAMGA SILSGKRLAE CLDKDIDV                           458

SEQ ID NO: 83           moltype = AA   length = 446
FEATURE                 Location/Qualifiers
source                  1..446
                        mol_type = protein
                        organism = Verrucomicrobia sp.
SEQUENCE: 83
MNTKKVCILG AGLSGISLGL SHENKGNQVT IFEKDLRVGG VLQSIKSEGF LMDYGGNTLS    60
IRTKKTVDFL KQYEILEHAM DANQESSKRF IIRKNRIISL PQGPLSFLFS SFLSPVGKLR   120
LCLEPFIGRK KDNGSDETMA EFVERRLGRE VLDYGVNPFI GGVYAARPES LILKYAFPSL   180
HDTELTFGSI FWGMIRGGTQ PSEKISKSRL ISPFREGMQEL HPNRLATRMHN PPVLGCEIKK   240
IEFKDDVQWC VQGETRDGKI QKEVFDQVIC TLPSHALDKI EWVGINSSHL LETLTRAYHP   300
PLALALAFQGYQ QRQIKHPLDG FGFLVPEKER RKILGTLFSS TLFQNRAPEN SVLLTTFIGG   360
ERNPELCDLP QNEILGHAFR ENQDLLGIEG NPIFEHLKLW PKSIPIPDHT LEDRKKAAST   420
LTLENKGLQI LGAHINGAPL PNCMVL                                        446

SEQ ID NO: 84           moltype = AA   length = 485
FEATURE                 Location/Qualifiers
source                  1..485
                        mol_type = protein
                        organism = Synechococcus sp.
SEQUENCE: 84
MNPATPEPLN AEVVVIGAGI SGLTLAWRLQ QGLSARGGSP QAVLLAEASS RVGGCISTQS    60
KDGYRWEEGP NSFTPTPALL NLIAEVGLTD QLVLADAKLP RYIYWEGALL PVPLSPAAAL   120
GSRLLSVGGK LRALQGLLGF VPPPPGHEET VRQFFRRQLG SEVAERLVEP FTSGVYAGDP   180
DQLSAVAAFP RVAGLEERYG SLFAGALQAL RQRPQPSPAA IQPPPKRGQL GNLRQGLQQL   240
PEALAQKLGD SLRLGWRALQ LKRAGELYWV GFETPEGSRW VAARQVVLAL PAYEAAALLQ   300
ELNPPASQLL AEILYPPVAV VALAYPQEAL PQPLRGFGHL IPRSQGLRTL GTIWASCLFP   360
ERAPQGYHSF LSFLGGATDA ALARRRGIPP IPALSPEERA QIAHAELSQV LLTRRAEPVY   420
LGERLWPRAI PQYTLGHRQR IAQVQAHLAS QTPGIWVCAN YLDGVALGDC VRRAEALAQQ   480
LLSQV                                                              485

SEQ ID NO: 85           moltype = AA   length = 443
FEATURE                 Location/Qualifiers
source                  1..443
                        mol_type = protein
                        organism = Hymenobacter sp.
SEQUENCE: 85
MTIAILGGGI SGLVVAWQLQ KAGVAYDLFE AETTPGGCLR SVSHPDGYLV ETGPNSLQLS    60
DELLELITEL GLVDEIQDAA AVSKNRYVLR NGRYQQLPST PPALLTNGFF SWKAKFNILR   120
ELRRPAAPLN PTETVDAFFR RRFGPEIVDY AVNPFISGIY AGDPAQLLIH KTFSKVAALE   180
QQYGSVLRGL AKTGGGAGRR RIISLQGGIQ KLTDTLAAKL THHHVRQRVL ALHRTTKGGY   240
QVQTSAGSNG GFSYDAVVLA LPTFAAAPLL APLFPEAAAA LAAVHYPPMA AVYTAYRRED   300
VGHPLDGFGA LHPKVEQPYA AGSIWTSSIF PNRVPDGQVL FTTFVGGAQY EANAQQSETA   360
QKAAVHEELS RFYDIKAAQP LWQYRYLWDK AIPQYDQRIM AAHTTTDALQ AQGIWSAANW   420
RGGVGVPDCI RHARHVADQL TGK                                           443

SEQ ID NO: 86           moltype = AA   length = 448
FEATURE                 Location/Qualifiers
source                  1..448
                        mol_type = protein
                        organism = Pontibacter sp.
SEQUENCE: 86
MRVAIIGAGI SGLSLAYYLQ RQGVAYDLFE AGSEVGGNMR TLRKNGYTFE LGPNTLQMNE    60
ELLQLITELK LETELLPLTP RNNKRYVLHD GKLYPVPASP KSFLANDLFS NEEKHRILQE   120
RKQPPAEVEN ETVSDFFERR FGVKQMDYLA APMISGLYGG DPRQLLVNKA HPELKELETQ   180
```

```
YGSVLEGMVQ  KKKRGVFQRA  FSFRNGMSTL  PHAIADKLIS  LHLDHKVEFI  TRIGKFIIS   240
CASNGDHDNE  EYDKLVLALP  AHQAAELIEF  TYPGMSAALQ  NINYPPMAVV  HTVYNRAEVG  300
HPLQGFGALH  PWEEQSFTSG  SIWTSSLFEG  RCRSHEVLIT  SYVGGTRFAE  HAQLEERSLL  360
EQVHQELCQT  YQIKALAPVY  QHLHLWQHAL  PQFDLYIEDA  HHMAEVLEQD  GLFISANWYA  420
GVSVPDCVRE  AKAIAAKINT  RAASRSIA                                       448

SEQ ID NO: 87           moltype = AA  length = 463
FEATURE                 Location/Qualifiers
source                  1..463
                        mol_type = protein
                        organism = Leptospirillum sp.
SEQUENCE: 87
MATEDVETLV  IGGGIAGLAC  ASHLKLAGRT  VRLVERNDYL  GGVIRTLSDS  GYRIETGPNS  60
LLVRTEEPLL  KYLSRPEIAA  RIQLAGRMGK  KRFILKDGHP  VALPMSLSEG  IFTQILSLPA  120
KVRLLKEPFI  PPAGGVDGVD  PEKETVADFV  RRRLGNEFLE  SLIDPFVKGV  YASDPHLLSM  180
ADTFPRLVQM  EKSYGSLIKG  GLALARQKKA  PAPAFAREIL  SFSEGMGTLP  ESLANILDDD  240
AGTNAEVIGC  APSESGFRTA  LLFEEETYYI  RSKHLVLALP  AAQTAELIEP  MAPGIPSLLG  300
QIPYAPIAVV  YLGYPRDRIS  HPLDGFGLLV  PSERRRKILG  ALFSSSLFPG  RSPDGHVLLT  360
VFVGGMTQPK  LAQAFDEDLL  PMVTKEIGSM  LGVLGAPSYV  RIQRWAGAIP  QSVPGHGERI  420
RSIESALPSG  LHLAGSYLSG  VSVSQTFSSG  IRAAEKILAQ  SPG                    463

SEQ ID NO: 88           moltype = AA  length = 451
FEATURE                 Location/Qualifiers
source                  1..451
                        mol_type = protein
                        organism = Prevotella sp.
SEQUENCE: 88
MERQRKIIVI  GAGLTGLTCA  AHLRHKGQDV  EVLEATERIG  GLMQTEDFDG  FIMEQGPSTG  60
TIKYPEVAEL  FDMLGDKCTL  EVAQSSAKCR  LIWKDGHFCA  LPSGLWSAVT  TPLFTLKDKF  120
RILGEPWRRK  GTDPNESVGA  LAERRLGRSF  VDYAVDPFLS  GVYAGDPYKL  PTRLALPKLY  180
NLEQHYGSFI  KGAMALAKAP  KSDRDKRATK  EVFSTRGGFR  SLVSALAKTI  GDDRITTGCA  240
HLHVEPLGDK  WKLSWGENTI  IADQVVTTCP  AYSLPDLLTF  LPKEQLDDLS  NLYYAPVIEI  300
GVGMKHTGNV  HWNAFGGLVP  SKEQQKVLGI  LMPSACFVGR  SPEEGATYAF  FIGGARHPEY  360
LDKTDEELRE  LVNTSLHTML  GYPKGTQADA  IRIYRHSHAI  PQYMTETDSR  LRAIDTVEHT  420
YPSLHIIGNL  KDGIGMGDRI  KQAVDLAERI  G                                  451

SEQ ID NO: 89           moltype = AA  length = 436
FEATURE                 Location/Qualifiers
source                  1..436
                        mol_type = protein
                        organism = Flexithrix sp.
SEQUENCE: 89
MVGIIGAGIS  GLSLAYHLQK  LGKAYCLFEA  GDKPGGNICS  VKKEGFLLEK  GPNSLLADSE  60
IIDLVKELGL  EDQMIIPETV  SKKRYIFKNG  KYQQLPSSPP  GLIFNNFFSW  HAKFSIYKEL  120
NNKSTSPQNE  TVADFFERRF  CKEIVDQAVN  PFISGIYAGD  PEKLIMEKTF  PAFLENEQKF  180
GSVIRGFIKN  KKNTQRKLTF  SFKEGLGILA  DKLAENLSVN  YNSPIKEIRQ  EAGGFLLITE  240
NGETKVTALV  FSIPAYAAGK  LIKDISPESA  QAWEGVNYPP  ICVVHTAFRR  KDLGFDFNGF  300
GGLNPKKEDL  FTAGSIWNSS  LFENRSPKDQ  FLITSFVGGA  QSLDNFQLTD  EEIKAKVTDE  360
LQQNFKIKGS  PTHQEITRWE  KSIPQYDIDI  FPAHQAIENL  QREGIYVCSN  WEGGVSVPDC  420
IKKGKQLAER  IKENKF                                                     436

SEQ ID NO: 90           moltype = AA  length = 469
FEATURE                 Location/Qualifiers
source                  1..469
                        mol_type = protein
                        organism = Geobacter sp.
SEQUENCE: 90
MKKVIVVGGG  ISGLATAFEL  RNKGAEAGIE  LDVTLLEKEE  RVGGKIWSIK  EEGYLCEWGP  60
NGFLDSKPQT  LDLCRDLGAS  ERLLRSNDNA  RKRPIYTGGV  LNRLPENGPT  FLKSSLISWP  120
GKLRLAMEPF  ISKRTDGTDE  TLASFGRRRL  GEEALQKLIS  PMVSGIFAGD  PETMSLRSCF  180
PRIAELEDEY  GSLIKAMIKL  AKKKQEAAQ   GKAVSSAAGP  GGVLTSFRWG  IQELTDILAE  240
QLGSATVVTG  QPVTGLTRGS  SVPWRLKTPT  VDIDADVVIL  ASPAHATAGI  VSGVDAAMAQ  300
VLGEIPYASM  TVVCFGFERE  RIAYDLNGFG  YLIPKDEGMN  TLGTLWDSSI  FENRAPEGKV  360
LLRSMLGGAC  FPEYVKLSDA  EVMQRVKADL  KATMGITADP  SFIRIFRHPQ  AIPQYTVGHG  420
KRLAALQERS  SALPGLFLTG  NSYRGIGLND  CATAANRTTD  EVVAYLKGR              469

SEQ ID NO: 91           moltype = AA  length = 498
FEATURE                 Location/Qualifiers
source                  1..498
                        mol_type = protein
                        organism = Synechococcus sp.
SEQUENCE: 91
MQAEVVVVGA  GISGLTLALR  LQQGLSPKDE  STQPLLLAEA  SSRVGGCIST  QSKDSYRWEE  60
GPNSFTPVPA  LLNLIAEVGL  AEHLVLADAK  LPRYIWEKE   LLPVPLSPSA  AIGSRLLSVG  120
GKLRALRGLL  GFVAPPPGGE  ETVRQFFRRQ  LGSEVVERLV  EPFTSGVYAG  DPDQLSALAA  180
FPPRIAGLEER  YGSLFAGAVQ  ALRSRYRYAT  LPRTRHQDSA  NSPIQPPPKR  GQLGNLRQGL  240
QQLPEAIAQK  LGSALRLGWR  AVHLKRDETG  YRVGFVIHDS  GAEHTAPEEI  HWVAQQVVL   300
TLPAYAAATL  LQDLNPQASR  LLREIPYPPV  AVVALAYPEE  ALPQPLRGFG  HLIPRSQGLR  360
TLGTIWASSL  FPERAPQGYH  CLISFIGGAT  DAAFARQKGI  PPITALSPDE  RAQIVHAELS  420
```

```
QILLTRPVEP IRLGERLWPQ AIPQYTLGHR QRIAQLQASL ADQTPGVWVC ANYLDGVALG   480
DCVRRAEALA QQILSVRR                                                498

SEQ ID NO: 92           moltype = AA  length = 475
FEATURE                 Location/Qualifiers
source                  1..475
                        mol_type = protein
                        organism = Crinalium sp.
SEQUENCE: 92
MVDTLIIGAG ISGLSLAYAL HQDGRKVLLC ERQERVGGNI TTGKAGGFLW EEGPTSFTPT    60
PALLKLAVDV GLREELVLAD HRLPRFVYWK GQLLPVPMSP PSAVTSKLLS LSGKFRALVG   120
ALGFIPPAIG NHLSQQGGEE TVAQFFKRHL GTEVAERLVA PFVSGVYAGD VHQLSARSAF   180
RRIAQLENVG GGLVSGAILS RKQRQQQKPP TDPSLPTVRR GELGSFKEGL QSLPKAIASH   240
LGENIKLNWT LTELRQTANQ TYIAEFSTPE GSQQVEARTV VLTTPAYVTA ELLHNLAPNA   300
SIALKEIPYP SVACVVLAYP DDALKFPLKG FGNLIPRGQG IRTLGTIWSS SLFPGRAPQG   360
WQMLTNFIGG ATDPEVGNLD NEQLVQAVHK DLQRVLLKKD VPPKAIAVHL WKRAIPQYTL   420
GHHLRLAQIN QDLAQLPGLY LCSNYTDGVS LGDCVQRAYD QLPIINKQLS IINDN        475

SEQ ID NO: 93           moltype = AA  length = 486
FEATURE                 Location/Qualifiers
source                  1..486
                        mol_type = protein
                        organism = Planctomyces sp.
SEQUENCE: 93
MNQSAPAKRI AVVGGGITGL SAAFHLQELA QEKNQPVEVT LFESQPEAGG WIGTISQDGY    60
RIDTGADMFI TNKPAAIELC QRLGLEDQLI STNQQYRGAL ILKDGTPVPV PLGFELMTPS   120
RILPMLKTPL LSPIGKLRMG LEYFLPRRTS ESGLDADDES LAQFVTRRFG REALTRLIQP   180
LVAGIYTSDP EKLSLRATLP RFLDMERDHR SLIKAIRKQK KQTKSADATG ARYGLFAAFK   240
EGMQTLIRTL ADRVSSTGTI LYEHRVTHVA AADSGYDLTI ESTVETQQH FDAVLLTTAA    300
PQAGQMLEAY APVLSGLLKQ IEYASTAIQV SVYRQENIKH PLHAFGLVIP AAEQRKIFAV   360
AFASRKFPGR APEGCVQLRT FVGGAMQPEL LEHSDDELNA IVNQELADIL GVSGEPIFSK   420
LLRHNQSMPQ YHLGHLQLVE RIEQSAATLA GLELAGNAYR GVGIPDCIHS AEQAAERLLV   480
DLTARV                                                              486

SEQ ID NO: 94           moltype = AA  length = 471
FEATURE                 Location/Qualifiers
source                  1..471
                        mol_type = protein
                        organism = Geobacter sp.
SEQUENCE: 94
MKKAIVVGGG ISGLASAYLL REKAKNSGME LEITIVEKED RTGGKIRSIK EDGYLCEWGP    60
NGFLDSKPQT LDLCRELKVD SQLLRSNDNA RKRFIYSGGV LNRLPENGPS FLKSRLISWP   120
GKLRLALEPT PFIAKAPEGV DETLAAFGRR RLGDEALRKL IAPMVSGIFA GDPETMSLVS   180
CFPPRIAELER EYGGLVKAMV KLAKKKKQEI AEGKQVASAA GPGGVLTSFR DGIQTLTDIL   240
NERLGKDMLV IGAEVTGVSR GNSTPYRVQT GGRELDADIV VLATPAYATA QALEGIDGGM   300
SATLNQIPYA TMTVVCFGYE QEKVAHDLNG FGYLIPKAEG MNILGTLWDS SIFENRAPEG   360
KVLLRSMMGG ACFPEYIRLS DAEVVQKVRD NLKTIMGIKE APEFVRIFRH EKAIPQYTVG   420
HGRRLAALEE QAKSHPGLFL SGNSYRGIGL NDCVAAANRT ADEVVAFLQS R            471

SEQ ID NO: 95           moltype = AA  length = 446
FEATURE                 Location/Qualifiers
source                  1..446
                        mol_type = protein
                        organism = Acidithiobacillus sp.
SEQUENCE: 95
MEDVIIIGAG ISGLATAYFL RKQGWSPLLL EAAAKPGGNL QSRQEEGYLR DMGPNSLMLK    60
GHIVPEWLRE LRLEEDIVEA NPLAKRRYIL NRHQPVALG PGVLFGGGLL SWRGRLRLLG   120
EPFRSPRRMQ DSEESVADFV RRRLGEEALT WLVDPFISGV FAGNPARLSV QATLPRLIAL   180
EQDGGSLLRG ALRARNKKSP DTPKTRLISF REGLQTLPLR VASALGDALA CNTPVEQLGN   240
SDGSWQVSSG SQTWQSKRLI LALPAGAAAR LLAPTDAALA HELDAIPYPA VGSLSIGFQR   300
MQVQHPLDGF GILIPRVMGL ETLGILFSST LFPGRAPADQ VLLTAFIGGS QNDISGRDDD   360
DLLATALREI CPLLGISGKP VFSRCQTWPK AIPQYEIGHL DRIKRIDALS ARHPGLYFRA   420
NWREGVALGD CMEEAYRFSQ DVGWQR                                        446

SEQ ID NO: 96           moltype = AA  length = 454
FEATURE                 Location/Qualifiers
source                  1..454
                        mol_type = protein
                        organism = Prevotella sp.
SEQUENCE: 96
MEERKIVVVG AGLTGLTCAA YLRRKGQDVV VLEAADRIGG LMQTEEVDGF VMEQGPSTGT    60
IKYPEVAELF DMLGDDCTLE VAQSSAKCRL IWKDGRFHAL PSGLWSAITT PLFTLKDKFR   120
ILGEPWRKKG IDPNESVGSL AERRLGRSFV DYAVDPYQLP VYAGDPYQLP TRLALPKLYD   180
LEQRYGSFIK GAMALAKQPK TDREKRATKA VFSTRGGFRS LVSALGRVIG DERIRTNCKE   240
LSIEPLGDKW KLSWGENTII AEQVITTCPA YALPKLLNFL PKEQLDDLSN LYYAPVIEIG   300
VGMKNTGDVH WNAFGGLVPS KEKQNVLGVL MPSACFQGRS PKEGANYACF IGGACHPEYI   360
NKTDEELIGL VNTSLHTMLG YPKGTCADVI RIYRHSHAIP QYMPETDARL RTIDAVELAY   420
PGLHIIGNLK DGIGMGDRIK QAVDMAEKIS LSVS                               454
```

```
SEQ ID NO: 97             moltype = AA  length = 458
FEATURE                   Location/Qualifiers
source                    1..458
                          mol_type = protein
                          organism = Thermovibrio sp.
SEQUENCE: 97
MRVCVIGGGV SGLSTAFYLK RGGAQVKLLE RENYPGGKAR TYYEKGYIVE SGPNGFLDGK    60
PDTLELVKLL GAEKLLYRSS DKARKRFIYK NGRLVRLPEN PIAFLSSYLL SWKGKVRVLG   120
ELLVPPSEKE DETLAEFVRR RLGKEALDYL LDPMVAGIFA GDPERMSLKA APFTIYRLER   180
EYGGLIRGLI AKAKEAKKKG AKSSGPAGPG GVLTSFVKGM SQFTQLLAQE LGESFTPEAQ   240
VKTLEKKKDK WLVTYTLRGK EKSEEFDAVV LSLPAYAAAQ VLKETSRELS ELLASIEYSP   300
ISVVALGFEK RGLGHNLDGF GFLVPKVEGR KILGALWDSS VFPNRAPEGK ALIRVMIGGA   360
RQPELALKSE EELTEIALKE LKRIMKIRHY PEMVKVFRHE KGIPHYTIGH AEKVERIFKL   420
GRELGNLFFC NNAYKGVGIN DCTKSARETA EEVLNSLC                           458

SEQ ID NO: 98             moltype = AA  length = 536
FEATURE                   Location/Qualifiers
source                    1..536
                          mol_type = protein
                          organism = Brassica sp.
SEQUENCE: 98
MDLSLLRPQP FLSPFSNPFP RSRPYKPLNL RCSVSGGSVV GSSTIEGGGG GKTVTADCVI    60
VGGGISGLCI AQALVTKHPD AAKNVMVTEA KDRVGGNIIT REEQGFLWEE GPNSFQPSDP   120
MLTMVVDSGL KDDLVLGDPT APRFVLWNGK LRPVPSKLTD LPFFDLMSIG GKIRAGFGAI   180
GIRPSPPGRE ESVEEFVRRN LGDEVFERLI EPFCSGVYAG DPAKLSMKAA FGKVWKLEEN   240
GGSIIGGAFK AIQAKNKAPK TTRDPRLPKP KGQTVGSFRK GLTMLPEAIS ARLGDKVKVS   300
WKLSSITKLA SGEYSLTYET PEGIVTVQSK SVVMTVPSHV ASSLLRPLSD SAAEALSKLY   360
YPPVAAVSIS YAKEAIRSEC LIDGELKGFG QLHPRTQKVE TLGTIYSSSL FPNRAPPGRV   420
LLLNYIGGAT NTGILSKSEG ELVEAVDRDL RKMLIKPSST DPLVLGVKVW PQAIPQFLIG   480
HIDLVDAAKA SLSSSGHEGL FLGGNYVAGV ALGRCVEGAY ETATQVNDFM SRYAYK       536

SEQ ID NO: 99             moltype = AA  length = 521
FEATURE                   Location/Qualifiers
source                    1..521
                          mol_type = protein
                          organism = Brassica sp.
SEQUENCE: 99
MASNAVADHD KPVSGKRVAV VGAGVSGLAA AYKLKSKGVN VTVFEADGRV GGKLRSVMHN    60
GLIWDEGANT MTEAEPEVGS LLLDDLGLREK QQFVSTFHAL SIMFQPLSQK KRYIVRNGLP   120
VMIPTNPIAL VTSSVLSTQS KFQILLEPFL WKKNDSSSKV SDASVVESVS GFFQRHFGQE   180
VVDYLIDPFM GGTSAADPES LSMKHSFPDL WNIEKSFGSI IVGAIRSKFA AKGSKNGETK   240
SSTGTKKGSR GSFSFKGGMQ ILPDMLCKDL SREDLNLDSK VLSLSYNTGP REENWSLSCV   300
SHNETQRQNL HYDAVVMTAP LCNVKEMKVM KGGEPFKLNF LPEIKYMPLS VIITTFTKEK   360
VKRPLEGFGV LIPSIEQKHG FKTLGTLFSS MMFPDRCPSD LHLYTTFIGG SRNQELAKAS   420
TDELKQVVTS DLQRLLGIEG EPVFVNHVYW NKAFPPLYDRS YDSVMEAIDK MEKDLPGFFY   480
AGNHRGGLSV GKSIASGCKA ADLVISYLES CSNDNKPEDS L                       521

SEQ ID NO: 100            moltype = AA  length = 539
FEATURE                   Location/Qualifiers
source                    1..539
                          mol_type = protein
                          organism = Gossypium sp.
SEQUENCE: 100
MTALIDLSLL RSSPSVSPFS IPHHQHPPRF RKPFKLRCSL AEGPTISSSK IDGGESSIAD    60
CVIVGGGISG LCIAQALATK HRDVASNVIV TEARDRVGCN ITTVERDGYL WEEGPNSFQP   120
SDPILTMAVD SGLKDDLVLG DPNAPRFVLW EGKLRPVPSK PTDLPFFDLM SIAGKLRAGF   180
GAIGIRPPPP GYEESVEEFV RRNLGAEVFPE RFIEPFCSGV YAGDPSKLSM KAAFGRVWKL   240
EEIGGSIIGG TFKTIQERNK TPKPPRDPRL PKPKGQTVGS FRKGLTMLPE AIANSLGSNV   300
KLSWKLSSIT KLGNGGYNLQ FETPEGMVSL QSRSVVMTIP SHVASNLLHP LSAAAADALS   360
QFYYPPVASV TVSYPKEAIR KECLIDGELK GFGQLHPRSQ GIETLGTIYS SSLFPNRAPS   420
GRVLLLNYIG GATNTGILSK TEGELVEAVD RDLRKMLINP NAKDPLVLGV RVWPKAIPQF   480
LVGHLDLLDS AKMALRDSGF HGLFLGGNYV SGVALGRCVE GAYEVAAEVK EFLSQYAYK    539

SEQ ID NO: 101            moltype = AA  length = 503
FEATURE                   Location/Qualifiers
source                    1..503
                          mol_type = protein
                          organism = Gossypium sp.
SEQUENCE: 101
MASTENKDDH SSAKRVAVIG AGVSGLAAAY KLKSQGLHVT VFESEGRAGG KLRSVSREGL    60
IWDEGANTMT ESEIEVRSLF DDLGIQDKEQ VPIAQNKRYI VRNGVPVLIP SNPLALFTSS   120
ILSAKSKFQI ILEPFLWRKS EASKVSDAYN QESVGGFFQR HFGQEVVDYL VDPFVAGTSA   180
GDPESLSMCH SFPELWDLEQ RFGSIIVGAV KSKFSAKRTN REETKNSVKR KALRGSFSFQ   240
GGMQTLADML CKDLSKDELK LKSKVLSLSY SHEGKSTSEN WSLSYASDRD KRSQGSSFDA   300
VIMTAPVCNV KEMKITKGGN VFPLNFIPEV SYMPLSVIIT AFKKENVKKP LEGFGVLIPS   360
KEQQNGLKTL GTLFSSVMFP DRAPNNLYLY TTFVGGNRNK ELAKASTDEL KHIVTSDLQQ   420
LLGVEGEPTF FNHFYWSKAF PLYGRNYASV LEAIEKIERD LPGFFYAGNH KGGLSVGKSI   480
ASGCKAADNV ITYLESSHDK LLK                                           503
```

```
SEQ ID NO: 102            moltype = AA  length = 535
FEATURE                   Location/Qualifiers
source                    1..535
                          mol_type = protein
                          organism = Conyza sp.
SEQUENCE: 102
MTSLTNFTPL KLTNPNYLTT TTTYNHRKLS NFRFRCSIAR DSPTAPSISG DSSSRPLLDC    60
VVVGAGISGL CIAQALSTKH GGDVVVTEAR ERVGGNISTV ERDGYLWEEG PNSFQPSDPM   120
LTMVVDSGLK DDLVLGDPTA PRFVLWDGDL KPVPSSPSDL PTFDLMSLGG KLRAGFGALG   180
IRPPPPDREE SVEEFVRRNL GDEVFERLIE PFCSGVYAGD PSKLSMKAAF GKVWKLEQNG   240
GSIVGGAFKA IQAKNKSTKP PRDPRLPTPK GQTVGSFRKG QAMLPNAISK GLGSRVKLSW   300
ELVGITKSEN RGYSLTYRTP DGLESLQTKT VVMTVPSYVA SDLLRPLSVE AADALSKFYY   360
PPVAAVSVSY PKEAIRADRL IDGQLKGFGQ LHPRSQGVET LGTIYSSSLF PNRAPPGRVL   420
LLNYIGGATN PGILSKTESQ IVEAVDRDLR KMLINPKAGE PLTLGVKVWP RAIPQFLIGH   480
YDILEAAKCA LSLAGYRGMF LGGNYVSGVA LGRCVENAYE VAADVSNFLS RGVYK        535

SEQ ID NO: 103            moltype = AA  length = 498
FEATURE                   Location/Qualifiers
source                    1..498
                          mol_type = protein
                          organism = Conyza sp.
SEQUENCE: 103
MASPTTTTDD NKEKAPAKRV AVVGAGVSGL AAAYKLKLHG INVTVFEAGE IAGGKLRSIS    60
QNGLIWDEGA NTMTESEPDV SRLLDDLGLR DKQQSPLSQH KRYIVRNGKP VLVPSNPIAL   120
IQSSLLSTQS KLQILLEPFS WKKKNSSDTQ ESVGAFFQRH FGKEVVEYLI NPVVAGTSGG   180
DPESLSMRYS FPELWDLERR FGSLISGAFQ SMISSRGRKK SPSGSSKRRR GSFSFLGGMQ   240
TLTNALSKEV GQHELNLQSK VLEMSYSCDD NTTGNWSIYC APDQNKQLNQ QPFDAVIMTA   300
PLGNVKEMKI TKTGSPFLLN FIPELSYMPV SVIIISTFKKE NVKRPLEGFG MLVPAKEQEN   360
GLKTLGTLFS SMMFPDRAPE DLYLYTTFVG GSRNKELANA SRDELKQIVT SDLRQLLGAE   420
GEPQFLTHYY WSKAYPLYGR DYGLVMEAIE KMERELPGYF YAGNHKGGLA VGKAISSGCK   480
AAESVISYLD SYSDEKRC                                                 498

SEQ ID NO: 104            moltype = AA  length = 565
FEATURE                   Location/Qualifiers
source                    1..565
                          mol_type = protein
                          organism = Kochia sp.
SEQUENCE: 104
MSAMASPSII PQSFLQRSPT SLQSRSNYSK NHIIISISTP CSHGKNQRRF LRKTTHFRSI    60
HCSTISTSTP TSSSNPGTLG EGGLLDCVIV GGGISGLCIA QALSTKYSSL STNFIVTEAK   120
DRVGGNITTK EDDGYIWEEG PNSFQPSDAV LTMAVDCGLK DELVFGDPKA PRFVLWNGKL   180
RRVPSKLTDL PFFDLMSFPG KIRAGLGALG FRPSPPGREE SVEDFVRRNL GDEVFERLIE   240
PFCSGVYAGD PAKLSMKAAF GRVWVLEQMG GNIIGGALKT IQEKKNKPKP PRDPRLPKGE   300
GQTVGSFRKG LIMLPNAISA RLGSKVKLSW TLASISKTHN GEYNLIYDTP DGPVSVRTKS   360
IVMTIPSYVA SSLLRPFSDA AADSLSKFHY PPVAAVSLSY PEEAIRPECL IDGKLQGFGQ   420
LHPRSQGVET LGSIYSSSLF PGRAPPGRTM ILSFIGGATN PGIVDKTQDE LAKTVDKDLR   480
RILINPSAKD PRVLGVKVWP QAIPQFLIGH FDLLDAAKAA LTDAGCKGLF LGGNYVSGVA   540
LGRCIEGAYE SAAEVVDFLS QYSDK                                         565

SEQ ID NO: 105            moltype = AA  length = 531
FEATURE                   Location/Qualifiers
source                    1..531
                          mol_type = protein
                          organism = Lolium sp.
SEQUENCE: 105
MVGATMATAT VTAALPLRLR VPARSRRGQT RCAVASDATE APAVPSARLS ADCIVGGGI    60
SGLCTAQALA TKYGVTDLLV TEARARAGGN ITTVERPDEG YLWEEGPNSF QPSDPVLTMA   120
VDSGLKDDLV FGDPNAPRFV LWQGKLRPVP SKPGDLPFFD LMSIPGKLRA GLGALGIRPP   180
PPGREESVEE FVRRNLGAEV FERLIEPFCS GVYAGDPSKL SMRAAFGKVW RLEENGGSII   240
GGTIKAIQDR GKNPKPPRDP RLPTPKGQTV ASFRKGLAML PNAIASRLGS KVKLSWKLTG   300
ITKSDNQGYV LAYETPEGVV SVQAKSVIMT IPSYIASEIL RPLSSDAADG LSKFYYPPVA   360
AVTVSYPTEA IRKECLIDGE LQGFGQLHPR SQGVETLGTI YSSSLFPNRA PAGRVLLLNY   420
IGGATNTGIV SKTESDLVEA VDRDLRKMLI NPTAPDPLAL GVRVWPQAIP QFLIGHLDRL   480
DAAKSALARG GCSGLFLGGN YVAGVALGRC IEGAYESASE VSDFLTKYAY K            531

SEQ ID NO: 106            moltype = AA  length = 509
FEATURE                   Location/Qualifiers
source                    1..509
                          mol_type = protein
                          organism = Lolium sp.
SEQUENCE: 106
MAASDDPRAA PARSVAVVGA GVSGLVAAYR LRKSGVRVTV FEADDRAGGK IRTNSDGGFL    60
WDEGANTMTE SALEASRLID DLGLEGRLQY PNSQHKRYTV KDGAPALIPS DPIALMKSSL   120
LSTKSKFKLF LEPFLYEKSS TNNSKKVSDE HIRESVGSFF ERHFGKEVVD YLIDPFVAGT   180
SAGDPESLSI RHAFPALWNL EKKYGSIIAG AILSKLTAKG DSTKKGSAVS GKGRNKRVSF   240
SFHGGMQTLV DALHKEIGDG NVKLATQVLS LACSCDGLSA SNGWSIFVDS KDASNRELAK   300
NQPFDAVIMT APLSNVQRMK FTKGGAPFVL DFLPKVDYLP LSLMVTAFKK EDVKRPLEGF   360
GVLVPYKEQQ KHGLKTLGTL FSSMMFPDRA PNDQHLFTTF VGGSHNRDLA GAPTAILKQL   420
VTSDLRKLLG VEGQPTFVRH IHWKNAFPLY GHDYDSALEA IGKMESDLPG FFYAGNNKDG   480
```

```
LAVGNVIASG SKTADLVISY LELGIKRDN                                              509

SEQ ID NO: 107           moltype = AA  length = 539
FEATURE                  Location/Qualifiers
source                   1..539
                         mol_type = protein
                         organism = Gossypium hirsutum
SEQUENCE: 107
MTALIDLSLL RSSPSVSPFS IPHHQLPPRS RKPFKLRCSL AEGPTISSSK IDGGESSIAD             60
CVVVGGGISG LCIAQALATK HRDVASNVIV TEARDRVGGN ITTVERDGYL WEEGPNSFQP            120
SDPILTMAVD SGLKDDLVLG DPNAPRFVLW EGKLRPVPSK PTDLPFFDLM SIAGKLRAGF            180
GAIGIRPPPP GYEESVEEFV RRNLGAEVFE RFIEPFCSGV YAGDPSKLSM KAAFGRVWKL            240
EEIGGSIIGG TFKTIQERNK TPKPPRDPRL PKPKGQTVGS FRKGLTMLPE AIANSLGGNV            300
KLSWKLSSIT KLGNGGYNLT FETPEGMVSL QSRSVVMTIP SHVASNLLHP LSAAAADALS            360
QFYYPPVASV TVSYPKEAIR KECLIDGELK GFGQLHPRSQ GIETLGTIYS SSLFPNRAPS            420
GRVLLLNYIG GATNTGILSK TEGELVEAVD RDLRKMLINP NAKDPLVLGV RVWPKAIPQF            480
LVGHLDLLDT AKMALRDSGF HGLFLGGNYV SGVALGRCVE GAYEVAAEVK EFLSQYAYK             539

SEQ ID NO: 108           moltype = AA  length = 560
FEATURE                  Location/Qualifiers
source                   1..560
                         mol_type = protein
                         organism = Beta vulgaris
SEQUENCE: 108
MKSMALSNCI PQTQCMPLHS SGHYRGNCIM LSIPCSLIGR RGYYSHKKRR MSMSCSTSSG             60
SKSAVKEAGS GSGSGAGGLL DCVIVGGGIS GLCIAQALCT KQSSLSPNFI VTEAKDRVGG            120
NIVTVEADGY IWEEGPNSFQ PSDAVLTMAV DSGLKDELVL GDPNAPRFVL WNDKLRPVPS            180
SLTDLPFFDL MTIPGKIRAA LGALGFRPSP PPHEESVEHF VRRNLGDEVF ERLIEPFCSG            240
VYAGDPAKLS MKAAFGKVWK LEQKGGSIIG GTLKAIQERG SNPKPPRDQR LPKPKGQTVG            300
SFRKGLVMLP TAISARLGSR VKLSWTLSSI VKSLNGEYSL TYDTPDGLVS VRTKSVVMTV            360
PSYVASRLLR PLSDSAADSL SKFYYPPVAA VSLSYPKEAI RSECLINGEL QGFGQLHPRS            420
QGVETLGTIY SSSLFPGRAP PGRILILSYI GGAKNPGILN KSKDELAETV DKDLRRMLIN            480
PDAKLPRVLG VRVWPQAIPQ FSIGHFDLLD AAKAALTDTG VKGLFLGGNY VSGVALGRCI            540
EGAYESAAEV VDFLSQYSDK                                                       560

SEQ ID NO: 109           moltype = AA  length = 530
FEATURE                  Location/Qualifiers
source                   1..530
                         mol_type = protein
                         organism = Hordeum vulgare
SEQUENCE: 109
MAGAGATMAT ATAPPLRGRV TRRPHGVRPR CAAAGSATET PAAPGVRLSA DCVIVGAGIS             60
GLCTAQALAT RHGVGDLLVT EARDRPGGNI TTVERPDEGY LWEEGPNSFQ PSDVLTMAV             120
DSGLKDDLVF GDPNAPRFVL WEGKLRPVPS KPGDLPFFSL MSVPGKLRAG LGALGIRPPP            180
PGREESVEEF VRRNLGAEVF ERLIEPFCSG VYAGDPSKLS MKAAFGKVWR LEEIGGSIIG            240
GTIKAIQDKG KNPKPPRDPR LPAPKGQTVA SFRKGLAMLP NAIASRLGSK VKLSWKLTSI            300
TKADNQGYVL GYETPEGLVS VQAKSVIMTI PSYVASDILR PLSIDAADAL SKFYYPPVAS            360
VTVSYPKEAI RKECLIDGEL QGFGQLHPRS QGVETLGTIY SSSLFPNRAP AGRVLLLNYI            420
GGSTNTGIVS KTESDLVEAV DRDLRKMLIN PRAADLPLALG VRVWPQAIPQ FLIGHLDRLA           480
AAKSALGRGG YDGLFLGGNY VAGVALGRCI EGAYESASQV SDFLTKYAYK                       530

SEQ ID NO: 110           moltype = AA  length = 554
FEATURE                  Location/Qualifiers
source                   1..554
                         mol_type = protein
                         organism = Hordeum vulgare
SEQUENCE: 110
MLTSATAPPS SSSCSSHAPA RFASPSRPRR SASASARGRG RRVRPVLAMA ASDDPRARSV             60
AVVGAVGSGL VAAYMLRKSG VRVTVFEAED RAGGKIRTNS DGGFLWDEGA NTMESALEA            120
SRLIDDLGLQ DRLQYPNSQH KRYTVKDGAP ALIPSDPIAL MKSTVLSTKS KFKLFLEPFL            180
YEKSSTRNSK KVSDEHLRES VGSFFERHFG KEVVDYLIDP FVAGTSAGDP ESLSIRHAFP            240
GLWNLEKKYG SLIVGAILSK LTAKGGSAKK GGASSGKGRN KRASFSFHGG MQTLVDALHK            300
EVGDTNVKLG TQVLSLACNC DGLSASDGWS IFVDSKDASS KELARNQSFD AVIMTAPLSN            360
VQRMKFTKGG RPFVLDFLPK VDYLPLSLMV TAFKKEDVKR PLEGFGVLIP FKEQQHGLK             420
TLGTLFSSMM FPDRAPNDQH LFTTFIGGSH NRDLAGAPTA ILKQFVTSDL TKLLGVEGQP            480
TFVKHIHWRN AFPLYGHDYD LALEAIGKME GDLPGFFYAG NNKDGLAVGN VIASGSNTAD            540
LVISYLESGI KHVN                                                             554

SEQ ID NO: 111           moltype = AA  length = 531
FEATURE                  Location/Qualifiers
source                   1..531
                         mol_type = protein
                         organism = Triticum aestivum
SEQUENCE: 111
MAGATMATAT VAAASPLRGR VTGRPHRVRP RCATASSATE TPAAPGVRLS AECVIVGAGI             60
SGLCTAQALA TRYGVSDLLV TEARDRPGGN ITTVERPDEG YLWEEGPNSF QPSDPVLTMA            120
VDSGLKDDLV FGDPNAPRFV LWEGKLRPVP SKPGDLPFFS LMSIPGKLRA GLGALGIRPP            180
PPGREESVEE FVRRNLGAEV FERLIEPFCS GVYAGDPSKL SMKAAFGKVW RLEEIGGSII            240
GGTIKAIQDK GKNPKPPRDP RLPAPKGQTV ASFRKGLAML PNAIASRLGS KVKLSWKLTS            300
```

```
ITKADNQGYV LGYETPEGLV SVQAKSVIMT IPSYVASDIL RPLSIDAADA LSKFYYPPVA  360
AVTVSYPKEA IRKECLIDGE LQGFGQLHPR SQGVETLGTI YSSSLFPNRA PAGRVLLLNY  420
IGGSTNTGIV SKTESDLVGA VDRDLRKMLI NPRAADPLAL GVRVWPQAIP QFLIGHLDRL  480
AAAKSALGQG GYDGLFLGGN YVAGVALGRC IEGAYESASQ VSDFLTKYAY K           531

SEQ ID NO: 112          moltype = AA  length = 501
FEATURE                 Location/Qualifiers
source                  1..501
                        mol_type = protein
                        organism = Solanum lycopersicum
SEQUENCE: 112
MAPSAGEDKQ KRVAVIGAGV SGLAAAYKLK VHGLNVTVFE AEGRAGGKLR SLSQDGLIWD  60
EGANTMTESE GDVTFLLDSL GLREKQQFPL SQNKRYIARN GTPTLIPSNP FDLFKSNFLS  120
TGSKLQMLFE PLLWKNKKLT KVSDKHESVS GFFQRHFGKE VVDYLIDPFV AGTCGGDPDS  180
LSMHLSFPDL WNLEKRFGSV IVGAIQSKLS PIKEKKQGPP RTSINKKRQR GSFSFLGGMQ  240
TLTDAICKNL KEDELRLNSR VLELSCSCSG DSAIDSWSIF SASPHKRQAE EESFDAVIMT  300
APLCDVKSMK IAKRGNPFLL NFIPEVDYVP LSVVITTFKK ESVKHPLEGF GVLVPSQEQK  360
HGLKTLGTLF SSMMFPDRAP NNVYLYTTFV GGSRNRELAK ASRTELKEIV TSDLKQLLGA  420
EGEPTYVNHL CWSKAFPLYG HNYDSVLDAI DKMEKSLPGL FYAGNHKGGL SVGKALSSGC  480
NAADLVISYL EAVSADTKNH S                                           501

SEQ ID NO: 113          moltype = AA  length = 546
FEATURE                 Location/Qualifiers
source                  1..546
                        mol_type = protein
                        organism = Triticum aestivum
SEQUENCE: 113
MGIHPAALTF PRATEMAGAT MATATVAAAS PLRGRVTGRP HRVRPRCATA SSATETPAAP  60
GVRLSAECVI VGAGISGLCT AQALATRYGV SDLLVTEARD RPGGNITTVE RPDEGYLWEE  120
GPNSFQPSDP VLTMAVDSGL KDDLVFGDPN APRFVLWEGK LRPVPSKPGD LPFFSLMSIP  180
GKLRAGLGAL GIRPPPPGRE ESVEEFVRRN LGAEVFERLI EPFCSGVYAG DPSKLSMKAA  240
FGKVWRLEEI GGSIIGGTIK AIQDKGKNPK PPRDPRLPAP KGQTVASFRK GLAMLPNAIA  300
SRLGSKVKLS WKLTSITKAD NQGYVLGYET PEGLVSVQAK SVIMTIPSYV ASDILRPLSI  360
DAADALSKFY YPPVAAVTVS YPKEAIRKEC LIDGELQGFG QLHPRSQGVE TLGTIYSSSL  420
FPNRAPAGRV LLLNYIGGST NTGIVSKTES DLVGAVDRDL RKMLINPRAA DPLALGVRVW  480
PQAIPQFLIG HLDRLAAAKS ALGQGGYDGL FLGGNYVAGV ALGRCIEGAY ESASQVSDFL  540
TKYAYK                                                            546

SEQ ID NO: 114          moltype = AA  length = 539
FEATURE                 Location/Qualifiers
VARIANT                 137
                        note = Xaa can be any naturally occurring amino acid
VARIANT                 156
VARIANT                 168
                        note = Xaa can be any naturally occurring amino acid
source                  1..539
                        mol_type = protein
                        organism = Gossypium hirsutum
SEQUENCE: 114
MTALIDLSLL RSSPSVSPFS IPHHQLPPRS RKPFRLRCSV AEGPTISSSK IDGGESSIAD  60
CVVVGGGISG LCIAQALATK HRDVASNVIV TEARDRVGGN ITTVERDGYL WEEGPNSFQP  120
SDPILTMAVD SGLKDDXVLG DPNAPRFVLW EGKLRXVPSK PTDLPFFXLM SIAGKLRAGF  180
GAIGIRPPPP GYEESVEEFV RRNLGAEVFE RFIEPFCSGV YAGDPSKLSM KAAFGRVWKL  240
EEIGGSIIGG TFKTIQERNK TPKPPRDPRL PKPKGQTVGS FRKGLTMLPE AIANSLGSNV  300
KLSWKLSSIT KLGNGGYNLT FETPEGMVSL QSRSVVMTIP SHVASNLLHP LSAAAADALS  360
QFYYPPVASV TVSYPKEAIR KECLIDGELK GFGQLHPRSQ GIETLGTIYS SSLFPNRAPS  420
GRVLLLNYIG GATNTGILSK TEGELVEAVD RDLRKMLINP NAKDPLVLGV RVWPKAIPQF  480
LVGHLDLLDS AKMALRDSGF HGLFLGGNYV SGVALGRCVE GAYEVAAEVK EFLSQYAYK   539

SEQ ID NO: 115          moltype = AA  length = 503
FEATURE                 Location/Qualifiers
source                  1..503
                        mol_type = protein
                        organism = Gossypium hirsutum
SEQUENCE: 115
MASTENKDDH SSAKRVAVIG AGVSGLAAAY KLKSQGLHVT VFESEGRAGG KLRSVSRDGL  60
IWDEGANTMT ESEIEVRSLF DDLGIQDKQQ VPIAQNKRYI MRNGVPVLIP SNPLSLFTSS  120
ILSAKSKFQI ILEPPLWRNS EASKVSDAYN QESVGGFFQR HFGQEVVDYL VDPFVAGTSA  180
GDPESLSMCH SFPGLWDLEQ RFGSIIVGAV KSKFSAKRTN REETKNSVKR KALRGSFSFK  240
GGMQTLADML CKDLSKDELK LKSKVLSLSY SHEGKSTSEN WSLSYASDRD KRSQGSSFDA  300
VIMTAPVCNV KEMKITKGGN VFPLNFIPEV SYMPLSVIIT AFKKENVKKP LEGFGVLIPS  360
KEQQNGLKTL GTLFSSVMFP DRAPNNLYLY TTFGGNRNE KLAKASTDEL KHIVTSDLQQ  420
LLGVEGEPTF PNHFYWSKAF PLYGRNYASV LEGIEKMERD LPGFFYAGNH KGGLSVGKSI  480
ASGCKAADNV ITYLESSHDK LLK                                         503

SEQ ID NO: 116          moltype = AA  length = 560
FEATURE                 Location/Qualifiers
source                  1..560
                        mol_type = protein
```

```
                         organism = Beta vulgaris
SEQUENCE: 116
MKSMALSNCI PQTQCMPLHS SGHYRGNCIM LSIPCSLIGR RGYYSHKKRR MSMSCSTSSG    60
SKSAVKEAGS GSGSGAGGLL DCVIVGGGIS GLCIAQALCT KQSSLSPNFI VTEAKDRVGG   120
NIVTVEADGY IWEEGPNSFQ PSDAVLTMAV DSGLKDELVL GDPNAPRFVL WNDKLRPVPS   180
SLTNLPFFDL MTIPGKIRAA LGALGFRPSP PPHEESVEHF VRRNLGDEVF ERLIEPFCSG   240
VYAGDPAKLS MKAAFGKVWK LEQKGGSIIG GTLKAIQERG SNPKPPRDQR LPKPKGQTVG   300
SFRKGLVMLP TAISARLGSR VKLSWTLSSI VKSLNGEYSL TYDTPDGLVS VRTKSVVMTV   360
PSYVASRLLR PLSDSAADSL SKFYYPPVAA VSLSYPKEAI RSECLINGEL QGFGQLHPRS   420
QGVETLGTIY SSSLFPGRAP PGRILILSYI GGAKNPGILN KSKDELAETV DKDLRRMLIN   480
PDAKLPRVLG VRVWPQAIPQ FSIGHFDLLD AAKAALTDTG VKGLFLGGNY VSGVALGRCI   540
EGAYESAAEV VDFLSQYSDK                                               560

SEQ ID NO: 117          moltype = AA  length = 508
FEATURE                 Location/Qualifiers
source                  1..508
                        mol_type = protein
                        organism = Brassica napus
SEQUENCE: 117
MASNAVADHD KLSGKRVAVV GAGVSGLAAA YKLKSKGVNV TVFEADGRVG GKLRSVMHNG    60
LIWDEGANTM TEAEPEVGSL LDDLGLREKQ QFPLSQKKRY IVRNGLPVMI PTNPIALVTS   120
SVLSTQSKFQ ILLEPFLWKK NDSSSKVSDA SVVESVSGFF QRHFGQEVVD YLIDPFMGGT   180
SAADPESLSM KHSFPDLWNI EKSFGSIIVG AIRSKFAAKG SKNGETKSST GTKKGSRGSF   240
SFKGGMQILP EMLCKDLSRD ELNLDSKVLS LSYNAGPRQE NWSLSCVSHN EAQGQNLHYD   300
AVIMTAPLCN VKEMKVMKGG EPFKLNFLPE IKYMPLSVII TTFTKEKVKR PLEGFGVLIP   360
TKEQKHGFKT LGTLFSSMMF PDRCPSDLHL YTTFIGGSRN QELAKASTDE LKQVATSDLQ   420
RLLGVEGEPV FVNHVYWNKA FPLYDRSYDS VMEAIDKMEK DLPGFFYAGN HRGGLSVGKS   480
IASGCKAADL VISYLESCSN DKKSEDSL                                      508

SEQ ID NO: 118          moltype = DNA  length = 1638
FEATURE                 Location/Qualifiers
source                  1..1638
                        mol_type = other DNA
                        organism = Triticum aestivum
SEQUENCE: 118
atggggatcc accccgccgc actgacattc ccccgagcga cagaaatggc cggcgcaaca    60
atggccaccg ccaccgtcgc ggccgcgtcg ccgctccgcg gcagggtcac cgggcgccca   120
caccgcgtcg gcccgcgttg cgctaccgcg agcagcgcga ccgagactcc ggcggcgccc   180
ggcgtggcgc tgtccgcgga atgcgtcatt gtgggcgcg gcatccagcg cctctgcacc   240
gcgcaggcgc tggccacccg atacggcgtc agcgacctgc tcgtcacgga ggcccgcgac   300
cgcccgggcg gcaacatcac caccgtcgag cgtcccgacg aggggtacct gtgggaggag   360
ggacccaaca gcttccagcc ctccgacccg gtcctcacca tggccgtgga cagcgggctc   420
aaggatgact tggtgttcgg ggaccccaac gcgccccggt tcgtgctgtg ggaggggaac   480
ctgaggccgg tgccgtcgaa gccaggcgac ctgcctttct tcagcctcat gagtatccct   540
gggaagctca gggccggcct tggcgcgctc ggcattcgcc cacctcctcc agggcgcgag   600
gagtcggtgg aggagtttgt gcgccgcaac ctcggtgccg aggtctttga gcgcctcatc   660
gagccttttct gctcaggtgt atatgctggt gatccttcga agcttagtat gaaggctgca   720
tttgggaagg tctggaggtt ggaggagatt ggaggtagta ttattggtgg aaccatcaag   780
gcgattcagg ataaagggaa gaaccccaaa ccgccaaggg atccccgact ccggcaccaa   840
aagggacaga cggtggcatc tttcaggaag ggtctagcca tgctcccgaa tgccatcgca   900
tctaggctgg gtagtaaagt caagctgtca tggaagctta cgagcattac aaaggccgga   960
aaccaaggat atgtattagg ttatgaaaca ccagaaggac ttgtttcagt gcaggctaaa  1020
agtgttatca tgaccatccc gtcatatgtt gctagtgata tcttgcgccc actttcaatt  1080
gatgcagcag atgcactctc aaaattctat tatccgccag ttgctgctgt aactgtttca  1140
tatccaaaag aagctattag aaaagaatgc ttaattgagg gggagctcca gggtttcggc  1200
cagttgcatc cacgtagcca aggagtcgag actttaggga caatatatag ctcttctctc  1260
tttcctaatc gtgctcctgc tggaagagtg ttacttctga actatatcgg gggttctaca  1320
aatacaggga tcgtctccaa gactgagagt gacttagtag gagccgttga ccgtgacctc  1380
agaaaaatgt tgataaaccc tagagcagca gaccctttag cattagggggt tcgagtgtgg  1440
ccacaagcaa taccacagtt tttgattggg caccttgatc gccttgctgc tgcaaaatct  1500
gcactgggcc aaggcggcta cgacgggmtg ttcctaggag gaaactacgt mgcaggagtt  1560
gccttggggcc gatgcatcga gggtgcgtac gagagtgcct cacaagtatc tgacttcttg  1620
accaagtatg cctacaag                                                1638

SEQ ID NO: 119          moltype = DNA  length = 1617
FEATURE                 Location/Qualifiers
misc_feature            411
                        note = /note="n is a, c, g, or t"
misc_feature            447
                        note = /note="n is a, c, g, or t"
misc_feature            467
                        note = /note="n is a, c, g, or t"
misc_feature            504
                        note = /note="n is a, c, g, or t"
misc_feature            564
                        note = /note="n is a, c, g, or t"
misc_feature            918
                        note = /note="n is a, c, g, or t"
misc_feature            939
```

|  | note = /note="n is a, c, g, or t" |  |
| --- | --- | --- |
| misc_feature | 1008 |  |
|  | note = /note="n is a, c, g, or t" |  |
| source | 1..1617 |  |
|  | mol_type = other DNA |  |
|  | organism = Gossypium hirsutum |  |

SEQUENCE: 119

```
atgacggctc taatcgacct ttctcttctc cgctcctcgc cctccgtttc cccttcctcc    60
atacccaccc accagcttcc gccccgctct cgtaaacctt tcaggctccg atgctccgtc   120
gccgagggtc ccacgatttc ctcatctaaa atcgacgggg gagaatcatc catcgcggat   180
tgcgtcgtcg ttggaggtgg tatcagtgga cttttgcattg ctcaagctct cgccaccaag   240
caccgtgacg tcgcttccaa tgtgattgtg acggaagcca gagaccgtgt tggtggcaac   300
atcactaccg ttgagagaga tggatatctg tgggaagaag gcccccaacag ttttcagccc   360
tccgatccta ttctaaccat ggccgtggat agtggattga aggacgattt ngttttaggt   420
gaccctaatg caccgcgatt tgtactntgg gagggaaaac taaggcntgt gccctccaag   480
ccaaccgact tgccgttttt tganttgatg agcattgctg gaaaacttag ggctgggttc   540
ggggctattg gcattcggcc tccncctccg ggttatgaag aatcggtgga ggagttttgtg   600
cgccgtaatc ttggtgctga gttttttgaa cgctttatttg aaccattttg ttcaggtgtt   660
tatgcagggg atccttcaaa attaagcatg aaagcagcat ttggaagagt atggaagcta   720
gaagagattg tgcagcagcat cattggtggc acttttcaaga caatccagga gagaaataag   780
acacctaagc cacccagaga cccgcgtctg ccaaaaccga agggccaaac agttggatct   840
tttaggaagg gacttaccat gctgcctgag gcaattgcaca acagttttggg tagcaatgta   900
aaattatctt ggaagctntc cagtattacc aaattgggna atggagggta aactttgaca   960
tttgaaacac ctgaaggaat ggtatctctt cagagtagaa gtgttgtnat gaccattcca  1020
tcccatgttg ccagtaactt gttgcatcct ctctcggctg ctgctgcaga tgcattatcc  1080
caattttatt atcctccagt tgcatcagtc acagtctctc atccaaaaga agcattcga  1140
aaagaatgtt tgattgatgg tgaacttaag gggtttggcc agttgcaccc acgcagccaa  1200
ggaattgaaa cttagggac gatatacagt tcatcacttt tccccaatcg agctccatct  1260
ggcagggtgt tgctcttgaa ctacatagga ggagctacca cactggaat tttgtccaag  1320
actgaagggg aactttgtaga agcagttgat cgtgatttga gaaaaatgct tataaatcct  1380
aatgcaaagg atcctcttgt tttgggtgta agagtatggc caaaagcccat tccacagttc  1440
ttggttggtc atttggatct ccttgatagt gcaaaaatgg ctctcaggga ttctgggttt  1500
catgactgt ttcttggggg caactatgta tctggtgtgg cattaggacg gtgtgtggaa  1560
ggtgcttacg aggttgcagc tgaagtgaag gaattcctgt cacaatatgc atacaaa     1617
```

| SEQ ID NO: 120 | moltype = DNA length = 1509 |
| --- | --- |
| FEATURE | Location/Qualifiers |
| misc_feature | 630 |
|  | note = /note="n is a, c, g, or t" |
| source | 1..1509 |
|  | mol_type = other DNA |
|  | organism = Gossypium hirsutum |

SEQUENCE: 120

```
atggcgtcaa ctgaaaacaa agatgaccac tcttctgcta aaagagtagc tgtcattggc    60
gctggtgtta gtggactcgc ggcagcttac aagttgaaat cacaaggttt acatgttacg   120
gtatttgaat ctgaaggaag agctggaggg aagttaagaa gtgtttcgag ggatggtttg   180
atatggagtg aaggagcaaa tacaatgact gaaagtgaga ttgaagtgag aagtttgttt   240
gatgatcttg gtattcaaga taagcaacaa gttccaattg cacagaacaa gcggtatatc   300
atgagaaatg cgtgcctgt attgatcccc tcaaatcctc tctcattatt cacaagcagc   360
attctttcag caaaatcgaa gtttcagatt attttggagc cttttctgtg gagaaacagt   420
gaagcctcaa aagtatctga tgcttataat caggaaagtg tgggaggatt ttttcagcgc   480
cattttgggc aggaggttgt ggattacctt gttgatccct tgttgctgg cacaagtgct   540
ggagatcctg aatctctatc tatgtgccat tcctttccgg ggctatggga tcttgagcaa   600
aggtttggct ctatcattgt tggagcagtn aaatctaaat tctctgccaa aaggacaaat   660
cgtgaagaaa caaaaaattc agtgaaaaga aaggctctac gtggctcatt ttccttcaag   720
ggtggaatgc agacacttgc tgatatgttg tgcaaagatc tttccaaaga tgagcttaaa   780
ctgaaatcaa aggttttgtc attatcttac agtcatgagg ggaagtctac atcagagaac   840
tggtctctct cttatgcttc tgatcagac aagcgctcac aaggctcatc atttgatgct   900
gtaataatga cggctccggt gtgcaatgtt aaagaaatga aaattactaa aggaggaaat   960
gtctttccac tgaacttcat ccctgaggtg agttatatgc cactatccgt cataattact  1020
gcttttaaga aggagaatgt caagaaaccc ctagaaggtt ttggagttct taaccttca  1080
aaggagcagc aaaatggttt aaaaactctc ggtacacttt ttcatctgt gatgtttcct  1140
gatcgtgcac ctaataattt gtatctctat acaaccttg ttggaggaaa tcgaaatgag  1200
aagctggcaa aagcctcaac agatgaattg aagcatattg ttacttccga ccttcagcag  1260
ttgttgggag tggagggaga accgacattc ttcaatcatt tctattggag caaggcatttt  1320
cccttgtatg gccgtaacta tgcttcggtc tggaaggca ttgaaagat gggagagat  1380
ctccctggat tcttctatgc aggtaaccac aaagggggat tatcggtggg caaatcgatt  1440
gcttctggtt gcaaagcagc agataatgta attacatatt tggaatcttc acatgacaag  1500
ctgctgaaa                                                          1509
```

| SEQ ID NO: 121 | moltype = DNA length = 1680 |
| --- | --- |
| FEATURE | Location/Qualifiers |
| source | 1..1680 |
|  | mol_type = other DNA |
|  | organism = Beta vulgaris |

SEQUENCE: 121

```
atgaaatcaa tggcgttatc aaactgcatt ccacagacac agtgcatgcc attgcacagc    60
agcgggcatt acagggggcaa ttgtatcatg ttgtcaattc catgtagttt aattggaaga   120
cgaggttatt attcacataa gaagaggagg atgagcatga gttgcagcac aagctcaggc   180
```

```
tcaaagtcag cggttaaaga agcaggatca ggatcaggat caggagcagg aggattgcta    240
gactgcgtaa tcgttggagg tggaattagc gggctttgca tcgcgcaggc tctttgtaca    300
aaacagtcct ctttatcccc aaattttata gtgacagagg ccaaagacag agttggcggc    360
aacatcgtca ctgtggaggc cgatggctat atctgggagg agggacccaa tagcttccag    420
ccttccgacg cggtgctcac catggcggtc gacagtggct tgaaagatga gttggtgctc    480
ggagatccca atgctcctcg ctttgtgctg tggaatgaca aattaaggcc cgtaccttcc    540
agtctcacca acctcccttt cttcgacctc atgaccattc ccgcaagat tagggctgct     600
cttggtgctc tcggatttcg cccttctcct ccacctcatg aggaatctgt tgaacacttt    660
gtgcgtcgta atctcggaga tgaggtcttt gaacgcttga ttgaacccctt ttgttcaggt    720
gtgtatgccg gtgatcctgc caagctgagt atgaaagctg cttttgggaa ggtctggaag    780
ttggagcaaa agggtggcag cataattggt ggcactctca aagctataca ggaaagaggg    840
agtaatccta agccgccccg tgaccagcgc ctccctaaac caaagggtca gactgttgga    900
tcctttagaa agggactcgt tatgttgcct accgccattc tgctcgact tggcagtaga     960
gtgaaactat cttggaccct ttctagtatc gtaaagtcac tcaatggaca atatagtctg   1020
acttatgata ccccagatgg cttggttcct gtaagaaccca aaagtgttgt gatgactgtc   1080
ccatcatatg ttgcaagtag gcttcttcgt ccactttcag actctgctgc agattctctt   1140
tcaaaatttt actatccacc agttgcagca gtgtcacttt cctatcctaa agaagcgatc   1200
agatcagaat gcttgattaa tggtgaactt caaggtttcg ggcaactaca tccccgcagt   1260
cagggtgtgg aaaccttggg aacaatttat agttcgtctc ttttccctgg tcgagcacca   1320
cctggtagga tcttgatctt gagctacatc ggaggtgcta aaaatcctgg catattaaac   1380
aagtcgaaag atgaacttgc cgagacagtt gacaaggacc tgagaagaat gcttataaat   1440
cctgatgcaa aacttcctcg tgtactgggt gtgagagtat ggcctcaagc aatacccag    1500
ttttctattg ggcactttga tctgctcgat gctgcaaaag ctgctctgac agatacaggg   1560
gtcaaaggac tgtttcttgg tggcaactat gtttcaggtg ttgccttggg gcggtgtata   1620
gagggtgctt atgagtctgc agctgaggta gtagatttcc tctcacagta ctcagacaaa   1680

SEQ ID NO: 122       moltype = DNA   length = 1593
FEATURE              Location/Qualifiers
source               1..1593
                     mol_type = other DNA
                     organism = Hordeum vulgare
SEQUENCE: 122
atggccggtg caggtgcaac catgccacc gccaccgcgc cgccgctccg cggcagggtc      60
accggcgcc cgcacggcgt ccgcccgcgt tgcgcggccg cgggcagcgc gaccgagacc     120
cccgcggcgc ccggcgtgcg tctgtccgcg gactcgtca tcgtgggcgc ggcatcagc      180
ggcctctgca ccgcgcaggc gctgccacc cggcacggcg tcggcgacct gctcgtcacg    240
gaggcccgcg accgcccggg cggcaacatc accaccgtcg agcgcccga cgaggggtac    300
ctctgggagg agggccccaa cagcttccag ccctccgacc ccgtcctcac catggccgtg    360
gacagcgggc tcaaggatga cctggtgttc ggggacccca acgcgccccg gttcgtcgtg    420
tgggagggga agctgaggcc ggtgccgtcc aagccaggcg acctgccgtt cttcagcctc    480
atgagcgtcc ccgggaagct cagggccggc ctcggcgccc tcggcattcg cccgcctcct   540
ccagggcgcg aggagtcggt ggaggagttt gtgcgccgca acctcggtgc cgaggtcttt    600
gagcgcctta tcgaaccttt ctgctcaggt gtgtatgctg gtgatccttc gaagctcagt    660
atgaaggctg catttgggaa ggtttggagg ttggaggaga ttgggggtag tattattggt    720
ggaaccatca aggcaattca ggataaaggg aagaacccca aacgccaag ggatcccga     780
cttccggcac aaagggcaca gacggtgcaa tcttttcagga agggtctggc catgctcccg   840
aatgccatcg catctaggtt gggtagtaaa gtcaagctgt catggaagct tacgagcatt   900
acaaaggcgg acaaccaagg atatgtatta ggttatgaaa caccagaagg acttgtttca   960
gtgcaggcta aaagtgttat catgaccatc ccgtcatatg ttgctagtga tatcttacgc   1020
ccactttcaa ttgatgcagc agatgcactc tcaaaattct attatccgcc agttgctgct   1080
gtaactgttt catatccaaa agaagctatt agaaaagaat gcttaattga tggggagctc   1140
cagggtttcg gccagctgca tccacgtagc caaggagtcg agactttagg gacaatatat   1200
agctcttctc tctttcccaa tcgtgctcct gctggaagag tgttacttct gaactatatc   1260
gggggttcta caaatacagg atcgtctcc aagaccgaga gtgacttagt agaagctgtt    1320
gatcgtgatc tcagaaaaat gttgataaac cctagagcag cagaccctta agcattaggg   1380
gtcagagtgt ggccacaagc aataccacag tttttgattg gacaccttga tcgccttgct   1440
gctgcaaaat ctgcactggg ccgaggcggg tacgacgggt tattcctagg aggaaactac   1500
gtagcaggag ttgccttggg ccgatgcatc gagggtgcgt acgagagtgc ctcacaagta   1560
tctgacttct tgaccaagta tgcctacaag tga                                1593

SEQ ID NO: 123       moltype = DNA   length = 1665
FEATURE              Location/Qualifiers
source               1..1665
                     mol_type = other DNA
                     organism = Hordeum vulgare
SEQUENCE: 123
atgctcactt ccgccaccgc tccccctcc tcctcctcct gctcgtccca cgctcccgcc      60
cgcttcgcct ccccgtcccg gccccgtcgc tccgcgtccg cgtccgcgcg cgggcgaggg    120
cgccgcgtcc gccccgtgct cgccatggcc gcctccgacg accccgcgcc caggtcggtc    180
gccgtcgtcg gcgccggcgt cagtgggctc gtgccggcgt acatgctgag gaagagcggc    240
gtgcggggtca ccgtgttcga ggcggaagac cgcgcggag ggaagatacg gaccaactcc    300
gacggcggat tcctctggga cgaaggacc aacaccatga cagaaagtgc actgaggct     360
agtaggctaa tcgacgatct tggtcttcag gacagactgc agtatcctaa ctcccagcac    420
aagcgttaca ccgttaagga tgggggcgca gcactgattc cttcagatcc cattgatgcta   480
atgaaagcag ctgttctttc tacgaaatca aagttcaagt tatttctgga accattctc    540
tatgaaaaat ctagcacaag gaactccaaa aaagtgtctg acgagcattt gcgcgagagc   600
gttgggagtt ttttttgaacg ccatttgggg aaagaggttg ttgactatct tattgatcca   660
tttgtagctg gaacaagtgc aggagatccc gagtcattat ctattcgtca tgcatttccg    720
gggttatgga atttagaaaa aaagtatggt ctctctcatcg ttggtgccat cttgtcaaaa    780
```

```
ctaacagcta aaggtggttc agcaaagaaa ggaggcgctt cgtcaggaaa aggaaggaac  840
aagcgggcct cattttcatt tcatggtggc atgcagacac tagtagacgc acttcacaag  900
gaagttggag atactaatgt gaagcttgga acacaagtat tgtcattggc gtgtaactgt  960
gatggactct ctgcatcaga tgggtggtca atttttgttg attcaaagga tgctagtagt 1020
aaggacttg caaggaacca atcctttgat gctgttataa tgacagctcc actgtccaat 1080
gtccagagga tgaagttcac aaaaggcgga cgtcccttg tgctagactt tcttcctaag 1140
gtggattatc tgccgttgtc cctcatggta acagcattta agaaggaaga cgtcaaaaga 1200
cccctcgaag gatttgggt cttaataccc tttaaggaac aacaaaaaca tggtttgaaa 1260
acgctcggaa ctctcttctc ctctatgatg ttcccagatc gagctcctaa tgaccagcac 1320
ttgtttacaa cattcattgg gggaagccac aatagagatc tcgctggagc tccaacggct 1380
atcttgaaac aatttgtgac atctgaccct acaaagctac tggggtaga ggggcagcca 1440
acttttgtga acatataca ttggagaaat gcttttcctt tgtatggcca tgattatgat 1500
ttggcactgg aagctatagg aaagatgaaa ggtgatctcc cagggttctt ctatgcagga 1560
aataacaagg atggggttggc tgttgaaat gtcatagctt caggaagtaa cactgcagac 1620
cttgtgatct cataccttga gtcaggcatc aagcatgtta attga              1665

SEQ ID NO: 124         moltype = DNA   length = 1593
FEATURE                Location/Qualifiers
source                 1..1593
                       mol_type = other DNA
                       organism = Triticum aestivum
SEQUENCE: 124
atggccggcg caacaatggc caccgccacc gtcgcggccg cgtcgccgct ccgcggcagg   60
gtcaccgggc gcccacaccg cgtccgcccg cgttgcgcta ccgcgagcag cgcgaccgag  120
actccggcgg cgcccggcgt gcggctgtcc gcggaatgcg tcattgtggg cgccggcatc  180
agcggcctct gcaccgcgca ggcgctggcc acccgatacg gcgtcagcga cctgctcgtc  240
acggaggccc gcgaccgccc gggcggcaac atcaccaccg tcgagcgtcc cgacgagggg  300
tacctgtggg aggagggacc caacagcttc cagccctccg acccggtcct caccatggcc  360
gtggacagcg ggctcaagga tgacttggtg ttcggggacc caacgcgcc ccggttcgtg  420
ctgtgggagg ggaagctgag gccggtgccg tcgaagccag ggacctgcc tttcttcagc  480
ctcatgagta tccctgggaa gctcagggcc ggccttggcg cgctcggcat tcgcccacct  540
cctccagggc gcgaggagtc ggtggaggag tttgtgcgcc gcaacctcgg tgccgaggtc  600
tttgagcgcc tcatcgagcc tttctgctca ggtgtatatg ctggtgatcc ttcgaagctt  660
agtatgaagg ctgcatttgg gaaggtctgg aggttggagg agattggagg tagtattatt  720
ggtgaaacca tcaaggcgat tcaggataaa gggaagaacc ccaaaccgtc aagggatccc  780
cgacttccgg caccaaaggg acagacggtg gcatctttca ggaagggtct agccatgctc  840
ccgaatgcca tcgcatctag gctgggtagt aaagtcaagc tgtcatggaa gcttacgagc  900
attacaaagg cggacaacca aggatatgta ttaggttatg aaaccagac aggacttgtt  960
tcagtgcagg ctaaagtgt tatcatgacc atccgtcat atgttgctag tgatatcttg 1020
cgcccacttt caattgatgc agcagatgca ctctcaaaat tctattatcc gccagttgct 1080
gctgtaactg tttcatatcc aaaagaagct attagaaaag aatgcttaat tgatgggag 1140
ctccaggggt tcggccagtt gcatccacgt agccaaggag tcgagacttt agggacaata 1200
tatagctctt ctctctttcc taatcgtgct cctgctggaa gagttgttact tctgaactat 1260
atcggggtt ctacaaatac agggatcgtc tccaagactg agagtgactt agtaggagc 1320
gttgaccgtg acctcagaaa aatgttgata accctcagag cagcagaccc tttagcatta 1380
gggggttcgag tgtggccaca agcaaatacca cagttttttga ttgggcacct tgatcgcctt 1440
gctgctgcaa aatctgcact gggccaaggc ggctacgacg ggttgttcct aggaggaaac 1500
tacgtcgcag gagttgcctt gggccgatgc atcgagggtg cgtacgagag tgcctcacaa 1560
gtatctgact tcttgaccaa gtatgcctac aag                              1593

SEQ ID NO: 125         moltype = DNA   length = 1506
FEATURE                Location/Qualifiers
source                 1..1506
                       mol_type = other DNA
                       organism = Solanum lycopersicum
SEQUENCE: 125
atggctccat ctgccggaga agataaacaa aagagagttg cagtcattgg tgctggcgtc   60
agtggacttg ctgcagcata caagttgaaa gttcatggct tgaatgtcac agtatttgaa  120
gcagaaggga gagctggagg gaagttacga agcctgagtc aagatggtca aatatgggat  180
gaaggcgcaa atactatgac tgaaagtgaa ggtgatgtca cattttgct tgattcgctt  240
ggactccgag aaaaacaaca attcccactt tcacagaaca agcgctacat tgccagaaat  300
ggtactccta ctctgatacc ttcaaatcca tttgacctat tcaaaagcaa ttttctttcc  360
actggatcaa agcttcagat gctttttcgag ccacttttgt ggaagaataa aaagcttaca  420
aaggtgtctg acaaacacga aagtgtcagt ggattcttcc gtgcatttt tggaaaggag  480
gttgtcgact atctcaattga cccttttgtt gctggaacat gtggtggtga tcctgattcg  540
ctttcaatgc accttttcatt tccagacttg tggaattttag agaaaggttt tggttcagtc  600
atagttgggg caattcaatc taagttatct cctataaagg aaaagaaca agggccaccc  660
agaacttcaa taaataagaa gcgccagcgg gggtccttct cattttttggg cggaatgcaa  720
acacttactg acgcaatatg caaaaatctc aaagaagatg aacttaggct aaactctaga  780
gttctggaat tatcttgtag ctgtagtggg gactctgcga tagatagctg gtcaatttt  840
tctgcctctc cacacaagcg gcaagcagaa aaagaatcat ttgatgctgt aattatgacg  900
gcccctctct gtgacgttaa gagtatgaag attgctaaga gaggaaatcc atttctgctc  960
aactttattc ctgaggtcga ttatgtacca ctatctgttg ttataaccac atttaagaag 1020
gagagtgtaa agcatcccct tgagggttt ggagtgttac taccctccca ggagcaaaaa 1080
catggtctga agacactagg caccctcttc tcttctatga tgtttccaga tcgtgcaccc 1140
aacaatgtct atctctatac tacatttgtt ggtggaagcc gaaatagaga actcgcgaaa 1200
gcctcgagga ctgagctgaa agagatagta acttctgacc ttaagcagtt gttgggtgct 1260
gagggagagc caacatatgt gaatcattta tgctggagta aagcatttcc attgtacggg 1320
cataactatg attcagtcct agacgcaatt gacaaaatgt agaaaagcct tcctggatta 1380
```

```
ttctatgcag gtaaccacaa gggggattg tcagttggca aagcattatc ttctggatgc  1440
aatgcagcag atcttgttat atcatatctt gaagcggttt cagctgacac caaaaaccat  1500
agctga                                                              1506

SEQ ID NO: 126          moltype = DNA   length = 1677
FEATURE                 Location/Qualifiers
source                  1..1677
                        mol_type = other DNA
                        organism = Solanum lycopersicum
SEQUENCE: 126
atgacaacaa cggccgtcgt caaccatcct agcattttca ctcaccggtc gccgctgccg  60
tcgccgtcct cctcctcatc ctcatcgccg tcatttttat ttttaaatcg tacgaatttt  120
attccatact tttccacctc caagcgcagt agtgtcaatt gcaatggctg gagaacacgg  180
tgttccgttg cgaagaatta tacagttcct ccctcagaag ttgacggtaa tcagttaccg  240
gagctggatt gtgtggtagt cggagcagga attagtggtc tctgcattgc taaggtgata  300
tcggctaatt atcccaattt gatggtgacg gaggcgaggg atcgtgccgg tggaaacata  360
acgacggtga aaagagatgg atacttatgg aagaaggtc ctaacagttt ccagccttcg  420
gatccatatg tgactatggc tgtagattgt ggattgaagg atgatttggt gttgggagat  480
cctgatgcgc ctcgctttgt cttgtggaag gataaactaa ggcctgttcc cggcaagctc  540
actgatcttc ccttctttga tttgatgagt attcctggca agctcagagc tggttttggt  600
gccattggcc ttcgccctc acctccaggt tatgaggaat cagttgagca gttcgtgcgt  660
cgtaatcttg gtgctgaagt cttttgaacgt ttgattgaac cattttgttc tggtgtttat  720
gctggcgacc catcaaaatt gagtatgaaa gcagcatttg ggaaagtgtg aagctagaa  780
caaactggtg gtagcattat tgggggaacc tttaaggcaa taaggagag atccagtaac  840
cctaaaccgc ctcgtgatcc gcgtttacca acaccaaaag gacaaactgt tggttcattt  900
aggaagggtc tgagaatgct gccagatgca aatttgtgaa gactgggaa caaagtgaaa  960
ctatcatgga agctttctag cattacaaag tcagataaag gaggatatct cttgacatac  1020
gagacaccag aaggagtagt ttctctgcga agtcgaagca ttgtcatgac tgttccatcc  1080
tatgtagcaa gcaacatatt acgccctctt tcggtcgccg cagcagatgc actttcaagt  1140
ttctactatc ccccagttgc agcagtgaca atttcatatc ctcaagaggc tattcgtagt  1200
gagcgtctgg ttgatggtga actaaaggga tttgggcagt tgcatccacg ttcacaggga  1260
gtggaaacac taggaacaat atatagttca tcactcttcc ctaaccgtgc tccaaatggc  1320
cgggtgctac tcttgaacta cattggagga gcaacaaata ctgaaattgt gtctaagaca  1380
gagagccaac ttgtggaagc agttgaccgt gacctcagaa agatgcttat aaaaaccaaa  1440
gcacaagatc cctttgttac gggtgtgcga gtatggccac aagctatccc acagttttg  1500
gtcggacatc tggatacact aggtactgct aaagctgctc taagtgataa tgggcttgac  1560
gggctattcc ttgggggtaa ttatgtgtct ggtgtagcat gggaaggtg tgttgaaggt  1620
gcttatgaaa ttgcatctga agtaactggg tttctgtctc agtatgcata caaatga      1677

SEQ ID NO: 127          moltype = DNA   length = 1620
FEATURE                 Location/Qualifiers
source                  1..1620
                        mol_type = other DNA
                        organism = Gossypium hirsutum
SEQUENCE: 127
atgacggctc taatcgacct ttctcttctc cgctcctcgc cctccgtttc ccctttctcc  60
ataccccacc accagcttcc gccccgtctc cgtaaacctt tcaagctccg atgctccctc  120
gccgagggtc ccacgatttc ctcatctaaa atcgacgggg agaatcatc catcgccggat  180
tgcgtcgtcg ttggaggtgg tatcagtgga cttttgcattg ctcaagctct cgccaccaag  240
caccgtgacg tcgcttccaa tgtgattgtg acggaagcca gagaccgtgt tggtggcaac  300
atcactaccg ttgagagaga tggatatctg tgggaagaag gacccaacag ttttcagccg  360
tccgatccta ttctaaccat ggccgttggat agtggattga aggacgattt agttttaggt  420
gaccctaatg caccgcgatt tgtactgtgg gagggaaaac taaggcctgt gcctccaag   480
ccaaccgact tgccgttttt tgacttgatg agcattgctg aaaacttag gctgggttc   540
ggggctattg gcattcggcc tccccctccg ggttatgagg aatcggtgga ggagtttgtg  600
cgccgtaatc ttggtgctga ggttttgaa cgctttattg aaccattttg ttcaggtgtc  660
tatgcagggg atccttcaaa attaagcatg aaagcagcat ttggaagagt atggaagcta  720
gaagagattg gtggcagcat cattggtggc actttcaaga caatccagga gagaaataag  780
acacctaagc cacccagaga cccgctctg ccaaaaccga agggccaaac agttggatct  840
tttaggaagg gacttaccat gctgcctgag gcaattgcta acagtttggg tagcaattga  900
aaattatctt ggaagctctc cagtattacc aaattgggta atggaggta taacttgaca  960
tttgaaacac ctgaaggaat ggtatctctt cagagtagaa gtgttgtcat gaccattcca  1020
tcccatgttg ccagtaactt gttgcatcct ctctcggctg ctgctgcaga tgcattatcc  1080
caatttttatt atcctccagt tgcatcagtc acagtctcat catccaaaaga agccatcga   1140
aaagaatgtt tgattgatgg tgaacttaag gggtttggcc agttgcaccc acgcagccaa  1200
ggaatcgaaa ctttagggac gatatacagt tcatcacttt tccccaatcg agctccatct  1260
ggcagggtgt tgctcttgaa ctacatagga ggagctacca cactggaat ttgtccaag   1320
actgaagggg aacttgtaga agcagttgat cgtgatttga gaaaaatgct tataaatcct  1380
aatgcaaaag atcctcttgt ttttgggtgta agatatggc caaaagccat tccacagttc  1440
ttggttggtc atctggatct ccttgatact gcaaaaatgg ctctcaggga ttctgggttt  1500
catggactgt tcttgggggg caactatgta tctggtgtgg cattaggacg gtgtgtggaa  1560
ggtgcttacg aggttgcagc tgaagtgaag gaattcctgt cacaatatgc atacaaataa  1620

SEQ ID NO: 128          moltype = DNA   length = 1683
FEATURE                 Location/Qualifiers
source                  1..1683
                        mol_type = other DNA
                        organism = Beta vulgaris
SEQUENCE: 128
```

```
atgaaatcaa tggcgttatc aaactgcatt ccacagacac agtgcatgcc attgcacagc    60
agcgggcatt acaggggcaa ttgtatcatg ttgtcaattc catgtagttt aattggaaga   120
cgaggttatt attcacataa gaagaggagg atgagcatga gttgcagcac aagctcaggc   180
tcaaagtcag cggttaaaga agcaggatca ggatcaggat caggagcagg aggattgcta   240
gactgcgtaa tcgttggagg tggaattagc gggctttgca tcgcgcaggc tctttgtaca   300
aaacagtcct cttttatcccc aaattttata gtgacagagg ccaaagacag agttggcggc   360
aacatcgtca ctgtggaggc cgatggctat atctgggagg agggacccaa tagcttccag   420
ccttccgacg cggtgctcac catggcggtc gacagtggct tgaaagatga gttggtgctc   480
ggagatccca atgctcctcg cttttgtgctg tggaatgaca aattaaggcc cgtaccttcc   540
agtctcaccg acctcccttt cttcgacctc atgaccattc ccggcaagat tagggctgct   600
cttggtgctc tcggatttcg cccttctcct ccacctcatg aggaatcgtt tgaacacttt   660
gtgcgtcgta atctcggaga tgaggtcttt gaacgcttga ttgaacccct tgttcaggt   720
gtgtatgccg gtgatcctgc caagctgagt atgaaagctg cttttgggaa ggtctggaag   780
tggagcaaa agggtggcag cataattggt ggcactctca aagctataca ggaaagaggg   840
agtaatccta gccgccccg tgaccagcgc tccctaaac caaagggtca gactgttgga   900
tcctttagaa agggactcgt tatgttgcct accgccattt ctgctcgact tggcagtaga   960
gtgaaactat cttggaccct ttctagtatc gtaaagtcac tcaatggaga atatagtctg  1020
acttatgata ccccagatgg cttggtttct gtaagaacca aaagtgttgt gatgactgtc  1080
ccatcatatg ttgcaagtag gcttcttcgt ccactttcag actctgctgc agattctctt  1140
tcaaaatttt actatccacc agttgcagca gtgtcacttt cctatcctaa agaagcgatc  1200
agatcagaat gcttgattaa tggtgaactt caaggtttcg ggcaactaca tccccgcagt  1260
cagggtgtgg aaaccttggg aacaatttat agttcgtctc ttttccctgg tcgagcacca  1320
cctggtagga tcttgatctt gagctacatc ggaggtgcta aaaatcctgg catattaaac  1380
aagtcgaaag atgaacttgc cgagacagtt gacaaggacc tgagaagaat gcttataaat  1440
cctgatgcaa aacttcctcg tgtactgggt gtgagatat ggcctcaagc aatacccag  1500
ttttctattg ggcactttga tctgctcgat gctgcaaaag ctgtctgac agatacaggg  1560
gtcaaaggac tgtttcttgg tggcaactat gtttcaggtg ttgccttggg gcggtgtata  1620
gagggtgctt atgagtctgc agctgaggta gtagatttcc tctcacagta ctcagacaaa  1680
tag                                                                1683

SEQ ID NO: 129         moltype = AA  length = 98
FEATURE                Location/Qualifiers
source                 1..98
                       mol_type = protein
                       organism = Amaranthus sp.
SEQUENCE: 129
MVIQSITHLS PNLALPSPLS VSTKNYPVAV MGNISEREEP TSAKRVAVVG AGVSGLAAAY    60
KLKSHGLSVT LFEADSRAGG KLKTVKKDGF IWDEGANT                            98

SEQ ID NO: 130         moltype = AA  length = 98
FEATURE                Location/Qualifiers
source                 1..98
                       mol_type = protein
                       organism = Amaranthus sp.
SEQUENCE: 130
MVIQSITHLS PNLALPSPLS VSTKNYPVAV MGNISEREEP TSAKRVAVVG AGVSGLAAAY    60
KLKSHGLSVT LFEANSRAGG KLKTVKKDGF IWDEGANT                            98

SEQ ID NO: 131         moltype = AA  length = 98
FEATURE                Location/Qualifiers
source                 1..98
                       mol_type = protein
                       organism = Amaranthus sp.
SEQUENCE: 131
MVIQSITHLS PKLALPSPLS VSTKNYPVAV MGNISEREEP TSAKRVAVVG AGVSGLAAAY    60
KLKSHGLNVT LFEADSRAGG KLKTVKKDGF IWDEGANT                            98

SEQ ID NO: 132         moltype = AA  length = 98
FEATURE                Location/Qualifiers
source                 1..98
                       mol_type = protein
                       organism = Amaranthus sp.
SEQUENCE: 132
MVIQSITHLS PKLALPSPLS VSTKNYPVAV MGNISEREEP TSAKRVAVVG AGVSGLAAAY    60
KLKSHGLNVT LFEADSRAGG KLKTVKKDGF IWDEGANT                            98

SEQ ID NO: 133         moltype = AA  length = 113
FEATURE                Location/Qualifiers
source                 1..113
                       mol_type = protein
                       organism = Echinochloa sp.
SEQUENCE: 133
MLTLLFGVTS AGRATMVIQS TTHLSPNLAL PSPLSVSTKN YPVAVMGNIS EREEPTSAKR    60
VAVVGAGVSG LAAAYKLKSH GLSVTLFEAD SRAGGKLKTV KKDGFIWDEG ANT          113

SEQ ID NO: 134         moltype = AA  length = 97
FEATURE                Location/Qualifiers
source                 1..97
                       mol_type = protein
```

```
                              organism = Spinacia oleracea
SEQUENCE: 134
MVILPVSQLS TNLGLSLVSP TKNNPVMGNV SERNQVNQPI SAKRVAVVGA GVSGLAAAYK    60
LKSNGLNVTL FEADSRAGGK LKTVVKDGLI WDEGANT                            97

SEQ ID NO: 135         moltype = AA   length = 96
FEATURE                Location/Qualifiers
source                 1..96
                       mol_type = protein
                       note = subsp. vulgaris
                       organism = Beta vulgaris
SEQUENCE: 135
MVMLYDSHLS GVSTHLQLSQ AFPRKNPLMA KVSEPGKPTS AKRIAVVGAG VSGLAAAYKL    60
KSHGLSVTLF EADTRAGGKL KTVAKDGLIW DEGANT                             96

SEQ ID NO: 136         moltype = AA   length = 94
FEATURE                Location/Qualifiers
source                 1..94
                       mol_type = protein
                       organism = Solanum tuberosum
SEQUENCE: 136
MAPSAGEDKQ SNLLYPHVSL HNSTISQAKL TQFFCVDCPK RVAVIGAGVS GLAAAYKLKI    60
HGLDVTVFEA EGRAGGKLRS LSQDGLIWDE GANT                               94

SEQ ID NO: 137         moltype = AA   length = 88
FEATURE                Location/Qualifiers
source                 1..88
                       mol_type = protein
                       organism = Gossypium sp.
SEQUENCE: 137
MLNIAPSCVL ASGISKPVTK MASTENKDDH SSAKRVAVIG AGVSGLAAAY KLKSQGLHVT    60
VFESEGRAGG KLRSVSREGL IWDEGANT                                      88

SEQ ID NO: 138         moltype = AA   length = 122
FEATURE                Location/Qualifiers
source                 1..122
                       mol_type = protein
                       organism = Eucalyptus sp.
SEQUENCE: 138
MTGSTICSWK TRTVDGPNPE LWSARRRRPP LSSLSISIGK PEQRGAHGQQ RHAKMSSAAG    60
ADISSKTLHA LSSSQLTYGL AAAHKLKSNG VDVTVYEAEG RIGGKLRSVS QGGLIWDEGA   120
NT                                                                 122

SEQ ID NO: 139         moltype = AA   length = 72
FEATURE                Location/Qualifiers
source                 1..72
                       mol_type = protein
                       organism = Coffea sp.
SEQUENCE: 139
MASPAPKEKD KSSTCTKKRV AVVGAGVSGL AAAYKLKLRG LNVTVFEADE RAGGKLKSVS    60
RDGLIWDEGA NT                                                       72

SEQ ID NO: 140         moltype = AA   length = 71
FEATURE                Location/Qualifiers
source                 1..71
                       mol_type = protein
                       organism = Arabidopsis thaliana
SEQUENCE: 140
MASGAVADHQ IEAVSGKRVA VVGAGVSGLA AAYKLKSRGL NVTVFEADGR VGGKLRSVMQ    60
NGLIWDEGAN T                                                        71

SEQ ID NO: 141         moltype = AA   length = 68
FEATURE                Location/Qualifiers
source                 1..68
                       mol_type = protein
                       organism = Helianthus annuus
SEQUENCE: 141
MASPTTPDNQ KPAKRVAVVG AGVSGCAAAY KLKLHGLNVT VFEADGRVGG KLRSVSQDGL    60
IWDEGANT                                                            68

SEQ ID NO: 142         moltype = AA   length = 73
FEATURE                Location/Qualifiers
source                 1..73
                       mol_type = protein
                       organism = Arabidopsis lyrata
SEQUENCE: 142
MESGAVGDHD TKFESISGKR VAVVGAGVSG LAAAYKLKSR GLNVTVFEAD ERAGGKLTSV    60
MQNGLIWDQG ANT                                                      73
```

```
SEQ ID NO: 143          moltype = AA   length = 99
FEATURE                 Location/Qualifiers
source                  1..99
                        mol_type = protein
                        organism = Erythranthe sp.
SEQUENCE: 143
MRLYSAQYCC PSLLLLSSPS PYPFPITRST VLSMASAAQQ DSAVKSVAVI GAGVSGLSAA     60
YKLKLHGLNV TVFEADARSG GKLRSISHDG LIWDEGANT                           99

SEQ ID NO: 144          moltype = AA   length = 69
FEATURE                 Location/Qualifiers
source                  1..69
                        mol_type = protein
                        organism = Brassica oleracea
SEQUENCE: 144
MASNAAADHD KLSGKRVAVV GAGVSGLAAA YKLKSKGVNV TLFEADGRVG GKLRSVMHNG     60
LIWDEGANT                                                            69

SEQ ID NO: 145          moltype = AA   length = 68
FEATURE                 Location/Qualifiers
source                  1..68
                        mol_type = protein
                        organism = Ambrosia artemisiifolia
SEQUENCE: 145
MASPTIVDNQ KPAKRVAIVG AGVSGCAAAY KLKLHGLNVT VFEADERVGG KPRSVSQDGL     60
IWDEGANT                                                             68

SEQ ID NO: 146          moltype = AA   length = 71
FEATURE                 Location/Qualifiers
source                  1..71
                        mol_type = protein
                        organism = Morus notabilis
SEQUENCE: 146
MGTSASKQDN PTSPVKSVAV IGAGVSGLAA AYKLKSHGLN VTVFEAEERA GGKLRSVSSH     60
HGLIWDEGAN T                                                         71

SEQ ID NO: 147          moltype = AA   length = 63
FEATURE                 Location/Qualifiers
source                  1..63
                        mol_type = protein
                        organism = Cucumis sativus
SEQUENCE: 147
MKSSQSSRKK VAVVGAGVSG LAAAYKLKSH GFDVTVLEAD ERVGGKLRSV SYKGLIWDEG     60
ANT                                                                  63

SEQ ID NO: 148          moltype = AA   length = 72
FEATURE                 Location/Qualifiers
source                  1..72
                        mol_type = protein
                        organism = Zostera marina
SEQUENCE: 148
MSLPAMSEIS CISTGPAHSV AVVGGGISGL AAAYKLKSNG LSVTVFETEE RPGGKIRSRS     60
QDGFIWDEGA NT                                                        72

SEQ ID NO: 149          moltype = AA   length = 77
FEATURE                 Location/Qualifiers
source                  1..77
                        mol_type = protein
                        organism = Chondrus crispus
SEQUENCE: 149
MAVAEGATPA PAAASATPSE VDALVIGSGI SGSSLAFTLS QASPATSLLL TEARPVVGGN     60
VISRNERGYT WEEGPNT                                                   77

SEQ ID NO: 150          moltype = AA   length = 66
FEATURE                 Location/Qualifiers
source                  1..66
                        mol_type = protein
                        organism = Chondrus crispus
SEQUENCE: 150
MPEPVKRNVA VLGGGPAGLS AAFRLLHDLP PGLSVKVDLY EATGRLGGAV TSACDAGFCY     60
ELGPNS                                                               66

SEQ ID NO: 151          moltype = AA   length = 109
FEATURE                 Location/Qualifiers
source                  1..109
                        mol_type = protein
                        organism = Oryza nivara
SEQUENCE: 151
MLSPATTFSS SSSSSSPSRA HARAPTRFAV VASARAARFR PARAMAASDD PRGGRSVAVV     60
```

```
GAGVSGLAAA YRLRKRGVQV TVFEAADRAG GKIRTNSEGG FIWDEGANT                109

SEQ ID NO: 152            moltype = AA  length = 108
FEATURE                   Location/Qualifiers
source                    1..108
                          mol_type = protein
                          organism = Oryza glumipatula
SEQUENCE: 152
MLSPATTFSS SSSSSPSRAH AHAPTRFAVA ASARAARFRP ARAMAASDDP RGGRSVAVVG    60
AGVSGLAAAY RLRKRGVQVT VFEAADRAGG KIRTNSEGGF IWDEGANT                 108

SEQ ID NO: 153            moltype = AA  length = 65
FEATURE                   Location/Qualifiers
source                    1..65
                          mol_type = protein
                          organism = Oryza sp.
SEQUENCE: 153
MAASDDPRGG RSVAVVGAGV SGLAAAYRLR KRGVQVTVFE AADRAGGKIR TNSEGGFIWD    60
EGANT                                                                65

SEQ ID NO: 154            moltype = AA  length = 109
FEATURE                   Location/Qualifiers
source                    1..109
                          mol_type = protein
                          organism = Oryza sativa
SEQUENCE: 154
MLSPATTFSS SSSSSPSRA HARAPTRFAV AASARAARFR PARAMAASDD PRGGRSVAVV     60
GAGVSGLAAA YRLRKRGVQV TVFEAADRAG GKIRTNSEGG FIWDEGANT                109

SEQ ID NO: 155            moltype = AA  length = 114
FEATURE                   Location/Qualifiers
source                    1..114
                          mol_type = protein
                          organism = Oryza sativa
SEQUENCE: 155
MAAAAAMAT ATSATAAPPL RIRDAARRTR RRGHVRCAVA SGAAEAPAAP GARVSADCVV     60
VGGGISGLCT AQALATKHGV GDVLVTEARA RPGGNITTAE RAGEGYLWEE GPNS          114

SEQ ID NO: 156            moltype = AA  length = 110
FEATURE                   Location/Qualifiers
source                    1..110
                          mol_type = protein
                          organism = Oryza punctata
SEQUENCE: 156
MLSPATTTTF SSSSSSSSS SRAHAPTRFA AASARAARF RPARAMAASD DPHGGRSVAV      60
VGAGVSGLAA AYRLRKRGVQ VTVFEAADRA GGKIRTNSEG GFIWDEGANT               110

SEQ ID NO: 157            moltype = AA  length = 108
FEATURE                   Location/Qualifiers
source                    1..108
                          mol_type = protein
                          organism = Oryza rufipogon
SEQUENCE: 157
MLSPATTFSS SSSSPSRAH ARAPTRFAVA ASARAARFRP ARAMAASDDP RGGRSVAVVG     60
AGVSGLAAAY RLRKRGVQVT VFEAADRAGG KIRTNSEGGF IWDEGANT                 108

SEQ ID NO: 158            moltype = AA  length = 113
FEATURE                   Location/Qualifiers
source                    1..113
                          mol_type = protein
                          organism = Oryza meridionalis
SEQUENCE: 158
MLSPATATTT TTTTFSSSSS PSRAHAHAST RFAVAASARA ARFRPARAMA ASNDPRGGRS    60
VAVVGAGVSG LAAAYRLRKR GVQVTVFEAA DRAGGKIRTN SEGGFIWDEG ANT           113

SEQ ID NO: 159            moltype = AA  length = 100
FEATURE                   Location/Qualifiers
source                    1..100
                          mol_type = protein
                          organism = Zea mays
SEQUENCE: 159
MLALTASASS ASSHPYRHAS AHTRRPRLRA VLAMAGSDDP RAAPARSVAV VGAGVSGLAA    60
AYRLRQSGVN VTVFEAADRA GGKIRTNSEG GFVWDEGANT                          100

SEQ ID NO: 160            moltype = AA  length = 109
FEATURE                   Location/Qualifiers
source                    1..109
                          mol_type = protein
                          organism = Oryza brachyantha
```

```
SEQUENCE: 160
MLSPAATTTT TTSYCSYSSR AHAPTRSASA GAARFRPARA MATSDNDPRG AAPARSVAVV    60
GAGVSGLAAA YKLRKRGVQV TVFEAADRAG GKIRTNSESG FIWDEGANT              109

SEQ ID NO: 161          moltype = AA  length = 131
FEATURE                 Location/Qualifiers
source                  1..131
                        mol_type = protein
                        organism = Musa acuminata
SEQUENCE: 161
MLKQHGSATN RGLLSKIWFA RRFGEPVCRD PILLFRLPLD LGRSRRRRCS RKPSCFGEFH    60
RQLAIAMASA DNHNSIKSVA VVGGGVSGLA AAYKLKSNGL KVTLFEAEER AGGKIKSSSE   120
NGLIWDEGAN T                                                        131

SEQ ID NO: 162          moltype = AA  length = 70
FEATURE                 Location/Qualifiers
source                  1..70
                        mol_type = protein
                        organism = Populus trichocarpa
SEQUENCE: 162
MTAAAKDDDF GSKQSKNVAV IGAGVSGLAA AYKLKSNGVK VTVFEAEGRA GGKLRSVSHH    60
DLVWDEGANT                                                          70

SEQ ID NO: 163          moltype = AA  length = 108
FEATURE                 Location/Qualifiers
source                  1..108
                        mol_type = protein
                        organism = Avena fatua
SEQUENCE: 163
MLASATTPSP SSSRASTLFA SSSRPRHTAS ARGRRLRPVL AMAASDDPRA APARSVAVVG    60
AGVSGLVAAY RLRKSGVRVT VFEADDRAGG KIRTNSDSGF LWDEGANT               108

SEQ ID NO: 164          moltype = AA  length = 98
FEATURE                 Location/Qualifiers
source                  1..98
                        mol_type = protein
                        organism = Setaria italica
SEQUENCE: 164
MLSSSTTTAS PASSHPYRPA YPRASLRPVL AMAGSDDPRA APARSVAVIG AGVSGLAAAY    60
RLRKSGVNVT VFEAADRAGG KIRTNSEAGF LWDEGANT                           98

SEQ ID NO: 165          moltype = AA  length = 108
FEATURE                 Location/Qualifiers
source                  1..108
                        mol_type = protein
                        organism = Poa annua
SEQUENCE: 165
MLTSATTPSS SSSASSRACA RFASSARPHH TASARGRRLR PVLAMAASDQ PRARSVAVVG    60
AGVSGLVAAY RLRKSGVRVT VFEADDRAGG KIRTNSDSGF LWDEGANT               108

SEQ ID NO: 166          moltype = AA  length = 100
FEATURE                 Location/Qualifiers
source                  1..100
                        mol_type = protein
                        organism = Sorghum bicolor
SEQUENCE: 166
MLARTATVSS TSSHSHPYRP TSARSLRLRP VLAMAGSDDS RAAPARSVAV VGAGVSGLVA    60
AYRLRKSGVN VTVFEAADRA GGKIRTNSEG GFLWDEGANT                         100

SEQ ID NO: 167          moltype = AA  length = 104
FEATURE                 Location/Qualifiers
source                  1..104
                        mol_type = protein
                        organism = Brachypodium distachyon
SEQUENCE: 167
MLTSATASPS ASTRFSSTCR PCRSDSVPAR RPRPVLAMAA SDDPRAAPAR SVAVVGAGVS    60
GLVAAHRLRK SGVRVTVFEA DDRAGGKIRT NSDSGFLWDE GANT                    104

SEQ ID NO: 168          moltype = AA  length = 107
FEATURE                 Location/Qualifiers
source                  1..107
                        mol_type = protein
                        organism = Alopecurus myosuroides
SEQUENCE: 168
MLTSATTPSS SSASSRASTR FASSSRPRRT ASARGRRLRP VLAMAASDDP RARSVAVVGA    60
GVSGLVAAYR LSKSGVRVTV FEADDRAGGK IRTNSDSGFL WDEGANT                 107

SEQ ID NO: 169          moltype = AA  length = 68
FEATURE                 Location/Qualifiers
```

```
source                   1..68
                         mol_type = protein
                         organism = Gossypium raimondii
SEQUENCE: 169
MASTENKDDH SSAKRVAVIG AGVSGLAAAY KLKSQGLHVT VFESEGRAGG KLRSVSREGL    60
IWDEGANT                                                            68

SEQ ID NO: 170           moltype = AA  length = 68
FEATURE                  Location/Qualifiers
source                   1..68
                         mol_type = protein
                         organism = Amaranthus tuberculatus
SEQUENCE: 170
MGNISERDEP TSAKRVAVVG AGVSGLAAAY KLKSHGLNVT LFEADSRAGG KLKTVKKDGF    60
IWDEGANT                                                            68

SEQ ID NO: 171           moltype = AA  length = 68
FEATURE                  Location/Qualifiers
source                   1..68
                         mol_type = protein
                         organism = Amaranthus tuberculatus
SEQUENCE: 171
MGNISERDEP TSAKRVAVVG AGVSGLAAAY KLKSHGLNVT LFEADSRAGG KLKTVKKDGF    60
IWDEGANT                                                            68

SEQ ID NO: 172           moltype = AA  length = 70
FEATURE                  Location/Qualifiers
source                   1..70
                         mol_type = protein
                         organism = Brassica rapa
SEQUENCE: 172
MASNAVADHD KPVSGKRVAV VGAGVSGLAA AYKLKSKGVN VTVFEADGRV GGKLRSVMHN    60
GLIWDEGANT                                                          70

SEQ ID NO: 173           moltype = AA  length = 70
FEATURE                  Location/Qualifiers
source                   1..70
                         mol_type = protein
                         organism = Jatropha curcas
SEQUENCE: 173
MASAPKDERR NPSSGKRVAV VGAGVSGLAA AYKLKSHGLK VTVFEAEGRA GGKLRSVSRD    60
GLIWDEGANT                                                          70

SEQ ID NO: 174           moltype = AA  length = 70
FEATURE                  Location/Qualifiers
source                   1..70
                         mol_type = protein
                         organism = Vitis vinifera
SEQUENCE: 174
MAEKSDAQSH YNGSGKRVAV VGAGVSGLAA AYKLKLHGVN ITLYEAEERA GGKLRSVSQH    60
GLVWDEGANT                                                          70

SEQ ID NO: 175           moltype = AA  length = 69
FEATURE                  Location/Qualifiers
source                   1..69
                         mol_type = protein
                         organism = Vitis vinifera
SEQUENCE: 175
MAEKSDAQSH YNGSGKRVAV VGAGVSGLAA AYKLKLHGVN TLYEAEERAG GKLRSVSQHG    60
LVWDEGANT                                                           69

SEQ ID NO: 176           moltype = AA  length = 69
FEATURE                  Location/Qualifiers
source                   1..69
                         mol_type = protein
                         organism = Ricinus communis
SEQUENCE: 176
MSSVIKEDRN PSHVKRVAVV GAGVSGLAAA YKLKSHGLKV TVFEAEERAG GKLRSVNHDG    60
LIWDEGANT                                                           69

SEQ ID NO: 177           moltype = AA  length = 65
FEATURE                  Location/Qualifiers
source                   1..65
                         mol_type = protein
                         organism = Solanum lycopersicum
SEQUENCE: 177
MAPSAGEDKQ KRVAVIGAGV SGLAAAYKLK VHGLNVTVFE AEGRAGGKLR SLSQDGLIWD    60
EGANT                                                               65
```

```
SEQ ID NO: 178          moltype = AA   length = 64
FEATURE                 Location/Qualifiers
source                  1..64
                        mol_type = protein
                        organism = Kochia sp.
SEQUENCE: 178
MADLSETSVK RVAVVGAGVS GLAAAYKLKS HGFNVTLFEA EPRAGGKIKT VAKDGLIWDE    60
GANT                                                                64

SEQ ID NO: 179          moltype = AA   length = 66
FEATURE                 Location/Qualifiers
source                  1..66
                        mol_type = protein
                        organism = Prunus persica
SEQUENCE: 179
MTSLTTKEGS VKRVAVVGAG VSGLAAAYKL KSHGFDVTVF EAEGRAGGKL RSVSHDGLIW    60
DEGANT                                                              66

SEQ ID NO: 180          moltype = AA   length = 68
FEATURE                 Location/Qualifiers
source                  1..68
                        mol_type = protein
                        organism = Theobroma cacao
SEQUENCE: 180
MAAAKNKDKQ TSAKRVAVVG AGVSGLAAAY KLKSHGLNVT MFEAEGRAGG KLRSVSQEGL    60
IWDEGANT                                                            68

SEQ ID NO: 181          moltype = AA   length = 68
FEATURE                 Location/Qualifiers
source                  1..68
                        mol_type = protein
                        organism = Glycine max
SEQUENCE: 181
MASSATDDNP RSVKRVAVVG AGVSGLAAAY KLKSHGLDVT VFEAEGRAGG RLRSVSQDGL    60
IWDEGANT                                                            68

SEQ ID NO: 182          moltype = AA   length = 68
FEATURE                 Location/Qualifiers
source                  1..68
                        mol_type = protein
                        organism = Citrus clementina
SEQUENCE: 182
MASAPGEDNQ RSAKRVAVVG AGVSGLAAAY KLKSNGVNVM VFEADERAGG KLRSISKDGL    60
IWDEGANT                                                            68

SEQ ID NO: 183          moltype = AA   length = 68
FEATURE                 Location/Qualifiers
source                  1..68
                        mol_type = protein
                        organism = Citrus clementina
SEQUENCE: 183
MTNKWRVDFS GSAKRVAVVG AGVSGLAAAY KLKSNGVNVM VFEADERAGG KLRSISKDGL    60
IWDEGANT                                                            68

SEQ ID NO: 184          moltype = AA   length = 68
FEATURE                 Location/Qualifiers
source                  1..68
                        mol_type = protein
                        organism = Medicago truncatula
SEQUENCE: 184
MASSAKDDNP RSVKRVAVVG AGVSGLAAAY KLKSHGLDVT VFEAEGRAGG RLRTVSRDGL    60
VWDEGANT                                                            68

SEQ ID NO: 185          moltype = AA   length = 68
FEATURE                 Location/Qualifiers
source                  1..68
                        mol_type = protein
                        organism = Phaseolus vulgaris
SEQUENCE: 185
MSSSATDDNP RSVKRVAVIG AGVSGLAAAY KLKSHGLDVT VFEAEGRAGG RLRSVSRDGL    60
IWDEGANT                                                            68

SEQ ID NO: 186          moltype = AA   length = 68
FEATURE                 Location/Qualifiers
source                  1..68
                        mol_type = protein
                        organism = Vigna angularis
SEQUENCE: 186
MSSSATDDNP RSVKRVAVIG AGVSGLAAAY KLKSHGVDVT VFEAEGRAGG RLRSVSRDGL    60
```

```
IWDEGANT                                                                   68

SEQ ID NO: 187          moltype = AA  length = 68
FEATURE                 Location/Qualifiers
source                  1..68
                        mol_type = protein
                        organism = Gossypium arboreum
SEQUENCE: 187
MASTENKDDH SSAKRVAVIG AGVSGLAAAY KLKSQGLHVT VFESEGRAGG KLRSVSRDGL           60
IWDEGANT                                                                   68

SEQ ID NO: 188          moltype = AA  length = 68
FEATURE                 Location/Qualifiers
source                  1..68
                        mol_type = protein
                        organism = Nicotiana tabacum
SEQUENCE: 188
MAPSAGEDKH SSAKRVAVIG AGVSGLAAAY KLKIHGLNVT VFEAEGKAGG KLRSVSQDGL           60
IWDEGANT                                                                   68

SEQ ID NO: 189          moltype = AA  length = 68
FEATURE                 Location/Qualifiers
source                  1..68
                        mol_type = protein
                        organism = Ambrosia artemisiifolia
SEQUENCE: 189
MASPTIVDNQ KPAKRVAIVG AGVSGCAAAY KLKLHGLNVT VFEADGRVGG KLRSVSQDGL           60
IWDEGANT                                                                   68

SEQ ID NO: 190          moltype = AA  length = 68
FEATURE                 Location/Qualifiers
source                  1..68
                        mol_type = protein
                        organism = Solanum tuberosum
SEQUENCE: 190
MAPSAGEDKQ NCPKRVAVIG AGVSGLAAAY KLKIHGLNVT VFEAEGRAGG KLRSLSQDGL           60
IWDEGANT                                                                   68

SEQ ID NO: 191          moltype = AA  length = 68
FEATURE                 Location/Qualifiers
source                  1..68
                        mol_type = protein
                        organism = Solanum tuberosum
SEQUENCE: 191
MAPSAGEDKQ NCPKRVAVIG AGVSGLAAAY KLKIHGLDVT VFEAEGRAGG KLRSLSQDGL           60
IWDEGANT                                                                   68

SEQ ID NO: 192          moltype = AA  length = 69
FEATURE                 Location/Qualifiers
source                  1..69
                        mol_type = protein
                        organism = Brassica napus
SEQUENCE: 192
MASNAAADHD KLSGKRVAVV GAGVSGLAAA YKLKSKGVNV TVFEADGRVG GKLRSVIRNG           60
LIWDEGANT                                                                  69

SEQ ID NO: 193          moltype = AA  length = 69
FEATURE                 Location/Qualifiers
source                  1..69
                        mol_type = protein
                        organism = Brassica napus
SEQUENCE: 193
MASNAVADHD KLSGKRVAVV GAGVSGLAAA YKLKSKGVNV TVFEADGRVG GKLRSVMHNG           60
LIWDEGANT                                                                  69

SEQ ID NO: 194          moltype = AA  length = 70
FEATURE                 Location/Qualifiers
source                  1..70
                        mol_type = protein
                        organism = Picea sitchensis
SEQUENCE: 194
MAEHIHTDQN DKRPLKSVAV VGAGISGLAA AYRLKSQGLA VTIFEADGTT GGKIKSFAQN           60
GLIWEKGANT                                                                 70

SEQ ID NO: 195          moltype = AA  length = 67
FEATURE                 Location/Qualifiers
source                  1..67
                        mol_type = protein
                        organism = Brachypodium distachyon
```

```
SEQUENCE: 195
MAASDDPRAA PARSVAVVGA GVSGLVAAHR LRKSGVRVTV FEADDRAGGK IRTNSDSGFL    60
WDEGANT                                                              67

SEQ ID NO: 196          moltype = AA   length = 64
FEATURE                 Location/Qualifiers
source                  1..64
                        mol_type = protein
                        organism = Triticum aestivum
SEQUENCE: 196
MAASDDPRAR SVAVVGAGVS GLVAAYRLRK SGVRVTVFEA EDRAGGKIRT NSDGGFLWDE    60
GANT                                                                 64

SEQ ID NO: 197          moltype = AA   length = 65
FEATURE                 Location/Qualifiers
source                  1..65
                        mol_type = protein
                        organism = Oryza glaberrima
SEQUENCE: 197
MAASDDPRGG RSVAVVGAGV SGLAAAYRLR KRGVQVTVFE AADRAGGKIR TNSEGGFIWD    60
EGANT                                                                65

SEQ ID NO: 198          moltype = AA   length = 67
FEATURE                 Location/Qualifiers
source                  1..67
                        mol_type = protein
                        organism = Selaginella moellendorffii
SEQUENCE: 198
MAMAEGETAP VLGSVAVVGA GASGLAAAYR LRAAGVSVTV YEAENSIGGK LKSVSENGFI    60
WEKGPNT                                                              67

SEQ ID NO: 199          moltype = AA   length = 67
FEATURE                 Location/Qualifiers
source                  1..67
                        mol_type = protein
                        organism = Selaginella moellendorffii
SEQUENCE: 199
MAMAEGETVP VLGSVAVVGA GASGLAAAYR LRAAGVSVTV YEAENSIGGK LKSVSENGFI    60
WEKGPNT                                                              67

SEQ ID NO: 200          moltype = AA   length = 97
FEATURE                 Location/Qualifiers
source                  1..97
                        mol_type = protein
                        organism = Triticum aestivum
SEQUENCE: 200
MLTSATAPSS SCSSHAPTRF ASARGRRLRP VLAMAASDDP RARSVAVIGA GVSGLVAAYR    60
LRKSGVRVTV FEAEDRAGGK IRTNSDGGFL WDEGANT                             97

SEQ ID NO: 201          moltype = AA   length = 112
FEATURE                 Location/Qualifiers
source                  1..112
                        mol_type = protein
                        organism = Hordeum vulgare
SEQUENCE: 201
MLTSATAPPS SSSCSSHAPA RFASPSRPRR SASASARGRG RRVRPVLAMA ASDDPRARSV    60
AVVGAGVSGL VAAYMLRKSG VRVTVFEAED RAGGKIRTNS DGGFLWDEGA NT           112

SEQ ID NO: 202          moltype = AA   length = 70
FEATURE                 Location/Qualifiers
source                  1..70
                        mol_type = protein
                        organism = Ginkgo sp.
SEQUENCE: 202
MAAPLHPDNN SRRPHKSVAI VGAGISGLAA AYRLKSEGLA VTVFEAEEST GGKIKSISQD    60
GLVWEKGPNT                                                           70

SEQ ID NO: 203          moltype = AA   length = 65
FEATURE                 Location/Qualifiers
source                  1..65
                        mol_type = protein
                        organism = Phytophthora capsici
SEQUENCE: 203
MAARDVVVLG GGISGLTLAY FLRQALPKAA ADATRIRVLD ASAISGGWVH TAKREGFLFE    60
EGPRG                                                                65

SEQ ID NO: 204          moltype = AA   length = 76
FEATURE                 Location/Qualifiers
source                  1..76
```

```
                         mol_type = protein
                         organism = Lemna sp.
SEQUENCE: 204
MEADAGKGSA GGAQILSHDS VRSVAVIGGG ISGLAAAYKL KSNGFRAVVF EAEGKAGGKI     60
RSGSQEGLIW DEGANT                                                    76

SEQ ID NO: 205           moltype = AA  length = 135
FEATURE                  Location/Qualifiers
source                   1..135
                         mol_type = protein
                         organism = Capsella rubella
SEQUENCE: 205
MHDAGDSHDP FEIHKHVDVE LKSGLDAKTL NKGPLDKRLK IIGPEELKTR FDAELSWLLL     60
ITMASAKVAD NDTKFEAVSG RRVAVVGGGV SGLAAAYKLK SKGLNVTVFE ADGRAGGKLR    120
SVMHNGLIWD EGANT                                                    135

SEQ ID NO: 206           moltype = AA  length = 66
FEATURE                  Location/Qualifiers
source                   1..66
                         mol_type = protein
                         organism = Eutrema salsugineum
SEQUENCE: 206
MAPDAVADHD KKFEALSGKR VAVVGAGVRL KSRGLNVTVF EADGRAGGKL RSVMHKGLIW     60
DEGANT                                                               66

SEQ ID NO: 207           moltype = AA  length = 121
FEATURE                  Location/Qualifiers
source                   1..121
                         mol_type = protein
                         organism = Glycine max
SEQUENCE: 207
MVSVFNEILF PPNQTLLRPS LHSPTSFFTS PTRKFPRSRP NPILRCSIAE ESTASPPKTR     60
DSAPVDCVVV GGGVSGLCIA QALATKHANA NVVVTEARDR VGGNITTMER DGYLWEEGPN    120
S                                                                   121

SEQ ID NO: 208           moltype = AA  length = 117
FEATURE                  Location/Qualifiers
source                   1..117
                         mol_type = protein
                         organism = Gossypium raimondii
SEQUENCE: 208
MTALIDLSLL RSSPSVSPFS IPHHQHPPRF RKPFKLRCSL AEGPTISSSK IDGGESSIAD     60
CVIVGGGISG LCIAQALATK HRDVASNVIV TEARDRVGGN ITTVERDGYL WEEGPNS       117

SEQ ID NO: 209           moltype = AA  length = 115
FEATURE                  Location/Qualifiers
source                   1..115
                         mol_type = protein
                         organism = Brassica napus
SEQUENCE: 209
MDLSLLRPQP FLSPFSNPFP RSRPYKPLNL RCSVSGGSVV VGSSTIEGGG GGKTVAADCV     60
IVGGGISGLC IAQALVTKHP DAAKSVMVTE AKDRVGGNII TREEQGFLWE EGPNS         115

SEQ ID NO: 210           moltype = AA  length = 114
FEATURE                  Location/Qualifiers
source                   1..114
                         mol_type = protein
                         organism = Brassica napus
SEQUENCE: 210
MDLSLLRPQP FLSPFSNPFP RSRPYKPLNL RCSVSGGSVV GSSTIEGGGG GKTVTADCVI     60
VGGGISGLCI AQALVTKHPD AAKNVMVTEA KDRVGGNIIT REEQGFLWEE GPNS          114

SEQ ID NO: 211           moltype = AA  length = 62
FEATURE                  Location/Qualifiers
source                   1..62
                         mol_type = protein
                         note = Bacteria sp.
                         organism = unidentified
SEQUENCE: 211
MTRHVVILGG GVTGLAAAYR LRRTVPSPDD LAITLVERRS RLGGSIGTER HEGYLIESGV     60
DS                                                                   62

SEQ ID NO: 212           moltype = AA  length = 113
FEATURE                  Location/Qualifiers
source                   1..113
                         mol_type = protein
                         organism = Setaria italica
SEQUENCE: 212
MVAAAMATAP SAGVPPLRGT RGPARFRIRG VSVRCAAVAG GAAEAPASAG ARVSADCVVV     60
```

```
GGGISGLCTA QALATKHGVG DVLVTEARAR PGGNITTVER PDEGYLWEEG PNS          113

SEQ ID NO: 213           moltype = AA   length = 115
FEATURE                  Location/Qualifiers
source                   1..115
                         mol_type = protein
                         organism = Zea mays
SEQUENCE: 213
MVAATATATA MATAASPLLN GTRIPARLRH RGLSVRCAAV AGGAAEAPAS TGARLSADCV    60
VVGGGISGLC TAQALATRHG VGDVLVTEAR ARPGGNITTV ERPEEGYLWE EGPNS        115

SEQ ID NO: 214           moltype = AA   length = 109
FEATURE                  Location/Qualifiers
source                   1..109
                         mol_type = protein
                         organism = Triticum aestivum
SEQUENCE: 214
MAGATMATAT VAAASPLRGR VTGRPHRVRP RCATASSATE TPAAPGVRLS AECVIVGAGI    60
SGLCTAQALA TRYGVSDLLV TEARDRPGGN ITTVERPDEG YLWEEGPNS              109

SEQ ID NO: 215           moltype = AA   length = 109
FEATURE                  Location/Qualifiers
source                   1..109
                         mol_type = protein
                         organism = Brachypodium distachyon
SEQUENCE: 215
MATATMATAA ATAAPPRRLR VPAPPRGGHA RCAVASNATE APAAPGARLS ADCVIVGGGI    60
SGLCTAQALA TKYGFGDVLV TEARARPGGN ITTVERPDEG YLWEEGPNS              109

SEQ ID NO: 216           moltype = AA   length = 162
FEATURE                  Location/Qualifiers
source                   1..162
                         mol_type = protein
                         organism = Populus trichocarpa
SEQUENCE: 216
MTVKQSSVAR IKGLINPSSS QITSLQGSGS FACQTESEPA MTSTFTDLSL LRPTIPSLIP    60
SSFSKFTTHR PLKLRCSLTE DSTTFIPFKL NGEAQSSAGH SATADCVIVG GISGLCIAQ   120
ALATKHWDVA PNVIVTEARD RVGGNITTLE RDGYLWEEGP NS                    162

SEQ ID NO: 217           moltype = AA   length = 121
FEATURE                  Location/Qualifiers
source                   1..121
                         mol_type = protein
                         organism = Populus trichocarpa
SEQUENCE: 217
MTTFIDFSLL RPTTPSLIPS SFSKFSTPRP FKLRCSLTEE SATITPSKLN GEAQSNGGHS    60
AAADCVIVGG GISGLCIAQA LATKHRDVAP NVIVTEARDR VGGNITTLER DGYLWEEGPN  120
S                                                                  121

SEQ ID NO: 218           moltype = AA   length = 147
FEATURE                  Location/Qualifiers
source                   1..147
                         mol_type = protein
                         note = Gingko
                         organism = unidentified
SEQUENCE: 218
MAMAVEMEAV LTVALQNYPI SPLKHFRGTH KKPATISSVF WQCKRNCLAG HAVWKGKTWI    60
GGGVNVVAKE ATMAPSGWVE NENENDDMYD CVVVGGGISG LSTAQALVSK HSSTVKNVVL  120
TEAKDRVGGN IMTMERDGYL WEEGPNS                                     147

SEQ ID NO: 219           moltype = AA   length = 157
FEATURE                  Location/Qualifiers
source                   1..157
                         mol_type = protein
                         organism = Alopecurus myosuroides
SEQUENCE: 219
MDFHTIRSPS LYPILVGHGK CKPTNQCSRS RIASSTPHRH LPRAQATEMV GATMAIATVT    60
AALPLRVRVP GRSRRGQARC AVASDATEAP AAPSARLSAD CVIVGGGISG LCTAQALATK  120
YGVSDLLVTE ARARPGGNIT TVERPDEGYL WEEGPNS                          157

SEQ ID NO: 220           moltype = AA   length = 62
FEATURE                  Location/Qualifiers
source                   1..62
                         mol_type = protein
                         note = Bacteria sp.
                         organism = unidentified
SEQUENCE: 220
MKRVVVIGGG ISGLSAAYFL KEAAAKKNID LDYTLIEKSD RLGGNIITEK LDHFIVEGGP    60
DN                                                                  62
```

```
SEQ ID NO: 221          moltype = AA   length = 139
FEATURE                 Location/Qualifiers
source                  1..139
                        mol_type = protein
                        organism = Cyanidioschyzon merolae
SEQUENCE: 221
MLRWSGSQQV TDRNRAEQHG LVVAFAFPAR APRHSEATHE RWTGLAQRER GLCVPLKATK   60
WKRDLWHSRK LQMQEPAQRN REQVQALVVG SGVTGSSFAF LLQHAGISDV ICTEARGEVG  120
GNLISRSKDG YLWEEGPNT                                               139

SEQ ID NO: 222          moltype = AA   length = 128
FEATURE                 Location/Qualifiers
source                  1..128
                        mol_type = protein
                        organism = Amaranthus tuberculatus
SEQUENCE: 222
MSAMALSSSI LQCPPHSDIS FRFFAHTRTQ SPIFFGRPRK LSYIHCSTSS SSTANYQNTI   60
TSQGEGDKVL DCVIVGAGIS GLCIAQALST KHIQSNLNFI VTEAKHRVGG NITTMESDGY  120
IWEEGPNS                                                           128

SEQ ID NO: 223          moltype = AA   length = 113
FEATURE                 Location/Qualifiers
source                  1..113
                        mol_type = protein
                        organism = Conyza canadensis
SEQUENCE: 223
MTSLTNFTPL KLTNPNYLTT TTTYNHRKLS NFRFRCSIAR DSPTAPSISG DSSSRPLLDC   60
VVVGAGISGL CIAQALSTKH GGDVVVTEAR ERVGGNISTV ERDGYLWEEG PNS          113

SEQ ID NO: 224          moltype = AA   length = 121
FEATURE                 Location/Qualifiers
source                  1..121
                        mol_type = protein
                        organism = Lemna sp.
SEQUENCE: 224
MASSAAISPL HFSPAPPRRR ELSHRCRVRC SIAGKPPATA ANDSSATSVT GGEPVRRLRA   60
DCVIVGAGIS GLCTAQALTV RPAAGRSSAP DVLVTEARDR VGGNITTVER DGYLWEEGPN  120
S                                                                  121

SEQ ID NO: 225          moltype = AA   length = 143
FEATURE                 Location/Qualifiers
source                  1..143
                        mol_type = protein
                        organism = Kochia sp.
SEQUENCE: 225
MSAMASPSII PQSFLQRSPT SLQSRSNYSK NHIIISISTP CSHGKNQRRF LRKTTHFRSI   60
HCSTISTSTP TSSSNPGTLG EGGLLDCVIV GGGISGLCIA QALSTKYSSL STNFIVTEAK  120
DRVGGNITTK EDDGYIWEEG PNS                                          143

SEQ ID NO: 226          moltype = AA   length = 115
FEATURE                 Location/Qualifiers
source                  1..115
                        mol_type = protein
                        organism = Arabidopsis thaliana
SEQUENCE: 226
MELSLLRPTT QSLLPSFSKP NLRLNVYKPL RLRCSVAGGP TVGSSKIEGG GGTTITTDCV   60
IVGGGISGLC IAQALATKHP DAAPNLIVTE AKDRVGGNII TREENGFLWE EGPNS        115

SEQ ID NO: 227          moltype = DNA  length = 639
FEATURE                 Location/Qualifiers
misc_feature            1..639
                        note = Expression cassette
source                  1..639
                        mol_type = other DNA
                        organism = synthetic construct
SEQUENCE: 227
atgactactg ctgttactgc tgctgtgtct ttcccaagta ccaagaccac ctctctcagt   60
gctaggtcta gttctgtgat ctctcctgat aagatctctt acaagaaggt gccactctac  120
tacagaaacg tgtcagctac cggaaagatg ggacctatca gggctcaaat cgcttcttgc  180
tctagtatgg atgctccttc tgatgcattc tctgggtga aggctctcca cattatcgct   240
gttgtttgct ggttcgctgc actcttctac ctccctagac tctacgtgta ccacgctatg  300
tctgaggatg atacctctca tagaaggttc gaggtgatga aagaaagct ctacagggt    360
atcatggc catctatgat cgctactctc atcaccgctc actttctcgt ggattgggga   420
gatgctacta gacactacca tgaggcactc tggttctaca tcaaggttgg acttgttgga  480
ctcctcgtga tctaccattt cgtgtgcggt tactatagaa agaagctcat cggaaacgct  540
cactacaagt ctcacaagtt ttggagatac ttcaacgaga tgcctaccct catcctcttc  600
gctgtggtta tcctcgttgt ggtgaagcct caattctga                         639
```

| SEQ ID NO: 228 | moltype = DNA   length = 747 |
| --- | --- |
| FEATURE | Location/Qualifiers |
| misc_feature | 1..747 |
| | note = Expression Cassette |
| source | 1..747 |
| | mol_type = other DNA |
| | organism = synthetic construct |

SEQUENCE: 228

```
atggttattc agtctattac ccacctctcc ccaaacctcg ctttgccatc tccactttct   60
gtgtccacca agaactaccc agttgctgtg atgggcaaca tctctgagag agaggaacct  120
acctctgcta agagggttgc agttgttgga gctggtgttt ctggacttgc tgctgcttac  180
aagctcaagt cccacggact ttcagtgacc cttttcgagg ctgattctag ggctggtgga  240
aagcttaaga ccgtgaagaa ggatggcttc atctgggatg agggtgctaa cactatggat  300
gccccatccg atgctttctt gtgggttaag gctctccaca ttatcgctgt ggtttgctgg  360
ttcgctgcac tcttctacct tccaaggctt tacgtgtacc acgccatgtc tgaggatgac  420
acctctcata aaggttcga ggtgatgaa cgtaagctct caggggcat tatgtggcca  480
tccatgattg ccacccttat taccgctcac ttcctcgtgg attggggaga tgctactagg  540
cattaccatg aggccctctg gttctacatt aaggtgggat tggtgggact cctcgtgatc  600
taccatttcg tgtgcggcta ctaccgtaag aagctcattg gaaacgccca ctacaagagc  660
cacaagtttt ggagatactt caacgagatg cccaccctga ttcttttcgc cgtggttatt  720
cttgtggtgg tgaagccaca gttctag                                       747
```

| SEQ ID NO: 229 | moltype = DNA   length = 1086 |
| --- | --- |
| FEATURE | Location/Qualifiers |
| misc_feature | 1..1086 |
| | note = Expression cassette |
| source | 1..1086 |
| | mol_type = other DNA |
| | organism = synthetic construct |

SEQUENCE: 229

```
atgactactg ctgttactgc tgctgtgtcc ttcccatcta ctaagaccac cagcctttcc   60
gccagatcct cctctgttat ctccccagac aagatctcct acaagaaggt gcccctctac  120
tacagaaacg tgtcagctac tggaaagatg ggcccaatca gggctcagat tgcttcctgc  180
tcatccatga agcagatgc tcatcaggtg aagcagttct tgcttaacct tcaggataco  240
atctgccagc agttgactgc tgttgatggt gctgagttcg ttgaggattc ttggcaaagg  300
gaagctggtg gtggtggaag gtctagagtt cttagaaacg gtggtgtttt cgagcaggct  360
ggcgtgaact ctctcatgt tcatggtgaa gctatgccag cttctgctac tgctcataga  420
ccagagcttg ccggaagatc tttcgaggct atgggagttt ctcttgtggt gcatccacac  480
aacccatacg ttccaacctc tcacgcaaac gtgagattct tcattgctga gaagccaggc  540
gctgatccag tttggtggtt cggtggtgga ttcgatctta ccccattcta cggcttcgaa  600
gaggatgcta ttcattggca taggaccgct agggatcttt gccttccatt cggagaggat  660
gtgtacccca ggtacaagaa gtggtgcgac gagtacttct acctcaagca cagaaacgag  720
cagaggggaa ttggaggcct cttcttcgat gatctcaaca cccagatttt cgaccgttgc  780
ttcgctttca tgcaggctgt tggaaaggga tacaccgatg cttacctccc catcgttgag  840
agaagaaagg ctatgcctta cggcgagaga gagaggaact ccaactttta cagacgtggc  900
cgttacgttg agttcaacct tgtttgggat cgtggaaccc ttttcggact tcaaactggt  960
ggtaggaccg agtccatcct catgtctatg ccaccacttg ttaggtggga gtacgactac 1020
caacctaagg atggatctcc agaggctgct ctctccgagt tcattaaggt tagggattgg 1080
gtgtga                                                             1086
```

| SEQ ID NO: 230 | moltype = DNA   length = 1194 |
| --- | --- |
| FEATURE | Location/Qualifiers |
| misc_feature | 1..1194 |
| | note = Expression Cassette |
| source | 1..1194 |
| | mol_type = other DNA |
| | organism = synthetic construct |

SEQUENCE: 230

```
atggttattc agtctattac ccacctctcc ccaaacctcg ctttgccatc tccactttct   60
gtgtccacca agaactaccc agttgctgtg atgggcaaca tctctgagag agaggaacct  120
acctctgcta agagggttgc agttgttgga gctggtgttt ctggacttgc tgctgcttac  180
aagctcaagt cccacggact ttcagtgacc cttttcgagg ctgattctag ggctggtgga  240
aagcttaaga ccgtgaagaa ggatggcttc atctgggatg agggtgccaa cactatgaag  300
ccagatgctc atcaggtgaa gcagttcttg cttaacctct aggataccat ctgccagcag  360
cttactgctg ttgatggtgc tgagttcgtt gaggattctt ggcaaaggga agctggtggt  420
ggtgaaggtc tagagttcct agaaacggt ggtgttttcg agcaggctgg cgtgaacttc  480
tctcatgttc atggtgaagc tatgccagct tctgctactg ctcatagacc agagcttgcc  540
ggaagatcat tcgaggctat gggagttct cttgtggtgc atccacacaa cccatacgtt  600
ccaacctctc acgcaaacgt gagattcttc attgctgaga agccaggcgc tgatccagtt  660
tggtggttcg gtggtggatt cgatcttacc ccattctacg gcttcgaaga ggatgctatt  720
cattggcata ggaccgctag ggatctttgc cttccattcg gagaggatgt gtaccccagg  780
tacaagaagt ggtgcgacga gtacttctac ctcaagcaca gaaacgagca gggggaatt  840
ggaggcctct cttcgatga tctcaacacc cagatttgc accgttgctt cgctttcatg  900
caggctgttg gaaagggata caccgatgct tacctcccca tcgttgagag aagaaaggct  960
atggcttacg gcgagcgtga gagaaacttc aactttaca gacgtggccg ttacgttgag 1020
ttcaaccttg tttgggatag gggaacccc ttccggcttc aaactggtgg aagaaccgag 1080
tccatcctca tgtctatgcc accacttgtt aggtgggagt acgactacca acctaaggat 1140
ggatctccag aggctgctct ctccgagttc attaaggtta gggattgggt gtga        1194
```

| SEQ ID NO: 231 | moltype = DNA length = 999 |
| --- | --- |
| FEATURE | Location/Qualifiers |
| misc_feature | 1..999 |
| | note = Expression Cassette |
| source | 1..999 |
| | mol_type = other DNA |
| | organism = synthetic construct |

SEQUENCE: 231

```
atggttattc agtctattac ccacctctcc ccaaacctcg ctttgccatc tccactttct   60
gtgtccacca agaactaccc agttgccgtg tgctcatcca tgaagccaga tgctcatcag  120
gtgaagcagt tcttgcttaa cctccaggat accatctgcc agcagcttac tgctgttgat  180
ggtgctgagt tcgttgagga ttcttggcaa agggaagctg gtggtggtgg aaggtctaga  240
gttcttagaa acggtggtgt tttcgagcag gctggcgtga acttctctca tgttcatggt  300
gaagctatgc cagcttctgc tactgctcat agaccagagc ttgccggaag atctttcgag  360
gctatgggag tttctcttgt ggtgcatcca cacaacccat acgttccaac ctctcacgca  420
aacgtgagat tcttcattgc tgagaagcca ggcgctgatc cagtttggtg gttcggtggt  480
ggattcgatc ttaccccatt ctacggcttc gaagaggatg ctattcattg cataggacc   540
gctagggatc tttgccttcc attcggagag gatgtgtacc ccaggtacaa gaagtggtgc  600
gacgagtact tctacctcaa gcacagaaac gagcagaggg gaattggagg cctcttcttc  660
gatgatctca acaccccaga tttcgaccgt tgcttcgctt tcatgcaggc tgttggaaag  720
ggatacaccg atgcttacct ccccatcgtt gagagaagaa aggctatggc ttacggcgag  780
agagagacta acttccaact ttacagacgt ggccgttacg ttgagttcaa ccttgttgg   840
gataggggaa ccctttttcgg acttcaaact ggtggtagga ccgagtccat cctcatgtct  900
atgccaccac ttgttaggtg ggagtacgac taccaaccta aggatggatc tccagaggct  960
gctctctccg agttcattaa ggttagggat tgggtgtga                         999
```

| SEQ ID NO: 232 | moltype = DNA length = 732 |
| --- | --- |
| FEATURE | Location/Qualifiers |
| misc_feature | 1..732 |
| | note = Expression Cassette |
| source | 1..732 |
| | mol_type = other DNA |
| | organism = synthetic construct |

SEQUENCE: 232

```
atgactactg ctgttactgc tgctgtgtcc ttcccatcta ctaagaccac cagccttttcc   60
gccagatcct cctctgttat ctccccagac aagatctcct acaagaaggt gccccctcta  120
tacagaaacg tgtcagctac tggaaagatg ggcccaatca gggctcagat tgcttcctgc  180
tcatccatga agaccctcat cttgttctcc accagggatg gacagaccag agagatcgct  240
tcttacctcg cctctgagct taaagagctt ggcattcagt tcgacgttgc aaacgttcac  300
aggatcgaag aaccacagtg ggagaactac gataggtgg tgattggagc ctccattagg   360
tacgacatt accactctgc cttccaagag ttcgtgaaga agcacgctac caggctcaac  420
tctatgccat ccgctttcta ctccgtgaac cttgttgcta ggaagccaga gaagaggact  480
ccacagacta actcctacgc ccgtaagttc ctcatgaact ctcaatggcg tccagatagg  540
tgcgctgtta ttgctggtgc tttgagatac ccaaggtaca ggtggtacga ccgtttcatg  600
atcaagctca ttatgaagat gtccggcgga gagactgaca ccagaaaaga agttgtgtac  660
accgactggg agcaggttgc aaaacttcgct agagagattc tcacctcac cgataagcca  720
accctcaagt aa                                                       732
```

| SEQ ID NO: 233 | moltype = DNA length = 840 |
| --- | --- |
| FEATURE | Location/Qualifiers |
| misc_feature | 1..840 |
| | note = Expression Cassette |
| source | 1..840 |
| | mol_type = other DNA |
| | organism = synthetic construct |

SEQUENCE: 233

```
atggttattc agtctattac ccacctctcc ccaaacctcg ctttgccatc tccactttct   60
gtgtccacca agaactaccc agttgctgtg atgggcaaca tctctgagag agaggaacct  120
acctctgcta agagggttgc agttgttgga gctggtgttt ctggacttgc tgctgcttac  180
aagctcaagt cccacggact ttcagtgacc cttttcgagg ctgattctag ggctggtgga  240
aagcttaaga ccgtgaagaa ggatggcttc atctgggatg agggtgccaa cactatgaag  300
accctgatct tgttctccac cagggatgga cagaccagag agattgcttc ctacctcgcc  360
tctgagctta aagagcttgg aatccaggct gacgttgcaa acgttcacag gattgaggaa  420
ccacagtggg agaactacga tagggttgtg atcggagcct ccattaggta cggacattac  480
cactctgcct tccaagagtt cgttaagaag cacgctacca ggctcaactc catgccatct  540
gcttttctact ccgtgaacct tgtggctagg aagccagaga gaggactcc acagactaac  600
tcctacgccc gtaagttcct catgaactct caatggcgtc cagataggtg cgctgttatt  660
gctggtgctc ttagataccc aaggtacagg tggtacgacc gtttcatgat caagctcatc  720
atgaagatgt ccggcggaga gactgacacc agaaaaag ttgtgtacac cgactgggag   780
caggttgcaa acttcgctag ggaaattgct cacctcaccg ataagccaac cctcaagtaa  840
```

| SEQ ID NO: 234 | moltype = DNA length = 645 |
| --- | --- |
| FEATURE | Location/Qualifiers |
| misc_feature | 1..645 |
| | note = Expression Cassette |
| source | 1..645 |
| | mol_type = other DNA |
| | organism = synthetic construct |

SEQUENCE: 234

```
atggttattc agtctattac ccacctctcc ccaaacctcg cttttgccatc tccactttct    60
gtgtccacca agaactaccc agttgccgtg tgctcatcca tgaagaccct catcttgttc   120
tccaccaggg atggacagac cagagagatt gcttcctacc tcgcctctga gcttaaagag   180
cttgaatcc aggctgacgt tgcaaacgtt cacaggattg aggaaccaca gtgggagaac    240
tacgataggg ttgtgatcgg agcctccatt aggtacggac attaccactc tgccttccaa   300
gagttcgtga agaagcacgc taccaggctc aactctatgc catccgcttt ctactccgtg   360
aaccttgttg ctaggaagcc agagaaggagg actccacaga ctaactccta cgcccgtaag  420
ttcctcatga actctcaatg gcgtccagat aggtgcgctg ttattgctgg tgctcttaga   480
tacccaaggt acaggtggta cgaccgtttc atgatcaagc tcattatgaa gatgtccggc   540
ggagagactg acaccagaaa agaagttgtg tacaccgagt gggagcaggt tgcaaacttc   600
gctagggaaa ttgctcacct caccgataag ccaaccctca agtaa                  645

SEQ ID NO: 235          moltype = DNA  length = 867
FEATURE                 Location/Qualifiers
misc_feature            1..867
                        note = Expression Cassette
source                  1..867
                        mol_type = other DNA
                        organism = synthetic construct
SEQUENCE: 235
atgcttactt cagctactac tccctccagc tcctctgctt cttctagagc ttctaccagg    60
ttcgcctcta gctcaagacc tagaagaact gcttacgctc ggggaagaag gcttaggcca   120
gttcttgcta tggctgcttc tgatgatcca agggctagat ctgttgctgt tgtgggagct   180
ggaatttccg gacttgttgc tgcttacagg ctctccaagt ctggtgttag ggttaccgtt   240
ttcgaggctg atgataggc tggcggaaag attaggacca actccgattc tggattcctc    300
tgggatgagg gtgctaaacac catgaagacc ctgatcttgt tctccaccag ggatgcacag   360
accagagaga ttgcttccta cctcgcctct gagcttaaag agcttggaat ccaggctgac   420
gttgcaaacg ttcacaggat tgaggaacca cagtgggaga actacgatag ggttgtgatc   480
ggcgcttcca ttaggtacgg acattaccac tctgccttcc aagagttcgt gaagaagcac   540
gctaccaggc tcaactctat gccatccgct ttctactccg tgaaccttgt gctaggaag   600
ccagagaaga ggactccaca gactaactcc tacgcccgta agttcctcat gaactctcaa   660
tggcgtccag ataggtgcgc tgttattgct ggtgctctta gatacccaag gtacaggtgg   720
tacgaccgtt tcatgatcaa gctcatcatg aagatgtccg gcggagagac tgacaccaga   780
aaagaagttg tgtacaccga ctgggagcag gttgcaaact tcgctaggga aattgctcac   840
ctcaccgata agccaaccct caagtaa                                      867

SEQ ID NO: 236          moltype = DNA  length = 1590
FEATURE                 Location/Qualifiers
misc_feature            1..1590
                        note = Expression Cassette
source                  1..1590
                        mol_type = other DNA
                        organism = synthetic construct
SEQUENCE: 236
atgactactg ctgttactgc tgctgtgtcc ttcccatcta ctaagaccac cagcctttcc    60
gccagatcct cctctgttat ctccccagac aagatctcct acaagaaggt gcccctctac   120
tacagaaacg tgtcagctac tggaaagatg ggcccaatca gggctcagat tgcttcctgc   180
tcatccatgt ctacctcccc attcaaccca tctgctactg cttcaggtag gccaccaaag   240
accttcgctg ttcttggagc ctggaattac cggacttaccg ctgctcatag gcttacccaa   300
cttggacata aggtgagggt gttcgagcag tctgataggt gggaggatc tatcaagacc   360
gaaagggttg acggatggct cattgaaggt ggaccaaaca cccttttgtc cggtgagctt   420
gctgtggata agctcattga tgagttggga ctcaacggcg agaggattgc tgctgatcca   480
gctgctaaga accgttacat tgtgagaagg ggaagggctc ttgctgctcc aatgtctcct   540
ccatcttttct tcgcctcatc cctgttctct ccagtggcta agttcaagct tctcgctgag   600
cttttcgcta ggcgtagggt taggactacc gatgtttctc ttgccgagtt cgttgagtct   660
cacttcggaa gggaattcgt ggattacgcc cttaacccat tcgtgggtgg tgtttatgct   720
ggcgatccag agaagctttc tgccaggcaa tcttttccaa agctctggga gattgagcag   780
acccacggat ctcttatcag gggacaaatt gctgcagcca aggctagaaa ggctagggga   840
gagccaagac caggcatctt ctcattcaag cacggacttc atgtgctccc tgaagctttg   900
gctgctagac ttccagctgg tgctattacc cttggagctt cccttgatgc tattgtgcca   960
ggcgataagt ggaacgttgt gtggcatgat gatgtggcta cccacaccca gtctttcgat  1020
tctgttgttg tggctttgcc agctccagct cttgctaggc ttcaaattgg aaccccttggt 1080
gagaagccac tcgctgctct tgctcttatt gagcaccctc cagtgtccag cttgttcctt  1140
ggattcagaa gagagcaggt tgcccaccca cttgatgagt tcggagttcgt tgttccagcc 1200
gttgagaaga gatctgtgct cggagtgctg ttctccagct cacttttccc aggtagggct  1260
ccacttggtc atgttgctct taccgttatg gttggaggaa ctaggcaacc acagcttgca  1320
tctttgcctc tgatcagtt gcttgctgct gttaggccag atcttaccca gcttcttgga   1380
gtgtctggtg atccagtttt cgtgaggcat aacttctggc aagggctatc ccacagtac   1440
aaccttggac acgagcactt cattgctgct tggcagtctg tgagagatt ccacccagga   1500
cttttcatgg gaggacaagc tagggatgga attgctgtgc ctgcttgcat tgctgccggt  1560
gaaaagcttg ctgagagagc tggacagtag                                  1590

SEQ ID NO: 237          moltype = DNA  length = 1596
FEATURE                 Location/Qualifiers
misc_feature            1..1596
                        note = Expression Cassette
source                  1..1596
                        mol_type = other DNA
                        organism = synthetic construct
```

```
SEQUENCE: 237
atgactactg ctgttactgc tgctgtgtcc ttcccatcta ctaagaccac cagcctttcc    60
gccagatcct cctctgttat ctccccagac aagatctcct acaagaaggt gcccctctac   120
tacagaaacg tgtcagctac tggaaagatg ggcccaatca gggctcagat tgcttcctgt   180
tcttccatgg cttccgtggg aattatcgga gctggaattg ctggacttac cgctgcttac   240
gagcttcaca aaggggact tgaggttacc gttttcgagg ctaccgatag gatcggagga   300
ttcattcagt ccgagaggat cgatggattc ctcgttgaac ttggaccaca gactcttcag   360
aggacctctg gtgatttcga ggaacttctc aggcaagtgg atctcgagga tgcttgcatt   420
ccagctagac cagttgctgc caacagattc attgtgaggg gaggacagcc aatcccactt   480
cctagatctc caagagagct tctcaggacc ccacttcttt caccaagagc taggcttagg   540
cttctcgctg agccattcat tcatagggct cataggtcca ccgaggaatc agttgctaag   600
ttcaccagaa aaggctcgg accagaggtt ctcgattacc ttgttgagcc tttcgtggct   660
ggaatcttcg ctggtgatcc agagcaactt tctgtgaggt acgcctttcc aaagctgttc   720
gagcttgagc aacagtacgg atccctttc tggggactca tcaggatag gatgaagcag   780
agataccacc cagccccaag acgttccatg ttctcattcg ttgagggact ccacatgctt   840
ccaagggctc ttgctgagag acttccagct catgctattg tgaggaacgc tgaggtgttg   900
gctattaggt gggatgagaa gaacccatgg acccttactt tcaggcaaca cggaagggct   960
tccaccagat tcttcgatat tatcgtgtgc gctgtgccac tccataggct tgctcaactt  1020
aggattcacc accagtggga tagaaggcca ctttctactg ttgagcaccc accaattgct  1080
cttgtggctc ttggattcag gcgtgagcaa gttgcacatc cacttgatgg attcggaatg  1140
cttgtgccag ctgttgagag ggacttccag attttgggaa ccctcttcag ctcctcactc  1200
ttcccagata gggctccaga gggacatgtt cttttgacca cttccgtggg aggaatgagg  1260
catccagagc ttgctttgct tccagaggat aggcttgagg ctcttgtgtt gcaggatctt  1320
agaaggctcc tcggaatttc tggtgctcca gttttcaggc atgtttggag gtgggagaga  1380
tccattccac agtacaggct tggatacgat gctgtgcttg cttgcgttca cgacgttgag  1440
atgtctaggt ccgacttttt cctcgctggc aactacatgg aaggcatctc tgtgattgat  1500
gctctccaca ccgacttaa ggctgctagg gctattattc agcacctcag agaagaggct  1560
gctggtggac ttgctaagct tgtgcttgga gattga                           1596

SEQ ID NO: 238          moltype = DNA  length = 1536
FEATURE                 Location/Qualifiers
misc_feature            1..1536
                        note = Expression Cassette
source                  1..1536
                        mol_type = other DNA
                        organism = synthetic construct
SEQUENCE: 238
atggttattc agtctattac ccacctctcc ccaaacctcg cttttgccatc tccactttct    60
gtgtccacca agaactaccc agttgctgtg atgggcaaca tctctgagag ggaagaacct   120
acctctatgg cttccgtggg aattatcgga gctggaattg ctggacttac cgctgcttac   180
gagcttcaca aaggggact tgaggttacc gttttcgagg ctaccgatag gatcggagga   240
ttcattcagt ccgagaggat cgatggattc ctcgttgaac ttggaccaca gactcttcag   300
aggacctctg gtgatttcga ggaacttctc aggcaagtgg atctcgagga tgcttgcatt   360
ccagctagac ctgttgctgc caacagattc attgtgaggg gaggacagcc aatcccactt   420
ccaagatctc aagagagct tctcaggacc ccacttcttt caccaagagc taggcttagg   480
cttctcgctg agccattcat tcatagggct cataggtcca ccgaggaatc agttgctaag   540
ttcaccagaa aaggctcgg accagaggtt ctcgattacc ttgttgagcc tttcgtggct   600
ggaatcttcg ctggtgatcc agagcaattg tctgtgaggt acgccttccc aaagctgttc   660
gagcttgagc aacagtacgg atccctttc tggggactca tcaggatag gatgaagcag   720
agataccacc cagccccaag acgttccatg ttctcattcg ttgagggact ccacatgctt   780
ccaagggctc ttgctgagag acttccagct catgctattg tgaggaacgc tgaggtgttg   840
gctattaggt gggatgagaa gaacccatgg acccttactt tcaggcaaca cggaagggct   900
tccaccagat tcttcgatat tatcgtgtgc gctgtgccac tccataggct tgctcaactt   960
aggattcacc accagtggga tagaaggcca ctttctactg ttgagcaccc accaattgct  1020
cttgtggctc ttggattcag gcgtgagcaa gttgcacatc cacttgatgg attcggaatg  1080
cttgtgccag ctgttgagag ggatttccag attctcggaa ccctcttcag ctcctcactt  1140
ttcccagata gggctccaga gggacatgtt cttttgacca cttccgtggg aggaatgagg  1200
catccagagc ttgctttgct tccagaggat aggcttgagg ctcttgtgtt gcaggatctt  1260
agaaggctcc tcggaatttc tggtgctcca gttttcaggc atgtttggag gtgggagaga  1320
tccattccac agtacaggct tggatacgat gctgtgcttg cttgcgttca cgacgttgag  1380
atgtctaggt ccgacttttt cctcgctggc aactacatgg aaggcatctc tgtgattgat  1440
gctctccaca ccgacttaa ggctgctagg gctattattc agcacctcag agaagaggct  1500
gctggtggac ttgctaagct tgtgcttgga gattga                           1536

SEQ ID NO: 239          moltype = DNA  length = 1611
FEATURE                 Location/Qualifiers
misc_feature            1..1611
                        note = Expression Cassette
source                  1..1611
                        mol_type = other DNA
                        organism = synthetic construct
SEQUENCE: 239
atgactactg ctgttactgc tgctgtgtcc ttcccatcta ctaagaccac cagcctttcc    60
gccagatcct cctctgttat ctccccagac aagatctcct acaagaaggt gcccctctac   120
tacagaaacg tgtcagctac tggaaagatg ggcccaatca gggctcagat tgcttcctgt   180
tcatctatga tggctggcta cgattctgtg gtgattggag gtggaattgc tggacttgct   240
gctgcttaca cccttcacaa gagggggatac agggttctcg ttatcgagtc tactaacagg   300
gtgggcggag tgattcaaac cattactact ccagagggct acatcctcga ttgcggacca   360
aacactgttg gaactggtga tgctaggctc tggcaagagc ttattgatct cggactcaga   420
```

```
                                                -continued gagaggatta ccccagctgc tccatgctcc aagaggcgtt tcattctcat taacggcacc    480
ccagttgaga tcccaacttc tccagtgggc cttatcacta ccaggctttt gtcttggagg    540
ggcaagctta gagttctcgc tgagccattc atcaacaggg gttctactga tccagatgag    600
tccgtggctc ctttcttcac cagaagaatt ggagctgagg ctaccgctca ccttttggat    660
ccattcgttg ctggtgtgta cgctggtgat ccacagagac tttctaccgc tgctgttttc    720
ccatctcttt gggaggctgc tcaaggtcc ggatctattg tgaggggaat gctctctaag    780
ccaaagccca agacccaagt gtctgagcca aagatgaggt ctaggacctt cacttttcagg   840
ggtggtcttg ctgaatggcc aagggctctt gctcaagctc ttggtgctgg aaacgtttgg    900
accgagagaa gggttgtgaa gttgcagcca agagactcat ggtgggaggt gaccattgag    960
ggtgttaacg gaccagagac tctcatctcc cgttccctca ttattgctac ccctgctttc   1020
accgccgctg atcttattga gtcgttgat caaagggctg ctggtgcttt gaggggtatt   1080
ccatatgctc cagttgctgt ggtgcacctc ggattcagaa gggatcagat ctcccaagag   1140
ttgtccggat tcggagttct tgctccatct tctgagcaga ggcagttcct tggaattctc   1200
tggaccctcca gcatcttccc acattgct ccacacgctc atgtgcttac cactaccctt   1260
tccggtggtg ctattagacc agagcttgct gaaaggtctg acgaaaccct tatcgaggct   1320
gctattaggg atcaccacca gcttctcgga attaggggac agccaatttt cacccatgtt   1380
accagatggc gtaccgctat tgctcagtac actttcggtc acagggaaag gattgctacc   1440
ttggtcaac tcgagcaaag gctcccaact attcagttcg ctgatccta caggatggt    1500
gttggagttc caaagacttg ggcttctggt gttcaagctc gtgagagaat tgctgcagct   1560
cttgctgctc atggaaccac tgctgttttc accgaaaccg cttctggatg a            1611

SEQ ID NO: 240          moltype = AA    length = 212
FEATURE                 Location/Qualifiers
REGION                  1..212
                        note = Expression Cassette
source                  1..212
                        mol_type = protein
                        organism = synthetic construct
SEQUENCE: 240
MTTAVTAAVS FPSTKTTSLS ARSSSVISPD KISYKKVPLY YRNVSATGKM GPIRAQIASC     60
SSMDAPSDAF LWVKALHIIA VVCWFAALFY LPRLYVYHAM SEDDTSHRRF EVMERKLYRG    120
IMWPSMIATL ITAHFLVDWG DATRHYHEAL WFYIKVGLVG LLVIYHFVCG YYRKKLIGNA    180
HYKSHKFWRY FNEMPTLILF AVVILVVVKP QF                                  212

SEQ ID NO: 241          moltype = AA    length = 248
FEATURE                 Location/Qualifiers
REGION                  1..248
                        note = Expression Cassette
source                  1..248
                        mol_type = protein
                        organism = synthetic construct
SEQUENCE: 241
MVIQSITHLS PNLALPSPLS VSTKNYPVAV MGNISEREEP TSAKRVAVVG AGVSGLAAAY     60
KLKSHGLSVT LFEADSRAGG KLKTVKKDGF IWDEGANTMD APSDAFLWVK ALHIIAVVCW    120
FAALFYLPRL YVYHAMSEDD TSHRRFEVME RKLYRGIMWP SMIATLITAH FLVDWGDATR    180
HYHEALWFYI KVGLVGLLVI YHFVCGYYRK KLIGNAHYKS HKFWRYFNEM PTLILFAVVI    240
LVVVKPQF                                                             248

SEQ ID NO: 242          moltype = AA    length = 361
FEATURE                 Location/Qualifiers
REGION                  1..361
                        note = Expression Cassette
source                  1..361
                        mol_type = protein
                        organism = synthetic construct
SEQUENCE: 242
MTTAVTAAVS FPSTKTTSLS ARSSSVISPD KISYKKVPLY YRNVSATGKM GPIRAQIASC     60
SSMKPDAHQV KQFLLNLQDT ICQQLTAVDG AEFVEDSWQR EAGGGGRSRV LRNGGVFEQA    120
GVNFSHVHGE AMPASATAHR PELAGRSFEA MGVSLVVHPH NPYVPTSHAN VRFFIAEKPG    180
ADPVWWFGGG FDLTPFYGFE EDAIHWHRTA RDLCLPFGED VYPRYKKWCD EYFYLKHRNE    240
QRGIGGLFFD DLNTPDFDRC FAFMQAVGKG YTDAYLPIVE RRKAMAYGER ERNFQLYRRG    300
RYVEFNLVWD RGTLFGLQTG GRTESILMSM PPLVRWEYDY QPKDGSPEAA LSEFIKVRDW    360
V                                                                    361

SEQ ID NO: 243          moltype = AA    length = 397
FEATURE                 Location/Qualifiers
REGION                  1..397
                        note = Expression Cassette
source                  1..397
                        mol_type = protein
                        organism = synthetic construct
SEQUENCE: 243
MVIQSITHLS PNLALPSPLS VSTKNYPVAV MGNISEREEP TSAKRVAVVG AGVSGLAAAY     60
KLKSHGLSVT LFEADSRAGG KLKTVKKDGF IWDEGANTMK PDAHQVKQFL NLQDTICQQ    120
LTAVDGAEFV EDSWQREAGG GGRSVLRNG VFEQAGVNF SHVHGEAMPA SATAHRPELA    180
GRSFEAMGVS LVVHPHNPYV PTSHANVRFF IAEKPGADPV WWFGGGFDLT PFYGFEEDAI    240
HWHRTARDLC LPFGEDVYPR YKKWCDEYFY LKHRNEQRGI GGLFFDDLNT PDFDRCFAFM    300
QAVGKGYTDA YLPIVERRKA MAYGERERNF QLYRRGRYVE FNLVWDRGTL FGLQTGGRTE    360
SILMSMPPLV RWEYDYQPKD GSPEAALSEF IKVRDWV                             397
```

```
SEQ ID NO: 244          moltype = AA  length = 332
FEATURE                 Location/Qualifiers
REGION                  1..332
                        note = Expression Cassette
source                  1..332
                        mol_type = protein
                        organism = synthetic construct
SEQUENCE: 244
MVIQSITHLS PNLALPSPLS VSTKNYPVAV CSSMKPDAHQ VKQFLLNLQD TICQQLTAVD   60
GAEFVEDSWQ REAGGGGRSR VLRNGGVFEQ AGVNFSHVHG EAMPASATAH RPELAGRSFE  120
AMGVSLVVHP HNPYVPTSHA NVRFFIAEKP GADPVWWFGG GFDLTPFYGF EEDAIHWHRT  180
ARDLCLPFGE DVYPRYKKWC DEYFYLKHRN EQRGIGGLFF DDLNTPDFDR CFAFMQAVGK  240
GYTDAYLPIV ERRKAMAYGE RERNFQLYRR GRYVEFNLVW DRGTLFGLQT GGRTESILMS  300
MPPLVRWEYD YQPKDGSPEA ALSEFIKVRD WV                                332

SEQ ID NO: 245          moltype = AA  length = 243
FEATURE                 Location/Qualifiers
REGION                  1..243
                        note = Expression Cassette
source                  1..243
                        mol_type = protein
                        organism = synthetic construct
SEQUENCE: 245
MTTAVTAAVS FPSTKTTSLS ARSSSVISPD KISYKKVPLY YRNVSATGKM GPIRAQIASC   60
SSMKTLILFS TRDGQTREIA SYLASELKEL GIQADVANVH RIEEPQWENY DRVVIGASIR  120
YGHYHSAFQE FVKKHATRLN SMPSAFYSVN LVARKPEKRT PQTNSYARKF LMNSQWRPDR  180
CAVIAGALRY PRYRWYDRFM IKLIMKMSGG ETDTRKEVVY TDWEQVANFA REIAHLTDKP  240
TLK                                                                243

SEQ ID NO: 246          moltype = AA  length = 279
FEATURE                 Location/Qualifiers
REGION                  1..279
                        note = Expression Cassette
source                  1..279
                        mol_type = protein
                        organism = synthetic construct
SEQUENCE: 246
MVIQSITHLS PNLALPSPLS VSTKNYPVAV MGNISEREEP TSAKRVAVVG AGVSGLAAAY   60
KLKSHGLSVT LFEADSRAGG KLKTVKKDGF IWDEGANTMK TLILFSTRDG QTREIASYLA  120
SELKELGIQA DVANVHRIEE PQWENYDRVV IGASIRYGHY HSAFQEFVKK HATRLNSMPS  180
AFYSVNLVAR KPEKRTPQTN SYARKFLMNS QWRPDRCAVI AGALRYPRYR WYDRFMIKLI  240
MKMSGGETDT RKEVVYTDWE QVANFAREIA HLTDKPTLK                         279

SEQ ID NO: 247          moltype = AA  length = 214
FEATURE                 Location/Qualifiers
REGION                  1..214
                        note = Expression Cassette
source                  1..214
                        mol_type = protein
                        organism = synthetic construct
SEQUENCE: 247
MVIQSITHLS PNLALPSPLS VSTKNYPVAV CSSMKTLILF STRDGQTREI ASYLASELKE   60
LGIQADVANV HRIEEPQWEN YDRVVIGASI RYGHYHSAFQ EFVKKHATRL NSMPSAFYSV  120
NLVARKPEKR TPQTNSYARK FLMNSQWRPD RCAVIAGALR YPRYRWYDRF MIKLIMKMSG  180
GETDTRKEVV YTDWEQVANF AREIAHLTDK PTLK                              214

SEQ ID NO: 248          moltype = AA  length = 288
FEATURE                 Location/Qualifiers
REGION                  1..288
                        note = Expression Cassette
source                  1..288
                        mol_type = protein
                        organism = synthetic construct
SEQUENCE: 248
MLTSATTPSS SSASSRASTR FASSSRPRRT AYARGRRLRP VLAMAASDDP RARSVAVVGA   60
GISGLVAAYR LSKSGVRVTV FEADDRAGGK IRTNSDSGFL WDEGANTMKT LILFSTRDGQ  120
TREIASYLAS ELKELGIQAD VANVHRIEEP QWENYDRVVI GASIRYGHYH SAFQEFVKKH  180
ATRLNSMPSA FYSVNLVARK PEKRTPQTNS YARKFLMNSQ WRPDRCAVIA GALRYPRYRW  240
YDRFMIKLIM KMSGGETDTR KEVVYTDWEQ VANFAREIAH LTDKPTLK               288

SEQ ID NO: 249          moltype = AA  length = 529
FEATURE                 Location/Qualifiers
REGION                  1..529
                        note = Expression Cassette
source                  1..529
                        mol_type = protein
                        organism = synthetic construct
SEQUENCE: 249
```

```
MTTAVTAAVS FPSTKTTSLS ARSSSVISPD KISYKKVPLY YRNVSATGKM GPIRAQIASC    60
SSMSTSPFNP SATASGRPPK TFAVLGAGIT GLTAAHRLTQ LGHKVRVFEQ SDRVGGSIKT   120
EEVDGWLIEG GPNTLLSGEL AVDKLIDELG LNGERIAADP AAKNRYIVRR GRALAAPMSP   180
PSFFASSLFS PVAKFKLLAE LFARRRVRTT DVSLAEFVES HFGREFVDYA LNPFVGGVYA   240
GDPEKLSARQ SFPKLWEIEQ THGSLIRGQI AAAKARKARG EPRPGIFSFK HGLHVLPEAL   300
AARLPAGAIT LGASLDAIVP GDKWNVVWHD DVATHTQSFD SVVVALPAPA LARLQIGTLG   360
EKPLAALALI EHPPVSSLFL GFRREQVAHP LDGFGVLVPA VEKRSVLGVL FSSSLFPGRA   420
PLGHVALTVM VGGTRQPQLA SLPADQLLAA VRPDLTQLLG VSGDPVFVRH NFWPRAIPQY   480
NLGHEHFIAA LAAGERFHPG LFMGGQARDG IAVPACIAAG EKLAERAGQ               529

SEQ ID NO: 250          moltype = AA  length = 565
FEATURE                 Location/Qualifiers
REGION                  1..565
                        note = Expression Cassette
source                  1..565
                        mol_type = protein
                        organism = synthetic construct
SEQUENCE: 250
MVIQSITHLS PNLALPSPLS VSTKNYPVAV MGNISEREEP TSAKRVAVVG AGVSGLAAAY    60
KLKSHGLSVT LFEADSRAGG KLKTVKKDGF IWDEGANTMS TSPFNPSATA SGRPPKTFAV   120
LGAGITGLTA AHRLTQLGHK VRVFEQSDRV GGSIKTEEVD GWLIEGGPNT LLSGELAVDK   180
LIDELGLNGE RIAADPAAKN RYIVRRGRAL AAPMSPPSFF ASSLFSPVAK FKLLAELFAR   240
RRVRTTDVSL AEFVESHFGR EFVDYALNPF VGGVYAGDPE KLSARQSFPK LWEIEQTHGS   300
LIRGQIAAAK ARKARGEPRP GIFSFKHGLH VLPEALAARL PAGAITLGAS LDAIVPGDKW   360
NVVWHDDVAT HTQSFDSVVV ALPAPALARL QIGTLGEKPL AALALIEHPP VSSLFLGFRR   420
EQVAHPLDGF GVLVPAVEKR SVLGVLFSSS LFPGRAPLGH VALTVMVGGT RQPQLASLPA   480
DQLLAAVRPD LTQLLGVSGD PVFVRHNFWP RAIPQYNLGH EHFIAALAAG ERFHPGLFMG   540
GQARDGIAVP ACIAAGEKLA ERAGQ                                        565

SEQ ID NO: 251          moltype = AA  length = 531
FEATURE                 Location/Qualifiers
REGION                  1..531
                        note = Expression Cassette
source                  1..531
                        mol_type = protein
                        organism = synthetic construct
SEQUENCE: 251
MTTAVTAAVS FPSTKTTSLS ARSSSVISPD KISYKKVPLY YRNVSATGKM GPIRAQIASC    60
SSMASVGIIG AGIAGLTAAY ELHRRGLEVT VFEATDRIGG FIQSERIDGF LVELGPQTLQ   120
RTSGDFEELL RQVDLEDACI PARPVAANRF IVRGGQPIPL PRSPRELLRT PLLSPRARLR   180
LLAEPFIHRA HRSTEESVAK FTRRRLGPEV LDYLVEPFVA GIFAGDPEQL SVRYAFPKLF   240
ELEQQYGSLF WGLIRDRMKQ RYHPAPRRSM FSFVEGLHML PRALAERLPA HAIVRNAEVL   300
AIRWDEKNPW TLTFRQHGRA STRFFDIIVC AVPLHRLAQL RIHPPVDRRP LSTVEHPPIA   360
LVALGFRREQ VAHPLDGFGM LVPAVERDFQ ILGTLFSSSL FPDRAPEGHV LLTTFVGGMR   420
HPELALLPED RLEALVLQDL RRLLGISGAP VFRHVWRWER SIPQYRLGYD AVLACVHDVE   480
MSRSGLFLAG NYMEGISVID ALHTGLKAAR AIIQHLREEA AGGLAKLVLG D            531

SEQ ID NO: 252          moltype = AA  length = 531
FEATURE                 Location/Qualifiers
REGION                  1..531
                        note = Expression Cassette
source                  1..531
                        mol_type = protein
                        organism = synthetic construct
SEQUENCE: 252
MTTAVTAAVS FPSTKTTSLS ARSSSVISPD KISYKKVPLY YRNVSATGKM GPIRAQIASC    60
SSMASVGIIG AGIAGLTAAY ELHRRGLEVT VFEATDRIGG FIQSERIDGF LVELGPQTLQ   120
RTSGDFEELL RQVDLEDACI PARPVAANRF IVRGGQPIPL PRSPRELLRT PLLSPRARLR   180
LLAEPFIHRA HRSTEESVAK FTRRRLGPEV LDYLVEPFVA GIFAGDPEQL SVRYAFPKLF   240
ELEQQYGSLF WGLIRDRMKQ RYHPAPRRSM FSFVEGLHML PRALAERLPA HAIVRNAEVL   300
AIRWDEKNPW TLTFRQHGRA STRFFDIIVC AVPLHRLAQL RIHPPVDRRP LSTVEHPPIA   360
LVALGFRREQ VAHPLDGFGM LVPAVERDFQ ILGTLFSSSL FPDRAPEGHV LLTTVVGGMR   420
HPELALLPED RLEALVLQDL RRLLGISGAP VFRHVWRWER SIPQYRLGYD AVLACVHDVE   480
MSRSGLFLAG NYMEGISVID ALHTGLKAAR AIIQHLREEA AGGLAKLVLG D            531

SEQ ID NO: 253          moltype = AA  length = 567
FEATURE                 Location/Qualifiers
REGION                  1..567
                        note = Expression Cassette
source                  1..567
                        mol_type = protein
                        organism = synthetic construct
SEQUENCE: 253
MVIQSITHLS PNLALPSPLS VSTKNYPVAV MGNISEREEP TSAKRVAVVG AGVSGLAAAY    60
KLKSHGLSVT LFEADSRAGG KLKTVKKDGF IWDEGANTMA SVGIIGAGIA GLTAAYELHR   120
RGLEVTVFEA TDRIGGFIQS ERIDGFLVEL GPQTLQRTSG DFEELLRQVD LEDACIPARP   180
VAANRFIVRG GQPIPLPRSP RELLRTPLLS PRARLRLLAE PFIHRAHRST EESVAKFTRR   240
RLGPEVLDYL VEPFVAGIFA GDPEQLSVRY AFPKLFELEQ QYGSLFWGLI RDRMKQRYHP   300
APRRSMFSFV EGLHMLPRAL AERLPAHAIV RNAEVLAIRW DEKNPWTLTF RQHGRASTRF   360
```

```
FDIIVCAVPL HRLAQLRIHP PVDRRPLSTV EHPPIALVAL GFRREQVAHP LDGFGMLVPA    420
VERDFQILGT LFSSSLFPDR APEGHVLLTT FVGGMRHPEL ALLPEDRLEA LVLQDLRRLL    480
GISGAPVFRH VWRWERSIPQ YRLGYDAVLA CVHDVEMSRS GLFLAGNYME GISVIDALHT    540
GLKAARAIIQ HLREEAAGGL AKLVLGD                                       567

SEQ ID NO: 254          moltype = AA  length = 567
FEATURE                 Location/Qualifiers
REGION                  1..567
                        note = Expression Cassette
source                  1..567
                        mol_type = protein
                        organism = synthetic construct
SEQUENCE: 254
MVIQSITHLS PNLALPSPLS VSTKNYPVAV MGNISEREEP TSAKRVAVVG AGVSGLAAAY    60
KLKSHGLSVT LFEADSRAGG KLKTVKKDGF IWDEGANTMA SVGIIGAGIA GLTAAYELHR    120
RGLEVTVFEA TDRIGGFIQS ERIDGFLVEL GPQTLQRTSG DFEELLRQVD LEDACIPARP    180
VAANRFIVRG GQPIPLPRSP RELLRTPLLS PRARLRLLAE PFIHRAHRST EESVAKFTRR    240
RLGPEVLDYL VEPFVAGIFA GDPEQLSVRY AFPKLFELEQ QYGSLFWGLI RDRMKQRYHP    300
APRRSMFSFV EGLHMLPRAL AERLPAHAIV RNAEVLAIRW DEKNPWTLTF RQHGRASTRF    360
FDIIVCAVPL HRLAQLRIHP PVDRRPLSTV EHPPIALVAL GFRREQVAHP LDGFGMLVPA    420
VERDFQILGT LFSSSLFPDR APEGHVLLTT VVGGMRHPEL ALLPEDRLEA LVLQDLRRLL    480
GISGAPVFRH VWRWERSIPQ YRLGYDAVLA CVHDVEMSRS GLFLAGNYME GISVIDALHT    540
GLKAARAIIQ HLREEAAGGL AKLVLGD                                       567

SEQ ID NO: 255          moltype = AA  length = 511
FEATURE                 Location/Qualifiers
REGION                  1..511
                        note = Expression Cassette
source                  1..511
                        mol_type = protein
                        organism = synthetic construct
SEQUENCE: 255
MVIQSITHLS PNLALPSPLS VSTKNYPVAV MGNISEREEP TSMASVGIIG AGIAGLTAAY    60
ELHRRGLEVT VFEATDRIGG FIQSERIDGF LVELGPQTLQ RTSGDFEELL RQVDLEDACI    120
PARPVAANRF IVRGGQPIPL PRSPRELLRT PLLSPRARLR LLAEPFIHRA HRSTEESVAK    180
FTRRRLGPEV LDYLVEPFVA GIFAGDPEQL SVRYAFPKLF ELEQQYGSLF WGLIRDRMKQ    240
RYHPAPRRSM FSFVEGLHML PRALAERLPA HAIVRNAEVL AIRWDEKNPW TLTFRQHGRA    300
STRFFDIIVC AVPLHRLAQL RIHPPVDRRP LSTVEHPPIA LVALGFRREQ VAHPLDGFGM    360
LVPAVERDFQ ILGTLFSSSL FPDRAPEGHV LLTTFVGGMR HPELALLPED RLEALVLQDL    420
RRLLGISGAP VFRHVWRWER SIPQYRLGYD AVLACVHDVE MSRSGLFLAG NYMEGISVID    480
ALHTGLKAAR AIIQHLREEA AGGLAKLVLG D                                  511

SEQ ID NO: 256          moltype = AA  length = 536
FEATURE                 Location/Qualifiers
REGION                  1..536
                        note = Expression Cassette
source                  1..536
                        mol_type = protein
                        organism = synthetic construct
SEQUENCE: 256
MTTAVTAAVS FPSTKTTSLS ARSSSVISPD KISYKKVPLY YRNVSATGKM GPIRAQIASC    60
SSMMAGYDSV VIGGGIAGLA AAYTLHKRGY RVLVIESTNR VGGVIQTITT PEGYILDCGP    120
NTVGTGDARL WQELIDLGLR ERITPAAPCS KRRFILINGT PVEIPTSPVG LITTRLLSWR    180
GKLRVLAEPF INRGSTDPDE SVAAFFTRRI GAEATAHLLD PFVAGVYAGD PQRLSTAAVF    240
PSLWEAAQRS GSIVRGMLSK PKPKTQVSEP KMRSRTFTFR GGLAEWPRAL AQALGAGNVW    300
TERRVVKLQP RDSWWEVTID GVNGPETLIS RSLIIATPAF TAADLIESVD QRAAGALRGI    360
PYAPVAVVHL GFRRDQISQE LSGFGVLAPS SEQRQFLGIL WTSSIFPHVA PHDHVLTTTL    420
SGGAIRPELA ERSDETLIEA AIRDHHQLLG IRGQPIFTHV TRWRTAIAQY TFGHRERIAT    480
LVQLEQRLPT IQFAGSYRDG VGVPKTWASG VQAGERIAAA LAAHGTTAVS TETASG       536

SEQ ID NO: 257          moltype = AA  length = 572
FEATURE                 Location/Qualifiers
REGION                  1..572
                        note = Expression Cassette
source                  1..572
                        mol_type = protein
                        organism = synthetic construct
SEQUENCE: 257
MVIQSITHLS PNLALPSPLS VSTKNYPVAV MGNISEREEP TSAKRVAVVG AGVSGLAAAY    60
KLKSHGLSVT LFEADSRAGG KLKTVKKDGF IWDEGANTMM AGYDSVVIGG GIAGLAAAYT    120
LHKRGYRVLV IESTNRVGGV IQTITTPEGY ILDCGPNTVG TGDARLWQEL IDLGLRERIT    180
PAAPCSKRRF ILINGTPVEI PTSPVGLITT RLLSWRGKLR VLAEPFINRG STDPDESVAA    240
FFTRRIGAEA TAHLLDPFVA GVYAGDPQRL STAAVFPSLW EAAQRSGSIV RGMLSKPKPK    300
TQVSEPKMRS RTFTFRGGLA EWPRALAQAL GAGNVWTERR VVKLQPRDSW WEVTIDGVNG    360
PETLISRSLI IATPAFTAAD LIESVDQRAA GALRGIPYAP VAVVHLGFRR DQISQELSGF    420
GVLAPSSEQR QFLGILWTSS IFPHVAPHDH VLTTTLSGGA IRPELAERSD ETLIEAAIRD    480
HHQLLGIRGQ PIFTHVTRWR TAIAQYTFGH RERIATLVQL EQRLPTIQFA GSYRDGVGVP    540
KTWASGVQAG ERIAAALAAH GTTAVSTETA SG                                 572
```

| SEQ ID NO: 258 | moltype = AA  length = 543 |
| --- | --- |
| FEATURE | Location/Qualifiers |
| REGION | 1..543 |
| | note = Expression Cassette |
| source | 1..543 |
| | mol_type = protein |
| | organism = synthetic construct |

SEQUENCE: 258
```
MLTSATTPSS SSASSRASTR FASSSRPRRT AYARGRRLRP VLAMAASDDP RARSVAVVGA   60
GISGLVAAYR LSKSGVRVTV FEADDRAGGK IRTNSDSGFL WDEGANTMTE SEAEVSSLID  120
DLGLREKQQL PISQNKMYIA RDGLPVLLPS NPAALLTSNI LSAKSKLQIM LEPFLWRKHN  180
ATELSDEHVQ ESVGEFFERH FGKEFVDYVI DPFVAGTCGG DPQSLSMHHT FPEVWNIEKR  240
FGSVFAGLIQ STLLSKKEKG GENASIKKPR VRGSFSFQGG MQTLVDTMCK QLGEDELKLQ  300
CEVLSLSYNQ KGIPSLGNWS VSSMSNNTSE DQSYDAVVVT APIRNVKEMK IMKFGNPFSL  360
DFIPEVTYVP LSVMITAFKK DKVKRPLEGF GVLIPSKEQH NGLKTLGTLF SSMMFPDRAP  420
SDMCLFTTIV GGSRNRKLAN ASTDELKQIV SSDLQQLLGT EDEPSFVNHL FWSNAFPLYG  480
HNYDSVLRAI DKMEKDLPGF FYAGNHKGGL SVGKAMASGC KAAELVISYL DSHIYVKMDE  540
KTA                                                                543
```

| SEQ ID NO: 259 | moltype = AA  length = 560 |
| --- | --- |
| FEATURE | Location/Qualifiers |
| REGION | 1..560 |
| | note = Expression Cassette |
| source | 1..560 |
| | mol_type = protein |
| | organism = synthetic construct |

SEQUENCE: 259
```
MVIQSITHLS PNLALPSPLS VSTKNYPVAV MGNISEREEP TSAKRVAVVG AGVSGLAAAY   60
KLKSHGLSVT LFEADSRAGG KLKTVKKDGF IWDEGANTAT KHPDAAPNLI VTEAKDRVGG  120
NIITREENGF LWEEGPNSFQ PSDPMLTMVV DSGLKDDLVL GDPTAPRFVL WNGKLRPVPS  180
KLTDLPFFDL MSIGGKIRAG FGALGIRPSP PGREESVEEF VRRNLGDEVF ERLIEPFCSG  240
VYAGDPSKLS MKAAFGKVWK LEQNGGSIIG GTFKAIQERK NAPKAERDPR LPKPQGQTVG  300
SFRKGLRMLP EAISARLGSK VKLSWKLSGI TKLESGGYNL TYETPDGLVS VQSKSVVMTV  360
PSHVASGLLR PLSESAANAL SKLYYPPVAA VSISYPKEAI RTECLIDGEL KGFGQLHPRT  420
QGVETLGTIY SSSLFPNRAP PGRILLLNYI GGSTNTGILS KSEGELVEAV DRDLRKMLIK  480
PNSTDPLKLG VRVWPQAIPQ FLVGHFDILD TAKSSLTSSG YEGLFLGGNY VAGVALGRCV  540
EGAYETAIEV NNFMSRYAYK                                              560
```

| SEQ ID NO: 260 | moltype = AA  length = 560 |
| --- | --- |
| FEATURE | Location/Qualifiers |
| REGION | 1..560 |
| | note = Expression Cassette |
| source | 1..560 |
| | mol_type = protein |
| | organism = synthetic construct |

SEQUENCE: 260
```
MVIQSITHLS PNLALPSPLS VSTKNYPVAV MGNISEREEP TSAKRVAVVG AGVSGLAAAY   60
KLKSHGLSVT LFEADSRAGG KLKTVKKDGF IWDEGANTAT KHPDAAPNLI VTEAKDRVGG  120
NIITREENGF LWEEGPNSFQ PSDPMLTMVV DSGLKDDLVL GDPTAPRFVL WNGKLRPVPS  180
KLTDLPFFDL MSIGGKIRAG FGALGIRPSP PGREESVEEF VRRNLGDEVF ERLIEPFCSG  240
VYAGDPSKLS MKAAFGKVWK LEQNGGSIIG GTFKAIQERK NAPKAERDPR LPKPQGQTVG  300
SFRKGLRMLP EAISARLGSK VKLSWKLLGI TKLESGGYNL TYETPDGLVS VQSKSVVMTV  360
PSHVASGLLR PLSESAANAL SKLYYPPVAA VSISYPKEAI RTECLIDGEL KGFGQLHPRT  420
QGVETLGTIY SSSLFPNRAP PGRILLLNMI GGSTNTGILS KSEGELVEAV DRDLRKMLIK  480
PNSTDPLKLG VRVWPQAIPQ FLVGHFDILD TAKSSLTSSG YEGLFLGGNY VAGVALGRCV  540
EGAYETAIEV NNFMSRYAYK                                              560
```

| SEQ ID NO: 261 | moltype = AA  length = 538 |
| --- | --- |
| FEATURE | Location/Qualifiers |
| REGION | 1..538 |
| | note = Expression Cassette |
| source | 1..538 |
| | mol_type = protein |
| | organism = synthetic construct |

SEQUENCE: 261
```
MVIQSITHLS PNLALPSPLS VSTKNYPVAV MGNISEREEP TSAKRVAVVG AGVSGLAAAY   60
KLKSHGLSVT LFEADSRAGG KLKTVKKDGF IWDEGANTMT ESALEASRLI DDLGLEDRLQ  120
YPNSQHKRYT VKDGAPALIP SDPIALMKSS LLSTKSKFKL FLEPFLYDKS STKSSKKVSD  180
EHISESVGSF FERHFGKEVV DYLIDPFVAG TSAGDPESLS IRHAFPGLWN LEKKYGSIIV  240
GAIMSKLTAK GDKKGSAVSG KGRNKRASFS FHGGMQTLVD ALHKEVGDGN VKLGAQVLSL  300
ACICDGLSAS DGWSISVDSK DASNKELTKN HSFDAVIMTA PLSNVQRMKF TKGGAPFVLD  360
FLPKVDYLPL SLMVTAFKKE DVKRPLEGFG VLIPYKEQQK HGLKTLGTLF SSMMFPDRAP  420
NDQHLFTTFV GGSHNRDLAG APTSILKQLV TSDLGKLLGV EGQPTFVKHI HWRNAFPLYG  480
HDYDSALEAI GKMESDLPGF FYAGNNKDGL AVGNVIASGS KTADLVISYL ESGIKQDN    538
```

| SEQ ID NO: 262 | moltype = AA  length = 538 |
| --- | --- |
| FEATURE | Location/Qualifiers |
| REGION | 1..538 |
| | note = Expression Cassette |

```
VGGSRNRKLA NASTDELKQI VSSDLQQLLG TEDEPSFVNH LFWSNAFPLY GHNYDSVLRA  480
IDKMEKDLPG FFYAGNHKGG LSVGKAMASG CKAAELVISY LDSHIYVKMD EKTA        534

SEQ ID NO: 266          moltype = AA  length = 461
FEATURE                 Location/Qualifiers
source                  1..461
                        mol_type = protein
                        organism = Salinibacter sp.
SEQUENCE: 266
MPNVGIIGAG ISGLAAAYRL QEHGHSVRVL EASGHTGGVI RSESSEGFLV EHGPNSIRAG  60
AAGLETLIDA LDLHEDRVWA NDAADTRYVV RDGRPTPLPR SVGSFLTTDL FSTRAKLRLL  120
AEPFIGRAAA EDESVARFTE RRLGPEVLNY AVAPFVGGVF AGRPDDLSVQ HAFRRLAALE  180
EESGSLLLGA IRRALTSDDG APPDTPSGLF SFRNGLQTLP NALADTLGDR IRLNAPVHAL  240
THDGTAWRVT VSPPDAPAHT RSFDALVCTV PLHRLAAMEI DTPVDLAPLG EVTYPPLSVL  300
ALGYERDAID HALDGFGMLV PPVEDTLDVL GTIFSSTLFP GRAPEGHVLL TTFVGGARAP  360
HHATSDAAAL QARVARDLDS LLGVDASPVF RRLVHWPHAI PQYELGYGTV KDTFDALEAA  420
HPHLAFAGNY RAGVSVGDAL TSGLEAADRL LETDERATQP H                      461

SEQ ID NO: 267          moltype = AA  length = 469
FEATURE                 Location/Qualifiers
source                  1..469
                        mol_type = protein
                        organism = Rhodothermus sp.
SEQUENCE: 267
MASVGIIGAG IAGLTAAYEL HRRGLEVTVF EATDRIGGFI QSERIDGFLV ELGPQTLQRT  60
SGDFEELLRQ VDLEDACIPA RPVAANRFIV RGGQPIPLPR SPRELLRTPL LSPRARLRLL  120
AEPFIHRAHR STEESVAKFT RRRLGPEVLD YLVEPFVAGI FAGDPEQLSV RYAFPKLFEL  180
EQQYGSLFWG LIRDRMKQRY HPAPRRSMFS FVEGLHMLPR ALAERLPAHA IVRNAEVLAI  240
RWDEKNPWTL TFRQHGRAST RFFDIIVCAV PLHRLAQLRI HPPVDRRPLS TVEHPPIALV  300
ALGFRREQVA HPLDGFGMLV PAVERDFQIL GTLFSSSLFP DRAPEGHVLL TTFVGGMRHP  360
ELALLPEDRL EALVLQDLRR LLGISGAPVF RHVWRWERSI PQYRLGYDAV LACVHDVEMS  420
RSGLFLAGNY MEGISVIDAL HTGLKAARAI IQHLREEAAG GLAKLVLGD             469

SEQ ID NO: 268          moltype = AA  length = 461
FEATURE                 Location/Qualifiers
source                  1..461
                        mol_type = protein
                        organism = Salinibacter sp.
SEQUENCE: 268
MPNVGIIGAG ISGLAAAYRL QEHGHSVRLL EASGHTGGVI RSESSEGFLV EHGPNSIRAG  60
AAGLETLIDA LDLHEDRVWA NDAADTRYVV RDGRPTPLPR SVGSFLTTDL FSTRAKLRLL  120
AEPFIGRAAA EEESVARFTE RRLGPEVLNY AVAPFVGGVF AGRPDDLSVQ HAFRRLAALE  180
EESGSLLLGA IRRALTSDDG APPDTPSGLF SFRNGLQTLP NALADTLGDR IRLNAPVHAL  240
AHDGTAWRVT VSPPDAPAHT RSFDALVCTV PLHRLAAMEI DTPVDLAPLG EVTYPPLSVL  300
ALGYGRDAID HALDGFGMLV PPVEDTLDVL GTIFSSTLFP GRAPEGHVLL TTFVGGARAP  360
HHATSDAAAL QARVARDLDS LLGVDASPVF RRLVHWPHAI PQYELGYGTV KDTFDALEAA  420
HPHLAFAGNY RAGVSVGDAL TSGLEAADRL LETDERAAQP H                      461

SEQ ID NO: 269          moltype = AA  length = 469
FEATURE                 Location/Qualifiers
source                  1..469
                        mol_type = protein
                        organism = Rhodothermus sp.
SEQUENCE: 269
MASVGIIGAG IAGLAAAYEL HRRGLEVTVF EATDRIGGFI QSERIDGFLV EHGPQTLQRT  60
SGDFEELLRQ VDLEDACITA RPIAANRFIV RGGRPIPLPR SPRELLRTPL LSPRARLRLL  120
AEPFIHRAHR STEESVAKFA RRRLGPEVLD YLVEPFVAGI FAGDPEQLSV RYAFPKLFEL  180
EQQYGSLFWG LIRDRMKQRY HPAPRRSMFS FVEGLHMLPR ALADRLPAHA IVRNAEVLAI  240
RWDEKNPWTL TFRQHGRAST RFFDIIVCAV PLHRLAQLRI HPPVDRRPLS TVEHPPIALV  300
ALGFRREQVA HPLDGFGMLV PAVERDFQIL GTLFSSSLFP DRAPEGHVLL TTFVGGMRHP  360
ELALLPEDRL EALVLQDLRR LLGISGAPVF RHVWRWERSI PQYRLGYDAV LACVHDVEMS  420
RSGLFLAGNY MEGISVIDAL HTGLKAARAI IQHLREEAAG GLAKLVLGD             469

SEQ ID NO: 270          moltype = AA  length = 472
FEATURE                 Location/Qualifiers
source                  1..472
                        mol_type = protein
                        organism = Halothiobacillus sp.
SEQUENCE: 270
MNTHSNASEP INCPYLVIGG GISGLATAYH LSRMGKTVTV LEATSRVGGA VGSIEEDGWL  60
RELGPNSLVQ TPEMAALMSA LDLVSEIIEA NTVAKKRFVA KNGHPVALPG SPLELLTSPL  120
FSMGDLWHLA REAWIKPVNK EETIAEFVRR RLGQGFLDWA VDPFVSGVYA GDPNRLSVQA  180
AIPKIYAFEQ ESGSLIRGGI AKMKAAKANP APVTLPAKGK LFSFKRGLQT LTDALATAIT  240
SSGRGNIQLD SAITNIQRLP EGGWSVKTVG GKTFHTRQLI LSTPAHVSAQ LLGEVDGPLA  300
ETLAAIEYPP VTSVVMGFDR SEVAHPLDGF GLLLPSKEKK RTLGVLFSST LFPDRTPAGK  360
VLLSAFIGGR KHPEAAQGDD QELLDRVLGD LSPLLGIKGK PEFLRVKRWQ QAIPQYEIGY  420
LELQEKISQR LTALPGLSLN GNWRGGIAVG DCLNNGNKLA ERLIENTRTE ES          472

SEQ ID NO: 271          moltype = AA  length = 441
```

```
FEATURE                 Location/Qualifiers
source                  1..441
                        mol_type = protein
                        organism = Coralibacter sp.
SEQUENCE: 271
MPDTCIIGAG ITGLATAWQY QRKGKDCVVL ESGPQVGGAI QSILQDGYLA EEGPNSIQLN    60
SLEIEDFLTS IPGLEAQIIE ANPAAQKRYI VRKGRLRAVP MNPLQAITTQ LWSIAGKLRV   120
LREPFIKAAP PEPDQSVADF VTRRLGKELY DYAINPLVGG IYAGKPEMLS LRYGFPKLYA   180
LEQEHGGLIR GALAKMKAAK ANKGPKAKKY ILSFKDGLQT LPQSIANNLN EPVQTGVSIE   240
SIRQIEDMWA VRWNGQVKAF KELIVTVPAH KLPGLPFEEP IRLPAIDYPP VSVISLGYPL   300
SAIKQPLDGF GALVPEREDR NILGVLFPSA VFDGRAPEGH GLLTVFVGGS RSPECSSPDT   360
DQLLKTIQPD LETLLGIQDE PSFVHHKHWP MAIPQYTLGY EKVLEAITRI EQQYIGLKLA   420
GNYRTGISLS YCLESAIAST N                                            441

SEQ ID NO: 272          moltype = AA  length = 463
FEATURE                 Location/Qualifiers
source                  1..463
                        mol_type = protein
                        organism = Magnetococcus sp.
SEQUENCE: 272
MTKNPILIIG GGISGLSTAW FLHKKGEKVI LLESRDRVGG NIRTSRNPEG YLIEHGPNST    60
LQKPGDEEDA LGRIITDMAL ESELQEANPL AARRFVMKGG QLHVLPTSPP GFIKTPLFSL   120
SAKLRLCLEP FIGKSEQEES IAQFVIRRLG QEFLDYAIEP FVSGVYAGDP KQLSVRAAVA   180
KIYALEAKYG SLIKGAIALG KIRKAAGMPR GRMISFETGM ETLPATIANR LPHQSIHTNA   240
QVTALCQHGA AWQVSWQQGG QHGGEPHSII ASQVVLATPA SVSAQLLRPL SPQAADLLES   300
IRYAPVDSVA LGYAKQDINH SLDGFGFLIP RKEQVTTLGG LFSTTLFPGR APQDKALLTC   360
FIGGMTNPSI TQWSEEKVVT QVDQDMMAAL GIQHGAEYVH LTRYTHAIAQ YEQGHLQRVG   420
DIDRALAGYK GLHLRANWRD GVSVSDCVLN GEKSAQKILA GVS                    463

SEQ ID NO: 273          moltype = AA  length = 467
FEATURE                 Location/Qualifiers
source                  1..467
                        mol_type = protein
                        organism = Opitutus sp.
SEQUENCE: 273
MSTSPFNPSA TASGRPPKTF AVLGAGITGL TAAHRLTQLG HKVRVFEQSD RVGGSIKTEE    60
VDGWLIEGGP NTLLSGELAV DKLIDELGLN GERIAADPAA KNRYIVRRGR ALAAPMSPPS   120
FFASSLFSPV AKFKLLAELF ARRRVRTTDV SLAEFVESHF GREFVDYALN PFVGGVYAGD   180
PEKLSARQSF PKLWEIEQTH GSLIRGQIAA AKARKARGEP RPGIFSFKHG LHVLPEALAA   240
RLPAGAITLG ASLDAIVPGD KWNVVWHDDV ATHTQSFDSV VVALPAPALA RLQIGTLGEK   300
PLAALALIEH PPVSSLFLGF RREQVAHPLD GFGVLVPAVE KRSVLGVLFS SSLFPGRAPL   360
GHVALTVMVG GTRQPQLASL PADQLLAAVR PDLTQLLGVS GDPVFVRHNF WPRAIPQYNL   420
GHEHFIAALA AGERFHPGLF MGGQARDGIA VPACIAAGEK LAERAGQ                467

SEQ ID NO: 274          moltype = AA  length = 451
FEATURE                 Location/Qualifiers
source                  1..451
                        mol_type = protein
                        organism = Melioribacter sp.
SEQUENCE: 274
MSKKIVVLGA GISGLSTAYW LVKKGYDVTI LETKNEPGGS MISRRLDNFL IDYGPNSGLE    60
TTPLIRKLVE EVNLSDKMIY ANAAASKRYI LKNGELIPLP MSPGSFIRTK LFSSGAKFRL   120
MAEPFVSKSD DGYYQSIAEF VRRRLGNEFL DYAIDPFVSG VFAGDPEKLS VKSAFPKLYR   180
LEEVYGGLIK GMIKGARERK QRNEESKQSA KMFSFLEGMQ SLPNAIADKL KDNIVFSAKV   240
LNVTGANDKQ WKVTYELNGN RESITADTVI STLPAYIAAG VFGELDQKLA ERLNSIYYPP   300
VMVLYLGYNK KDIKRKLDGF GFLIPSKEKK HFLGAIWSSS IFPGRSPEDM AAFTLFVGGA   360
RSPQLFEMEK SDLIKKVLSE FHQIMNIKGE PVLIENKLWQ KAIPQYNLGY IEHEKYFEVF   420
EENHRGIYLR GNYRGGISVG DCIKNSELEI K                                 451

SEQ ID NO: 275          moltype = AA  length = 501
FEATURE                 Location/Qualifiers
source                  1..501
                        mol_type = protein
                        organism = Physcomitrella sp.
SEQUENCE: 275
VAVVGAGVSG LAAAHRLRSA GVAVTVFEAQ NAVGGKIQSF SNDGLIWEQG PNTMVETEPE    60
VSSLIDELGL REKQQWPVMQ NKRYVVRDGK AVQLPSNPLG LITTKLLSAQ AKCQILLEPF   120
LWKRKEVPLK EAANGRENVG NFITRHFGRE VVDYLVDPFI AGTSGSDPDS VSIRHTFPDL   180
FAIEERYGSL LIGGVKSSFK KKSGSKKESF KVQSDSAKVT PAQKRPRGSF SFVGGMQTLA   240
HALSERLDEE SLELNSSVLN LASDQQGNPS RNNWTVTYKK ENSQQKEKHF DAVILTTPLH   300
NLQELGIEKN GIPYALDFIP EIVYQPMSVI VTAFKESDVK NSLKGFGVLV PRMEKKNGFF   360
TLGTMFSSSM FPDRAPPGQV VFTTFVGGSR NRALASAPFE EVKAVALEDL RKIVGVQGPP   420
VAVVKHIFWKQ AFPQYSLDYN EFLSSLEKME SDLPGLFYAG NHRGGLSVGK SVASGCKAAE   480
HVLSMLEGTG GRKIFTMAST K                                            501

SEQ ID NO: 276          moltype = AA  length = 511
FEATURE                 Location/Qualifiers
source                  1..511
                        mol_type = protein
```

```
                    note         = Angiosperm
                    organism     = Ricinus sp.
SEQUENCE: 276
MSSVIKEDRN PSHVKRVAVV GAGVSGLAAA YKLKSHGLKV TVFEAEERAG GKLRSVNHDG    60
LIWDEGANTM TESEMEVKSL IGNLGIREKQ QFPISQNKRY IVRNGKPILI PTNPIALITS   120
NILSAQSKFQ IILEPFLWKK RESSETHNAY TEESVGEFFQ RHFGKEVVDY LIDPFVAGTS   180
AGDPESLSVC HSFPELWNLE KRFGSIIAGV VQAKLSTKRG KSQETKGSSV KKKQQRGSFS   240
FFGGMQTLTD TLCKALAKDE LRLESKVFSL SYNPDSKSAV ENWSLSYAFK GAKHLQNSSY   300
DAIVMTAPLC NVKEMKITKN RNIFSLNFLP EVSYMPLSVV ITTFKKDNVK SPLEGFGVLV   360
PSKEQQNGLK TLGTLFSSMM FPDRAPNDLY LYTTFVGGSR NKELAKASTD DLKQIVTSDL   420
RQLLGAEGEP TFVNHFYWSK AFPLYGRNYD AVLEAIDTME KDLPGFFYAG NHKGGLSVGK   480
AIASGCKAAD LVISYLESSS DDKMLKEGPS N                                  511

SEQ ID NO: 277              moltype = AA  length = 476
FEATURE                     Location/Qualifiers
source                      1..476
                            mol_type = protein
                            organism = Chromohalobacter sp.
SEQUENCE: 277
MQHEEQLDAT DQAVGEARRD VVVVGGGASG LAAARAAARR GLAVSVLERG SHAGGNLRTH    60
RDGAWQVEVG PNTLVMKPPL HTLLDELGLL DEAQPANPDA RRRYIAFHGR PVALPTHVLK   120
APANPLIGLR GSWSVLREPF RAGPPRDEES LADFVVRRLG RHVLDHLVDP FVSGVYAGDP   180
ARLSAQAAMP RLVALEREYG SLVRGGLRRL RQSRREPPAL PREWRGQLVS FPAGLQRLAE   240
RLAEDIADQP GASVQCGCEV VAVGREADGW QVETAAGQRI RTRELVLAVP APTAAALLAP   300
LDAALAAPLE EIAYPPVNAV SVGFRRADVD HPLDGFGMLI PGVERRRTLG ALFSSTLPFG   360
RAPSDHVLLT AFLGGRRQPE AAAGDDAEQV AQVVADLGDL LGIHAEPVWQ CVSRWPQAIP   420
QYERGHLARI AALDAALEAH PGLSLLGNWR DGIAVGDCLE NGRRLGERLA ETPDRR       476

SEQ ID NO: 278              moltype = AA  length = 462
FEATURE                     Location/Qualifiers
source                      1..462
                            mol_type = protein
                            organism = Leptospirillum sp.
SEQUENCE: 278
MAGFDCDTLV VGGGVSGLAA ALTLKNRGVD VRLLESRGYL GGAIRTVRED GYLLEFGPNS    60
LMVRPEDAID TVLGDPELRA RIVPASGLSK NRYVVKAGHL YPVPLSPWAF FRTPLLSWRG   120
RRDILSEWKV PPRTGGPEET LSHFVRRRLG EEALDYFVDP FVKGVYASHP DLLSVEAAFP   180
LLVRLEREHG GLLRGALKTF LKRRKRPSGS SPRGIFSFAG GMTDLVEAMG KRLGEDVGTN   240
VDVIKYTRLE EGFRVALMYD ETEYYMTSRR LILATSAPQA AELLEGDPDG PSSELKSIPY   300
APVTIAYAGF LREQVTHPLD GFGLLCPTVE NRKVLGVIFS SSLFPGRAPE GKVLLTVFVG   360
GMTGQKLAQA FDEDLERIVL KELTELLGVK GAPSFFRIHR WEKAIPQLIL GHRETVRTIR   420
KKLPSGLRLA GNYLDGISIA RAFASGVRAA EELLSEDGGT PG                     462

SEQ ID NO: 279              moltype = AA  length = 514
FEATURE                     Location/Qualifiers
source                      1..514
                            mol_type = protein
                            organism = Selaginella sp.
SEQUENCE: 279
MAMAEGETVP VLGSVAVVGA GASGLAAAYR LRAAGVSVTV YEAENSIGGK LKSVSENGFI    60
WEKGPNTMTE NDPSISRMFD DLHLRDKQQF PVEQKKRYIV RNASPTMLPS NPLGFITTGL   120
FSAQAKLKLL TEPFSWKRTK AESNEDESVG AFMERHFGDE IVDYAVDPFV AGTSGSDPSS   180
ISIRHSFPEL WSLEKNYGSL FVGAIKSGFS KKKKQKLRPV EFEDEDSDFP ARTRPRRGGS   240
FSFVGGMQTL ANELVSRIGK EKFKLNTFVT GLACNQQGNP SRQSWTVTGL ETSGKRSKRS   300
DKTFDAVIMT APVDDVRTMK VVKDGKPYAL DYLPTVIYEP MSVLITMFNK DSVKRALPGF   360
GVLVPSKEQQ ANGFQTLGTL FSSFMFPDRA PEDQLLFTTF IGGSRNTLLA SRSKEELLDV   420
TLKDLSRLIG VEGQPTAMRH VYWEKAFPRY SIGYDNVLNS IQKLESDLPG LFYAGNHRGG   480
LAVGKTIVSG LDAAEQVLQY LQGSGGKKVF TMAS                              514

SEQ ID NO: 280              moltype = AA  length = 520
FEATURE                     Location/Qualifiers
source                      1..520
                            mol_type = protein
                            organism = Selaginella sp.
SEQUENCE: 280
MAMAEGETAP VLGSVAVVGA GASGLAAAYR LRAAGVSVTV YEAENSIGGK LKSVSENGFI    60
WEKGPNTMTE NDPSISRMFD DLHLRDKQQF PVEQKKRYIV RNASPTMLPS NPLGFITTGL   120
FSAQAKLKLL TEPFSWKRTK AESNEDESVG AFMERHFGDE IVDYAVDPFV AGTSGSDPSS   180
ISIRHSFPEL WSLEKNYGSL FVGAIKSGFS KKKKQKLRPV EFEDEDSDFP ARTRPRRGGS   240
FSFVGGMQTL ANELVSRIGK EKFKLNTFVT GLACNQQGNP SRQSWTVTGL ETSGKRSKRS   300
DKTFDAVIMT APVDDVRAMK VVKDGKPYAL DYLPTVIYEP MSVLITMFNK DSVKRALPGF   360
GVLVPSKEQQ ANGFQTLGTL FSSFMFPDRA PEDQLLFTTF IGGSRNTLLA SRSKEELLDI   420
TLKDLSRLIG VEGQPTAIRH VYWEKAFPRY SIGYDNVLHS IQKLESDLPG LFYAGNHRGG   480
LAVGKTIVSG LDAAEQVLQY LQGSGGKKVF TMASLEQPVS                        520

SEQ ID NO: 281              moltype = AA  length = 508
FEATURE                     Location/Qualifiers
source                      1..508
                            mol_type = protein
```

```
                              organism = Arabidopsis sp.
SEQUENCE: 281
MASGAVADHQ  IEAVSGKRVA  VVGAGVSGLA  AAYKLKSRGL  NVTVFEADGR  VGGKLRSVMQ   60
NGLIWDEGAN  TMTEAEPEVG  SLLDDLGLRE  KQQFPISQKK  RYIVRNGVPV  MLPTNPIELV  120
TSSVLSTQSK  FQILLEPFLW  KKKSSKVSDA  SAEEVSEFF   QRHFGQEVVD  YLIDPFVGGT  180
SAADPDSLSM  KHSFPDLWNV  EKSFGSIIVG  AIRTKFAAKG  GKSRDTKSSP  GTKKGSRGSF  240
SFKGGMQILP  DTLCKSLSHD  EINLDSKVLS  LSYNSGSRQE  NWSLSCVSHN  ETQRQNPHYD  300
AVIMTAPLCN  VKEMKVMKGG  QPFQLNFLPE  INYMPLSVLI  TTFTKEKVKR  PLEGFGVLIP  360
SKEQKHGFKT  LGTLFSSMMF  PDRSPSDVHL  YTTFIGGSRN  QELAKASTDE  LKQVVTSDLQ  420
RLLGVEGEPV  SVNHYYWRKA  FPLYDSSYDS  VMEAIDKMEN  DLPGFFYAGN  HRGGLSVGKS  480
IASGCKAADL  VISYLESCSN  DKKPNDSL                                        508

SEQ ID NO: 282          moltype = AA  length = 454
FEATURE                 Location/Qualifiers
source                  1..454
                        mol_type = protein
                        organism = Acidithiobacillus sp.
SEQUENCE: 282
MSSETVIVVG  AGLTGLSATW  YLHQRGIPAL  LLEAEAEVGG  NLRSRSEDGF  LRDLGPNSLM   60
IKGDLLPDLI  RQLQLEDRVV  EANPLARRRF  VLNRRGHPVA  LGPDVLFSSS  LLSLSARLRL  120
LSEPWRPRRP  QSQNDESIAD  FVRRRLGPEA  LTWMVDPFVS  GVFAGDPEKL  SVTAALPRLA  180
AMEAESGSLL  RAALRRRRAG  KKEGSSRLVS  FRGGLQEATR  AAARLPPDR   LALSRPLTHL  240
QRRGELWHLQ  TPAGDLECRR  LVLALPAAES  ARLLRAEAPE  LAAELEAIVY  PAVATVALGF  300
PREAVDHRLD  GFGLLIPRRL  GIETLGVLFS  STLFPERAPP  GMVLLTAFLG  GAQQDISGRS  360
PAELEAQALA  DLRPILGIRG  DPAYHRCALW  PRAIPQYALG  HRQRVERIHE  LRRQLAGLEL  420
LGNWQGGVAL  GDCVVQADAF  QRTFAQVDTA  TGPS                                454

SEQ ID NO: 283          moltype = AA  length = 512
FEATURE                 Location/Qualifiers
source                  1..512
                        mol_type = protein
                        organism = Arabidopsis sp.
SEQUENCE: 283
MESGAVGDHD  TKFESISGKR  VAVVGAGVSG  LAAAYKLKSR  GLNVTVFEAD  ERAGGKLTSV   60
MQNGLIWDQG  ANTMTEAEPE  VGSLLDDLGL  RDKQQFPISQ  KKRYIVRNGL  PMMLPTNPIE  120
LVTSSVLSTQ  AKIQILLEPF  LWKKNDSSSK  VSDASAEESV  SGFFQRHFGQ  EVVDYLIDPF  180
VGGTSAADPD  SLSMKHSFPD  LWNVEKSFGS  IIVGAIRTKL  AAKGGKSGEA  KSSPGTKRGS  240
RRSFSFKGGM  QILPDMLCKS  LSHDEINLDS  KVLSLSYNSG  SRQENWSLSC  VSHNETQRQN  300
LHYDAVVMTA  PLCNVKEMKV  TKGGQPFLLN  FLPEINYMPL  SVLITTFTKE  KVKRPLEGFG  360
VLIPSKEKKH  GFKTLGTLFS  SMMFPDRCPS  DLHYTTFIG   GSRNQELAKA  STDELKQVVT  420
SDLQRLLGVE  GEPVSNHYY   WRKAFPLYDS  SYGSVMEAID  KMEKDLPGFF  YAGNHRGGLS  480
IGKSIASGCK  AADLVISYLE  SCSNDKKPDE  SL                                  512

SEQ ID NO: 284          moltype = AA  length = 502
FEATURE                 Location/Qualifiers
source                  1..502
                        mol_type = protein
                        organism = Glycine sp.
SEQUENCE: 284
MASSATDDNP  RSVKRVAVVG  AGVSGLAAAY  KLKSHGLDVT  VFEAEGRAGG  RLRSVSQDGL   60
IWDEGANTMT  ESEIEVKGLI  DALGLQEKQQ  FPISQHKRYI  VKNGAPLLVP  TNPAALLKSK  120
LLSAQSKIHL  IFEPFMWKRS  DPSNVCDENS  VESVGRFFER  HFGKEVVDYL  IDPFVGGTSA  180
ADPESLSMRH  SFPELWNLEK  RFGSIIAGAL  QSKLFAKREK  TGENRTALRK  NKHKRGSFSF  240
QGGMQTLTDT  LCKELGKDDL  KLNEKVLTLA  YGHDGSSSSQ  NWSITSASNQ  STQDVDAVIM  300
TAPLYNVKDI  KITKRGTPFP  LNFLPEVSYV  PISVMITTFK  KENVKRPLEG  FGVLVPSKEQ  360
KNGLKTLGTL  FSSMMFPDRA  PSDLYLYTTF  IGGTQNRELA  QASTDELRKI  VTSDLRKLLG  420
AEGEPTFVNH  FYWSKGFPLY  GRNYGSVLQA  IDKIEKDLPG  FFFAGNYKGG  LSVGKAIASG  480
CKAADLVISY  LNSASDNTVP  DK                                              502

SEQ ID NO: 285          moltype = AA  length = 474
FEATURE                 Location/Qualifiers
source                  1..474
                        mol_type = protein
                        organism = Chloroflexus sp.
SEQUENCE: 285
MMAGYDSVVI  GGGIAGLAAA  YTLHKRGYRV  LVIESTNRVG  GVIQTITTPE  GYILDCGPNT   60
VGTGDARLWQ  ELIDLGLRER  ITPAAPCSKR  RFILINGTPV  EIPTSPVGLI  TTRLLSWRGK  120
LRVLAEPFIN  RGSTDPDESV  AAFFTRRIGA  EATAHLLDPF  VAGVYAGDPQ  RLSTAAVFPS  180
LWEAAQRSGS  IVRGMLSKPK  PKTQVSEPKM  RSRTFTFRGG  LAEWPRALAQ  ALGAGNVWTE  240
RRVVKLQPRD  SWWEVTIDGV  NGPETLISRS  LIIATPAFTA  ADLIESVDQR  AAGALRGIPY  300
APVAVVHLGF  RRDQISQELS  GFGVLAPSSE  QRQFLGILWT  SSIFPHVAPH  DHVLTTTLSG  360
GAIRPELAER  SDETLIEAAI  RDHHQLLGIR  GQPIFTHVTR  WRTAIAQYTF  GHRERIATLV  420
QLEQRLPTIQ  FAGSYRDGVG  VPKTWASGVQ  AGERIAAALA  AHGTTAVSTE  TASG        474

SEQ ID NO: 286          moltype = AA  length = 499
FEATURE                 Location/Qualifiers
source                  1..499
                        mol_type = protein
                        organism = Medicago sp.
```

```
SEQUENCE: 286
MASSAKDDNP RSVKRVAVVG AGVSGLAAAY KLKSHGLDVT VFEAEGRAGG RLRTVSRDGL    60
VWDEGANTMT ENEIEVKGLI DALGLHEKQQ YPLSQHKRYI VKNGTPVLVP ANPAALLKSK   120
LLSAQSKIQV IFEPFMWKRS DSSAVRDENS EESVSRFFER HFGKEVVDYL IDPFVGGTSA   180
AGPESLSIRH SFPELWNLEK RFGSIIAGAL QSSVFGKKDK AGETKDVPRK NKHQRGSFSF   240
QGGMQTLTDT LCKELGKDDI KLNAKVLTLA YSHDGSSPSQ NWSITCTSNR KAQDVDAVIM   300
TAPLGNVRDI QIKKKGNPFP LNFLPEVTYL PLSVLITTFK KENVKRPLEG FGVLVPSKEQ   360
QNGFKTLGTL FSSMMFPDRA PSDMHLYTTF IGGTRNRELA QASTDELTKI VTSDLRKLLG   420
AEGEPAFVNH FFWSKGFPLY GHNYGSVLEA IDKMEKDLPG FFYAGNHRGG LSVGRAIASG   480
CKAADLVISY LNNASDNSV                                                499

SEQ ID NO: 287           moltype = AA  length = 475
FEATURE                  Location/Qualifiers
source                   1..475
                         mol_type = protein
                         organism = Chloroflexus sp.
SEQUENCE: 287
MMMANYDSVV IGGGIGGLAA AYTLYKRGYR VLVIEAANRV GGVIHSITTP EGFTLDCGPN    60
TIGTNDVRLW QELIDLGLRD RIRPAARCGR RRYILINGTP IEIPSSPVGL ITTRLLSWRG   120
KLRVLGEPFV NIGTPTGEES VAAFFSRRIG HEAVAHLLDP FVAGVYAGDP NQLSAAAVFP   180
SLWEAVQRGG SIVRGMLRRP KQKTLISEPK MRSRTFSFQG GLADWPRAIA RALGTGNVWT   240
GRRAVGLRDL GTYWEVTVDG TGRLETITTR SVIIATPAYV AAELVEALDP AAASALRSIP   300
YAPVSVVHLG FRRDQLSHEL NGFGVLAPSS ERRQFLGILW ASSLFPHVAP PDRVLTITLS   360
GGAIRPEVAE QSEEALIESA IRDNQEVLGI RGQPLLTHVT RWHHAIAQYT LGHRERIATL   420
ERLEQRRPTL QLTGSYRGGI GIPKTWASGV GAGERIAAAL DAQGTTADTL EQARG        475

SEQ ID NO: 288           moltype = AA  length = 508
FEATURE                  Location/Qualifiers
source                   1..508
                         mol_type = protein
                         organism = Vitis sp.
SEQUENCE: 288
MAEKSDAQSH YNGSGKRVAV VGAGVSGLAA AYKLKLHGVN ITLYEAEERA GGKLRSVSQH    60
GLVWDEGANT MTESEIEVGS LLDNLRLREK QQFPISQNKR YIVRNGMPVL LPSNPIALIK   120
SNILSAKSKF QIILEPFLWK KSDLSKVSDD HMKESVGGFF QRHFGKEVVD YLIDPFVAGT   180
SGGDPESLSM HHTFPELWNL EKRFGSIIAG AVLSKLSAKR EKRGETKGSS EKKKRQRGSF   240
SFQGGMQTLT DTLCKELGKD KLRLSKVLS LSYSHGEKSA LENWSVAYAS NPGKQSKDLS    300
FDAVIMTAPL CNVREMKIMK KGNPFLLDFL PEVSYLPLSV ITTFKKENV KRPLEGFGVL    360
VPSKEQQNGL KTLGTLFSSM MFPDRAPNDL YLYTTFIGGS RNRELAKAST DELKQIVTSD   420
LRQLLGAEGE PTFVNHFYWS KAFPLFGHNY DSVLEAIDKM EKDLPGFFYA GNHKGGLSVG   480
KAIASGCKAA DLVISYLNSS SDGKMFKE                                      508

SEQ ID NO: 289           moltype = AA  length = 544
FEATURE                  Location/Qualifiers
source                   1..544
                         mol_type = protein
                         organism = Zea sp.
SEQUENCE: 289
MLALTASASS ASSHPYRHAS AHTRRPRLRA VLAMAGSDDP RAAPARSVAV VGAGVSGLAA    60
AYRLRQSGVN VTVFEAADRA GGKIRTNSEG GFVWDEGANT MTEGEWEASR LIDDLGLQDK   120
QQYPNSQHKR YIVKDGAPAL IPSDPISLMK SSVLSTKSKI ALFFEPFLYK KANTRNSGKV   180
SEEHLSESVG SFCERHFGRE VVDYFVDDPFV AGTSAGDPES LSIRHAFPAL WNLERKYGSV   240
IVGAILSKLA AKGDPVKTRH DSSGKRRNRR VSFSFHGGMQ SLINALHNEV GDDNVKLGTE   300
VLSLACTFDG VPALGRWSIS VDSKDSGDKD LASNQTFDAV IMTAPLSNVR RMKFTKGGAP   360
VVLDFLPKMD YLPLSLMVTA FKKDDVKKPL EGFGVLIPYK EQQKHGLKTL GTLFSSMMFP   420
DRAPPDDQYLY TTFVGGSHNR DLAGAPTSIL KQLVTSDLKK LLGVEGQPTF VKHVYGNAF    480
PLYGHDYSSV LEAIEKMEKN LPGFFYAGNS KDGLAVGSVI ASGSKAADLA ISYLESHTKH   540
NNSH                                                                544

SEQ ID NO: 290           moltype = AA  length = 478
FEATURE                  Location/Qualifiers
source                   1..478
                         mol_type = protein
                         organism = Arabidopsis sp.
SEQUENCE: 290
MASGAVADHQ IEAVSGKRVA VVGAGVSGLA AAYKLKSRGL NVTVFEADGR VGGKLRSVMQ    60
NGLIWDEGAN TMTEAEPEVG SLLDDLGLRE KQQFPISQKK RYIVRNGVPV MKKSSKVSDA   120
SAEESVSEFF QRHFGQEVVD YLIDPFVGGT SAADPDSLSM KHSFPDLWNV EKSFGSIIVG   180
AIRTKFAAKG GKSRDTKSSP GTKKGSRGSF SFKGGMQILP DTLCKSLSHD EINLDSKVLS   240
LSYNSGSRQE NWSLSCVSHN ETQRQNPHYD AVIMTAPLCN VKEMKVMKGG QPFQLNFLPE   300
INYMPLSVLI TTFKEKVKR PLEGFGVLIP SKEQKHGFKT LGTLFSSMMF PDRSPSDVHL    360
YTTFIGGSRN QELAKASTDE LKQVVTSDLQ RLLGVEGEPV SVNHYYWRKA FPLYDSSYDS   420
VMEAIDKMEN DLPGFFYAGN HRGGLSVGKS IASGCKAADL VISYLESCSN DKKPNDSL     478

SEQ ID NO: 291           moltype = AA  length = 441
FEATURE                  Location/Qualifiers
source                   1..441
                         mol_type = protein
                         organism = Hydrogenobacter sp.
```

```
SEQUENCE: 291
MIDVAVVGAG ISGLSIAYHL KKAGLEVKVF EKEDAVGGNI QTAYIDGYVC ELGPQTILAD    60
SKVEEFLKDA GIKPIYANPS SKKRYIYRKG KLVALPLSPV EFLLSPFLSL GGKLRVLKEP   120
FVPRSPKQEE SIAEFVRRRF GREFLDYVVA PFVSGVYAGD PEELSVKYAV RKVYELEQKY   180
GSVIKGAIKL KALGPSGKLI SFEGGNATLI RKLSESLEVH KENVVLRIRR KDDIFILDTK   240
EGKVTAKAVV VSTPATSTGY LLRDLSWSIS EEFDKIYYAP VLVVHVAVKF GVLPEGFGFL   300
VPKKENKRIL GVIFSSNLFE GRSPEGKSLI TVYIGGATDP EIIEYEDEAI VSVLERELRE   360
TVDIRDWDLL KITRWKKGIP QYTVGYGRYL ELANSIEMEQ PGLFLSGNYL YGVSVADCIR   420
VSHHIAKRVI DFLEVKGRTV V                                            441

SEQ ID NO: 292         moltype = AA  length = 458
FEATURE                Location/Qualifiers
source                 1..458
                       mol_type = protein
                       organism = Thermovibrio sp.
SEQUENCE: 292
MRVCVIGGGV SGLSTAFYLK RGGAQVKLLE RENYPGGKAR TYYEKGYIVE SGPNGFLDGK    60
PDTLELVKLL GAEKLLYRSS DKARKRFIYK NGRLVRLPEN PIAFLSSYLL SWKGKVRVLG   120
ELLVPPSEKE DETLAEFVRR RLGKEALDYL LDPMVAGIFA GDPERMSLKA AFPTIYRLER   180
EYGGLIRGLI AKAKEAKKKG AKSSGPAGPG GVLTSFVKGM SQFTQLLAQE LGESFTPEAQ   240
VKTLEKKKDK WLVTYTLRGK EKSEEFDAVV LSLPAYAAAQ VLKETSRELS ELLASIEYSP   300
ISVVALGFEK RGLGHNLDGF GFLVPKVEGR KILGALWDSS VFPNRAPEGK ALIRVMIGGA   360
RQPELALKSE EELTEIALKE LKRIMKIRHY PEMVKVFRHE KGIPHYTIGH AEKVERIFKL   420
GRELGNLFFC NNAYKGVGIN DCTKSARETA EEVLNSLC                          458

SEQ ID NO: 293         moltype = AA  length = 462
FEATURE                Location/Qualifiers
source                 1..462
                       mol_type = protein
                       organism = Ignavibacterium sp.
SEQUENCE: 293
MTKTIVVIGA GISGLTTAYL LSKRGFNIRI LERKSEVGGS IESIKENGFL FDRGPNSALE    60
TTPLISQLVE ELNLKDELLY ANKAANKRYI LRNNELHALP MSPPALIKTK LFSAKAKLRL   120
LTEPFIGRSE DGYYQSLAEF VRRRLGQEFL DYAINPFVAG VYAGKPEELS VKSAFPKLYA   180
LEEKFGGLII GTIRSIRERK KRAEKSKQSA RMLSFKSGMI SLPKAIANYF ADKLILSAEV   240
ISVDKTAEGF IVSYRHSGID EAIVCDAVLS TVPSYVAGNL FSKFDKKFKV HSDEIYYPPV   300
LVYFLAYEKK NIGQTLDGFG FLIPEKENKS FLGALWSSVI PPYRADNNFA TFTLFIGGSR   360
YPDFVKEDRN KLLEKVRKEF EQLMKIKSDP VFSAYRFWEK AIPQYNIGYI EHERFFDEFE   420
KQNPGLFISG NFRGGISVGD CIKNAELVAN KICVQFTMHN VQ                     462

SEQ ID NO: 294         moltype = AA  length = 544
FEATURE                Location/Qualifiers
source                 1..544
                       mol_type = protein
                       organism = Sorghum sp.
SEQUENCE: 294
MLARTATVSS TSSHSHPYRP TSARSLRLRP VLAMAGSDDS RAAPARSVAV VGAGVSGLVA    60
AYRLRKSGVN VTVFEAADRA GGKIRTNSEG GFLWDEGANT MTEGELEASR LIDDLGLQDK   120
QQYPNSQHKR YIVKDGAPAL IPSDPISLMK SSVLSTKSKI ALFFEPFLYK KANTRNPGKV   180
SDEHLSESVG SFFERHFGRE VVDYLIDPFV AGTSAGDPES LSICHAFPAL WNLERKYGSV   240
VVGAILSKLT AKGDPVKTRR DSSAKRRNRR VSFSFHGGMQ SLINALHNEV GDDNVKLGTE   300
VLSLACTLDG APAPGGWSIS DDSKDASGKD LAKNQTFDAV IMTAPLSNVQ RMKFTKGGAP   360
FVLDFLPKVD YLPLSLMVTA FKKEDVKKPL EGFGVLIPYK EQQHGLKTL GTLFSSMMFP   420
DRAPDDQYLY TTFVGGSHNR DLAGAPTSIL KQLVTSDLKK LLGVQGQPTF VKHIYWGNAF   480
PLYGHDYNSV LEAIEKMEKN LPGFFYAGNN KDGLAVGSVI ASGSKAADLA ISYLESHTKH   540
NNLH                                                               544

SEQ ID NO: 295         moltype = AA  length = 456
FEATURE                Location/Qualifiers
source                 1..456
                       mol_type = protein
                       organism = Desulfurobacterium sp.
SEQUENCE: 295
MKVAVIGAGI SGLSVAFYLK KGGAEVKVFE KEKTVGGKMK TIHEDGYIIE TGPNGFLDGK    60
PYTLNLVKEL GIESKLYRSS DKARKRFIYT NGRLVRLPES PIAFLASYLL SWKGKLRLVG   120
EFLVPPKKED IDESLSEFAK RRIGEEALEK LLDPMVAGIF AGDPDRLSLK AAFPAIYYLE   180
KQYGGLIKGL IAKMKEAKKS GKKSGPAGPG GVLTSFKGGV KDLIDSLSEF LGDSIETEVE   240
ILGLDRIEKG WKVKYKKENE VFEETFDAIV FSTPAYITAK LLNDLNLELS KLLSEIEYSP   300
ISVVALGFEK KGLGHDLDGF GFLVPRSEKR KILGALWDSS VFPNRAPSGK ALIRVMIGGA   360
RQPELALLPD EELVNIALKE LRRIMKIRHY PEKIVFKHE KGIPHYTVGH AERVEKIFRL   420
ISKYPGLYLC NNAYTGVGVN DCTKAAEEVA RRILDG                            456

SEQ ID NO: 296         moltype = AA  length = 446
FEATURE                Location/Qualifiers
source                 1..446
                       mol_type = protein
                       organism = Acidithiobacillus sp.
SEQUENCE: 296
MEDVIIIGAG ISGLATAYFL RKQGWSPLLL EAAAKPGGNL QSRQEEGYLR DMGPNSLMLK    60
```

```
GHIVPEWLRE LRLEEDIVEA NPLAKRRYIL NRHRQPVALG PGVLFGGGLL SWRGRLRLLG    120
EPFRSPRRMQ DSEESVADFV RRRLGEEALT WLVDPFISGV FAGNPARLSV QATLPRLIAL    180
EQDGGSLLRG ALRARNKKSP DTPKTRLISF REGLQTLPLR VASALGDALR CNTPVEQLGN    240
SDGSWQVSSG SQTWQSKRLI LALPAGAAAR LLAPTDAALA HELDAIPYPA VGSLSIGFQR    300
MQVQHPLDGF GILIPRVMGL ETLGILFSST LFPGRAPADQ VLLTAFIGGS QNDISGRDDD    360
DLLATALREI CPLLGISGKP VFSRCQTWPK AIPQYEIGHL DRIKRIDALS ARHPGLYFRA    420
NWREGVALGD CMEEAYRFSQ DVGWQR                                        446

SEQ ID NO: 297         moltype = AA  length = 433
FEATURE                Location/Qualifiers
source                 1..433
                       mol_type = protein
                       organism = Thermocrinis sp.
SEQUENCE: 297
MMDVIVVGAG ISGLSVAFRL SKEGLKVKVL EKEEEPGGNI RTRKVGDFLC ELGPQTVLAD     60
GEVVDFFREV GIQPQEASPS SSVRYIYKRG KLIPLPNSPV KFLTSPLLSL GGKLRVLMEP    120
FVAPSVKTEE TVAQFVRRRL GEEFLHYVIT PFVRGVYAGD PEELSIKYAF RRVYQLEREY    180
GSLIRAAIKL KRLGPPGKII SFEGGNQSII QQLASYVDLE TENVALRIRR KDDRYILDTK    240
EGKYEARCVV VASPATSAGY LLRDISWSAA QELDKIYYAP VVVVHVATSQ NIPDGFGFLA    300
PQKEDLRILG VLFSSRIFPN KAPQGKELLT IYMGGATDPE VVEYEDELIM RIVEEDLRKS    360
LGLTQLEFLL VTRWKRAIPQ YTLGYGRYIE LVEALQRENP GLFITGNYLE GVSVADCIKR    420
SKRVVQEVVK FFR                                                      433

SEQ ID NO: 298         moltype = AA  length = 440
FEATURE                Location/Qualifiers
source                 1..440
                       mol_type = protein
                       organism = Laribacter sp.
SEQUENCE: 298
MVVVIGAGIS GLSCAWHLQQ RGIPVVVLEA GSRVGGKIGT VAADGYRLEL GPNTLYGHAG     60
HLDLLERLGL TAAIRPAAAV VRHRFVLRGD RYEALPSGPL SFLTGSQFGA RSKWLALTEP    120
FRRNRPVREP ETVAAFFRRR LGDEFVERAI SPFVGGIFAG DPEELVAGLT LPVIHEAERQ    180
SGSIVRGMFA RRKTFRRKAT FTLNEGLQQL PETLAQGLDV RLDTSVQALE RLETGWRVRT    240
PAGELDADEV VLAVPADVAG QLLASHFPAI AANLANVTYA PVAVLHTAWP RSTVGHDLDG    300
FGGLNPKVEK PFAAGSIWSG SLFPDRTPAG ETLLTTFVGG MQFLDRYRHD DATLVALALE    360
ELRRLYRIQG EPTLCRLTRQ EQAIPQYDSH ALPLASAVSD LHEHGIRVCA NWHGGVSVVD    420
CLDKGQQVAV QCLLDYPPAS                                               440

SEQ ID NO: 299         moltype = AA  length = 446
FEATURE                Location/Qualifiers
source                 1..446
                       mol_type = protein
                       organism = Acidithiobacillus sp.
SEQUENCE: 299
MEEVIIIGGG ISGLATAYFL RKRGWSPLLL EAGAAPGGNL QSRQEEGYLR DMGPNSLMLK     60
GRIVPEWLRE LQLEGDIVEA NPLAGRRYVL NRHRQPVALG PGVLFGGGLL SIRGRLRLLG    120
EPFQPPHPTP DGEESIADFV RRRLGEDEALT WLVDPFVSGV FAGNPARLSV QATLPRLAAL   180
EQDGGSLLRG ALRARKKKLP GTPKTRLVSF REGLQVLPLR VANTLGDTLR CDTPVDQLAY    240
SGDMWQVSSG NQTWQSKRLV LALPAGAAAR LLAQTDATLA RELDAIPYPA VGSLSIGFRR    300
PQVEHPLDGF GMLIPRVMGL ETLGVLFSST LFPGRAPAGQ VLLTAFIGGS QNVLAGRDDD    360
DLLATVLREI GPLLGISGDP VFSRCRVWPK AIPQYEIGHL DRMKRIDTLS AGHPGLHFRA    420
NWQGGVALGD CIEQAWEFSQ TADWQH                                        446

SEQ ID NO: 300         moltype = AA  length = 453
FEATURE                Location/Qualifiers
source                 1..453
                       mol_type = protein
                       organism = Deferribacter sp.
SEQUENCE: 300
MKIAIIGGGI SGISTAFWLE YFAKERLKSI DITIFEKNKR LGGTINTFYK DNFIIESGPN     60
GFLDSKPYTV ETFEKAGLGD NLIRSNELAK KRYIMRGGVL HKLPEKPNEF FSSKLLSFKG    120
KLRVISELFI PAKKDEYDET IEEFAYRRLG KEAADYLISP MVSGVFAGDP SKLSLKSCFP    180
VIYNLEKEYG GLFKAMFKKK GKKSGPAGPG GNLTSYKGGL IKGINALTEQ LSNTKIYLGE    240
EVTGLDKTNG SFKVKTTNSC DNYDIVIITS PAYVAAEFIK GLSVELSDKL LKLNYAPMYV    300
IGFGFKEEDV LDPLDGFGFL VPHNENRKIL GALFTSSIFP ERAPKGYKLI RVMIGGDKNR    360
WVLNCSEDEL RDIAFNEIKD ILGVKGNSVV EKSFYWERAI PQYYQGHEKL VEDIESICMD    420
INNIYIGGNL LYGIGINDCT KRSIDIARGV LGG                                453

SEQ ID NO: 301         moltype = AA  length = 471
FEATURE                Location/Qualifiers
source                 1..471
                       mol_type = protein
                       organism = Geobacter sp.
SEQUENCE: 301
MKKAIVVGGG ISGLASAYLL REKAKNSGME LEITIVEKED RTGGKIRSIK EDGYLCEWGP     60
NGFLDSKPQT LDLCRELKVD SQLLRSNDNA RKRPIYSGGV LNRLPENGPS FLKSRLISWP    120
GKLRLALEPT PFIAKAPEGV DETLAAFGRR RLGDEALRKL IAPMVSGIFA GDPETMSLVS    180
CFPRIAELER EYGGLVKAMV KLAKKKKQEI AEGKQVASAA GPGGVLTSFR DGIQTLTDIL    240
NERLGKDMLV IGAEVTGVSR GNSTPYRVQT GGRELDADIV VLATPAYATA QALEGIDGGM    300
```

```
SATLNQIPYA TMTVVCFGYE QEKVAHDLNG FGYLIPKAEG MNILGTLWDS SIFENRAPEG   360
KVLLRSMMGG ACFPEYIRLS DAEVVQKVRD NLKTIMGIKE APEFVRIFRH EKAIPQYTVG   420
HGRRLAALEE QAKSHPGLFL SGNSYRGIGL NDCVAAANRT ADEVVAFLQS R            471

SEQ ID NO: 302              moltype = AA  length = 450
FEATURE                     Location/Qualifiers
source                      1..450
                            mol_type = protein
                            organism = Thermodesulfovibrio sp.
SEQUENCE: 302
MGSAEIVIVG GGISGLSLAY FLIQKNSQLN IKIVEAEKRA GGKIITENIS GFLCEGGVNG    60
FLSNKPSTIS LAKELNIEPL RGSESSKIRY ILIDGKLIRV PENPIKFFLT PLLSFSGKIR   120
MLREYFTPPL KEEIDETVES FVSRRVGKEF YEKLIDAMST GIYAGDPSKM SMKSCFPKVY   180
WLEKRHGGLL KGLIALKKEK KDTKAQPSGV LMSFKGGMSE LIQSLERHLS SRILKGKKVL   240
SIDRKNTYYT VHLDDGNFIE AEKVILACPA HESAEILKEL SSELSDILKT IPYPPLSVVA   300
FGFKKEQIGF GTSLYGFLIP YREQRKILGT LFDSSIFPNR APESYVLLRS MIGGRRAPEL   360
AMLPDEKLID TALSELKPLL NIKGDPEFIK IFRWEKAIPQ YELGHEDKLN RIEQILSEFS   420
GLYLTGNAYR GVSVNDCIEN SLKLAEGIMV                                   450

SEQ ID NO: 303              moltype = AA  length = 469
FEATURE                     Location/Qualifiers
source                      1..469
                            mol_type = protein
                            organism = Geobacter sp.
SEQUENCE: 303
MKKAIVAGGG ISGLATAYLL KTRAAEEGLE LDVTLVEREE RLGGKIWSIK EEGYLCEWGP    60
NGFLDSKPQT LDLCRELGAS DLLLRSNDNA RKRFIYTGGA LNRLPENGPM FLKSGLISWP   120
GKLRLAMEPF IPKKAGDEDE TLAAFGRRRL GDEALRKLIA PMVSGIFAGN PETMSLRSCF   180
PRIAELEDEY GSLVRAMIRL AKKKKQEVAQ GKAVASAAGP GGVLTSFRDG IQALTDILAE   240
RLGPDTIVSG QEVLEVSRGG SLPWRVRTGS IDMDADLVIL ATPAYATASI IQGVDSDMAG   300
ILRQIPYATM TVVCFGYDRE RIAHDLNGFG YLIPKEEGMN TLGTLWDSSI FENRAPEGQV   360
LLRSMMGGAC FPEYVNLTDE EVTGRVKNDL ATIMGITAPP SFVRIFRHHQ AIPQYTVGHS   420
TRVAALEQRA ASLPGLFLTG NSYRGIGLND CVAAANRTAG EAIAQLTSR              469

SEQ ID NO: 304              moltype = AA  length = 469
FEATURE                     Location/Qualifiers
source                      1..469
                            mol_type = protein
                            organism = Geobacter sp.
SEQUENCE: 304
MKKAIVAGGG ISGLATAYLL KTRAAEEGLE LDVTLVEREE RLGGKIWSIK EEGYLCEWGP    60
NGFLDSKPQT LDLCRELGAS DLLLRSNDNA RKRFIYTGGA LNRLPENGPM FLKSGLISWP   120
GKLRLAMEPF IPKKAGDEDE TLAAFGRRRL GDEALRKLIA PMVSGIFAGN PETMSLRSCF   180
PRIAELEDEY GSLVRAMIRL AKKKKQEVAQ GKAVASAAGP GGVLTSFRDG IQALTDILAE   240
RLGPDTIVSG QEVLEVSRGG SLPWRVRTGS IDMDADLVIL ATPAYATASI IQGVDSDMAG   300
ILRQIPYATM TVVCFGYDRE RIAHDLNGFG YLIPKEEGMN TLGTLWDSSI FENRAPEGQV   360
LLRSMMGGAC FPEYVNLTDE EVTGRVKNDL ATIMGITAPP SFVRIFRHHQ AIPQYTVGHS   420
TRVAALEQRA ASLPGLFLTG NSYRGIGLND CVAAANRTAG EAIAQVTSR              469

SEQ ID NO: 305              moltype = AA  length = 436
FEATURE                     Location/Qualifiers
source                      1..436
                            mol_type = protein
                            organism = Aquifex sp.
SEQUENCE: 305
MDMREVVVIG AGISGLSTAY RLKKEGVDVV VYEKDDRIGG TIHTVKEKGY LFEVGAQTIL    60
ADQEVIDFLK EAGIEPVEAS PSSKYRYIYK KGRLIPLPMS PVEFLKTPLL SLKTKLKVLT   120
EIFKRGVDED ISIADFVREH FGEEFLNYVV APFISGVYAG DPEKLSLKHA TPKLYEAQKK   180
YGSLIKAFIK EKTAGPKGKL ISFGEGLGEL INALAQKLEV HTENVVLRMR KFEDFFRLDV   240
RGKKVETKSV VVASPAYTSS YLLKEVSFSA SEEFDKIDYP PVVVVNVGVE GKFPKVRLLS   300
SESGKKRILG AMFMSKLFPG RAPQGKELLT VFLGGATDRE VIELSEEEIE NIVERELKEI   360
LQIDCIDFMH VQKWKRAIPQ YTLGYDRFLN LAQEMEKDYP GLFLTGNWLY GVSTADCIRA   420
SKKVAQKVLS FLRPQA                                                  436

SEQ ID NO: 306              moltype = AA  length = 470
FEATURE                     Location/Qualifiers
source                      1..470
                            mol_type = protein
                            organism = Pelobacter sp.
SEQUENCE: 306
MNISVVGAGI SGLATAFAIQ QQARRLGLEW TLDIFEKEDC SGGKIRSEKV DGYLCEWGPN    60
GFLDSKPMTL DLCREAGLAE QLLRSNDAAR KRFIFSGGRL QRVPESAADF FRSSLVSWPG   120
KLRLAAELLV PRRKDLTDET LADFVRRRLG REALDQMVGP MAAGIFAGDP ETMSLRSCFP   180
RIHELEQQYG GLIRALLLLA RKKRAERRAG KAVAGAAGPG GILTSFGGGI QELTDGLSRL   240
LAPNLHLGDA VAAITPLKEG FSLRTHKGRV HETDIVVAAV PAMALATQVE GFSAPMAAQL   300
RQIPYAPLQI ACFGYRREAL PLSLDGFGYL AARRSGMHSL GTLWSSSIFP GRAPAGYVLL   360
RTMFGGATRP DAAQLSADEV QQRVEEDLSR SMGIKQAPDF VRIIRHTAAI PQYVSGHGAR   420
LKVLEDKAAA YPGLFLVGNA FYGVGLNDCV AAADRVASRV LTLMQQRQQA              470
```

```
SEQ ID NO: 307          moltype = AA  length = 469
FEATURE                 Location/Qualifiers
source                  1..469
                        mol_type = protein
                        organism = Geobacter sp.
SEQUENCE: 307
MKKVIVVGGG ISGLATAFEL RNKGAEAGIE LDVTLLEKEE RVGGKIWSIK EEGYLCEWGP    60
NGFLDSKPQT LDLCRDLGAS ERLLRSNDNA RKRFIYTGGV LNRLPENGPT FLKSSLISWP   120
GKLRLAMEPF ISKRTDGTDE TLASFGRRRL GEEALQKLIS PMVSGIFAGD PETMSLRSCF   180
PRIAELEDEY GSLIKAMIKL AKKKKQEAAQ GKAVSSAAGP GGVLTSFRWG IQELTDILAE   240
QLGSATVVTG QPVTGLTRGS SVPWRLKTPT VDIDADVVIL ASPAHATAGI VSGVDAAMAQ   300
VLGEIPYASM TVVCFGFERE RIAYDLNGFG YLIPKDEGMN TLGTLWDSSI FENRAPEGKV   360
LLRSMLGGAC FPEYVKLSDA EVMQRVKADL KATMGITADP SFIRIFRHPQ AIPQYTVGHG   420
KRLAALQERS SALPGLFLTG NSYRGIGLND CATAANRTTD EVVAYLKGR              469

SEQ ID NO: 308          moltype = AA  length = 435
FEATURE                 Location/Qualifiers
source                  1..435
                        mol_type = protein
                        organism = Cytophaga sp.
SEQUENCE: 308
MIAIIGAGIS GLTLAYQLQQ AGKPYILFES NSRPGGYINS QRFGKYLLEV GPNSILVDKK    60
LEEFIHELNL DKLFEPAAII NKNRFIYKDA NIQQVPSGPL SFLTGRFFSA KTKYAIFKEL   120
FNKSISKENE TVYDFFARRF SAPFTQYTID PFATGVYAGD IKQLLIEETF PQLVELEKQY   180
GSIIKGIFKK GFGEKRKTGT FVHGLQTLTD TLAAQLHSLQ LNTRVLNLRK QMDKIVLTTD   240
TKHGIEELTF DKVVVCGTTF QAATLIKDSY PDLSAILSQV QYASMKAVFA AFKRTDVTHP   300
MNGFGCLYPS AEQSFLAGTI WNSSIFNDRC PADEVLTTSF IGGMHHPEYT ALSESELEQR   360
AIQQLSKDLG ITGKPTFTHV AGWNKAIPQY DIYLKKARLA SKLLSDDHIY FRSNWTNGIS   420
LGNCIQSARD LALIL                                                    435

SEQ ID NO: 309          moltype = AA  length = 471
FEATURE                 Location/Qualifiers
source                  1..471
                        mol_type = protein
                        organism = Geobacter sp.
SEQUENCE: 309
MKKAIIVGGG ITGLATAWLL REKAKKAGME LEIALLEKEE RVGGKIRSIK ADGYLCEWGP    60
NGFLDNKPQT LDLCRDLQAD SQLLRSNDNA RKRFIYSEGF LHQLPENGPS FFKSKLISWP   120
GKLRLALEPT PFIAKAPDGV DETLAAFGRR RLGDEALRKL IAPMVSGIFA GDPETMSLQS   180
CFPRIAELER EYGGLVMAMV KLAKKKKQEL AEGKAVASAA GPGGILTSFR DGLQTLTEII   240
RGQLGCEVLS VGEEVVRIRK GSSVPYRVET TSRELDADVV VLATPAYATG QMLEGLDSAM   300
TGILGQIPYA TMSVVCLGYE QDKISHDLNG FGYLIPKGEG MNILGTLWDS SIFENRAPQG   360
RVLLRSMMGG ACFPEYIKLS DEEVQRRVCD NLKTIMGIAA PPDFVRIFRH EKAIPQYTVG   420
HGKRLQALLD AGRNHQGLLL TGNSYRGIGL NDCVAAAVRS SNEVMEHLQK R            471

SEQ ID NO: 310          moltype = AA  length = 465
FEATURE                 Location/Qualifiers
source                  1..465
                        mol_type = protein
                        organism = Porphyromonas sp.
SEQUENCE: 310
MDHLTVIIGA GLTGLTTAAF LRAAGRPVLV LERAAHIGGQ IRTYREDGFV FETGPNTGTI    60
SSPEVAELFE LLGLEPEIAT PAASNRLIWK GNKLYPLPRN IAEAVATPLF SLWDKWRILG   120
EPFRRRGGQP NETVGALARR RLGKSFVDYA VDPFLGGIYA GDPDQLVTRF ALPKLYDLEQ   180
RYGSFVLGAV RKARQPQSER DRKASRKVFS VQGGLGLLVE ALADYIGREH ILTETQIRYI   240
NHPGAHTFGL TYTDASEEEH TIPCRHLVST VAAHHIPTLF DHFPADESAV FEQLYYAPMI   300
EVAVGFRRNV ATHLPAFGCL IPSRENRRIL GILFPSDCFR GRAPEGGALY SIFMGGVRNA   360
SLIDLSDEEI STIAMEELRD MLRIPHTCKP DLLHISRHRH AIPQYYADTE LRQDIIRRME   420
MRWPGLHLGG NMHGGIGMAH RISQGVEMAR SIIEETAIAE RSARG                   465

SEQ ID NO: 311          moltype = AA  length = 464
FEATURE                 Location/Qualifiers
source                  1..464
                        mol_type = protein
                        organism = Corallococcus sp.
SEQUENCE: 311
MTVAVIGGGI TGLALAYQLR ARGTDAVVLE STSRVGGNVQ THARGGYLLE AGPNSFLDRE    60
PTTRELADAL GVSSRIRPAD VAAKNRYVFT RGALRALPTS PPAFLKSDIL PLASRLRVVG   120
ELFSGRNPTG ADESLAQLGR RHLGREATAV LLDDAMQTGTY AGDPEQLSAE ATFPQLVKFE   180
REHRSLILGA IRAQRAARQA KGAVETGPRL TGQMSTFDGG LGVLVDALAK ALGDSVRTDA   240
KVEGLERAAD GWTVRYQQRG QPAELSASHV VLAVPAHVAA SLVRPLDAEL AQKADAIPYA   300
PIAVVHLGFA PGTVPKPDGF GFLVPAVEGT AMLGTIHVST TFPFRVEGGR VLLTCLMGGA   360
RRPEVVSRDE DALVALAREE LKAMAGLTAT PELTAVFRWP RGIPQYTVGH LERLAAMEER   420
LKRWPGLHLA GNAYRGVGVN DCLKEAARLA EALGGPAAGA TRSA                    464

SEQ ID NO: 312          moltype = AA  length = 454
FEATURE                 Location/Qualifiers
source                  1..454
                        mol_type = protein
```

```
                        organism = Calditerrivibrio sp.
SEQUENCE: 312
MRVAIIGGGI SGISTAFLLE NLKNELNLDM EITIIEKRLR WGGSIETSRE DGFIVEAGPN    60
GFLDSKPHTL ELLSMAGLSN NLVKSNDLAR KRYIMRNGIL HRLPENPPMF FKTKLLSFSA   120
KMRILSEYFI QKSVLEDESV ADFARRRLGK EALEYLISPM VSGIFAGDPE KMSLRSCFPV   180
IRDLEINYGG LFKGMIKKKG KKSGPSGPGG ILTSYKNGLD NMITDLLEST SITKMLNTEV   240
FSIDKKINRY ILNTNKGIME FDKIFINAPA YAVSQMLSVL DKDLSRDLNN ITYPPVFVAG   300
FIFKPEDLED PLDGFGYLIP HSENKRILGA LFDSSIFPDR TRDGYKIVRT IMGGDKNRWI   360
IEKSDDELIR MAFDDIKETL KIKREPYKIK YFRWEKAIPQ YYIGHHKIVE KVEEFYKKFD   420
DIFIGGNILY GVGINDCTRT SFMNVDRFKN LLNK                               454

SEQ ID NO: 313          moltype = AA  length = 465
FEATURE                 Location/Qualifiers
source                  1..465
                        mol_type = protein
                        organism = Porphyromonas sp.
SEQUENCE: 313
MDHLTVIIGA GLTGLTTAAF LRAAGRPVLV LERAAHIGGQ IRTYREDGFV FETGPNTGTI    60
SSPEVAELFE LLGLEPEIAT PAASNRLIWK GNKLYPLPRN IAEAVGTPLF SLWDKWRILG   120
EPFRRRGGQP NETVGALARR RLGKSFVDYA VDPFLGGIYA GDPDQLVTRF ALPKLYDLEQ   180
RYGSFVLGAV RKARQPQSER DRKASRKVFS VQGGLGLLVE ALADYIGREH ILTETQIRYI   240
NHPGAHTFGL TYTDASEEEH TIPCRHLVST VAAHHIPTLF DHFPADESAV FEQLYYAPMI   300
EVAVGFRRNV ATHLPAFGCL IPSRENRRIL GILFPSDCFR GRAPEGGALY SIFMGGVRNA   360
SLIDLSDEEI STIAMEELRD MLHIPHTCKP DLLHISRHRH AIPQYYADTE LRQDIIRRME   420
MRWPGLHLGG NMHGGIGMAH RISQGVEMAR SIIEETAIAE RSARG                   465

SEQ ID NO: 314          moltype = AA  length = 454
FEATURE                 Location/Qualifiers
source                  1..454
                        mol_type = protein
                        organism = Stigmatella sp.
SEQUENCE: 314
MAVIAVVGGG ITGLALAHRL RSRGKDAVVL EAGAHLGGVI QTRQRDGFST ETGPNSFLDR    60
EPATRELAAS LGIEERIRMA DPSAKSRSLY TRGQLRPVPA SPPAFLKSDL LPLGTRLRVL   120
AELFTGRAPP GQDESLGDFG RRHVGARATS VLLDAMQTGT YAGDVEALSA EAAFPTLKQL   180
EREHRSLLLG AVRTQGRQRA PAPAGTKLKG AMCTFEGGLG TLVEALARAL GPAARTGAAV   240
EGLARSQNGW RLSVRERGQQ AELEASQVVL TSPAHVSAEL LAPLDPSLAG HLKGIPYAPI   300
AVVHLGFAPG KTPPPDGFGF LVPGQEQRQL LGVIHVSTVF PFRAEGGRVL YTCLMGGARR   360
PDLVGLNEEA LAALAQQELR EMAGVTASPD FTEAVRWPRG IPQYTVGHLE RLSAIDSALA   420
RLPGLHLAGN AYKGVGLNDC IRNAAALAET LASR                               454

SEQ ID NO: 315          moltype = AA  length = 465
FEATURE                 Location/Qualifiers
source                  1..465
                        mol_type = protein
                        organism = Porphyromonas sp.
SEQUENCE: 315
MDHLTVIIGA GLTGLTTAAF LRAAGRPVLV LERAAHIGGQ IRTYRENGFV FETGPNTGTI    60
SSPEVAELFE LLGLEPEIAT PAASNRLIWK GNKLYPLPRN IAEAVATPLF SLWDKWRILG   120
EPFRRRGGQP NETVGALARR RLGKSFVDYA VDPFLGGIYA GDADQLVTRF ALPKLYDLEQ   180
RYGSFVLGAV RKARQPQNER DRKASRKVFS VQGGLGLLVE ALADYIGREH ILTETQIRYI   240
NHPGAHTFGL TYTDASEEEH TIPCRHLVST VAAHHIPTLF DRFPADESAV FEQLYYAPMI   300
EVAVGFRRNV ATHLPAFGCL IPSRENRRIL GILFPSDCFR GRAPEGGALY SIFMGGVRNA   360
SLIDLSDEEI STIAMEELRD MLHIPHTCKP DLLHISRHRH AIPQYYADTE LRQDIIRRME   420
MRWPGLHLGG NMHGGIGMAH RISQGVEMAR SIIEETAIAE RSARG                   465

SEQ ID NO: 316          moltype = AA  length = 462
FEATURE                 Location/Qualifiers
source                  1..462
                        mol_type = protein
                        organism = Leptospirillum sp.
SEQUENCE: 316
MSTVFRCDVL IVGGGISGLA AAMVLHQAGK NILLVESRGY LGGAIRSVED SGYLLEMGPN    60
SMMLGPEDPI NVWLDKLGLS EKLLKASPEA QNRYVWCQGK LIPVPLSPSS FLTTPLFSLS   120
EKMRVAKEFF ISPGSGLPEG SDETVGHFVR RRLGNEFLEK LIDPFVKGVY ASHPDLLSLN   180
SAFPLLARLE QESGGLIRGA IRLSREKKRK KANLTGPPGG LYSFSGGLGE MVRAFSGYLK   240
DESLIHGELI HWNRLPSGEF QCVLLQDEER VEVISQKMIL ATSPADAGRI LEKNQPEIAS   300
VLSSIPMAPI AIAYIGVDRK ALPGYLPGFG VLFPTSEKRK ILGIIQNSDL FPNRSPDGKV   360
LLTIFAGGML SPKIAMSFDE DFEQIVLGEL KTVFGLDSRP EFFRIQRWAE GISQYSPGHA   420
SRIQRIRDLT PEGMILTGNY LGGISVLKTF TNGLEAGKAF LS                      462

SEQ ID NO: 317          moltype = AA  length = 454
FEATURE                 Location/Qualifiers
source                  1..454
                        mol_type = protein
                        organism = Spirosoma sp.
SEQUENCE: 317
MTIGIIGAGI SGLTLAYELQ RRGIAYHLWE AAGQAGGYIR SQRDWPDGPS GRNYLRELGP    60
NSLLGDAELL NWLDELGLTP ELTSFQPVSK ARFIFRDGKY RQLPSGPPSL LFGNFFSWKT   120
```

```
KLAILRERNN KTVSPPGETL GQFFRRRFSS EIVDYALGPF VAGIYAGDPE QLLVSETFPS   180
LLQYEKEYGS VLRGLIKSQS AGGSAIGRRQ SFSFREGMQM LPNALAAKLT NLSLNEAVSS   240
ISPTPNGWEV ETNTGTTTVD KLVLAVGTDA AARLVDQRYP DLARTLQAIT YPPMTAVHSA   300
YKRADVRHPL NGFGGLNPAV EGRFAAGHIW SSSIFTGRCP DDEVLFTTFV GGQTGAHNTR   360
HPDSVLAHNV HKELVDGFGI TAATPVYQSV FRWERAIPQY DATLASAKES VKAMEADQLF   420
VCANWYGGVS LSDCIGKSRK LADQLAVKPF IKNF                              454

SEQ ID NO: 318          moltype = AA  length = 495
FEATURE                 Location/Qualifiers
source                  1..495
                        mol_type = protein
                        note = Candidatus prokaryotic phyla
                        organism = unidentified
SEQUENCE: 318
MATEQHSGSR RIVVVGSGIA GLAAAYRLQE RCEQDGPPCE VRVLEAAARP GGAISTTHRD    60
GFVLESGPDT IFTDKPWGLD LIRRLGLSEQ VIGTNEAHRR TFVVRDGALH PLPEGFALMG   120
PTKPWPFLQS GLLSWRGKAR AALDLVLPRG GPSDDESLAS FVRRRFGQEF LDRLAQPMIG   180
GIYGADPERL SLRATFPQFL QMEATHRSVI LGLRRMRPAG RGVGHTSSGP RYGLFVTLDH   240
GLQALVDAMV KRLPAGTLRL RAPVDRIAHT EQGWTVRLGD GASLQADGLI LAVPAFEIAR   300
LTHDLDQDLA RQLEAMPYAS SVTINLAYRR EAIHHPLDGF GFVVPACEGR TIIACSFSSV   360
KFAHRAPAGH VLLRAFAGGA LQPEPFTWDD ETLLSAVRRD LEELLAIHAP PLWSQLVRHP   420
RVMPQYQVGH LGRLAALEET LRRWPTLKLT GNAYRGVGVP DVVHSGETAA DSLLAELAPS   480
PTEPTPACTE GDSRL                                                   495

SEQ ID NO: 319          moltype = AA  length = 469
FEATURE                 Location/Qualifiers
source                  1..469
                        mol_type = protein
                        organism = Pelobacter sp.
SEQUENCE: 319
MKRAIIVGGG ISGLATAWLL REKALACGIQ LELVLLEKDQ RPGGKIRSIH EGGYVCEWGP    60
NGFLDSKPQT LELCDAVGVS SDLLRSNDNA RKRFIYSDGE LHRLPEGGGT FLKSRLISWP   120
GKLRLALEPT PFIARTPAGV DESLADFARR RLGGEALDKL ISPMVSGIFA GDPETMSLVS   180
CFPRIAQLER EYGGLIRAMV RLARQKKRER AAGKAVSSAA PGGVLTSFR PGIQYLTDSL    240
AASLGGIVMA DREVSWVRRG KSAAWRVGCR DGGEYDADLV IVASPAHAAS AILHDCDAGI   300
ASILESIPYA SMTVVCLGYE RELVSHPLDG FGYLIPKKEG RSILGTLWDS SMFENRAPTG   360
KVLLRSMVGG ACFPDYVHMG DDELLGRVRG DMKDVMGIVA EPSFIRIFRH PQAIPQYTVG   420
HGERLKHLEE RLACHPGLIL TGNSYRGIGL NDCVAAAQRA SDQALELLR              469

SEQ ID NO: 320          moltype = AA  length = 436
FEATURE                 Location/Qualifiers
source                  1..436
                        mol_type = protein
                        organism = Aquifex sp.
SEQUENCE: 320
MDMREVVVIG AGISGLSTAY RLKKEGVDVV VYEKDDRIGG TIHTVKEKGY LFEVGAQTIL    60
ADQEVIDFLK EAGIEPVEAS PSSKYRYIYK KGRLIPLPMS PVEFLKTPLL SLKTKLKVLT   120
EIFKRGVDED ISIADFVREH FGEEFLNYVV APFISGVYAG DPEKLSLKHA TPKLYEAQKK   180
YGSLIKAFIK EKTAGPKGKL ISFGEGLGEL INALAQKLEV HTENVVLRMR KFEDFFRLDV   240
RGKKVETKSV VVASPAYTSS YLLKEVSFSA SEEFDKIDYP PVVVVNVGVE GKFPKVRLLS   300
SESGKKRILG AMFMSKLFPG RAPQGKELLT VFLGGATDRE VIELSEEEIE NIVERELKEI   360
LQIDCIDFMH VQKWKRAIPQ YTLGYDRFLN LAQEMEKDYP GLFLTGNWLY GVSTADCIRA   420
SKKVAQKVLS FLRPQA                                                  436

SEQ ID NO: 321          moltype = AA  length = 495
FEATURE                 Location/Qualifiers
source                  1..495
                        mol_type = protein
                        organism = Candidatus sp.
SEQUENCE: 321
MATEQHSGSR RIVVVGSGIA GLAAAYRLQE RCEQDGPPCE VRVLEAAARP GGAISTTHRD    60
GFVLESGPDT IFTDKPWGLD LIRRLGLSEQ VIGTNEAHRR TFVVRDGALH PLPEGFALMG   120
PTKPWPFLQS GLLSWRGKAR AALDLVLPRG GPSDDESLAS FVRRRFGQEF LDRLAQPMIG   180
GIYGADPERL SLRATFPQFL QMEATHRSVI LGLRRMRPAG RGVGHTSSGP RYGLFVTLDH   240
GLQALVDAMV KRLPAGTLRL RAPVDRIAHT EQGWTVRLGD GASLQADGLI LAVPAFEIAR   300
LTHDLDQDLA RQLEAMPYAS SVTINLAYRR EAIHHPLDGF GFVVPACEGR TIIACSFSSV   360
KFAHRAPAGH VLLRAFAGGA LQPEPFTWDD ETLLSAVRRD LEELLAIHAP PLWSQLVRHP   420
RVMPQYQVGH LGRLAALEET LRRWPTLKLT GNAYRGVGVP DVVHSGETAA DSLLAELAPS   480
PTEPTPACTE GDSRL                                                   495

SEQ ID NO: 322          moltype = AA  length = 457
FEATURE                 Location/Qualifiers
REGION                  1..457
                        note = Unknown
source                  1..457
                        mol_type = protein
                        organism = unidentified
SEQUENCE: 322
MGVEVAIIGA GISGLSVAFF LKRAGAGVLV LEAEEDVGGT MRSRRFKGYL IELGPNSALE    60
```

```
TTPLFQELIA  AAGLAGERVY  ASEAARNRYI  VRGGELHPLP  LTPLAFLRSR  LWSWKGKLRV   120
LAEPFHGRAD  REESVADFAR  RRVGQEFLDY  AVNPFVAGIY  AGDPERLSVR  FAFPRLYALE   180
AQYGGLFLGM  LRGARERRRR  GEAPKIAARL  FSFREGMGAL  PRALAAALGN  TVWCATRALC   240
VERAGAAFEI  AFERDGRRDT  LRAERVVLAT  PAYAAASLLK  RLAPEAARAL  DRIVYPPVSA   300
VILGYPETAI  GRPLDGFGPL  VPEKEQRRIL  GTIWNSTIFP  ARAPQGFVTL  TTFVGGMRQP   360
ELARRPNEEL  IALVAEELTD  LLRLRGEPEF  AYVSRWERAI  PQYELGYGEI  LDALDRAERE   420
HVGLYFCANY  RGGIAVGDCV  MSAHATAERI  LRDRARS                              457

SEQ ID NO: 323         moltype = AA  length = 462
FEATURE                Location/Qualifiers
REGION                 1..462
                       note = Unknown
source                 1..462
                       mol_type = protein
                       organism = unidentified
SEQUENCE: 323
MAGFDCDTLV  VGGGVSGLAA  ALTLKNRGVD  VRLLESRGYL  GGAIRTVRED  GYLLEFGPNS    60
LMVRPEDAID  TVLGDPELRA  RIVPASGLSK  NRYVVKAGHL  YPVPLSPWAF  FRTPLLSWRG   120
RRDILSEWKV  PPRTGGPEET  LSHFVRRRLG  EEALDYFVDP  FVKGVYASHP  DLLSVEAAFP   180
LLVRLEREHG  GLLRGALKTF  LKRRKRPSGS  SPRGIFSFAG  GMTDLVEAMG  KRLGEDVGTN   240
VDVIKYTRLE  EGFRVALMYD  ETEYYMTSRR  LILATSAPQA  AELLEGDPDG  PSSELKSIPY   300
APVTIAYAGF  LREQVTHPLD  GFGLLCPTVE  NRKVLGVIFS  SSLFPGRAPE  GKVLLTVFVG   360
GMTGQKLAQA  FDEDLERIVL  KELTELLGVK  GAPSFFRIHR  WEKAIPQLIL  GHGETVRTIR   420
KKLPSGLRLA  GNYLDGISIA  RAFASGVRAA  EELLSEDGGT  PG                      462

SEQ ID NO: 324         moltype = AA  length = 467
FEATURE                Location/Qualifiers
REGION                 1..467
                       note = Unknown
source                 1..467
                       mol_type = protein
                       organism = unidentified
SEQUENCE: 324
GCAAAYKLKL  HGLNVTVFEA  DERVGGKLRS  VSQDGLIWDE  GANTMTESEA  DVSSLIDDLG    60
LRDKQQFPIS  QHKRYIVRNG  KPVLIPSNPI  ALIRSSFLST  QSKVQILLEP  FLWKKTKSSD   120
EPESVGGFFQ  RHFGKEVVEY  LIDPVVAGTS  GGDPESLSMR  HAFPELWDLE  RRFGSIISGA   180
FQSMVSSRGG  KRKPSGNSKR  RRGSFSFFGG  MQTLTDALSK  EIGPHEINLQ  SKVLEMSYSC   240
DDNAVGNWSI  YCAPDQNKQF  QQSFDAVIMT  APLNNLKEMK  ITKTGSPFLL  NFIPEVSYLP   300
ISVIISTFKK  ENVKQPLEGF  GVLVPAKEQE  NGLRTLGTLF  SSMMFPDRAS  EDVYLYTTFV   360
GGSRNKELAK  ASRDELKQIV  TSDLRQLLGT  EGEPKFLTHY  YWSKAFPLYG  RDYGSVIEAI   420
EKMEKELPGY  FYAGNHKGGL  SVGKAISSGC  KAAESVIAYL  DSYSNQK                  467

SEQ ID NO: 325         moltype = AA  length = 535
FEATURE                Location/Qualifiers
source                 1..535
                       mol_type = protein
                       organism = Amaranthus sp.
SEQUENCE: 325
MVIQSITHLS  PKLALPSPLS  VSTKNYPVAV  MGNISEREEP  TSAKRVAVVG  AGVSGLAAAY    60
KLKSHGLNVT  LFEADSRAGG  KLKTVKKDGF  IWDEGANTMT  ESEAEVSSLI  DDLGREKQQ    120
LPISQNKRYI  ARDGLPVLLP  SNPAALLSSN  ILSAKSKLQI  MLEPFLWRKR  NATELSDEHV   180
QESVGEFFER  HFGKEFVDYV  IDPFVAGTCG  GDPQSLSVHH  TFPDVWNVEK  RFGSVFAGLI   240
QSTLLSKKEK  GGGENASIKK  PRVRGSFSPH  GGMQTLVDTM  CKQIGEDELK  LQCEVLSLSY   300
NQKGIPSLGN  WSVSSMSNNT  SEDQSYDAVV  VTAPIRNVKE  MKIMKFGNPF  SLDFIPEVTY   360
VPLSVMITAF  KKDKVKRPLE  GFGVLIPSKE  QHNGLKTLVF  LFSSMMFPDR  APSDMCLFTT   420
FVGGSRNRKL  AKASTDELKQ  IVSSDLQQLL  GTEDEPSFVN  HLFWSNAFPL  YGHNYDSVLR   480
AIDKMEKDLP  GFFYAGNHKG  GLSVGKAMAS  GCKAAELVIS  YLDSHLYVKM  NEKTA        535

SEQ ID NO: 326         moltype = AA  length = 493
FEATURE                Location/Qualifiers
source                 1..493
                       mol_type = protein
                       organism = Silene sp.
SEQUENCE: 326
TSDPDKLQSS  AKRVAVIGAG  VSGLAAAYKL  KSNGLNVTLI  EADERAGGKI  RSAAKNGYIW    60
DEGANTMTES  ESEVTSLLDD  LGIRDKQQLP  LSQNKRYVVR  DGLPVLLPSG  PISIFTSNFL   120
SPKSKLRLLC  EPFSWRRRDN  AKVSDEQADE  SVSDFFGRHF  GEEFVDYLID  PFVGGTSAAD   180
PKTISMRHSF  PELWDIEDRF  GSIIAGAIQS  RLTPKPGEQK  KPVKKTRVRG  SFSFKGGMQT   240
LVDTICERFS  EDELKLKCKV  LSLSYSHEGH  SNNWSLSCLS  NKSIEDRPYD  AVVVTAPLTN   300
VKDMKILNGG  SPFSLDFVPE  VDYLPVSIIV  TAFKKANVER  PLEGFGVLIP  SKEQEKGLKT   360
LGTLFSSMMF  PDRSPADQYL  YTTFVGGSRN  RELARATTDE  LKQVVLSDLQ  QLLGVKGDPS   420
FINHVYWSKA  FPRYGQNYES  VKMAIAKMEN  DLPGFFYAGN  HKDGLSVGKA  LASGYKAADL   480
VMSYLNSYSN  TNQ                                                          493

SEQ ID NO: 327         moltype = AA  length = 493
FEATURE                Location/Qualifiers
source                 1..493
                       mol_type = protein
                       organism = Silene sp.
```

```
SEQUENCE: 327
TSDPDKLQSS AKRVAVIGAG VSGLAAAYKL KSNGLNVTLI EADERAGGKI RSAAKNGYIW      60
DEGANTMTES ESEVTSLLDD LGIRDKQQLP LSQNKRYVVR DGLPVLLPSG PISIFTSNFL     120
SAKSKLRLLC EPFSWRRRDN AKVSDEQADE SVSDFFGRHF GEEFVDYLID PFVGGTSAAD    180
PKTISMRHSF PELWDIEDRF GSIIAGAIQS RLTPKPGEQK KPVKKTRVCG SFSFKGGMQT    240
LVDTICERFS EDELKLKCKV LSLSYSHEGH SNNWSLSCLS NKSIEDRPYD AVVVTAPLTN    300
VKDMKILNGG SPFSLDFVPE VDYLPVSIIV TAFKKANVER PLEGFGVLIP SKEQEKGLKT    360
LGTLFSSMMF PDRSPADQYL YTTFIGGSRN RELARATTDE LKQVVLSDLQ QLLGVKGDPS    420
FINHVYWSKA PPRYGQNYES VKMAIAKMEN DLPGFFYAGN HKDGLSVGKA LASGYKAADL    480
VMSYLNSYSN TNQ                                                     493

SEQ ID NO: 328          moltype = AA  length = 501
FEATURE                 Location/Qualifiers
source                  1..501
                        mol_type = protein
                        organism = Solanum sp.
SEQUENCE: 328
MAPSAGEDKQ KRVAVIGAGV SGLAAAYKLK VHGLNVTVFE AEGRAGGKLR SLSQDGLIWD     60
EGANTMTESE GDVTFLLDSL GLREKQQFPL SQNKRYIARN GTPTLIPSNP FDLFKSNFLS    120
TGSKLQMLFE PLLWKNKKLT KVSDKHESVS GFFQRHFGKE VVDYLIDPFV AGTCGGDPDS    180
LSMHLSFPDL WNLEKRFGSV IVGAIQSKLS PIKEKKQGPP RTSINKKRQR GSFSFLGGMQ    240
TLTDAICKNL KEDELRLNSR VLELSCSCSG DSAIDSWSIF SASPHKRQAE EESFDAVIMT    300
APLCDVKSMK IAKRGNPFLL NFIPEVDYVP LSVVITTFKK ESVKHPLEGF GVLVPSQEQK    360
HGLKTLGTLF SSMMFPDRAP NNVYLYTTFV GGSRNRELAK ASRTELKEIV TSDLKQLLGA    420
EGEPTYVNHL CWSKAFPLYG HNYDSVLDAI DKMEKSLPGL FYAGNHKGGL SVGKALSSGC    480
NAADLVISYL EAVSADTKNH S                                             501

SEQ ID NO: 329          moltype = AA  length = 463
FEATURE                 Location/Qualifiers
REGION                  1..463
                        note = Unknown
source                  1..463
                        mol_type = protein
                        organism = unidentified
SEQUENCE: 329
MATEDVETLV IGGGIAGLAC ASHLKLAGRT VRLVERNDYL GGVIRTLSDS GYRIETGPNS     60
LLVRTEEPLL KYLSRPEIAA RIQLAGRMGK KRFILKDGHP VALPMSLSEG IFTQILSLPA    120
KVRLLKEPFI PPAGGVDGVD PEKETVADFV RRRLGNEFLE SLIDPFVKGV YASDPHLLSM    180
ADTFPRLVQM EKSYGSLIKG GLALARQKKA PAPAFAREIL SFSEGMGTLP ESLANILDDD    240
AGTNAEVIGC APSESGFRTA LLFEEETYYI RSKHLVLALP AAQTAELIEP MAPGIPSLLG    300
QIPYAPIAVV YLGYPRDRIS HPLDGFGLLV PSRERRKILG ALFSSSLFPG RSPDGHVLLT    360
VFVGGMTQPK LAQAFDEDLL PMVTKEIGSM LGVLGAPSYV RIQRWAGAIP QSVPGHGERI    420
RSIESALPSG LHLAGSYLSG VSVSQTFSSG IRAAEKILAQ SPG                     463

SEQ ID NO: 330          moltype = AA  length = 544
FEATURE                 Location/Qualifiers
source                  1..544
                        mol_type = protein
                        organism = Zea sp.
SEQUENCE: 330
MLALTASASS ASSHPYRHAS AHTRRPRLRA VLAMAGSDDP RAAPARSVAV VGAGVSGLAA     60
AYRLRQSGVN VTVFEAADRA GGKIRTNSEG GFVWDEGANT MTEGEWEASR LIDDLGLQDK    120
QQYPNSQHKR YIVKDGAPAL IPSDPISLMK SSVLSTKSKI ALFFEPFLYK KANTRNSGKV    180
SEEHLSESVG SFCERHFGRE VVDYFVDPFV AGTSAGDPES LSIRHAFPAL WNLERKYGSV    240
IVGAILSKLA AKGDPVKTRH DSSGKRRNRR VSFSFHGGMQ SLINALHNEV GDDNVKLGTE    300
VLSLACTFDG VPALGRWSIS VDSKDSGDKD LASNQTFDAV IMTAPLSNVR RMKFTKGGAP    360
VVLDFLPKMD YLPLSLMVTA FKKDDVKKPL EGFGVLIPYK EQQKHGLKTL GTLFSSMMFP    420
DRAPDDQYLY TTFVGGSHNR DLAGAPTSIL KQLVTSDLKK LLGVEGQPTF VKHVYWGNAF    480
PLYGHDYSSV LEAIEKMEKN LPGFFYAGNN KDGLAVGSVI ASGSKAADLA ISYLESHTKH    540
NNSH                                                               544

SEQ ID NO: 331          moltype = AA  length = 507
FEATURE                 Location/Qualifiers
source                  1..507
                        mol_type = protein
                        organism = Oryza sp.
SEQUENCE: 331
MAASDDPRGG RSVAVVGAGV SGLAAAYRLR KRGVQVTVFE AADRAGGKIR TNSEGGFIWD     60
EGANTMTESE LEASRLIDDL GLQGKQQYPN SQHKRYIVKD GAPTLIPSDP IALMKSTVLS    120
TKSKLKLFLE PFLYEKSSRR TSGKVSDEHL SESVASFFER HFGKEVVDYL IDPFVAGTSG    180
GDPESLSIRH AFPALWNLEN KYGSVIAGAI LSKLSTKGDS VKTGGASPGK GRNKRVSFSF    240
HGGMQSLIDA LHNEVGDGNV KLGTEVLSLA CCCDGVSSSG GWSISVDSKD AKGKDLRKNQ    300
SFDAVIMTAP LSNVQRMKFT KGGVPFVLDF LPKVDYLPLS LMVTAFKKED VKKPLEGFGV    360
LIPYKEQQKH GLKTLGTLFS SMMFPDRAPN DQYLYTSFIG GSHNRDLAGA PTAVLKQLVT    420
SDLRKLLGVE GQPTFVKHVH WRNAFPLYGQ NYDLVLEAIA KMENNLPGFF YAGNNKDGLA    480
VGNVIASGSK AADLVISYLE SCTDQDN                                       507

SEQ ID NO: 332          moltype = AA  length = 542
FEATURE                 Location/Qualifiers
```

```
source                          1..542
                                mol_type = protein
                                organism = Setaria sp.
SEQUENCE: 332
MLSSSTTTAS PASSHPYRPA YPRASLRPVL AMAGSDDPRA APARSVAVIG AGVSGLAAAY    60
RLRKSGVNVT VFEAADRAGG KIRTNSEAGF LWDEGANTMT EGELEVSRLI DDLGLQDRQQ   120
YPNSQHKRYI VKDGAPALIP ADPISLMKSS VLSTKSKLAL FLEPFLYKKS NTRNSGKVSD   180
EHLSESVGSF FERHFGREVV DYLIDPFVAG TSAGDPESLS IRHAFPALWN LERKYHSIIV   240
GAILSKLTAK GDPVKTGSDL SGKRRNRRAS FSFHGGMQSL INALHNEVGD DNVKLGTEVL   300
SLACTFDGLP STGGWSISVD SKDAGSKDLA KNQTFDAVIM TAPLSNVQRM KFRKGGAPFV   360
LDFLPKVNYL PLSLMVTAFK KEDVKKPLEG FGVLIPYKEQ QKHGLKTLGT LFSSMMFPDR   420
APDDQYLYTT FVGGSHNRDL AGAPTSILKQ LVTSDLKKLL GVEGQPTFVK HIYWRNAFPL   480
YGRDYGSVLD AIEKMEKNLP GFFYAGNNKD GLAVGNVIAS GSKAAELAIS YLESQTKHNN   540
SH                                                                 542

SEQ ID NO: 333                  moltype = AA   length = 507
FEATURE                         Location/Qualifiers
source                          1..507
                                mol_type = protein
                                organism = Brachypodium sp.
SEQUENCE: 333
MAASDDPRAA PARSVAVVGA GVSGLVAAHR LRKSGVRVTV FEADDRAGGK IRTNSDSGFL    60
WDEGANTMTE SALEASRLID DLGLQDKQQY PNSQHKRYTV KDGAPTLIPS DPIALMKSTV   120
LSTKSKFKLF LEPFLYEKSH TRNSQKVSDN HLSESVGSFF ERHFGKEVVD YLIDPFVAGT   180
SAGDPESLSI RHAFPGLWDL EKKYGSIIVG AILSKLTAKG DSTKKADTSS GKGRNKQASF   240
SPHGGMQTLV EGLHKDVGDG NVKLGTQVLS LACSCDRLSA SDGWSISVNS KDASSKLAAK   300
NQLFDAVIMT APLSNVQRMK FTKGGVPFVL DFLPKVDYLP LSLMVTAFRK EDVKRPLEGF   360
GVLIPYKEQQ KYGLKTLGTL FSSMMFPDRA PNDQHLFTTF VGGSHNRDLA AAPTAILKQL   420
VTSDLRKLLG VEGQPTFVKH VHWKNAFPLY GHDYDLALEA IGKMENELPG FFYAGNNKDG   480
LAVGNVIASG SKTADLVISY LESHQAR                                      507

SEQ ID NO: 334                  moltype = AA   length = 551
FEATURE                         Location/Qualifiers
source                          1..551
                                mol_type = protein
                                organism = Oryza sp.
SEQUENCE: 334
MLSPAATTTT TTSYCSYSSR AHAPTRSASA GAARFRPARA MATSDNDPRG AAPARSVAVV    60
GAGVSGLAAA YKLRKRGVQV TVFEAADRAG GKIRTNSESG FIWDEGANTM TESESEAGRL   120
IDDLDLQGKL QYPNSQHKRY IVKDGAPTLI PSDPIGLMKS TVLSTKSKLK LFLEPFLYEK   180
SSKRNSGKVS DEHLSESVAS FFERHFGKEV VDYLIDPFVA GTSGGDPESL SIRHAFPALW   240
NLENKYGSVI AGAILSKLST KGESVKTGGA TPGKGRNKRV SFSFHGGMQS LIDALHNEVG   300
DGNVKLGTEV LSLACSCDEI SSSGGWSIAV DSRDAKGKDL RKNQSFDAVI MTAPLSNVQR   360
MKFTKNGAPF VLDFLPKVDY LPLSLMVTAF KKEDVKRPLE GFGVLIPYKE QQKHGLKTLG   420
TLFSSMMFPN RAPNDQYLYT SFIGGSHNRD LAGASTAILK QLVTSDLRKL LGIEGQPTFV   480
KHVHWGNAFP LYGRNYDLVL EAIAKMEKNL PGFFYAGNNK DGLAVGNVIA SGSKAAELVL   540
SYLESHTDQD N                                                       551

SEQ ID NO: 335                  moltype = AA   length = 494
FEATURE                         Location/Qualifiers
source                          1..494
                                mol_type = protein
                                organism = Picris sp.
SEQUENCE: 335
MAEHIHTDQN DKRPLKSVAV VGAGISGLAA AYRLKSQGLA VTIFEADGTT GGKIKSFAQN    60
GLIWEKGANT MTETEPEVGK LIDDLGIRGK QQFPIMQSKR YIVRDGKPQL LPSNPVAFIG   120
SKTLSAQAKL NIFLEPILWK HKNSKEKTPN SPDIYQEESV GDFFRRHFGQ EVVDYIVDPF   180
VAGTAGADAE SLSIRHMFPE IWDLEERFGS IITGAIKSSW SRKKAQRDAK HVTHGQKRQR   240
GSFSFMGGLQ TLTNALSKKL GEEESLRMHCS VLSLSCNLQG NPPHNNWSVC YARNDASYKE   300
PLKEQSFDAV VMTVTYLPMS IIITTFKKQD VKHPLEGFGI LVPSKEEKNG FQTLGTLFSS   360
NMFPDRAPTD QYLFTTFIGG NRNRKLAKSQ LKDLQEVAVN DLNKILGVGS DPLSVKHIYW   420
NEAFPLYSLD YNSVVAAIDK LGKSLPGIYF AGNYRGGLSV GKALTSGFKA ADLAISDFNS   480
KGLCTMIGTD HEVK                                                    494

SEQ ID NO: 336                  moltype = AA   length = 506
FEATURE                         Location/Qualifiers
source                          1..506
                                mol_type = protein
                                organism = Oryza sp.
SEQUENCE: 336
MAASDDPRGG RSVAVVGAGV SGLAAAYRLR KRGVQVTVFE AADRAGGKIR TNSEGGFIWD    60
EGANTMTESE LEASRLIDDL GLQGKQQYPN SQHKRYIVKD GAPTLIPSDP IALMKSTVLS   120
TKSKLKLFLE PFLYEKSSRR TSGKVSDEHL SESVIFLCIC RDNQVVDYLI DPFVAGTSGG   180
DPESLSIRHA FPALWNLENK YGSVIAGAIL SKLSTKGDSV KTGGASPGKG RNKRVSFSFH   240
GGMQSLIDAL HNEVGDGNVK LGTEVLSLAC CCDGVSSSGG WSISVDSKDA KGKDLRKNQS   300
FDAVIMTAPL SNVQRMKFTK GGVPPVLDFL PKVDYLPLSL MVTAFKKEDV KKPLEGFGAL   360
IPYKEQQKHG LKTLGTLFSS MMFPDRAPND QYLTYSFIGG SHNRDLAGAP TAILKQLVTS   420
DLRKLLGVEG QPTFVKHVHW RNAFPLYGQN YDLVLEAIAK MENNLPGFFY AGNNKDGLAV   480
GNVIASGSKA ADLVISYLES CTDQDN                                       506
```

```
SEQ ID NO: 337          moltype = AA  length = 465
FEATURE                 Location/Qualifiers
REGION                  1..465
                        note = Unknown
source                  1..465
                        mol_type = protein
                        organism = unidentified
SEQUENCE: 337
MDHLTVIIGA GLTGLTTAAF LRAAGRPVLV LERAAHIGGQ IRTYREDGFV FETGPNTGTI   60
SSPEVAELFE LLGLEPEIAT PAASNRLIWK GNKLYPLPRN IAEAVGTPLF SLWDKWRILG  120
EPFRRRGGQP NETVGALARR RLGKSFVDYA VDPFLGGIYA GDPDQLVTRF ALPKLYDLEQ  180
RYGSFVLGAV RKARQPQSER DRKASRKVFS VQGGLGLLVE ALADYIGREH ILTETQIRYI  240
NHPGAHTFGL TYTDASEEEH TIPCRHLVST VAAHHIPTLF DRFPANESAV FEQLYYAPMI  300
EVAVGFRRNV ATHLPAFGCL IPSRENRRIL GILFPSDCFR GRAPEGGALY SIFMGGVRNA  360
SLIDLSDEEI STIAMEELRD MLHIPHTCKP DLLHISRHRH AIPQYYADTE LRQDIIRRME  420
MRWPGLHLGG NMHGGIGMAH RISQGVEMAR SIIEETAIAE RSARG                  465

SEQ ID NO: 338          moltype = AA  length = 505
FEATURE                 Location/Qualifiers
source                  1..505
                        mol_type = protein
                        organism = Oryza sp.
SEQUENCE: 338
MAASDDPRGG RSVAVVGAGV SGLAAAYRLR KRGVQVTVFE AADRAGGKIR TNSEGGFIWD   60
EGANTMTESE LEASRLIDDL GLQGKQQYPN SQHKRYIVKD GAPTLIPSDP IALMKSTVLS  120
TKSKLKLFLE PFLYEKSSRR TSGKVSDEHL SESMFSDQRE YICSVIFLCI CRDNQVVDYL  180
IDPFVAGTSG GDPESLSIRH AFPALWNLEN KYGSVIAGAI LSKLSTKGDS VKTGGASPGK  240
GRDKRVSFSF HGGMQSLIDA LHNEVGDGNV KLGTEVLSLA CCCDGVSSSG GWSISVDSKD  300
AKGKDLRKNQ SFDAVIMTAP LSNVQRMKFT KGGVPFVLDF LPKVDYLPLS LMVTAFKKED  360
VKKPLEGFGA LIPYKEQQKH GLKTLGTLFS SMMFPDRAPN DQYLYTSFIG GSHNRDLAGA  420
PTAILKQLVT SDLRKLLGVE GQPTFVKHVH WRNAFPLYGQ NYDLVLEAIA KMENNLPGFF  480
YAGKSMKAPL LYKRNLRYLK HIPVD                                       505

SEQ ID NO: 339          moltype = AA  length = 461
FEATURE                 Location/Qualifiers
source                  1..461
                        mol_type = protein
                        organism = Salinibacter sp.
SEQUENCE: 339
MPNVGIIGAG ISGLAAAYRL QEHGHSVRVL EASGHTGGVI RSESSEGFLV EHGPNSIRAG   60
AAGLETLIDA LDLHEDRVWA NDAADTRYVV RDGRPTPLPR SVGSFLTTDL FSTRAKLRLL  120
AEPFIGRAAA EDESVARFTE RRLGPEVLNY AVAPFVGGVF AGRPDDLSVQ HAFRRLAALE  180
EESGSLLLGA IRRALTSDDG APPDTPSGLF SFRNGLQTLP NALADTLGDR IRLNAPVHAL  240
THDGTAWRVT VSPPDAPAHT RSFDALVCTV PLHRLAAMEI DTPVDLAPLG EVTYPPLSVL  300
ALGYERDAID HALDGFGMLV PPVEDTLDVL GTIFSSTLFP GRAPEGHVLL TTFVGGARAP  360
HHATSDAAAL QARVARDLDS LLGVDASPVF RRLVHWPHAI PQYELGYGTV KDTFDALEAA  420
HPHLAFAGNY RAGVSVGDAL TSGLEAADRL LETDERATQP H                     461

SEQ ID NO: 340          moltype = AA  length = 469
FEATURE                 Location/Qualifiers
source                  1..469
                        mol_type = protein
                        organism = Rhodothermus sp.
SEQUENCE: 340
MASVGIIGAG IAGLTAAYEL HRRGLEVTVF EATDRIGGFI QSERIDGFLV ELGPQTLQRT   60
SGDFEELLRQ VDLEDACIPA RPVAANRFIV RGGQPIPLPR SPRELLRTPL LSPRARLRLL  120
AEPFIHRAHR STEESVAKFT RRRLGPEVLD YLVEPFVAGI FAGDPEQLSV RYAFPKLFEL  180
EQQYGSLFWG LIRDRMKQRY HPAPRRSMFS FVEGLHMLPR ALAERLPAHA IVRNAEVLAT  240
RWDEKNPWTL TFRQHGRAST RFFDIIVCAV PLHRLAQLRI HPPVDRRPLS TVEHPPIALV  300
ALGFRREQVA HPLDGFGMLV PAVERDFQIL GTLFSSSLFP DRAPEGHVLL TTFVGGMRHP  360
ELALLPEDRL EALVLQDLRR LLGISGAPVF RHVWRWERSI PQYRLGYDAV LACVHDVEMS  420
RSGLFLAGNY MEGISVIDAL HTGLKAARAI IQHLREEAAG GLAKLVLGD             469

SEQ ID NO: 341          moltype = AA  length = 483
FEATURE                 Location/Qualifiers
source                  1..483
                        mol_type = protein
                        organism = Tribolium sp.
SEQUENCE: 341
NMSLRLVLFL VFCIGKVLGN FSVIVIGAGP SGIAAATKLL QHSVNVTVLE AENRIGGRIN   60
TVKFGDGLVE LGAEYCHGEV GNIVKELVNG YDLLEPNFNY LNGEIYYSNG SKLDHGFVRE  120
MQDLILSENK EENYDTRGKS IGEVPMHKYN STLVEKYKSD ENKLKLLKEG LHFAERSILI  180
SEGSFSWFDA SADSDWLECP GNQTLVWKGV GYKTVLEILM KSYPNPDEKL PLDDKLFLNS  240
KVTKINWGEK PIKVHTSDKV YSADYVIFTP SIGVLKAGSD LFTPSLPPKK HKAIDSIGFA  300
GVVKLFLRFP VKWWDDNDKY FAFFWSDDDL KSENFPEGPP EKRKIVGYPA VGLVPSWAQH  360
QRLDDLDLGE MVPEIEQLPI ETLKKGVNFT LEKFLGKDYN ITEIGEVLRS GWVTNENFRG  420
TYSFTRNGLY QKGVSYQNDL AEPLEGLFFA GEATNPVHFA TVHGAIESGH REARRILDPR  480
NKN                                                               483
```

```
SEQ ID NO: 342          moltype = AA  length = 453
FEATURE                 Location/Qualifiers
source                  1..453
                        mol_type = protein
                        organism = Tribolium sp.
SEQUENCE: 342
SVIIVGAGVS GISAAVKLFE NGIANLKIFE AEDRIGGRIH TVKFGDNFID LGAQYCHGEN    60
VVYDTVKDLD LLEHAQLFST PKMYYSNGSH LDNQLTQDLQ KVVSSYDHDI TRSKELSLGD   120
AFLKKYNSTI LEKYKNDPEN FKLASDGLTF AHSTILMHEG AFHWSRPASG RHYKAVKGDQ   180
MMVWKQRGYD MILDVLLKRY PDPSLKIPIE EKLFLNKRVT KITWTGDKAS VKLSDGTSHE   240
ADHVIFTPSV GVLTHDDLFE PVVPPRKQQA IKSMGFDGII KLILYFPEKW WHDSDSTFFF   300
LWDRKDLEGI TKEFNEGPSK DGISWVSNLV ALVKVPSNPH VLIGWVSGGL IPEMEKMSLD   360
VVKKGSMFVI RKFLGRDYNV TEPGEVLWSD WHNNPNFRGT YSYEKNGYFE EEVHYQDHLA   420
EPLTQGTTPV VLFAGEATHP THYSTVHGAI ESG                                453

SEQ ID NO: 343          moltype = AA  length = 612
FEATURE                 Location/Qualifiers
source                  1..612
                        mol_type = protein
                        organism = Mycosphaerella sp.
SEQUENCE: 343
MASSSSPNHG KKAIVIGAGV GGVSTAARLA AAGFSVTVLE KNSFTGGRCS LIHHDGYRFD    60
QGPSLLLLPH LFHATFADLG TTLEKEGVHL LKCEPNYNIH FGDGEKFTLS TDLSVMKEEI   120
EKWEGKDGYD RYLAFLRESH AHYELSVTHV LLKNFTSLLS MLRISFLQHL VALHPFESIW   180
SRASRYFWTE RLRRVFTFGS MYMGMSPFDA PGTYSLLQYT ELAEGIWYPV GGFHKVVGAL   240
VGIAERMGAE FRLETAVKRI CVTADGARAT GVELENGEVL EADVVVNNSD LVYAYNHLLQ   300
PQAYAESLSD RPGSCSSISF YWALDRKVPE LSAHNIFLAD DYRESFDSIF KKHLIPDQPS   360
FYVNVPSRVD STAAPEGKDT VVVLVPVGHL TGEAAASHFS QPASSPSKPN GGTIKSASPS   420
TQTGIPPTLD QDWPAMIALA RQTIIKTIHH RTGVDLHPLI IHEQSNDPVT WRSAFNLDKG   480
AILGLSHSFF NVLCFRPSTR ARRAGPLDPL LKYLSGLYMV GASAHPGTGV PIVLAGGKLV   540
AEQVCGDMGV RVPWVVEEGR GKGKEEVKKL DRMEKPETWV KWVGILIALG MVPWILGWVV   600
VLFLAKVASV GW                                                      612

SEQ ID NO: 344          moltype = AA  length = 936
FEATURE                 Location/Qualifiers
source                  1..936
                        mol_type = protein
                        organism = Mycosphaerella sp.
SEQUENCE: 344
MSIDTEEATC QVPVELSAGS ESEEELNDIA EHELEDDFDP HFHREGQATP MVDIAGPASE    60
SQHQQPPAFS RWVSKLRRRK HNHPQLLSPR KERWTLDDFD TRAASPGQQY LSPGRHYHSD   120
SQGSSVRFVT AVRSATATLA SASMATLSRR TTRFRRGHQR SSIVSGSEIR LSIESRRSII   180
DEAAKQRARK RREKLEELIR TEESYVADVK ALSNAYFTIL AHQPTATSFA RTSTQRTIAD   240
ILHLHDDILG CLHRIVPFAE YDQTIARLPL PLRAHNRWHS MDAVPQRTTP NRSTLATIRQ   300
GRRSLNISRS SSDDAQVVLR CSPQTIAAVA KAFSDNMLRF AAYEDYGANY DLIQRDVDDT   360
QRAISGWADF DKAIEAISAH VNPMRTREAN RKRAMTVKDL LIKPIQRLPR YELLFSDLHK   420
LTPACDDPIS HAEIEELRLK LNSVCHRMNA AKENPARARA LEMTWLIGDR LTFSSQVPRS   480
IFLQLLGRVS LCGSLYIAYR SRDRIKGAYV ICVLFESCLL LASCDEDQSK YSILVSITLA   540
NATIEETDNA KGLQCHTAPH AWKVVFEQGA RMYELIFTAC SAVESEVWRT HIASGIETQI   600
AAVAEGKANV FELQSPLTAD MKSIGKAFGK PGSFVRRMSV QRAATIGPTA DLNQVIIKNT   660
QAVKEVMDNS SQGSFQIPRS QSVATPSHVQ TLAPRRADRH RLETILSDVW SRDLLPYPGM   720
VRRSDPIRAG ANHVIRKFSM ASITSNFSSS KRTGSYTSMS SWRKEDMPPP RNRGESGREG   780
SSMSSRQSRP PLIDFHTAPD AFLPADFEIG RPSKDKRKRS ALRTFTMTME RPFTPLLGNE   840
NKQSGLRRAQ SVKDVVDDQA RPGPSPIQLK RREEKRTGTP VYSVVQERAR TPAMLHVKDE   900
SLEMGMGVGE ASNGAVAGKA PRKSKSRLLR LFGQER                            936

SEQ ID NO: 345          moltype = AA  length = 573
FEATURE                 Location/Qualifiers
source                  1..573
                        mol_type = protein
                        organism = Mycosphaerella sp.
SEQUENCE: 345
MLHSRSCTYR LLAPAVARRI TPLVPSQCLL QTHRSRTYSA EAAPSHDVAV LGGGITGLAA    60
AHYVTREHPR AKVTLYEASD RVGGWVSSKR ADVHDGTVLF EGGPRTLRPN GNGVLAANAS   120
QMQELDLTKD AIFTQKSSPA AQNRFVYYPD HIVRMPHPSA GLFNNLWSLM TEPVFATALK   180
SGFMEAFTTG RDGSIQDESI AEFFSRRLSP TMVDRILSAV IHGIYAGDVN KLSAKSLFPN   240
QWRHEAKYDS LIKGVIQERA EGTMVTKREA DFLQAMKVYE WDPLLKATLK DNSVFTFKDG   300
LQMLPDRLHS RLFEDGRVEF KTGSPVESIV QSQGNSGIQV TTKGSTESKT HTHVISALSP   360
EHLNTVCRHG SASSRLIDSI PTVTVMTVSM YFRTPDLHEP GFGYLIPQAT PFENNPERAL   420
GVVFDTAYSP GSSDSRGTKV TVMLGGHWWD GWPAFPDEEE GVTMARAVLE RHLGIKEAPE   480
AWQVNLQADC IPQYTVGHET RLKKAHNNIW QEYKGRLRVA GNWMSGVGVN DCLRSAYEVA   540
RNLSKDGTGL QHVGEAPTLR MKPVRPGEKT EES                                573

SEQ ID NO: 346          moltype = AA  length = 239
FEATURE                 Location/Qualifiers
source                  1..239
                        mol_type = protein
                        organism = Apisum sp.
```

```
SEQUENCE: 346
KREGGIEKNQ SIQIIEASDH TGGWIQSWKD ENTNVISELG PRTIRGRGKS ANNTYSLIKD   60
LGIEDLVRNV GIDASARYIF ANGNIHQLPM SVWKALFTVN QPPTKPWIYY VLRECFSSNN  120
SKDKLSDVQN NDESAYDFFC RTFGQEFADY LISPLLCGVC GGNAKQMSVK FMFGALYEAE  180
RKHGTVGLGL LKEQLSSIWN REKVKDTKGT NTVKPPPSVY YLDGGLQRLI HALDIENES   239

SEQ ID NO: 347          moltype = AA  length = 502
FEATURE                 Location/Qualifiers
source                  1..502
                        mol_type = protein
                        organism = Schizophyllum sp.
SEQUENCE: 347
MAPHHIAVLG GGLTGLSSAY HLSHRFPNAL ITLVERSTRV GGWAESERVS LKDPKDGSEA   60
SILIEGGPRT LRPTAKSVLE LVTRLDLLDD LILVPRTSPS AKNKYFHMPG QPGLLAVPSS  120
FKGLISSPLG ACLTRAVAKE AMAFSNRDDL KDESFDSFLC RRFTAEFAEK VGSALVHGIF  180
AADSRKLSVR AAFPVLWEAE EYGWGSVVRG FIRGRREEDV EESYYISNPV QKAMEETAVF  240
SFRNGMDTVA RATEHHLSKL KNVTILKGAD VKSLGVNSKD KSIEVQIRPT HVVSTLPLPA  300
LHRVLTPTSN LPHLTTNPYS TVTVYNLIFR TDTPTPIHPA GFGYLIPRPP GGYEQPQANK  360
EGILGCVFDS CALSAQDVMP GPTKYTKMTV MTGGPYQNKP PALDTVLQAL ARHLDWPEVY  420
EPVYTRVREN RDCIPVPAPG HLERVAELRR VLKEGEWQGR MEVVGAGVGG VSVGDCVEAG  480
RWVGEGWGPS TPQMEDDECD DE                                          502

SEQ ID NO: 348          moltype = AA  length = 150
FEATURE                 Location/Qualifiers
source                  1..150
                        mol_type = protein
                        organism = Acinetobacter sp.
SEQUENCE: 348
MDAPSDAFLW VKALHIIAVV CWFAALFYLP RLYVYHAMSE DDTSHRRFEV MERKLYRGIM   60
WPSMIATLIT AHFLVDWGDA TRHYHEALWF YIKVGLVGLL VIYHFVCGYY RKKLIGNAHY  120
KSHKFWRYFN EMPTLILFAV VILVVVKPQF                                  150

SEQ ID NO: 349          moltype = AA  length = 150
FEATURE                 Location/Qualifiers
source                  1..150
                        mol_type = protein
                        organism = Acinetobacter sp.
SEQUENCE: 349
MDAPSDAFLW VKALHIIAVV CWFAALFYLP RLYVYHAMSE DEISHRRFEI MERKLYRGIM   60
WPSMIATLIT AHFLVDWGDA TRHYHEALWF YIKVGLVGLL VIYHFVCGYY RKKLIGNAHY  120
KSHKFWRYFN EMPTLILFAV VILVVVKPQF                                  150

SEQ ID NO: 350          moltype = AA  length = 150
FEATURE                 Location/Qualifiers
source                  1..150
                        mol_type = protein
                        organism = Acinetobacter sp.
SEQUENCE: 350
MDAPSDAFLW VKALHIIAVV CWFAALFYLP RLYVYHAMSE DEISHRRFEI MERKLYRGIM   60
WPSMIATLIT AHFLVDWGDA TRHYHQALWF YIKVGLVGLL VIYHFVCGYY RKKLIGNAHY  120
KSHKFWRYFN EMPTLILFAV VILVVVKPQF                                  150

SEQ ID NO: 351          moltype = AA  length = 150
FEATURE                 Location/Qualifiers
source                  1..150
                        mol_type = protein
                        organism = Acinetobacter sp.
SEQUENCE: 351
MDAPSDAFLW VKALHIIAVV CWFAALFYLP RLYVYHAMSE DTVSHQRFEV MERKLYRGIM   60
WPSMIATLIT AHFLVDWGDA TRHYHEALWF YLKVGLVGLL VIYHFVCGYY RKKLIGNAHY  120
KSHKFWRFFN EMPTLILFAV VILVVVKPQF                                  150

SEQ ID NO: 352          moltype = AA  length = 150
FEATURE                 Location/Qualifiers
source                  1..150
                        mol_type = protein
                        organism = Acinetobacter sp.
SEQUENCE: 352
MDAPSDAFLW VKALHIIAVV CWFAALFYLP RLYVYHAMSE DAVSHQRFEV MERKLYRGIM   60
WPSMIATLIT AHFLVDWGDA TRHYHEALWF YLKVGLVGLL VIYHFVCGYY RKKLIGNAHY  120
KSHKFWRFFN EMPTLILFAV VILVVVKPQF                                  150

SEQ ID NO: 353          moltype = AA  length = 150
FEATURE                 Location/Qualifiers
source                  1..150
                        mol_type = protein
                        organism = Acinetobacter sp.
SEQUENCE: 353
MDAPSDAFLW VKALHIIAVV CWFAALFYLP RLYVYHAMSE DAVSHQRFEV MERKLYRGIM   60
```

```
WPSMIATLIT AHFLVDWGDA TRHYHEALWF YLKVGMVGLL VIYHFVCGYY RKKLIGNAHY    120
KSHKFWRFFN EMPTLILFAV VILVVVKPQF                                    150

SEQ ID NO: 354          moltype = AA  length = 150
FEATURE                 Location/Qualifiers
source                  1..150
                        mol_type = protein
                        organism = Acinetobacter sp.
SEQUENCE: 354
MDAPSDAFLW VKALHIIAVV CWFAALFYLP RLYVYHAMSE DVVSHQRFEV MERKLYRGIM    60
WPSMIATLIT AHFLVDWGDA TRHYHEALWF YLKVGLVGLL VIYHFVCGYY RKKLIGNAHY    120
KSHKFWRFFN EMPTLILFAV VILVVVKPQF                                    150

SEQ ID NO: 355          moltype = AA  length = 150
FEATURE                 Location/Qualifiers
source                  1..150
                        mol_type = protein
                        organism = Acinetobacter sp.
SEQUENCE: 355
MDAPSDAFLW VKALHIIAVV CWFAALFYLP RLFVYHAMSE DTVSHQRFEV MERKLYRGIM    60
WPSMIATLIT AHFLVDWGDA TRHYHEALWF YLKVGLVGLL VIYHFVCGYY RKKLIGNAHY    120
KSHKFWRFFN EMPTLILFAV VILVVVKPQF                                    150

SEQ ID NO: 356          moltype = AA  length = 150
FEATURE                 Location/Qualifiers
source                  1..150
                        mol_type = protein
                        organism = Acinetobacter sp.
SEQUENCE: 356
MDAPSDAFLW VKALHIIAVV CWFAALFYLP RLYVYHAMSE DAVSHQRFEV MERKLYRGIM    60
WPSMIATLIT AHFLVDWGDA SRHYHEALWF YLKVGLVGLL VIYHFVCGYY RKKLIGNAHY    120
KSHKFWRFFN EMPTLILFAV VILVVVKPQF                                    150

SEQ ID NO: 357          moltype = AA  length = 150
FEATURE                 Location/Qualifiers
source                  1..150
                        mol_type = protein
                        organism = Acinetobacter sp.
SEQUENCE: 357
MDAPSDAFLW VKALHIIAVV CWFAALFYLP RLFVYHAMSE DAVSHQRFEV MERKLYRGIM    60
WPSMIATLIT AHFLVDWGDA TRHYHEALWF YLKVGLVGLL VIYHFVCGYY RKKLIGNAHY    120
KSHKFWRFFN EMPTLILFAV VILVVVKPQF                                    150

SEQ ID NO: 358          moltype = AA  length = 150
FEATURE                 Location/Qualifiers
source                  1..150
                        mol_type = protein
                        organism = Acinetobacter sp.
SEQUENCE: 358
MDAPSDAFLW VKALHIIAVV CWFAALFYLP RLFVYHAMSE DAVSHQRFEV MERKLYRGIM    60
WPSMIATLIT AHFLVDWGDA TRHYHEALWF YLKVGLVGLL VIYHFICGYY RKKLIGNAHY    120
KSHKFWRFFN EMPTLILFAV VILVVVKPQF                                    150

SEQ ID NO: 359          moltype = AA  length = 150
FEATURE                 Location/Qualifiers
source                  1..150
                        mol_type = protein
                        organism = Acinetobacter sp.
SEQUENCE: 359
MDAPSDAFLW VKALHIIAVV CWFAALFYLP RLYVYHAMSE DAVSHQRFEV MERKLYRGIM    60
WPSMIATLIT AHFLVDWGDA TRHYHEALWF YLKVGLVGLL VIYHLVCGYY RKKLIGNAHY    120
KSHKFWRFFN EMPTLILFAV VILVVVKPQF                                    150

SEQ ID NO: 360          moltype = AA  length = 150
FEATURE                 Location/Qualifiers
source                  1..150
                        mol_type = protein
                        organism = Acinetobacter sp.
SEQUENCE: 360
MDAPSDAFLW VKALHIIAVV CWFAALFYLP RLFVYHAMSE DAVSHQRFEV MERKLYRGIM    60
WPSMIATLIT AHFLVDWGDA SRHYHEALWF YLKVGLVGLL VIYHFVCGYY RKKLIGNAHY    120
KSHKFWRFFN EMPTLILFAV VILVVVKPQF                                    150

SEQ ID NO: 361          moltype = AA  length = 150
FEATURE                 Location/Qualifiers
source                  1..150
                        mol_type = protein
                        organism = Acinetobacter sp.
SEQUENCE: 361
```

```
MDAPSDAFLW VKALHIIAVV CWFAALFYLP RLYVYHAMSE DAVSHQRFEV MERKLYRGIM    60
WPSMIATLIT AHFLVDWGDA TRHYHEALWF YLKVGLVGLL VIYHLVCGYY RKKLIGNAHY   120
KTHKFWRFFN EMPTLILFAV VILVVVKPQF                                    150

SEQ ID NO: 362          moltype = AA   length = 150
FEATURE                 Location/Qualifiers
source                  1..150
                        mol_type = protein
                        organism = Acinetobacter sp.
SEQUENCE: 362
MDAPSDAFLW VKALHIIAVV CWFAALFYLP RLFVYHAMSE DALSHQRFEV MERKLYRGIM    60
WPSMIATLIT AHFLVDWGDA TRHYHDALWF YLKVGLVGLL VIYHFVCGYY RKKLIGNAHY   120
KSHKFWRFFN EMPTLILFAV VILVVVKPQF                                    150

SEQ ID NO: 363          moltype = AA   length = 150
FEATURE                 Location/Qualifiers
source                  1..150
                        mol_type = protein
                        organism = Acinetobacter sp.
SEQUENCE: 363
MDAPSDAFLW VKALHIIAVV CWFAALFYLP RLYVYHAMSE DAISHQRFEV MERKLYRGIM    60
WPSMIATLIT AHFLVDWGDA TRHYHEALWF YLKVGLVGLL VIYHLVCGYY RKKLIGNAHY   120
KTHKFWRFFN EMPTLILFAV VILVVVKPQF                                    150

SEQ ID NO: 364          moltype = AA   length = 150
FEATURE                 Location/Qualifiers
source                  1..150
                        mol_type = protein
                        organism = Acinetobacter sp.
SEQUENCE: 364
MDAPSDAFLW VKALHIIAVV CWFAALFYLP RLYVYHAMSE DKVSHQRFEV MERKLYRGIM    60
WPSMLATLIT AHFLVDWGDA TRHYHEALWF YLKVGLVGLL VIYHFVCGYY RKKLISNAHY   120
KSHQFWRFFN EMPTLILFAV VILVVVKPQF                                    150

SEQ ID NO: 365          moltype = AA   length = 150
FEATURE                 Location/Qualifiers
source                  1..150
                        mol_type = protein
                        organism = Acinetobacter sp.
SEQUENCE: 365
MDAPSDAFLW VKALHIIAVV CWFAALFYLP RLYVYHAMSE DEISHQRFEV MERKLYRGIM    60
WPSMIATLVT AHFLVEWGDA TRHYHEAIWF YLKVGLVGLL VIYHFVCGYY RKKLIGNAHY   120
KSHKFWRFFN EMPTLLLFAI IILVVVKPQF                                    150

SEQ ID NO: 366          moltype = AA   length = 150
FEATURE                 Location/Qualifiers
source                  1..150
                        mol_type = protein
                        organism = Acinetobacter sp.
SEQUENCE: 366
MDAPSDAFLW VKALHIIAVV CWFAALFYLP RLYVYHAMSE DAISHQRFEV MERKLYRGIM    60
WPSMIATLVT AHFLVEWGDA TRHYHEALWF YLKVGLVGLL VIYHFVCGYY RKKLIGNAHY   120
KSHKFWRFFN EMPTLLLFAI IILVVVKPQF                                    150

SEQ ID NO: 367          moltype = AA   length = 150
FEATURE                 Location/Qualifiers
source                  1..150
                        mol_type = protein
                        organism = Acinetobacter sp.
SEQUENCE: 367
MDAPSDAFLW VKALHIIAVV CWFAALFYLP RLYVYHAMSD DAVSHQRFEV MERKLYRGIM    60
WPSMIATLIT AHFLVDWGDA TRHYHEALWF YLKVGLVGLL VIYHFVCGYY RKKLIGNAHY   120
KSHKFWRFFN EMPTLILFAV VILVVVKPTF                                    150

SEQ ID NO: 368          moltype = AA   length = 150
FEATURE                 Location/Qualifiers
source                  1..150
                        mol_type = protein
                        organism = Acinetobacter sp.
SEQUENCE: 368
MDAPSDAFLW VKALHIIAVV CWFAALFYLP RLYVYHAMSE DAISHQRFEV MERKLYRGIM    60
WPSMIATLLT AHFLVDWGDA TRHYHEALWF YMKVGLVGLL VIYHFVCGYY RKKLIGNAHY   120
KSHRFWRFFN EMPTLLLFAI IILVVVKPQF                                    150

SEQ ID NO: 369          moltype = AA   length = 150
FEATURE                 Location/Qualifiers
source                  1..150
                        mol_type = protein
                        organism = Acinetobacter sp.
```

```
SEQUENCE: 369
MDAPSDAFLW VKALHIIAVV CWFAALFYLP RLYVYHAMSE DAVSHQRFEV MERKLYRGIM    60
WPSMIATLIT AHFLVDWGDA TRHYHDALWF YLKVGLVGLL VIYHFVCGYY RKKLIGHAHY   120
KSHKFWRFFN EMPTLILFAV VILVVVKPQF                                   150

SEQ ID NO: 370          moltype = AA   length = 150
FEATURE                 Location/Qualifiers
source                  1..150
                        mol_type = protein
                        organism = Acinetobacter sp.
SEQUENCE: 370
MDAPSEAFLW VKALHIIAVV CWFAALFYLP RLYVYHAMSE DTVSHQRFEI MERKLYRGIM    60
WPSMIATLIT AHFLVDWGDA TRHYHEALWF YLKVGLVGLL VIYHFVCGYY RKKLIGNAHY   120
KSHKFWRFFN EMPTLILFAV IILVVVKPTF                                   150

SEQ ID NO: 371          moltype = AA   length = 150
FEATURE                 Location/Qualifiers
source                  1..150
                        mol_type = protein
                        organism = Acinetobacter sp.
SEQUENCE: 371
MDAPSDAFLW VKALHIIAVV CWFAALFYLP RLYVYHAMSE DAISHQRFEV MERKLYRGIM    60
WPSMIATLVT AHFLVEWGDA TRHYHEAIWF YLKVGLVGLL VIYHFVCGYY RKKLIGNAHY   120
KSHKFWRFFN EMPTLLLFAI IILVVVKPQF                                   150

SEQ ID NO: 372          moltype = AA   length = 150
FEATURE                 Location/Qualifiers
source                  1..150
                        mol_type = protein
                        organism = Acinetobacter sp.
SEQUENCE: 372
MDAPSDAFLW VKALHIIAVV CWFAALFYLP RLYVYHAMSD DATSHQRFEV MERKLYRGIM    60
WPSMIATLIT AHFLVDWGDA TRHYHEATWF YLKVGLVALL VIYHLVCGYY RKKLIGNAHY   120
KSHKFWRFFN EMPTLILFAV VILVVVKPQF                                   150

SEQ ID NO: 373          moltype = AA   length = 150
FEATURE                 Location/Qualifiers
source                  1..150
                        mol_type = protein
                        organism = Acinetobacter sp.
SEQUENCE: 373
MDAPSDAFLW VKALHIIAVV CWFAALFYLP RLYVYHAMSE DAVSHQRFEV MERKLYRGIM    60
WPSMIATLVT AHFLVDWGDA TRHYHDALWF YLKVGLVGLL VIYHLVCGYY RKKLIGNAHY   120
KSHRFWRFFN EMPTLILFAV VILVVVKPQF                                   150

SEQ ID NO: 374          moltype = AA   length = 150
FEATURE                 Location/Qualifiers
source                  1..150
                        mol_type = protein
                        organism = Acinetobacter sp.
SEQUENCE: 374
MDAPSDAFLW VKALHIIAVV CWFAALFYLP RLYVYHAMSE DAVSHQRFEV MERKLYRGIM    60
WPAMLATLIT AHFLVDWGDA TRHYHEALWF YLKVGLVGLL VIYHLVCGYY RKKLIGNAHY   120
KSHKFWRYFN EMPTLILFAV VILVVVKPTF                                   150

SEQ ID NO: 375          moltype = AA   length = 150
FEATURE                 Location/Qualifiers
source                  1..150
                        mol_type = protein
                        organism = Acinetobacter sp.
SEQUENCE: 375
MDAPSDAFLW VKALHIIAVV CWFAALFYLP RLFVYHAMSE DALSHQRFEV MERKLYRGIM    60
WPSMIATLIT AHFLVDWGDA TRHYHDALWF YLKVGLVGLL VIYHLVCGYY RKKLIGNAHY   120
KSHKFWRFFN EMPTLILFAV VILVVVKPQF                                   150

SEQ ID NO: 376          moltype = AA   length = 150
FEATURE                 Location/Qualifiers
source                  1..150
                        mol_type = protein
                        organism = Acinetobacter sp.
SEQUENCE: 376
MDAPSDAFLW VKALHIIAVV CWFAALFYLP RLYVYHAMSE DAASHQRFEV MERKLYRGIM    60
WPSMIATLIT AHFLVDWGDA TRHYHEATWF YLKVGLVALL VIYHLVCGYY RKKLIGNAHY   120
KSHKFWRFFN EMPTLILFAV VILVVVKPQF                                   150

SEQ ID NO: 377          moltype = AA   length = 150
FEATURE                 Location/Qualifiers
source                  1..150
                        mol_type = protein
```

```
                          organism = Acinetobacter sp.
SEQUENCE: 377
MDAPSDAFLW VKALHIIAVV CWFAALFYLP RLYVYHAMSE DEISHQRFEV MERKLYRGIM      60
WPSMIATLVT AHLLVEWGDA TRHYHEAIWF YLKVGLVGLL VIYHFVCGYY RKKLIGNAHY     120
KSHKFWRFFN EMPTLLLFAI IILVVVKPQF                                     150

SEQ ID NO: 378            moltype = AA   length = 150
FEATURE                   Location/Qualifiers
source                    1..150
                          mol_type = protein
                          organism = Acinetobacter sp.
SEQUENCE: 378
MDAPSDAFLW VKALHIIAVV CWFAALFYLP RLYVYHAMSD DATSHQRFEV MERKLYRGIM      60
WPSMIATLIT AHFLVEWGDA TRHYHEATWF YLKIGLVALL VVYHFVCGYY RKKLIGNAHY     120
KSHKFWRFFN EMPTLILFAV VILVVVKPQF                                     150

SEQ ID NO: 379            moltype = AA   length = 150
FEATURE                   Location/Qualifiers
REGION                    1..150
                          note = Bacteria
source                    1..150
                          mol_type = protein
                          organism = unidentified
SEQUENCE: 379
MDAPSDAFLW VKALHIIAVV CWFAALFYLP RLYVYHAMSD DAVSHQRFEV MERKLYRGIM      60
WPAMIATLIT AHFLVDWGDA TRHYHEALWF YLKVGLVGLL VIYHFVCGYY RKKLIGNAHY     120
KSHKFWRFFN EMPTLILFAV VILVVVKPTF                                     150

SEQ ID NO: 380            moltype = AA   length = 150
FEATURE                   Location/Qualifiers
source                    1..150
                          mol_type = protein
                          organism = Acinetobacter sp.
SEQUENCE: 380
MDAPSDAFLW VKALHIIAVV CWFAALFYLP RLYVYHAMSE DAISHQRFEV MERKLYRGIM      60
WPAMLATLIT AHFLVDWGDA TRHYHEALWF YLKVGLVGLL VIYHLVCGYY RKKLIGNAHY     120
KSHKFWRYFN EMPTLILFAV VILVVVKPTF                                     150

SEQ ID NO: 381            moltype = AA   length = 150
FEATURE                   Location/Qualifiers
source                    1..150
                          mol_type = protein
                          organism = Acinetobacter sp.
SEQUENCE: 381
MDAPSDAFLW VKALHIIAVV CWFAALFYLP RLYVYHAMSD DATSHQRFEI MERKLYRGIM      60
WPSMIATLIT AHFLVDWGDA TRHYHEATWF YLKVGLVALL VIYHLVCGYY RKKLIGNAHY     120
KSHKFWRFFN EMPTLILFAV VILVVVKPQF                                     150

SEQ ID NO: 382            moltype = AA   length = 150
FEATURE                   Location/Qualifiers
source                    1..150
                          mol_type = protein
                          organism = Acinetobacter sp.
SEQUENCE: 382
MDAPSDAFLW VKALHIIAVV CWFAALFYLP RLYVYHAMSE DAVSHQRFEV MERKLYRGIM      60
WPSMIATLVT AHFLVDWGDA TRHYHEALWF YLKVALVGLL VIYHLVCGYY RKKLIGNAHY     120
KSHKFWRFFN EMPTVILFAV VILVVVKPQF                                     150

SEQ ID NO: 383            moltype = AA   length = 150
FEATURE                   Location/Qualifiers
source                    1..150
                          mol_type = protein
                          organism = Acinetobacter sp.
SEQUENCE: 383
MDAPSDAFLW VKALHIIAVV CWFAALFYLP RLYVYHAMSD DTVSHQRFEV MERKLYRGIM      60
WPSMVATLIT AHFLVDWGDA TRHYHEALWF YIKVALVGLL VIYHFVCGYY RKKLIGNAHY     120
KSHKFWRFFN EMPTLILFAV VILVVVKPHF                                     150

SEQ ID NO: 384            moltype = AA   length = 150
FEATURE                   Location/Qualifiers
source                    1..150
                          mol_type = protein
                          organism = Acinetobacter sp.
SEQUENCE: 384
MDAPSDAFLW VKALHIIAVV CWFAALFYLP RLYVYHAMSE DAASHQRFEV MERKLYRGIM      60
WPSMIATLIT AHFLVDWGDA TRHYHQATWF YLKVGLVALL VIYHLVCGYY RKKLIGNAHY     120
KSHKFWRFFN EMPTLILFAV VILVVVKPQF                                     150

SEQ ID NO: 385            moltype = AA   length = 150
```

```
FEATURE                 Location/Qualifiers
source                  1..150
                        mol_type = protein
                        organism = Acinetobacter sp.
SEQUENCE: 385
MDAPSEAFLW VKALHIIAVV CWFAALFYLP RLFVYHAMSD DNLSHQRFEI MERKLYRGIM    60
WPSMIATLIT AHFLVDWGDA TRHYHEALWF YLKVGLVGLL VIYHFVCGYY RKKLIGNAHY   120
KSHKFWRFFN EMPTLILFAV VILVVVKPTF                                   150

SEQ ID NO: 386          moltype = AA  length = 150
FEATURE                 Location/Qualifiers
source                  1..150
                        mol_type = protein
                        organism = Acinetobacter sp.
SEQUENCE: 386
MDAPSDAFLW VKALHIIAVV CWFAALFYLP RLYVYHAMSD DATSHHRFEV MERKLYRGIM    60
WPSMIATLIT AHFLVDWGDA TRHYHEATWF YLKVGLVALL VIYHLVCGYY RKKLIGNAHY   120
KSHKFWRFFN EMPTLILFAV VILVVVKPQF                                   150

SEQ ID NO: 387          moltype = AA  length = 150
FEATURE                 Location/Qualifiers
source                  1..150
                        mol_type = protein
                        organism = Acinetobacter sp.
SEQUENCE: 387
MDAPSDAFLW VKALHIIAVV CWFAALFYLP RLYVYHAMSD DATSHQRFEV MERKLYRGIM    60
WPSMIATLIT AHFLVEWGDA TRHYHEATWF YLKVGLVALL VIYHLVCGYY RKKLIGNAHY   120
KSHKFWRFFN EMPTLILFAV VILVVVKPQF                                   150

SEQ ID NO: 388          moltype = AA  length = 150
FEATURE                 Location/Qualifiers
source                  1..150
                        mol_type = protein
                        organism = Acinetobacter sp.
SEQUENCE: 388
MDAPSNAFLW VKALHIIAVV CWFAALFYLP RLYVYHAMSD DATSHQRFEV MERKLYRGIM    60
WPSMIATLIT AHFLVDWGDA TRHYHEATWF YLKVGLVALL VIYHLVCGYY RKKLIGNAHY   120
KSHKFWRFFN EMPTLILFAV VILVVVKPQF                                   150

SEQ ID NO: 389          moltype = AA  length = 150
FEATURE                 Location/Qualifiers
source                  1..150
                        mol_type = protein
                        organism = Acinetobacter sp.
SEQUENCE: 389
MDAPSDAFLW VKALHIIAVV CWFAALFYLP RLYVYHAMSE DVISHQRFEV MERKLYRGIM    60
WPSMIATLLT AHFLVDWGDA TRHYHEALWF YLKVSLVGLL VIYHFVCGYY RKKLIGNAHY   120
KSHRFWRFFN EMPTLLLFAI IILVVVKPQF                                   150

SEQ ID NO: 390          moltype = AA  length = 150
FEATURE                 Location/Qualifiers
source                  1..150
                        mol_type = protein
                        organism = Acinetobacter sp.
SEQUENCE: 390
MDAPSDAFLW VKALHIIAVV CWFAALFYLP RLYVYHAMSD DATSHQRFEV MERKLYRGIM    60
WPSMIATLIT AHFLVDWGDA TRHYHEATWF YLKVGLVALL VIYHLVCGYY RKKLIGNAHY   120
KSHKFWRFFN EMPTFILFAV VILVVVKPQF                                   150

SEQ ID NO: 391          moltype = AA  length = 150
FEATURE                 Location/Qualifiers
source                  1..150
                        mol_type = protein
                        organism = Acinetobacter sp.
SEQUENCE: 391
MDAPSDAFLW VKALHIIAVV CWLAALFYLP RLYVYHAMSD DATSHQRFEV MERKLYRGIM    60
WPSMIATLIT AHFLVDWGDA TRHYHEATWF YLKVGLVALL VIYHLVCGYY RKKLIGNAHY   120
KSHKFWRFFN EMPTLILFAV VILVVVKPQF                                   150

SEQ ID NO: 392          moltype = AA  length = 150
FEATURE                 Location/Qualifiers
source                  1..150
                        mol_type = protein
                        organism = Acinetobacter sp.
SEQUENCE: 392
MDAPSDAFLW VKALHIIAVV CWFAALFYLP RLYVYHAMSD DAVSHQRFEV MERKLYRGIM    60
WPSMIATLIT AHFLVDWGDA TRHYHEALWF YLKVGLVGLL VIYHFVCGYY RKKLIGHAHY   120
KSHKFWRFFN EMPTLILFAV VILVVVKPTF                                   150
```

```
SEQ ID NO: 393           moltype = AA  length = 150
FEATURE                  Location/Qualifiers
source                   1..150
                         mol_type = protein
                         organism = Acinetobacter sp.
SEQUENCE: 393
MDAPSDAFLW VKALHIIAVV CWFAALFYLP RLYVYNAMSD DATSHQRFEV MERKLYRGIM    60
WPSMIATLIT AHFLVDWGDA TRHYHEATWF YLKVGLVALL VIYHLVCGYY RKKLIGNAHY   120
KSHKFWRFFN EMPTLILFAV VILVVVKPQF                                    150

SEQ ID NO: 394           moltype = AA  length = 150
FEATURE                  Location/Qualifiers
source                   1..150
                         mol_type = protein
                         organism = Acinetobacter sp.
SEQUENCE: 394
MDAPSDAFLW VKALHIIAVV CWFAALFYLP RLYVYHAMSD DAASHQRFEV MERKLYRGIM    60
WPSMIATLIT AHFLVDWGDA TRHYHEATWF YLKVGLVALL VIYHLVCGYY RKKLIGNAHY   120
KSHKFWRFFN EMPTLILFAV VILVVVKPQF                                    150

SEQ ID NO: 395           moltype = AA  length = 150
FEATURE                  Location/Qualifiers
source                   1..150
                         mol_type = protein
                         organism = Acinetobacter sp.
SEQUENCE: 395
MDAPSDAFLW VKALHIIAVV CWFAALFYLP RLYVYHAMSD DAASHQRFEV MERKLYRGIM    60
WPSMIATLIT AHFLVEWGDA TRHYHEATWF YLKVGLVALL VVYHFVCGYY RKKLIGNAHY   120
KSHKFWRFFN EMPTLILFAV VILVVVKPQF                                    150

SEQ ID NO: 396           moltype = AA  length = 150
FEATURE                  Location/Qualifiers
source                   1..150
                         mol_type = protein
                         organism = Acinetobacter sp.
SEQUENCE: 396
MDAPSDAFLW VKALHIIAVV CWFAALFYLP RLYVYHAMSE DAASHQRFEV MERKLYRGIM    60
WPSMIATLIT AHFLVEWGDA TRHYHEATWF YLKVGLVALL VVYHLVCGYY RKKLIGNAHY   120
KSHKFWRFFN EMPTLILFAV VILVVVKPQF                                    150

SEQ ID NO: 397           moltype = AA  length = 150
FEATURE                  Location/Qualifiers
source                   1..150
                         mol_type = protein
                         organism = Acinetobacter sp.
SEQUENCE: 397
MDAPSDAFLW VKALHIIAVV CWFAALFYLP RLYVYHAMSE DAVSHQRFEV MERKLYRGIM    60
WPAMLATLIT AHFLVDWGDA TRHYHEALWF YLKVGLVGLL VIYHLVCGYY RKKLINNAHY   120
KSHKFWRYFN EMPTLILFAV VILVVVKPTF                                    150

SEQ ID NO: 398           moltype = AA  length = 150
FEATURE                  Location/Qualifiers
source                   1..150
                         mol_type = protein
                         organism = Acinetobacter sp.
SEQUENCE: 398
MDAPSDAFLW VKALHIIAVV CWFAALFYLP RLYVYHAMSE DAASHQRFEV MERKLYRGIM    60
WPSMIATLIT AHFLVEWGDA TRHYHQATWF YLKVGLVALL VIYHLVCGYY RKKLIGNAHY   120
KSHKFWRFFN EMPTLILFAV VILVVVKPQF                                    150

SEQ ID NO: 399           moltype = AA  length = 150
FEATURE                  Location/Qualifiers
source                   1..150
                         mol_type = protein
                         organism = Acinetobacter sp.
SEQUENCE: 399
MDAPSDAFLW VKALHIIAVV CWFAALFYLQ RLYVYHAMSD DATSHQRFEV MERKLYRGIM    60
WPSMIATLIT AHFLVDWGDA TRHYHEATWF YLKVGLVALL VIYHLVCGYY RKKLIGNAHY   120
KSHKFWRFFN EMPTLILFAV VILVVVKPQF                                    150

SEQ ID NO: 400           moltype = AA  length = 150
FEATURE                  Location/Qualifiers
source                   1..150
                         mol_type = protein
                         organism = Acinetobacter sp.
SEQUENCE: 400
MDAPSEAFLW VKALHIIAVV CWFAALFYLP RLFVYHAMSD DNLSHQRFEI MERKLYRGIM    60
WPSMIATLIT AHFLVDWGDA TRHYHEALWF YLKVGLVGLL VIYHFACGYY RKKLIGNAHY   120
KSHKFWRFFN EMPTLILFAV VILVVVKPTF                                    150
```

```
SEQ ID NO: 401          moltype = AA   length = 150
FEATURE                 Location/Qualifiers
source                  1..150
                        mol_type = protein
                        organism = Acinetobacter sp.
SEQUENCE: 401
MDAPSDAFLW VKALHIIAVV CWFAALFYLP RLYVYHAMSE DTASHQRFEV MERKLYRGIM    60
WPSMIATLIT AHFLVDWGDA TRHYHQATWF YLKVGLVALL VIYHLACGYY RKKLIGNAHY   120
KSHKFWRFFN EMPTLILFAV IILVVVKPQF                                   150

SEQ ID NO: 402          moltype = AA   length = 150
FEATURE                 Location/Qualifiers
source                  1..150
                        mol_type = protein
                        organism = Acinetobacter sp.
SEQUENCE: 402
MDAPSDAFLW VKALHIIAVV CWFAALFYLP RLYVYHAMSE DAVSHQRFEV MERKLYRGIM    60
WPSLIATLIT AHFLVDWGDA TRHYHQATWF YLKVGLVALL VIYHLVCGYY RKKLIGNAHY   120
KSHKFWRFFN EMPTLILFAV VILVVVKPQF                                   150

SEQ ID NO: 403          moltype = AA   length = 150
FEATURE                 Location/Qualifiers
source                  1..150
                        mol_type = protein
                        organism = Acinetobacter sp.
SEQUENCE: 403
MDAPSDAFLW VKALHIIAVV CWFAALFYLP RLYVYHAMSK DAASHQRFEV MERKLYRGIM    60
WPSMIATLIT AHFLVDWGDA TRHYHQATWF YLKVGLVALL VIYHLVCGYY RKKLIGNAHY   120
KSHKFWRFFN EMPTLILFAV VILVVVKPQF                                   150

SEQ ID NO: 404          moltype = AA   length = 150
FEATURE                 Location/Qualifiers
source                  1..150
                        mol_type = protein
                        organism = Acinetobacter sp.
SEQUENCE: 404
MDAPSDAFLW VKALHIIAVV CWFAALFYLP RLYVYHAMSE DAVSHQRFEV MERKLYRGIM    60
WPAMLATLIT AHFLVDWGDA TRHYHEALWF YLKVGLVGLL VIYHLVCGYY RKKLIDNAHY   120
KSHKFWRYFN EMPTLILFAV VILVVVKPTF                                   150

SEQ ID NO: 405          moltype = AA   length = 150
FEATURE                 Location/Qualifiers
source                  1..150
                        mol_type = protein
                        organism = Acinetobacter sp.
SEQUENCE: 405
MDAPSDAFLW VKALHIIAVV CWFAALFYLP RLYVYHAMSE DAASHQRFEV MERKLYRGIM    60
WPSMIATLIT AHFLVEWGDA TRHYHQATWF YLKVGLVTLL VIYHLVCGYY RKKLIGNAHY   120
KSHKFWRFFN EMPTLILFAV VILVVVKPQF                                   150

SEQ ID NO: 406          moltype = AA   length = 150
FEATURE                 Location/Qualifiers
source                  1..150
                        mol_type = protein
                        organism = Acinetobacter sp.
SEQUENCE: 406
MDAPTDAFLW VKALHIIAVV CWFAALFYLP RLYVYHAMSE DTISHQRFEV MERKLYRGIM    60
WPSMIATLIT AHFLVDWGDA TQHYHQAVWF YLKVALVALL VIYHFVCGYY RKKLIGNAHY   120
KSHKFWRFFN EMPTLILFAV VILVVVKPQF                                   150

SEQ ID NO: 407          moltype = AA   length = 150
FEATURE                 Location/Qualifiers
source                  1..150
                        mol_type = protein
                        organism = Acinetobacter sp.
SEQUENCE: 407
MDAPSDAFLW VKALHIIAVV CWFAALFYLP RLYVYHAMSD DATSHQRFEV MERKLYRGIM    60
WPSMIATLIT AHFLVEWGDA TRHYHEATWF YLKVGLVALL VIYNLVCGYY RKKLIGNAHY   120
KSHKFWRFFN EMPTLILFAV VILVVVKPQF                                   150

SEQ ID NO: 408          moltype = AA   length = 150
FEATURE                 Location/Qualifiers
source                  1..150
                        mol_type = protein
                        organism = Acinetobacter sp.
SEQUENCE: 408
MDAPSDAFLW VKALHIIAVV CWFAALFYLP RLYVYHAMSD DAVSHQRFEV MERKLYRGIM    60
WPSMIATLIT AHFLVEWGDA TRHYHEALWF YLKVGLVGLL VIYHFVCGYY RKKLIGHAHY   120
```

```
KSHKFWRFFN EMPTLILFAV VILVVVKPTF                                          150

SEQ ID NO: 409         moltype = AA  length = 150
FEATURE                Location/Qualifiers
source                 1..150
                       mol_type = protein
                       organism = Acinetobacter sp.
SEQUENCE: 409
MDAPSDAFLW VKALHIIAVV CWFAALFYLP RLYVYHAMSE DAASHQRFEV MERKLYRGIM          60
WPSMIATLIT AHFLVEWGDA TRHYHDATWF YLKVGLVALL VIYHLVCGYY RKKLIGNAHY         120
KSHKFWRFFN EMPTLILFAV VILVVVKPQF                                          150

SEQ ID NO: 410         moltype = AA  length = 150
FEATURE                Location/Qualifiers
source                 1..150
                       mol_type = protein
                       organism = Acinetobacter sp.
SEQUENCE: 410
MDAPSDAFLW VKALHIIAVV CWFAALFYLP RLYVYHAMSD DAASHQRFEV MERKLYRGIM          60
WPSMIATLIT AHFLVEWGDA TRHYHEATWF YLKVGLVALL VIYHLVCGYY RKKLIGNAHY         120
KSHKFWRFFN EMPTLILFAV VILVVVKPQF                                          150

SEQ ID NO: 411         moltype = AA  length = 150
FEATURE                Location/Qualifiers
source                 1..150
                       mol_type = protein
                       organism = Acinetobacter sp.
SEQUENCE: 411
MDVPSDAFLW VKALHIIAVV CWFAALFYLP RLYVYHAMSD DATSHQRFEV MERKLYRGIM          60
WPSMIATLIT AHFLVEWGDA TRHYHEATWF YLKVGLVALL VIYHLVCGYY RKKLIGNAHY         120
KSHKFWRFFN EMPTLILFAV VILVVVKPQF                                          150

SEQ ID NO: 412         moltype = AA  length = 150
FEATURE                Location/Qualifiers
source                 1..150
                       mol_type = protein
                       organism = Acinetobacter sp.
SEQUENCE: 412
MDAPSDAFLW VKALHIIAVV CWFAALFYLP RLYVYHAMSE DTVSHQRFEV MERKLYRGIM          60
WPAMLATLIT AHFLVDWGDA TRHYHEALWF YLKVGLVGLL VIYHLVCGYY RKKLIDNAHY         120
KSHKFWRYFN EMPTLLLFAV VILVVVKPTF                                          150

SEQ ID NO: 413         moltype = AA  length = 150
FEATURE                Location/Qualifiers
source                 1..150
                       mol_type = protein
                       organism = Acinetobacter sp.
SEQUENCE: 413
MDAPSDAFLW VKALHIIAVV CWFAALFYLP RLYVYHAMSE DAASHQRFEV MERKLYRGIM          60
WPSMIATLIT AHFLVEWGDA TRHYHQATWF YLKVGLVALL MIYHLVCGYY RKKLIGNAHY         120
KSHKFWRFFN EMPTLILFAV VILVVVKPQF                                          150

SEQ ID NO: 414         moltype = AA  length = 150
FEATURE                Location/Qualifiers
source                 1..150
                       mol_type = protein
                       organism = Acinetobacter sp.
SEQUENCE: 414
MDAPSDAFLW VKALHIIAVV CWFAALFYLP RLYVYHAMSE DAVSHQRFEV MERKLYRGIM          60
WPAMLATLIT AHFLVDWGDA TRHYHEALWF YLKVGLVGLL VIYHLVCGYY RKKLIDNAHY         120
KSHKFWRYFN EMPTLLLFAV VILVVVKPTF                                          150

SEQ ID NO: 415         moltype = AA  length = 150
FEATURE                Location/Qualifiers
source                 1..150
                       mol_type = protein
                       organism = Acinetobacter sp.
SEQUENCE: 415
MDAPSDAFLW VKALHIIAVV CWFAALFYLP RLYVYHAMSE DAVSHQRFEV MERKLYRGIM          60
WPSLIATLIT AHFLVDWGDA TRHYHQATWF YLKVGLVALL VIYHLACGYY RKKLIGNAHY         120
KSHKFWRFFN EMPTLILFAV VILVVVKPQF                                          150

SEQ ID NO: 416         moltype = AA  length = 150
FEATURE                Location/Qualifiers
source                 1..150
                       mol_type = protein
                       organism = Acinetobacter sp.
SEQUENCE: 416
MDAPSDAFLW VKALHIIAVV CWFAALFYLP RLYVYHAMSE DAASHQRFEI MERKLYRGIM          60
```

```
WPSMIATLIT AHFLVEWGDA TRHYHQATWF YLKVGLVALL VIYHLVCGYY RKKLIGNAHY    120
KSHRFWRFFN EMPTLILFAV VILVVVKPQF                                    150

SEQ ID NO: 417          moltype = AA  length = 150
FEATURE                 Location/Qualifiers
source                  1..150
                        mol_type = protein
                        organism = Acinetobacter sp.
SEQUENCE: 417
MDAPSDAFLW VKALHIIAVV CWFAALFYLP RLYVYHAMSE DAVSHQRFEV MERKLYRGIM    60
WPAMLATLIT AHFLVDWGDA TRHYHEALWF YLKVGLVGLL VIYHLICGYY RKKLINNAHY    120
KSHKFWRYFN EMPTLILFAV VILVVVKPTL                                    150

SEQ ID NO: 418          moltype = AA  length = 150
FEATURE                 Location/Qualifiers
source                  1..150
                        mol_type = protein
                        organism = Acinetobacter sp.
SEQUENCE: 418
MDAPSDAFLW VKALHIIAVV CWFAALFYLP RLYVYHAMSD DAISHQRFEV MERKLYRGIM    60
WPAMIATLIT AHFLVDWGDA TRHYHEALWF YLKVGLVGLL VIYHLMCGYY RKKLIDNAHY    120
KSHKFWRYFN EMPTLILFAV VILVVVKPTF                                    150

SEQ ID NO: 419          moltype = AA  length = 150
FEATURE                 Location/Qualifiers
source                  1..150
                        mol_type = protein
                        organism = Acinetobacter sp.
SEQUENCE: 419
MDAPSDAFLW VKALHIIAVV CWFAALFYLP RLYVYHAMSE DAASHQRFEI MERKLYRGIM    60
WPSMIATLIT AHFLVEWGDA TRHYHQATWF YLKVALVALL VIYHLVCGYY RKKLIGNAHY    120
KSHKFWRFFN EMPTLILFAV VILVVVKPQF                                    150

SEQ ID NO: 420          moltype = AA  length = 150
FEATURE                 Location/Qualifiers
source                  1..150
                        mol_type = protein
                        organism = Acinetobacter sp.
SEQUENCE: 420
MDAPSDAFLW VKALHIIAVV CWFAALFYLP RLYVYHAMSD DAVSHQRFEV MERKLYRGIM    60
WPSMIATLIT AHFLVDWGDA TRHYHEALWF YLKVGLVGLL VIYHFVCGYY RKKLIRHAHY    120
KSHKFWRFFN EMPTLILFAV VILVVVKPTF                                    150

SEQ ID NO: 421          moltype = AA  length = 150
FEATURE                 Location/Qualifiers
source                  1..150
                        mol_type = protein
                        organism = Acinetobacter sp.
SEQUENCE: 421
MDAPSDAFLW VKALHIIAVV CWFAALFYLP RLYVYHAMSE DTVSHERFQV MERKLYRGIM    60
WPAMVATLIT AHFLVDWGDA TRHYHEALWF YLKVGLVGLL VIYHLCGYY RKKLIENAHY     120
KSHKFWRFFN EMPTLILFAV VILVVVKPTF                                    150

SEQ ID NO: 422          moltype = AA  length = 150
FEATURE                 Location/Qualifiers
source                  1..150
                        mol_type = protein
                        organism = Acinetobacter sp.
SEQUENCE: 422
MDAPSDAFLW VKALHIIAVV CWFAALFYLP RLYVYHAMSE DAASHQRFEV MERKLYRGIM    60
WPSMIATLIT AHFLVEWGDA TRHYHQATWF YLKVALVALL VIYHLVCGYY RKKLIGNAHY    120
KSHRFWRFFN EMPTLILFAV VILVVVKPQF                                    150

SEQ ID NO: 423          moltype = AA  length = 150
FEATURE                 Location/Qualifiers
source                  1..150
                        mol_type = protein
                        organism = Acinetobacter sp.
SEQUENCE: 423
MDAPSDAFLW VKALHIIAVV CWFAALFYLP RLYVYHAMSE DAVSHQRFEV MERKLYRGIM    60
WPSLIATLIT AHFLVDWGDA TRHYHQATWF YLKVALVALL VIYHLACGYY RKKLIGNAHY    120
KSHKFWRFFN EMPTLILFAV VILVVVKPQF                                    150

SEQ ID NO: 424          moltype = AA  length = 150
FEATURE                 Location/Qualifiers
source                  1..150
                        mol_type = protein
SEQUENCE: 424
```

```
MDAPSDAFLW VKALHIIAVV CWFAALFYLP RLYVYHAMSE DAVSHQRFEV MERKLYRGIM    60
WPAMLATLIT AHFLVDWGDA TRHYHEALWF YLKVGLVGLL VIYHLVCGHY RKKLMENAHY   120
KSHKFWRYFN EMPTLILFAV VILVVVKPTF                                   150

SEQ ID NO: 425            moltype = AA  length = 150
FEATURE                   Location/Qualifiers
source                    1..150
                          mol_type = protein
                          organism = Acinetobacter sp.
SEQUENCE: 425
MDAPSDAFLW VKALHIIAVV CWFAALFYLP RLYVYHAMSE DVVSHQRFEI MERKLYRGIM    60
WPAMVATLIT AHFLVDWGDA TRHYHEALWF YLKVGLVGLL VIYHLVCGYY RKKLMENAHY   120
KSHKFWRFFN EMPTLILFAV VILVVVKPTF                                   150

SEQ ID NO: 426            moltype = AA  length = 150
FEATURE                   Location/Qualifiers
source                    1..150
                          mol_type = protein
                          organism = Acinetobacter sp.
SEQUENCE: 426
MDAPSDAFLW VKALHIIAVV CWFAALFYLP RLYVYHAMSE DAASHQRFEV MERKLYRGIM    60
WPSMIATLIT AHFLVEWGDA TRHYHQATWF YLKVALVALL IIYHLVCGYY RKKLIGNAHY   120
KSHRFWRFFN EMPTLILFAV VILVVVKPQF                                   150

SEQ ID NO: 427            moltype = AA  length = 150
FEATURE                   Location/Qualifiers
source                    1..150
                          mol_type = protein
                          organism = Acinetobacter sp.
SEQUENCE: 427
MDAPSDAFLW VKALHIIAVV CWFAALFYLP RLYVYHAMSE DAASHQRFEI MERKLYRGIM    60
WPSMIATLIT AHFLVEWGDA TRHYHQATWF YLKVALVALL VIYHLVCGYY RKKLIGNAHY   120
KSHRFWRFFN EMPTLILFAV VILVVVKPQF                                   150

SEQ ID NO: 428            moltype = AA  length = 150
FEATURE                   Location/Qualifiers
source                    1..150
                          mol_type = protein
                          organism = Acinetobacter sp.
SEQUENCE: 428
MDAPTDAFLW VKALHIIAVV CWFAALFYLP RLYVYHAMSE DTISHQRFEV MERKLYRGIM    60
WPSMIATLIT AHFLVDWGDG TQHYHQAGWF YLKVALVALL VIYHFVCGYY RKKLIGNAHY   120
KSHKFWRFFN EMPTLILFAV VILVVVKPQF                                   150

SEQ ID NO: 429            moltype = AA  length = 150
FEATURE                   Location/Qualifiers
source                    1..150
                          mol_type = protein
                          organism = Acinetobacter sp.
SEQUENCE: 429
MDAPSDAFLW VKALHIIAVV CWFAALFYLP RLYVYHAMSE DAASHQRFEI MERKLYRGIM    60
WPSLIATLIT AHFLVDWGDA TRHYHQATWF YLKVALVALL VIYHLACGYY RKKLIGNAHY   120
KSHKFWRFFN EMPTLILFAV VILVVVKPQF                                   150

SEQ ID NO: 430            moltype = AA  length = 150
FEATURE                   Location/Qualifiers
source                    1..150
                          mol_type = protein
                          organism = Acinetobacter sp.
SEQUENCE: 430
MDAPSDAFLW VKALHIIAVV CWFAALFYLP RLYVYHAMSE DVVSHQRFEI MERKLYRGIM    60
WPAMVATLIT AHFLVDWGDA TRHYHEALWF YLKVGLVGLL VIYHLICGYY RKKLMENAHY   120
KSHKFWRFFN EMPTLILFAV VILVVVKPTF                                   150

SEQ ID NO: 431            moltype = AA  length = 150
FEATURE                   Location/Qualifiers
source                    1..150
                          mol_type = protein
                          organism = Acinetobacter sp.
SEQUENCE: 431
MDAPSDAFLW VKALHIIAVV CWFAALFYLP RLYVYHAMSE DAASHQRFEV MERKLYRGIM    60
WPSMIATLIT AHFLVEWGDA TRHYHQATWF YLKVALVALL VIYHLVCGYY RKKLIGNAHY   120
KSHRFWRFFN EMPTVILFAV VILVVVKPQF                                   150

SEQ ID NO: 432            moltype = AA  length = 150
FEATURE                   Location/Qualifiers
source                    1..150
                          mol_type = protein
                          organism = Acinetobacter sp.
```

```
SEQUENCE: 432
MDAPSDAFLW VKALHIIAVV CWFAALFYLP RLYVYHAMSE DTLSHQRFEI MERKLYRGIM    60
WPSMIATLIT AHFLVDWGDA TRNYHDALWF YLKVALVGLL VIYHLVCGYY RQKLIGNAHY   120
KSHKFWRFFN EMPTVLLLAI VILVVVKPQF                                   150

SEQ ID NO: 433         moltype = AA   length = 150
FEATURE                Location/Qualifiers
source                 1..150
                       mol_type = protein
                       organism = Acinetobacter sp.
SEQUENCE: 433
MDAPSDAFLW VKALHIIAVV CWFAALFYLP RLYVYHAMSE DAVSHARFQV MERKLYRGIM    60
WPAMLATLIT AHFLVDWGDA TRHYHEAVWF YLKVGLVGLL VIYHLVCGHY RKKLMENAHY   120
KSHKFWRYFN EMPTLILFAV VILVVVKPTF                                   150

SEQ ID NO: 434         moltype = AA   length = 150
FEATURE                Location/Qualifiers
source                 1..150
                       mol_type = protein
                       organism = Acinetobacter sp.
SEQUENCE: 434
MDAPSDAFLW VKALHIIAVV CWFAALFYLP RLYVYHAMSE DAVSHQRFEV MERKLYRGIM    60
WPSMIATLIT AHFLVDWGDA TRNYHDALWF YLKVALVGLL VIYHLVCGYY RLKLIGNAHY   120
KSHKFWRFFN EMPTVLLFAI VILVVVKPVF                                   150

SEQ ID NO: 435         moltype = AA   length = 150
FEATURE                Location/Qualifiers
source                 1..150
                       mol_type = protein
                       organism = Acinetobacter sp.
SEQUENCE: 435
MDAPSDAFLW VKALHIIAVV CWFAALFYLP RLYVYHAMSE DAVSHQRFEV MERKLYRGIM    60
WPSMIATLIT AHFLVDWGDA TRHYHEALWF YLKVGLVGLL VIYHLVCGYY RKKLIGNAHY   120
KTHKFWRFFN EMPTLILFAV VVLVVVKPQF                                   150

SEQ ID NO: 436         moltype = AA   length = 150
FEATURE                Location/Qualifiers
source                 1..150
                       mol_type = protein
                       organism = Acinetobacter sp.
SEQUENCE: 436
MDAPSSAFLW VKALHIIAVV CWFAALFYLP RLYVYHAMSK DQASYERFQI MERKLYRGIM    60
WPAMIATLIT AHFLVDWGDA TRHYHEALWF YFKVGLVGLL IIYHFVCGYY RKKLIDNAHY   120
KTHKFWRMFN ELPTVILFAV VILVVVKPQF                                   150

SEQ ID NO: 437         moltype = AA   length = 149
FEATURE                Location/Qualifiers
source                 1..149
                       mol_type = protein
                       organism = Acinetobacter sp.
SEQUENCE: 437
MNAPSDAFFW IKALHIIAVV CWFAALFYLP RLYVYHAMSD DTVSHQRFEV MERKLYRGIM    60
WPAMIATLIT AHFLVDWGDQ FYHYHEALWF YLKVALVGLL VIYHFVCGYY RKKLIGNAHY   120
KTHKFWRFFN EMPTLLLFAI VILVVVKPF                                    149

SEQ ID NO: 438         moltype = AA   length = 150
FEATURE                Location/Qualifiers
source                 1..150
                       mol_type = protein
                       organism = Acinetobacter sp.
SEQUENCE: 438
MDAPSDAFLW VKALHIIAVV CWFAALFYLP RLYVYHAMSE DTVSHQRFEV MERKLYRGIM    60
WPSMIATLIT AHFLVDWGDA TRHYHEALWF YLKVGLVGLL VIYHFVCGYY RKKLIGNAHY   120
KSHKFWRFFN EMPTLILLAV VILVVVKPQF                                   150

SEQ ID NO: 439         moltype = AA   length = 142
FEATURE                Location/Qualifiers
source                 1..142
                       mol_type = protein
                       organism = Acinetobacter sp.
SEQUENCE: 439
MWVKALHIIA VVCWFAALFY LPRLYVYHAM SDDATSHQRF EVMERKLYRG IMWPSMIATL    60
ITAHFLVDWG DATRHYHEAT WFYLKVGLVA LLVIYHLVCG YYRKKLIGNA HYKSHKFWRF   120
FNEMPTLILF AVVILVVVKP QF                                           142

SEQ ID NO: 440         moltype = AA   length = 150
FEATURE                Location/Qualifiers
source                 1..150
                       mol_type = protein
```

```
                        organism = Acinetobacter sp.
SEQUENCE: 440
MDAPSDAFLW VKALHIIAVV CWFAALFYLP RLYVYHAMSD DAVSHQRFEV MERKLYRGIM    60
WPSMIATLIT AHFLVDWGDA TRHYHEALWF YLKVGLVGLL VIYHFVCGYY RKKLIGNAHY   120
KSHKFWRFFN EMPTLILVAV IILVVVKPQF                                   150

SEQ ID NO: 441          moltype = AA   length = 150
FEATURE                 Location/Qualifiers
source                  1..150
                        mol_type = protein
                        organism = Acinetobacter sp.
SEQUENCE: 441
MDAPSDAFLW VKALHIIAVV CWFAALFYLP RLYVYHAMSE DAVSHQRFEV MERKLYRGIM    60
WPSMIATLVT AHFLVDWGDA TRHYHEALWF YLKVALVGLL VIYHLVCGYY RKKLIGNAHY   120
KSHKFWRFFN EMPTVILLAV VILVVVKPQF                                   150

SEQ ID NO: 442          moltype = AA   length = 150
FEATURE                 Location/Qualifiers
source                  1..150
                        mol_type = protein
                        organism = Acinetobacter sp.
SEQUENCE: 442
MDAPSDAFLW VKALHIIAVV CWFAALFYLP RLYVYHAMSE DGTSHQRFQI MERKLYRGIM    60
WPSMLATLIT AHFLVDWGDA TRHYHEALWF YLKVGLVGLL VIYHFVCGYY RKKLMENPHY   120
KSHKFWRFFN EMPTLILLAV VILVVVKPQF                                   150

SEQ ID NO: 443          moltype = AA   length = 150
FEATURE                 Location/Qualifiers
source                  1..150
                        mol_type = protein
                        organism = Acinetobacter sp.
SEQUENCE: 443
MNAPSEAFLW VKALHIIAVV CWFAALFYLP RLYVYHAMSD DDASHQRFEV MERKLYRGIM    60
WPAMIATLIT AHFLVDWGDA TYHYHEALWF YLKVGLVGLL VIYHFVCGYY RKKLIGNAHY   120
KSHKFWRVFN EMPTLILLAV VILVVVKPTF                                   150

SEQ ID NO: 444          moltype = AA   length = 148
FEATURE                 Location/Qualifiers
source                  1..148
                        mol_type = protein
                        organism = Acinetobacter sp.
SEQUENCE: 444
MVSEAFLWVK ALHIIAVVCW FAALFYLPRL YVYHAMSDDL ASHQRFEVME RKLYRGIMWP    60
AMIATLITAH FLVDWGDATQ HYHEATWFYI KVALVGLLVI YHFVCGYYRK KLIGNAHYKS   120
HKFWRFFNEM PTLLLLAIVI LVVVKPQF                                     148

SEQ ID NO: 445          moltype = AA   length = 150
FEATURE                 Location/Qualifiers
source                  1..150
                        mol_type = protein
                        organism = Acinetobacter sp.
SEQUENCE: 445
MNAPSDAFLW VKALHIIAVV CWFAALFYLP RLYVYHAMSD DAISHQRFQV MERKLYRGIM    60
WPAMIATLIT AHFLVAWGDA TQHYHLAHWF YVKVALVGLL VIYHFVCGYY RKKLIENAHY   120
KSHKFWRFFN EMPTVILLAV VILVVVKPQF                                   150

SEQ ID NO: 446          moltype = AA   length = 150
FEATURE                 Location/Qualifiers
source                  1..150
                        mol_type = protein
                        organism = Acinetobacter sp.
SEQUENCE: 446
MNAPSDAFLW VKALHIIAVV CWFAALFYLP RLYVYHAMSD DAISHQRFQV MERKLYRGIM    60
WPAMIATLIT AHFLVAWGDA TQHYHLAHWF YLKVALVGLL VIYHFVCGYY RKKLIENAHY   120
KSHKFWRFFN EMPTVILLAV VILVVVKPQF                                   150

SEQ ID NO: 447          moltype = AA   length = 150
FEATURE                 Location/Qualifiers
source                  1..150
                        mol_type = protein
                        organism = Acinetobacter sp.
SEQUENCE: 447
MDVPSDAFLW VKAFHIISIV CWFAALFYLP RLYVYHAMSN DAVSHQRFQV MERKLYRGIM    60
WPSMIATLIT AHFLVDWGDA TQHYHEALWF YLKLGLVGLL VIYHLFCGYY RQKLILDAHY   120
KSHKFWRFFN EMPTFILVAV IILVVVKPHF                                   150

SEQ ID NO: 448          moltype = AA   length = 181
FEATURE                 Location/Qualifiers
source                  1..181
```

```
                        mol_type = protein
                        organism = Escherichia sp.
SEQUENCE: 448
MKTLILFSTR DGQTREIASY LASELKELGI QADVANVHRI EEPQWENYDR VVIGASIRYG      60
HYHSAFQEFV KKHATRLNSM PSAFYSVNLV ARKPEKRTPQ TNSYARKFLM NSQWRPDRCA     120
VIAGALRYPR YRWYDRFMIK LIMKMSGGET DTRKEVVYTD WEQVANFARE IAHLTDKPTL     180
K                                                                     181

SEQ ID NO: 449          moltype = AA  length = 181
FEATURE                 Location/Qualifiers
source                  1..181
                        mol_type = protein
                        organism = Escherichia sp.
SEQUENCE: 449
MKTLILFSTR DGQTREIASY LASELKELGI QADVANVHRI EEPQWENYDR VVIGASIRYG      60
HYHSAFQEFV KKHATRLNSM PSAFYSVNLV ARKPEKRTPQ TNSYARKFLM NSQWRPDRCA     120
VIAGALRYPR YRWYDRFMIK LIMKMSGGET DTRKEVVYTD WEQVANFARE IAHLTDKPTL     180
K                                                                     181

SEQ ID NO: 450          moltype = AA  length = 181
FEATURE                 Location/Qualifiers
source                  1..181
                        mol_type = protein
                        organism = Enterobacter sp.
SEQUENCE: 450
MKTLILFSTR DGQTREIASY LASELKELGI QADVTNVHRI EEPQWENYDR VVIGASIRYG      60
HYHSAFQEFV KKHATRLNSM PSAFYSVNLV ARKPEKRTPQ TNSYARKFLM NSQWRPDRCA     120
VIAGALRYPR YRWYDRFMIK LIMKMSGGET DTRKEVVYTD WEQVANFARE IAHLTDKPTL     180
K                                                                     181

SEQ ID NO: 451          moltype = AA  length = 181
FEATURE                 Location/Qualifiers
source                  1..181
                        mol_type = protein
                        organism = Shigella sp.
SEQUENCE: 451
MKTLILFSTR DGQTREIASY LASELKELGI QTDVANVHRI EEPQWENYDR VVIGASIRYG      60
HYHSAFQEFV KKHATRLNSM PSAFYSVNLV ARKPEKRTPQ TNSYARKFLM NSQWRPDRCA     120
VIAGALRYPR YRWYDRFMLK LIMKMSGGET DTRKEVVYTD WEQVANFARE IAHLTDKPTL     180
K                                                                     181

SEQ ID NO: 452          moltype = AA  length = 181
FEATURE                 Location/Qualifiers
source                  1..181
                        mol_type = protein
                        organism = Escherichia sp.
SEQUENCE: 452
MKTLILFSTR DGQTREIAAY LASELKELGI QADVANVHRI EEPQWENYDR VVIGASIRYG      60
HYHSAFQEFV KKHATRLNSM PSAFYSVNLV ARKPEKRTPQ TNSYARKFLM SSQWRPDRCA     120
VIAGALRYPR YRWYDRFMIK LIMKMSGGET DTRKEVVYTD WEQVANFARE IAHLTDKPTL     180
K                                                                     181

SEQ ID NO: 453          moltype = AA  length = 180
FEATURE                 Location/Qualifiers
source                  1..180
                        mol_type = protein
                        organism = Shigella sp.
SEQUENCE: 453
MKTLILFSTR DGQTREISSY LASELKELGI QTDVANVHRI EEPQWENYDR VVIGASIRYG      60
HYHSAFQEFV KKHATRLNSM PSAFYSVNLV ARKPEKRTPQ TNSYARKFLM NSQWRPDRCA     120
VIAGALRYPR YRWYDRFMLK LIMKMSGGET DTRKEVVTDW EQVANFAREI AHLTDKPTLK     180

SEQ ID NO: 454          moltype = AA  length = 181
FEATURE                 Location/Qualifiers
source                  1..181
                        mol_type = protein
                        organism = Escherichia sp.
SEQUENCE: 454
MKTLILFSTR DGQTREIASY LASELKELGI QADVANVHRT EEPQWENYDR VVIGASIRYG      60
HYHSAFQEFV KKHATRLNSM PSAFYSVNLV ARKPEKRTPQ TNSYARKFLM SSQWRPDRCA     120
VIAGALRYPR YRWYDRFMIK LIMKMSGGET DTRKEVVYTD WEQVANFARE IAHLTDKPTL     180
K                                                                     181

SEQ ID NO: 455          moltype = AA  length = 181
FEATURE                 Location/Qualifiers
source                  1..181
                        mol_type = protein
                        organism = Escherichia sp.
SEQUENCE: 455
```

```
MKTLILFSTR DGQTREIASY LASELKELGI QADVANVHRI EEPQWENYDR VVIGASIRYG    60
HYHSAFQEFV KKHATQLNSM PSAFYSVNLV ARKPEKRTPQ TNSYARKFLM NSQWRPDRCA   120
VIAGALRYPR YRWYDRFMIK LIMKMSGGET DTRKEVVYTD WEQVANFARE IAHLTDKPTP   180
K                                                                  181

SEQ ID NO: 456          moltype = AA   length = 181
FEATURE                 Location/Qualifiers
source                  1..181
                        mol_type = protein
                        organism = Shigella sp.
SEQUENCE: 456
MKTLILFSTR DGQTREIASY LASELKELGI QTDVANVHRI EEPQWENYGR VVIGASIRYG    60
HYHSAFQEFV KKHATRLNSM PSAFYSVNLV ARKPEKRTPQ TNSYARKFLM NSQWRPDRCA   120
VIAGALRYPR YRWYDRFMLK LIMKMSGGET DTRKEVVYTD WEQVANFARE IAHLTDKPTL   180
K                                                                  181

SEQ ID NO: 457          moltype = AA   length = 181
FEATURE                 Location/Qualifiers
source                  1..181
                        mol_type = protein
                        organism = Escherichia sp.
SEQUENCE: 457
MKTLILFSTR DGQTREIASY LASELKELGI QADVANVHRI EEPQWENYDR VVIGASIRYG    60
HYHSAFQEFV KKHATRLNSM PSAFYSVNLV ARKPEKRTPQ TNSYARKFLM SSQWRPDRCA   120
VIAGALRYPR YRWYDRFMIK LIMKMSGGET DTRKEVVYTD WQQVENFARE IAHLTDKPTL   180
K                                                                  181

SEQ ID NO: 458          moltype = AA   length = 181
FEATURE                 Location/Qualifiers
source                  1..181
                        mol_type = protein
                        organism = Shigella sp.
SEQUENCE: 458
MKTLILFSTR DGQTREIASY LASELKELGI QTDVANVHRI EEPQWENYDR VVIGASIRYG    60
HYHSAFQEFV KKHATRLNSM PSAFYSVNLV ARKPEKRTPQ TNSYARKFLM NSQWRPDRCA   120
VIAGALRYPR YRWYDRFMIK LIMKMSGGET DTRKEVVYTD WEQVANFARE IAQLTNKPTL   180
K                                                                  181

SEQ ID NO: 459          moltype = AA   length = 181
FEATURE                 Location/Qualifiers
source                  1..181
                        mol_type = protein
                        organism = Escherichia sp.
SEQUENCE: 459
MKTLILFSTR DGQTREIASY LASELKELGI QADVANVHRT EEPQWENYDR VVIGASIRYG    60
HYHSAFEEFV KKHETRLNSM PSAFYSVNLV ARKPEKRTPQ TNSYARKFLM SSQWRPDRCA   120
VIAGALRYPR YRWYDRFMIK LIMKMSGGET DTRKEVVYTD WEQVANFARE IAHLTDKPTL   180
K                                                                  181

SEQ ID NO: 460          moltype = AA   length = 181
FEATURE                 Location/Qualifiers
source                  1..181
                        mol_type = protein
                        organism = Escherichia sp.
SEQUENCE: 460
MKTLILFSTR DGQTREIASY LASELKELGI LADVANVHRT EEPQWENYDR VVIGASIRYG    60
HYHSAFQEFV KKHATRLNSM PSAFYSVNLV ARKPEKRTPQ TNSYARKFLM SSQWRPDRCA   120
VIAGALRYPR YRWYDRFMIK LIMKMSGGET DTRKEVVYTD WEQVANFARE IAHLTDKPTM   180
K                                                                  181

SEQ ID NO: 461          moltype = AA   length = 181
FEATURE                 Location/Qualifiers
source                  1..181
                        mol_type = protein
                        organism = Enterobacter sp.
SEQUENCE: 461
MKTLILFSTR DGQTREIASY LASELKELGI QTDVANVHRI EEPQWENYDR VVIGASIRYG    60
HYHSAFQEFV KKHATRLNSM PSAFYSVNLV ARKPEKRTPQ TNSYARKFLM SSQWRPDRCA   120
VIAGALRYPR YRWYDRFMIK LIMKMSGGET DTRKEVVYTD WEQVANFARE IAQLTNKPTL   180
K                                                                  181

SEQ ID NO: 462          moltype = AA   length = 181
FEATURE                 Location/Qualifiers
source                  1..181
                        mol_type = protein
                        organism = Shigella sp.
SEQUENCE: 462
MKTLILFSTR DGQTREIASY LASELKELGI QTDVANVHRI EEPQWKNYDR VVIGASIRYG    60
HYHSAFQEFV KKHATRLNSM PSAFYSVNLV ARKPEKRTPQ TNSYARKFLM SSQWRPDRCA   120
```

```
VIAGALRYPR YRWYDRFMIK LIMKMSGGET DTRKEVVYTD WEQVANFARE IAQLTNKPTL    180
K                                                                  181

SEQ ID NO: 463          moltype = AA  length = 181
FEATURE                 Location/Qualifiers
source                  1..181
                        mol_type = protein
                        organism = Shigella sp.
SEQUENCE: 463
MKTLILFSTR DGQTREIASY LASELKELGI QTDVANVHRI EEPQWENYDR VVIGASIRYG    60
HYHSAFQEFV KKHATRLNSM PSAFYSVNLV ARKPEKRTPQ TNSYARKFLM SSQWRPDRCA   120
VIAGALRYPR YCWYDRFMIK LIMKMSGGET DTRKEVVYTD WEQVANFARE IAQLTNKPTL   180
K                                                                  181

SEQ ID NO: 464          moltype = AA  length = 181
FEATURE                 Location/Qualifiers
source                  1..181
                        mol_type = protein
                        organism = Salmonella sp.
SEQUENCE: 464
MKTLILFSTR DGQTREIASY LASELKEMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK LIMKMSGGET DTRKEVVYTD WEQVANFARE IAHLTNKSSA   180
K                                                                  181

SEQ ID NO: 465          moltype = AA  length = 161
FEATURE                 Location/Qualifiers
source                  1..161
                        mol_type = protein
                        organism = Shigella sp.
SEQUENCE: 465
MASELKELGI QADVANVHRI EEPQWENYDR VVIGASIRYG HYHSAFQEFV KKHATRLNSM    60
PSAFYSVNLV ARKPEKRTPQ TNSYARKFLM NSQWRPDRCA VIAGALRYPR YRWYDRFMIK   120
LIMKMSGGET DTRKEVVYTD WEQVANFARE IAHLTDKPTL K                       161

SEQ ID NO: 466          moltype = AA  length = 181
FEATURE                 Location/Qualifiers
source                  1..181
                        mol_type = protein
                        organism = Citrobacter sp.
SEQUENCE: 466
MKTLILFSTR DGQTREIASY LASELKELGI WADVVNLHRT EEPEWDSYDR VVIGASIRYG    60
HYHTAFQEFV KKHATRLNGM PSAFYSVNLV ARKPEKRTPQ TNSYARKFLM SSQWRPDRCA   120
VIAGALLYPR YRWYDRIMIK LIMKMSGGET DTNKEVIYTD WEQVAGFARE IAQLTVKSPV   180
K                                                                  181

SEQ ID NO: 467          moltype = AA  length = 181
FEATURE                 Location/Qualifiers
source                  1..181
                        mol_type = protein
                        organism = Salmonella sp.
SEQUENCE: 467
MKTLILFSTR DGQTREIASY LASELKEMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDHCA   120
VIAGALRYPR YRWYDRLMIK LIMKMSGGET DTSKEVVYTD WEQVANFARE IAHLTNKSSA   180
K                                                                  181

SEQ ID NO: 468          moltype = AA  length = 181
FEATURE                 Location/Qualifiers
source                  1..181
                        mol_type = protein
                        organism = Citrobacter sp.
SEQUENCE: 468
MKTLILFSTR DGQTREIASY LASELKELGI WADVINLHRT EELDWQSYDR VVIGASIRYG    60
HYHAAFQEFV KKHATRLNAM PSAFYSVNLV ARKPEKRTPQ TNSYARKFLM SSQWRPDLCA   120
VIAGALRYPR YRWYDRLMIK LIMKMSGGET DTSKEVVYTD WEQVANFARD IAQLTNKSLA   180
K                                                                  181

SEQ ID NO: 469          moltype = AA  length = 181
FEATURE                 Location/Qualifiers
source                  1..181
                        mol_type = protein
                        organism = Salmonella sp.
SEQUENCE: 469
MKTLILFSTR DGQTREIASY LASELKEMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDHCA   120
VIAGALRYPR YRWYDRLMIK LIMKMSGGET DTSKEVVYTD WDQVANFARE IAHLTNKSSA   180
K                                                                  181
```

```
SEQ ID NO: 470          moltype = AA  length = 181
FEATURE                 Location/Qualifiers
source                  1..181
                        mol_type = protein
                        organism = Salmonella sp.
SEQUENCE: 470
MKTLILFSTR DGQTREIASY LASELKEMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDHCA   120
VIAGALRYPR YRWYDRLMIK LIMKLSGGET DTSKEVVYTD WEQVANFARE IAHLTNKSSA   180
K                                                                   181

SEQ ID NO: 471          moltype = AA  length = 181
FEATURE                 Location/Qualifiers
source                  1..181
                        mol_type = protein
                        organism = Salmonella sp.
SEQUENCE: 471
MKTLILFSTR DGQTREIASY LASELKEMGI WADVVNLHRA EEPDWDKYDR VVIGASIRYG    60
HYHSAFQEFV KKYSTRLNGM PSAFYSVNLV ARKPEKRTPQ TNSYARKFLM NSPWRPDHCA   120
VIAGALRYPC YRWYDRLMIK LIMKMSGGET DTSKEVVYTD WDQVAKFARE IAHLTNKPSS   180
K                                                                   181

SEQ ID NO: 472          moltype = AA  length = 181
FEATURE                 Location/Qualifiers
source                  1..181
                        mol_type = protein
                        organism = Citrobacter sp.
SEQUENCE: 472
MKTLILFSTR DGQTREIASY LASELKELGI WADVINLHRT EELDWQSYDR VVIGASIRYG    60
HYHSAFQEFV KKHATRLNAM PSAFYSVNLV ARKPEKRTPQ TNSYARKFLM SAQWRPDLCA   120
VIAGALRYPR YRWYDRLMIK LIMKMSGGET DTSKEVVYTD WEQVANFARD IAQLTNKSLA   180
K                                                                   181

SEQ ID NO: 473          moltype = AA  length = 181
FEATURE                 Location/Qualifiers
source                  1..181
                        mol_type = protein
                        organism = Salmonella sp.
SEQUENCE: 473
MKTLILFSTR DGQTREIASY LASELKEMGI RADVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK LIMKMSGGET DTSKEVVYTD WEQVAHFARE IAHLTNKSSA   180
K                                                                   181

SEQ ID NO: 474          moltype = AA  length = 181
FEATURE                 Location/Qualifiers
source                  1..181
                        mol_type = protein
                        organism = Citrobacter sp.
SEQUENCE: 474
MKTLILFSSR DGQTREIAAY LASELKELGI WADVFNLHRT EEPDWESYDR VVIGASIRYG    60
HYHSAFLDFV KKHATRLNQM PSAFYSVNLV ARKPEKRTPQ TNSYARKFLM HSQWRPDRSA   120
VIAGALLYPR YRWYDRIMIK LIMKMSGGET DTRKEVIYTD WEQVASFARE IAQLTDKSSV   180
K                                                                   181

SEQ ID NO: 475          moltype = AA  length = 181
FEATURE                 Location/Qualifiers
source                  1..181
                        mol_type = protein
                        organism = Salmonella sp.
SEQUENCE: 475
MKTLILFSTR DGQTREIASY LASELKEMGI WADVVNLHRA EEPDWDKYDR VVIGASIRYG    60
HYHSAFQEFV KKYATRLNGM PSAFYSVNLV ARKPEKRTPQ TNSYARKFLM SSPWRPDHCA   120
VIAGALRYPC YRWYDRLMIK LIMKMSGGET DTSKEVVYTD WDQVAKFARE IAHLTNKPSS   180
K                                                                   181

SEQ ID NO: 476          moltype = AA  length = 181
FEATURE                 Location/Qualifiers
source                  1..181
                        mol_type = protein
                        organism = Citrobacter sp.
SEQUENCE: 476
MKTLILFSTR DGQTREIASY LASELKALGI WADVINLHRT EELDWQSYDR VVIGASIRYG    60
HYHAAFQEFV KKHATRLNAM PSAFYSVNLV ARKPEKRTPQ TNSYARKFLM SSQWRPDLCA   120
VIAGALRYPR YRWYDRLMIK LIMKMSGGET DTSKEVVYTD WEQVANFARD IAQLTNKSLA   180
K                                                                   181

SEQ ID NO: 477          moltype = AA  length = 181
FEATURE                 Location/Qualifiers
```

```
source                        1..181
                              mol_type = protein
                              organism = Salmonella sp.
SEQUENCE: 477
MKTLILFSTR DGQTREIASY LASELKEMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK LIMKMSGGET DTSKEVVYTD WEQVAHFARE IAHLTNKSSA   180
K                                                                  181

SEQ ID NO: 478                moltype = AA   length = 181
FEATURE                       Location/Qualifiers
source                        1..181
                              mol_type = protein
                              organism = Salmonella sp.
SEQUENCE: 478
MKTLILFSTR DGQTREIASY LASELKEMGI WADVVNLHRA EEPDWDCYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK LIMKMSGGET DTSKEVVYTD WEQVAHFARE IAHLTNKSSA   180
K                                                                  181

SEQ ID NO: 479                moltype = AA   length = 181
FEATURE                       Location/Qualifiers
source                        1..181
                              mol_type = protein
                              organism = Salmonella sp.
SEQUENCE: 479
MKTLILFSTR DGQTREIASY LASELKEMGI WADVVNLHRA EEPDWDSYDR VVIGASIRYG    60
HYHSAFQEFV KKYATRLNGM PSAFYSVNLV SRKAEKRTPQ TNSYARKFLM SSPWRPDYCA   120
VIAGALRYPR YRWYDRLMIK LIMKMSGGET DTSKEVVYTD WEQVAHFARE IAHLTNKSSA   180
K                                                                  181

SEQ ID NO: 480                moltype = AA   length = 181
FEATURE                       Location/Qualifiers
source                        1..181
                              mol_type = protein
                              organism = Salmonella sp.
SEQUENCE: 480
MKTLILFSTR DGQTREIASY LASELKDMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK LIMKMSGGET DTSKEVVYTD WEQVAHFARE IAHLTNKSSA   180
K                                                                  181

SEQ ID NO: 481                moltype = AA   length = 181
FEATURE                       Location/Qualifiers
source                        1..181
                              mol_type = protein
                              organism = Salmonella sp.
SEQUENCE: 481
MKTLILFSTR DGQTREIASY LASELKEMGI WGDVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK LIMKMSGGET DTSKEVVYTD WEQVAHFARE IAHLTNKSSA   180
K                                                                  181

SEQ ID NO: 482                moltype = AA   length = 181
FEATURE                       Location/Qualifiers
source                        1..181
                              mol_type = protein
                              organism = Salmonella sp.
SEQUENCE: 482
MKTLILFSTR DGQTREIASY LASELKEMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK FIMKMSGGET DTSKEVVYTD WEQVAHFARE IAHLTNKSSA   180
K                                                                  181

SEQ ID NO: 483                moltype = AA   length = 181
FEATURE                       Location/Qualifiers
source                        1..181
                              mol_type = protein
                              organism = Salmonella sp.
SEQUENCE: 483
MKTLILFSTR DGQTREIASY LASELKEMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK LIMKMSGGET DTSKEAVYTD WEQVAHFARE IAHLTNKSSA   180
K                                                                  181

SEQ ID NO: 484                moltype = AA   length = 181
FEATURE                       Location/Qualifiers
source                        1..181
                              mol_type = protein
```

```
                              organism = Salmonella sp.
SEQUENCE: 484
MKTLILFSTR DGQTREIASY LASELKEMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK LIMKMSGGET DTSKEVVYTD WEQVTHFARE IAHLTNKSSA   180
K                                                                  181

SEQ ID NO: 485           moltype = AA  length = 181
FEATURE                  Location/Qualifiers
source                   1..181
                         mol_type = protein
                         organism = Salmonella sp.
SEQUENCE: 485
MKTLILFSTR DGQTHEIASY LASELKEMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK LIMKMSGGET DTSKEVVYTD WEQVAHFARE IAHLTNKSSA   180
K                                                                  181

SEQ ID NO: 486           moltype = AA  length = 181
FEATURE                  Location/Qualifiers
source                   1..181
                         mol_type = protein
                         organism = Salmonella sp.
SEQUENCE: 486
MKTLILFSTR DGQTREIASY LASELKEMGI WADVVNLHRA EEPDWDSYDR VVIGASIRYG    60
HYHSAFQEFV KKYAKRLNGM PSAFYSVNLV ARKAEKRTPQ TNSYARKFLM SSPWRPDYCA   120
VIAGALRYPR YRWYDRLMIK LIMKMSGGET DTSKEVVYTD WEQVAHFARE IAHLTNKSSA   180
K                                                                  181

SEQ ID NO: 487           moltype = AA  length = 181
FEATURE                  Location/Qualifiers
source                   1..181
                         mol_type = protein
                         organism = Salmonella sp.
SEQUENCE: 487
MKTLILFSTR DGQTREIASY LASELKEMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK LIMQMSGGET DTSKEVVYTD WEQVTHFARE IAHLTNKSSA   180
K                                                                  181

SEQ ID NO: 488           moltype = AA  length = 181
FEATURE                  Location/Qualifiers
source                   1..181
                         mol_type = protein
                         organism = Salmonella sp.
SEQUENCE: 488
MKTLILFSTW DGQTREIASY LASELKEMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK LIMKMSGGET DTSKEVVYTD WEQVAHFARE IAHLTNKSSA   180
K                                                                  181

SEQ ID NO: 489           moltype = AA  length = 181
FEATURE                  Location/Qualifiers
source                   1..181
                         mol_type = protein
                         organism = Salmonella sp.
SEQUENCE: 489
MKTLILFSTR DGQTREIASY LASELKEMGI WADVVNLHRA EEPDWDKYDR VVIGASIRYG    60
HYHSAFQEFV KKYATRLNGM PSAFYSVNLV ARKPEKRTPQ TNSYARKFLM SSPWRPDYCA   120
VIAGALRYPC YRWYDRLMIK LIMKMSGGET DTSKEVVYTD WDQVAKFARE IAHLTNKLSS   180
K                                                                  181

SEQ ID NO: 490           moltype = AA  length = 181
FEATURE                  Location/Qualifiers
source                   1..181
                         mol_type = protein
                         organism = Salmonella sp.
SEQUENCE: 490
MKTLILFSTR DGQTREIASY LASELKEMGI WGDVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPS YRWYDRLMIK LIMKMSGGET DTSKEVVYTD WEQVAHFARE IAHLTNKSSA   180
K                                                                  181

SEQ ID NO: 491           moltype = AA  length = 181
FEATURE                  Location/Qualifiers
source                   1..181
                         mol_type = protein
                         organism = Salmonella sp.
SEQUENCE: 491
```

```
MKTLILFSTR DGQTREIASY LASELKEMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK LIMKMSGGET DTSKEVVYTD WEQVTHFARE IAHLNNKSSA   180
K                                                                  181

SEQ ID NO: 492          moltype = AA  length = 181
FEATURE                 Location/Qualifiers
source                  1..181
                        mol_type = protein
                        organism = Salmonella sp.
SEQUENCE: 492
MKILILFSTR DGQTREIASY LASELKEMGI WADVVNLHRA EEPDWDSYDR VVIGASIRYG    60
HYHSAFQEFV KKYAPRLNGM PSAFYSVNLV ARKAEKRTPQ TNSYARKFLM SSPWRPDHCA   120
VIAGALRYPR YRWYDRLMIK LIMKMSGGET DTSKEVVYTD WDQVANFARE IAHLTNKSSA   180
K                                                                  181

SEQ ID NO: 493          moltype = AA  length = 181
FEATURE                 Location/Qualifiers
source                  1..181
                        mol_type = protein
                        organism = Citrobacter sp.
SEQUENCE: 493
MKTLILFSSR DGQTREIAAY LASELKELGI CTDVVNLHRI EEPDWERYDR VVIGASIRYG    60
HYHSAFLEFV KKHATRLNHM PSAFYSVNLV ARKPEKRTPQ TNSYARKFLM NSQWRPDRSA   120
VIAGALLYPR YRWYDRMMIQ LIMKMSGGET DTRKEVIYTD WEQVASFARE VAQLTPDSLV   180
K                                                                  181

SEQ ID NO: 494          moltype = AA  length = 176
FEATURE                 Location/Qualifiers
source                  1..176
                        mol_type = protein
                        organism = Salmonella sp.
SEQUENCE: 494
MKTLILFSTR DGQTREIASY LASELKEMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK LIMKMSGGET DTSKEVVYTD WEQVAHFARE IAHLTN       176

SEQ ID NO: 495          moltype = AA  length = 181
FEATURE                 Location/Qualifiers
source                  1..181
                        mol_type = protein
                        organism = Salmonella sp.
SEQUENCE: 495
MKTLILFSTR DGQTREIASY LASELKEMGI WADVVNLHRA EEPDWDSYDR VVIGASIRYG    60
HYHSAFQEFV KKYATRLNGM SSAFYSVNLV ARKAEKRTPQ TNSYARKFLM SSPWRPDYCA   120
VIAGALRYPR YRWYDRLMIK LIMKMSGGET DTSKEVVYTD WEQVTHFARE IAHLTNKSSA   180
K                                                                  181

SEQ ID NO: 496          moltype = AA  length = 181
FEATURE                 Location/Qualifiers
source                  1..181
                        mol_type = protein
                        organism = Salmonella sp.
SEQUENCE: 496
MKTLILFSTR DGQTREIASY LASELKEMGI WADVVNLHRA EELDWDSYDR VVIGASIRYG    60
HYHSSFQEFV KKYATRLNGM PSAFYSVNLV ARKAEKRTPQ TNSYARKFLM SSPWRPDYCA   120
VIAGALRYPR YRWYDRLMIK LIMKMSGGET DTSKEVVYTD WEQVAHFARE IAHLTNKSSA   180
K                                                                  181

SEQ ID NO: 497          moltype = AA  length = 181
FEATURE                 Location/Qualifiers
source                  1..181
                        mol_type = protein
                        organism = Citrobacter sp.
SEQUENCE: 497
MKTLILFSSR DGQTREIAEY LASELKELGV WADVVNLHRT EEPDWKNYDS VVIGASIRYG    60
HYHTAFQEFV KKHATRLNAM PSAFYSVNLV ARKPEKRTPQ TNSYARKFLM SSPWRPDRSA   120
VIAGALLYPR YRWYDRVMIK LIMKMSGGET DTSKEVVYTD WEQVAIFARE IAQLTNKALL   180
K                                                                  181

SEQ ID NO: 498          moltype = AA  length = 181
FEATURE                 Location/Qualifiers
source                  1..181
                        mol_type = protein
                        organism = Citrobacter sp.
SEQUENCE: 498
MKTLILFSSR DGQTREIAAY LASELKELGV CTDVVNLHRT EEPDWERYDR VVIGASIRYG    60
HYHSAFLEFV KKHATRLNHM PSAFYSVNLV ARKPEKRTPQ TNSYARKFLM NSQWRPDRSA   120
VIAGALLYPR YRWYDRMMIQ LIMKMSGGET DTRKEVIYTD WEQVASFARE IAQLTPDSVV   180
```

```
K                                                                          181

SEQ ID NO: 499            moltype = AA  length = 181
FEATURE                   Location/Qualifiers
source                    1..181
                          mol_type = protein
                          organism = Shigella sp.
SEQUENCE: 499
MKTLILFSSR DGQTREIAEY LASELKELGV WADVMNLHRT EEPEWKNYDS VVIGASIRYG    60
HYHSAFQEFV KKHATQLNTM PSAFYSVNLV ARKPEKRTPQ TNSYARKFLM SSPWRPDHSA   120
VIAGAGALLYPR YRWYDRVMIQ LIMKMSGGET DTKKEVIYTD WEQVAGFARE IAQLTNKTLL  180
K                                                                          181

SEQ ID NO: 500            moltype = AA  length = 181
FEATURE                   Location/Qualifiers
source                    1..181
                          mol_type = protein
                          organism = Citrobacter sp.
SEQUENCE: 500
MKTLILFSSR DGQTREIAEY LASELKELGV WADVVNLHRT AEPDWQNYDS VVIGASIRYG    60
HYHAAFQEFV KKHATRLNSM PSAFYSVNLV ARKPEKRTPQ TNSYARKFLM SSPWRPDHSA   120
VIAGALLYPR YRWYDRVMIQ LIMKMSGGET DTNKEVVYTD WEQVARFARE IAQLTNKASL   180
K                                                                          181

SEQ ID NO: 501            moltype = AA  length = 181
FEATURE                   Location/Qualifiers
source                    1..181
                          mol_type = protein
                          organism = Enterobacter sp.
SEQUENCE: 501
MKTLILFSSR DGQTREIAEY LASELKELGV WADVVNLHRT AEPDWQNYDS VVIGASIRYG    60
HYHAAFQEFV KKHATRLNSM PSAFYSVNLV ARKPEKRTPQ TNSYARKFLM SSPWRPDHSA   120
VIAGALLYPR YRWYDRVMIQ LIMKMSGGET DTNKEVVYTD WEQVARFARE IAQLTNKTSL   180
K                                                                          181

SEQ ID NO: 502            moltype = AA  length = 174
FEATURE                   Location/Qualifiers
source                    1..174
                          mol_type = protein
                          organism = Salmonella sp.
SEQUENCE: 502
MKTLILFSTR DGQTREIASY LASELKEMGI WADVVNLHRA EEPDWDSYDR VVIGASIRYG    60
HYHSAFQEFV KKYATRLNGM PSAFYSVNLV ARKAEKRTPQ TNSYARKFLM SSPWRPDYCA   120
VIAGALRYPR YRWYDRLMIK LIMKMSGGET DTSKEVVYTD WEQVTHFARE IAHL         174

SEQ ID NO: 503            moltype = AA  length = 181
FEATURE                   Location/Qualifiers
source                    1..181
                          mol_type = protein
                          organism = Citrobacter sp.
SEQUENCE: 503
MKTLILFSSR DGQTREIAEY LASELKELGV WADVVNLHRT AEPDWQNYDS VVIGASIRYG    60
HYHAAFQEFV KKHATRLNSM PSAFYSVNLV ARKPEKRTPQ TNSYARKFLM GSPWRPDHSA   120
VIAGALLYPR YRWYDRVMIQ LIMKMSGGET DTNKEVVYTD WEQVARFARE IAQLTNKTSL   180
K                                                                          181

SEQ ID NO: 504            moltype = AA  length = 181
FEATURE                   Location/Qualifiers
source                    1..181
                          mol_type = protein
                          organism = Citrobacter sp.
SEQUENCE: 504
MKTLILFSSR DGQTREIAEY LASELKELGV WADVLNLHRT AEPDWQNYDS VVIGASIRYG    60
HYHAAFQEFV KKHATRLNAM PSAFYSVNLV ARKPEKRTPQ TNSYARKFLM SSPWRPDRSA   120
VIAGALRYPR YRWYDRVMIQ LIMKMSGGET DTHKEVVYTD WEQVAGFARE IAQLTHKTVS   180
K                                                                          181

SEQ ID NO: 505            moltype = AA  length = 181
FEATURE                   Location/Qualifiers
source                    1..181
                          mol_type = protein
                          organism = Citrobacter sp.
SEQUENCE: 505
MKTLILFSSR DGQTREIAEY LASELKELGV WADVVNLHRT AEPDWQNYDS VVIGASIRYG    60
HYHAAFQEFV KKHATRLNSM PSAFYSVNLV ARKPEKRTPQ TNSYARKFLM SSPWRPDHSA   120
VIAGALLYPR YRWYDRVMIQ LIMKMSGGET DTNKEVVYTD WEQVARFARE IAQLTNKALL   180
K                                                                          181

SEQ ID NO: 506            moltype = AA  length = 181
```

```
FEATURE                 Location/Qualifiers
source                  1..181
                        mol_type = protein
                        organism = Citrobacter sp.
SEQUENCE: 506
MKTLILFSSR DGQTREIAEY LASELKELGV WADVVNLHRT AEPDWQNYDS VVIGASIRYG     60
HYHAAFQEFV KKHATRLNAM PSAFYSVNLV ARKPEKRTPQ TNSYARKFLM SSPWRPDRSA    120
VIAGALLYPR YRWYDRVMIQ LIMKMSGGET DTNKEVVYTD WEQVAGFARE IAQLTNKTLS    180
K                                                                   181

SEQ ID NO: 507          moltype = AA  length = 181
FEATURE                 Location/Qualifiers
source                  1..181
                        mol_type = protein
                        organism = Citrobacter sp.
SEQUENCE: 507
MKTLILFSSR DGQTREIAEY LASELKELGV WADVVNLHRT AEPDWQNYDS VVVGASIRYG     60
HYHAAFQEFV KKHATRLNAM PSAFYSVNLV ARKPEKRTPQ TNSYARKFLM SSPWRPDRSA    120
VIAGALLYPR YRWYDRVMIQ LIMKMSGGET DTNKEVVYTD WEQVAGFARE IAQLTNKTLS    180
K                                                                   181

SEQ ID NO: 508          moltype = AA  length = 181
FEATURE                 Location/Qualifiers
source                  1..181
                        mol_type = protein
                        organism = Citrobacter sp.
SEQUENCE: 508
MKTLILFSSR DGQTREIAEY LASELKELGV WADVVNLHRT AEPDWQNYDS VVIGASIRYG     60
HYHAAFQEFV KKHATRLNAM PSAFYSVNLV ARKPEKRTPQ TNSYARKFLM SSPWRPDRSA    120
VIAGALLYPR YRWYDRVMIQ LIMKMSGGET DTNKEVVYTD WEQVADFARE IAQLTHKTLS    180
K                                                                   181

SEQ ID NO: 509          moltype = AA  length = 181
FEATURE                 Location/Qualifiers
source                  1..181
                        mol_type = protein
                        organism = Citrobacter sp.
SEQUENCE: 509
MKTLILFSSR DGQTQEIAAY LASELKELGI STDVVNLHRT DEPDWERYDR VVIGASIRYG     60
HYHSAFLAFV KKHATRLNRM PSAFYSVNLV ARKPEKRTPQ TNSYARKFLM NSQWRPDRSA    120
VIAGALLYPR YRWYDRMMIQ LIMKMSGGET DTRKEVIYTD WAQVASFARE IAQLTPDSLV    180
K                                                                   181

SEQ ID NO: 510          moltype = AA  length = 181
FEATURE                 Location/Qualifiers
source                  1..181
                        mol_type = protein
                        organism = Citrobacter sp.
SEQUENCE: 510
MKTLILFSSR DGQTREIAEY LASELKELGV WADVVNLHRT AEPDWQNYDS VVIGASIRYG     60
HYHAAFQEFV KKYATRLNSM PSAFYSVNLV ARKPEKRTPQ TNSYARKFLM SSPWRPDHSA    120
VIAGALLYPR YRWYDRVMIQ LIMKMSGGET DTNKEVVYTD WEQVARFARE IAQLTNKALL    180
K                                                                   181

SEQ ID NO: 511          moltype = AA  length = 181
FEATURE                 Location/Qualifiers
source                  1..181
                        mol_type = protein
                        organism = Citrobacter sp.
SEQUENCE: 511
MKTLILFSSR DGQTREIAEY LASELKELGV WADVVNLHRT AEPDWQHYDS VVIGASIRYG     60
HYHAAFQEFV KKHATRLNAM PSAFYSVNLV ARKPEKRTPQ TNSYARKFLM SSPWRPDRSA    120
VIAGALLYPR YRWYDRVMIQ LIMKMSGGET DTNKEVVYTD WEQVADFARE IAQLTHKTLS    180
K                                                                   181

SEQ ID NO: 512          moltype = AA  length = 181
FEATURE                 Location/Qualifiers
source                  1..181
                        mol_type = protein
                        organism = Citrobacter sp.
SEQUENCE: 512
MKTLILFSSR DGQTREIAEY LASELKELGV WTDVVNLHRT AEPDWQNYDS VVIGASIRYG     60
HYHAAFQEFV KKHATRLNAM PSAFYSVNLV ARKPEKRTPQ TNSYARKFLM SSPWRPDRSA    120
VIAGALLYPR YRWYDRVMIQ LIMKMSGGET DTHKEVVYTD WEQVAGFARE IAQLTHKTLP    180
K                                                                   181

SEQ ID NO: 513          moltype = AA  length = 187
FEATURE                 Location/Qualifiers
source                  1..187
```

```
                              mol_type = protein
                              organism = Salmonella sp.
SEQUENCE: 513
MNNGVTRENI DSFSTRDGQT REIASYLASE LKEMGIWADV VNLHRAEEPD WDSYDRVVIG    60
ASIRYGHYHS AFQEFVKKYA TRLNGMPSAF YSVNLVARKA EKRTPQTNSY ARKFLMSSPW   120
RPDYCAVIAG ALRYPRYRWY DRLMIKLIMK MSGGETDTSK EVVYTDWEQV THFAREIAHL   180
TNKSSAK                                                             187

SEQ ID NO: 514            moltype = AA  length = 181
FEATURE                   Location/Qualifiers
source                    1..181
                          mol_type = protein
                          organism = Citrobacter sp.
SEQUENCE: 514
MKTLILFSSR DGQTREIAEY LASELKELGV WTDVVNLHRT AEPDWKNYDS VVIGASIRYG    60
HYHSAFQEFV KKYATRLNAM PSAFYSVNLV ARKPEKRTPQ TNSYARKFLM SSPWRPDRSA   120
VIAGALLYPR YRWYDRVMIQ LIMKMSGGET DTNKEVVYTD WEQVAGFARE IAQLTHKTLP   180
K                                                                   181

SEQ ID NO: 515            moltype = AA  length = 171
FEATURE                   Location/Qualifiers
source                    1..171
                          mol_type = protein
                          organism = Salmonella sp.
SEQUENCE: 515
DGQTREIASY LASELKEMGI WADVVNLHRA EEPDWDSYDR VVIGASIRYG HYHSAFQEFV    60
KKYATRLNGM PSAFYSVNLV ARKAEKRTPQ TNSYARKFLM SSPWRPDYCA VIAGALRYPR   120
YRWYDRLMIK LIMKMSGGET DTSKEVVYTD WEQVAHFARE IAHLTNKSSA K            171

SEQ ID NO: 516            moltype = AA  length = 181
FEATURE                   Location/Qualifiers
source                    1..181
                          mol_type = protein
                          organism = Enterobacter sp.
SEQUENCE: 516
MKTLILFSTR DGQTREIAAY LASELKELGI YSDVVNLNRA EQIAWQDYDR VVIGASIRYG    60
HFHPALDRFV KKHTAVLNKL PGAFYSVNLV ARKAEKRTPQ TNSYTRKFLL NSPWQPDLCA   120
VFAGALRYPR YRWYDRFMIR LIMKMTGGET DTRKEVVYTD WSQVASFARE IAHLTDNSRL   180
K                                                                   181

SEQ ID NO: 517            moltype = AA  length = 181
FEATURE                   Location/Qualifiers
source                    1..181
                          mol_type = protein
                          organism = Enterobacter sp.
SEQUENCE: 517
MKTLILFSTR DGQTREIAAY LASELKELGI YSDVVNLNRV EQISWQDYDR VVIGASIRYG    60
HFHPALDRFV KKHTAVLNKL PGAFYSVNLV ARKPEKRTPQ TNSYTRKFLL SSPWQPELCA   120
VFAGALRYPR YRWYDRFMIR LIMKMTGGET DTRKEVVYTD WSQVASFARE IAHLTDDSRH   180
K                                                                   181

SEQ ID NO: 518            moltype = AA  length = 181
FEATURE                   Location/Qualifiers
source                    1..181
                          mol_type = protein
                          organism = Enterobacter sp.
SEQUENCE: 518
MKTLILFSTR DGQTREIAAY LASELKELGI YSDVVNLNRA EQISWQDYDR VVIGASIRYG    60
HFHPALDRFV KKHTAVLNKL PGAFYSVNLV ARKPEKRTPQ TNSYTRKFLL NSPWQPDLCA   120
VFAGALRYPR YRWYDRFMIR LIMKMTGGET DTRKEVVYTD WSQVASFARE IAHLTGDSRH   180
K                                                                   181

SEQ ID NO: 519            moltype = AA  length = 181
FEATURE                   Location/Qualifiers
source                    1..181
                          mol_type = protein
                          organism = Enterobacter sp.
SEQUENCE: 519
MKTLILFSTR DGQTREIAAY LASELKELGI YSDVVNLNRA EQIAWQDYDR VVIGASIRYG    60
HFHPALDRFV KKHAAVLNKM PGAFYSVNLV ARKAEKRTPQ TNSYTRKFLL SSPWQPDLCA   120
VFAGALRYPR YRWYDRFMIR LIMKMTGGET DTRKEVVYTD WSQVASFARE IAHLTGDSRL   180
K                                                                   181

SEQ ID NO: 520            moltype = AA  length = 181
FEATURE                   Location/Qualifiers
source                    1..181
                          mol_type = protein
                          organism = Enterobacter sp.
SEQUENCE: 520
```

```
MKTLILFSTR DGQTREIAAY LASELKELGI YSDVVNLNRA EQIAWQDYDR VVIGASIRYG    60
HFHPALDRFV KKHTAVLNKL PGAFYSVNLV ARKAEKRTPQ TNSYTRKFLL NSPWQPDLCA   120
VFAGALRYPR YRWYDRFMIR LIMKMTGGET DTRKEVVYTD WSQVASFARE IAHLTGNSRL   180
K                                                                  181

SEQ ID NO: 521         moltype = AA   length = 181
FEATURE                Location/Qualifiers
source                 1..181
                       mol_type = protein
                       organism = Enterobacter sp.
SEQUENCE: 521
MKTLILFSTR DGQTREIAAY LASELKELGI YSDVVNLNRA DQITWQDYDR VVIGASIRYG    60
HFHPALDRFV KKHTAKLNTL PGAFYSVNLV ARKPEKRTPQ TNSYTRKFLL NSPWQPELCA   120
VFAGALRYPR YRWYDRFMIR LIMKMTGGET DTRKEVVYTD WSQVASFARE IAHLTGDSRH   180
K                                                                  181

SEQ ID NO: 522         moltype = AA   length = 181
FEATURE                Location/Qualifiers
source                 1..181
                       mol_type = protein
                       organism = Enterobacter sp.
SEQUENCE: 522
MKTLILFSTR DGQTREIASY LASELKELGI YSDVVNLNRT EQITWQDYDR VVIGASIRYG    60
HFHPALDRFV KKHTAVLNKL PGAFYSVNLV ARKAEKRTPQ TNSYTRKFLL NSPWRPDLCA   120
VFAGALRYPR YRWYDRFMIR LIMKMTGGET DTRKEVVYTD WSQVASFARE IAHLSRDSQR   180
K                                                                  181

SEQ ID NO: 523         moltype = AA   length = 181
FEATURE                Location/Qualifiers
source                 1..181
                       mol_type = protein
                       organism = Enterobacter sp.
SEQUENCE: 523
MKTLILFSTR DGQTREIAAY LASELKELGI YSDVVNLNRA EQITWQEYDR VVIGASIRYG    60
HFHPALDRFV KKHTAVLNKL PGAFYSVNLV ARKAEKRTPQ TNSYTRKFLL SSPWQPDLCA   120
VFAGALRYPR YRWYDRFMIR LIMKMTGGET DTRKEVVYTD WSQVASFARE IAHLTDDSRL   180
K                                                                  181

SEQ ID NO: 524         moltype = AA   length = 181
FEATURE                Location/Qualifiers
source                 1..181
                       mol_type = protein
                       organism = Enterobacter sp.
SEQUENCE: 524
MKTLILFSTR DGQTREIAAY LASELKELGI YSDVVNLNRA EQIAWQDYDR VVIGASIRYG    60
HFHPALDRFV KKHTAVLNKM PGAFYSVNLV ARKAEKRTPQ TNSYTRKFLL SSPWQPDLCA   120
VFAGALRYPR YRWYDRFMIR LIMKMTGGET DTRKEVVYTD WSQVASFARE IAHLTGDSRL   180
K                                                                  181

SEQ ID NO: 525         moltype = AA   length = 181
FEATURE                Location/Qualifiers
source                 1..181
                       mol_type = protein
                       organism = Enterobacter sp.
SEQUENCE: 525
MKTLILFSTR DGQTREIAAY LASELKELGI YSDVVNLNRA EQIAWQDYDR VVIGASIRYG    60
HFHPALDRFV KKHTAILNKM PGAFYSVNLV ARKAEKRTPQ TNSYTRKFLL SSPWQPDLCA   120
VFAGALRYPR YRWYDRFMIR LIMKMTGGET DTRKEVVYTD WSQVASFARE IAHLTGDSRL   180
K                                                                  181

SEQ ID NO: 526         moltype = AA   length = 180
FEATURE                Location/Qualifiers
source                 1..180
                       mol_type = protein
                       organism = Enterobacter sp.
SEQUENCE: 526
MKTLILFSTR DGQTREIAAY LASELKELGI YSDVVNLNRA EQIAWQDYDR VVIGASIRYG    60
HFHPALDRFV KKHTAVLNKM PGAFYSVNLV ARKAEKRTPQ TNSYTRKFLL SSPWQPDLCA   120
VFAGALRYPR YRWYDRFMIR LIMKMTGGET DTRKEVVTDW SQVATFAREI AHLTGDSRLK   180

SEQ ID NO: 527         moltype = AA   length = 181
FEATURE                Location/Qualifiers
source                 1..181
                       mol_type = protein
                       organism = Enterobacter sp.
SEQUENCE: 527
MKTLILFSTR DGQTREIASY LASELKELGV YADVVNLNRT EEISWQDYDR VVIGASIRYG    60
HFHPALDSFV KKHTAVLNAL PGAFYSVNLV ARKAEKRTPQ TNSYTRKFLL GSPWQPDLCA   120
VFAGALRYPR YRWYDRFMIR LIMKMTGGET DTRKEVVYTD WAQVASFARE IAQLTADSKV   180
```

```
K                                                                        181

SEQ ID NO: 528          moltype = AA  length = 181
FEATURE                 Location/Qualifiers
source                  1..181
                        mol_type = protein
                        organism = Enterobacter sp.
SEQUENCE: 528
MKTLILFSTR DGQTREIASY LASELQELGI YSDVVNLNRT EQIAWQDYDR VVIGASIRYG        60
HFHPALDRFV KKHTAALNKL PGAFYSVNLV ARKPEKRTPQ TNSYTRKFLL NSPWQPDLCA        120
VFAGALRYPR YRWYDRFMIR LIMKMTGGET DTRKEVVYTD WTQVSSFARE IAHLSPESRR        180
I                                                                        181

SEQ ID NO: 529          moltype = AA  length = 181
FEATURE                 Location/Qualifiers
source                  1..181
                        mol_type = protein
                        organism = Enterobacter sp.
SEQUENCE: 529
MKTLILFSTR DGQTREIAAY LASELKELGI YSDVVNLNRA EQIAWHDYDR VVIGASIRYG        60
HFHPALDRFV KKHTAVLNKM PGAFYSVNLV ARKAEKRTPQ TNSYTRKFLL SSPWQPDLCA        120
VFAGALRYPR YRWYDRFMIR LIMKMTGGET DTRKEVVYTD WSQVASFARE IAHLTGDSRL        180
K                                                                        181

SEQ ID NO: 530          moltype = AA  length = 181
FEATURE                 Location/Qualifiers
source                  1..181
                        mol_type = protein
                        organism = Enterobacter sp.
SEQUENCE: 530
MKTLILFSTR DGQTREIAAY LASELKELGI YSDVVNLNRA EQIAWQDYDR VVIGASIRYG        60
HFHPALDRFV KKHTAKLNAL PGAFYSVNLV ARKAEKRTPQ TNSYTRKFLL SSPWQPDLCA        120
VFAGALRYPR YRWYDRFMIR LIMKMTGGET DTRKEVVYTD WSQVASFARE IAHLTGDSRH        180
K                                                                        181

SEQ ID NO: 531          moltype = AA  length = 181
FEATURE                 Location/Qualifiers
source                  1..181
                        mol_type = protein
                        organism = Enterobacter sp.
SEQUENCE: 531
MKTLILFSTR DGQTREIASY LASELQELGI YSDVVNLNRT EQIAWQDYDR VVIGASIRYG        60
HFHPALDRFV KKHTAALNKL PGAFYSVNLV ARKPEKRTPQ TNSYTRKFLL NSPWQPDLCA        120
VFAGALRYPR YRWYDRFMIR LIMKMTGGET DTRKEVVYTD WTQVSSFARD IAHLSPESRR        180
I                                                                        181

SEQ ID NO: 532          moltype = AA  length = 181
FEATURE                 Location/Qualifiers
source                  1..181
                        mol_type = protein
                        organism = Enterobacter sp.
SEQUENCE: 532
MKTLILFSTR DGQTREIAAY LASELKELGI YSDVVNLNRA EQIAWQEYDR VVIGASIRYG        60
HFHPALDRFV KKHTAVLNKL PGAFYSVNLV ARKAEKRTPQ TNSYTRKFLL SSPWQPDLCA        120
VFAGALRYPR YRWYDRFMIR LIMKMTGGET DTRKEVVYTD WSQVASFARE IAHLTGDSRL        180
K                                                                        181

SEQ ID NO: 533          moltype = AA  length = 181
FEATURE                 Location/Qualifiers
source                  1..181
                        mol_type = protein
                        organism = Enterobacter sp.
SEQUENCE: 533
MKTLILFSTR DGQTREIAAY LASELKELGI YSDVVNLNRA EEIAWQEYDR VVIGASIRYG        60
HFHPALDRFV KKHTAVLNTL PGAFYSVNLV ARKAEKRTPQ TNSYTRKFLL GSPWQPDLCA        120
VFAGALRYPR YRWYDRFMIR LIMKMTGGET DTRKEVVYTD WSQVASFARE IAHLAGDSRL        180
K                                                                        181

SEQ ID NO: 534          moltype = AA  length = 181
FEATURE                 Location/Qualifiers
source                  1..181
                        mol_type = protein
                        organism = Enterobacter sp.
SEQUENCE: 534
MKTLILFSTR DGQTREIAAY LASELKELGI YSDVVNLNRA EQIAWQDYDR VVIGASIRYG        60
HFHPALDRFV KKHTAVLNKM PGAFYSVNLV ARKAEKRTPQ TNSYTRKFLL SSPWQPDLCA        120
VFAGALRYPR YRWYDRFMIR LIMKMTGGET DTHKEVVYTD WSQVASFARE IAHLTGDSRL        180
K                                                                        181
```

```
SEQ ID NO: 535         moltype = AA   length = 181
FEATURE                Location/Qualifiers
source                 1..181
                       mol_type = protein
                       organism = Enterobacter sp.
SEQUENCE: 535
MKTLILFSTR DGQTREIASY LASELKELGI YSDVVNLNRT EQIAWQDYDR VVIGASIRYG   60
HFHPALDRFV KKHTAVLNKL PGAFYSVNLV ARKPEKRTPQ TNSYTRKFLL SSPWQPDISA  120
VFAGALRYPR YRWYDRFMIR LIMKMTGGET DTRKEVVYTD WSQVASFARE IAHLSGDSRL  180
K                                                                 181

SEQ ID NO: 536         moltype = AA   length = 181
FEATURE                Location/Qualifiers
source                 1..181
                       mol_type = protein
                       organism = Enterobacter sp.
SEQUENCE: 536
MKTLILFSTR DGQTREIAAY LASELKELGI YSDVVNLNRA EQIAWQEYDR VVIGASIRYG   60
HFHPALDRFV KKHTAVLNKL PGAFYSVNLV ARKAEKRTPQ TNSYTRKFLL GSPWQPDLCA  120
VFAGALRYPR YRWYDRFMIR LIMKMTGGET DTRKEVVYTD WSQVASFARE IAHLTGDSRL  180
K                                                                 181

SEQ ID NO: 537         moltype = AA   length = 181
FEATURE                Location/Qualifiers
source                 1..181
                       mol_type = protein
                       organism = Enterobacter sp.
SEQUENCE: 537
MKTLILFSTR DGQTREIAAY LASELKELGI YSDVVNLNRA EQITWQEYDR VVIGASIRYG   60
HFHPALVRFV KKHTAVLNKL PGAFYSVNLV ARKAEKRTPQ TNSYTRKFLL SSPWQPALCA  120
VFAGALRYPR YRWYDRFMIR LIMKMTGGET DTRKEVVYTD WSQVASFARE IAHLTDDSRL  180
K                                                                 181

SEQ ID NO: 538         moltype = AA   length = 181
FEATURE                Location/Qualifiers
source                 1..181
                       mol_type = protein
                       organism = Enterobacter sp.
SEQUENCE: 538
MKTLILFSTR DGQTREIAAY LASELKELGI YSDVVNLNRV GQITWQDYDR VVIGASIRYG   60
HFHPALDRFV KKHTAVLNKL PGAFYSVNLV ARKAEKRTPQ TNSYTRKFLL NSPWQPDLCA  120
VFAGALRYPR YRWYDRFMIR LIMKMTGGET DTRKEVVYTD WSQVASFARE IAHLSGDSRV  180
K                                                                 181

SEQ ID NO: 539         moltype = AA   length = 299
FEATURE                Location/Qualifiers
source                 1..299
                       mol_type = protein
                       organism = Escherichia sp.
SEQUENCE: 539
MKPDAHQVKQ FLLNLQDTIC QQLTAVDGAE FVEDSWQREA GGGGRSRVLR NGGVFEQAGV   60
NFSHVHGEAM PASATAHRPE LAGRSFEAMG VSLVVHPHNP YVPTSHANVR FFIAEKPGAD  120
PVWWFGGGFD LTPYGFEED  AIHWHRTARD LCLPFGEDVY PRYKKWCDEY FYLKHRNEQR  180
GIGGLFFDDL NTPDFDRCFA FMQAVGKGYT DAYLPIVERR KAMAYGERER NFQLYRRGRY  240
VEFNLVWDRG TLFGLQTGGR TESILMSMPP LVRWEYDYQP KDGSPEAALS EFIKVRDWV   299

SEQ ID NO: 540         moltype = AA   length = 299
FEATURE                Location/Qualifiers
source                 1..299
                       mol_type = protein
                       organism = Escherichia sp.
SEQUENCE: 540
MKPDAHQVKQ FLLNLQDTIC QQLTAVDGAE FVEDSWQREA GGGGRSRVLR NGGVFEQAGV   60
NFSHVHGEAM PASATAHRPE LAGRSFEAMG ASLVVHPHNP YVPTSHANVR FFIAEKPGAD  120
PVWWFGGGFD LTPYGFEED  AIHWHRTARD LCLPFGEDVY PRYKKWCDEY FYLKHRNEQR  180
GIGGLFFDDL NTPDFDRCFA FMQAVGKGYT DAYLPIVERR KAMAYGERER NFQLYRRGRY  240
VEFNLVWDRG TLFGLQTGGR TESILMSMPP LVRWEYDYQP KDGSPEAALS EFIKVRDWV   299

SEQ ID NO: 541         moltype = AA   length = 299
FEATURE                Location/Qualifiers
source                 1..299
                       mol_type = protein
                       organism = Shigella sp.
SEQUENCE: 541
MKPDAHQVKQ FLLNLQDTIC QQLTAVDGAE FVEDSWQREA GGGGRSRVLR NGGIFEQAGV   60
NFSHVHGEAM PASATAHRPE LAGRSFEAMG VSLVVHPHNP YVPTSHANVR FFIAEKPGAE  120
PVWWFGGGFD LTPYGFEED  AIHWHRTARD LCLPFGEDVY PRYKKWCDDY FYLKHRNEQR  180
GIGGLFFDDL NTPDFDHCFA FMQAVGKGYT DAYLPIVERR KAMAYGERER NFQLYRRGRY  240
VEFNLVWDRG TLFGLQTGGR TESILMSMPP LVRWEYDYQP KDGSPEAALS EFIKVRDWV   299
```

```
SEQ ID NO: 542           moltype = AA  length = 299
FEATURE                  Location/Qualifiers
source                   1..299
                         mol_type = protein
                         organism = Citrobacter sp.
SEQUENCE: 542
MKPDAQRVKQ FLLSLQDDIC QRLSAVDGAE FIEDSWQREA GGGGRSRVLR NGGIFEQAGV    60
NFSHVHGDAM PASATAHRPE LAGRSFEAMG VSLVVHPLNP YIPTSHANVR FFIAEKPGAD   120
PVWWFGGGFD LTPYYGIEED AVHWHRTARD LCQPFGEDVY PRYKKWCDDY FFLKHRNEQR   180
GIGGGLFFDDL NTPDFDRCFA FMQAVGKGYT DAYLPIVGRR KTMSWGERER NFQLYRRGRY  240
VEFNLVWDRG TLFGLQTGGR TESILMSMPP LVRWEYDYHP EDGSPEAALS DFIQVRDWV   299

SEQ ID NO: 543           moltype = AA  length = 299
FEATURE                  Location/Qualifiers
source                   1..299
                         mol_type = protein
                         organism = Citrobacter sp.
SEQUENCE: 543
MKPDAQRVKQ FLLTLQESIC GQLCAVDGAQ FVEDSWQREA GGGGRSRVLR NGGVFEQAGV    60
NFSHVHGDAM PASATAHRPE LAGRSFEAMG VSLVVHPLNP YIPTSHANVR FFIAEKPGAD   120
PVWWFGGGFD LTPYYGFAED AVHWHRTARD LCLPFGEEVY PRYKKWCDEY FLKHRNEQR    180
GIGGLFFDDL NTPDFDHCFA FMQAVGKGYT EAYLPIVERR KAMIWGERER NFQLYRRGRY   240
VEFNLVWDRG TLFGLQTGGR TESILMSMPP LVRWEYDWQP EDGSPEAALS EFIKARDWV   299

SEQ ID NO: 544           moltype = AA  length = 308
FEATURE                  Location/Qualifiers
source                   1..308
                         mol_type = protein
                         organism = Salmonella sp.
SEQUENCE: 544
MKPDAHHVKQ FLLRLQDDIC QTLSAVDGVN FVEDSWRREA GGGGRSRVLR NGGIFEQAGV    60
NFSHVHGDAM PASATAHRPE LAGRSFEAMG VSLVVHPHNP YIPTSHANVR FFIAEKPGAD   120
PVWWFGGGFD LTPYYGFEED AVHWHRTARD LCQPFGDDVY PRYKKWCDDY FYLKHRNEQR   180
GVGGLFFDDL NTPDFDHCFA FMQAVGHGYT GAYLPIVERR KAMVWGERER NFQLYRRGRY   240
VEFNLVWDRG TLFGLQTGGR TESILMSMPP LVRWEYGYQP EEGSPEAALC EFIQVRDWVS  300
LPDNSSVS                                                          308

SEQ ID NO: 545           moltype = AA  length = 299
FEATURE                  Location/Qualifiers
source                   1..299
                         mol_type = protein
                         organism = Citrobacter sp.
SEQUENCE: 545
MKPDAQRVKQ FLLSLQDNIC QQLSAVDGAE FVEDNWQREA GGGGRSRVLR NGGIFEQAGV    60
NFSHVHGEAM PASATAHRPE LAGRSFEAMG VSLVVHPQNP YIPTSHANVR FFIAEKPGAD   120
PVWWFGGGFD LTPYYGFDED AVHWHRTARD LCQPFGDDVY PRYKKWCDDY FFLKHRNEQR   180
GIGGLFFDDL NTPDFDHCFA FMQAVGQGYT EAYLPIVERR KAMSWSERER DFQLYRRGRY   240
VEFNLVWDRG TLFGLQTGGR TESILMSMPP LVRWEYDWQP EANSPEAALS EFIQVRDWV   299

SEQ ID NO: 546           moltype = AA  length = 299
FEATURE                  Location/Qualifiers
source                   1..299
                         mol_type = protein
                         organism = Rhizobium sp.
SEQUENCE: 546
MKPDAHQVKQ FLLNLQDTIC QQLTAVDGAE FVEDSWQREA GGGGRSRVLR NGGVFEQAGV    60
NFSHVHGEAM PASATAHRPE LAGRSFEAMG VSLVVHPHNP YVPTSHANVR FFIAEKPGAD   120
PVWWFGGGFD LTPFYGFEED AIHWHRTARD LCLPFGEDVY PRYKKWCDEY FYLKHRNEQR   180
GIGGLFFDDL NTPDFDRCFA FMQAVGKGYT DAYLPIVERR KAMAYGERER NFQLYRRGRY   240
VEFNLVWDRG TLFGLQTGGR TESILMSMPP LVRWEYDYQP KDGSPEAALS EFIKVRDWV   299

SEQ ID NO: 547           moltype = AA  length = 299
FEATURE                  Location/Qualifiers
source                   1..299
                         mol_type = protein
                         organism = Vibrio sp.
SEQUENCE: 547
MKPDALRVKQ FLLNLQDAIC QQLTAIDGAE FVEDSWQRDA GGGGRSRVLR NGGIFEQAGV    60
NFSHVHGDAM PASATAHRPE LAGRSFEAMG VSLVVHPLNP YIPTSHANVR FFIAEKPDAD   120
PVWWFGGGFD LTPYYGFEED AIHWHRTARD LCQPFGDDVY PRYKKWCDDY FFLKHRNEQR   180
GIGGLFFDDL NTPDFDHCFA FMQAVGEGYT EAYLPIVERR KAMSWGERER NFQLYRRGRY   240
VEFNLVWDRG TLFGLQTGGR TESILMSMPP LVRWEYDWQP DAGSPEAALS DFIQVREWV   299

SEQ ID NO: 548           moltype = AA  length = 299
FEATURE                  Location/Qualifiers
source                   1..299
                         mol_type = protein
                         organism = Enterobacter sp.
```

```
SEQUENCE: 548
MKPDAQQVKT FLLALQDSIC QQLAAVDGQT FSEDNWQRDG GGGGRSRVLR NGGVFEQAGV    60
NFSHVHGDAM PASATAHRPE LAGRSFEAMG VSLVVHPHNP YVPTSHANVR FFIAEKPGAD   120
PVWWFGGGFD LTPYYGFEED AVHWHRTARD LCLPFGEDVY PRYKKWCDDY FYLRHRQEQR   180
GIGGLFFDDL NTPDFDRCFA FMQAVGNGYT DAYLPIVERR KAMAFGERER DFQLYRRGRY   240
VEFNLVWDRG TLFGLQTGGR TESILMSMPP LVRWEYDYQP EDGSPEAALS EFIRVRDWV    299

SEQ ID NO: 549          moltype = AA  length = 299
FEATURE                 Location/Qualifiers
source                  1..299
                        mol_type = protein
                        organism = Enterobacter sp.
SEQUENCE: 549
MTVDANKVKT FLLQLQDDIC QQLSALDGGA FIEDSWQRDA GGGGRSRVLR DGGIFEQAGV    60
NFSHVHGDAM PASATAHRPE LAGRSFEAMG VSLVVHPRNP YVPTSHANVR FFIAEKPGAD   120
PVWWFGGGFD LTPFYGFEED AIHWHRTARD LCQPFGEDVY PRYKKWCDDY FFIKHRNEQR   180
GIGGLFFDDL NTPDFDSCFA FMQAVGNGFT DAYLPIVKRR KAAIWGERER NFQLYRRGRY   240
VEFNLVWDRG TLFGLQTGGR TESILMSMPP LVRWEYDYQP QAGSPEAALS EFIKVRDWV    299

SEQ ID NO: 550          moltype = AA  length = 299
FEATURE                 Location/Qualifiers
source                  1..299
                        mol_type = protein
                        organism = Enterobacter sp.
SEQUENCE: 550
MKPDVQQVKA FLLQLQDAIC AKLSAVDGKD FVEDSWQREG GGSGRSRVLR DGGIFEQAGV    60
NFSHVHGDAM PASATAHRPE LAGRSFEAMG VSLVVHPRNP YVPTSHANVR FFIAEKPGAD   120
PVWWFGGGFD LTPYYGFEED AIHWHRTARD LCLPYGDEVY PRYKKWCDDY FFLKHRNEQR   180
GIGGLFFDDL NTPDFDHCFA FMQAVGNGFT DAYLPIVERR KTTPYGERER DFQLYRRGRY   240
VEFNLVWDRG TLFGLQTGGR TESILMSMPP LVRWEYDYHP QEGSPEAALS EFIKVKEWI    299

SEQ ID NO: 551          moltype = AA  length = 300
FEATURE                 Location/Qualifiers
source                  1..300
                        mol_type = protein
                        organism = Kluyvera sp.
SEQUENCE: 551
MTINVQQVKA FLLKLQDDIC QQLERVDGGT FIEDSWQREA GGGGRSRVLR DGSVFEQAGV    60
NFSHVHGDAM PASATAHRPE LAGRSFEAMG VSLVVHPRNP YVPTSHANVR FFIAEKPGAE   120
PVWWFGGGFD LTPYYGFQED AVHWHTVARD LCLPFGEDVY PRYKKWCDDY FHLKHRNEQR   180
GIGGLFFDDL NTPDFDHCFG FMQAVGKGFT DAYLPIVERR KAMAYGERER DFQLYRRGRY   240
VEFNLVWDRG TLFGLQTGGR TESILMSMPP LVRWEYNYQP EEGSPEAALS EFIKVKDWLL   300

SEQ ID NO: 552          moltype = AA  length = 299
FEATURE                 Location/Qualifiers
source                  1..299
                        mol_type = protein
                        organism = Trabulsiella sp.
SEQUENCE: 552
MKPDAQQVKT VLLTLQDTLC QQLSATDGSG FTEDLWQRAA GGGGRSRVLR NGGVFEQAGV    60
NFSHVHGDAM PASATAHRPE LVGRSFEAMG VSLVVIHPYNP YVPTSHANVR FFIAEKPGAD   120
PVWWFGGGFD LTPFYGFNED AVHWHTTARD LCLPFGDEVY PRYKKWCDDY FWLKHRNEQR   180
GIGGLFFDDL NTPDFDHCFA FMQAVGNGFT DAYLPIVERR KMMPFGERER EFQLYRRGRY   240
VEFNLVWDRG TLFGLQTGGR TESILMSMPP LVRWEYNYEP EKGSPEAALS EFLQVRDWI    299

SEQ ID NO: 553          moltype = AA  length = 299
FEATURE                 Location/Qualifiers
source                  1..299
                        mol_type = protein
                        organism = Raoultella sp.
SEQUENCE: 553
MKPDAHQVKR YLLQLQETIC QKLSAIDGGE FVEDSWQREG GGGGRSRVLR DGGVFEQAGV    60
NFSHVHGDAM PASATAHRPE LAGRSFEAMG VSLVVHPWNP YVPTSHANVR FFIAEKPGAE   120
PVWWFGGGFD LTPFYGFEED AVHWHRTAHD LCQPFGEEVY PRYKKWCDDY FYLKHRHEQR   180
GIGGLFFDDL NTPDFDHAFA FMQAVGNGYT DAYLPIVEQR KAMPYGERER NFQLYRRGRY   240
VEFNLVWDRG TLFGLQTGGR TESILMSMPP LVRWEYDYQP EEGSPEAALS EFIQVREWI    299

SEQ ID NO: 554          moltype = AA  length = 299
FEATURE                 Location/Qualifiers
source                  1..299
                        mol_type = protein
                        organism = Kosakonia sp.
SEQUENCE: 554
MTPEIAPVKN ALLALQDKIC RQLSDIDGAT FVEDAWQRAE GGGGRSRVLR DGGVFEQAGV    60
NFSHVHGDAM PASATAHRPE LAGRSFEAMG VSLVVHPRNP YVPTSHANVR FFIAQKPGAD   120
PVWWFGGGFD LTPYYGFEED AIHWHRTARD ICLPFGEEIY PRYKKWCDDY FYLKHRNEQR   180
GIGGLFFDDL NTPDFDHCFA FMQAVGNGYL DAYLPIVARR KALPYGERER DFQLYRRGRY   240
VEFNLVWDRG TLFGLQTGGR TESILMSMPP LVRWEYNYQP AEGSPEAALS EFIQVKDWV    299
```

```
SEQ ID NO: 555          moltype = AA  length = 299
FEATURE                 Location/Qualifiers
source                  1..299
                        mol_type = protein
                        organism = Enterococcus sp.
SEQUENCE: 555
MKPDAAQVKT FLLQLQDNLC QQLSAVDGAP FIEDAWQREG GGGGRSRVLR EGRVFEQAGV  60
NFSHVHGDAM PASATAHRPE LAGRSFEAMG VSLVVHPLNP YVPTSHANVR FFIAEKPGAD  120
PVWWFGGGFD LTPYYGFEED AVHWHRTARD LCLPFGEEVY PRYKKWCDDY FYLKHRQEEP  180
GIGGLFFDDL NTPDFDHCFA FMQAVGNGYA DAYLPIVERR KATPYGERER HFQLYRRGRY  240
VEFNLVWDRG TLFGLQTGGR TESILMSMPP LVRWEYDYQP EPGSPEAALS EFIQVRDWL   299

SEQ ID NO: 556          moltype = AA  length = 307
FEATURE                 Location/Qualifiers
REGION                  1..307
                        note = gamma proteobacterium
source                  1..307
                        mol_type = protein
                        organism = unidentified
SEQUENCE: 556
MNQLPDINQV KAFLLSLQDQ ICQKLSAVDG RAQFKQDQWV REEGGGGQSR VLTGGAIFEQ  60
AGVNFSHVSG ATLPASATAH RPELAGRSFQ AMGVSLVIHP LSPYIPTSHA NVRFFIAEKP  120
GEAPVWWFGG GFDLTPYYGF EEDARHWHQT AADLCQPFGD DVYPKYKKWC DDYFFIKHRN  180
EARGIGGLFF DDLNSPDFAH CFAFMQAVAN GFTDAYLPIV ERRKTLTWGE REREFQLYRR  240
GRYVEFNLVW DRGTLFGLQT GGRTESILMS MPPLVRWEYG FEPDENSPEA ALYRDFLPVR  300
DWLAESE                                                           307

SEQ ID NO: 557          moltype = AA  length = 303
FEATURE                 Location/Qualifiers
source                  1..303
                        mol_type = protein
                        organism = Shewanella sp.
SEQUENCE: 557
MKPDATQVKA FLLDLQQRIC EGLEQLDGEA KFVADSWERE EGGGGTSRVL TKGKVFEQAG  60
VNFSHVTGAA MPASATAHRP ELAGRSFEAM GVSLVIHPNN PYVPTTHANV RFFIAEKEGA  120
DPVWWFGGGF DLTPYYPFEE DVVAWHQSAK ALCEPFGEDV YPKYKKWCDE YFFLPHRNET  180
RGVGGLFFDD LNEPGFENSF AFMQAVGEGF LKAYAPIVEK RKETAYGERE RDFQLYRRGR  240
YVEFNLVYDR GTLFGLQTGG RTESILMSMP PLVRWQYAYT PEAGSPEAKL YSDFLKPREW  300
LEA                                                               303

SEQ ID NO: 558          moltype = AA  length = 302
FEATURE                 Location/Qualifiers
source                  1..302
                        mol_type = protein
                        organism = Oceanimonas sp.
SEQUENCE: 558
MSSKPDTSAV KAFLLALQDN ICRQLEQADG SGRFIEDSWT REEGGGGRSR VLRNGTVIEQ  60
GGVNFSHVYG AAMPASATAH RPELAGRSFE AMGVSLVIHP HNPHVPTSHA NVRFFIAEKE  120
GAEPVWWFGG GFDLTPFYPV EEDCRHWHQV SKDLCEPFGE DVYPKYKEWC DRYFYLKHRN  180
ETRGVGGLFF DDLNEWPFER CFAFMKAVGE GYLDAYLPII ARRKDTPYGE DERQFQLYRR  240
GRYVEFNLVY DRGTLFGLQT GGRTESILMS MPPLARWEYD WQPEAGSREA RLQAFLVPRS  300
WV                                                                302

SEQ ID NO: 559          moltype = AA  length = 302
FEATURE                 Location/Qualifiers
source                  1..302
                        mol_type = protein
                        organism = Chromobacterium sp.
SEQUENCE: 559
MSHPHSDAVK AILLLDLQDRI CAALEGADGD GRFVEDAWQR EAGGGGRSRV LSNGAVFEQA  60
GVNFSHVHGD ALPASATAHR PELAGRRFEA MGVSLVIHPH NPHVPTSHAN VRFFIAEKAG  120
EAPVWWFGGG FDLTPYPVR EDVVHWHTVA RDLCAPFGPE VYPRYKKWCD EYFYLKHRNE  180
ARGVGGLFFD DLNEWGFDQS FAFMQAVGNG YLDAYLPIVQ ARKDTAWGAR ERQFQLYRRG  240
RYVEFNLVWD RGTLFGLQSG GRTESILMSM PPLVRWEYGY QPEPGSAEAL LYTDFLPPRD  300
WV                                                                302

SEQ ID NO: 560          moltype = AA  length = 302
FEATURE                 Location/Qualifiers
source                  1..302
                        mol_type = protein
                        organism = Pseudogulbenkiania sp.
SEQUENCE: 560
MSHPHSDAVK SFLLDLQDRI CAALEQADGK AQFAEDAWSR EAGGGGRSRV LAGGGVFEQA  60
GVNFSHVHGD ALPASATAHR PELADRRFEA MGVSLVIHPS NPHVPTSHAN VRFFIAEKDG  120
EAPVWWFGGG FDLTPYYPQE EDAVHWHTVA RDLCAPFGGE VYPRYKKWCD EYFHLKHRNE  180
ARGIGGLFFD DLNEWGFDKS FAFTRAVGDG YLDAYLPIVA RRKEQAWGDR ERQFQLYRRG  240
RYVEFNLVWD RGTLFGLQSG GRTESILMSM PPLVRWEYGY QPEPGSPEAR LYTDFLPPRD  300
WV                                                                302
```

```
SEQ ID NO: 561           moltype = AA   length = 302
FEATURE                  Location/Qualifiers
source                   1..302
                         mol_type = protein
                         organism = Chromobacterium sp.
SEQUENCE: 561
MSHPHSNAVK SFLLDLQDRI CAALEQADGK AQFAEDAWSR EAGGGGRSRV LTGGEVFEQA    60
GVNFSHVHGD ALPPSASAHR PELAGRRFEA MGVSLVIHPS NPHVPTSHAN VRFFIAEKDG   120
EAPVWWFGGG FDLTPFYPQE EDAVHWHTVA RDLCAPFGGD VYPRYKKWCD EYFHLKHRNE   180
ARGIGGLFFD DLNEWGFDKS FAFTRAVGDG YLDAYLPIVA RRKEQAWGDR ERQFQLYRRG   240
RYVEFNLVWD RGTLFGLQSG GRTESILMSM PPLVRWEYGY QPEPGSPEAR LYTDFLPPRD   300
WV                                                                 302

SEQ ID NO: 562           moltype = AA   length = 302
FEATURE                  Location/Qualifiers
source                   1..302
                         mol_type = protein
                         organism = Aeromonas sp.
SEQUENCE: 562
MSKPDVAQVK AFLLQLQDEI CRGLELADGV GHFVEDAWLR EGGGGGRTRV LRHGAVIEQG    60
GVNFSHVHGD AMPASATAHR PELAGRRFEA MGVSLVIHPH NPYVPTSHAN VRFFIAEKEG   120
EEPIWWFGGG FDLTPFYPFE EDVRHWHQVS RDLCQPFGTD IYPEFKSWCD RYFFLKHRDE   180
TRGVGGLFFD DLNRWPFADC FAFMQVVGKG YLDAYLPIVE RRKALAYGER EREFQLYRRG   240
RYVEFNLVYD RGTLFGLQTG GRTESILMSM PPLARWEYDW QPPAGSPEAL LYSDYLKPRE   300
WL                                                                 302

SEQ ID NO: 563           moltype = AA   length = 310
FEATURE                  Location/Qualifiers
source                   1..310
                         mol_type = protein
                         organism = Glaciecola sp.
SEQUENCE: 563
MNTELPSHEK IAQVKAFLLK LQDNICQTLE LSDGKARFVE DEWEREQGGG GRTRVLTNGA    60
VIEQGGVNFS HVFGDQMPAS ATAARPELAG RRFQAMGVSL VIHPHNPYIP TSHANVRFFI   120
AEKEGEAPIW WFGGGFDLTP FFPFKEDVVH WHKVAHDLCL PFGEDVYPKY KKWCDDYFYL   180
KHRNETRGVG GLFFDDLNTP DFETAFGFMQ AVGNGYLDAY VPIIEKRKNT EYGNMERDFQ   240
LYRRGRYVEF NLVYDRGTLF GLQTGGRTES ILMSMPPLVR WEYNYVPDEH SAQGKLAAYL   300
TPQDWLAGQS                                                         310

SEQ ID NO: 564           moltype = AA   length = 304
FEATURE                  Location/Qualifiers
source                   1..304
                         mol_type = protein
                         organism = Alteromonas sp.
SEQUENCE: 564
MDGKNAAEVI EQVKSYLLGL QDTICQTLEL ADGKGQFVED SWQREEGGGG RSRVLKNGAV    60
IEQGGVNFSH VFGSQMPASA TANRPELAGR RFQAMGVSLV IHPHSNPYIP SHANVRFFIA   120
EKEGEAPIWW FGGGFDLTPF YPFKDDVVHW HDTAKKLCKP FGEDVYPKYK KWCDEYFYLK   180
HRNETRGVGG LFFDDLNEWG FEQSFAFMQA VGNGFIDAYV PIVERRKQTD YGERERDFQL   240
YRRGRYVEFN LVFDRGTLFG LQTGGRTESI LMSMPPLARW EYCYTPAPGS AEAKLTDWLK   300
PTPW                                                               304

SEQ ID NO: 565           moltype = AA   length = 305
FEATURE                  Location/Qualifiers
source                   1..305
                         mol_type = protein
                         organism = Gilvimarinus sp.
SEQUENCE: 565
MTTTPDKHAV KAYLMDLQER ICDSLAAVDG GRFAEDTWQR AEGGGGRSRV LADGAVIEKG    60
GVNFSHVMGD AMPASATAHR PELAGRSFEA MGVSLVIHPA NPYAPTSHAN VRFFIAEKEG   120
ADPVWWFGGG YDLTPFYGFV EDCVHWHKTA FEACAPFGDD VYPRYKNWCD EYFYLKHRNE   180
ARGVGGLFFD DLNELGFDQS FAFMRAVGDS YLQAYRPILE RRKDSPYGER EREFQLYRRG   240
RYVEFNLVYD RGTLFGLQTG GRTESILMSL PPLVRWEYDF HPEPDSPEAR LSRDFLPHQD   300
WLARQ                                                              305

SEQ ID NO: 566           moltype = DNA   length = 453
FEATURE                  Location/Qualifiers
source                   1..453
                         mol_type = other DNA
                         organism = Acinetobacter sp.
SEQUENCE: 566
atggatgcac cttctgatgc tttcttatgg gtaaaagcat acatatatt tgccgtagta    60
tgttggtttg ctgccttatt ctatttacct cgactctatg tttaccatgc catgagtgag   120
gatgacacta gtcatcgtcg ttttgaagtc atggagcgta aacttatcg tgggattatg   180
tggccttcta tgattgcgac actgatcact gctcatttt tggtagaatt gggcgatgca   240
acacgacatt atcatgaagc actctggttt tatatcaaag tcggattggt gggactttta   300
gttatctatc attttgtttg cggctactac cgtaaaaaac tgattggcaa tgcccattat   360
aaatcacaca aattctggcg ttattttaat gaaatgccga cactgatttt atttgcagtc   420
gtgatcctgg tcgtggtcaa accacaattt taa                               453
```

```
SEQ ID NO: 567          moltype = DNA  length = 1365
FEATURE                 Location/Qualifiers
source                  1..1365
                        mol_type = other DNA
                        organism = Calditerrivibrio sp.
SEQUENCE: 567
ttatttgttt aagagatttt taaatctatc cacattcata aagcttgttc tggtgcaatc    60
atttataccc acaccatata agatattacc accgataaaa atgtcatcaa attttttata   120
gaactcttca accttttcaa ctattttgtg gtgcccgatg tagtactggg ggattgcttt   180
ttcccatcta aaatatttta ttttgtaagg ctctctttt attttaaag tttcttttat    240
gtcatcgaaa gccatcctga taagttcatc gtcggatttt tcaattatcc atctattttt   300
atctccaccc attatcgttc taacgatttt gtatccatcc cttgttctat cagggaatat   360
cgaagaatca aacagtgctc ccaaaattct tttattctct gaatggggta tcagatagcc   420
gaagccatcc agaggatctt ccagatcctc cggcttgaat ataaacccag caacaaaaac   480
aggagggtaa gtgatgttat ttagatccct ggatagatct ttatcaagaa ctgagagcat   540
ttgggaaaca gcataggccg gggcatttat gaatatttta tcgaactcca tgatgccttt   600
attggtattt aatatatatc tgtttatttt tttatctatt gaaaatactt ccgtattcaa   660
catctttgtg atgcttgtgg attcgagtaa atcgttatc atattatcca gtccattttt   720
gtatgaagta aggattccgc cggggcctga tgggccactt ttttttccctt ttttctttat  780
catcccttta aaaaggccac cataaattat ttccagatcc cttattacgg ggaaacagga   840
tcttaagctc atcttttcgg gatcacctgc aaaaatgcca agaccattg ggctgataag    900
gtattcaaga gcttctttcc ccaatccttc tctggcaaag tctgccacag attcatcttc   960
aaggacactt ttttgtatga atattcgga tagtatcctc attttgctg agaaggagag    1020
tagcttagtt ttgaaaaaca ttggtggatt tcaggtaat ctatgtaaaa tcccattgcg    1080
catgatatat ctttttcttg ctaagtcatt acttttgaca agattgttgc ttaatcgtgc   1140
cattgataga agttcaaggg tatgggttt gctgtctaaa aaaccatttg gccctgcttc    1200
tactatgaac ccatcttccc gtgaggtctc tattgaaccg ccccacctca atctcttttc   1260
tatgattgtt atttccatat ccagattcag ttcattttc aaattttcca ataaaaaagc    1320
ggtggatatc cctgatattc cgcctcctat tatggctact ctcat                   1365

SEQ ID NO: 568          moltype = DNA  length = 1488
FEATURE                 Location/Qualifiers
source                  1..1488
                        mol_type = other DNA
                        organism = Candidatus sp.
SEQUENCE: 568
atggcgacgg aacagcacag cggcagcagg cgtatcgtgg tggtggggag cggcatcgcg    60
ggtctggctg ccgcctatcg gctgcaggag cggtgcgagc aggacggccc gccttgcagg   120
gtgcgcgtat tggaggccgc tgcacggccc ggcggtgcga tcagtaccac gcaccgggat   180
ggttttgttc ttgaatctgg gcccgatacc attttcaccg ataagccgtg gggattggat   240
ctgatcgagc gcctcggtct gagcgagcag gtcatcggga ccaatgaggc gcaccgccgg   300
accttttgtg tgcgggacgg cgcactgcac ccgctgccgg aagggttcgc cttgatgggg   360
ccgaccaagc cttggccgtt tctgcaatca gggctgctgt catggcgcgg caaggcaagg   420
gcggctctgg acctggtact gccgcgaggg ggaccatccg acgacgagag cctggcgtcg   480
ttcgttcggc gtcgtttcgg acaggagttt ctcgatcggc tggcccaacc gatgatcggt   540
ggaatctatg gcgcgaccc ggagcggttg agtctgccgg ctaccttccc gcagtttctg    600
cagatggaag cgacgcatcg cagcgtgatc ctcggcctgc gacgaatgcg ccccgccggc   660
cgcggcgtag gtcataccag cagcggcccg cgctatggcc tgtttgtcac gctggatcac   720
gggctgcagg ccctcgtcga tgccatggta aaaaggctgc cggctgggac gctgcgtctc   780
cgcgcgcccg ttgatagaat cgcgcacaca gagcaaggct ggaccgttcg acttggagga   840
ggcgcgagcc tgcaggccga tggccttatt ctcgccgtcc ccgcatttga gattgccagg   900
cttacccacg acctggacca agacctggct cgtcagctcg aggccatgcc ctacgcctct   960
tcggtcacga tcaatctggc ctatcgtaga gaggcgatcc accatccgct cgacgggttt   1020
ggatttgtgg tgccggcctg cgaggggcgc accatcattg cctgttcgtt cagcagcgtg   1080
aagttcgctc atcgggcgcc ggccggtcac gtcctgctgc gtgccttcgc gggcggcgcg   1140
ctgcagccgg agccgttcac ctgggatgac gagacgctgc tgagcgcagt gcgccgcgat   1200
ctggaggagc tgctggcgat tcacgcgccg cctttgtgga gccagttggt ccgacatcct   1260
cgtgtgatgc cccagtacca ggtcggccac ctgggccggt tggcggcgct cgaagagacg   1320
cttcggcggt ggccgaccct caagctgacc ggtaacgcct acagaggtgt cgtgtgccg    1380
gatgtggttc acagcgggga gacggccgcc gattcattat tggcagagct ggccccgtca   1440
ccgaccgagc cgaccccgc ttgtaccgaa ggcgattctc gcctataa                 1488

SEQ ID NO: 569          moltype = DNA  length = 1425
FEATURE                 Location/Qualifiers
source                  1..1425
                        mol_type = other DNA
                        organism = Chloroflexus sp.
SEQUENCE: 569
atgatggcgg gatacgacag tgtagtgatt ggcggtggca ttgccggttt agctgcggct    60
tacacgctcc acaagcgtgg ttatcgggtc ctggtcatcg agtcgaccaa tcgcgttggc   120
ggtgtgatcc agaccatcac cacaccagaa ggctacattc tcgattgtgg gccgaacacg   180
gtgggtaccg gcgatgcgcg attgtggcag gaactgatcg atctgggtct gcgcgagcgg   240
atcacaccgg cagcgccatg tagcaaacgg cggttcatca tgatcaattg tacaccggtt   300
gaaatcccaa cctcaccagt cgggctgatt accacgcgat tactctcgtg gcgggggaaa   360
ttgcgggtac tggccgaacc gttcatcaac cgtggatcga ccgatcccga tgaaagcgtt   420
gctgccttct tcacccgccg gattggtgca gaggctaccg cccacctcct cgatccatt    480
gttgccggcg tctacgctgg cgatccgcaa cggctctcga ctgcgcagt cttttccatca   540
ctgtgggaag cggcccagcg cagtggcagc atcgtgcgcg gcatgctgag caaacccaaa   600
```

```
ccgaagactc aggtgagtga gccaaagatg cgcagccgca cctttacctt ccgcggtggc    660
ctggccgaat ggccacgcgc tctgcgcaa gccctgggtg ccggcaatgt ctggacagaa    720
cggcgcgtgg tcaagctcca accacgcgac tcctggtggg aagtgacgat tgatggtgtg    780
aacgccccgg agacactcat cagtcgcagc ctcattatcg ccaccccagc ctttacggcg    840
gctgatctca ttgagtcggt tgatcaaaga gcggtcggtg ccctacgcgg cattccgtat    900
gcgccggtag cagtggtaca tctcggcttt cgtcgtgacc agatcagcca ggaattgagc    960
ggctttggtg tgctggcccc ctcaagcgaa cagcgtcagt tcctcggcat tctctggaca   1020
tcaagcatct tcccgcacgt tgcaccacac gatcatgtcc tcaccacaac cctcagtggt   1080
ggtgctatcc ggcccgaact ggccgaacgg agtgacgaaa cactgattga agcggccatt   1140
cgcgatcatc accagctcct ggggatcaga gggcaaccga tcttcaccca tgttactcgc   1200
tggcgaaccg ccattgccca gtataccttt gggcaccgcg agcggattgc caccctcgtg   1260
caactcgaac agcgcctgcc gaccatccag tttgccggca gctaccgcga cggcgttgga   1320
gtgcccaaaa cctgggccag cggtgtgcag gcaggcgagc ggatcgctgc ggcactggca   1380
gcccatggaa ctaccgcagt ttccacagag acggcgtcgg ggtga                    1425

SEQ ID NO: 570        moltype = DNA   length = 546
FEATURE               Location/Qualifiers
source                1..546
                      mol_type = other DNA
                      organism = Escherichia sp.
SEQUENCE: 570
gtgaaaacat taattctttt ctcaacaagg gacggacaaa cgcgcgagat tgcctcctac     60
ctggcttcgg aactgaaaga actggggatc caggcggatg tcgccaatgt gcaccgcatt    120
gaagaaccac agtgggaaaa ctatgaccgt gtggtcattg gtgcttctat tcgctatggt    180
cactaccatt cagcgttcca ggaatttgtc aaaaaacatg cgacgcggct gaattcgatg    240
ccgagcgcct tttactccgt gaatctggtg gcgcgcaaac cggagaagcg tactccacag    300
accaacagct acgcgcgcaa gtttctgatg aactcgcaat ggcgtcccga tcgctgcgcg    360
gtcattgccg gggcgctgcg ttacccacgt tatcgctggt acgaccgttt tatgatcaag    420
ctgattatga agatgtcagg cggtgaaacg gatacgcgca aagaagttgt ctataccgat    480
tgggagcagg tggcgaattt cgcccgagaa atcgcccatt taaccgacaa accgacgctg    540
aaataa                                                                546

SEQ ID NO: 571        moltype = DNA   length = 900
FEATURE               Location/Qualifiers
source                1..900
                      mol_type = other DNA
                      organism = Escherichia sp.
SEQUENCE: 571
atgaaacccg acgcacacca ggttaaacag tttctgctca accttcagga tacgatttgt     60
cagcagctga ccgccgtcga tggcgcagaa tttgtcgaag atagttggca gcgcgaagct    120
ggcggcggcg gcgtagtcg ggtgttgcgt aatggtggtg ttttcgaaca ggcaggcgtc    180
aacttttcgc atgtccacgg tgaggcgatg cctgcttccg ccaccgctca tcgcccggaa    240
cttgccgggc gcagtttcga ggcgatgggc gtttcactgg tagtgcatcc gcataaccga    300
tatgttccca ccagccacgc gaatgtgcgg ttttttattg ccgaaaaaacc gggtgccgat    360
cccgtctggt ggtttggcgg tggcttcgac ttaaccccat tctatggttt tgaagaagat    420
gctattcact ggcatcgcac cgcccgtgac ctgtgcctgc catttggcga agacgtttat    480
ccccgttaca aaaagtggtg cgacgaatac ttctacctca aacatcgcaa cgaacagcga    540
ggtattggcg gctgttctt tgatgacctg aacacgccag atttcgaccg ctgtttttgcc    600
tttatgcagg cggtaggcaa aggctacacc gacgcttatt taccaattgt cgagcgacgg    660
aaagcgatgg cctacggcga gcgcgagcgc aatttccagt tatatcgtcg cggtcgttat    720
gtcgggttca atctggtctg ggatcgcggc acgctgtttg gcctgcaaac tggcgggcgc    780
accgagtcta tcctgatgtc aatgccgcca ctggtacgct gggaatatga ttatcagcca    840
aaagatggca gcccagaagc ggcgttaagt gagtttatta aggtcaggga ttgggtgtaa    900

SEQ ID NO: 572        moltype = DNA   length = 1326
FEATURE               Location/Qualifiers
source                1..1326
                      mol_type = other DNA
                      organism = Hydrogenobacter sp.
SEQUENCE: 572
atgatagatg tagcggtagt aggggcaggt tatatccggg ctatccatag cctatcacctt    60
aaaaggctg gacttgaggt aaaggttttt gaaaagaag atgccgtagg tggaaacata    120
caaacagcat acatagacgg ttatgttttgc gagcttggac ctcagaccat tcttgcggac    180
agtaaagtag aagagttttt aaaagatgca cgcatatatgc caatccttct tcttgggga   ...continued
```

```
caatacactg tggggtacgg aaggtatctt gagctggcaa actccataga gatggagcaa   1200
cccggacttt tcttgagtgg caattatctt tatggtgttt ccgttgcaga ctgtataaga   1260
gtttcacatc acatagcaaa gagggtaata gacttttttgg aagttaaggg gcgtactgtt   1320
gtataa                                                              1326

SEQ ID NO: 573           moltype = DNA   length = 1323
FEATURE                  Location/Qualifiers
source                   1..1323
                         mol_type = other DNA
                         organism = Laribacter sp.
SEQUENCE: 573
tcagctggcc ggcgggtagt ccagcaagca ctggacagcc acctgctgcc ccttgtcgag   60
acagtcgacg accgataccc cgccatgcca gttggcacac acgcggatac cgtgttcatg   120
caggtcactg accgcgctgg ccagcggcag ggcatggctg tcgtactgcg gaatggcctg   180
ctcctgacgg gtcagccggc aaaggggtcgg ctcgccctgg atgcggtaga gccgccgcag   240
ttcttccagc gccagcgcca ccagcgtggc gtcatcgtgc cggtaacggt caaggaactg   300
catgccgccg acaaaggtgg tcagcagggt ttcgcctgcc ggcgtgcggt cgggaaacag   360
cgagccggac cagatggagc cggcggcaaa cggttttttcg actttggggt tcagcccgcc   420
aaaaccgtcg aggtcatgcc cgaccgtgct gcgtggccag gccgtatgca ggacggccac   480
cgggggcgtag gttacgttgg caaggttcgc tgcaatggcc ggaaaatggc tggccagcag   540
ttgcccggcc acgtcggccg gcacggccag caccacttcg tcggcgtcca gttcacctgc   600
tggggttctg acccgccagc cggtttccag ccgctccagt cgctcgacaa acgtatccag   660
ccgtacgtcc agccctgcg ccagcgtttc gggcagctgc tgcaaaccct cgttcagggt   720
gaaggtggcc ttgcgccgga aggttttgcg gcgggcaaac atgccgcgca cgatggagcc   780
tgactggcgc tcggcttcgt ggatgaccgg cagcgtcagt ccggccacca gctcttcggg   840
atcaccggca aaaatgccgc cgacaaacgg cgaaatgccc cgctcgacaa attcgtcgcc   900
cagacgacgc cggaaaaagg cagccacggt ttccggctca cgcaccggcc ggttgcgccg   960
gaaaggctcg gtcagcgcca gccatttgct ccgggcaccg aactgcgatc cggtcaggaa   1020
cgacagcggt ccggacggca gggcctcgta gcgatcgccg cgcagcacga aacggtgccg   1080
gaccacggcc gccgcggcc ggatggctgc cgtgaggccc agccgttcca gaaggtccag   1140
atgcccggca tggccgtaaa gggtattggg gccgagttcc agccggtaac cgtcggccgc   1200
taccgtcccg atcttgccgc cgacccggct gccggcctcc agcaccacga cggggatgcc   1260
ccgctgttgc aggtgccagg cacacgacag gccggaaatg ccggcaccga tcaccaccac   1320
cat                                                                1323

SEQ ID NO: 574           moltype = DNA   length = 1404
FEATURE                  Location/Qualifiers
source                   1..1404
                         mol_type = other DNA
                         organism = Opitutus sp.
SEQUENCE: 574
ctattgcccg gcgcgttccg ccagttttttc gccggccgcg atgcaggccg ggacggcgat   60
cccgtcgcgg gcctgtcccc ccatgaacag tcccggatgg aagcgttcgc cggcggcaag   120
agcggcgatg aagtgctcgt gaccgaggtt gtactgcggg atggcgcgag gccagaagtt   180
gtgccggaca aaaaccgggt cgccgctgac gccgagcaac tgcgtgagat cgggccgcac   240
ggcggcaagc agctgatcgg cgggcaggct ggcgagttgc ggctggcgtg ttccgcccac   300
catccacgtc agcgccacgt gtcccagcgg cgcgcggccg ggaacacgg aggacgagaa   360
cagcacgcca aggaccgagc gcttctcgac ggccggcacg agcacgccga acccgtcgag   420
cggatgcgcg acctgctcgc ggcggaagcc gaggaagagc gacgagaccg gcgggtgttc   480
gatcagcgcc agcgcggcga gcggttttttc gccgagcgtg ccgatctgga gtcgcgcgag   540
ggcgggcgg ggcagcgcga ccacgacgct gtcgaagctt tgcgtgtgcg tcgccacgtc   600
gtcgtgccaa accacgttcc acttgtcgcc gggcacgatg gcgtcgagcg aagcgccgag   660
tgtgatggcg ccggcgggga gacgcgcgg gagcgcctcc ggcagcacgt gcaggccgtg   720
tttgaaggaa aagatgccgg ggcgcggctc accgcgggcc ttccgggctt tggccgcggc   780
gatctcgccg cggatcagcg agccgtgggt ttgttcgatt tcccagagct tggggaacga   840
ctgccgcgcg gagagctttt cgggatcgcg ggcatacacg ccgcccacga acggattgag   900
cgcgtagtcg acgaactcgc gcccgaagtg cgactcgacg aattcggcga ggctgacgtc   960
ggtcgtgcgg acgcgccgcc gggcgaacag ctcggcgagg agcttgaact tggcgacggg   1020
cgaaaacagt gaggaggcga agaacgacgg tggggacatc ggccggcca gcgcgcggcc   1080
ggggcgaacg atgtagcggt ttttcgcggc gggatccgcg gcgatgcgtt cgccgttcag   1140
cccgagttcg tcgatgagct tgtcgacggc gagttcgccg gagagcagcg tgtttgggtcc   1200
gccttcgatc agccagccgt cgacttcctc cgtcttgatc gagccgccga cgcggtcgga   1260
ttgctcgaac acgcgcacct tgtggccgag ctgggtgagc cggtgggcgg cggtgagccc   1320
ggtgatgccg cgccaagca cggcgaacgt tttgggcggc cggcctgagg cggtggcgga   1380
aggattaaaa ggcgaggtgc tcat                                         1404

SEQ ID NO: 575           moltype = DNA   length = 1410
FEATURE                  Location/Qualifiers
source                   1..1410
                         mol_type = other DNA
                         organism = Rhodothermus sp.
SEQUENCE: 575
atggcttctg tgggaatcat cggagccggc attgccggtc tgacggccgc ctacgaactg   60
caccgtcgtg gcctggaagt gacggtcttt gaagccacag accgcatcgg cggcttcatt   120
cagtcggagc ggatcgacgg cttttctggtg gagctcggtc ctcagacgct ccagcgcacc   180
tcgggcgact cgaagagtt gctgcagacag gtggatctgg aggacgcgtg cattccggcc   240
cgaccggtcg cggcgaatcg cttcatcgtg cggggtggcc agccgatacc cctgccacgc   300
tcgccgcgcg aactgctgcg cacgccgctg ctttcgcccc gggcgcgcct gcgcctgctg   360
gccgagccgt tcattcaccg ggcccaccgg agcaccgagg aaagcgtggc caaattcacc   420
```

-continued

```
cggcgtcgac tgggtccgga ggtgctcgac tatctggtag agcccttcgt ggccggcatc    480
tttgcgggcg atcccgagca gctttcggtg cgctacgcct tcccgaaact gttcgaactg    540
gagcagcagt acggctcgct tttctggggc ctgatccgcg atcggatgaa gcagcggtat    600
catccggccc cgcgccgctc gatgttctcg tttgtcgagg cctgcacat gctgccccgg    660
gcgctggccg agcggttgcc gcgcacgcg atcgtgccga acgcggaggt gctggccatc    720
cgctgggacg agaaaaaccc ctggacgctc acgttccggc agcacggccg cgttcgacc    780
cgttttttcg atatcatcgt ctgtgccgtg ccgctacacc ggctggcgca actccggatt    840
catccccgcg tggatcgccg gccgctcagc ccgtcgagc acccgcccat gcgctggtg    900
gcgctgggct tccggcgcga gcaggttggcc catccgctgg acggcttcgg gatgctggta    960
ccggccggcg agcgcgactt tcagattctg ggcacgtcgt tctcctcgtc gctctttccg    1020
gaccgggcgc ccgaaggcca cgtgctgctg accacgttcg tcgcggcat gcggcatccc    1080
gaactggcgt tgctgcccga agatcggctg gaggcgctgg tgctgcagga cctgcgccgg    1140
ctgctgggca tctcgggcgc gccggtcttc cggcacgtgt ggcgctggga cgctcgatc    1200
ccgcagtacc ggctgggcta cgatgcggtt ctcgcctgcg ttcacgatgt ggaaatgcag    1260
cgctccggtc tgtttctggc cggcaactac atggaaggca tctccgtgat cgacgcgctc    1320
cataccggcc tgaaggccgc ccgcgcgatc atccagcacc tgcgcgaaga agcagccggc    1380
ggtctggcca agctggtgct gggagattga                                      1410
```

SEQ ID NO: 576          moltype =   length =
SEQUENCE: 576
000

SEQ ID NO: 577          moltype = AA   length = 534
FEATURE                 Location/Qualifiers
source                  1..534
                        mol_type = protein
                        organism = Amaranthus tuberculatus
SEQUENCE: 577
MVIQSITHLS PNLALPSPLS VSTKNYPVAV MGNISEREEP TSAKRVAVVG AGVSGLAAAY    60
KLKSHGLSVT LFEADSRAGG KLKTVKKDGF IWDEGANTMT ESEAEVSSLI DDLGLREKQQ    120
LPISQNKRYI ARDGLPVLLP SNPAALLTSN ILSAKSKLQI MLEPFLWRKH NATELSDEHV    180
QESVGEFFER HFGKEFVDYV IDPFVAGTCG GDPQSLSMHH TFPEVWNIEK RFGSVFAGLI    240
QSTLLSKKEK GGENASIKKP RVRGSFSFQG GMQTLVDTMC KQLGEDELKL QCEVLSLSYN    300
QKGIPSLGNW SVSSMSNNTS EDQSYDAVVV TAPIRNVKEM KIMKFGNPFS LDFIPEVTYV    360
PLSVMITAFK KDKVKRPLEG FGVLIPSKEQ HNGLKTLGTL FSSMMFPDRA PSDMCLFTTF    420
VGGSRNRKLA NASTDELKQI VSSDLQQLLG TEDEPSFVNH LFWSNAFPLY GHNYDSVLRA    480
IDKMEKDLPG FFYAGNHKGG LSVGKAMASG CKAAELVISY LDSHIYVKMD EKTA          534

SEQ ID NO: 578          moltype =   length =
SEQUENCE: 578
000

SEQ ID NO: 579          moltype = AA   length = 534
FEATURE                 Location/Qualifiers
source                  1..534
                        mol_type = protein
                        organism = Amaranthus tuberculatus
SEQUENCE: 579
MVIQSITHLS PNLALPSPLS VSTKNYPVAV MGNISEREEP TSAKRVAVVG AGVSGLAAAY    60
KLKSHGLSVT LFEADSRAGG KLKTVKKDGF IWDEGANTMT ESEAEVSSLI DDLGLREKQQ    120
LPISQNKRYI ARAGLPVLLP SNPAALLTSN ILSAKSKLQI MLEPFLWRKH NATELSDEHV    180
QESVGEFFER HFGKEFVDYV IDPFVAGTCG GDPQSLSMHH TFPEVWNIEK RFGSVFAGLI    240
QSTLLSKKEK GGENASIKKP RVRGSFSFQG GMQTLVDTMC KQLGEDELKL QCEVLSLSYN    300
QKGIPSLGNW SVSSMSNNTS EDQSYDAVVV TAPIRNVKEM KIMKFGNPFS LDFIPEVTYV    360
PLSVMITAFK KDKVKRPLEG FGVLIPSKEQ HNGLKTLGTL FSSMMFPDRA PSDMCLFTTF    420
VGGSRNRKLA NASTDELKQI VSSDLQQLLG TEDEPSFVNH LFWSNAFPLY GHNYDSVLRA    480
IDKMEKDLPG FFYAGNHKGG LSVGKAMASG CKAAELVISY LDSHIYVKMD EKTA          534

SEQ ID NO: 580          moltype =   length =
SEQUENCE: 580
000

SEQ ID NO: 581          moltype = AA   length = 533
FEATURE                 Location/Qualifiers
source                  1..533
                        mol_type = protein
                        organism = Amaranthus tuberculatus
SEQUENCE: 581
MVIQSITHLS PNLALPSPLS VSTKNYPVAV MGNISEREEP TSAKRVAVVG AGVSGLAAAY    60
KLKSHGLSVT LFEADSRAGG KLKTVKKDGF IWDEGANTMT ESEAEVSSLI DDLGLREKQQ    120
LPISQNKRYI ARDGLPVLLP SNPAALLTSN ILSAKSKLQI MLEPFLWRKH NATELSDEHV    180
QESVGEFFER HFGKEFVDYV IDPFVAGTCG DPQSLSMHHT FPEVWNIEKR FGSVFAGLIQ    240
STLLSKKEKG GENASIKKPR VRGSFSFQGG MQTLVDTMCK QLGEDELKLQ CEVLSLSYNQ    300
KGIPSLGNWS VSSMSNNTSE DQSYDAVVVT APIRNVKEMK IMKFGNPFSL DFIPEVTYVP    360
LSVMITAFKK DKVKRPLEGF GVLIPSKEQH NGLKTLGTLF SSMMFPDRAP SDMCLFTTFV    420
GGSRNRKLAN ASTDELKQIV SSDLQQLLGT EDEPSFVNHL FWSNAFPLYG HNYDCVLRAI    480
DKMEKDLPGF FYAGNHKGGL SVGKAMASGC KAAELVISYL DSHIYVKMDE KTA           533

SEQ ID NO: 582          moltype =   length =
```

```
SEQUENCE: 582
000

SEQ ID NO: 583           moltype = AA   length = 533
FEATURE                  Location/Qualifiers
source                   1..533
                         mol_type = protein
                         organism = Amaranthus tuberculatus
SEQUENCE: 583
MVIQSITHLS PNLALPSPLS VSTKNYPVAV MGNISEREEP TSAKRVAVVG AGVSGLAAAY    60
KLKSHGLSVT LFEANSRAGG KLKTVKKDGF IWDEGANTMT ESEAEVSSLI DDLGLREKQQ   120
LPISQNKRYI ARDGLPVLLP SNPAALLTSN ILSAKSKLQI MLEPFLWRKH NATELSDEHV   180
QESVGEFFER HFGKEFVDYV IDPFVAGTCG DPQSLSMYHT FPEVWNIEKR FGSVFAGLIQ   240
STLLSKKEKG GENASIKKPR VRGSFSFQGG MQTLVDTMCK QLGEDELKLQ CEVLSLSYNQ   300
KGIPSLGNWS VSSMSNNTSE DQSYDAVVVT APIRNVKEMK IMKFGNPFSL DFIPEVTYVP   360
LSVMITAFKK DKVKRPLEGF GVLIPSKEQH NGLKTLGTLF SSMMFPDRAP SDMCLFTTFV   420
GGSRNRKLAN ASTDELKQIV SSDLQQLLGT EDEPSFVNHL FWSNAFPLYG HNYDSVLRAI   480
DKMEKDLPGF FYAGNHKGGL SVGKAMASGC KAAELVISYL DSHIYVKMDE KTA          533

SEQ ID NO: 584           moltype =    length =
SEQUENCE: 584
000

SEQ ID NO: 585           moltype = AA   length = 547
FEATURE                  Location/Qualifiers
source                   1..547
                         mol_type = protein
                         organism = Arabidopsis thaliana
SEQUENCE: 585
MGLIKNGTLY CRFGISWNFA AVFFSTYFRH CFRLVRDFDS ELLQIAMASG AVADHQIEAV    60
SGKRVAVVGA GVSGLAAAYK LKSRGLNVTV FEADGRVGGK LRSVMQNGLI WDEGANTMTE   120
AEPEVGSLLD DLGLREKQQF PISQKKRYIV RNGVPVMLPT NPIELVTSSV LSTQSKFQIL   180
LEPFLWKKKS SKVSDASAEE SVSEFFQRHF GQEVVDYLID PFVGGTSAAD PDSLSMKHSF   240
PDLWNSFGSI IVGAIRTKFA AKGGKSRDTK SSPGTKKGSR GSFSFKGGMQ ILPDTLCKSL   300
SHDEINLDSK VLSLSYNSGS RQENWSLSCV SHNETQRQNP HYDAAPLCNV KEMKVMKGGQ   360
PPFQLNFLPEI NYMPLSVLIT TFTKEKVKRP LEGFGVLIPS KEQHGFKTL GTLFSSMMFP   420
DRSPSDVHLY TTFIGGSRNQ ELAKASTDEL KQVVTSDLQR LLGVEGEPVS VNHYYWRKAF   480
PLYDSSYDSV MEAIDKMEND LPGFFYAGNH RGGLSVGKSI ASGCKAADLV ISYLESCSND   540
KKPNDSL                                                             547

SEQ ID NO: 586           moltype =    length =
SEQUENCE: 586
000

SEQ ID NO: 587           moltype = AA   length = 548
FEATURE                  Location/Qualifiers
source                   1..548
                         mol_type = protein
                         organism = Nicotiana tabacum
SEQUENCE: 587
MTTTPIANHP NIFTHQSSSS PLAFLNRTSF IPFSSISKRN SVNCNGWRTR CSVAKDYTVP    60
SSAVDGGPAA ELDCVIVGAG ISGLCIAQVM SANYPNLMVT EARDRAGGNI TTVERDGYLW   120
EEGPNSFQPS DPMLTMAVDC GLKDDLVLGD PNAPRFVLWK GKLRPVPSKL TDLPFFDLMS   180
IPGKLRAGFG AIGLRPSPPG HEESVEQFVR RNLGGEVFER LIEPFCSGVY AGDPSKLSMK   240
AAFGKVWKLE ETGGSIIGGT FKAIKERSST PKAPRDPRLP KPKGQTVGSF RKGLRMLPDA   300
ISARLGSKLK LSWKLSSITK SEKGGYHLTY ETPEGVVSLQ SRSIVMTVPS YVASNILRPL   360
SVAAADALSN FYYPPVGAVT ISYPQEAIRD ERLVDGELKG FGQLHPRTQG VETLGTIYSS   420
SLFPNRAPKG RVLLLNYIGG AKNPEILSKT ESQLVEVVDR DLRKMLIKPK AQDPLVVGVR   480
VWPQAIPQFL VGHLDTLSTA KAAMNDNGLE GLFLGGNYVS GVALGRCVEG AYEVASEVTG   540
FLSRYAYK                                                            548

SEQ ID NO: 588           moltype =    length =
SEQUENCE: 588
000

SEQ ID NO: 589           moltype = AA   length = 555
FEATURE                  Location/Qualifiers
source                   1..555
                         mol_type = protein
                         organism = Cichorium sp.
SEQUENCE: 589
MTSLTDVCSL NCCRSWSSLP PPVSGGSLTS KNPRYLITYS PAHRKCNRWR FRCSIAKDSP    60
ITPPISNEFN SQPLLDCVIV GAGISGLCIA QALATKHASV SPDVIVTEAR DRVGGNISTV   120
ERDGYLWEEG PNSFQPSDAM LTMVVDSGLK DDLVLGGSLK PRFVLWGGDL KPVPSKPADL   180
PFFDLMSFPG KLRAGFGALG FRPSPPDREE SVEEFVRRNL GDEVFERLIE PFCSGVYAGD   240
PSKLSMKAAF GKVWNLEQNG GSIVGGAFKA IQDRKNSQKP PRDPRLPKPK GQTVGSFRKG   300
QAMLPNAIST RLGSRVKLCW KLTSISKLEN RGYNLTYETP QGFESLQTKT IVMTVPSYVA   360
SDLLRPLSLG AADALSKFYY PPVAAVSISY PKDAIRADRL IDGQLKGFGQ LHPRSQGVET   420
LGTIYSSSLF PNRAPPGRVL LLNYIGGATN PEILSKTEGE IVDAVDRDLR TMLIRRDAED   480
```

```
PLTLGVRVWP RAIPQFLIGH YDILDSAKAA LSSGGFQGMF LGGNYVSGVA LGKCVEAAYD    540
VAAEVMNFLS QGVYK                                                   555

SEQ ID NO: 590           moltype =    length =
SEQUENCE: 590
000

SEQ ID NO: 591           moltype = AA   length = 562
FEATURE                  Location/Qualifiers
source                   1..562
                         mol_type = protein
                         organism = Spinacia sp.
SEQUENCE: 591
MSAMALSSTM ALSLPQSSMS LSHCRHNRIT ILIPSSSLRR RGGSSIRCST ISTSNSAAAA    60
NYQNKNIGTN GVDGGGGGGG VLDCVIVGGG ISGLCIAQAL STKYSNLSTN FIVTEAKDRV   120
GGNITTMEAD GYLWEEGPNS FQPSDAVLTM AVDSGLKEEL VLGDPNSPRF VLWNGKLRPV   180
PSKLTDLPFF DLMSFPGKIR AGLGALGLRP SPPAHEESVE QFVRRNLGDE VFERLIEPFC   240
SGVYAGDPSK LSMKAAFGRV WVLEQKGGSI IGGTLKTIQE RKDNPKPPRD PRLPKPKGQT   300
VGSFRKGLSM LPTAISERLG NKVKVSWTLS GIAKSSNGEY NLTYETPDGL VSVRTKSVVM   360
TVPSYVASSL LRPLSDVAAE SLSKFHYPPV AAVSLSYPKE AIRSECLIDG ELKGFGQLHS   420
RSQGVETLGT IYSSSLFPGR APPGRTLILN YIGGDTNPGI LDKTKDELAE AVDRDLRRIL   480
INPNAKAPRV LGVRVWPQAI PQFLIGHFDL LDAAKAALTD GGHKGLFLGG NYVSGVALGR   540
CIEGAYESAA EVVDFLSQYS DK                                           562

SEQ ID NO: 592           moltype =    length =
SEQUENCE: 592
000

SEQ ID NO: 593           moltype = AA   length = 531
FEATURE                  Location/Qualifiers
source                   1..531
                         mol_type = protein
                         organism = Spinacia sp.
SEQUENCE: 593
MVILPVSQLS TNLGLSLVSP TKNNPVMGNV SERNQVNQPI SAKRVAVVGA GVSGLAAAYK    60
LKSNGLNVTL FEADSRAGGK LKTVVKDGLI WDEGANTMTE SDEEVTSLFD DLGIREKLQL   120
PISQNKRYIA RDGLPVLLPS NPVALLKSNI LSAKSKLQIM LEPFLWKKHN GAKVSDENAQ   180
ESVAEFFERH FGKEFVDYLI DPFVAGTSGG DPQSLSMRHA FPELWNIENR FGSVISGFIQ   240
SKLSSKKEKG GEKQSSNKKP RVRGSFSFQG GMQTLVDTIC KEFGEDELKL QSEVLSLSYS   300
HNGSLTSENW SVSSMSNSTI QDQPYDAVVV TAPINNVKEL KIMKVENPFS LDFIPEVSCL   360
PLSVIITTFK KTNVKRPLEG FGVLVPSNEQ HNGLKTLGTL FSSMMFPDRA PSDVYLYTTF   420
VGGSRNRELA KASTDELKQI VSSDQQLLG TEGEPTFVNH FYWSKAFPLY GRNYDSVLRA   480
IEKMERDLPG LFYAGNHKGG LSVGKSIASG YKAAELAISY LESNKMTEET I            531

SEQ ID NO: 594           moltype =    length =
SEQUENCE: 594
000

SEQ ID NO: 595           moltype = AA   length = 557
FEATURE                  Location/Qualifiers
source                   1..557
                         mol_type = protein
                         organism = Solanum tuberosum
SEQUENCE: 595
MTTTAVANHP SIFTHRSPLP SPSSSSSSPS FLFLNRTNFI PYFSTSKRNS VNCNGWRTRC    60
SVAKDYTVPP SEVDGNQFPE LDCVVVGAGI SGLCIAKVIS ANYPNLMVTE ARDRAGGNIT   120
TVERDGYLWE EGPNSFQPSD PMLTMAVDCG LKDDLVLGDP DAPRFVLWKD KLRPVPGKLT   180
DLPFFDLMSI PGKLRAGFGA IGLRPSPPGY EESVEQFVRR NLGAEVFERL IEPFCSGVYA   240
GDPSKLIMKA AFGKVWKLEQ TGGSIIGGTF KAIKERSSNP KPPRDPRLPT PKGQTVGSFR   300
KGLRMLPDAI CERLGSKVKL SWKLSSITKS EKGGYLLTYE TPEGVVSLRS RSIVMTVPSY   360
VASNILRPLS VAAADALSSF YYPPVAAVTI SYPQEAIRDE RLVDGELKGF GQLHPRSQGV   420
ETLGTIYSSS LFPNRAPNGR VLLLNYIGGA TNTEIVSKTE SQLVEAVDRD LRKMLIKPKA   480
QDPFVTGVRV WPQAIPQFLV GHLDTLGTAK TALSDNGLDG LFLGGNYVSG VALGRCVEGA   540
YEIASEVTGF LSQYAYK                                                 557

SEQ ID NO: 596           moltype =    length =
SEQUENCE: 596
000

SEQ ID NO: 597           moltype = AA   length = 535
FEATURE                  Location/Qualifiers
source                   1..535
                         mol_type = protein
                         organism = Zea mays
SEQUENCE: 597
MVAATATAMA TAASPLLNGT RIPARLRHRG LSVRCAAVAG GAAEAPASTG ARLSADCVVV    60
GGGISGLCTA QALATRHGVG DVLVTEARAR PGGNITTVER PEEGYLWEEG PNSFQPSDPV   120
LTMAVDSGLK DDLVFGDPNA PRFVLWEGKL RPVPSKPADL PFFDLMSIPG KLRAGLGALG   180
IRPPPPGREE SVEEFVRRNL GAEVFERLIE PFCSGVYAGD PSKLSMKAAF GKVWRLEETG   240
```

-continued

```
GSIIGGTIKT IQERSKNPKP PRDARLPKPK GQTVASFRKG LAMLPNAITS SLGSKVKLSW  300
KLTSITKSDD KGYVLEYETP EGVVSVQAKS VIMTIPSYVA SNILRPLSSD AADALSRFYY  360
PPVAAVTVSY PKEAIRKECL IDGELQGFGQ LHPRSQGVET LGTIYSSSLF PNRAPDGRVL  420
LLNYIGGATN TGIVSKTESE LVEAVDRDLR KMLINSTAVD PLVLGVRVWP QAIPQFLVGH  480
LDLLEAAKAA LDRGGYDGLF LGGNYVAGVA LGRCVEGAYE SASQISDFLT KYAYK       535

SEQ ID NO: 598          moltype =    length =
SEQUENCE: 598
000

SEQ ID NO: 599          moltype = AA   length = 544
FEATURE                 Location/Qualifiers
source                  1..544
                        mol_type = protein
                        organism = Zea mays
SEQUENCE: 599
MLALTASASS ASSHPYRHAS AHTRRPRLRA VLAMAGSDDP RAAPARSVAV VGAGVSGLAA   60
AYRLRQSGVN VTVFEAADRA GGKIRTNSEG GFVWDEGANT MTEGEWEASR LIDDLGLQDK  120
QQYPNSQHKR YIVKDGAPAL IPSDPISLMK SSVLSTKSKI ALFFEPFLYK KANTRNSGKV  180
SEEHLSESVG SFCERHFGRE VVDYFVDPFV AGTSAGDPES LSIRHAFPAL WNLERKYGSV  240
IVGAILSKLA AKGDPVKTRH DSSGKRRNRR VSFSFHGGMQ SLINALHNEV GDDNVKLGTE  300
VLSLACTFDG VPALGRWSIS VDSKDSGDKD LASNQTFDAV IMTAPLSNVR RMKFTKGGAP  360
VVLDFLPKMD YLPLSLMVTA FKKDDVKKPL EGFGVLIPYK EQQKHGLKTL GTLFSSMMFP  420
DRAPDDQYLY TTFVGGSSHNR DLAGAPTSIL KQLVTSDLKK LLGVEGQPTF VKHVYWGNAF  480
PLYGHDYSSV LEAIEKMEKN LPGFFYAGNS KDGLAVGSVI ASGSKAADLA ISYLESHTKH  540
NNSH                                                              544

SEQ ID NO: 600          moltype =    length =
SEQUENCE: 600
000

SEQ ID NO: 601          moltype = AA   length = 563
FEATURE                 Location/Qualifiers
source                  1..563
                        mol_type = protein
                        organism = Chlamydomonas sp.
SEQUENCE: 601
MMLTQTPGTA TASSRRSQIR SAAHVSAKVA PRPTPFSVAS PATAASPATA AARRTLHRTA   60
AAATGAPTAS GAGVAKTLDN VYDVIVVGGG LSGLVTGQAL AAQHKIQNFL VTEARERVGG  120
NITSMSGDGY VWEEGPNSFQ PNDSMLQIAV DSGCEKDLVF GDPTAPRFVW WEGKLRPVPS  180
GLDAFTFDLM SIPGKIRAGL GAIGLINGAM PSFEESVEQF IRRNLGDEVF FRLIEPFCSG  240
VYAGDPSKLS MKAAFNRIWI LEKNGGSLVG GAIKLFQERQ SNPAPPRDPR LPPKPKGQTV  300
GSFRKGLKML PDAIERNIPD KIRVNWKLVS LGREADGRYG LVYDTPEGRV KVFARAVALT  360
APSYVVADLV KEQAPAAAEA LGSFDYPPVG AVTLSYPLSA VREERKASDG SVPGFGQLHP  420
RTQGITTLGT IYSSSLFPGR APEGHMLLLN YIGGTTNRGI VNQTTEQLVE QVDKDLRNMV  480
IKPDAPKPRV VGVRVWPRAI PQFNLGHLEQ LDKARKALDA AGLQGVHLGG NYVSGVALGK  540
VVEHGYESAA NLAKSVSKAA VKA                                          563

SEQ ID NO: 602          moltype =    length =
SEQUENCE: 602
000

SEQ ID NO: 603          moltype = AA   length = 577
FEATURE                 Location/Qualifiers
source                  1..577
                        mol_type = protein
                        organism = Polytomella sp.
SEQUENCE: 603
MSSSALRLLC GRTSFFNLCQ KYPPSFLSQL STLNFSTHSP FDSTYDVVVV GAGISGLSTA   60
QALSIQHKID NVLVTEADHR VGGKITTKRN KDFLWEEGPN SCLMNDALYR AARDAGVESK  120
ILSADPKLPR WILWGRRLRV APIGSYALKS DLLSTQGLLR AIRGVTGFGV SPAPPKGQEE  180
SVEGFVRRTL GDEIFERLVE PFCSGVYAGD PSKLSMRAAF GKLVEFEETG DGSLLRGVFR  240
YVMNKRRERR TGGAKDGDTV PLNETAKAPK SSSGPTVSSF EGGIEILPKA IAQKLGDRVR  300
LGLRLVRIDP TQLADGTTAY RLSYRRMSHQ GDDDSSRTAG AVPRTAEGDV AAGDEDAVVE  360
VVAKKVVLTT PAFDAADILS RSGLVAAANP LKEVDYPPVA LVVVLSYDVDS ISAIHRVSHV  420
AHGLSGFGQL HPRPEGLRTL GTIYGSTLFP NRSPVARTTL LNFVGGSTDR AVGSADPMAL  480
AMEVDLDLKK SGLIREGAAK PEVLGVKVYP KAIPQFDIGH LDRVEKAKMM LKNERGGADW  540
SGVKLAGNYV CGVAVGRCIE FGFEIAENLA QELARKK                           577

SEQ ID NO: 604          moltype =    length =
SEQUENCE: 604
000

SEQ ID NO: 605          moltype = AA   length = 544
FEATURE                 Location/Qualifiers
source                  1..544
                        mol_type = protein
                        organism = Sorghum sp.
SEQUENCE: 605
```

```
MLARTATVSS TSSHSHPYRP TSARSLRLRP VLAMAGSDDS RAAPARSVAV VGAGVSGLVA    60
AYRLRKSGVN VTVFEAADRA GGKIRTNSEG GFLWDEGANT MTEGELEASR LIDDLGLQDK   120
QQYPNSQHKR YIVKDGAPAL IPSDPISLMK SSVLSTKSKI ALFFEPFLYK KANTRNPGKV   180
SDEHLSESVG SFFERHFGRE VVDYLIDPFV AGTSAGDPES LSICHAFPAL WNLERKYGSV   240
VVGAILSKLT AKGDPVKTRR DSSAKRRNRR VSFSFHGGMQ SLINALHNEV GDDNVKLGTE   300
VLSLACTLDG APAPGGWSIS DDSKDASGKD LAKNQTFDAV IMTAPLSNVQ RMKFTKGGAP   360
FVLDFLPKVD YLPLSLMVTA FKKEDVKKPL EGFGVLIPYK EQQHGLKTL GTLFSSMMFP    420
DRAPDDQYLY TTFVGGSHNR DLAGAPTSIL KQLVTSDLKK LLGVQGQPTF VKHIYWGNAF   480
PLYGHDYNSV LEAIEKMEKN LPGFFYAGNN KDGLAVGSVI ASGSKAADLA ISYLESHTKH   540
NNLH                                                               544

SEQ ID NO: 606          moltype =    length =
SEQUENCE: 606
000

SEQ ID NO: 607          moltype = AA   length = 536
FEATURE                 Location/Qualifiers
source                  1..536
                        mol_type = protein
                        organism = Oryza sativa
SEQUENCE: 607
MAAAAAAMAT ATSATAAPPL RIRDAARRTR RRGHVRCAVA SGAAEAPAAP GARVSADCVV    60
VGGGISGLCT AQALATKHGV GDVLVTEARA RPGGNITTAE RAGEGYLWEE GPNSFQPSDP   120
VLTMAVDSGL KDDLVFGDPN APRFVLWEGK LRPVPSKPGD LPFFDLMSIP GKLRAGLGAL   180
GVRAPPPGRE ESVEDFVRRN LGAEVFERLI EPFCSGVYAG DPSKLSMKAA FGKVWRLEDT   240
GGSIIGGTIK TIQERGKNPK PPRDPRLPTP KGQTVASFRK GLTMLPDAIT SRLGSKVKLS   300
WKLTSITKSD NKGYALVYET PEGVVSVQAK TVVMTIPSYV ASDILRPLSS DAADALSIFY   360
YPPVAAVTVS YPKEAIRKEC LIDGELQGFG QLHPRSQGVE TLGTIYSSSL FPNRAPAGRV   420
LLLNYIGGST NTGIVSKTES ELVEAVDRDL RKMLINPKAV DPLVLGVRVW PQAIPQFLIG   480
HLDHLEAAKS ALGKGGYDGL FLGGNYVAGV ALGRCVEGAY ESASQISDYL TKYAYK       536

SEQ ID NO: 608          moltype =    length =
SEQUENCE: 608
000

SEQ ID NO: 609          moltype = AA   length = 505
FEATURE                 Location/Qualifiers
source                  1..505
                        mol_type = protein
                        organism = Amaranthus sp.
SEQUENCE: 609
MGNISERDEP TSAKRVAVVG AGVSGLAAAY KLKSHGLNVT LFEADSRAGG KLKTVKKDGF    60
IWDEGANTMT ESEAEVSSLI DDLGLREKQQ LPISQNKRYI ARDGLPVLLP SNPAALLTSN   120
ILSAKSKLQI MLEPFFWRKH NATELSDEHV QESVGEFFER HFGKEFVDYV IDPFVAGTCG   180
GDPQSLSMHH TFPEVWNIEK RFGSVFAGLI QSTLLSKKEK GGGGNASIKK PRVRGSFSFH   240
GGMQTLVDTI CKQLGEDELK LQCEVLSLSY NQKGIPSLGN WSVSSMSNNT SEDQSYDAVV   300
VTAPIRNVKE MKIMKFGNPF SLDFIPEVSY VPLSVMITAF VGGSRNRKL ANASTDELKQ    360
QHNGLKTLGT LFSSMMFPDR APSDMCLFTT FVGGSRNRKL ANASTDELKQ IVSSDLQQLL   420
GTEDEPSFVN HLFWSNAFPL YGHNYDSVLR AIDKMEKDLP GFFYAGNHKG GLSVGKAMAS   480
GCKAAELVIS YLDSHIYVKM DEKTA                                        505

SEQ ID NO: 610          moltype =    length =
SEQUENCE: 610
000

SEQ ID NO: 611          moltype = AA   length = 506
FEATURE                 Location/Qualifiers
source                  1..506
                        mol_type = protein
                        organism = Arabidopsis sp.
SEQUENCE: 611
MELSLLRPTT QSLLPSFSKP NLRLNVYKPL RLRCSVAGGP TVGSSKIEGG GGTTITTDCV    60
IVGGGISGLC IAQALATKHP DAAPNLIVTE AKDRVGGNII TREENGFLWE EGPNSFQPSD   120
PMLTMVVDSG LKDDLVLGDP TAPRFVLWNG KLRPVPSKLT DLPFFDLMSI GGKIRAGFGA   180
LGIRPSPPGR EESVEEFVRR NLGDEVFERL IEPFCSGVYA GDPSKLSMKA AFGKVWKLEQ   240
NGGSIIGGTF KAIQERKNAP KAERDPRLPK PQGQTVGSFR KGLRMLPEAI SARLGSKVKL   300
SWKLSGITKL ESGGYNLTYE TPDGLVSVQS KSVVMTVPSH VASGLLRPLS ESAANALSKL   360
YYPPVAAVSI SYPKEAIRTE CLIDGELKGF GQLHPRTQGV ETLGTIYSSS LPNRAPPGRV   420
ILLLNYIGGS TNTGILSKSE GELVEAFLVG HFDILDTAKS SLTSSGYEGL FLGGNYVAGV   480
ALGRCVEGAY ETAIEVNNFM SRYAYK                                       506

SEQ ID NO: 612          moltype =    length =
SEQUENCE: 612
000

SEQ ID NO: 613          moltype = AA   length = 504
FEATURE                 Location/Qualifiers
source                  1..504
                        mol_type = protein
```

```
                        organism = Nicotiana sp.
SEQUENCE: 613
MAPSAGEDKH  SSAKRVAVIG  AGVSGLAAAY  KLKIHGLNVT  VFEAEGKAGG  KLRSVSQDGL   60
IWDEGANTMT  ESEGDVTFLI  DSLGLREKQQ  FPLSQNKRYI  ARNGTPVLLP  SNPIDLIKSN  120
FLSTGSKLQM  LLEPILWKNK  KLSQVSDSHE  SVSGFFQRHF  GKEVVDYLID  PFVAGTCGGD  180
PDSLSMHHSF  PELWNLEKRF  GSVILGAIRS  KLSPKNEKKQ  GPPKTSANKK  RQRGSFSFLG  240
GMQTLTDAIC  KDLREDELRL  NSRVLELSCS  CTEDSAIDSW  SIISASPHKR  QSEEESFDAV  300
IMTAPLCDVK  SMKIAKRGNP  FLLNFIPEVD  YVPLSVVITT  FKRENVKYPL  EGFGVLVPSK  360
EQQHGLKTLG  TLFSSMMFPD  RAPNNVYLYT  TFVGGSRNRE  LAKASRTELK  EIVTSDLKQL  420
LGAEGEPTYV  NHLYWSKAFP  LYGHNYDSVL  DAIDKMEKNL  PGLFYAGNHR  GGLSVGKALS  480
SGCNAADLVI  SYLESVSTDS  KRHC                                           504

SEQ ID NO: 614          moltype =   length =
SEQUENCE: 614
000

SEQ ID NO: 615          moltype = AA   length = 502
FEATURE                 Location/Qualifiers
source                  1..502
                        mol_type = protein
                        organism = Glycine sp.
SEQUENCE: 615
MASSATDDNP  RSVKRVAVVG  AGVSGLAAAY  KLKSHGLDVT  VFEAEGRAGG  RLRSVSQDGL   60
IWDEGANTMT  ESEIEVKGLI  DALGLQEKQQ  FPISQKRYI   VKNGAPLLVP  TNPAALLKSK  120
LLSAQSKIHL  IFEPFMWKRS  DPSNVCDENS  VESVGRFFER  HFGKEVVDYL  IDPFVGGTSA  180
ADPESLSMRH  SFPELWNLEK  RFGSIIAGAL  QSKLFAKREK  TGENRTALRK  NKHKRGSFSF  240
QGGMQTLTDT  LCKELGKDDL  KLNEKVLTLA  YGHDGSSSSQ  NWSITSASNQ  STQDVDAVIM  300
TAPLYNVKDI  KITKRGTPFP  LNFLPEVSYV  PISVMITTFK  KENVKRPLEG  FGVLVPSKEQ  360
KNGLKTLGTL  FSSMMFPDRA  PSDLYLYTTF  IGGTQNRELA  QASTDELRKI  VTSDLRKLLG  420
AEGEPTFVNH  FYWSKGFPLY  GRNYGSVLQA  IDKIEKDLPG  FFFAGNYKGG  LSVGKAIASG  480
CKAADLVISY  LNSASDNTVP  DK                                             502

SEQ ID NO: 616          moltype =   length =
SEQUENCE: 616
000

SEQ ID NO: 617          moltype = AA   length = 401
FEATURE                 Location/Qualifiers
source                  1..401
                        mol_type = protein
                        organism = Cucumis sp.
SEQUENCE: 617
SFQPSDPILT  MVVDSGLKDD  LVLGDPDAPR  FVLWNGKLRP  VPAKPNDLPF  FDLMSIGGKI   60
RAGFGALGIR  PPPPGREESV  EEFVRRNLGN  EVFERLIEPF  CSGVYAGDPS  KLSMKAAFGK  120
VWRLEQNGGS  IIGGTFKALQ  ERNKTTKPPR  DPRLPKPKGQ  TVGSFRKGLT  MLPNAISTCL  180
GSKVKVSWKL  SSISKVDDGG  YSLTYETPEG  LVSILSRSVI  MTVPSYIAGT  LLRPISGKAA  240
DALSKFYYPP  VASVTISYPK  GAIRKECLID  GELKGFGQLH  PRSQGVTTLG  TIYSSSLFPN  300
RAPDGRVLLL  NYIGGATNTG  ILSQTESELI  EVVDRDLRKI  LINPNAEDPL  PLSVRVWPQA  360
IPQFLIGHLD  VLDTAKAGLR  EAGMEGLFLG  GNYVCGVALG  R                      401

SEQ ID NO: 618          moltype =   length =
SEQUENCE: 618
000

SEQ ID NO: 619          moltype = AA   length = 506
FEATURE                 Location/Qualifiers
source                  1..506
                        mol_type = protein
                        organism = Oryza sativa
SEQUENCE: 619
MAASDDPRGG  RSVAVVGAGV  SGLAAAYRLR  KRGVQVTVFE  AADRAGGKIR  TNSEGGFIWD   60
EGANTMTESE  LEASRLIDDL  GLQGKQQYPN  SQHKRYIVKD  GAPTLIPSDP  IALMKSTVLS  120
TKSKLKLFLE  PFLYEKSSRR  TSGKVSDEHL  SESVIFLCIC  RDNQVVDYLI  DPFVAGTSGD  180
DPESLSIRHA  FPALWNLENK  YGSVIAGAIL  SKLSTKGDSV  KTGGASPGKG  RNKRVSFSFH  240
GGMQSLIDAL  HNEVGDGNVK  LGTEVLSLAC  CCDGVSSSGG  WSISVDSKDA  KGKDLRKNQS  300
FDAVIMTAPL  SNVQRMKFTK  GGVPFVLDFL  PKVDYLPLSL  MVTAFKKEDV  KKPLEGFGAL  360
IPYKEQQKHG  LKTLGTLFSS  MMFPDRAPND  QYLYTSFIGG  SHNRDLAGAP  TAILKQLVTS  420
DLRKLLGVEG  QPTFVKHVHW  RNAFPPLYGQN YDLVLEAIAK  MENNLPGFFY  AGNNKDGLAV  480
GNVIASGSKA  ADLVISYLES  CTDQDN                                         506

SEQ ID NO: 620          moltype =   length =
SEQUENCE: 620
000

SEQ ID NO: 621          moltype = AA   length = 574
FEATURE                 Location/Qualifiers
source                  1..574
                        mol_type = protein
                        organism = Oryza sativa
```

```
SEQUENCE: 621
MLSPATTFSS SSSSSSPSRA HARAPTRFAV AASARAARFR PARAMAASDD PRGGRSVAVV    60
GAGVSGLAAA YRLRKRGVQV TVFEAADRAG GKIRTNSEGG FIWDEGANTM TESELEASRL   120
IDDLGLQGKQ QYPNSQHKRY IVKDGAPTLI PSDPIALMKS TVLSTKSKLK LFLEPFLYEK   180
SSRRTSGKVS DEHLSESVAS FFERHFGKEV VDYLIDPFVA GTSGGDPESL SIRHAFPALW   240
NLENKYGSVI AGAILSKLST KGDSVKTGGA SPGKGRNKRV SFSFHGGMQS LIDALHNEVG   300
DGNVKLGTEV LSLACCCDGV SSSGGWSISV DSKDAKGKDL RKNQSFDAVI MTAPLSNVQR   360
MKFTKGGVPF VLDFLPKVDY LPLSLMVTAF KKEDVKKPLE GFGALIPYKE QQKHGLKTLG   420
HPASCIELNI QINLATLLYF FSGTLFSSMM FPDRAPNDQY LYTSFIGGSH NRDLAGAPTA   480
ILKQLVTSDL RKLLGVEGQP TFVKHVHWRN AFPLYGQNYD LVLEAIAKME NNLPGFFYAG   540
NNKDGLAVGN VIASGSKAAD LVISYLESCT DQDN                              574

SEQ ID NO: 622          moltype =    length =
SEQUENCE: 622
000

SEQ ID NO: 623          moltype = AA   length = 550
FEATURE                 Location/Qualifiers
source                  1..550
                        mol_type = protein
                        organism = Amaranthus tuberculatus
SEQUENCE: 623
MSAMALSSSI LQCPPHSDIS FRFFAHTRTQ PPIFFGRPRK LSYIHCSTSS SSTANYQNTI    60
TSQGEGDKVL DCVIVGAGIS GLCIAQALST KHIQSNLNFI VTEAKHRVGG NITTMESDGY   120
IWEEGPNSFQ PSDPVLTMAV DSGLKDDLVL GDPNAPRFVL WNGKLRPVPS KPTDLPFFDL   180
MSFPGKIRAG LGALGLRPPP PSYEEESVEEF VRRNLGDEVF ERLIEPFCSG VYAGDPAKLS   240
MKAAFGKVWT LEQKGGSIIA GTLKTIQERK NNPPPPRDPR LPKPKGQTVG SFRKGLIMLP   300
TAIAARLGSK VKLSWTLSNI DKSLNGEYNL TYQTPDGPVS VRTKAVVMTV PSYIASSLLR   360
PLSDVAADSL SKFYYPPVAA VSLSYPKEAI RPECLIDGEL KGFGQLHPRS QGVETLGTIY   420
SSSLFPGRAP PGRTLILSYI GGATNLGILQ KSEDELAETV DKDLRKILIN PNAKGSRVLG   480
VRVWPKAIPQ FLVGHFDVLD AAKAGLANAG QKGLFLGGNY VSGVALGRCI EGAYDSASEV   540
VDFLSQYKDK                                                         550

SEQ ID NO: 624          moltype =    length =
SEQUENCE: 624
000

SEQ ID NO: 625          moltype = AA   length = 547
FEATURE                 Location/Qualifiers
source                  1..547
                        mol_type = protein
                        organism = Alopecurus myosuroides
SEQUENCE: 625
MLTSATTPSS SSASSRASTR FASSSRPRRT AYARGRRLRP VLAMAASDDP RARSVAVVGA    60
GISGLVAAYR LSKSGVRVTV FEADDRAGGK IRTNSDSGFL WDEGANTMTE SALEASRLID   120
DLGLEDRLQY PNSQHKRYTV KDGAPALIPS DPIALMKSSL LSTKSKFKLF LEPFLYDKSS   180
TKSSKKVSDE HISESVGSFF ERHFGKEVVD YLIDPFVAGT SAGDPESLSI RHAFPGLWNL   240
EKKYGSIIVG AIMSKLTAKG DKKGSAVSGK GRNKRASFSF HGGMQTLVDA LHKEVGDGNV   300
KLGAQVLSLA CICDGLSASD GWSISVDSKD ASNKELTKNH SFDAVIMTAP LSNVQRMKFT   360
KGGAPFVLDF LPKVDYLPLS LMVTAFKKED VKRPLEGFGV LIPYKEQQKH GLKTLGTLFS   420
SMMFPDRAPN DQHLFTTFVG GSHNRDLAGA PTSILKQLVT SDLGKLLGVE GQPTFVKHIH   480
WRNAFPLYGH DYDSALEAIG KMESDLPGFF YAGNNKDGLA VGNVIASGSK TADLVISYLE   540
SGIKQDN                                                            547

SEQ ID NO: 626          moltype =    length =
SEQUENCE: 626
000

SEQ ID NO: 627          moltype = AA   length = 531
FEATURE                 Location/Qualifiers
source                  1..531
                        mol_type = protein
                        organism = Alopecurus myosuroides
SEQUENCE: 627
MVGATMAIAT VTAALPLRVR VPGRSRRGQA RCAVASDATE APAAPSARLS ADCVIVGGGI    60
SGLCTAQALA TKYGVSDLLV TEARARPGGN ITTVERPDEG YLWEEGPNSF QPSDPVLTMA   120
VDSGLKDELV FGDPNAPRFV LWEGKLRPVP SKPGDLPFFD LMSIPGKLRA GLGALGIRPP   180
PPGREESVEE FVRRNLGAEV FERLIEPFCS GVYAGDPAKL SMRAAFGKVW RLEENGGSII   240
GGTIKAIQDK GKNPKPPRDP RLPAPKGQTV ASFRKGLAML PNAIASRLGS KVKLSWKLTS   300
ITKSENQGYV LGYETPEGVV SVQAKSVIMT IPSYIASDIL RPLSSDAADG LSKFYYPPVA   360
AVTVSYPKEA IRKECLIDGE LQGFGQLHPS SQGVETLGTI YSSSLFPNRA PAGRVLLLNY   420
IGGATNTGIV SKTESDLVEA VDRDLRKMLI NPRAADPLAL GVRVWPQAIP QFLIGHLDRL   480
DAAKSALVRS GCSGLFLGGN YVAGVALGRC IEGAYDSASE VSDFLNKYAY K            531

SEQ ID NO: 628          moltype = AA   length = 551
FEATURE                 Location/Qualifiers
source                  1..551
                        mol_type = protein
                        organism = Oryza sativa
```

```
SEQUENCE: 628
MLSPATTFSS SSSSSSPSRA HARAPTRFAV AASARAARFR PARAMAASDD PRGGRSAVVV    60
GAGVSGLAAA YRLRKRGVQV TVFEAADRAG GKIRTNSEGG FIWDEGANTM TESELEASRL   120
IDDLGLQGKQ QYPNSQHKRY IVKDGAPTLI PSDPIALMKS TVLSTKSKLK LFLEPFLYEK   180
SSRRTSGKVS DEHLSESVAS FFERHFGKEV VDYLIDPFVA GTSGGDPESL SIRHAFPALW   240
NLENKYGSVI AGAILSKLST KGDSVKTGGA SPGKGRNKRV SFSFHGGMQS LIDALHNEVG   300
DGNVKLGTEV LSLACCCDGV SSSGGWSISV DSKDAKGKDL RKNQSFDAVI MTAPLSNVQR   360
MKFTKGGVPF VLDFLPKVDY LPLSLMVTAF KKEDVKKPLE GFGALIPYKE QQKHGLKTLG   420
TLFSSMMFPD RAPNDQYLYT SIIGGSHNRD LAGAPTAILK QLVTSDLRKL LGVEGQPTFV   480
KHVHWRNAFP LYGQNYDLVL EAIAKMENNL PGFFYAGNNK DGLAVGNVIA SGSKAADLVI   540
SYLESCTDQD N                                                       551

SEQ ID NO: 629          moltype = AA  length = 551
FEATURE                 Location/Qualifiers
source                  1..551
                        mol_type = protein
                        organism = Oryza sativa
SEQUENCE: 629
MLSPATTFSS SSSSSSPSRA HARAPTRFAV AASARAARFR PARAMAASDD PRGGRSAVVV    60
GAGVSGLAAA YRLRKRGVQV TVFEAADRAG GKIRTNSEGG FIWDEGANTM TESELEASRL   120
IDDLGLQGKQ QYPNSQHKRY IVKDGAPTLI PSDPIALMKS TVLSTKSKLK LFLEPFLYEK   180
SSRRTSGKVS DEHLSESVAS FFERHFGKEV VDYLIDPFVA GTSGGDPESL SIRHAFPALW   240
NLENKYGSVI AGAILSKLST KGDSVKTGGA SPGKGRNKRV SFSFHGGMQS LIDALHNEVG   300
DGNVKLGTEV LSLACCCDGV SSSGGWSISV DSKDAKGKDL RKNQSFDAVI MTAPLSNVQR   360
MKFTKGGVPF VLDFLPKVDY LPLSLMVTAF KKEDVKKPLE GFGALIPYKE QQKHGLKTLG   420
TLFSSMMFPD RAPNDQYLYT SLIGGSHNRD LAGAPTAILK QLVTSDLRKL LGVEGQPTFV   480
KHVHWRNAFP LYGQNYDLVL EAIAKMENNL PGFFYAGNNK DGLAVGNVIA SGSKAADLVI   540
SYLESCTDQD N                                                       551

SEQ ID NO: 630          moltype = AA  length = 551
FEATURE                 Location/Qualifiers
source                  1..551
                        mol_type = protein
                        organism = Oryza sativa
SEQUENCE: 630
MLSPATTFSS SSSSSSPSRA HARAPTRFAV AASARAARFR PARAMAASDD PRGGRSAVVV    60
GAGVSGLAAA YRLRKRGVQV TVFEAADRAG GKIRTNSEGG FIWDEGANTM TESELEASRL   120
IDDLGLQGKQ QYPNSQHKRY IVKDGAPTLI PSDPIALMKS TVLSTKSKLK LFLEPFLYEK   180
SSRRTSGKVS DEHLSESVAS FFERHFGKEV VDYLIDPFVA GTSGGDPESL SIRHAFPALW   240
NLENKYGSVI AGAILSKLST KGDSVKTGGA SPGKGRNKRV SFSFHGGMQS LIDALHNEVG   300
DGNVKLGTEV LSLACCCDGV SSSGGWSISV DSKDAKGKDL RKNQSFDAVI MTAPLSNVQR   360
MKFTKGGVPF VLDFLPKVDY LPLSLMVTAF KKEDVKKPLE GFGALIPYKE QQKHGLKTLG   420
TLFSSMMFPD RAPNDQYLYT SVIGGSHNRD LAGAPTAILK QLVTSDLRKL LGVEGQPTFV   480
KHVHWRNAFP LYGQNYDLVL EAIAKMENNL PGFFYAGNNK DGLAVGNVIA SGSKAADLVI   540
SYLESCTDQD N                                                       551

SEQ ID NO: 631          moltype = AA  length = 551
FEATURE                 Location/Qualifiers
source                  1..551
                        mol_type = protein
                        organism = Oryza sativa
SEQUENCE: 631
MLSPATTFSS SSSSSSPSRA HARAPTRFAV AASARAARFR PARAMAASDD PRGGRSAVVV    60
GAGVSGLAAA YRLRKRGVQV TVFEAADRAG GKIRTNSEGG FIWDEGANTM TESELEASRL   120
IDDLGLQGKQ QYPNSQHKRY IVKDGAPTLI PSDPIALMKS TVLSTKSKLK LFLEPFLYEK   180
SSRRTSGKVS DEHLSESVAS FFERHFGKEV VDYLIDPFVA GTSGRDPESL SIRHAFPALW   240
NLENKYGSVI AGAILSKLST KGDSVKTGGA SPGKGRNKRV SFSFHGGMQS LIDALHNEVG   300
DGNVKLGTEV LSLACCCDGV SSSGGWSISV DSKDAKGKDL RKNQSFDAVI MTAPLSNVQR   360
MKFTKGGVPF VLDFLPKVDY LPLSLMVTAF KKEDVKKPLE GFGALIPYKE QQKHGLKTLG   420
TLFSSMMFPD RAPNDQYLYT SFIGGSHNRD LAGAPTAILK QLVTSDLRKL LGVEGQPTFV   480
KHVHWRNAFP LYGQNYDLVL EAIAKMENNL PGFFYAGNNK DGLAVGNVIA SGSKAADLVI   540
SYLESCTDQD N                                                       551

SEQ ID NO: 632          moltype = AA  length = 551
FEATURE                 Location/Qualifiers
source                  1..551
                        mol_type = protein
                        organism = Oryza sativa
SEQUENCE: 632
MLSPATTFSS SSSSSSPSRA HARAPTRFAV AASARAARFR PARAMAASDD PRGGRSAVVV    60
GAGVSGLAAA YRLRKRGVQV TVFEAADRAG GKIRTNSEGG FIWDEGANTM TESELEASRL   120
IDDLGLQGKQ QYPNSQHKRY IVKDGAPTLI PSDPIALMKS TVLSTKSKLK LFLEPFLYEK   180
SSRRTSGKVS DEHLSESVAS FFERHFGKEV VDYLIDPFVA GTSGGDPESL SIRHAFPALW   240
NLENKYGSVI AGAILSKLST KGDSVKTGGA SPGKGRNKRV SFSFHGGMQS LIDALHNEVG   300
DGNVKLGTEV LSLACCCDGV SSSGGWSISV DSKDAKGKDL RKNQSFDAVI MTAPLSNVQR   360
MKFTKGGVPF VLDFLPKVDY LPLSLMVTAF KKEDVKKPLE GFGALIPYKE QQKHGLKTLA   420
TLFSSMMFPD RAPNDQYLYT SFIGGSHNRD LAGAPTAILK QLVTSDLRKL LGVEGQPTFV   480
KHVHWRNAFP LYGQNYDLVL EAIAKMENNL PGFFYAGNNK DGLAVGNVIA SGSKAADLVI   540
SYLESCTDQD N                                                       551
```

```
SEQ ID NO: 633           moltype = AA   length = 551
FEATURE                  Location/Qualifiers
source                   1..551
                         mol_type = protein
                         organism = Oryza sativa
SEQUENCE: 633
MLSPATTFSS SSSSSSPSRA HARAPTRFAV AASARAARFR PARAMAASDD PRGGRSVAVV    60
GAGVSGLAAA YRLRKRGVQV TVFEAADRAG GKIRTNSEGG FIWDEGANTM TESELEASRL   120
IDDLGLQGKQ QYPNSQHKRY IVKDGAPTLI PSDPIALMKS TVLSTKSKLK LFLEPFLYEK   180
SSRRTSGKVS DEHLSESVAS FFERHFGKEV VDYLIDPFVA GTSGGDPESL SIRHAFPALW   240
NLENKYGSVI AGAILSKLST KGDSVKTGGA SPGKGRNKRV SFSFHGGMQS LIDALHNEVG   300
DGNVKLGTEV LSLACCCDGV SSSGGWSISV DSKDAKGKDL RKNQSFDAVI MTAPLSNVQR   360
MKFTKGGVPF VLDFLPKVDY LPLSLMVTAF KKEDVKKPLE GFGALIPYKE QQKHGLKTFG   420
TLFSSMMFPD RAPNDQYLYT SFIGGSHNRD LAGAPTAILK QLVTSDLRKL LGVEGQPTFV   480
KHVHWRNAFP LYGQNYDLVL EAIAKMENNL PGFFYAGNNK DGLAVGNVIA SGSKAADLVI   540
SYLESCTDQD N                                                       551

SEQ ID NO: 634           moltype = AA   length = 551
FEATURE                  Location/Qualifiers
source                   1..551
                         mol_type = protein
                         organism = Oryza sativa
SEQUENCE: 634
MLSPATTFSS SSSSSSPSRA HARAPTRFAV AASARAARFR PARAMAASDD PRGGRSVAVV    60
GAGVSGLAAA YRLRKRGVQV TVFEAADRAG GKIRTNSEGG FIWDEGANTM TESELEASRL   120
IDDLGLQGKQ QYPNSQHKRY IVKDGAPTLI PSDPIALMKS TVLSTKSKLK LFLEPFLYEK   180
SSRRTSGKVS DEHLSESVAS FFERHFGKEV VDYLIDPFVA GTSGGDPESL SIRHAFPALW   240
NLENKYGSVI AGAILSKLST KGDSVKTGGA SPGKGRNKRV SFSFHGGMQS LIDALHNEVG   300
DGNVKLGTEV LSLACCCDGV SSSGGWSISV DSKDAKGKDL RKNQSFDAVI MTAPLSNVQR   360
MKFTKGGVPF VLDFLPKVDY LPLSLMVTAF KKEDVKKPLE GFGALIPYKE QQKHGLKTLG   420
TFFSSMMFPD RAPNDQYLYT SFIGGSHNRD LAGAPTAILK QLVTSDLRKL LGVEGQPTFV   480
KHVHWRNAFP LYGQNYDLVL EAIAKMENNL PGFFYAGNNK DGLAVGNVIA SGSKAADLVI   540
SYLESCTDQD N                                                       551

SEQ ID NO: 635           moltype = AA   length = 551
FEATURE                  Location/Qualifiers
source                   1..551
                         mol_type = protein
                         organism = Oryza sativa
SEQUENCE: 635
MLSPATTFSS SSSSSSPSRA HARAPTRFAV AASARAARFR PARAMAASDD PRGGRSVAVV    60
GAGVSGLAAA YRLRKRGVQV TVFEAADRAG GKIRTNSEGG FIWDEGANTM TESELEASRL   120
IDDLGLQGKQ QYPNSQHKGY IVKDGAPTLI PSDPIALMKS TVLSTKSKLK LFLEPFLYEK   180
SSRRTSGKVS DEHLSESVAS FFERHFGKEV VDYLIDPFVA GTSGGDPESL SIRHAFPALW   240
NLENKYGSVI AGAILSKLST KGDSVKTGGA SPGKGRNKRV SFSFHGGMQS LIDALHNEVG   300
DGNVKLGTEV LSLACCCDGV SSSGGWSISV DSKDAKGKDL RKNQSFDAVI MTAPLSNVQR   360
MKFTKGGVPF VLDFLPKVDY LPLSLMVTAF KKEDVKKPLE GFGALIPYKE QQKHGLKTLG   420
TLFSSMMFPD RAPNDQYLYT SFIGGSHNRD LAGAPTAILK QLVTSDLRKL LGVEGQPTFV   480
KHVHWRNAFP LYGQNYDLVL EAIAKMENNL PGFFYAGNNK DGLAVGNVIA SGSKAADLVI   540
SYLESCTDQD N                                                       551

SEQ ID NO: 636           moltype = AA   length = 551
FEATURE                  Location/Qualifiers
source                   1..551
                         mol_type = protein
                         organism = Oryza sativa
SEQUENCE: 636
MLSPATTFSS SSSSSSPSRA HARAPTRFAV AASARAARFR PARAMAASDD PRGGRSVAVV    60
GAGVSGLAAA YRLRKRGVQV TVFEAADRAG GKIRTNSEGG FIWDEGANTM TESELEASRL   120
IDDLGLQGKQ QYPNSQHKLY IVKDGAPTLI PSDPIALMKS TVLSTKSKLK LFLEPFLYEK   180
SSRRTSGKVS DEHLSESVAS FFERHFGKEV VDYLIDPFVA GTSGGDPESL SIRHAFPALW   240
NLENKYGSVI AGAILSKLST KGDSVKTGGA SPGKGRNKRV SFSFHGGMQS LIDALHNEVG   300
DGNVKLGTEV LSLACCCDGV SSSGGWSISV DSKDAKGKDL RKNQSFDAVI MTAPLSNVQR   360
MKFTKGGVPF VLDFLPKVDY LPLSLMVTAF KKEDVKKPLE GFGALIPYKE QQKHGLKTLG   420
TLFSSMMFPD RAPNDQYLYT SFIGGSHNRD LAGAPTAILK QLVTSDLRKL LGVEGQPTFV   480
KHVHWRNAFP LYGQNYDLVL EAIAKMENNL PGFFYAGNNK DGLAVGNVIA SGSKAADLVI   540
SYLESCTDQD N                                                       551

SEQ ID NO: 637           moltype = AA   length = 551
FEATURE                  Location/Qualifiers
source                   1..551
                         mol_type = protein
                         organism = Oryza sativa
SEQUENCE: 637
MLSPATTFSS SSSSSSPSRA HARAPTRFAV AASARAARFR PARAMAASDD PRGGRSVAVV    60
GAGVSGLAAA YRLRKRGVQV TVFEAADRAG GKIRTNSEGG FIWDEGANTM TESELEASRL   120
IDDLGLQGKQ QYPNSQHKRY IVKDGAPTLI PSDPIALMKS TVLSTKSKLK LFLEPFLYEK   180
SSRRTSGKVS DEHLSESVAS FFERHFGKEV VDYLIDPFVA GTSGGDPESL SIRHAFPALW   240
```

```
NLENKYGSVI AGAILSKLST KGDSVKTGGA SPGKGRNKRV SFSFHGGMQS LIDALHNEVG   300
DGNVKLGTEV LSLACCCDGV SSSGGWSISV DSKDAKGKDL RKNQSFDAVI MTAPLSNVQR   360
MKFTKGGVPF VLDFLPKVDY LPLSLMVTAF KKEDVKKPLE GFGALIPYKE QQKHGLKTLG   420
TLFSSMMFPD RAPNDQYLYT SFIGGSHNRD LAGAPTAILK QLVTSDLRKL LGVEGQPTFV   480
KHVHWRNAFP LYGQNYDLVL EAIAKMENNL PGFFYAGNNK DGLAVGNVIA SGSKAADLVI   540
SYLESCTDQD N                                                       551

SEQ ID NO: 638          moltype = DNA   length = 1656
FEATURE                 Location/Qualifiers
source                  1..1656
                        mol_type = other DNA
                        organism = Oryza sativa
SEQUENCE: 638
atgctctctc ctgccaccac cttctcctcc tcctcctcct cctcgtcgcc gtcgcgcgcc     60
cacgctcgcg ctcccacccg cttgcggtc gcagcatccg cgcgcgccgc acggttccgc    120
cccgcgcgcg ccatggccgc ctccgacgac ccccgcggcg ggaggtccgt cgccgtcgtc    180
ggcgccggcg tcagtgggct cgcggcggcg tacaggctga ggaagcgcgg cgtgcaggtg    240
acggtgttcg aggcggccga cagggcgggt gggaagatac ggaccaactc cgagggcggg    300
ttcatctggg acgaaggggc caacaccatg acagagagtg aattggaggc aagcaggctt    360
attgacgatc ttggcctaca aggcaaacag cagtatccta actcacaaca caagcgttac    420
attgtcaaag atggagcacc aacactgatt ccctcagatc ccattgcgct catgaaaagc    480
actgttcttt ctacaaaatc aaagctcaag ctatttctgg aaccattcct ctatgagaaa    540
tctagcagaa ggacctcggg aaaagtgtct gatgaacatt taagtgagag tgttgcaagt    600
ttctttgaac gccactttgg aaaagaggtt gttgattatc ttattgatcc atttgtggct    660
ggaacaagcg gaggagatcc tgagtcatta tcaattcgtc atgcatttcc agcattatgg    720
aatttggaga ataagtatgg ctctgtcatt gctggtgcca tcttgtccaa actatccact    780
aagggtgatt cagtgaagac aggaggtgct tcgccaggga aggaaggaa taaacgtgtg    840
tcattttcat ttcatggtgg aatgcagtca ctaatagatg cacttcacaa tgaagttgga    900
gatggtaacg tgaagcttgg tacagaagtg ttgtcattgg catgttgctg tgatggagtc    960
tcttcttctg gtggttggtc aatttctgtt gattcaaaag atgctaaagg gaaagatctc   1020
agaaagaacc aatctttcga tgctgttata atgactgctc cattgtctaa tgtccagagg   1080
atgaagttta caaaaggtgg agttcccttt gtgctagact tcttcctaa ggtcgattat   1140
ctaccactat ctctcatggt aacagctttt aagaaggaag atgtcaaaaa accattggaa   1200
ggatttggtg ccttgatacc ctataaggaa cagcaaaagc atggtctcaa aaccctttgg   1260
accctcttct cctcgatgat gtttccagat cgagctccta atgatcaata tctatataca   1320
tctttgattg ggggagcca taatagagac ctcgctgggg ctccaacggc tattctgaaa   1380
caacttgtga cctctgacct aagaaagctc ttgggtgttg agggacaacc tactttgtg    1440
aagcatgtac attggagaaa tgcttttcct ttatatggcc agaattatga tctggtactg   1500
gaagctatag caaaaatgga gaacaatctt ccagggttct tttacgcagg aaataacaag   1560
gatgggttgg ctgttggaaa tgttatagct tcaggaagca aggctgctga ccttgtgatc   1620
tcttatcttg aatcttgcac agatcaggac aattag                            1656

SEQ ID NO: 639          moltype = DNA   length = 1656
FEATURE                 Location/Qualifiers
source                  1..1656
                        mol_type = other DNA
                        organism = Oryza sativa
SEQUENCE: 639
atgctctctc ctgccaccac cttctcctcc tcctcctcct cctcgtcgcc gtcgcgcgcc     60
cacgctcgcg ctcccacccg cttgcggtc gcagcatccg cgcgcgccgc acggttccgc    120
cccgcgcgcg ccatggccgc ctccgacgac ccccgcggcg ggaggtccgt cgccgtcgtc    180
ggcgccggcg tcagtgggct cgcggcggcg tacaggctga ggaagcgcgg cgtgcaggtg    240
acggtgttcg aggcggccga cagggcgggt gggaagatac ggaccaactc cgagggcggg    300
ttcatctggg acgaaggggc caacaccatg acagagagtg aattggaggc aagcaggctt    360
attgacgatc ttggcctaca aggcaaacag cagtatccta actcacaaca caagcgttac    420
attgtcaaag atggagcacc aacactgatt ccctcagatc ccattgcgct catgaaaagc    480
actgttcttt ctacaaaatc aaagctcaag ctatttctgg aaccattcct ctatgagaaa    540
tctagcagaa ggacctcggg aaaagtgtct gatgaacatt taagtgagag tgttgcaagt    600
ttctttgaac gccactttgg aaaagaggtt gttgattatc ttattgatcc atttgtggct    660
ggaacaagcg gaggagatcc tgagtcatta tcaattcgtc atgcatttcc agcattatgg    720
aatttggaga ataagtatgg ctctgtcatt gctggtgcca tcttgtccaa actatccact    780
aagggtgatt cagtgaagac aggaggtgct tcgccaggga aggaaggaa taaacgtgtg    840
tcattttcat ttcatggtgg aatgcagtca ctaatagatg cacttcacaa tgaagttgga    900
gatggtaacg tgaagcttgg tacagaagtg ttgtcattgg catgttgctg tgatggagtc    960
tcttcttctg gtggttggtc aatttctgtt gattcaaaag atgctaaagg gaaagatctc   1020
agaaagaacc aatctttcga tgctgttata atgactgctc cattgtctaa tgtccagagg   1080
atgaagttta caaaaggtgg agttcccttt gtgctagact tcttcctaa ggtcgattat   1140
ctaccactat ctctcatggt aacagctttt aagaaggaag atgtcaaaaa accattggaa   1200
ggatttggtg ccttgatacc ctataaggaa cagcaaaagc atggtctcaa aaccctttgg   1260
accctcttct cctcgatgat gtttccagat cgagctccta atgatcaata tctatataca   1320
tctttaattg ggggagcca taatagagac ctcgctgggg ctccaacggc tattctgaaa   1380
caacttgtga cctctgacct aagaaagctc ttgggtgttg agggacaacc tactttgtg    1440
aagcatgtac attggagaaa tgcttttcct ttatatggcc agaattatga tctggtactg   1500
gaagctatag caaaaatgga gaacaatctt ccagggttct tttacgcagg aaataacaag   1560
gatgggttgg ctgttggaaa tgttatagct tcaggaagca aggctgctga ccttgtgatc   1620
tcttatcttg aatcttgcac agatcaggac aattag                            1656

SEQ ID NO: 640          moltype = DNA   length = 1656
FEATURE                 Location/Qualifiers
```

```
source                  1..1656
                        mol_type = other DNA
                        organism = Oryza sativa
SEQUENCE: 640
atgctctctc ctgccaccac cttctcctcc tcctcctcct cctcgtcgcc gtcgcgcgcc    60
cacgctcgcg ctcccacccg cttcgcggtc gcagcatccg cgcgcgccgc acggttccgc   120
cccgcgcgcg ccatggccgc ctccgacgac cccgcggcg ggaggtccgt cgccgtcgtc   180
ggcgccggcg tcagtgggct cgcggcggcg tacaggctga ggaagcgcgg cgtgcaggtg   240
acggtgttcg aggcggccga cagggcgggt gggaagatac ggaccaactc cgagggcggg   300
ttcatctggg acgaaggggc caacaccatg acagagagtg aattggaggc aagcaggctt   360
attgacgatc ttggcctaca aggcaaacag cagtatccta actcacaaca caagcgttac   420
attgtcaaag atggagcacc aacactgatt ccctcagatc ccattgcgct catgaaaagc   480
actgttcttt ctacaaaatc aaagctcaag ctatttctgg aaccattttct ctatgagaaa   540
tctagcagaa ggacctcggg aaaagtgtct gatgaacatt taagtgagag tgttgcaagt   600
ttctttgaac gccactttgg aaaagaggtt gttgattatc ttattgatcc atttgtggct   660
ggaacaagcg gaggagatcc tgagtcatta tcaattcgtc atgcatttcc agcattatgg   720
aatttggaga ataagtatgg ctctgtcatt gctggtgcca tcttgtccaa actatccact   780
aagggtgatt cagtgaagac aggaggtgct tcgccaggga aaggaaggaa taaacgtgtg   840
tcatttttcat ttcatggtgg aatgcagtca ctaatagatg cacttcacaa tgaagttgga   900
gatggtaacg tgaagcttgg tacagaagtg ttgtcattgg catgttgctg tgatggagtc   960
tcttcttctg gtggttggtc aatttctgtt gattcaaaag atgctaaagg gaaagatctc  1020
agaaagaacc aatctttcga tgctgttata atgactgctc cattgtctaa tgtccagagg  1080
atgaagttta caaaaggtgg agttcccttt gtgctagact ttcttcctaa ggtcgattat  1140
ctaccactat ctctcatggt aacagctttt aagaaggaag atgtcaaaaa accattggaa  1200
ggatttggtg ccttgatacc ctataaggaa cagcaaaagc atggtctcaa aacccttggg  1260
accctcttct cctcgatgat gtttccagat cgagctccta atgatcaata tctatataca  1320
tctctcattg gggggagcca taatagagac ctcgctgggg ctccaacggc tattctgaaa  1380
caacttgtga cctctgacct aagaaagctc ttgggtgttg agggacaacc tacttttgtg  1440
aagcatgtac attggagaaa tgcttttcct ttatatggcc agaattatga tctggtactg  1500
gaagctatag caaaaatgga gaacaatctt ccagggttct tttacgcagg aaataacaag  1560
gatgggttgg ctgttggaaa tgttatagct tcaggaagca aggctgctga ccttgtgatc  1620
tcttatcttg aatcttgcac agatcaggac aattag                            1656

SEQ ID NO: 641          moltype = DNA  length = 1656
FEATURE                 Location/Qualifiers
source                  1..1656
                        mol_type = other DNA
                        organism = Oryza sativa
SEQUENCE: 641
atgctctctc ctgccaccac cttctcctcc tcctcctcct cctcgtcgcc gtcgcgcgcc    60
cacgctcgcg ctcccacccg cttcgcggtc gcagcatccg cgcgcgccgc acggttccgc   120
cccgcgcgcg ccatggccgc ctccgacgac cccgcggcg ggaggtccgt cgccgtcgtc   180
ggcgccggcg tcagtgggct cgcggcggcg tacaggctga ggaagcgcgg cgtgcaggtg   240
acggtgttcg aggcggccga cagggcgggt gggaagatac ggaccaactc cgagggcggg   300
ttcatctggg acgaaggggc caacaccatg acagagagtg aattggaggc aagcaggctt   360
attgacgatc ttggcctaca aggcaaacag cagtatccta actcacaaca caagcgttac   420
attgtcaaag atggagcacc aacactgatt ccctcagatc ccattgcgct catgaaaagc   480
actgttcttt ctacaaaatc aaagctcaag ctatttctgg aaccattttct ctatgagaaa   540
tctagcagaa ggacctcggg aaaagtgtct gatgaacatt taagtgagag tgttgcaagt   600
ttctttgaac gccactttgg aaaagaggtt gttgattatc ttattgatcc atttgtggct   660
ggaacaagcg gaggagatcc tgagtcatta tcaattcgtc atgcatttcc agcattatgg   720
aatttggaga ataagtatgg ctctgtcatt gctggtgcca tcttgtccaa actatccact   780
aagggtgatt cagtgaagac aggaggtgct tcgccaggga aaggaaggaa taaacgtgtg   840
tcatttttcat ttcatggtgg aatgcagtca ctaatagatg cacttcacaa tgaagttgga   900
gatggtaacg tgaagcttgg tacagaagtg ttgtcattgg catgttgctg tgatggagtc   960
tcttcttctg gtggttggtc aatttctgtt gattcaaaag atgctaaagg gaaagatctc  1020
agaaagaacc aatctttcga tgctgttata atgactgctc cattgtctaa tgtccagagg  1080
atgaagttta caaaaggtgg agttcccttt gtgctagact ttcttcctaa ggtcgattat  1140
ctaccactat ctctcatggt aacagctttt aagaaggaag atgtcaaaaa accattggaa  1200
ggatttggtg ccttgatacc ctataaggaa cagcaaaagc atggtctcaa aacccttggg  1260
accctcttct cctcgatgat gtttccagat cgagctccta atgatcaata tctatataca  1320
tctctcattg gggggagcca taatagagac ctcgctgggg ctccaacggc tattctgaaa  1380
caacttgtga cctctgacct aagaaagctc ttgggtgttg agggacaacc tacttttgtg  1440
aagcatgtac attggagaaa tgcttttcct ttatatggcc agaattatga tctggtactg  1500
gaagctatag caaaaatgga gaacaatctt ccagggttct tttacgcagg aaataacaag  1560
gatgggttgg ctgttggaaa tgttatagct tcaggaagca aggctgctga ccttgtgatc  1620
tcttatcttg aatcttgcac agatcaggac aattag                            1656

SEQ ID NO: 642          moltype = DNA  length = 1656
FEATURE                 Location/Qualifiers
source                  1..1656
                        mol_type = other DNA
                        organism = Oryza sativa
SEQUENCE: 642
atgctctctc ctgccaccac cttctcctcc tcctcctcct cctcgtcgcc gtcgcgcgcc    60
cacgctcgcg ctcccacccg cttcgcggtc gcagcatccg cgcgcgccgc acggttccgc   120
cccgcgcgcg ccatggccgc ctccgacgac cccgcggcg ggaggtccgt cgccgtcgtc   180
ggcgccggcg tcagtgggct cgcggcggcg tacaggctga ggaagcgcgg cgtgcaggtg   240
acggtgttcg aggcggccga cagggcgggt gggaagatac ggaccaactc cgagggcggg   300
```

```
ttcatctggg acgaaggggc caacaccatg acagagagtg aattggaggc aagcaggctt   360
attgacgatc ttggcctaca aggcaaacag cagtatccta actcacaaca caagcgttac   420
attgtcaaag atggagcacc aacactgatt ccctcagatc ccattgcgct catgaaaagc   480
actgttcttt ctacaaaatc aaagctcaag ctatttctgg aaccatttct ctatgagaaa   540
tctagcagaa ggacctcggg aaaagtgtct gatgaacatt taagtgagag tgttgcaagt   600
ttctttgaac gccactttgg aaaagaggtt gttgattatc ttattgatcc atttgtggct   660
ggaacaagcg gaggagatcc tgagtcatta tcaattcgtc atgcatttcc agcattatgg   720
aatttggaga ataagtatgg ctctgtcatt gctggtgcca tcttgtccaa actatccact   780
aagggtgatt cagtgaagac aggaggtgct tcgccaggga aaggaaggaa taaacgtgtg   840
tcattttcat ttcatggtgg aatgcagtca ctaatagatg cacttcacaa tgaagttgga   900
gatggtaacg tgaagcttgg tacagaagtg ttgtcattgg catgttgctg tgatggagtc   960
tcttcttctg gtggttggtc aatttctgtt gattcaaaag atgctaaagg aaagatctc   1020
agaaagaacc aatctttcga tgctgttata atgactgctc cattgtctaa tgtccagagg   1080
atgaagttta caaaaggtgg agttcccttt gtgctagact ttcttcctaa ggtcgattat   1140
ctaccactat ctctcatggt aacagctttt aagaaggaag atgtcaaaaa accattggaa   1200
ggatttggtg ccttgatacc ctataaggaa cagcaaaagc atggtctcaa aacccttggg   1260
accctcttct cctcgatgat gtttccagat cgagctccta atgatcaata tctatataca   1320
tctatcattg gggggagcca taatagagac ctcgctgggg ctccaacggc tattctgaaa   1380
caacttgtga cctctgacct aagaaagctc ttgggtgttg agggacaacc tacttttgtg   1440
aagcatgtac attggagaaa tgcttttcct ttatatggcc agaattatga tctggtactg   1500
gaagctatag caaaaatgga gaacaatctt ccagggttct tttacgcagg aaataacaag   1560
gatgggttgg ctgttggaaa tgttatagct tcaggaagca aggctgctga ccttgtgatc   1620
tcttatcttg aatcttgcac agatcaggac aattag                             1656

SEQ ID NO: 643           moltype = DNA  length = 1656
FEATURE                  Location/Qualifiers
source                   1..1656
                         mol_type = other DNA
                         organism = Oryza sativa
SEQUENCE: 643
atgctctctc ctgccaccac cttctcctcc tcctcctcct cctcgtcgcc gtcgcgcgcc    60
cacgctcgcg ctcccacccg cttcgcggtc gcagcatccg cgcgcgccgc acggttccgc   120
cccgcgcgcg ccatggccgc ctccgacgac ccccgcggcg ggaggtccgt cgccgtcgtc   180
ggcgccgtcg tcagtgggct cgcggcggcg tacaggctga ggaagcgcgg cgtgcaggtg   240
acggtgttcg aggcggccga cagggcgggt gggaagatac ggaccaactc cgagggcggg   300
ttcatctggg acgaaggggc caacaccatg acagagagtg aattggaggc aagcaggctt   360
attgacgatc ttggcctaca aggcaaacag cagtatccta actcacaaca caagcgttac   420
attgtcaaag atggagcacc aacactgatt ccctcagatc ccattgcgct catgaaaagc   480
actgttcttt ctacaaaatc aaagctcaag ctatttctgg aaccatttct ctatgagaaa   540
tctagcagaa ggacctcggg aaaagtgtct gatgaacatt taagtgagag tgttgcaagt   600
ttctttgaac gccactttgg aaaagaggtt gttgattatc ttattgatcc atttgtggct   660
ggaacaagcg gaggagatcc tgagtcatta tcaattcgtc atgcatttcc agcattatgg   720
aatttggaga ataagtatgg ctctgtcatt gctggtgcca tcttgtccaa actatccact   780
aagggtgatt cagtgaagac aggaggtgct tcgccaggga aaggaaggaa taaacgtgtg   840
tcattttcat ttcatggtgg aatgcagtca ctaatagatg cacttcacaa tgaagttgga   900
gatggtaacg tgaagcttgg tacagaagtg ttgtcattgg catgttgctg tgatggagtc   960
tcttcttctg gtggttggtc aatttctgtt gattcaaaag atgctaaagg aaagatctc   1020
agaaagaacc aatctttcga tgctgttata atgactgctc cattgtctaa tgtccagagg   1080
atgaagttta caaaaggtgg agttcccttt gtgctagact ttcttcctaa ggtcgattat   1140
ctaccactat ctctcatggt aacagctttt aagaaggaag atgtcaaaaa accattggaa   1200
ggatttggtg ccttgatacc ctataaggaa cagcaaaagc atggtctcaa aacccttggg   1260
accctcttct cctcgatgat gtttccagat cgagctccta atgatcaata tctatataca   1320
tcttttcattg gggggagcca taatagagac ctcgctgggg ctccaacggc tattctgaaa   1380
caacttgtga cctctgacct aagaaagctc ttgggtgttg agggacaacc tacttttgtg   1440
aagcatgtac attggagaaa tgcttttcct ttatatggcc agaattatga tctggtactg   1500
gaagctatag caaaaatgga gaacaatctt ccagggttct tttacgcagg aaataacaag   1560
gatgggttgg ctgttggaaa tgttatagct tcaggaagca aggctgctga ccttgtgatc   1620
tcttatcttg aatcttgcac agatcaggac aattag                             1656

SEQ ID NO: 644           moltype = DNA  length = 1656
FEATURE                  Location/Qualifiers
source                   1..1656
                         mol_type = other DNA
                         organism = Oryza sativa
SEQUENCE: 644
atgctctctc ctgccaccac cttctcctcc tcctcctcct cctcgtcgcc gtcgcgcgcc    60
cacgctcgcg ctcccacccg cttcgcggtc gcagcatccg cgcgcgccgc acggttccgc   120
cccgcgcgcg ccatggccgc ctccgacgac ccccgcggcg ggaggtccgt cgccgtcgtc   180
ggcgccgtcg tcagtgggct cgcggcggcg tacaggctga ggaagcgcgg cgtgcaggtg   240
acggtgttcg aggcggccga cagggcgggt gggaagatac ggaccaactc cgagggcggg   300
ttcatctggg acgaaggggc caacaccatg acagagagtg aattggaggc aagcaggctt   360
attgacgatc ttggcctaca aggcaaacag cagtatccta actcacaaca caagcgttac   420
attgtcaaag atggagcacc aacactgatt ccctcagatc ccattgcgct catgaaaagc   480
actgttcttt ctacaaaatc aaagctcaag ctatttctgg aaccatttct ctatgagaaa   540
tctagcagaa ggacctcggg aaaagtgtct gatgaacatt taagtgagag tgttgcaagt   600
ttctttgaac gccactttgg aaaagaggtt gttgattatc ttattgatcc atttgtggct   660
ggaacaagcg gaggagatcc tgagtcatta tcaattcgtc atgcatttcc agcattatgg   720
aatttggaga ataagtatgg ctctgtcatt gctggtgcca tcttgtccaa actatccact   780
aagggtgatt cagtgaagac aggaggtgct tcgccaggga aaggaaggaa taaacgtgtg   840
```

```
tcatttcat ttcatggtgg aatgcagtca ctaatagatg cacttcacaa tgaagttgga    900
gatggtaacg tgaagcttgg tacagaagtg ttgtcattgg catgttgctg tgatggagtc    960
tcttcttctg gtggttggtc aatttctgtt gattcaaaag atgctaaagg gaaagatctc   1020
agaaagaacc aatctttcga tgctgttata atgactgctc cattgtctaa tgtccagagg   1080
atgaagttta caaaaggtgg agttcccttt gtgctagact ttcttcctaa ggtcgattat   1140
ctaccactat ctctcatggt aacagctttt aagaaggaag atgtcaaaaa accattggaa   1200
ggatttggtg ccttgatacc ctataaggaa cagcaaaagc atggtctcaa aacccttgcg   1260
accctcttct cctcgatgat gtttccagat cgagctccta atgatcaata tctatataca   1320
tctttcattg gggggagcca taatagagac ctcgctgggg ctccaacggc tattctgaaa   1380
caacttgtga cctctgacct aagaaagctc ttgggtgttg agggacaacc tacttttgtg   1440
aagcatgtac attggagaaa tgcttttcct ttatatggcc agaattatga tctggtactg   1500
gaagctatag caaaaatgga gaacaatctt ccagggttct tttacgcagg aaataacaag   1560
gatgggttgg ctgttggaaa tgttatagct tcaggaagca aggctgctga ccttgtgatc   1620
tcttatcttg aatcttgcac agatcaggac aattag                              1656

SEQ ID NO: 645         moltype = DNA   length = 1656
FEATURE                Location/Qualifiers
source                 1..1656
                       mol_type = other DNA
                       organism = Oryza sativa
SEQUENCE: 645
atgctctctc ctgccaccac cttctcctcc tcctcctcct cctcgtcgcc gtcgcgcgcc     60
cacgctcgcg ctcccacccg cttcgcggtc gcagcatccg cgcgcgccgc acggttccgc    120
cccgcgcgcg ccatggccgc ctccgacgac ccccgcggcg ggaggtccgt cgccgtcgtc    180
ggcgccggcg tcagtgggct cgcggcggcg tacaggctga ggaagcgcgg cgtgcaggtg    240
acggtgttcg aggcggccga cagggcgggt gggaagatac ggaccaactc cgagggcggg    300
ttcatctggg acgaagggc caacaccatg acagagagtg aattggaggc aagcaggctt    360
attgacgatc ttggcctaca aggcaaacag cagtatccta actcacaaca caagcgttac    420
attgtcaaag atggagcacc aacactgatt ccctcagatc ccattgcgct catgaaaagc    480
actgttcttt ctacaaaatc aaagctcaag ctatttctgg aaccattct ctatgagaaa    540
tctagcagaa ggacctcggg aaaagtgtct gatgaacatt taagtgagag tgttgcaagt    600
ttctttgaac gccactttgg aaaagaggtt gttgattatc ttattgatcc atttgtggct    660
ggaacaagcg gaggagatcc tgagtcatta tcaattcgtc atgcatttcc agcattatgg    720
aatttggaga ataagtatgg ctctgtcatt gctggtgcca tcttgtccaa actatccact    780
aagggtgatt cagtgaagac aggaggtgct tcgccaggga aggaaggaa taacgctgtg    840
tcatttcat ttcatggtgg aatgcagtca ctaatagatg cacttcacaa tgaagttgga    900
gatggtaacg tgaagcttgg tacagaagtg ttgtcattgg catgttgctg tgatggagtc    960
tcttcttctg gtggttggtc aatttctgtt gattcaaaag atgctaaagg gaaagatctc   1020
agaaagaacc aatctttcga tgctgttata atgactgctc cattgtctaa tgtccagagg   1080
atgaagttta caaaaggtgg agttcccttt gtgctagact ttcttcctaa ggtcgattat   1140
ctaccactat ctctcatggt aacagctttt aagaaggaag atgtcaaaaa accattggaa   1200
ggatttggtg ccttgatacc ctataaggaa cagcaaaagc atggtctcaa aacccttggg   1260
accctcttct cctcgatgat gtttccagat cgagctccta atgatcaata tctatataca   1320
tctttcattg gggggagcca taatagagac ctcgctgggg ctccaacggc tattctgaaa   1380
caacttgtga cctctgacct aagaaagctc ttgggtgttg agggacaacc tacttttgtg   1440
aagcatgtac attggagaaa tgcttttcct ttatatggcc agaattatga tctggtactg   1500
gaagctatag caaaaatgga gaacaatctt ccagggttct tttacgcagg aaataacaag   1560
gatgggttgg ctgttggaaa tgttatagct tcaggaagca aggctgctga ccttgtgatc   1620
tcttatcttg aatcttgcac agatcaggac aattag                              1656

SEQ ID NO: 646         moltype = DNA   length = 1656
FEATURE                Location/Qualifiers
source                 1..1656
                       mol_type = other DNA
                       organism = Oryza sativa
SEQUENCE: 646
atgctctctc ctgccaccac cttctcctcc tcctcctcct cctcgtcgcc gtcgcgcgcc     60
cacgctcgcg ctcccacccg cttcgcggtc gcagcatccg cgcgcgccgc acggttccgc    120
cccgcgcgcg ccatggccgc ctccgacgac ccccgcggcg ggaggtccgt cgccgtcgtc    180
ggcgccggcg tcagtgggct cgcggcggcg tacaggctga ggaagcgcgg cgtgcaggtg    240
acggtgttcg aggcggccga cagggcgggt gggaagatac ggaccaactc cgagggcggg    300
ttcatctggg acgaagggc caacaccatg acagagagtg aattggaggc aagcaggctt    360
attgacgatc ttggcctaca aggcaaacag cagtatccta actcacaaca caagcgttac    420
attgtcaaag atggagcacc aacactgatt ccctcagatc ccattgcgct catgaaaagc    480
actgttcttt ctacaaaatc aaagctcaag ctatttctgg aaccattct ctatgagaaa    540
tctagcagaa ggacctcggg aaaagtgtct gatgaacatt taagtgagag tgttgcaagt    600
ttctttgaac gccactttgg aaaagaggtt gttgattatc ttattgatcc atttgtggct    660
ggaacaagcg gaagagatcc tgagtcatta tcaattcgtc atgcatttcc agcattatgg    720
aatttggaga ataagtatgg ctctgtcatt gctggtgcca tcttgtccaa actatccact    780
aagggtgatt cagtgaagac aggaggtgct tcgccaggga aggaaggaa taacgctgtg    840
tcatttcat ttcatggtgg aatgcagtca ctaatagatg cacttcacaa tgaagttgga    900
gatggtaacg tgaagcttgg tacagaagtg ttgtcattgg catgttgctg tgatggagtc    960
tcttcttctg gtggttggtc aatttctgtt gattcaaaag atgctaaagg gaaagatctc   1020
agaaagaacc aatctttcga tgctgttata atgactgctc cattgtctaa tgtccagagg   1080
atgaagttta caaaaggtgg agttcccttt gtgctagact ttcttcctaa ggtcgattat   1140
ctaccactat ctctcatggt aacagctttt aagaaggaag atgtcaaaaa accattggaa   1200
ggatttggtg ccttgatacc ctataaggaa cagcaaaagc atggtctcaa aacccttggg   1260
accctcttct cctcgatgat gtttccagat cgagctccta atgatcaata tctatataca   1320
tctttcattg gggggagcca taatagagac ctcgctgggg ctccaacggc tattctgaaa   1380
```

-continued

```
caacttgtga cctctgacct aagaaagctc ttgggtgttg agggacaacc tactttgtg      1440
aagcatgtac attggagaaa tgcttttcct ttatatggcc agaattatga tctggtactg      1500
gaagctatag caaaaatgga gaacaatctt ccagggttct tttacgcagg aaataacaag     1560
gatgggttgg ctgttggaaa tgttatagct tcaggaagca aggctgctga ccttgtgatc     1620
tcttatcttg aatcttgcac agatcaggac aattag                                1656

SEQ ID NO: 647         moltype = DNA  length = 1656
FEATURE                Location/Qualifiers
source                 1..1656
                       mol_type = other DNA
                       organism = Oryza sativa
SEQUENCE: 647
atgctctctc ctgccaccac cttctcctcc tcctcctcct cctcgtcgcc gtcgcgcgcc       60
cacgctcgcg ctcccacccg cttcgcggtc gcagcatccg cgcgcgccgc acggttccgc      120
cccgcgcgcg ccatggccgc ctccgacgac ccccgcggcg ggaggtccgt cgccgtcgtc      180
ggcgccggcg tcagtgggct cgcggcggcg tacaggctga ggaagcgcgg cgtgcaggtg      240
acggtgttcg aggcggccga cagggcgggt gggaagatac ggaccaactc cgagggcggg      300
ttcatctggg acgaagggc caacaccatg acagagagtg aattggaggc aagcaggctt       360
attgacgatc ttggcctaca aggcaaacag cagtatccta actcacaaca caagcgttac      420
attgtcaaag atggagcacc aacactgatt ccctcagatc ccattgcgct catgaaaagc      480
actgttcttt ctacaaaatc aaagctcaag ctatttctgg aaccattct ctatgagaaa       540
tctagcagaa ggacctcggg aaaagtgtct gatgaacatt taagtgagag tgttgcaagt      600
ttctttgaac gccactttgg aaaagaggtt gttgattatc ttattgatcc atttgtggct      660
ggaacaagcg gaagagatcc tgagtcatta tcaattcgtc atgcatttcc agcattatgg      720
aatttggaga ataagtatgg ctctgtcatt gctggtgcca tcttgtccaa actatccact      780
aagggtgatt cagtgaagac aggaggtgct tcgccaggga aggaaggaa taaacgtgtg      840
tcattttcat ttcatggtgg aatgcagtca ctaatagatg cacttcacaa tgaagttgga    900
gatggtaacg tgaagcttgg tacagaagtg ttgtcattgg catgttgctg tgatggagtc     960
tcttcttctg tgtggttggtc aatttctgtt gattcaaaag atgctaaagg aaagatctc    1020
agaaagaacc aatctttcga tgctgttata atgactgctc cattgtctaa tgtccagagg    1080
atgaagtta caaaaggtgg agttcccttt gtgctagact tcttcctaa ggtcgattat      1140
ctaccactat ctctcatggt aacagctttt aagaaggaag atgtcaaaaa accattggaa    1200
ggatttggtg ccttgatacc ctataaggaa cagcaaaagc atggtctcaa aacccttggg    1260
accctcttct cctcgatgat gtttccagat cgagctccta atgatcaata tctatataca    1320
tctttcattg gggggagcca taatagagac ctcgctgggg ctccaacggc tattctgaaa     1380
caacttgtga cctctgacct aagaaagctc ttgggtgttg agggacaacc tactttgtg     1440
aagcatgtac attggagaaa tgcttttcct ttatatggcc agaattatga tctggtactg    1500
gaagctatag caaaaatgga gaacaatctt ccagggttct tttacgcagg aaataacaag    1560
gatgggttgg ctgttggaaa tgttatagct tcaggaagca aggctgctga ccttgtgatc    1620
tcttatcttg aatcttgcac agatcaggac aattag                              1656

SEQ ID NO: 648         moltype = DNA  length = 1656
FEATURE                Location/Qualifiers
source                 1..1656
                       mol_type = other DNA
                       organism = Oryza sativa
SEQUENCE: 648
atgctctctc ctgccaccac cttctcctcc tcctcctcct cctcgtcgcc gtcgcgcgcc       60
cacgctcgcg ctcccacccg cttcgcggtc gcagcatccg cgcgcgccgc acggttccgc      120
cccgcgcgcg ccatggccgc ctccgacgac ccccgcggcg ggaggtccgt cgccgtcgtc      180
ggcgccggcg tcagtgggct cgcggcggcg tacaggctga ggaagcgcgg cgtgcaggtg      240
acggtgttcg aggcggccga cagggcgggt gggaagatac ggaccaactc cgagggcggg      300
ttcatctggg acgaagggc caacaccatg acagagagtg aattggaggc aagcaggctt       360
attgacgatc ttggcctaca aggcaaacag cagtatccta actcacaaca caagctttac      420
attgtcaaag atggagcacc aacactgatt ccctcagatc ccattgcgct catgaaaagc      480
actgttcttt ctacaaaatc aaagctcaag ctatttctgg aaccattct ctatgagaaa       540
tctagcagaa ggacctcggg aaaagtgtct gatgaacatt taagtgagag tgttgcaagt      600
ttctttgaac gccactttgg aaaagaggtt gttgattatc ttattgatcc atttgtggct      660
ggaacaagcg gaggagatcc tgagtcatta tcaattcgtc atgcatttcc agcattatgg      720
aatttggaga ataagtatgg ctctgtcatt gctggtgcca tcttgtccaa actatccact      780
aagggtgatt cagtgaagac aggaggtgct tcgccaggga aggaaggaa taaacgtgtg       840
tcattttcat ttcatggtgg aatgcagtca ctaatagatg cacttcacaa tgaagttgga    900
gatggtaacg tgaagcttgg tacagaagtg ttgtcattgg catgttgctg tgatggagtc     960
tcttcttctg tgtggttggtc aatttctgtt gattcaaaag atgctaaagg aaagatctc    1020
agaaagaacc aatctttcga tgctgttata atgactgctc cattgtctaa tgtccagagg    1080
atgaagtta caaaaggtgg agttcccttt gtgctagact tcttcctaa ggtcgattat      1140
ctaccactat ctctcatggt aacagctttt aagaaggaag atgtcaaaaa accattggaa    1200
ggatttggtg ccttgatacc ctataaggaa cagcaaaagc atggtctcaa aacccttggg    1260
accctcttct cctcgatcct gtttccagat cgagctccta atgatcaata tctatataca    1320
tctttcattg gggggagcca taatagagac ctcgctgggg ctccaacggc tattctgaaa     1380
caacttgtga cctctgacct aagaaagctc ttgggtgttg agggacaacc tactttgtg     1440
aagcatgtac attggagaaa tgcttttcct ttatatggcc agaattatga tctggtactg    1500
gaagctatag caaaaatgga gaacaatctt ccagggttct tttacgcagg aaataacaag    1560
gatgggttgg ctgttggaaa tgttatagct tcaggaagca aggctgctga ccttgtgatc    1620
tcttatcttg aatcttgcac agatcaggac aattag                              1656

SEQ ID NO: 649         moltype = DNA  length = 1656
FEATURE                Location/Qualifiers
source                 1..1656
```

```
                    mol_type = other DNA
                    organism = Oryza sativa
SEQUENCE: 649
atgctctctc ctgccaccac ctttctcctcc tcctcctcct cctcgtcgcc gtcgcgcgcc    60
cacgctcgcg ctcccacccg cttcgcggtc gcagcatccg cgcgcgccgc acggttccgc   120
cccgcgcgcg ccatggccgc ctccgacgac ccccgcggcg ggaggtccgt cgccgtcgtc   180
ggcgccggcg tcagtgggct cgcggcggcg tacaggctga ggaagcgcgg cgtgcaggtg   240
acggtgttcg aggcggccga cagggcgggt gggaagatac ggaccaactc cgagggcggg   300
ttcatctggg acgaaggggc caacaccatg acagagagtg aattggaggc aagcaggctt   360
attgacgatc ttggcctaca aggcaaacag cagtatccta actcacaaca caagggttac   420
attgtcaaag atggagcacc aacactgatt ccctcagatc ccattgcgct catgaaaagc   480
actgttcttt ctacaaaatc aaagctcaag ctatttctgg aaccatttct ctatgagaaa   540
tctagcagaa ggacctcggg aaaagtgtct gatgaacatt taagtgagag tgttgcaagt   600
ttctttgaac gccactttgg aaaagaggtt gttgattatc ttattgatcc atttgtggct   660
ggaacaagcg gaggagatcc tgagtcatta tcaattcgtc atgcatttcc agcattatgg   720
aatttggaga ataagtatgg ctctgtcatt gctggtgcca tcttgtccaa actatccact   780
aagggtgatt cagtgaagac aggaggtgct tcgccaggga aaggaaggaa taaacgtgtg   840
tcattttcat ttcatggtgg aatgcagtca ctaatagatg cacttcacaa tgaagttgga   900
gatggtaacg tgaagcttgg tacagaagtg ttgtcattgg catgttgctg tgatggagtc   960
tcttcttctg gtggttggtc aatttctgtt gattcaaaag atgctaaagg gaaagatctc  1020
agaaagaacc aatctttcga tgctgttata atgactgctc cattgtctaa tgtccagagg  1080
atgaagttta caaaaggtgg agttcccttt gtgctagact ttcttcctaa ggtcgattat  1140
ctaccactat ctctcatggt aacagctttt aagaaggaag atgtcaaaaa accattggaa  1200
ggatttggtg ccttgatacc ctataaggaa cagcaaaagc atggtctcaa aacccttggg  1260
accctcttct cctcgatgat gtttccagat cgagctccta atgatcaata tctatataca  1320
tctttcattg gggggagcca taatagagac ctcgctgggg ctccaacggc tattctgaaa  1380
caacttgtga cctctgacct aagaaagctc ttgggtgttg agggacaacc tacttttgtg  1440
aagcatgtac attggagaaa tgcttttcct ttatatggcc agaattatga tctggtactg  1500
gaagctatag caaaaatgga gaacaatctt ccagggttct tttacgcagg aaataacaag  1560
gatgggttgg ctgttggaaa tgttatagct tcaggaagca aggctgctga ccttgtgatc  1620
tcttatcttg aatcttgcac agatcaggac aattag                            1656

SEQ ID NO: 650              moltype = DNA  length = 1656
FEATURE                     Location/Qualifiers
source                      1..1656
                            mol_type = other DNA
                            organism = Oryza sativa
SEQUENCE: 650
atgctctctc ctgccaccac ctttctcctcc tcctcctcct cctcgtcgcc gtcgcgcgcc    60
cacgctcgcg ctcccacccg cttcgcggtc gcagcatccg cgcgcgccgc acggttccgc   120
cccgcgcgcg ccatggccgc ctccgacgac ccccgcggcg ggaggtccgt cgccgtcgtc   180
ggcgccggcg tcagtgggct cgcggcggcg tacaggctga ggaagcgcgg cgtgcaggtg   240
acggtgttcg aggcggccga cagggcgggt gggaagatac ggaccaactc cgagggcggg   300
ttcatctggg acgaaggggc caacaccatg acagagagtg aattggaggc aagcaggctt   360
attgacgatc ttggcctaca aggcaaacag cagtatccta actcacaaca caagcgttac   420
attgtcaaag atggagcacc aacactgatt ccctcagatc ccattgcgct catgaaaagc   480
actgttcttt ctacaaaatc aaagctcaag ctatttctgg aaccatttct ctatgagaaa   540
tctagcagaa ggacctcggg aaaagtgtct gatgaacatt taagtgagag tgttgcaagt   600
ttctttgaac gccactttgg aaaagaggtt gttgattatc ttattgatcc atttgtggct   660
ggaacaagcg gaggagatcc tgagtcatta tcaattcgtc atgcatttcc agcattatgg   720
aatttggaga ataagtatgg ctctgtcatt gctggtgcca tcttgtccaa actatccact   780
aagggtgatt cagtgaagac aggaggtgct tcgccaggga aaggaaggaa taaacgtgtg   840
tcattttcat ttcatggtgg aatgcagtca ctaatagatg cacttcacaa tgaagttgga   900
gatggtaacg tgaagcttgg tacagaagtg ttgtcattgg catgttgctg tgatggagtc   960
tcttcttctg gtggttggtc aatttctgtt gattcaaaag atgctaaagg gaaagatctc  1020
agaaagaacc aatctttcga tgctgttata atgactgctc cattgtctaa tgtccagagg  1080
atgaagttta caaaaggtgg agttcccttt gtgctagact ttcttcctaa ggtcgattat  1140
ctaccactat ctctcatggt aacagctttt aagaaggaag atgtcaaaaa accattggaa  1200
ggatttggtg ccttgatacc ctataaggaa cagcaaaagc atggtctcaa aacccttggg  1260
accctcttct cctcgatgat gtttccagat cgagctccta atgatcaata tctatataca  1320
tctttcattg gggggagcca taatagagac ctcgctgggg ctccaacggc tattctgaaa  1380
caacttgtga cctctgacct aagaaagctc ttgggtgttg agggacaacc tacttttgtg  1440
aagcatgtac attggagaaa tgcttttcct ttatatggcc agaattatga tctggtactg  1500
gaagctatag caaaaatgga gaacaatctt ccagggttct tttacgcagg aaataacaag  1560
gatgggttgg ctgttggaaa tgttatagct tcaggaagca aggctgctga ccttgtgatc  1620
tcttatcttg aatcttgcac agatcaggac aattag                            1656
```